(12) United States Patent
Itoh et al.

(10) Patent No.: US 8,492,378 B2
(45) Date of Patent: Jul. 23, 2013

(54) GSK-3β INHIBITOR

(75) Inventors: Fumio Itoh, Osaka (JP); Jun Kunitomo, Osaka (JP); Hiromi Kobayashi, Ibaraki (JP); Eiji Kimura, Osaka (JP); Morihisa Saitoh, Osaka (JP); Tomohiro Kawamoto, Osaka (JP); Hiroki Iwashita, Osaka (JP); Katsuhito Murase, Prospect Heights, IL (US)

(73) Assignee: Takeda Pharmaceutical Company Limited, Osaka (JP)

( * ) Notice: Subject to any disclaimer, the term of this patent is extended or adjusted under 35 U.S.C. 154(b) by 51 days.

(21) Appl. No.: 12/309,906

(22) PCT Filed: Aug. 2, 2007

(86) PCT No.: PCT/JP2007/065203
§ 371 (c)(1),
(2), (4) Date: Feb. 3, 2009

(87) PCT Pub. No.: WO2008/016123
PCT Pub. Date: Feb. 7, 2008

(65) Prior Publication Data
US 2010/0069381 A1 Mar. 18, 2010

(30) Foreign Application Priority Data

Aug. 3, 2006 (JP) ................................. 2006-212642

(51) Int. Cl.
*A61K 31/535* (2006.01)

(52) U.S. Cl.
USPC ................... 514/233.5; 514/254.03; 514/264; 514/303; 546/121; 548/144; 544/138; 544/367

(58) Field of Classification Search
USPC ... 548/145, 144; 546/269.4, 121; 514/254.03, 514/303; 544/138, 367
See application file for complete search history.

(56) References Cited

U.S. PATENT DOCUMENTS

| 5,371,074 | A | 12/1994 | Dunlap et al. |
| 6,391,874 | B1 | 5/2002 | Cockerill et al. |
| 6,420,367 | B1 | 7/2002 | Ueda et al. |
| 2003/0232869 | A1 | 12/2003 | Wallace et al. |
| 2004/0127536 | A1 | 7/2004 | Bhagwat et al. |
| 2005/0009876 | A1 | 1/2005 | Bhagwat et al. |
| 2005/0261339 | A1 | 11/2005 | Ohi et al. |
| 2006/0004011 | A1 | 1/2006 | Ladouceur et al. |
| 2006/0252790 | A1 | 11/2006 | Allen et al. |

FOREIGN PATENT DOCUMENTS

| EP | 1 847 531 | 10/2007 |
| JP | 5-194444 | 8/1993 |
| JP | 8-12579 | 1/1996 |
| JP | 2000-514445 | 10/2000 |
| JP | 2000-514806 | 11/2000 |
| JP | 2000-515136 | 11/2000 |
| JP | 2004-513882 | 5/2004 |
| JP | 2004-536782 | 12/2004 |
| JP | 2005-298437 | 10/2005 |
| JP | 2005-530709 | 10/2005 |
| JP | 2006-503062 | 1/2006 |
| JP | 2006-509840 | 3/2006 |
| JP | 2006-513258 | 4/2006 |
| WO | 95/09159 | 4/1995 |
| WO | 98/02434 | 1/1998 |
| WO | 98/02437 | 1/1998 |
| WO | 98/02438 | 1/1998 |
| WO | 00/04014 | 1/2000 |
| WO | 02/10137 | 2/2002 |
| WO | 02/50062 | 6/2002 |
| WO | 02/060879 | 8/2002 |
| WO | 03/101968 | 12/2003 |
| WO | 2004/014910 | 2/2004 |
| WO | 2004/029053 | 4/2004 |
| WO | 2004/094388 | 11/2004 |
| WO | 2005/023251 | 3/2005 |
| WO | 2005/032550 | 4/2005 |
| WO | 2005/037259 | 4/2005 |
| WO | 2005/040157 | 5/2005 |
| WO | 2005/051308 | 6/2005 |
| WO | 2005/051942 | 6/2005 |
| WO | 2005/105780 | 11/2005 |
| WO | 2005/111018 | 11/2005 |
| WO | 2006/044860 | 4/2006 |
| WO | 2006/058007 | 6/2006 |
| WO | 2006/069155 | 6/2006 |
| WO | 2006/085685 | 8/2006 |
| WO | 2006/124780 | 11/2006 |
| WO | 2007/071598 | 6/2007 |

OTHER PUBLICATIONS

STN Accession No. 1977:495447.*
International Search Report issued Oct. 23, 2007 in International Application No. PCT/JP2007/065203.
L. Nærum et al. "Scaffold Hopping and Optimization towards Libraries of Glycogen Synthase Kinase-3 Inhibitors", Bioorganic & Medicinal Chemistry Letters, vol. 12, No. 11, pp. 1525-1528 (2002).
G. Mazzone et al. "2,5 Diaryl-substituted 1,3,4-oxadiazoles: Synthesis and Preliminary Pharmacological Research", Farmaco, Edizione Scientifica, vol. 39, No. 5, pp. 414-420 (1984).

(Continued)

*Primary Examiner* — Brandon Fetterolf
*Assistant Examiner* — Jean Cornet
(74) *Attorney, Agent, or Firm* — Wenderoth, Lind & Ponack, L.L.P.

(57) ABSTRACT

For the purpose of providing a GSK-3β inhibitor containing an oxadiazole compound or a salt thereof or a prodrug thereof useful as an agent for the prophylaxis or treatment of a GSK-3β-related pathology or disease, the present invention provides a GSK-3β inhibitor containing a compound represented by the formula (I):

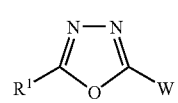

wherein each symbol is as defined in the specification, or a salt thereof or a prodrug thereof.

5 Claims, No Drawings

OTHER PUBLICATIONS

D. Rusnak et al. "The Characterization of Novel, Dual ErbB-2/EGFR, Tyrosine Kinase Inhibitors: Potential Therapy for Cancer", Cancer Research, vol. 61, No. 19, pp. 7196-7203 (2001).
STN Search Result No. 1 by the Applicants (2006).
STN Search Result No. 2 by the Applicants (2006).
STN Search Result No. 3 by the Applicants (2006).
STN Search Result No. 4 by the Applicants (2006).
FA Omar et al., "Design, Synthesis and Antiinflammatory Activity of Some 1,3,4-oxadiazole derivatives", European Journal of Medical Chemistry, 31 (10), pp. 819-825 (1996).
S.N. Sawhney, et al. "Benzothiazole Derivatives: Part IV. Synthesis of some 2- and 6- (1,3,4-Oxadiazol-2-yl) benzothiazoles and 2- and 6-(1,3,4-Thiadiazol-2-yl) benzothiazoles as Potential Antiinflammatory Agents", Journal of the Indian Chemical Society, vol. LI, pp. 886-890 (1974).
B.M. Culbertson et al. "Poly(Phenylene-1,3,4-Oxadiazolyl Benzoxazoles)", Journal of Polymer Science, Polymer Letters, Part B, vol. 4 (4), pp. 249-253 (1966).
STN Search Result No. 5 by the Applicants (2007).
STN Search Results No. 6 by the Applicants (2007).

\* cited by examiner

SEQUENCE LISTING

<160> NUMBER OF SEQ ID NOS: 2

<210> SEQ ID NO 1
<211> LENGTH: 65
<212> TYPE: DNA
<213> ORGANISM: Artificial
<220> FEATURE:
<223> OTHER INFORMATION: Primer for cloning human GSK3beta gene

<400> SEQUENCE: 1
aaagaattca ccatggacta caaggacgac gatgacaagt cagggcggcc cagaaccacc    60
tcctt    65

```
<210> SEQ ID NO 2
<211> LENGTH: 39
<212> TYPE: DNA
<213> ORGANISM: Artificial
<220> FEATURE:
<223> OTHER INFORMATION: Primer for cloning human GSK3beta gene

<400> SEQUENCE: 2
aaaagtcgac tcaggtggag ttggaagctg atgcagaag                            39
```

GSK-3β INHIBITOR

This application is a U.S. national stage of International Application No. PCT/JP2007/065203 filed Aug. 2, 2007.

TECHNICAL FIELD

The present invention relates to oxadiazole compounds having a Glycogen Synthase Kinase 3 (GSK-3) inhibitory activity, which are useful as pharmaceutical agents, and use thereof.

BACKGROUND OF THE INVENTION

GSK-3 was found to be a kinase that phosphorylates and deactivates glycogen synthase. It has been clarified at present that it is involved in the oxidation and synthesis of fatty acid, or abnormality in insulin signaling pathway via phosphates of various protein groups related to metabolism and signal is transduction such as AcylCoA carboxylase, ATP-citrate lyase, Insulin receptor substrate-1 and the like. Moreover, GSK-3 is known to phosphorylate various structural proteins and regulate functions thereof. Particularly, phosphorylation of tau protein has been attracting attention in relation to the onset of Alzheimer's disease. In addition, GSK-3 is involved in phosphorylation of various transcription factors, and particularly, activates activator protein-1, cyclic AMP response element binding protein, nuclear factor of activated T cells, heat shock factor-1, β-catenin, Myc, C/EBP, NFκ-b or the like. Therefore, its inhibitor is expected to be a therapeutic drug for Alzheimer's disease, cerebral stroke, bipolar disorder, schizophrenia, cancer, bone disease, type II diabetes and obesity.

In insulin signaling pathway, GSK-3 is negatively regulated by phosphorylation via Akt (protein kinase B: also described as PKB). In diabetic patients, increased activity of GSK-3 and synthesis of fatty acids and/or insulin resistance are considered to be synergistically induced by the overlapped occurrence of promoted GSK-3 gene expression and insulin dysfunction. Since GSK-3 positively regulates the process of adipocyte differentiation and/or maturation via phosphorylation of C/EBP, increased GSK-3 activity triggers obesity, which in turn aggravates diabetes. In fact, it has been reported that administration of GSK-3 inhibitor improves insulin resistance of model animals of Type II diabetes. We have elucidated as our own findings that GSK-3 inhibitor suppresses adipocyte differentiation and/or maturation, expresses an antiobesity effect, and promotes sugar-dependent insulin secretory action of pancreatic β cells. Given these findings in combination, GSK-3 is considered to be additively and/or synergistically involved in the onset of diabetes in the insulin targeting tissues such as liver, skeletal muscle, fat, pancreas and the like, and GSK-3 inhibitor can be an effective therapeutic drug for obesity and/or diabetes because it eliminates these factors.

Activation of GSK-3 in Alzheimer's brain has been reported, and therefore, GSK-3 is considered to be involved in senile plaque and neurofibrillary tangle, which are the two major pathological findings in Alzheimer's disease. In the metabolism of amyloid precursor proteins, GSK-3 is linked to γ secretase to positively regulate the production of β amyloid protein, a main constituent component of senile plaque. As for tau protein, which is a main constituent component of neurofibrillary tangle, GSK-3 is considered to facilitate phosphorylation of the protein, prevent axonal transport, and finally induce neurodegeneration. It is also known that GSK-3 is located downstream of the PI3 kinase-Akt system signal transduction important for the neuronal cell survival, and activated during neuronal cell death. Accordingly, GSK-3 inhibitor is expected to not only suppress neurodegeneration but also suppress two major pathological findings of Alzheimer's disease. As our own findings, we have clarified that PI3 kinase-Akt system signal transduction plays a key role in neurogenesis and neuroregeneration and found that inhibition of GSK-3 located downstream thereof can facilitate neurogenesis. Considering our new findings in combination, there is a possibility that GSK-3 inhibitor suppresses two major pathological findings of Alzheimer's disease and additionally suppresses neurodegeneration, induces neurogenesis and achieves regeneration of function. It is assumed that GSK-3 inhibitor having the above-mentioned properties can be an ultimate therapeutic drug for Alzheimer's disease, and can also be effective as a therapeutic drug for neurodegenerative diseases such as Parkinson's disease and the like, cerebrovascular disorders and the like. Since a report has recently documented that Akt system signal transduction decreases in schizophrenia, GSK-3 inhibitor may become a completely new type of therapeutic drug for schizophrenia.

The following are known as regards the relationship between GSK-3 and diseases such as neurological disorder, diabetes, cancer, inflammatory disease (sepsis shock etc.), osteoporosis, alopecia and the like.

In neurological disorder, GSK-3 relates to neuronal cell death and nerve cell survival, and induces apoptosis by over-expression of GSK-3 (non-patent document 1). In addition, GSK-3 phosphorylates tau protein which causes neurofibrillary tangle (non-patent document 2).

In diabetes, GSK-3 phosphorylates glycogen synthase to decrease the activity, and inhibits glucose uptake in skeletal muscle to decrease the insulin reactivity (non-patent documents 3 and 4).

In cancer, a GSK-3 inhibitor induced apoptosis in a certain kind of cancer cells (non-patent document 5).

In inflammatory disease (sepsis shock etc.), GSK-3 acts on Toll-like receptor signal, and controls the production of inflammatory and anti-inflammatory cytokines. Since inhibition of GSK-3 suppresses production of inflammatory cytokine and increases production of anti-inflammatory cytokine, a GSK-3 inhibitor is useful for inflammatory diseases (non-patent document 6).

In osteoporosis and alopecia, GSK-3 stabilizes β-catenin via Wnt signal, and is involved in bone mass increase and hair development (non-patent documents 7 and 8).

As a compound having a GSK-3β inhibitory activity, a compound represented by the formula:

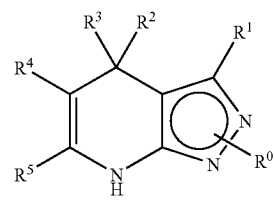

wherein $R^0$ is hydrogen, alkyl and the like; $R^1$ is hydrogen; $R^2$ is hydrogen, alkyl and the like; $R^3$ is (1) alkyl or haloalkyl, (2) cycloalkyl optionally having substituents and the like; $R^4$ is alkoxycarbonyl, alkylcarbonyl and the like; and $R^5$ is alkyl, phenylaminoalkyl etc. is known (patent document 1).

Non-patent document 9 describes a compound represented by the following formula:

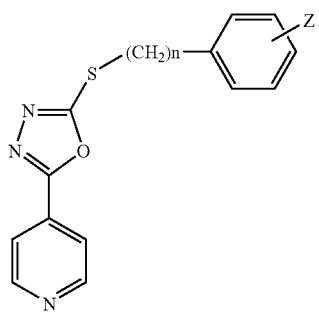

wherein (1) n=1, Z=H; (2) n=2, Z=H; (3) n=1, Z=3-Cl; (4) n=1, Z=2-Cl; (5) n=1, Z=3-I; (6) n=1, Z=4-I; (7) n=1, Z=3-F; (8) n=1, Z=3-COOH; (9) n=1, Z=3-COOCH$_3$; (10) n=1, Z=3-(5-methyl-1,3,4-oxadiazol-2-yl); (11) n=1, Z=4-COOH; (12) n=1, Z=4-CH$_2$COOH; (13) n=1, Z=4-(2-fluorobenzylcarbamoylmethyl), which has a GSK-3β inhibitory activity.

In addition, patent document 2 describes a compound represented by the following formula:

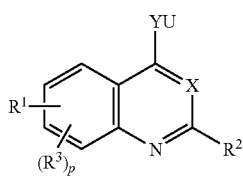

wherein X is N or CH; Y is a group: W(CH$_2$), (CH$_2$)W and the like; R$^1$ is a phenyl group or a heterocyclic group containing 1 to 4 hetero atoms selected from N, O and S(O)$_m$, which is optionally substituted by one or more R$^3$; each R$^3$ is selected from the group comprising amino, hydrogen and the like; R$^2$ is selected from the group comprising hydrogen, halogen and the like; U is phenyl or 5- to 10-membered monocyclic or bicyclic system wherein one or more carbon atoms are optionally substituted by a hetero atom selected from N, O and S(O)$_m$, which is substituted by at least one R$^6$ and optionally substituted by at least one R$^4$.

On the other hand, as an oxadiazole compound, the following compound is known.

(1) As a melanin-concentrating hormone antagonist, a compound represented by the formula:

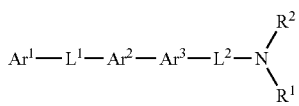

wherein Ar$^1$ is a cyclic group optionally substituted by 1 to 5 groups selected from a C$_1$-C$_8$ alkyl group etc.; L$^1$ is a bond or a divalent linker represented by the formula: X$_2$—(CR$^3$R$^4$)m-X$_3$; Ar$^2$ is a 5-membered monocyclic aromatic heterocyclic group or its positional isomer, which is optionally substituted by 1 to 3 substituents selected from a C$_1$-C$_8$ alkyl group etc.; Ar$^3$ is an optionally substituted bicyclic aromatic or nonaromatic group; L$^2$ is a divalent linker represented by the formula: X$_4$—(CR$^3$R$^4$)$_m$—X$_3$; and R$^1$ and R$^2$ are each independently hydrogen, C$_1$-C$_8$ alkyl etc., which is useful for the treatment of type 2 diabetes, diabetes-associated disease or obesity, is reported (patent document 3).

(2) A compound represented by the formula:

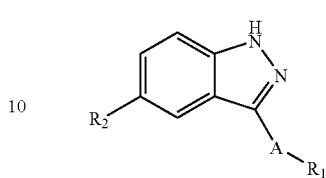

wherein A is a bond, —(CR$_2$)$_a$— and the like; R$_1$ is aryl, heteroaryl and the like; and R$_2$ is —R$_3$, —R$_4$, —(CH$_2$)$_b$C(=O)R$_5$ etc., which is used for the treatment or prophylaxis of protein kinase associated disease, for example, inflammatory disease, diabetes, obesity and the like, is reported (patent document 4).

(3) As a JNK inhibitor, a compound represented by the formula:

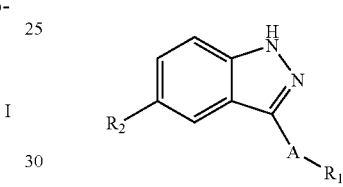

wherein A is a bond, —(CH$_2$)$_a$— and the like; R$_1$ is aryl, heteroaryl and the like; and R$_2$ is —R$_3$, —R$_4$, —(CH$_2$)$_b$C(=O)R$_5$ etc., is reported (patent document 5).

(4) As a compound having a JNK inhibitory activity, a compound represented by the formula:

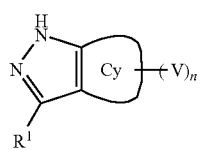

wherein R$^1$ is a group represented by the formula: —(CO)$_h$—(NR$^a$)$_j$—(CR$^b$=CR$^c$)$_k$—Ar; Cy is a 5- or 6-membered aromatic heterocyclic group; V is a group represented by the formula: -L-X—Y; and n is 0, 1, 2, 3 or 4, is reported (patent document 6).

(5) A compound represented by the formula:

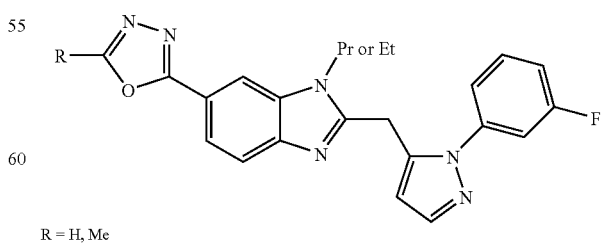

R = H, Me and the like, which is used for the treatment of a central neurological disease, is reported (patent document 7).

(6) As a JNK inhibitor, a compound represented by the formula:

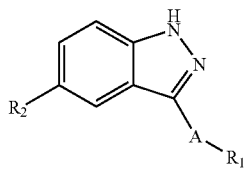

wherein A is a bond, —(CR$_2$)$_a$— and the like; R$_1$ is aryl, heteroaryl and the like; and R$_2$ is —R$_3$, —R$_4$, —(CR$_2$)$_b$C(=O)R$_5$ etc., is reported (patent document 8).

(7) A compound represented by the formula:

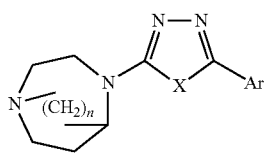

wherein n is 1, 2 or 3; X is O, S or Se; Ar is an aromatic cyclic hydrocarbon (aryl) group or an aromatic heterocyclic (heteroaryl) group, which is useful for the treatment of central neurological diseases, is reported (patent document 9).

(8) The following compounds

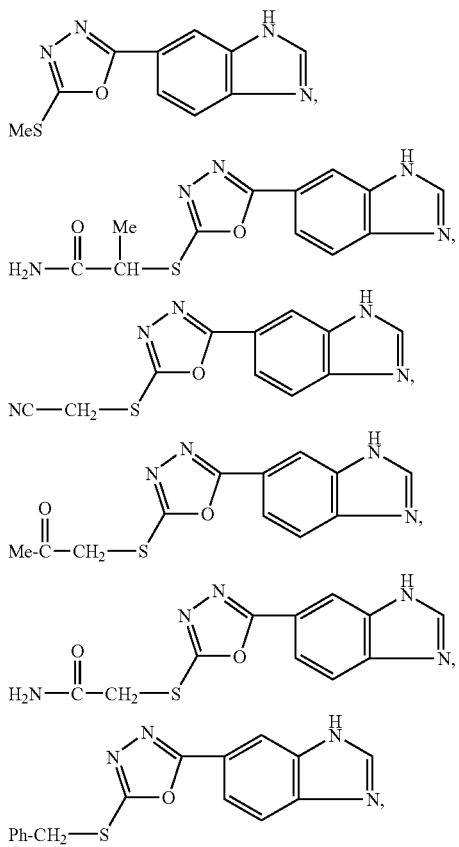

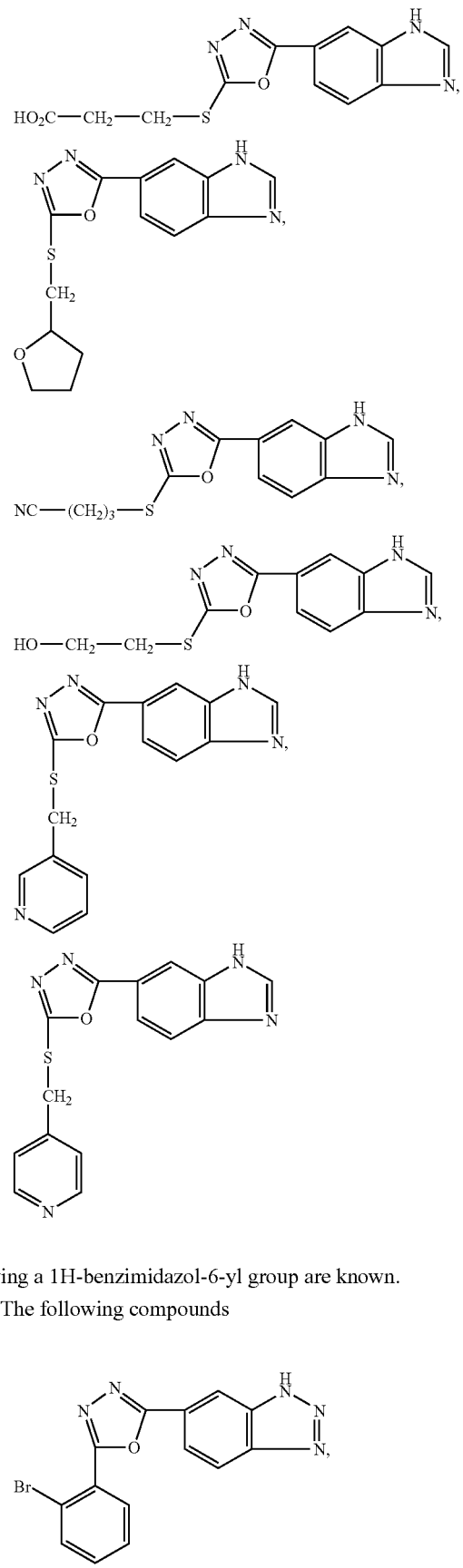

having a 1H-benzimidazol-6-yl group are known.

(9) The following compounds

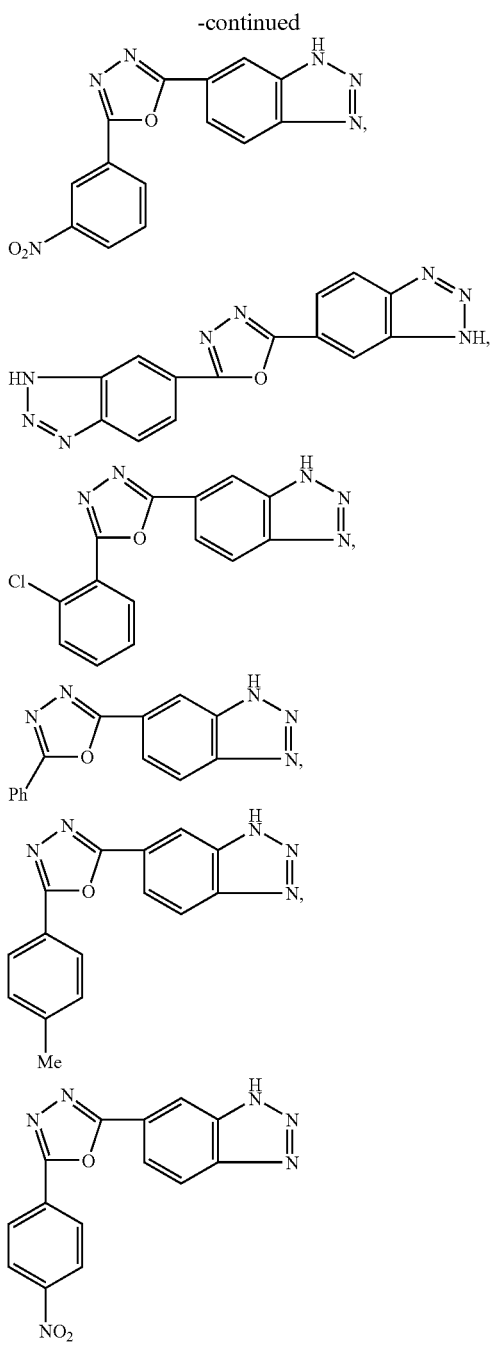

having a 1H-benzotriazol-6-yl group are known.

(10) Non-patent documents 10 and 11 describe the following compound (2,5-bis(3-phenyl-2,1-benzisoxazol-5-yl)-1,3,4-oxadiazole)

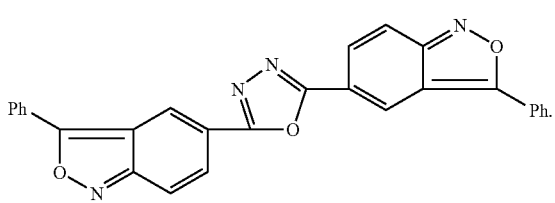 [SMILES: c1ccc(-c2onc3ccc(-c4nnc(-c5ccc6noc(-c7ccccc7)c6c5)o4)cc23)cc1]

(11) Patent document 10 describes the following compounds (N-ethyl-N'-[6-(5-methyl-1,3,4-oxadiazol-2-yl)-1H-benzimidazol-2-yl]urea and N-ethyl-N'-[6-(1,3,4-oxadiazol-2-yl)-1H-benzimidazol-2-yl]urea):

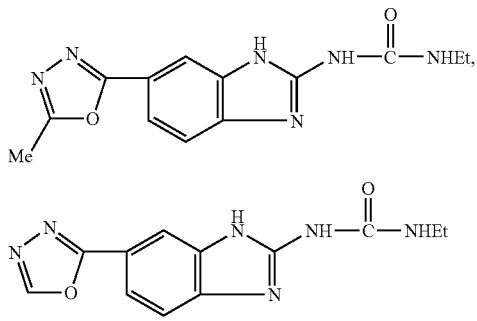

(12) Non-patent documents 12, 13 and 14 describe the following compound (2,5-bis(benzo[1,3]dioxol-5-yl)-1,3,4-oxadiazole):

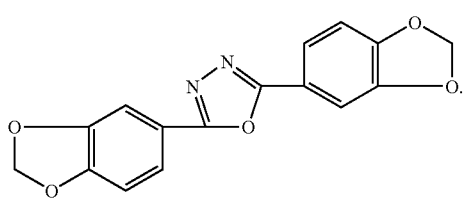 [SMILES: c1cc2c(cc1-c1nnc(-c3ccc4c(c3)OCO4)o1)OCO2]

(13) Patent document 11 describes the following compound (N,N'-diethyl-N''-{5-[5-(quinoxalin-6-yl)-1,3,4-oxadiazol-2-ylsulfanylmethyl]pyrimidin-4-yl}guanidine):

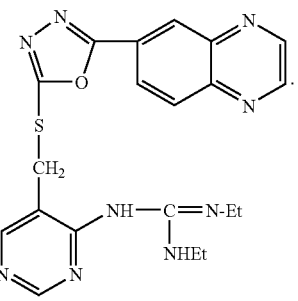

(14) Non-patent document 15 describes the following compounds (phenyl-[5-(6-quinolyl)-1,3,4-oxadiazol-2-yl]amine, cyclohexyl-[5-(6-quinolyl)-1,3,4-oxadiazol-2-yl]amine, ethyl-[5-(6-quinolyl)-1,3,4-oxadiazol-2-yl]amine, and [5-(6-quinolyl)-1,3,4-oxadiazol-2-yl]-4-tolylamine):

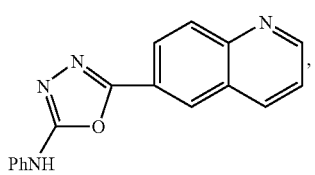

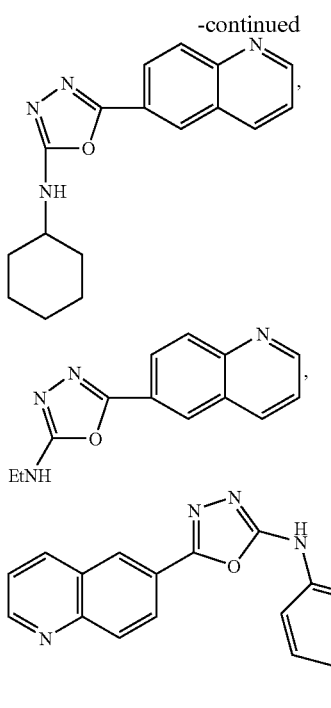

However, it has not been known heretofore that these oxadiazole compounds have a GSK-3 inhibitory action.
patent document 1: WO04/014910
patent document 2: U.S. Pat. No. 6,391,874
patent document 3: WO05/040157
patent document 4: US-A-2005/0009876
patent document 5: US-A-2004/0127536
patent document 6: WO03/101968
patent document 7: WO02/050062
patent document 8: WO02/010137
patent document 9: WO04/029053
patent document 10: WO02/060879
patent document 11: WO00/004014
non-patent document 1: J. Biol. Chem. 273, 19929-19932 (1998)
non-patent document 2: Acta Neuropathology, 103, 91 (2002)
non-patent document 3: Diabetes 49, 263-271 (2000)
non-patent document 4: Diabetes 50, 937-946 (2001)
non-patent document 5: Mol. Cancer Ther. 2, 1215-1222 (2003)
non-patent document 6: Nature Immunology, 6, 777-784 (2005)
non-patent document 7: Journal of Bone Mineral Research, 21, 910-920 (2006)
non-patent document 8: Cell, 95, 605 (1998)
non-patent document 9: Bioorg. Med. Chem. Lett. (2002), 12, 1525-1528
non-patent document 10: Materialy Mezhdunarodnoi Konferentsii, "Khimiya i Biologicheskaya Aktivnost Azotistykh Geterotsiklov i Alkaloidov", Oct. 9-12, 2001 (2001), Volume 1, 452-457
non-patent document 11: Izvestiya Vysshikh Uchebnykh Zavedenii, Khimiya i Khimicheskaya Tekhnologiya (1998), 41(6), 15-19
non-patent document 12: Tap Chi Hoa Hoc (2005), 43(3), 265-269
non-patent document 13: Farmaco, Edizione Scientifica (1984), 39(5), 414-20
non-patent document 14: Monatshefte fuer Chemie (1960), 91, 294-304
non-patent document 15: Eur. J. Med. Chem. Chim. Ther. (1996), 31(10), 819-826

DISCLOSURE OF THE INVENTION

Problems to be Solved by the Invention

Conventional compounds having a GSK-3 inhibitory action have some problems to be solved, such as effectiveness (e.g., insufficient GSK-3 inhibitory action, insufficient selectivity to other kinase inhibitory action and the like), and safety (e.g., possible side effects and the like). In addition, since they are not sufficient in the property (stability, solubility and the like), oral absorbability, transferability to target organ and the like, practically satisfactory results as a pharmaceutical agent have not been achieved entirely. Thus, the development of a superior GSK-3 inhibitor effective as a pharmaceutical agent for GSK-3 related pathology or disease has been demanded.

The present invention aims at providing a safe GSK-3 inhibitor useful as an agent for the prophylaxis or treatment of GSK-3 related pathology or disease.

Means of Solving the Problems

The present inventors have conducted intensive studies and found that the oxadiazole compounds represented by the following formulas (I) and (II) or salts thereof unexpectedly have a superior GSK-3 specific inhibitory activity based on their specific chemical structures, and further, superior properties of pharmaceutical product such as stability, solubility and the like, and can be safe and useful pharmaceutical agents for the prophylaxis or treatment of GSK-3 related pathology or disease in mammal, which resulted in the completion of the present invention.

Accordingly, the present invention provides the following.
[1] A GSK-3β inhibitor comprising a compound represented by the formula (I):

(I)

wherein
$R^1$ is a hydrogen atom, an optionally substituted hydrocarbon group, an optionally substituted heterocyclic group excluding a diazabicycloalkyl group, an optionally substituted alkanoyl group, an optionally substituted hydroxy group, an optionally substituted amino group, a substituted sulfonyl group, a substituted sulfinyl group, or an optionally substituted mercapto group, and
W is a group represented by the formula:

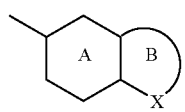

wherein
ring A is a 6-membered aromatic ring,
X is a carbon atom, a nitrogen atom, an oxygen atom or a sulfur atom, ring B is a 5- or 6-membered heterocycle optionally having substituent(s) at any position(s) other than X and optionally further having, as a hetero atom other than X, 1 to 3 nitrogen atoms or one sulfur atom or oxygen atom, or a group represented by the formula:

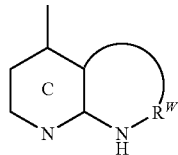

wherein
ring C is a nitrogen-containing 6-membered aromatic ring optionally having substituent(s), and
$R^W$ is a hydrogen atom, an acyl group, an optionally substituted hydrocarbon group, or an optionally substituted heterocyclic group, or optionally forms, together with the adjacent —NH— and a carbon atom on ring C, an optionally substituted nitrogen-containing 5- to 7-membered ring,
or a salt thereof or a prodrug thereof.

[2] A GSK-3β inhibitor comprising a compound represented by the formula (I):

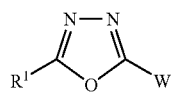

(I)

wherein
$R^1$ is a hydrogen atom, an optionally substituted hydrocarbon group, an optionally substituted heterocyclic group excluding a diazabicycloalkyl group, an optionally substituted hydroxy group, an optionally substituted amino group, a substituted sulfonyl group, or an optionally substituted mercapto group, and
W is a group represented by the formula:

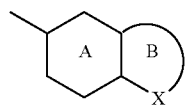

wherein
ring A is a 6-membered aromatic ring,
X is a carbon atom, a nitrogen atom, an oxygen atom or a sulfur atom, and
ring B is a 5- or 6-membered heterocycle optionally having substituent(s) at any position(s) other than X and optionally further having, as a hetero atom other than X, 1 to 3 nitrogen atoms or one sulfur atom or oxygen atom, excluding
(1) a group represented by the formula:

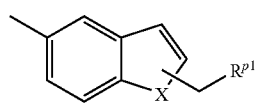

wherein X is a nitrogen atom or an oxygen atom, and $R^{p1}$ is a disubstituted amino group,
(2) a group represented by the formula:

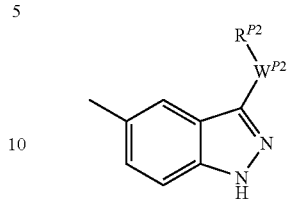

wherein $R^{p2}$ is an optionally substituted aryl group, an optionally substituted heteroaryl group, or an optionally substituted fused ring group, and $W^{p2}$ is a bond or a spacer, and
(3) a group represented by the formula:

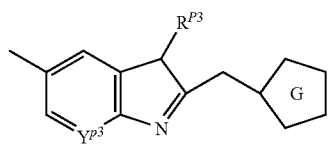

wherein $Y^{p3}$ is a carbon atom or a nitrogen atom, $R^{p3}$ is a $C_{1-6}$ alkyl group, and G is an azole ring having substituent(s), or a group represented by the formula:

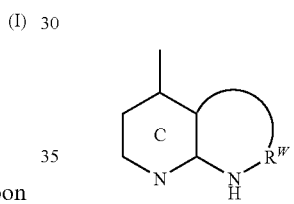

wherein
ring C is a nitrogen-containing 6-membered aromatic ring optionally having substituent(s), and
$R^W$ is a hydrogen atom, an acyl group, an optionally substituted hydrocarbon group, or an optionally substituted heterocyclic group, or optionally forms, together with the adjacent —NH— and a carbon atom on ring C, an optionally substituted nitrogen-containing 5- to 7-membered ring,
or a salt thereof or a prodrug thereof.

[3] The GSK-3β inhibitor of the above-mentioned [2], wherein $R^1$ is a group represented by the formula: $R^{1a}$—Y— wherein Y is a bond, a sulfur atom, or —$NR^y$— ($R^y$ is a hydrogen atom, or a lower alkyl group),
$R^{1a}$ is (1) a hydrogen atom, (2) a $C_{1-2}$ alkyl group optionally substituted by one or more substituents selected from a halogen atom, an optionally substituted carbamoyl group, an optionally substituted $C_{6-10}$ aryl group and an optionally substituted 5- to 10-membered aromatic heterocyclic group, or (3) a cyano group.

[4] A GSK-3β inhibitor of the above-mentioned [2], wherein W is a group represented by the formula:

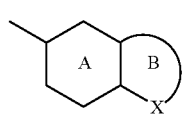

wherein each symbol is as defined in the above-mentioned [2], excluding (1) a group represented by the formula:

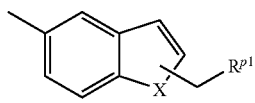

wherein each symbol is as defined in the above-mentioned [2], (2) a group represented by the formula:

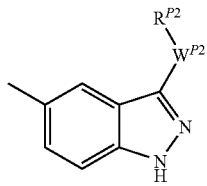

wherein each symbol is as defined in the above-mentioned [2], and (3) a group represented by the formula:

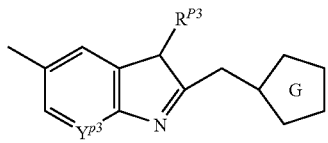

wherein each symbol is as defined in the above-mentioned [2].

[5] The GSK-3β inhibitor of the above-mentioned [4], wherein the ring B optionally has one or more substituents selected from an optionally substituted hydrocarbon group, an optionally substituted heterocyclic group, an acyl group, an amino group, and a monosubstituted amino group.

[6] The GSK-3β inhibitor of the above-mentioned [4], wherein the ring B is a 5- or 6-membered heterocycle represented by

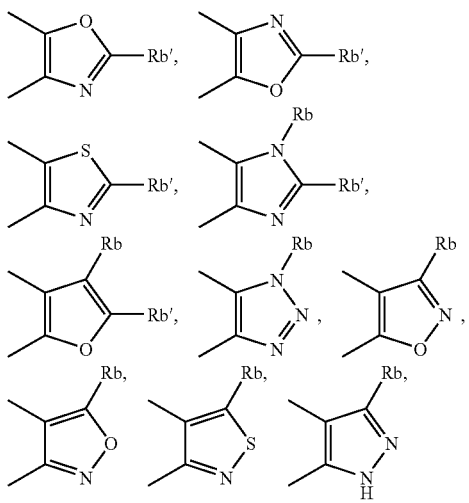

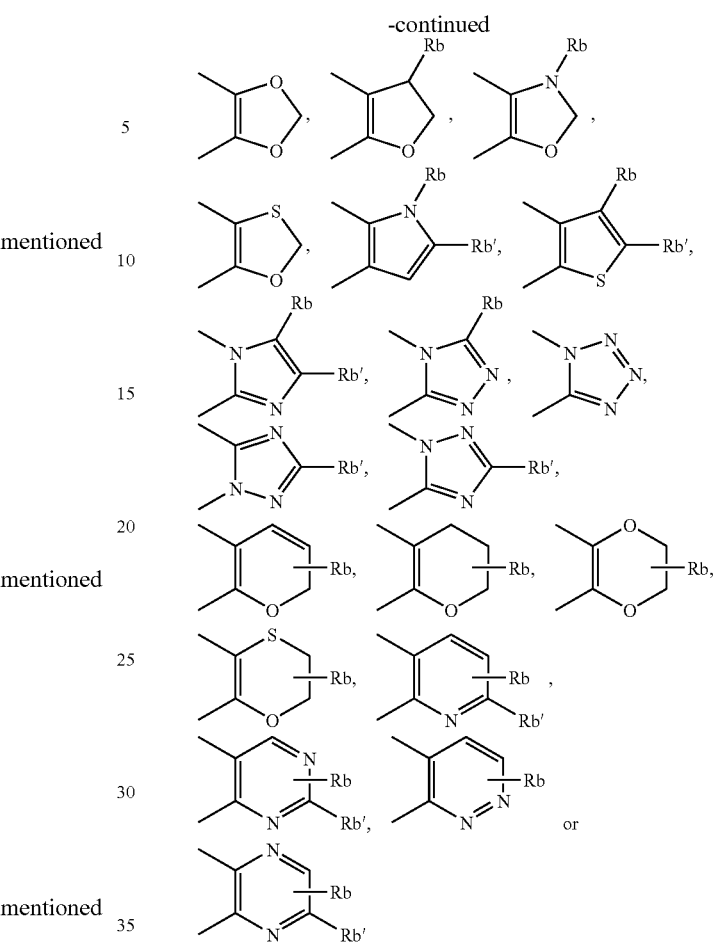

wherein
Rb is a hydrogen atom, an optionally substituted hydrocarbon group, an optionally substituted heterocyclic group, an optionally substituted alkanoyl group, an optionally substituted carboxy group, an optionally substituted carbamoyl group, an optionally substituted heterocyclyl-carbonyl group, or an optionally substituted hydrocarbon-carbonyl group, and Rb' is a hydrogen atom, an amino group, or a monosubstituted amino group.

[7] The GSK-3β inhibitor of the above-mentioned [6], wherein $R^1$ is a group represented by the formula: $R^{1a}$—Y—
wherein
Y is a bond, a sulfur atom, or —$NR^y$— ($R^y$ is a hydrogen atom, or a lower alkyl group), and
$R^{1a}$ is a hydrogen atom, or an optionally fluorinated $C_{1-2}$ alkyl group, and
Rb is an optionally substituted phenyl group, or an optionally substituted 5- or 6-membered heterocyclic group.

[8] The GSK-3β inhibitor of the above-mentioned [6], wherein $R^1$ is a group represented by the formula: $R^{1a}$—Y—
wherein
Y is a bond, a sulfur atom, or —$NR^y$— ($R^y$ is a hydrogen atom, or a lower alkyl group),
$R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and Rb is a hydrogen atom or a lower alkyl group.

[9] The GSK-3β inhibitor of the above-mentioned [6], wherein $R^1$ is a group represented by the formula: $R^{1a}$—Y— wherein

Y is a bond, a sulfur atom, or —$NR^y$— ($R^y$ is a hydrogen atom, or a lower alkyl group), and $R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and Rb is an optionally substituted phenyl group, or an optionally substituted 5- or 6-membered heterocyclic group.

[10] The GSK-3β inhibitor of the above-mentioned [2], wherein W is a group represented by the formula:

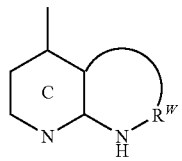

wherein each symbol is as defined in the above-mentioned [2].

[11] The GSK-3β inhibitor of the above-mentioned [1], which is an agent for the prophylaxis or treatment of a neurodegenerative disease.

[12] The GSK-3β inhibitor of the above-mentioned [1], which is an agent for the prophylaxis or treatment of Alzheimer's disease.

[13] The GSK-3β inhibitor of the above-mentioned [1], which is a neural stem cell differentiation promoter.

[14] The GSK-3β inhibitor of the above-mentioned [1], which is an agent for the prophylaxis or treatment of diabetes.

[15] The GSK-3β inhibitor of the above-mentioned [1], which is a hypoglycemic agent.

[16] A compound represented by the formula (II):

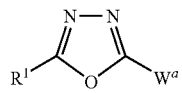

wherein $R^1$ is a hydrogen atom, an optionally substituted hydrocarbon group, an optionally substituted heterocyclic group excluding a diazabicycloalkyl group, an optionally substituted alkanoyl group, an optionally substituted hydroxy group, an optionally substituted amino group, a substituted sulfonyl group, a substituted sulfinyl group, or an optionally substituted mercapto group, and $W^a$ is a group represented by the formula:

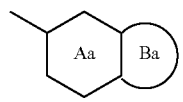

wherein ring Aa is a 6-membered aromatic ring; and ring Ba is a 5- or 6-membered heterocycle represented by

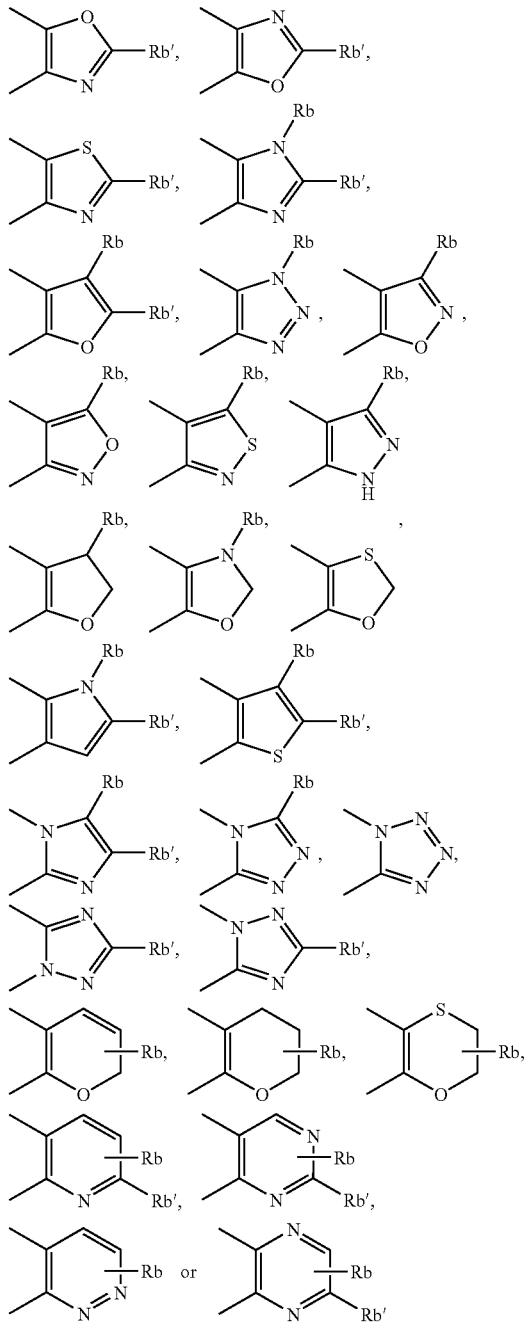

wherein

Rb is a hydrogen atom, an optionally substituted hydrocarbon group, an optionally substituted heterocyclic group, an optionally substituted alkanoyl group, an optionally substituted carboxy group, an optionally substituted carbamoyl group, an optionally substituted heterocyclyl-carbonyl group, or an optionally substituted hydrocarbon-carbonyl group, Rb' is a hydrogen atom, an amino group, or a mono-substituted amino group, excluding
(1) a group represented by the formula:

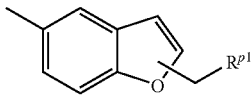

wherein $R^{p1}$ is a disubstituted amino group, and
(2) a group represented by the formula:

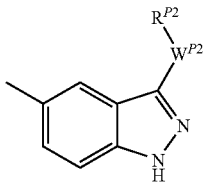

wherein $R^{p2}$ is an optionally substituted aryl group, an optionally substituted heteroaryl group, or an optionally substituted fused ring group, and $W^{p2}$ is a bond or a spacer, or
a group represented by the formula:

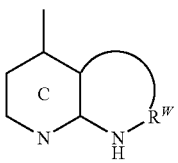

wherein
ring C is a nitrogen-containing 6-membered aromatic ring optionally having substituent(s), and
$R^W$ is a hydrogen atom, an acyl group, an optionally substituted hydrocarbon group or an optionally substituted heterocyclic group, or optionally forms, together with the adjacent —NH— and a carbon atom on ring C, an optionally substituted nitrogen-containing 5- to 7-membered ring,
or a salt thereof,
provided that
(1) when $R^1$ is an optionally substituted mercapto group, $W^a$ should not be 1H-benzimidazol-6-yl,
(2) when $R^1$ is an optionally substituted phenyl group or a phenyl group optionally condensed with a heterocycle, $W^a$ should not be 1H-benzotriazol-6-yl, and
(3) the following compounds are excluded:
(a) 2,5-bis(3-phenyl-2,1-benzisoxazol-5-yl)-1,3,4-oxadiazole,
(b) N-ethyl-N'-[6-(5-methyl-1,3,4-oxadiazol-2-yl)-1H-benzimidazol-2-yl]urea,
(c) N-ethyl-N'-[6-(1,3,4-oxadiazol-2-yl)-1H-benzimidazol-2-yl]urea,
(d) N,N'-diethyl-N''-{5-[5-(quinoxalin-6-yl)-1,3,4-oxadiazol-2-ylsulfanylmethyl]pyrimidin-4-yl}guanidine,
(e) phenyl[5-(6-quinolyl)-1,3,4-oxadiazol-2-yl]amine,
(f) cyclohexyl[5-(6-quinolyl)-1,3,4-oxadiazol-2-yl]amine,
(g) ethyl[5-(6-quinolyl)-1,3,4-oxadiazol-2-yl]amine,
(h) [5-(6-quinolyl)-1,3,4-oxadiazol-2-yl]-4-tolylamine,
(i) 6-(5-phenyl-1,3,4-oxadiazol-2-yl)-1,3-benzothiazole,
(j) 6-[5-(4-chlorophenyl)-1,3,4-oxadiazol-2-yl]-1,3-benzothiazole,
(k) 6-[5-(3-methylphenyl)-1,3,4-oxadiazol-2-yl]-1,3-benzothiazole,
(l) 6-(1,3,4-oxadiazol-2-yl)-1,3-benzoxazole,
(m) N-{3-[5-[5-(1,3-benzothiazol-6-yl)-1,3,4-oxadiazol-2-yl]-3-(trifluoromethyl)-1H-pyrazol-1-yl]benzyl}-L-alaninamide,
(n) 6-[5-(4-chlorophenyl)-1,3,4-oxadiazol-2-yl]quinoline,
(o) 6-[5-(4-methylphenyl)-1,3,4-oxadiazol-2-yl]quinoline,
(p) 6-[5-(1-naphthyl)-1,3,4-oxadiazol-2-yl]quinoxaline, and
(q) 6-{5-[4-(trifluoromethyl)phenyl]-1,3,4-oxadiazol-2-yl}quinoxaline.
[17] The compound of the above-mentioned [16], wherein $R^1$ is a group represented by the formula: $R^{1a}$—Y—
wherein
Y is a bond, a sulfur atom, or —$NR^y$— ($R^y$ is a hydrogen atom or a lower alkyl group), and
$R^{1a}$ is (1) a hydrogen atom, (2) a $C_{1-2}$ alkyl group optionally substituted by one or more substituents selected from a halogen atom, an optionally substituted carbamoyl group, an optionally substituted $C_{6-10}$ aryl group and an optionally substituted 5- to 10-membered aromatic heterocyclic group, or (3) a cyano group.
[18] The compound of the above-mentioned [16], wherein $W^a$ is a group represented by the formula:

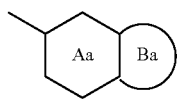

wherein each symbol is as defined in the above-mentioned [16], excluding
(1) a group represented by the formula:

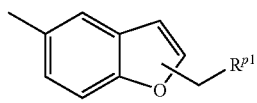

wherein each symbol is as defined in the above-mentioned [16], and
(2) a group represented by the formula:

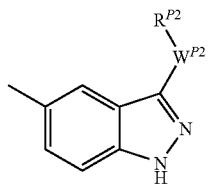

wherein each symbol is as defined in the above-mentioned [16].
[19] The compound of the above-mentioned [18], wherein ring Aa is benzene or pyridine.
[20] The compound of the above-mentioned [18], wherein Rb is a hydrogen atom, an optionally substituted hydrocarbon group, or an optionally substituted heterocyclic group, and
Rb' is a hydrogen atom, an amino group, or a monosubstituted amino group.
[21] The compound of the above-mentioned [18], wherein $R^1$ is a group represented by the formula: $R^{1a}$—Y—
wherein
Y is a bond, a sulfur atom, or —$NR^y$— ($R^y$ is a hydrogen atom or a lower alkyl group), and $R^{1a}$ is a hydrogen atom, or an optionally fluorinated $C_{1-2}$ alkyl group, and Rb is an optionally substituted phenyl group, or an optionally substituted 5- or 6-membered heterocyclic group.

[22] The compound of the above-mentioned [18], wherein $R^1$ is a group represented by the formula: $R^{1a}$—Y— wherein

Y is a bond, a sulfur atom, or —$NR^y$— ($R^y$ is a hydrogen atom or a lower alkyl group), and $R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and Rb is a hydrogen atom or a lower alkyl group.

[23] The compound of the above-mentioned [18], wherein $R^1$ is a group represented by the formula: $R^{1a}$—Y— wherein

Y is a bond, a sulfur atom, or —$NR^y$— ($R^y$ is a hydrogen atom or a lower alkyl group, and $R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and Rb is an optionally substituted phenyl group, or an optionally substituted 5- or 6-membered heterocyclic group.

[24] The compound of the above-mentioned [16], wherein $W^a$ is a group represented by the formula:

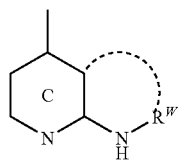

wherein each symbol is as defined in the above-mentioned [16].

[25] The compound of the above-mentioned [24], wherein $R^1$ is a group represented by the formula: $R^{1a}$—Y— wherein

Y is a bond, a sulfur atom, or —$NR^y$— ($R^y$ is a hydrogen atom or a lower alkyl group, and $R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and ring C is pyridine.

[26] The compound of the above-mentioned [16], which is 6-[5-[[4-methoxy-3-(trifluoromethyl)benzyl]thio]-1,3,4-oxadiazol-2-yl]benzothiazole, 2-methyl-5-[3-[4-(methylsulfinyl)phenyl]-1-benzofuran-5-yl]-1,3,4-oxadiazole, 6-[5-[(3-fluorobenzyl)thio]-1,3,4-oxadiazol-2-yl]-1-(4-methoxyphenyl)-1H-benzimidazole.

N-[4-[5-[(3-fluorobenzyl)thio]-1,3,4-oxadiazol-2-yl]-2-pyridyl]-N'-(2-pyridylmethyl)urea, 3-[[[5-[3-[4-(methylsulfinyl)phenyl]-1-benzofuran-5-yl]-1,3,4-oxadiazol-2-yl]thio]methyl]benzonitrile, 2-[3-[4-(ethylsulfinyl)phenyl]-1-benzofuran-5-yl]-5-methyl-1,3,4-oxadiazole, 2-[3-[2-chloro-4-(methylsulfinyl)phenyl]-1-benzofuran-5-yl]-5-methyl-1,3,4-oxadiazole, 2-[3-(3,3-dimethyl-1-oxido-2,3-dihydro-1-benzothien-5-yl)-1-benzofuran-5-yl]-5-methyl-1,3,4-oxadiazole, 5-[3-(2,5-difluorophenyl)-1-benzofuran-5-yl]-1,3,4-oxadiazol-2-amine, or 5-[1-[3-(trifluoromethoxy)phenyl]-1H-benzimidazol-6-yl]-1,3,4-oxadiazol-2-amine, or a salt thereof.

[27] A prodrug of the compound of the above-mentioned [16].

[28] A pharmaceutical agent comprising the compound of the above-mentioned [16] or the prodrug of the above-mentioned [27].

[29] Use of a compound represented by the formula (I):

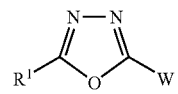

(I)

wherein $R^1$ is a hydrogen atom, an optionally substituted hydrocarbon group, an optionally substituted heterocyclic group excluding a diazabicycloalkyl group, an optionally substituted alkanoyl group, an optionally substituted hydroxy group, an optionally substituted amino group, a substituted sulfonyl group, a substituted sulfinyl group, or an optionally substituted mercapto group, and W is a group represented by the formula:

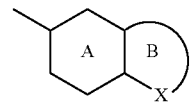

wherein ring A is a 6-membered aromatic ring,

X is a carbon atom, a nitrogen atom, an oxygen atom or a sulfur atom, and ring B is a 5- or 6-membered heterocycle optionally having substituent(s) at any position(s) other than X and optionally further having, as a hetero atom other than X, 1 to 3 nitrogen atoms or one sulfur atom or oxygen atom, or a group represented by the formula:

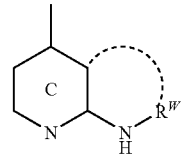

wherein ring C is a nitrogen-containing 6-membered aromatic ring optionally having substituent(s), and $R^W$ is a hydrogen atom, an acyl group, an optionally substituted hydrocarbon group, or an optionally substituted heterocyclic group, or optionally forms, together with the adjacent —NH— and a carbon atom on ring C, an optionally substituted nitrogen-containing 5- to 7-membered ring, or a salt thereof or a prodrug thereof for the production of a GSK-3β inhibitor.

[30] The use of the above-mentioned [29], wherein the GSK-3β inhibitor is an agent for the prophylaxis or treatment of a neurodegenerative disease.

[31] The use of the above-mentioned [29], wherein the GSK-3β inhibitor is an agent for the prophylaxis or treatment of Alzheimer's disease.

[32] The use of the above-mentioned [29], wherein the GSK-3β inhibitor is a neural stem cell differentiation promoter.

[33] The use of the above-mentioned [29], wherein the GSK-3β inhibitor is an agent for the prophylaxis or treatment of diabetes.

[34] The use of the above-mentioned [29], wherein the GSK-3β inhibitor is a hypoglycemic agent.

[35] A method of inhibiting GSK-3β, comprising administering a compound represented by the formula (I):

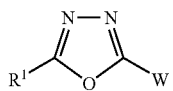
(I)

wherein
R$^1$ is a hydrogen atom, an optionally substituted hydrocarbon group, an optionally substituted heterocyclic group excluding a diazabicycloalkyl group, an optionally substituted alkanoyl group, an optionally substituted hydroxy group, an optionally substituted amino group, a substituted sulfonyl group, a substituted sulfinyl group, or an optionally substituted mercapto group, and
W is a group represented by the formula:

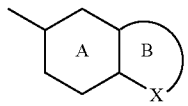

wherein
ring A is a 6-membered aromatic ring,
X is a carbon atom, a nitrogen atom, an oxygen atom or a sulfur atom, and
ring B is a 5- or 6-membered heterocycle optionally having substituent(s) at any position(s) other than X and optionally further having, as a hetero atom other than X, 1 to 3 nitrogen atoms or one sulfur atom or oxygen atom, or
a group represented by the formula:

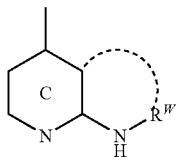

wherein
ring C is a nitrogen-containing 6-membered aromatic ring optionally having substituent(s), and
R$^W$ is a hydrogen atom, an acyl group, an optionally substituted hydrocarbon group, or an optionally substituted heterocyclic group, or optionally forms, together with the adjacent —NH— and a carbon atom on ring C, an optionally substituted nitrogen-containing 5- to 7-membered ring, or a salt thereof or a prodrug thereof to a subject.

[36] The method of the above-mentioned [35], which is used for the prophylaxis or treatment of a neurodegenerative disease.

[37] The method of the above-mentioned [35], which is used for the prophylaxis or treatment of Alzheimer's disease.

[38] The method of the above-mentioned [35], which promotes differentiation of neural stem cells.

[39] The method of the above-mentioned [35], which is used for the prophylaxis or treatment of diabetes.

[40] The method of the above-mentioned [35], which decreases blood glucose.

In the present specification, unless otherwise specified, the "lower" means that the carbon number is 1 to 6.

In the present specification, examples of the "halogen atom" include, unless otherwise specified, fluorine atom, chlorine atom, bromine atom and iodine atom.

In the present specification, examples of the "optionally substituted hydrocarbon group" include, unless otherwise specified, "optionally substituted $C_{1-6}$ alkyl group", "optionally substituted $C_{2-6}$ alkenyl group", "optionally substituted $C_{2-6}$ alkynyl group", "optionally substituted $C_{3-8}$ cycloalkyl group", "optionally substituted $C_{6-14}$ aryl group", "optionally substituted $C_{7-16}$ aralkyl group" and the like.

In the present specification, examples of the "$C_{1-6}$ alkyl group" include, unless otherwise specified, methyl, ethyl, propyl, isopropyl, butyl, isobutyl, sec-butyl, tert-butyl, pentyl, isopentyl, neopentyl, hexyl and the like.

In the present specification, examples of the "$C_{2-6}$ alkenyl group" include, unless otherwise specified, vinyl, propenyl, isopropenyl, 2-buten-1-yl, 4-penten-1-yl, 5-hexen-1-yl and the like.

In the present specification, examples of the "$C_{2-6}$ alkynyl group" include, unless otherwise specified, 2-butyn-1-yl, 4-pentyn-1-yl, 5-hexyn-1-yl and the like.

In the present specification, examples of the "$C_{3-8}$ cycloalkyl group" include, unless otherwise specified, cyclopropyl, cyclobutyl, cyclopentyl, cyclohexyl, cycloheptyl, cyclooctyl, bicyclo[2.2.1]heptyl, oxobicyclo[2.2.1]heptyl, bicyclo[2.2.2]octyl and the like.

In the present specification, examples of the "$C_{6-14}$ aryl group" include, unless otherwise specified, phenyl, 1-naphthyl, 2-naphthyl, 2-biphenylyl, 3-biphenylyl, 4-biphenylyl, 2-anthryl and the like. The $C_{6-14}$ aryl may be partially saturated, and examples of the partially saturated $C_{6-14}$ aryl include indanyl, tetrahydronaphthyl and the like.

In the present specification, examples of the "$C_{7-16}$ aralkyl group" include, unless otherwise specified, benzyl, phenethyl, 1-phenylethyl, diphenylmethyl, 1-naphthylmethyl, 2-naphthylmethyl, 2,2-diphenylethyl, 3-phenylpropyl, 3,3-diphenylpropyl, 4-phenylbutyl, 5-phenylpentyl, 2-biphenylylmethyl, 3-biphenylylmethyl, 4-biphenylylmethyl and the like.

In the present specification, examples of the "optionally substituted hydroxy group" include, unless otherwise specified, "hydroxy group", "optionally substituted $C_{1-10}$ alkoxy group", "optionally substituted heterocyclic oxy group", "optionally substituted $C_{6-14}$ aryloxy group", "optionally substituted $C_{7-16}$ aralkyloxy group", "tri-$C_{1-6}$ alkyl-silyloxy group", "optionally substituted $C_{1-6}$ alkylsulfonyloxy group", "optionally substituted heterocyclic sulfonyloxy group" and the like.

In the present specification, examples of the "$C_{1-6}$ alkoxy group" include, unless otherwise specified, methoxy, ethoxy, propoxy, isopropoxy, butoxy, isobutoxy, tert-butoxy, pentyloxy, hexyloxy and the like.

In the present specification, examples of the "$C_{1-10}$ alkoxy group" include, in addition to the above-mentioned $C_{1-6}$ alkoxy group, heptyloxy, octyloxy, nonyloxy, decyloxy and the like.

In the present specification, examples of the "heterocyclic oxy group" include hydroxy group substituted by the below-mentioned "heterocyclic group". Preferable examples of the heterocyclic oxy group include tetrahydropyranyloxy, thiazolyloxy, pyridyloxy, pyrazolyloxy, oxazolyloxy, thienyloxy, furyloxy, tetrahydrothiopyranyloxy, 1,1-dioxidotetrahydrothiopyranyloxy and the like.

In the present specification, examples of the "$C_{6-14}$ aryloxy group" include, unless otherwise specified, phenoxy, 1-naphthyloxy, 2-naphthyloxy and the like.

In the present specification, examples of the "$C_{7-16}$ aralkyloxy group" include, unless otherwise specified, benzyloxy, phenethyloxy, 1-phenylethyloxy and the like.

In the present specification, examples of the "tri-$C_{1-6}$ alkylsilyloxy group" include, unless otherwise specified, trimethylsilyloxy, tert-butyl(dimethyl)silyloxy and the like.

In the present specification, examples of the "$C_{1-6}$ alkylsulfonyloxy group" include, unless otherwise specified, methylsulfonyloxy, ethylsulfonyloxy and the like.

In the present specification, examples of the "heterocyclic sulfonyloxy group" include sulfonyloxy group substituted by the below-mentioned "heterocyclic group". Preferable examples of the heterocyclic sulfonyloxy group include thienylsulfonyloxy, furylsulfonyloxy and the like.

In the present specification, examples of the "optionally substituted mercapto group" include, unless otherwise specified, "mercapto group", "optionally substituted $C_{1-10}$ alkylthio group", "optionally substituted heterocyclic thio group", "optionally substituted $C_{6-14}$ arylthio group", "optionally substituted $C_{7-16}$ aralkylthio group" and the like.

In the present specification, examples of the "$C_{1-6}$ alkylthio group" include, unless otherwise specified, methylthio, ethylthio, propylthio, isopropylthio, butylthio, sec-butylthio, tert-butylthio and the like. In the present specification, examples of the "$C_{1-10}$ alkylthio group" include, in addition to the above-mentioned $C_{1-6}$ alkylthio group, heptylthio, octylthio, nonylthio, decylthio and the like.

In the present specification, examples of the "heterocyclic thio group" include mercapto group substituted by the below-mentioned "heterocyclic group". Preferable examples of the heterocyclic thio group include tetrahydropyranylthio, thiazolylthio, pyridylthio, pyrazolylthio, oxazolylthio, thienylthio, furylthio, tetrahydrothiopyranylthio, 1,1-dioxidotetrahydrothiopyranylthio and the like.

In the present specification, examples of the "$C_{6-14}$ arylthio group" include, unless otherwise specified, phenylthio, 1-naphthylthio, 2-naphthylthio and the like.

In the present specification, examples of the "$C_{7-16}$ aralkylthio group" include, unless otherwise specified, benzylthio, phenethylthio, 1-phenylethylthio and the like.

In the present specification, examples of the "heterocyclic group" include, unless otherwise specified, a 5- to 14-membered (monocyclic, bicyclic or tricyclic) heterocyclic group, preferably (i) 5- to 14-membered (preferably 5- to 10-membered) aromatic heterocyclic group, (ii) 5- to 10-membered nonaromatic heterocyclic group containing, as a ring constituting atom besides carbon atom, 1 to 4 hetero atoms of 1 or 2 kinds selected from a nitrogen atom, a sulfur atom and an oxygen atom, and the like. Particularly, 5 or 6-membered aromatic heterocyclic group is preferable.

Specific examples include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), oxadiazolyl (e.g., 2-oxadiazolyl), quinolyl (e.g., 2-quinolyl, 3-quinolyl, 4-quinolyl, 5-quinolyl, 6-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), indazolyl (e.g., 1-indazolyl, 3-indazolyl, 5-indazolyl), benzothiazolyl (e.g., 2-benzothiazolyl), benzoxazolyl (e.g., 2-benzoxazolyl), benzimidazolyl (e.g., 1-benzimidazolyl, 2-benzimidazolyl), benzo[b]thienyl (e.g., 2-benzo[b]thienyl, 3-benzo[b]thienyl, 5-benzo[b]thienyl), benzo[b]furanyl (e.g., 2-benzo[b]furanyl, 3-benzo[b]furanyl), benzotriazolyl (e.g., 1-benzotriazolyl, 5-benzotriazolyl), imidazo[1,2-a]pyridinyl (e.g., 2-imidazo[1,2-a]pyridinyl, 3-imidazo[1,2-a]pyridinyl, 6-imidazo[1,2-a]pyridinyl), imidazo[1,2-a]pyrimidinyl (e.g., 2-imidazo[1,2-a]pyrimidinyl, 3-imidazo[1,2-a]pyrimidinyl, 5-imidazo[1,2-a]pyrimidinyl), pyrrolo[2,3-b]pyridinyl (e.g., 2-1H-pyrrolo[2,3-b]pyridinyl, 3-1H-pyrrolo[2,3-b]pyridinyl, 4-1H-pyrrolo[2,3-b]pyridinyl), [1,2,4]triazolo[1,5-a]pyridinyl (e.g., 2-[1,2,4]triazolo[1,5-a]pyridinyl, 6-1[1,2,4]triazolo[1,5-a]pyridinyl, 7-[1,2,4]triazolo[1,5-a]pyridinyl) and the like; nonaromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), tetrahydropyranyl (e.g., 2-tetrahydropyranyl, 3-tetrahydropyranyl, 4-tetrahydropyranyl), oxetanyl (e.g., 2-oxetanyl, 3-oxetanyl), oxopyrrolidinyl (e.g., 2-oxopyrrolidin-1-yl, 2-oxopyrrolidin-3-yl, 2-oxopyrrolidin-4-yl, 2-oxopyrrolidin-5-yl, 3-oxopyrrolidin-1-yl), dioxopyrrolidinyl (e.g., 2,5-dioxopyrrolidin-1-yl, 2,5-dioxopyrrolidin-3-yl), tetrahydrothiopyranyl (e.g., 2-tetrahydrothiopyranyl, 3-tetrahydrothiopyranyl, 4-tetrahydrothiopyranyl), 1,1-dioxide tetrahydrothiopyranyl (e.g., 1,1-dioxide tetrahydrothiopyran-2-yl, 1,1-dioxide tetrahydrothiopyran-3-yl, 1,1-dioxide tetrahydrothiopyran-4-yl), dihydrobenzofuranyl (e.g., 2,3-dihydro-1-benzofuran-4-yl, 2,3-dihydro-1-benzofuran-5-yl, 2,3-dihydro-1-benzofuran-6-yl, 2,3-dihydro-1-benzofuran-7-yl), tetrahydrobenzo[c]azepinyl (e.g., 1,3,4,5-tetrahydrobenzo[c]azepin-2-yl), tetrahydroisoquinolinyl (e.g., 1,2,3,4-tetrahydroisoquinolin-2-yl) and the like; and the like.

In the present specification, examples of the 5- or 6-membered heterocyclic group include 5- or 6-membered ones from among the "heterocyclic groups".

In the present specification, unless otherwise specified, examples of the "substituted sulfonyl group" include "optionally substituted $C_{1-6}$ alkylsulfonyl group", "optionally substituted heterocyclylsulfonyl group", "optionally substituted $C_{6-14}$ arylsulfonyl group", "optionally substituted $C_{7-16}$ aralkylsulfonyl group" and the like.

In the present specification, unless otherwise specified, examples of the "$C_{1-6}$ alkylsulfonyl group" include methylsulfonyl, ethylsulfonyl and the like.

In the present specification, unless otherwise specified, examples of the "heterocyclylsulfonyl group" include a sulfonyl group substituted by the aforementioned "heterocyclic group". Preferable examples of the heterocyclylthio group include tetrahydropyranylsulfonyl, thiazolylsulfonyl, pyridylsulfonyl, pyrazolylsulfonyl, oxazolylsulfonyl, thienylsulfonyl, furylsulfonyl, tetrahydrothiopyranylsulfonyl, 1,1-dioxide tetrahydrothiopyranylsulfonyl and the like.

In the present specification, unless otherwise specified, examples of the "$C_{6-14}$ arylsulfonyl group" include phenylsulfonyl, 1-naphthylsulfonyl, 2-naphthylsulfonyl and the like.

In the present specification, unless otherwise specified, examples of the "$C_{7-16}$ aralkylsulfonyl group" include benzylsulfonyl, 1-phenylethylsulfonyl, phenethylsulfonyl and the like.

In the present specification, unless otherwise specified, examples of the "substituted sulfinyl group" include "optionally substituted $C_{1-6}$ alkylsulfinyl group", "optionally substituted $C_{6-14}$ arylsulfinyl group" and the like.

In the present specification, unless otherwise specified, examples of the "$C_{1-6}$ alkylsulfinyl group" include methylsulfinyl, ethylsulfinyl and the like.

In the present specification, unless otherwise specified, examples of the "$C_{6-14}$ arylsulfinyl group" include phenylsulfinyl, 1-naphthylsulfinyl, 2-naphthylsulfinyl and the like.

In the present specification, unless otherwise specified, examples of the "$C_{1-6}$ alkyl-carbonyl group" include acetyl, isobutanoyl, isopentanoyl and the like.

In the present specification, unless otherwise specified, examples of the "$C_{6-14}$ aryl-carbonyl group" include benzoyl, 1-naphthylcarbonyl, 2-naphthylcarbonyl and the like.

In the present specification, unless otherwise specified, examples of the "heterocyclyl-carbonyl group" include a carbonyl group substituted by the aforementioned "heterocyclic group". For example, pyrrolidinylcarbonyl, piperidinocarbonyl, piperazinylcarbonyl, morpholinocarbonyl, thiomorpholinocarbonyl, thienylcarbonyl, tetrahydrobenzo[c]azepinylcarbonyl, tetrahydroisoquinolinylcarbonyl and the like can be mentioned.

In the present specification, unless otherwise specified, examples of the "optionally esterified carboxyl group" include carboxyl group, $C_{1-6}$ alkoxy-carbonyl group (e.g., methoxycarbonyl, ethoxycarbonyl, propoxycarbonyl, tert-butoxycarbonyl etc.), $C_{6-14}$ aryloxy-carbonyl group (e.g., phenoxycarbonyl etc.), $C_{7-16}$ aralkyloxy-carbonyl group (e.g., benzyloxycarbonyl, phenethyloxycarbonyl etc.) and the like.

In the present specification, unless otherwise specified, examples of the "optionally halogenated $C_{1-6}$ alkyl group" include the above-mentioned "$C_{1-6}$ alkyl group" optionally substituted by 1 to 5 "halogen atoms" mentioned above. Examples thereof include methyl, ethyl, propyl, isopropyl, butyl, tert-butyl, isobutyl, trifluoromethyl and the like.

In the present specification, unless otherwise specified, examples of the "optionally halogenated $C_{1-6}$ alkoxy group" include the above-mentioned "$C_{1-6}$ alkoxy group" optionally substituted by 1 to 5 "halogen atoms" mentioned above. Examples thereof include methoxy, ethoxy, isopropoxy, tert-butoxy, trifluoromethoxy and the like.

In the present specification, unless otherwise specified, examples of the "mono- or di-$C_{1-6}$ alkyl-amino group" include an amino group mono- or di-substituted by the above-mentioned "$C_{1-6}$ alkyl group(s)". Examples thereof include methylamino, ethylamino, propylamino, dimethylamino, diethylamino and the like.

In the present specification, unless otherwise specified, examples of the "mono- or di-$C_{3-8}$ cycloalkyl-amino group" include an amino group mono- or di-substituted by the above-mentioned "$C_{3-8}$ alkyl group(s)". For example, cyclopropylamino and the like can be mentioned.

In the present specification, unless otherwise specified, examples of the "mono- or di-$C_{6-14}$ aryl-amino group" include an amino group mono- or di-substituted by the above-mentioned "$C_{6-14}$ aryl group(s)". Examples thereof include phenylamino, diphenylamino, 1-naphthylamino, 2-naphthylamino and the like.

In the present specification, unless otherwise specified, examples of the "mono- or di-$C_{7-16}$ aralkyl-amino group" include an amino group mono- or di-substituted by the above-mentioned "$C_{7-16}$ aralkyl group(s)". Examples thereof include benzylamino, phenethylamino and the like.

In the present specification, unless otherwise specified, examples of the "N—$C_{1-6}$ alkyl-N—$C_{6-14}$ aryl-amino group" include an amino group substituted by the above-mentioned "$C_{1-6}$ alkyl group" and the above-mentioned "$C_{6-14}$ aryl group". Examples thereof include N-methyl-N-phenylamino, N-ethyl-N-phenylamino and the like.

In the present specification, unless otherwise specified, examples of the "N—$C_{1-6}$ alkyl-N—$C_{7-16}$ aralkyl-amino group" include an amino group substituted by the above-mentioned "$C_{1-6}$ alkyl group" and the above-mentioned "$C_{7-16}$ aralkyl group". Examples thereof include N-methyl-N-benzylamino, N-ethyl-N-benzylamino and the like.

In the present specification, unless otherwise specified, examples of the "mono- or di-($C_{1-6}$ alkyl-carbonyl)-amino group" include an amino group mono- or di-substituted by the aforementioned "$C_{1-6}$ alkyl-carbonyl group(s)". For example, acetylamino and the like can be mentioned.

In the present specification, unless otherwise specified, examples of the "N—$C_{1-6}$ alkyl-N—($C_{1-6}$ alkyl-carbonyl)-amino group" include an amino group substituted by the aforementioned "$C_{1-6}$ alkyl group" and "$C_{1-6}$ alkyl-carbonyl group". Examples thereof include N-acetyl-N-methylamino, N-acetyl-N-ethylamino and the like.

In the present specification, unless otherwise specified, examples of the "mono- or di-$C_{1-6}$ alkyl-carbamoyl group" include a carbamoyl group mono- or di-substituted by the above-mentioned "$C_{1-6}$ alkyl group(s)". Examples thereof include methylcarbamoyl, ethylcarbamoyl, dimethylcarbamoyl, diethylcarbamoyl, ethylmethylcarbamoyl and the like.

In the present specification, unless otherwise specified, examples of the "mono- or di-$C_{6-14}$ aryl-carbamoyl group" include a carbamoyl group mono- or di-substituted by the above-mentioned "$C_{6-14}$ aryl group(s)". Examples thereof include phenylcarbamoyl, 1-naphthylcarbamoyl, 2-naphthylcarbamoyl and the like.

In the present specification, unless otherwise specified, examples of the "mono- or di-5- to 7-membered heterocyclyl-carbamoyl group" include a carbamoyl group mono- or di-substituted by a 5- to 7-membered heterocyclic group(s). Examples of the 5- to 7-membered heterocyclic group include heterocyclic group containing, as a ring constituting atom besides carbon atom, 1 to 4 hetero atoms of 1 or 2 kinds selected from a nitrogen atom, a sulfur atom and an oxygen atom. Preferable examples of the "mono- or di-5- to 7-membered heterocyclyl-carbamoyl group" include 2-pyridylcarbamoyl, 3-pyridylcarbamoyl, 4-pyridylcarbamoyl, 2-thienylcarbamoyl, 3-thienylcarbamoyl and the like.

In the present specification, unless otherwise specified, examples of the "N—$C_{1-6}$ alkyl-N—$C_{1-6}$ alkoxy-carbamoyl group" include a carbamoyl group substituted by the above-mentioned "$C_{1-6}$ alkyl group" and the above-mentioned "$C_{1-6}$ alkoxy group". For example, N-methyl-N-methoxycarbamoyl and the like can be mentioned.

In the present specification, unless otherwise specified, examples of the "mono- or di-$C_{1-6}$ alkyl-sulfamoyl group" include a sulfamoyl group mono- or di-substituted by the above-mentioned "$C_{1-6}$ alkyl group(s)" and, for example, methylsulfamoyl, ethylsulfamoyl, dimethylsulfamoyl, diethylsulfamoyl and the like can be mentioned.

In the present specification, unless otherwise specified, examples of the "mono- or di-$C_{6-14}$ aryl-sulfamoyl group" include a sulfamoyl group mono- or di-substituted by the above-mentioned "$C_{6-14}$ aryl group(s)" and, for example, phenylsulfamoyl, diphenylsulfamoyl, 1-naphthylsulfamoyl, 2-naphthylsulfamoyl and the like can be mentioned.

In the present specification, examples of the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (including optionally substituted $C_{1-6}$ alkoxy group)", "optionally substituted $C_{1-6}$ alkylsulfonyloxy group", "optionally substituted $C_{1-10}$ alkylthio group (including optionally substituted $C_{1-6}$ alkylthio group)", "optionally substituted $C_{1-6}$ alkyl-carbonyl group" and "optionally substituted $C_{1-6}$ alkylsulfonyl group" include "$C_{1-6}$ alkyl group", "$C_{2-6}$ alkenyl group", "$C_{2-6}$ alkynyl group", "$C_{1-10}$ alkoxy group (including $C_{1-6}$ alkoxy group)", "$C_{1-6}$ alkylsulfonyloxy group", "$C_{1-10}$ alkylthio group (including $C_{1-6}$ alkylthio group)", "$C_{1-6}$ alkyl-carbonyl group" and "$C_{1-6}$ alkylsulfonyl group", each optionally having, at substitutable positions, 1 to 5 substituents selected from (1) a halogen atom;
(2) a hydroxy group;
(3) an amino group;
(4) a nitro group;
(5) a cyano group;
(6) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxide tetrahydrothiopyranyl, dihydrobenzofuranyl, benzofuranyl, benzothiazolyl, imidazo[1,2-a]pyridyl, oxodihydropyridyl, oxo-5H-thiazolo[3,2-a]pyrimidinyl, oxodihydrothieno[3,2-d]pyrimidinyl, imidazolyl, oxodihydrothieno[2,3-d]pyrimidinyl, imidazo[1,2-a]pyrimidinyl, dioxodihydroindolyl, oxadiazolyl) optionally substituted 1 to 3 substituents selected from a halogen atom, a hydroxy group, an amino group, a nitro group, a cyano group, a $C_{1-6}$ alkyl group (said $C_{1-6}$ alkyl group is optionally substituted by 1 to 3 substituents selected from a halogen atom, a cyano group and a $C_{3-8}$ cycloalkyl group), a $C_{2-6}$ alkenyl group (said $C_{2-6}$ alkenyl group is optionally substituted by a $C_{6-14}$ aryl group optionally substituted by 1 to 3 halogen atoms), a mono- or di-$C_{1-6}$ alkyl-amino group, a $C_{6-14}$ aryl group (said $C_{6-14}$ aryl group is optionally substituted by 1 to 3 $C_{1-6}$ alkoxy groups), a mono- or di-$C_{6-14}$ aryl-amino group, a $C_{3-8}$ cycloalkyl group, a $C_{1-6}$ alkoxy group, $C_{7-16}$ aralkyloxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group, a mono- or di-$C_{6-14}$ aryl-sulfamoyl group and a heterocyclic group (e.g., thienyl);
(7) a mono- or di-$C_{1-6}$ alkyl-amino group;
(8) a mono- or di-$C_{3-8}$ cycloalkyl-amino group;
(9) a mono- or di-$C_{6-14}$ aryl-amino group optionally substituted by 1 to 3 halogen atoms;
(10) a mono- or di-$C_{7-16}$ aralkyl-amino group;
(11) a N—$C_{1-6}$ alkyl-N—$C_{6-14}$ aryl-amino group;
(12) a N—$C_{1-6}$ alkyl-N—$C_{7-16}$ aralkyl-amino group;
(13) a $C_{3-8}$ cycloalkyl group optionally substituted by a $C_{1-6}$ alkyl group;
(14) an optionally halogenated $C_{1-6}$ alkoxy group;
(15) a $C_{1-6}$ alkylthio group optionally substituted by a $C_{1-6}$ alkoxy group;
(16) a $C_{1-6}$ alkylsulfinyl group optionally substituted by a $C_{1-6}$ alkoxy group;
(17) a $C_{1-6}$ alkylsulfonyl group optionally substituted by a $C_{1-6}$ alkoxy group;
(18) an optionally esterified carboxyl group;
(19) a carbamoyl group;
(20) a thiocarbamoyl group;
(21) a mono- or di-$C_{1-6}$ alkyl-carbamoyl group;
(22) a mono- or di-$C_{6-14}$ aryl-carbamoyl group;
(23) a mono- or di-5- to 7-membered heterocyclyl-carbamoyl group;
(24) a N—$C_{1-6}$ alkoxy-carbamoyl group;
(25) a $C_{1-6}$ alkyl-carbonylamino group (e.g., acetylamino, propionylamino) optionally substituted by a carboxyl group;
(26) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkoxy-carbonyl group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(27) a $C_{6-14}$ aryl group optionally substituted by 1 to 3 substituents selected from a halogen atom, a hydroxy group, an amino group, a nitro group, a cyano group, a $C_{1-6}$ alkyl group (said $C_{1-6}$ alkyl group is optionally substituted by 1 to 3 substituents selected from a halogen atom and a hydroxy group), a mono- or di-$C_{1-6}$ alkyl-amino group, a $C_{6-14}$ aryl group, a mono- or di-$C_{6-14}$ aryl-amino group, a mono- or di-($C_{1-6}$ alkyl-carbonyl)-amino group, a $C_{3-8}$ cycloalkyl group, a $C_{1-6}$ alkoxy group (said $C_{1-6}$ alkoxy group is optionally substituted by 1 to 3 halogen atoms), a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group, a mono- or di-$C_{6-14}$ aryl-sulfamoyl group, a $C_{1-6}$ alkyl-carbonyl group, a heterocyclic group (e.g., pyrrolyl) and a heterocyclyl-carbonyl group (e.g., piperazinylcarbonyl, morpholinocarbonyl);
(28) a heterocyclyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(29) a sulfamoyl group;
(30) a mono- or di-$C_{1-6}$ alkyl-sulfamoyl group;
(31) a mono- or di-$C_{6-14}$ aryl-sulfamoyl group;
(32) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(33) a $C_{1-6}$ alkylsulfonyloxy group;
(34) a tri-$C_{1-6}$ alkyl-silyloxy group;
(35) a heterocyclyl-carbonyl group (e.g., thienylcarbonyl, tetrahydrobenzo[c]azepinylcarbonyl, tetrahydroisoquinolinylcarbonyl);
(36) a $C_{6-14}$ aryl-carbonyl group;
(37) a $C_{6-14}$ aryl-thio group optionally substituted by 1 to 3 substituents selected from a halogen atom and a cyano group;
(38) a $C_{6-14}$ aryl-sulfinyl group optionally substituted by 1 to 3 halogen atoms;
(39) a $C_{6-14}$ aryl-sulfonyl group optionally substituted by 1 to 3 halogen atoms;
(40) a nitrogen-containing heterocyclyl-sulfonyl group (e.g., pyridylsulfonyl);
(41) a nitrogen-containing heterocyclyl-amino group (e.g., pyridylamino) optionally substituted by a cyano group; and the like.

In the present specification, examples of the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylsulfonyloxy group", "optionally substituted heterocyclylthio group", "optionally substituted $C_{6-14}$ arylthio group", "optionally substituted $C_{7-16}$ aralkylthio group", "optionally substituted heterocyclylsulfonyl group", "optionally substituted $C_{6-14}$ arylsulfonyl group" and "optionally substituted $C_{7-16}$ aralkylsulfonyl group" include "$C_{3-8}$ cycloalkyl group", "$C_{6-14}$ aryl group", "$C_{7-16}$ aralkyl group", "heterocyclic group", "heterocyclyloxy group", "$C_{6-14}$ aryloxy group", "$C_{7-16}$ aralkyloxy group", "heterocyclylsulfonyloxy group", "heterocyclylthio group", "$C_{6-14}$ arylthio group", "$C_{7-16}$ aralkylthio group", "heterocyclylsulfonyl group", "$C_{6-14}$ arylsulfonyl group" and "$C_{7-16}$ aralkylsulfonyl group", each optionally having, at substitutable positions, 1 to 5 substituents selected from (1) a halogen atom;
(2) a hydroxy group;
(3) an amino group;
(4) a nitro group;
(5) a cyano group;
(6) an optionally substituted $C_{1-6}$ alkyl group;
(7) an optionally substituted $C_{2-6}$ alkenyl group;
(8) an optionally substituted $C_{2-6}$ alkynyl group;
(9) a $C_{6-14}$ aryl group optionally substituted by 1 to 3 substituents selected from a halogen atom, a hydroxy group, an amino group, a nitro group, a cyano group; an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(10) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(11) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(12) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxide tetrahydrothiopyranyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(13) a mono- or di-$C_{1-6}$ alkyl-amino group;
(14) a mono- or di-$C_{6-14}$ aryl-amino group;
(15) a mono- or di-$C_{7-16}$ aralkyl-amino group;
(16) a N—$C_{1-6}$ alkyl-N—$C_{6-14}$ aryl-amino group;
(17) a N—$C_{1-6}$ alkyl-N—$C_{7-16}$ aralkyl-amino group;
(18) a $C_{3-8}$ cycloalkyl group;
(19) an optionally substituted $C_{1-6}$ alkoxy group;

(20) a $C_{1-6}$ alkylthio group optionally substituted by a $C_{1-6}$ alkoxy group;
(21) a $C_{1-6}$ alkylsulfinyl group optionally substituted by a $C_{1-6}$ alkoxy group;
(22) a $C_{1-6}$ alkylsulfonyl group optionally substituted by a $C_{1-6}$ alkoxy group;
(23) an optionally esterified carboxyl group;
(24) a carbamoyl group;
(25) a thiocarbamoyl group;
(26) a mono- or di-$C_{1-6}$ alkyl-carbamoyl group;
(27) a mono- or di-$C_{6-14}$ aryl-carbamoyl group;
(28) a mono- or di-5- to 7-membered heterocyclyl-carbamoyl group;
(29) a sulfamoyl group;
(30) a mono- or di-$C_{1-6}$ alkyl-sulfamoyl group;
(31) a mono- or di-$C_{6-14}$ aryl-sulfamoyl group;
(32) a $C_{1-6}$ alkylsulfonyloxy group;
(33) a tri-$C_{1-6}$ alkyl-silyloxy group;
(34) a nitrogen-containing heterocyclyl-carbonyl group (e.g., pyrrolidinylcarbonyl, piperidinocarbonyl, morpholinocarbonyl, thiomorpholinocarbonyl);
(35) a heterocyclyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(36) an optionally substituted $C_{1-4}$ alkylenedioxy group (e.g., methylenedioxy, ethylenedioxy);
(37) a $C_{1-6}$ alkyl-carbonylamino group (e.g., acetylamino);
(38) a N—$C_{1-6}$ alkyl-N—($C_{1-6}$ alkyl-carbonyl)-amino group (e.g., N-acetyl-N-ethylamino);
(39) a formyl group; and the like.

In the present specification, unless otherwise specified, examples of the "optionally substituted amino group" include an amino group optionally substituted by 1 or 2 substituents selected from
(1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-8}$ cycloalkyl group;
(5) an optionally substituted $C_{6-14}$ aryl group;
(6) an optionally substituted $C_{1-6}$ alkoxy group;
(7) an acyl group;
(8) an optionally substituted heterocyclic group (preferably furyl, pyridyl, thienyl, pyrazolyl, thiazolyl, oxazolyl);
(9) a sulfamoyl group;
(10) a mono- or di-$C_{1-6}$ alkyl-sulfamoyl group;
(11) a mono- or di-$C_{6-14}$ aryl-sulfamoyl group and the like.

When the "optionally substituted amino group" is an amino group substituted by two substituents, these substituents may form, together with the adjacent nitrogen atom, nitrogen-containing heterocycle. Examples of the "nitrogen-containing heterocycle" include 5- to 7-membered nitrogen-containing heterocycle containing, as a ring constituting atom besides carbon atom, at least one nitrogen atom, and further optionally containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

In the present specification, unless otherwise specified, examples of the "acyl group" include groups represented by the formulas: —$COR^7$, —CO—$OR^7$, —$SO_2R^7$, —$SOR^7$, —PO($OR^7$)($OR^8$), —CO—$NR^{7a}R^{8a}$ and —CS—$NR^{7a}R^{8a}$ wherein $R^7$ and $R^8$ are the same or different and each is a hydrogen atom, an optionally substituted hydrocarbon group or an optionally substituted heterocyclic group, and $R^{7a}$ and $R^{8a}$ are the same or different and each is a hydrogen atom, an optionally substituted hydrocarbon group or an optionally substituted heterocyclic group, or $R^{7a}$ and $R^{8a}$ may form, together with the adjacent nitrogen atom, an optionally substituted nitrogen-containing heterocycle, and the like.

In the present specification, unless otherwise specified, the "optionally substituted alkanoyl group" is a group represented by the formula: —$COR^7$ wherein $R^7$ is as defined above, from among the aforementioned "acyl group", and particularly, a $C_{1-7}$ alkanoyl group (e.g., formyl, and a $C_{1-6}$ alkyl-carbonyl group such as acetyl and the like) and the like can be mentioned.

Examples of the "nitrogen-containing heterocycle" of the "optionally substituted nitrogen-containing heterocycle" formed by $R^{7a}$ and $R^{8a}$, together with the adjacent nitrogen atom, include 5- to 7-membered nitrogen-containing heterocycle containing, as a ring constituting atom besides carbon atom, at least one nitrogen atom, and further optionally containing 1 or 2 hetero atoms selected from oxygen atom, a sulfur atom and nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle optionally has 1 or 2 substituents at substitutable positions. Examples of the substituent include a hydroxy group, an optionally halogenated $C_{1-6}$ alkyl group, a $C_{6-14}$ aryl group, a $C_{7-16}$ aralkyl group and the like.

Preferable examples of the "acyl group" include a formyl group; a carboxyl group; a carbamoyl group; a $C_{1-6}$ alkyl-carbonyl group (e.g., acetyl, isobutanoyl, isopentanoyl) optionally substituted by 1 to 3 halogen atoms; $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms; $C_{3-8}$ cycloalkyl-carbonyl group (e.g., cyclopentylcarbonyl, cyclohexylcarbonyl); $C_{6-14}$ aryl-carbonyl group (e.g., benzoyl, 1-naphthoyl, 2-naphthoyl); $C_{7-16}$ aralkyl-carbonyl group (e.g., phenylacetyl, 2-phenylpropanoyl); $C_{6-14}$ aryloxy-carbonyl group (e.g., phenyloxycarbonyl, naphthyloxycarbonyl); $C_{7-16}$ aralkyloxy-carbonyl group (e.g., benzyloxycarbonyl, phenethyloxycarbonyl); mono- or di-$C_{1-6}$ alkyl-carbamoyl group; mono- or di-$C_{6-14}$ aryl-carbamoyl group; $C_{3-8}$ cycloalkyl-carbamoyl group (e.g., cyclopropylcarbamoyl); $C_{7-16}$ aralkyl-carbamoyl group (e.g., benzylcarbamoyl); $C_{1-6}$ alkylsulfonyl group optionally substituted by 1 to 3 halogen atoms; $C_{6-14}$ arylsulfonyl group (e.g., phenylsulfonyl) optionally substituted by nitro group; nitrogen-containing heterocyclyl-carbonyl group (e.g., pyrrolidinylcarbonyl, piperidinocarbonyl, morpholinocarbonyl, thiomorpholinocarbonyl); $C_{1-6}$ alkylsulfinyl group optionally substituted by 1 to 3 halogen atoms; $C_{6-14}$ arylsulfinyl group; thiocarbamoyl group; and the like.

In the present specification, as the "optionally substituted hydrocarbon (group)" of the "optionally substituted hydrocarbon-carbonyl group", those similar to the above-mentioned groups exemplified for the "optionally substituted hydrocarbon group" can be mentioned.

As the "optionally substituted hydrocarbon (group)", "optionally substituted $C_{1-6}$ alkyl-carbonyl group" and "optionally substituted $C_{6-14}$ aryl-carbonyl group" are preferable.

As the "optionally substituted $C_{1-6}$ alkyl" of the "optionally substituted $C_{1-6}$ alkyl-carbonyl group", those similar to the above-mentioned groups exemplified for the "optionally substituted $C_{1-6}$ alkyl group" can be mentioned.

As the "optionally substituted $C_{6-14}$ aryl" of the "optionally substituted $C_{6-14}$ aryl-carbonyl group", those similar to the above-mentioned groups exemplified for the above-mentioned "optionally substituted $C_{6-14}$ aryl" can be mentioned. As the "$C_{6-14}$ aryl-carbonyl group", benzoyl is particularly preferable.

In the present specification, as the "optionally substituted heterocycle (group)" of the "optionally substituted heterocyclyl-carbonyl group", those similar to the above-mentioned groups exemplified for the "optionally substituted heterocyclic group" can be mentioned. As the "heterocyclic group", a 5- or 6-membered heterocyclic group is particularly preferable.

In the present specification, as the substituent that the carboxy group of the "optionally substituted carboxy group" optionally has, for example, an optionally substituted hydrocarbon group, an optionally substituted heterocyclic group and the like can be mentioned.

In the present specification, as the substituent that the carbamoyl group of the "optionally substituted carbamoyl group" optionally has, for example, an optionally substituted hydrocarbon group, an optionally substituted heterocyclic group and the like can be mentioned.

In the present specification, unless otherwise specified, examples of the "$C_{1-4}$ alkylenedioxy group" of the "optionally substituted $C_{1-4}$ alkylenedioxy group" include methylenedioxy, ethylenedioxy, propylenedioxy, tetrafluoroethylenedioxy and the like. The $C_{1-4}$ alkylenedioxy group optionally has 1 to 3 substituents at substitutable positions. Examples of the substituent include a halogen atom, a hydroxy group, an amino group, a mono- or di-$C_{1-6}$ alkyl-amino group, a mono- or di-$C_{6-14}$ aryl-amino group, a mono- or di-$C_{7-16}$ aralkyl-amino group, a nitro group, a cyano group, a $C_{1-6}$ alkoxy group, a $C_{1-6}$ alkylthio group and the like.

Each symbol in the formulas (I) and (II) is described in detail in the following.

$R^1$ in the formula (I) or the formula (II) is a hydrogen atom, an optionally substituted hydrocarbon group, an optionally substituted heterocyclic group excluding a diazabicycloalkyl group, an optionally substituted alkanoyl group, an optionally substituted hydroxy group, an optionally substituted amino group, a substituted sulfonyl group, a substituted sulfinyl group, or an optionally substituted mercapto group.

As $R^1$, an optionally substituted hydrocarbon group, an optionally substituted amino group or an optionally substituted mercapto group is preferable.

Particularly, as $R^1$, a group represented by the formula:

wherein
Y is a bond, a sulfur atom, or —$NR^y$— ($R^y$ is a hydrogen atom, or a lower alkyl group, and
$R^{1a}$ is a $C_{1-2}$ alkyl group optionally substituted by one or more substituents selected from a hydrogen atom, or a halogen atom (preferably, a fluorine atom), an optionally substituted carbamoyl group, an optionally substituted $C_{6-10}$ aryl group and an optionally substituted 5- to 10-membered aromatic heterocyclic group, is more preferable.

Specific examples of $R^1$ include
(1) a hydrogen atom;
(2) a $C_{3-8}$ cycloalkyl group (e.g., cyclopropyl);
(3) a $C_{1-10}$ alkoxy group (e.g., methoxy) optionally substituted by a substituent selected from
　(a) a carboxyl group,
　(b) a $C_{1-6}$ alkoxy-carbonyl group (e.g., ethoxycarbonyl),
　(c) a N—$C_{1-6}$ alkoxy-carbamoyl group (e.g., N-methyl-N-methoxycarbamoyl) and the like;
(4) a $C_{7-16}$ aralkyloxy group (e.g., benzyloxy) optionally substituted by 1 to 3 halogen atoms (e.g., fluorine atom) and the like;
(5) a $C_{1-6}$ alkylsulfonyl group (e.g., methylsulfonyl);
(6) a $C_{1-6}$ alkylsulfinyl group (e.g., methylsulfinyl);
(7) a hydroxy group;
(8) a $C_{1-7}$ alkanoyl group (e.g., acetyl);
(9) a 5- or 6-membered heterocyclic group (e.g., 5- or 6-membered nonaromatic heterocyclic group such as piperazino, morpholino and the like); or
(10) a group represented by the formula: $R^{1a}$—Y—
wherein
　Y is a bond, a sulfur atom, or —NRy- wherein Ry is a hydrogen atom or a lower alkyl (e.g., methyl) and
　$R^{1a}$ is
(1') a hydrogen atom,
(2') a $C_{1-6}$ alkyl group (e.g., $C_{1-3}$ alkyl group such as methyl, ethyl, propyl, isopropyl and the like (preferably $C_{1-2}$ alkyl group)) optionally substituted by 1 to 3 substituents selected from
　(a) a halogen atom (e.g., fluorine atom),
　(b) a carboxyl group,
　(c) a $C_{1-6}$ alkoxy-carbonyl group (e.g., ethoxycarbonyl),
　(d) a N—$C_{1-6}$ alkyl-N—$C_{1-6}$ alkoxy-carbamoyl group (e.g., N-methyl-N-methoxycarbamoyl),
　(e) a $C_{6-14}$ aryloxy group (e.g., phenoxy) optionally substituted by 1 to 3 substituents selected from
　　(i) a halogen atom (e.g., fluorine atom),
　　(ii) a cyano group,
　　(iii) a $C_{1-6}$ alkoxy-carbonyl group (e.g., methoxycarbonyl) and the like,
　(f) an amino group optionally substituted by 1 or 2 substituents selected from a mono- or di-$C_{6-14}$ aryl group optionally substituted by 1 to 3 halogen atoms (e.g., fluorine atom) and the like, and a $C_{1-6}$ alkyl group (e.g., phenylamino, methylamino),
　(g) a heterocyclyl-carbonyl group (e.g., thienylcarbonyl, tetrahydrobenzo[c]azepinylcarbonyl, tetrahydroisoquinolinylcarbonyl) optionally substituted by 1 to 3 $C_{1-6}$ alkyl groups (e.g., methyl) and the like,
　(h) a $C_{6-14}$ arylthio group (e.g., phenylthio, 2-naphthylthio) optionally substituted by 1 to 3 substituents selected from a halogen atom (e.g., fluorine atom, chlorine atom), a cyano group and the like,
　(i) a $C_{6-14}$ aryl-sulfinyl group (e.g., phenylsulfinyl) optionally substituted by 1 to 3 halogen atoms (e.g., fluorine atom) and the like,
　(j) a $C_{6-14}$ aryl-sulfonyl group (e.g., phenylsulfonyl) optionally substituted by 1 to 3 halogen atoms (e.g., fluorine atom) and the like,
　(k) a $C_{1-6}$ alkoxy-carbonyl group (e.g., ethoxycarbonyl),
　(l) a $C_{3-8}$ cycloalkyl group (e.g., cyclopropyl),
　(m) a heterocyclic group (e.g., dihydrobenzofuranyl, benzofuranyl, pyridyl, thiazolyl, benzothiazolyl, imidazo[1,2-a]pyridyl, oxodihydropyridinyl, oxo-5H-thiazolo[3,2-a]pyrimidinyl, oxodihydrothieno[3,2-d]pyrimidinyl, imidazolyl, oxazolyl, morpholinyl, oxodihydrothieno[2,3-d]pyrimidinyl, imidazo[1,2-a]pyrimidinyl, dioxodihydroindolyl, oxadiazolyl) optionally substituted by substituent(s) selected from
  (i) a $C_{7-16}$ aralkyloxy group (e.g., benzyloxy),
  (ii) a $C_{1-6}$ alkyl group (e.g., methyl, propyl) optionally substituted by 1 to 3 $C_{3-8}$ cycloalkyl groups (e.g., cyclopropyl) and the like,
  (iii) a $C_{2-6}$ alkynyl group (e.g., 2-propynyl),
  (iv) a $C_{2-6}$ alkenyl group (e.g., vinyl) optionally substituted by a $C_{6-14}$ aryl group (e.g., phenyl) optionally substituted by 1 to 3 halogen atoms (e.g., fluorine atom) and the like,
  (v) a $C_{1-6}$ alkoxy group (e.g., methoxy),
  (vi) a heterocyclic group (e.g., thienyl),
  (vii) a $C_{6-14}$ aryl group (e.g., phenyl) optionally substituted by 1 to 3 $C_{1-6}$ alkoxy groups (e.g., methoxy) and the like, and the like,
(n) a carbamoyl group,
(o) a mono- or di-$C_{1-6}$ alkyl-carbamoyl group (e.g., diethylcarbamoyl),
(p) a $C_{6-14}$ aryl group (e.g., $C_{6-10}$ aryl group such as phenyl, 1-naphthyl, 2-naphthyl and the like) optionally substituted by substituent(s) selected from
  (i) a halogen atom (e.g., fluorine atom, chlorine atom),
  (ii) a cyano group,
  (iii) a heterocyclic group (e.g., 1-pyrrolyl),
  (iv) a $C_{1-6}$ alkyl group (e.g., methyl, tert-butyl) optionally substituted by 1 to 3 substituents selected from a halogen atom (e.g., fluorine atom), a hydroxy group and the like,
  (v) a $C_{1-6}$ alkoxy group (e.g., methoxy) optionally substituted by 1 to 3 halogen atoms (e.g., fluorine atom) and the like,
  (vi) a mono- or di-($C_{1-7}$ alkanoyl)-amino group (e.g., acetylamino),
  (vii) a $C_{1-6}$ alkylsulfonyl group (e.g., methylsulfonyl),
  (viii) a carboxyl group,
  (iv) a $C_{1-6}$ alkoxy-carbonyl group (e.g., methoxycarbonyl),
  (x) a heterocyclyl-carbonyl group (e.g., piperazinylcarbonyl, morpholinocarbonyl) optionally substituted by 1 to 3 $C_{1-6}$ alkyl groups (e.g., methyl),
  (xi) a $C_{1-7}$ alkanoyl group (e.g., acetyl),
  (xii) a $C_{1-6}$ alkylthio group (e.g., methylthio),
  (xiii) a $C_{1-6}$ alkylsulfinyl group (e.g., methylsulfinyl), and the like;
(q) a $C_{1-7}$ alkanoyloxy group (e.g., acetyloxy),
(r) a hydroxy group,
(s) a $C_{1-6}$ alkylthio group (e.g., methylthio),
(t) a $C_{1-6}$ alkylsulfinyl group (e.g., methylsulfinyl),
(u) a $C_{1-6}$ alkylsulfonyl group (e.g., methylsulfonyl),
(v) a $C_{1-6}$ alkoxy group (e.g., methoxy),
(w) a group represented by the formula:

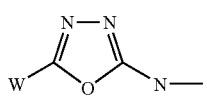

wherein each symbol is as defined above, and the like, or
(3') a cyano group;
and the like can be mentioned.

In the formula (I), W is a group represented by the formula:

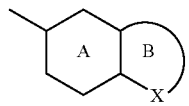

wherein
ring A is a 6-membered aromatic ring,
X is a carbon atom, a nitrogen atom, an oxygen atom or a sulfur atom, and
ring B is a 5- or 6-membered heterocycle optionally having substituent(s) at any position(s) other than X and optionally further having, as hetero atom other than X, 1 to 3 nitrogen atoms or one sulfur atom or oxygen atom, or a group represented by the formula:

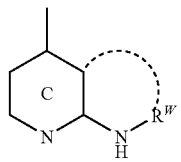

wherein
ring C is a 6-membered nitrogen-containing aromatic ring optionally having substituent(s), and
$R^W$ is a hydrogen atom, an acyl group, an optionally substituted hydrocarbon group, or an optionally substituted heterocyclic group, or optionally forms, together with the adjacent —NH— and a carbon atom on ring C, a nitrogen-containing 5- to 7-membered ring.

As the "6-membered aromatic ring" for ring A, benzene and 6-membered aromatic heterocycle can be mentioned. The 6-membered aromatic heterocycle may be any as long as it can be fused with ring B to form a bicyclic fused ring, and 6-membered heterocycle (e.g., pyridine, pyridazine, pyrimidine, pyrazine, triazine etc.) containing, besides carbon atom, 1 to 3 nitrogen atoms, can be mentioned. Specific examples of ring A include benzene, pyridine and the like.

X is a carbon atom, a nitrogen atom, an oxygen atom or a sulfur atom. Ring B does not have a substituent on X. That is, it is clear to those of ordinary skill in the art that "—X—" in ring B shows —CH$_2$—, —CH=, =CH—, —NH—, —N=, =N—, —O— or —S—.

As the "5- or 6-membered heterocycle optionally having substituent(s) at any position(s) other than X, and optionally further having, as a hetero atom other than X, 1 to 3 nitrogen atoms or one sulfur atom or oxygen atom" for ring B, a 5- or 6-membered heterocycle containing one nitrogen atom or oxygen atom for X, and optionally further containing 1 to 3 nitrogen atoms or one sulfur atom or oxygen atom besides X for hetero atom (e.g., oxazole, thiazole, imidazole, furan, triazole, isoxazole, isothiazole, pyrazole, dioxole, dihydrofuran, oxazoline, oxathiol, triazole, tetrazole, pyran, dihydropyran, dihydrodioxin, dihydrooxathiin, pyridine, pyrimidine, pyridazine, pyrazine etc.), can be mentioned. Specific examples thereof include, furan, pyrazole, thiazole, imidazole, oxazole, triazole, dihydrofuran, pyridine and the like can be mentioned.

The 5- or 6-membered heterocycle optionally has substituent(s) at any position(s) other than X. As such substituent, an optionally substituted hydrocarbon group, an optionally substituted heterocyclic group, an optionally substituted hydroxy group, an optionally substituted amino group, an optionally substituted mercapto group, and an acyl group can be mentioned. Of these, an optionally substituted hydrocarbon group, an optionally substituted heterocyclic group, an acyl group, an amino group, a monosubstituted amino group and the like are preferable.

As the substituent that the amino group of the monosubstituted amino group may have, for example, an optionally substituted hydrocarbon group, an optionally substituted heterocyclic group, a substituted sulfonyl group, an acyl group and the like can be mentioned. Of these, an optionally substituted hydrocarbon group, an optionally substituted heterocyclic group, and an acyl group are preferable, and an optionally substituted $C_{1-6}$ alkyl group, an optionally substituted $C_{3-6}$ cycloalkyl group, an optionally substituted $C_{6-10}$ aryl group, an optionally substituted 5- or 6-membered heterocyclic group, and an acyl group are more preferable.

Specific examples of the substituent that the 5- or 6-membered heterocycle may have include (1) a $C_{1-6}$ alkyl group (e.g., methyl) optionally substituted by a hydroxy group;

(2) a $C_{6-14}$ aryl group (e.g., phenyl) optionally substituted by 1 to 3 substituents selected from
   (a) a halogen atom (e.g., fluorine atom, chlorine atom),
   (b) a cyano group,
   (c) a $C_{1-6}$ alkyl group (e.g., methyl) optionally substituted by 1 to 3 substituents selected from
     (i) a halogen atom (e.g., fluorine atom),
     (ii) a hydroxy group,
     (iii) a $C_{1-6}$ alkoxy group (e.g., methoxy),
     (iv) a $C_{1-6}$ alkylsulfonyl group (e.g., methylsulfonyl), etc.,
   (d) a di-$C_{1-6}$ alkyl-amino group (e.g., dimethylamino),
   (e) a $C_{1-6}$ alkoxy group (e.g., methoxy, ethoxy) optionally substituted by 1 to 3 substituents selected from
     (i) a halogen atom,
     (ii) a $C_{1-6}$ alkylthio group (e.g., methylthio),
     (iii) a $C_{1-6}$ alkylsulfinyl group (e.g., methylsulfinyl),
     (iv) a $C_{1-6}$ alkylsulfonyl group (e.g., methylsulfonyl),
     (v) a $C_{6-14}$ aryl group (e.g., phenyl), etc.,
   (f) a $C_{1-6}$ alkylthio group (e.g., methylthio, ethylthio, propylthio, isopropylthio) optionally substituted by 1 to 3 substituents selected from
     (i) a halogen atom (e.g., fluorine atom),
     (ii) a $C_{6-14}$ aryl group (e.g., phenyl) optionally substituted by a cyano group, etc.,
   (g) a $C_{1-6}$ alkylsulfinyl group (e.g., methylsulfinyl, ethylsulfinyl, propylsulfinyl, isopropylsulfinyl) optionally substituted by 1 to 3 substituents selected from
     (i) a halogen atom (e.g., fluorine atom),
     (ii) a $C_{6-14}$ aryl group (e.g., phenyl) optionally substituted by cyano, etc.,
   (h) a $C_{1-6}$ alkylsulfonyl group (e.g., methylsulfonyl, ethylsulfonyl, propylsulfonyl, isopropylsulfonyl) optionally substituted by 1 to 3 substituents selected from
     (i) a halogen atom (e.g., fluorine atom),
     (ii) a $C_{6-14}$ aryl group (e.g., phenyl) optionally substituted by a cyano group, etc.,
   (i) a carboxyl group,
   (j) a $C_{1-6}$ alkoxy-carbonyl group (e.g., methoxycarbonyl),
   (k) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
   (l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., methylaminosulfonyl, dimethylaminosulfonyl),
   (m) a $C_{1-7}$ alkanoyl group (e.g., formyl group, $C_{1-6}$ alkyl-carbonyl group (e.g., acetyl)),
   (n) a $C_{1-6}$ alkylsulfonyloxy group (e.g., sulfonyloxy) optionally substituted by 1 to 3 halogen atoms (e.g., fluorine atom),
   (o) a $C_{1-6}$ alkylsulfonylamino group (e.g., methylsulfonylamino),
   (p) a di-$C_{1-6}$ alkoxyphosphoryl group (e.g., dimethoxyphosphoryl),
   (q) a $C_{1-6}$ alkoxy-carbonyl group (e.g., methoxycarbonyl),
   (r) a hydroxy group,
etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group;

(3) a heterocyclic group (e.g., pyridyl, oxazolyl, benzothienyl, quinolyl, piperidinyl) optionally substituted by 1 to 3 substituents selected from
   (a) a halogen atom (e.g., fluorine atom, chlorine atom),
   (b) a $C_{1-6}$ alkyl group (e.g., methyl),
   (c) a carboxyl group,
   (d) a $C_{1-6}$ alkoxy-carbonyl group (e.g., ethoxycarbonyl),
   (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
   (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl)
   (g) a $C_{6-14}$ aryl-carbonyl group (e.g., benzoyl),
   (h) a $C_{1-6}$ alkylsulfonyl group (e.g., methylsulfonyl),
   (i) a $C_{1-6}$ alkylsulfonylamino group,
   (j) a $C_{7-10}$ aralkyl group (e.g., benzyl),
   (k) a $C_{1-7}$ alkanoyl group (e.g., acetyl), etc.;

(4) a carboxyl group;

(5) a $C_{1-6}$ alkoxy-carbonyl group (e.g., ethoxycarbonyl);

(6) a heterocyclyl-carbonyl group (e.g., morpholinocarbonyl);

(7) a $C_{1-6}$ alkyl-carbamoyl group (e.g., ethylcarbamoyl) optionally substituted by 1 to 3 carbamoyl groups;

(8) an amino group;

(9) a cyano group;

(10) a $C_{1-7}$ alkanoyl group (e.g., formyl);

and the like.

As ring B,

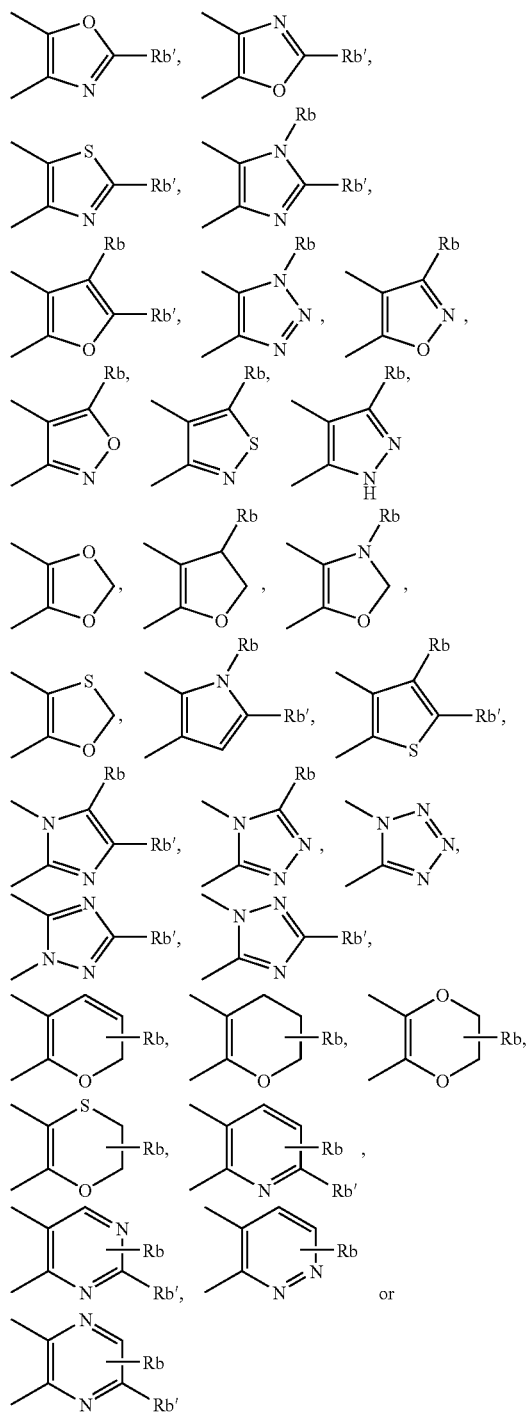

wherein
Rb is a hydrogen atom, an optionally substituted hydrocarbon group, an optionally substituted heterocyclic group, an optionally substituted alkanoyl group, an optionally substituted carboxy group, an optionally substituted carbamoyl group, an optionally substituted heterocyclyl-carbonyl group, m or an optionally substituted hydrocarbon-carbonyl group, and Rb' is a hydrogen atom, an amino group, or a monosubstituted amino group, and the like are preferable.

As the "monosubstituted amino group" for Rb', groups similar to those exemplified as the substituents of the "5- or 6-membered heterocycle" for ring B can be mentioned.

Specific examples of Rb include
(1) a hydrogen atom;
(2) a $C_{1-6}$ alkyl group (e.g., methyl) optionally substituted by a hydroxy group;
(3) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group,
    (iii) a $C_{1-6}$ alkoxy group (e.g., methoxy),
    (iv) a $C_{1-6}$ alkylsulfonyl group (e.g., methylsulfonyl), etc.,
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from
    (i) a halogen atom,
    (ii) a $C_{1-6}$ alkylthio group (e.g., methylthio),
    (iii) a C1-6 alkylsulfinyl group (e.g., methylsulfinyl),
    (iv) a $C_{1-6}$ alkylsulfonyl group (e.g., methylsulfonyl),
    (v) a $C_{6-14}$ aryl group (e.g., phenyl), etc.,
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by cyano, etc.,
  (h) a $C_{1-6}$ alkylsulfonyl group (e.g., methylsulfonyl, ethylsulfonyl, propylsulfonyl, isopropylsulfonyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (i) a carboxyl group,
  (j) a $C_{1-6}$ alkoxy-carbonyl group (e.g., methoxycarbonyl),
  (k) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
  (l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., methylaminosulfonyl, dimethylaminosulfonyl),
  (m) a $C_{1-7}$ alkanoyl group (e.g., formyl group, $C_{1-6}$ alkyl-carbonyl group (e.g., acetyl)),
  (n) a $C_{1-6}$ alkylsulfonyloxy group optionally substituted by 1 to 3 halogen atoms (e.g., fluorine atom) (e.g., trifluoromethylsulfonyloxy), (o) a $C_{1-6}$ alkylsulfonylamino group (e.g., methylsulfonylamino),
(p) a alkoxyphosphoryl group (e.g., dimethoxyphosphoryl),
(q) a $C_{1-6}$ alkoxy-carbonyl group (e.g., methoxycarbonyl),
(r) a hydroxy group, etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group;

(4) a heterocyclic group (e.g., pyridyl, oxazolyl, benzothienyl, quinolyl, piperidinyl) optionally substituted by 1 to 3 substituents selected from
  (a) a halogen atom (e.g., fluorine atom, chlorine atom),
  (b) a $C_{1-6}$ alkyl group (e.g., methyl),
  (c) a carboxyl group,
  (d) a $C_{1-6}$ alkoxy-carbonyl group (e.g., ethoxycarbonyl),
  (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
  (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl),
  (g) a $C_{6-14}$ aryl-carbonyl group (e.g., benzoyl),
  (h) a $C_{1-6}$ alkylsulfonyl group (e.g., methylsulfonyl),
  (i) a $C_{1-6}$ alkylsulfonylamino group,
  (j) a $C_{7-10}$ aralkyl group (e.g., benzyl),
  (k) a $C_{1-7}$ alkanoyl group (e.g., acetyl), etc.;
(5) a carboxyl group;
(6) a $C_{1-6}$ alkoxy-carbonyl group (e.g., ethoxycarbonyl);
(7) a heterocyclyl-carbonyl group (e.g., morpholinocarbonyl);
(8) a $C_{1-6}$ alkyl-carbamoyl group (e.g., ethylcarbamoyl) optionally substituted by 1 to 3 carbamoyl groups;
(9) a cyano group;
(10) a $C_{1-7}$ alkanoyl group (e.g., formyl);
and the like.

Specific examples of Rb' include
(a) a hydrogen atom;
(b) an amino group;
and the like.

As the "6-membered nitrogen-containing aromatic ring" of the "6-membered nitrogen-containing aromatic ring optionally having substituents" for ring C, a 6-membered nitrogen-containing aromatic ring containing, as a ring constituting atom besides carbon atom, at least one nitrogen atom (e.g., pyridine, pyrimidine, pyridazine, triazine etc.) can be mentioned. Specific examples include pyridine, pyrimidine and the like.

The 6-membered nitrogen-containing aromatic ring may have substituent(s). As such substituent, an optionally substituted hydrocarbon group, an optionally substituted heterocyclic group, an optionally substituted hydroxy group, an optionally substituted amino group, an optionally substituted mercapto group, and an acyl group can be mentioned. As the "6-membered nitrogen-containing aromatic ring optionally having substituents" for ring C, an unsubstituted 6-membered nitrogen-containing aromatic ring is preferable.

R$^W$ is a hydrogen atom, an acyl group, an optionally substituted hydrocarbon group, or an optionally substituted heterocyclic group, or optionally forms, together with the adjacent —NH— and a carbon atom on ring C, an optionally substituted nitrogen-containing 5- to 7-membered ring.

As the "nitrogen-containing 5- to 7-membered ring" of the optionally substituted nitrogen-containing 5- to 7-membered ring formed by R$^W$ together with the adjacent —NH— and a carbon atom on ring C, a 5- to 7-membered nitrogen-containing heterocycle containing at least one nitrogen atom besides carbon atom, and optionally further containing 1 or 2 hetero atoms selected from an oxygen atom, a sulfur atom and a nitrogen atom (e.g., pyrrole, imidazole, triazole, 2,3-dihydropyrrole, 2,3-dihydroimidazole, 2,3-dihydrooxazole, 2,3-dihydrothiazole, 1,2-dihydropyridine, 1,2,3,4-tetrahydropyridine, 1,2,3,4-tetrahydropyrazine, 2,3-dehydro-1,4-oxazine, 2,3-dehydro-1,4-thiazine, azepine, 1,2-dihydroazepine, 1,4-diazepine, 4,1-oxazepine, 4,1-thiazepine etc.) can be mentioned. Specific examples include pyrrole and the like.

As the substituent of the "optionally substituted nitrogen-containing 5- to 7-membered ring", for example, a $C_{7-16}$ aralkyl group (e.g., phenethyl) can be mentioned.

Specific examples of R$^W$ include
(1) a hydrogen atom;
(2) a $C_{1-7}$ alkanoyl group (e.g., propionyl) optionally substituted by 1 to 3 substituents selected from
  (a) a heterocyclic group (e.g., morpholino, pyrrolidinyl),
  (b) a $C_{3-8}$ cycloalkylamino group (e.g., cyclopropylamino),
  (c) a $C_{6-14}$ aryl group (e.g., phenyl), etc.;
(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl);
(6) a $C_{7-16}$ aralkyl group (e.g., 3-phenylpropionyl);
(7) a $C_{6-10}$ aryl group (e.g., phenyl) optionally substituted by 1 to 3 substituents selected from
  (a) an optionally halogenated $C_{1-6}$ alkyl group (e.g., trifluoromethyl),
  (b) a $C_{1-6}$ alkoxy group (e.g., methoxy),
  (c) a $C_{1-6}$ alkylthio group (e.g., methylthio)
  (d) a $C_{1-6}$ alkylsulfinyl group (e.g., methylsulfinyl),
  (e) a $C_{1-6}$ alkylsulfonyl group (e.g., methylsulfonyl), etc.;
(8) a $C_{1-6}$ alkyl-carbamoyl group (e.g., methylcarbamoyl) optionally substituted by a heterocyclic group (e.g., pyridyl);
(9) a heterocyclic group (e.g., pyridyl) etc., or R$^W$ optionally forms, together with the adjacent —NH— and a carbon atom on ring C, a nitrogen-containing 5- to 7-membered ring (e.g., pyrrole) optionally substituted by substituent(s) such as a $C_{7-16}$ aralkyl group (e.g., phenethyl) and the like.

A group represented by the formula:

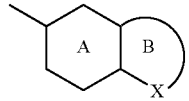

wherein each symbol is as defined above, for W is preferably other than (1) a group represented by the formula:

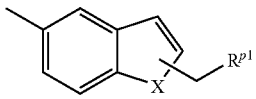

wherein X is a nitrogen atom or an oxygen atom, and $R^{p1}$ is a disubstituted amino group, (2) a group represented by the formula:

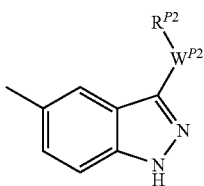

wherein $R^{p2}$ is an optionally substituted aryl group, an optionally substituted heteroaryl group, or an optionally substituted fused ring group, and $W^{p2}$ is a bond or a spacer, and (3) a group represented by the formula:

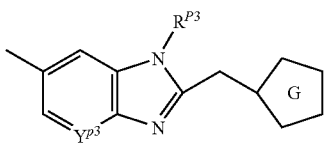

wherein $Y^{p3}$ is a carbon atom or a nitrogen atom, $R^{p3}$ is a $C_{1-6}$ alkyl group, and G is an azole ring having substituent(s).

In the present specification, $R^{p1}$ is a disubstituted amino group. As the "disubstituted amino group" for $R^{p1}$, for example, an amino group disubstituted by $C_{1-6}$ alkyl groups (e.g., dimethylamino) can be mentioned.

In the present specification, $R^{p2}$ is an optionally substituted aryl group, an optionally substituted heteroaryl group, or an optionally substituted fused ring group.

As the "aryl group" of the "optionally substituted aryl group" for $R^{p2}$, a $C_{6-14}$ aryl group (e.g., phenyl) can be mentioned. As the substituent that the aryl group may have, a halogen atom (e.g., fluorine atom) can be mentioned.

As the "optionally substituted heteroaryl group" for $R^{p2}$, a 6-membered heteroaryl group containing, as a ring constituting atom other than carbon atom, 1 to 4 hetero atoms of 1 or 2 kinds selected from a nitrogen atom, a sulfur atom and an oxygen atom (e.g., pyridine) can be mentioned. As the substituent that the heteroaryl group may have, groups similar to those that the "aryl group" of the "optionally substituted aryl group" for $R^{p2}$ optionally have can be mentioned.

As the "optionally substituted fused ring group" for $R^{p2}$, a fused ring of a ring constituting the heteroaryl group of the "optionally substituted heteroaryl group" for $R^{p2}$ and a benzene ring can be mentioned. As the substituent that the fused ring group may have, groups similar to those that the "aryl group" of the "optionally substituted aryl group" for $R^{p2}$ optionally have can be mentioned.

In the present specification, $W^{p2}$ is a bond or a spacer. As the "spacer" for $W^{p2}$, for example, a $C_{2-6}$ alkenylene group (e.g., vinylene) can be mentioned.

In the present specification, $Y^{p3}$ is a carbon atom or a nitrogen atom, $R^{p3}$ is a $C_{1-6}$ alkyl group, and G is an azole ring having substituent(s).

As the "azole ring" of the azole ring having substituent(s) for G, a 5-membered azole ring containing, as a ring constituting atom, a carbon atom and 1 or 2 nitrogen atoms (e.g., pyrazole, imidazole) can be mentioned. As the substituent that the azole ring has, for example, a $C_{6-14}$ aryl group (e.g., phenyl) and a 6-membered aromatic heterocyclic group (e.g., pyridyl), each optionally substituted by 1 to 3 halogen atoms (e.g., fluorine atom, chlorine atom), can be mentioned.

Specific examples of W include, for example, a group represented by the formula:

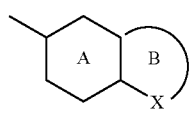

wherein
ring A is a 6-membered aromatic ring (e.g., benzene, pyridine);
X is a nitrogen atom or an oxygen atom; and
ring B is a 5- or 6-membered heterocycle (e.g., furan, pyrazole, thiazole, imidazole, oxazole, triazole, dihydrofuran, pyridine) optionally having substituent(s) at any position(s) other than X, optionally further having, as a hetero atom other than X, 1 to 3 nitrogen atoms or one sulfur atom or oxygen atom, the substituent that the ring B may have is
(1) a $C_{1-6}$ alkyl group (e.g., methyl);
(2) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group,
    (iii) a $C_{1-6}$ alkoxy group (e.g., methoxy),
    (iv) a $C_{1-6}$ alkylsulfonyl group (e.g., methylsulfonyl), etc.,
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from
    (i) a halogen atom
    (ii) a $C_{1-6}$ alkylthio group (e.g., methylthio)
    (iii) a $C_{1-6}$ alkylsulfinyl group (e.g., methylsulfinyl)
    (iv) a $C_{1-6}$ alkylsulfonyl group (e.g., methylsulfonyl)
    (v) a $C_{6-10}$ aryl group (e.g., phenyl), etc.,
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (h) a $C_{1-6}$ alkylsulfonyl group (e.g., methylsulfonyl, ethylsulfonyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc., (i) a carboxyl group,
(j) a $C_{1-6}$ alkoxy-carbonyl group (e.g., methoxycarbonyl),
(k) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
(l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle (e.g., methylaminosulfonyl, dimethylaminosulfonyl),
(m) a $C_{1-7}$ alkanoyl group (e.g., formyl group, $C_{1-6}$ alkylcarbonyl group (e.g., acetyl)),
(n) a $C_{1-6}$ alkylsulfonyloxy group (e.g., sulfonyloxy) optionally substituted by 1 to 3 halogen atoms (e.g., fluorine is atom),
(o) a $C_{1-6}$ alkylsulfonylamino group (e.g., methylsulfonylamino),
(p) a alkoxy-phosphoryl group (e.g., dimethoxyphosphoryl),
(q) a $C_{1-6}$ alkoxy-carbonyl group (e.g., methoxycarbonyl),
(r) a hydroxy group,
etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group;
(3) a heterocyclic group (e.g., pyridyl, oxazolyl, benzothienyl, quinolyl, piperidinyl) optionally substituted by 1 to 3 substituents selected from
  (a) a halogen atom (e.g., fluorine atom, chlorine atom),
  (b) a $C_{1-6}$ alkyl group (e.g., methyl),
  (c) a carboxyl group,
  (d) a $C_{1-6}$ alkoxy-carbonyl group (e.g., ethoxycarbonyl),
  (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
  (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl),
  (g) a $C_{6-14}$ aryl-carbonyl group (e.g., benzoyl),
  (h) a $C_{1-6}$ alkylsulfonyl group (e.g., methylsulfonyl),
  (i) a $C_{1-6}$ alkylsulfonylamino group,
  (j) a $C_{7-10}$ aralkyl group (e.g., benzyl),
  (k) a $C_{1-7}$ alkanoyl group (e.g., acetyl) etc.;
(4) a carboxyl group;
(5) a $C_{1-6}$ alkoxy-carbonyl group (e.g., ethoxycarbonyl);
(6) a heterocyclyl-carbonyl group (e.g., morpholinocarbonyl);
(7) a $C_{1-6}$ alkyl-carbamoyl group (e.g., ethylcarbamoyl) optionally substituted by 1 to 3 carbamoyl groups;
(8) an amino group;
(9) a cyano group;
(10) a $C_{1-7}$ alkanoyl group (e.g., formyl) etc., excluding
(2) a group represented by the formula:

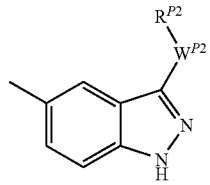

wherein each symbol is as defined above, or
a group represented by the formula:

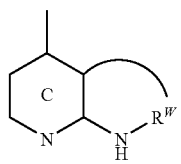

wherein
ring C is a 6-membered nitrogen-containing aromatic ring (e.g., pyridine, pyrimidine), and
R$^W$ is
(1) a hydrogen atom;
(2) a $C_{1-7}$ alkanoyl group (e.g., propionyl) optionally substituted by 1 to 3 substituents selected from
  (a) a heterocyclic group (e.g., morpholino, pyrrolidinyl),
  (b) a $C_{3-8}$ cycloalkylamino group (e.g., cyclopropylamino),
  (c) a $C_{6-14}$ aryl group (e.g., phenyl), etc.;
(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl);
(6) a $C_{7-16}$ aralkyl group (e.g., 3-phenylpropionyl);
(7) a $C_{6-10}$ aryl group (e.g., phenyl) optionally substituted by 1 to 3 substituents selected from
  (a) an optionally halogenated $C_{1-6}$ alkyl group (e.g., trifluoromethyl),
  (b) a $C_{1-6}$ alkoxy group (e.g., methoxy),
  (c) a $C_{1-6}$ alkylthio group (e.g., methylthio),
  (d) a $C_{1-6}$ alkylsulfinyl group (e.g., methylsulfinyl),
  (e) a $C_{1-6}$ alkylsulfonyl group (e.g., methylsulfonyl)
  (f) a halogen atom (e.g., fluorine), etc.;
(8) a $C_{1-6}$ alkyl-carbamoyl group (e.g., methylcarbamoyl) optionally substituted by a heterocyclic group (e.g., pyridyl);
(9) a heterocyclic group (e.g., pyridyl);
(10) a 5- or 6-membered heterocyclyl-$C_{1-6}$ alkyl group (e.g., pyridylmethyl) etc., or
optionally forms, together with the adjacent —NH— and a carbon atom on ring C, a nitrogen-containing 5- to 7-membered ring (e.g., pyrrole) optionally substituted by substituent(s) such as a $C_{7-16}$ aralkyl group (e.g., phenethyl) and the like.

$W^a$ in the formula (II) is a group represented by the formula:

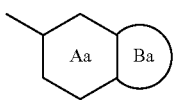

wherein
ring Aa is a 6-membered aromatic ring; and
ring Ba is a 5- or 6-membered heterocycle represented by

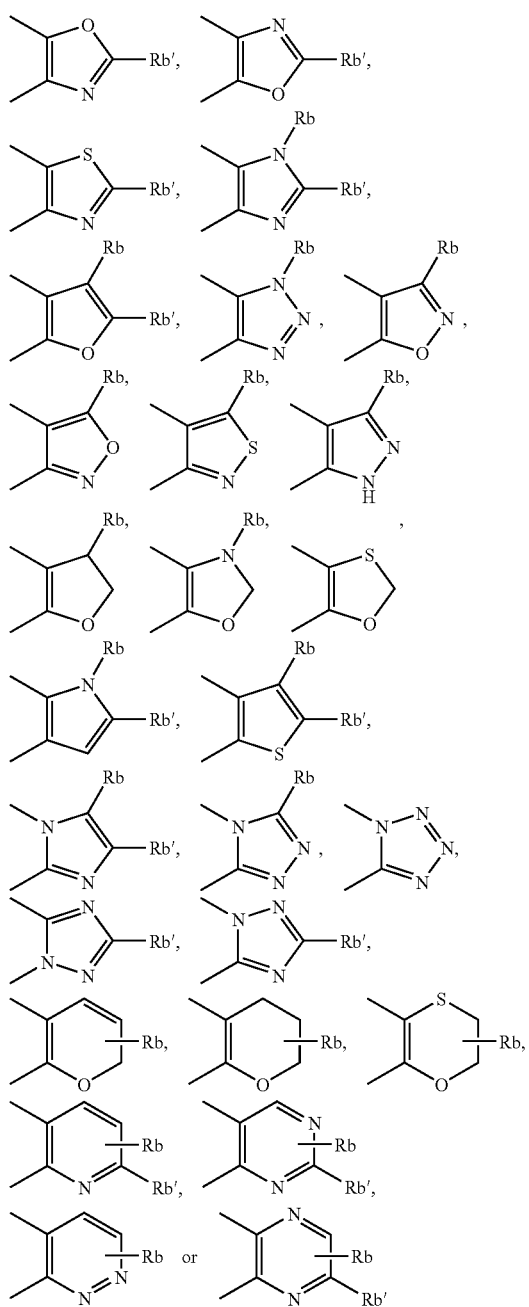

wherein Rb is a hydrogen atom, an optionally substituted hydrocarbon group, an optionally substituted heterocyclic group, an optionally substituted alkanoyl group, an optionally substituted carboxy group, an optionally substituted carbamoyl group, an optionally substituted heterocyclyl-carbonyl group, or an optionally substituted hydrocarbon-carbonyl group, and Rb' is a hydrogen atom, an amino group, or a monosubstituted amino group, excluding
(1) a group represented by the formula:

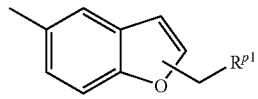

wherein $R^{p1}$ is a disubstituted amino group,
(2) a group represented by the formula:

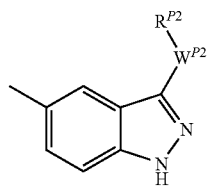

wherein $R^{p2}$ is an optionally substituted aryl group, an optionally substituted heteroaryl group, or an optionally substituted fused ring group, and $W^{p2}$ is a bond or a spacer, and
(3) a group represented by the formula:

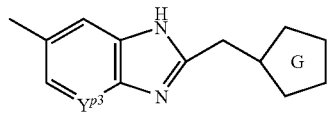

wherein $Y^{p3}$ is a carbon atom or a nitrogen atom, and G is an azole ring having substituent(s), or
a group represented by the formula:

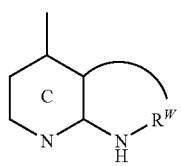

wherein
ring C is a nitrogen-containing 6-membered aromatic ring optionally having substituent(s), and
$R^W$ is a hydrogen atom, an acyl group, an optionally substituted hydrocarbon group, or an optionally substituted heterocyclic group, or optionally forms, together with the adjacent —NH— and a carbon atom on ring C, a nitrogen-containing 5- to 7-membered ring.

As the "6-membered aromatic ring" for ring Aa, those similar to the "6-membered aromatic ring" exemplified for ring A can be mentioned, such as benzene, pyridine, pyridazine, pyrazine and the like. Specific examples of ring Aa include benzene, pyridine and the like.

As the "monosubstituted amino group" for Rb', groups similar to the "monosubstituted amino group" exemplified as the substituent of the "5- or 6-membered heterocycle" for ring B can be mentioned.

As Rb, an optionally substituted $C_{1-6}$ alkyl group, an optionally substituted phenyl group, an optionally substituted pyridyl group, an optionally substituted piperidinyl group, or an optionally substituted benzoyl group is preferable.

Specific examples of Rb include
(1) a hydrogen atom;
(2) a $C_{1-6}$ alkyl group (e.g., methyl) optionally substituted by a hydroxy group;
(3) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group,
    (iii) a $C_{1-6}$ alkoxy group (e.g., methoxy),
    (iv) a $C_{1-6}$ alkylsulfonyl group (e.g., methylsulfonyl), etc.,
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from is (i) a halogen atom,
    (ii) a $C_{1-6}$ alkylthio group (e.g., methylthio),
    (iii) a $C_{1-6}$ alkylsulfinyl group (e.g., methylsulfinyl),
    (iv) a $C_{1-6}$ alkylsulfonyl group (e.g., methylsulfonyl),
    (v) a $C_{6-14}$ aryl group (e.g., phenyl), etc.,
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by a cyano group etc.,
  (h) a $C_{1-6}$ alkylsulfonyl group (e.g., methylsulfonyl, ethylsulfonyl, propylsulfonyl, isopropylsulfonyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (i) a carboxyl group,
  (j) a $C_{1-6}$ alkoxy-carbonyl group (e.g., methoxycarbonyl),
  (k) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
  (l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., methylaminosulfonyl, dimethylaminosulfonyl),
  (m) a $C_{1-7}$ alkanoyl group (e.g., formyl group, $C_{1-6}$ alkyl-carbonyl group (e.g., acetyl)),
  (n) a $C_{1-6}$ alkylsulfonyloxy group (e.g., sulfonyloxy) optionally substituted by 1 to 3 halogen atoms (e.g., fluorine atom),
  (o) a $C_{1-6}$ alkylsulfonylamino group (e.g., methylsulfonylamino),
  (p) a di-$C_{1-6}$ alkoxyphosphoryl group (e.g., dimethoxyphosphoryl),
  (q) a $C_{1-6}$ alkoxy-carbonyl group (e.g., methoxycarbonyl),
  (r) a hydroxy group
etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group;
(4) a heterocyclic group (e.g., pyridyl, oxazolyl, benzothienyl, quinolyl, piperidinyl) optionally substituted by 1 to 3 substituents selected from
  (a) a halogen atom (e.g., fluorine atom, chlorine atom),
  (b) a $C_{1-6}$ alkyl group (e.g., methyl),
  (c) a carboxyl group,
  (d) a $C_{1-6}$ alkoxy-carbonyl group (e.g., ethoxycarbonyl),
  (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
  (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl),
  (g) a $C_{6-14}$ aryl-carbonyl group (e.g., benzoyl),
  (h) a $C_{1-6}$ alkylsulfonyl group (e.g., methylsulfonyl),
  (i) a $C_{1-6}$ alkylsulfonylamino group,
  (j) a $C_{7-10}$ aralkyl group (e.g., benzyl),
  (k) a $C_{1-7}$ alkanoyl group (e.g., acetyl),
  (l) a $C_{1-6}$ alkoxy-carbonyl group (e.g., ethoxycarbonyl), etc.;
(5) a carboxyl group;
(6) a $C_{1-6}$ alkoxy-carbonyl group (e.g., ethoxycarbonyl);
(7) a heterocyclyl-carbonyl group (e.g., morpholinocarbonyl);
(8) a $C_{1-6}$ alkyl-carbamoyl group (e.g., ethylcarbamoyl) optionally substituted by 1 to 3 carbamoyl groups;
(9) a cyano group;
(10) a $C_{1-7}$ alkanoyl group (e.g., formyl);
and the like.

Specific examples of Rb' include
(a) a hydrogen atom;
(b) an amino group;
and the like.

A group represented by the formula:

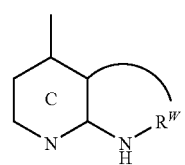

Wherein each symbol is as defined above, for $W^a$ is a group similar to a group represented by the formula:

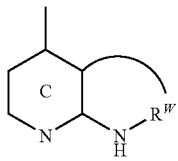

wherein each symbol is as defined above, for W.

Specific examples of $W^a$ include a group represented by the formula:

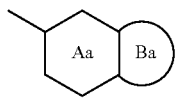

wherein
ring Aa is a 6-membered aromatic ring (e.g., benzene, pyridine); and
ring Ba is

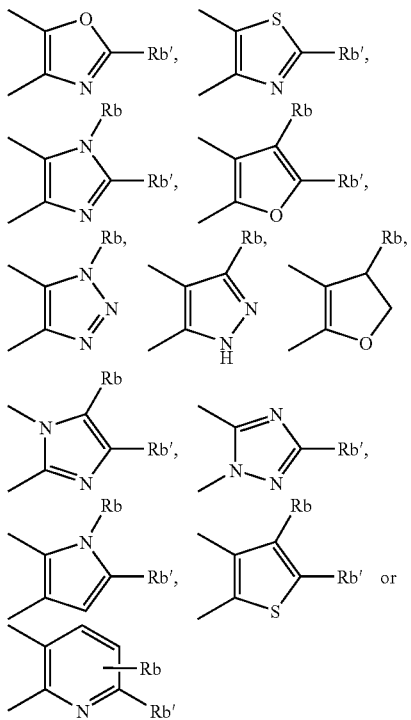

wherein Rb is
(1) a hydrogen atom;
(2) a $C_{1-6}$ alkyl group (e.g., methyl) optionally substituted by a hydroxy group;
(3) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group,
    (iii) a $C_{1-6}$ alkoxy group (e.g., methoxy),
    (iv) a $C_{1-6}$ alkylsulfonyl group (e.g., methylsulfonyl), etc.,
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from
    (i) a halogen atom,
    (ii) a $C_{1-6}$ alkylthio group (e.g., methylthio),
    (iii) a $C_{1-6}$ alkylsulfinyl group (e.g., methylsulfinyl),
    (iv) a $C_{1-6}$ alkylsulfonyl group (e.g., methylsulfonyl),
    (v) a $C_{6-14}$ aryl group (e.g., phenyl), etc.,
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by cyano, etc.,
  (h) a $C_{1-6}$ alkylsulfonyl group (e.g., methylsulfonyl, ethylsulfonyl, propylsulfonyl, isopropylsulfonyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (i) a carboxyl group,
  (j) a $C_{1-6}$ alkoxy-carbonyl group (e.g., methoxycarbonyl),
  (k) a group represented by —CO—$NR^sR^t$ wherein $R^s$ and $R^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
  (l) a group represented by —$SO_2$—$NR^sR^t$ wherein $R^s$ and $R^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a is sulfur atom (e.g., methylaminosulfonyl, dimethylaminosulfonyl),
  (m) a $C_{1-7}$ alkanoyl group (e.g., formyl group, $C_{1-6}$ alkyl-carbonyl group (e.g., acetyl)),
  (n) a $C_{1-6}$ alkylsulfonyloxy group optionally substituted by 1 to 3 halogen atoms (e.g., fluorine atom) (e.g., trifluoromethylsulfonyloxy),
  (o) a $C_{1-6}$ alkylsulfonylamino group (e.g., methylsulfonylamino),
  (p) a di-$C_{1-6}$ alkoxyphosphoryl group (e.g., dimethoxyphosphoryl),
  (q) a $C_{1-6}$ alkoxy-carbonyl group (e.g., methoxycarbonyl),
  (r) a hydroxy group
etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group;
(4) a heterocyclic group (e.g., pyridyl, oxazolyl, benzothienyl, quinolyl, piperidinyl) optionally substituted by 1 to 3 substituents selected from (a) a halogen atom (e.g., fluorine atom, chlorine atom),
(b) a $C_{1-6}$ alkyl group (e.g., methyl),
(c) a carboxyl group,
(d) a $C_{1-6}$ alkoxy-carbonyl group (e.g., ethoxycarbonyl),
(e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
(f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl),
(g) a $C_{6-14}$ aryl-carbonyl group (e.g., benzoyl),
(h) a $C_{1-6}$ alkylsulfonyl group (e.g., methylsulfonyl),
(i) a $C_{1-6}$ alkylsulfonylamino group,
(j) a $C_{7-10}$ aralkyl group (e.g., benzyl),
(k) a $C_{1-7}$ alkanoyl group (e.g., acetyl), etc.;
(5) a carboxyl group;
(6) a $C_{1-6}$ alkoxy-carbonyl group (e.g., ethoxycarbonyl);
(7) a heterocyclyl-carbonyl group (e.g., morpholinocarbonyl);
(8) a $C_{1-6}$ alkyl-carbamoyl group (e.g., ethylcarbamoyl) optionally substituted by 1 to 3 carbamoyl groups;
(9) a cyano group;
(10) a $C_{1-7}$ alkanoyl group (e.g., formyl);
and the like, and
Rb' is
(1) a hydrogen atom;
(2) an amino group;
and the like, excluding
(2) a group represented by the formula:

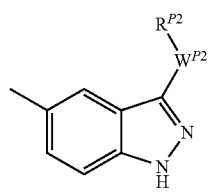

wherein each symbol is as defined above, or
a group represented by the formula:

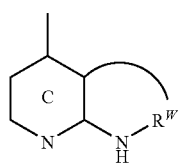

wherein
ring C is a 6-membered nitrogen-containing aromatic ring (e.g., pyridine), and R$^W$ is
(1) a hydrogen atom;
(2) a $C_{1-7}$ alkanoyl group (e.g., propionyl) optionally substituted by 1 to 3 substituents selected from
    (a) a heterocyclic group (e.g., morpholino, pyrrolidinyl),
    (b) a $C_{3-8}$ cycloalkylamino group (e.g., cyclopropylamino),
    (c) a $C_{6-14}$ aryl group (e.g., phenyl), etc.;
(4) a $C_{1-6}$ alkoxy-carbonyl group (e.g., tert-butoxycarbonyl);
(5) a $C_{7-16}$ aralkyloxy-carbonyl group (e.g., benzyloxycarbonyl);
(6) a $C_{7-16}$ aralkyl-carbamoyl group (e.g., benzylcarbamoyl);
(7) a $C_{7-16}$ aralkyl group (e.g., 3-phenylpropionyl);
and the like, or optionally forms, together with the adjacent —NH— and a carbon atom on ring C, a nitrogen-containing 5- to 7-membered ring (e.g., pyrrole).

As compound (I), a compound wherein, when W is a group represented by the formula:

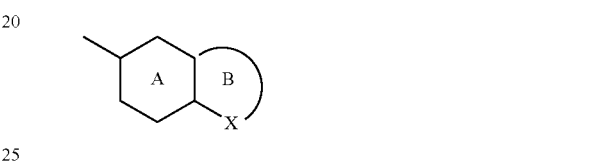

wherein each symbol is as defined above,
ring B is a 5- or 6-membered heterocycle represented by

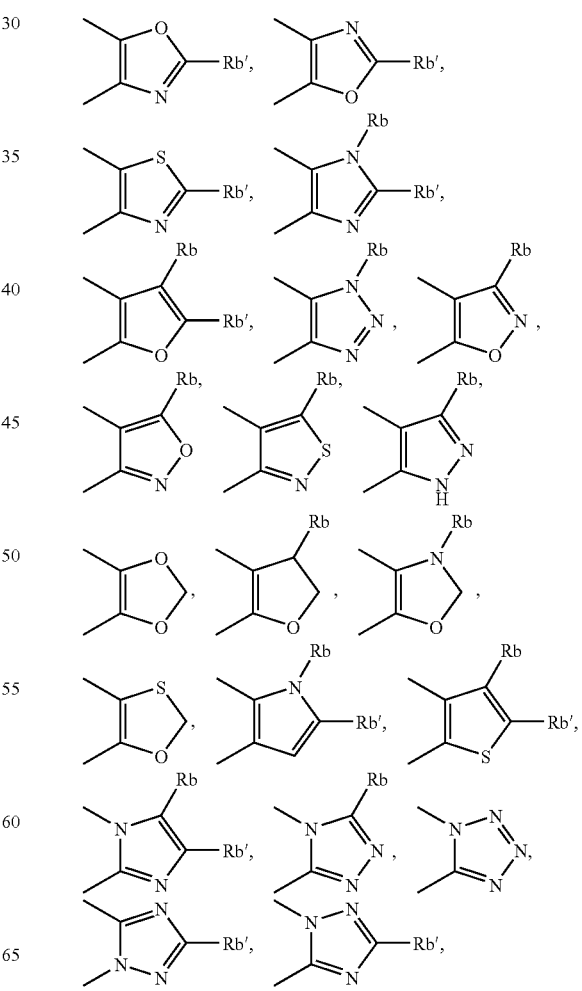

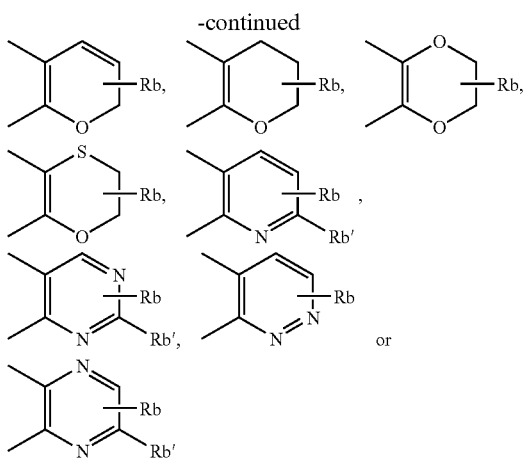

wherein each symbol is as defined above, is preferable. Of these,
(1) a compound wherein
R¹ is a group represented by the formula: $R^{1a}$—Y—
wherein
Y is a bond, a sulfur atom, or —$NR^y$— ($R^y$ is a hydrogen atom, or a lower alkyl group),
$R^{1a}$ is a hydrogen atom, or an optionally fluorinated $C_{1-2}$ alkyl group, and
Rb is an optionally substituted phenyl group, or an optionally substituted 5- or 6-membered heterocyclic group;
(2) a compound wherein
R¹ is a group represented by the formula: $R^{1a}$—Y—
wherein
Y is a bond, a sulfur atom, or —$NR^y$— ($R^y$ is a hydrogen atom, or a lower alkyl group),
$R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and
Rb is a hydrogen atom or a lower alkyl group;
(3) a compound wherein
R¹ is a group represented by the formula: $R^{1a}$—Y—
wherein
Y is a bond, a sulfur atom, or —$NR^y$— ($R^y$ is a hydrogen atom, or a lower alkyl group),
$R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and
Rb is an optionally substituted phenyl group, or an optionally substituted 5- or 6-membered heterocyclic group;
and the like are more preferable.

Specific examples of compound (I) include the following compounds.

[Compound (I)-A]
A compound wherein
R¹ is
(1) a hydrogen atom;
(2) a $C_{3-8}$ cycloalkyl group (e.g., cyclopropyl);
(3) a $C_{1-10}$ alkoxy group (e.g., methoxy) optionally substituted by a substituent selected from
   (a) a carboxyl group,
   (b) a $C_{1-6}$ alkoxy-carbonyl group (e.g., ethoxycarbonyl),
   (c) a N—$C_{1-6}$ alkyl-N—$C_{1-6}$ alkoxy-carbamoyl group (e.g., N-methyl-N-methoxycarbamoyl), etc.;
(4) a $C_{7-16}$ aralkyloxy group (e.g., benzyloxy) optionally m substituted by 1 to 3 halogen atoms (e.g., fluorine atom);
(5) a $C_{1-6}$ alkylsulfonyl group (e.g., methylsulfonyl);
(6) a $C_{1-6}$ alkylsulfinyl group (e.g., methylsulfinyl);
(7) a hydroxy group;
(8) a $C_{1-7}$ alkanoyl group (e.g., acetyl);
(9) a 5- or 6-membered heterocyclic group (e.g., 5- or 6-membered nonaromatic heterocyclic group such as piperazino, morpholino and the like), or
(10) a group represented by the formula: $R^{1a}$—Y—
wherein
Y is a bond, a sulfur atom, or —$NR^y$— ($R^y$ is a hydrogen atom, or a lower alkyl group (e.g., $C_{1-6}$ alkyl group such as methyl and the like)), and
$R^{1a}$ is
(1') a hydrogen atom,
(2') a $C_{1-6}$ alkyl group (e.g., $C_{1-3}$ alkyl group such as methyl, ethyl, propyl, isopropyl and the like (preferably $C_{1-2}$ alkyl group)) optionally substituted by 1 to 3 substituents selected from
   (a) a halogen atom (e.g., fluorine atom),
   (b) a carboxyl group,
   (c) a $C_{1-6}$ alkoxy-carbonyl group (e.g., ethoxycarbonyl),
   (d) a N—$C_{1-6}$ alkyl-N—$C_{1-6}$ alkoxy-carbamoyl group (e.g., N-methyl-N-methoxycarbamoyl),
   (e) a $C_{6-14}$ aryloxy group (e.g., phenoxy) optionally substituted by 1 to 3 substituents selected from
      (i) a halogen atom (e.g., fluorine atom),
      (ii) a cyano group, and
      (iii) a $C_{1-6}$ alkoxy-carbonyl group (e.g., methoxycarbonyl),
   (f) an amino group optionally substituted by 1 or 2 substituents selected from a mono- or di-$C_{6-14}$ aryl group optionally substituted by 1 to 3 halogen atoms (e.g., fluorine atom), and a $C_{1-6}$ alkyl group (e.g., phenylamino, methylamino),
   (g) a heterocyclyl-carbonyl group (e.g., thienylcarbonyl, tetrahydrobenzo[c]azepinylcarbonyl, tetrahydroisoquinolinylcarbonyl) optionally substituted by 1 to 3 $C_{1-6}$ alkyl groups (e.g., methyl),
   (h) a $C_{6-14}$ arylthio group (e.g., phenylthio, 2-naphthylthio) optionally substituted by 1 to 3 substituents selected from a halogen atom (e.g., fluorine atom, chlorine atom) and a cyano group,
   (i) a $C_{6-14}$ aryl-sulfinyl group (e.g., phenylsulfinyl) optionally substituted by 1 to 3 halogen atoms (e.g., fluorine atom),
   (j) a $C_{6-14}$ aryl-sulfonyl group (e.g., phenylsulfonyl) optionally substituted by 1 to 3 halogen atoms (e.g., fluorine atom),
   (k) a $C_{1-6}$ alkoxy-carbonyl group (e.g., ethoxycarbonyl),
   (l) a $C_{3-8}$ cycloalkyl group (e.g., cyclopropyl),
   (m) a heterocyclic group (e.g., dihydrobenzofuranyl, benzofuranyl, pyridyl, thiazolyl, benzothiazolyl, imidazo[1,2-a]pyridyl, oxodihydropyridinyl, oxo-5H-thiazolo[3,2-a]pyrimidinyl, oxodihydrothieno[3,2-d]pyrimidinyl, imidazolyl, oxazolyl, morpholinyl, oxodihydrothieno[2,3-d]pyrimidinyl, imidazo[1,2-a]pyrimidinyl, dioxodihydroindolyl, oxadiazolyl) optionally substituted by substituent(s) selected from
      (i) a $C_{7-16}$ aralkyloxy group (e.g., benzyloxy),
      (ii) a $C_{1-6}$ alkyl group (e.g., methyl, propyl) optionally substituted by 1 to 3 $C_{3-8}$ cycloalkyl groups (e.g., cyclopropyl),
      (iii) a $C_{2-6}$ alkynyl group (e.g., 2-propynyl), (iv) a $C_{2-6}$ alkenyl group (e.g., vinyl) optionally substituted by a $C_{6-14}$ aryl group (e.g., phenyl) optionally substituted by 1 to 3 halogen atoms (e.g., fluorine atom),
(v) a $C_{1-6}$ alkoxy group (e.g., methoxy),
(vi) a heterocyclic group (e.g., thienyl), and
(vii) a $C_{6-14}$ aryl group (e.g., phenyl) optionally substituted by 1 to 3 $C_{1-6}$ alkoxy groups (e.g., methoxy),
(n) a carbamoyl group,
(o) a mono- or di-$C_{1-6}$ alkyl-carbamoyl group (e.g., diethylcarbamoyl), and
(p) a $C_{6-14}$ aryl group (e.g., a $C_{6-14}$ aryl group such as phenyl, 1-naphthyl, 2-naphthyl and the like) optionally substituted by substituent(s) selected from
  (i) a halogen atom (e.g., fluorine atom, chlorine atom),
  (ii) a cyano group,
  (iii) a heterocyclic group (e.g., 1-pyrrolyl),
  (iv) a $C_{1-6}$ alkyl group (e.g., methyl, tert-butyl) optionally substituted by 1 to 3 substituents selected from a halogen atom (e.g., fluorine atom) and a hydroxy group,
  (v) a $C_{1-6}$ alkoxy group (e.g., methoxy) optionally substituted by 1 to 3 halogen atoms (e.g., fluorine atom) etc.,
  (vi) a mono- or di-($C_{1-7}$ alkanoyl)-amino group (e.g., acetylamino),
  (vii) a $C_{1-6}$ alkylsulfonyl group (e.g., methylsulfonyl),
  (viii) a carboxyl group,
  (iv) a $C_{1-6}$ alkoxy-carbonyl group (e.g., methoxycarbonyl),
  (x) a heterocyclyl-carbonyl group (e.g., piperazinylcarbonyl, morpholinocarbonyl) optionally substituted by 1 to 3 $C_{1-6}$ alkyl groups (e.g., methyl),
  (xi) a $C_{1-7}$ alkanoyl group (e.g., acetyl),
  (xii) a $C_{1-6}$ alkylthio group (e.g., methylthio),
  (xiii) a $C_{1-6}$ alkylsulfinyl group (e.g., methylsulfinyl), etc.,
(q) a $C_{1-7}$ alkanoyloxy group (e.g., acetyloxy),
(r) a hydroxy group,
(s) a $C_{1-6}$ alkylthio group (e.g., methylthio),
(t) a $C_{1-6}$ alkylsulfinyl group (e.g., methylsulfinyl),
(u) a $C_{1-6}$ alkylsulfonyl group (e.g., methylsulfonyl),
(v) a $C_{1-6}$ alkoxy group (e.g., methoxy),
(w) a group represented by the formula:

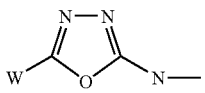

wherein each symbol is as defined above; etc., or
(3') a cyano group; and
W is a group represented by the formula:

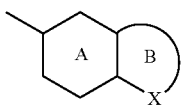

wherein
ring A is benzene or pyridine;
X is a nitrogen atom or an oxygen atom; and
ring B is furan, pyrazole, thiazole, imidazole, oxazole, triazole, dihydrofuran or pyridine, each optionally having 1 to 3 substituents selected from (1) a $C_{1-6}$ alkyl group (e.g., methyl) optionally substituted by a hydroxy group;
(2) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group, and
    (iii) a $C_{1-6}$ alkoxy group (e.g., methoxy),
    (iv) a $C_{1-6}$ alkylsulfonyl group (e.g., methylsulfonyl),
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from
    (i) a halogen atom,
    (ii) a $C_{1-6}$ alkylthio group (e.g., methylthio)
    (iii) a $C_{1-6}$ alkylsulfinyl group (e.g., methylsulfinyl)
    (iv) a $C_{1-6}$ alkylsulfonyl group (e.g., methylsulfonyl) and
    (v) a $C_{6-14}$ aryl group (e.g., phenyl),
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (h) a $C_{1-6}$ alkylsulfonyl group (e.g., methylsulfonyl, ethylsulfonyl, propylsulfonyl, isopropylsulfonyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (i) a carboxyl group,
  (j) a $C_{1-6}$ alkoxy-carbonyl group (e.g., methoxycarbonyl),
  (k) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
  (l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., methylaminosulfonyl, dimethylaminosulfonyl),
  (m) a $C_{1-7}$ alkanoyl group (e.g., formyl group, $C_{1-6}$ alkyl-carbonyl group (e.g., acetyl)),
  (n) a $C_{1-6}$ alkylsulfonyloxy group (e.g., sulfonyloxy) optionally substituted by 1 to 3 halogen atoms (e.g., fluorine atom),
  (o) a $C_{1-6}$ alkylsulfonylamino group (e.g., methylsulfonylamino),
  (p) a di-$C_{1-6}$ alkoxyphosphoryl group (e.g., dimethoxyphosphoryl),
  (q) a $C_{1-6}$ alkoxy-carbonyl group (e.g., methoxycarbonyl),
  (r) a hydroxy group,
etc., and optionally fused with a 5- or 6-membered heterocyclic group (e.g., dihydrothiophene, thiophene, pyridine)

optionally substituted by 1 to 4 substituents selected from a $C_{1-6}$ alkyl group (e.g., methyl) and an oxo group [examples of such "$C_{6-14}$ aryl group fused with substituted 5- or 6-membered heterocyclic group" include dimethyldihydrothiophene, dimethyltetrahydrothiophene 1-oxide, and dimethyldihydrothiophene 1,1-dioxide];

(3) a heterocyclic group (e.g., 5- or 6-membered heterocyclic group such as pyridyl, piperidyl, oxazolyl, pyrazolyl and the like) optionally substituted by 1 to 3 substituents selected from
- (a) a halogen atom (e.g., fluorine atom, chlorine atom),
- (b) a $C_{1-6}$ alkyl group (e.g., methyl) optionally substituted by a $C_{1-6}$ alkoxy group (e.g., methoxy),
- (c) a carboxyl group,
- (d) a $C_{1-6}$ alkoxy-carbonyl group (e.g., ethoxycarbonyl),
- (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
- (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl)
- (g) a $C_{6-14}$ aryl-carbonyl group (e.g., benzoyl),
- (h) a $C_{1-6}$ alkylsulfonyl group (e.g., methylsulfonyl),
- (i) a $C_{1-6}$ alkylsulfonylamino group,
- (j) a $C_{7-10}$ aralkyl group (e.g., benzyl) optionally substituted by cyano, an optionally halogenated $C_{1-6}$ alkyl group (e.g., trifluoromethyl) or a halogen atom (e.g., fluorine),
- (k) a $C_{1-7}$ alkanoyl group (e.g., acetyl),
- (l) a 5- or 6-membered heterocyclyl-$C_{1-6}$ alkyl group (e.g., pyridylmethyl), etc.;

(4) a carboxyl group;
(5) a $C_{1-8}$ alkoxy-carbonyl group (e.g., ethoxycarbonyl);
(6) a heterocyclyl-carbonyl group (e.g., morpholinocarbonyl);
(7) a $C_{1-8}$ alkyl-carbamoyl group (e.g., ethylcarbamoyl) optionally substituted by 1 to 3 carbamoyl groups;
(8) an amino group;
(9) a cyano group; and
(10) a $C_{1-7}$ alkanoyl group (e.g., formyl);
excluding
(2) a group represented by the formula:

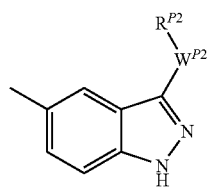

wherein each symbol is as defined above, or a group represented by the formula:

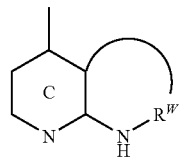

wherein
ring C is pyridine, and
R$^W$ is
(1) a hydrogen atom;
(2) a $C_{1-7}$ alkanoyl group (e.g., propionyl) optionally substituted by 1 to 3 substituents selected from
- (a) a heterocyclic group (e.g., morpholino, pyrrolidinyl),
- (b) a $C_{3-8}$ cycloalkylamino group (e.g., cyclopropylamino),
and
- (c) a $C_{6-14}$ aryl group (e.g., phenyl);

(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl);
(6) a $C_{7-16}$ aralkyl group (e.g., 3-phenylpropionyl); or
(7) a $C_{6-10}$ aryl group (e.g., phenyl) optionally substituted by 1 to 3 substituents selected from
- (a) optionally halogenated $C_{1-6}$ alkyl (e.g., trifluoromethyl),
- (b) a $C_{1-6}$ alkoxy group (e.g., methoxy),
- (c) a $C_{1-6}$ alkylthio group (e.g., methylthio)
- (d) a $C_{1-6}$ alkylsulfinyl group (e.g., methylsulfinyl),
- (e) a $C_{1-6}$ alkylsulfonyl group (e.g., methylsulfonyl)
- (f) a halogen atom (e.g., fluorine), etc.;

(8) a $C_{1-6}$ alkyl-carbamoyl group (e.g., methylcarbamoyl) optionally substituted by a heterocyclic group (e.g., pyridyl);
(9) a heterocyclic group (e.g., pyridyl);
(10) a 5- or 6-membered heterocyclyl-$C_{1-6}$ alkyl group (e.g., pyridylmethyl)
and the like, or optionally forms, together with the adjacent —NH— and a carbon atom on ring C, a nitrogen-containing 5- to 7-membered ring (e.g., pyrrole) optionally substituted by substituent(s) such as a $C_{7-16}$ aralkyl group (e.g., phenethyl) and the like.

[Compound (I)-A']
A compound wherein
R$^1$ is
(1) a hydrogen atom;
(2) a $C_{3-8}$ cycloalkyl group (e.g., cyclopropyl);
(3) a $C_{1-10}$ alkoxy group (e.g., methoxy) optionally substituted by a substituent selected from
- (a) a carboxyl group,
- (b) a $C_{1-6}$ alkoxy-carbonyl group (e.g., ethoxycarbonyl), and
- (c) a N—$C_{1-6}$ alkyl-N—$C_{1-6}$ alkoxy-carbamoyl group (e.g., N-methyl-N-methoxycarbamoyl);

(4) a $C_{7-16}$ aralkyloxy group (e.g., benzyloxy) optionally substituted by 1 to 3 halogen atoms (e.g., fluorine atom);
(5) a $C_{1-6}$ alkylsulfonyl group (e.g., methylsulfonyl); or
(6) a group represented by the formula: R$^{1a}$—Y— wherein
Y is a bond, a sulfur atom, or —NH—, and
$R^{1a}$ is
(1') a hydrogen atom, or
(2') a $C_{1-6}$ alkyl group (e.g., a $C_{1-3}$ alkyl group such as methyl, ethyl, propyl and the like (preferably a $C_{1-2}$ alkyl group)) optionally substituted by 1 to 3 substituents selected from
(a) a halogen atom (e.g., fluorine atom),
(b) a carboxyl group,
(c) a $C_{1-6}$ alkoxy-carbonyl group (e.g., ethoxycarbonyl),
(d) a N—$C_{1-6}$ alkyl-N—$C_{1-6}$ alkoxy-carbamoyl group (e.g., N-methyl-N-methoxycarbamoyl),
(e) a $C_{6-14}$ aryloxy group (e.g., phenoxy) optionally substituted by 1 to 3 substituents selected from
  (i) a halogen atom (e.g., fluorine atom),
  (ii) a cyano group, and
  (iii) a $C_{1-6}$ alkoxy-carbonyl group (e.g., methoxycarbonyl),
(f) a mono- or di-$C_{6-14}$ aryl-amino group (e.g., phenylamino) optionally substituted by 1 to 3 halogen atoms (e.g., fluorine atom),
(g) a heterocyclyl-carbonyl group (e.g., thienylcarbonyl, tetrahydrobenzo[c]azepinylcarbonyl, tetrahydroisoquinolinylcarbonyl) optionally substituted by 1 to 3 $C_{1-6}$ alkyl groups (e.g., methyl),
(h) a $C_{6-14}$ arylthio group (e.g., phenylthio, 2-naphthylthio) optionally substituted by 1 to 3 substituents selected from a halogen atom (e.g., fluorine atom, chlorine atom) and a cyano group,
(i) a $C_{6-14}$ aryl-sulfinyl group (e.g., phenylsulfinyl) optionally substituted by 1 to 3 halogen atoms (e.g., fluorine atom),
(j) a $C_{6-14}$ aryl-sulfonyl group (e.g., phenylsulfonyl) optionally substituted by 1 to 3 halogen atoms (e.g., fluorine atom),
(k) a $C_{1-6}$ alkoxy-carbonyl group (e.g., ethoxycarbonyl),
(l) a $C_{3-8}$ cycloalkyl group (e.g., cyclopropyl),
(m) a heterocyclic group (e.g., dihydrobenzofuranyl, benzofuranyl, pyridyl, thiazolyl, benzothiazolyl, imidazo[1,2-a]pyridyl, oxodihydropyridinyl, oxo-5H-thiazolo[3,2-a]pyrimidinyl, oxodihydrothieno[3,2-d]pyrimidinyl, imidazolyl, oxazolyl, morpholinyl, oxodihydrothieno[2,3-d]pyrimidinyl, imidazo[1,2-a]pyrimidinyl, dioxodihydroindolyl, oxadiazolyl) optionally substituted by substituent(s) selected from
  (i) a $C_{7-16}$ aralkyloxy group (e.g., benzyloxy),
  (ii) a alkyl group (e.g., methyl, propyl) optionally substituted by 1 to 3 $C_{3-8}$ cycloalkyl groups (e.g., cyclopropyl),
  (iii) a $C_{2-6}$ alkynyl group (e.g., 2-propynyl),
  (iv) a $C_{2-6}$ alkenyl group (e.g., vinyl) optionally substituted by a $C_{6-14}$ aryl group (e.g., phenyl) optionally substituted by 1 to 3 halogen atoms (e.g., fluorine atom),
  (v) a $C_{1-6}$ alkoxy group (e.g., methoxy),
  (vi) a heterocyclic group (e.g., thienyl), and
  (vii) a $C_{6-14}$ aryl group (e.g., phenyl) optionally substituted by 1 to 3 $C_{1-6}$ alkoxy groups (e.g., methoxy),
(n) a carbamoyl group,
(o) a mono- or di-$C_{1-6}$ alkyl-carbamoyl group (e.g., diethylcarbamoyl), and
(p) a $C_{6-14}$ aryl group (e.g., $C_{6-10}$ aryl group such as phenyl, 1-naphthyl, 2-naphthyl and the like) optionally substituted by substituent(s) selected from
  (i) a halogen atom (e.g., fluorine atom, chlorine atom),
  (ii) a cyano group,
  (iii) a heterocyclic group (e.g., 1-pyrrolyl),
  (iv) a $C_{1-6}$ alkyl group (e.g., methyl, tert-butyl) optionally substituted by 1 to 3 substituents selected from a halogen atom (e.g., fluorine atom) and a hydroxy group,
  (v) a $C_{1-6}$ alkoxy group (e.g., methoxy) optionally substituted by 1 to 3 halogen atoms (e.g., fluorine atom) etc.,
  (vi) a mono- or di-($C_{1-6}$ alkyl-carbonyl)-amino group (e.g., acetylamino),
  (vii) a $C_{1-6}$ alkylsulfonyl group (e.g., methylsulfonyl),
  (viii) a carboxyl group,
  (iv) a $C_{1-6}$ alkoxy-carbonyl group (e.g., methoxycarbonyl),
  (x) a heterocyclyl-carbonyl group (e.g., piperazinylcarbonyl, morpholinocarbonyl) optionally substituted by 1 to 3 $C_{1-6}$ alkyl groups (e.g., methyl), and
  (xi) a $C_{1-6}$ alkyl-carbonyl group (e.g., acetyl); and W is a group represented by the formula:

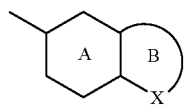

wherein
ring A is benzene or pyridine;
X is a nitrogen atom or an oxygen atom; and
ring B is furan, pyrazole, thiazole, imidazole, oxazole, triazole, dihydrofuran or pyridine, each optionally having 1 to 3 substituents selected from
(1) a $C_{1-6}$ alkyl group (e.g., methyl);
(2) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group, and
    (iii) a $C_{1-6}$ alkoxy group (e.g., methoxy),
  (d) a di-$C_{1-6}$ alkyl-amino group (e.g., dimethylamino),
  (e) a $C_{1-6}$ alkoxy group (e.g., methoxy) optionally substituted by 1 to 3 halogen atoms,
  (f) a $C_{1-6}$ alkylthio group (e.g., methylthio),
  (g) a $C_{1-6}$ alkylsulfinyl group (e.g., methylsulfinyl),
  (h) a $C_{1-6}$ alkylsulfonyl group (e.g., methylsulfonyl),
  (i) a carboxyl group,
  (j) a $C_{1-6}$ alkoxy-carbonyl group (e.g., methoxycarbonyl),
  (k) a carbamoyl group, and
  (l) a formyl group;
(3) a heterocyclic group (e.g., pyridyl);
(4) a carboxyl group;
(5) a $C_{1-6}$ alkoxy-carbonyl group (e.g., ethoxycarbonyl);
(6) a heterocyclyl-carbonyl group (e.g., morpholinocarbonyl);
(7) a $C_{1-6}$ alkyl-carbamoyl group (e.g., ethylcarbamoyl) optionally substituted by 1 to 3 carbamoyl groups; and
(8) an amino group;

excluding
(2) a group represented by the formula:

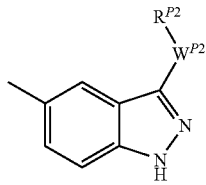

wherein each symbol is as defined above, or
a group represented by the formula:

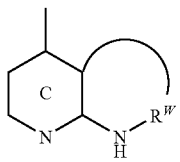

wherein
ring C is pyridine, and
$R^W$ is
(1) a hydrogen atom;
(2) a $C_{1-6}$ alkyl-carbonyl group (e.g., propionyl) optionally substituted by 1 to 3 substituents selected from
 (a) a heterocyclic group (e.g., morpholino, pyrrolidinyl),
 (b) a $C_{3-8}$ cycloalkylamino group (e.g., cyclopropylamino), and
 (c) a $C_{6-14}$ aryl group (e.g., phenyl);
(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl); or
(6) a $C_{7-16}$ aralkyl group (e.g., 3-phenylpropionyl);
or optionally forms, together with the adjacent —NH— and a carbon atom on ring C, a nitrogen-containing 5- to 7-membered ring (e.g., pyrrole).
As compound (II), when $W^a$ is a group represented by the formula:

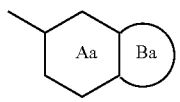

wherein each symbol is as defined above,
a compound wherein ring Aa is benzene or pyridine;
a compound wherein Rb is a hydrogen atom, an optionally substituted hydrocarbon group, or an optionally substituted heterocyclic group, and
Rb' is a hydrogen atom, an amino group, or a monosubstituted amino group;
and the like are preferable. Of these,
(1) a compound wherein $R^1$ is a group represented by the formula: $R^{1a}$—Y—
wherein
Y is a bond, a sulfur atom, or —$NR^y$— ($R^y$ is a hydrogen atom, or a lower alkyl group), and
$R^{1a}$ is a hydrogen atom, or an optionally fluorinated $C_{1-2}$ alkyl group, and Rb is an optionally substituted phenyl group, or an optionally substituted 5- or 6-membered heterocyclic group;
(2) a compound wherein $R^1$ is a group represented by the formula: $R^{1a}$—Y—
wherein
Y is a bond, a sulfur atom, or —$NR^y$— ($R^y$ is a hydrogen atom, or a lower alkyl group), and
$R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and
Rb is a hydrogen atom or a lower alkyl group;
(3) a compound wherein $R^1$ is a group represented by the formula: $R^{1a}$—Y—
wherein
Y is a bond, a sulfur atom, or —$NR^y$— ($R^y$ is a hydrogen atom, or a lower alkyl group), and
$R^{1a}$ is a $C_{1-2}$ alkyl group optionally substituted by one or more substituents selected from an optionally substituted carbamoyl group, an optionally substituted $C_{6-10}$ aryl group and an optionally substituted 5- to 10-membered aromatic heterocyclic group, and
Rb is an optionally substituted phenyl group, or an optionally substituted 5- or 6-membered heterocyclic group; and the like are more preferable.
Specific examples of compound (II) include the following compounds.
[Compound (II)-A]
A compound wherein $R^1$ is
(1) a hydrogen atom;
(2) a $C_{3-8}$ cycloalkyl group (e.g., cyclopropyl);
(3) a $C_{1-10}$ alkoxy group (e.g., methoxy) optionally substituted by a substituent selected from
 (a) a carboxyl group,
 (b) a $C_{1-6}$ alkoxy-carbonyl group (e.g., ethoxycarbonyl), and
 (c) a N—$C_{1-6}$ alkyl-N—$C_{1-6}$ alkoxy-carbamoyl group (e.g., N-methyl-N-methoxycarbamoyl);
(4) a $C_{7-16}$ aralkyloxy group (e.g., benzyloxy) optionally substituted by 1 to 3 halogen atoms (e.g., fluorine atom);
(5) a $C_{1-6}$ alkylsulfonyl group (e.g., methylsulfonyl);
(6) a $C_{1-6}$ alkylsulfinyl group (e.g., methylsulfinyl);
(7) a hydroxy group;
(8) a $C_{1-7}$ alkanoyl group (e.g., acetyl);
(9) a 5- or 6-membered heterocyclic group (e.g., a 5- or 6-membered nonaromatic heterocyclic group such as piperazino, morpholino and the like); or
(10) a group represented by the formula: $R^{1a}$—Y—
wherein
Y is a bond, a sulfur atom, or —$NR^y$—($R^y$ is a hydrogen atom, or a lower alkyl group (e.g., $C_{1-6}$ alkyl group such as methyl and the like)), and
$R^{1a}$ is
(1') a hydrogen atom,
(2') a $C_{1-6}$ alkyl group (e.g., $C_{1-3}$ alkyl group such as methyl, ethyl, propyl, isopropyl and the like (preferably $C_{1-2}$ alkyl group)) optionally substituted by 1 to 3 substituents selected from
 (a) a halogen atom (e.g., fluorine atom),
 (b) a carboxyl group,
 (c) a $C_{1-6}$ alkoxy-carbonyl group (e.g., ethoxycarbonyl),
 (d) a N—$C_{1-6}$ alkoxy-carbamoyl group (e.g., N-methyl-N-methoxycarbamoyl), (e) a $C_{6-14}$ aryloxy group (e.g., phenoxy) optionally substituted by 1 to 3 substituents selected from
  (i) a halogen atom (e.g., fluorine atom),
  (ii) a cyano group, and
  (iii) a $C_{1-6}$ alkoxy-carbonyl group (e.g., methoxycarbonyl),
(f) an amino group optionally substituted by 1 or 2 substituents selected from a mono- or di-$C_{6-14}$ aryl group optionally substituted by 1 to 3 halogen atoms (e.g., fluorine atom) and a $C_{1-6}$ alkyl group (e.g., phenylamino, methylamino),
(g) a heterocyclyl-carbonyl group (e.g., thienylcarbonyl, tetrahydrobenzo[c]azepinylcarbonyl, tetrahydroisoquinolinylcarbonyl) optionally substituted by 1 to 3 $C_{1-6}$ alkyl groups (e.g., methyl),
(h) a $C_{6-14}$ arylthio group (e.g., phenylthio, 2-naphthylthio) optionally substituted by 1 to 3 substituents selected from a halogen atom (e.g., fluorine atom, chlorine atom) and a cyano group,
(i) a $C_{6-14}$ aryl-sulfinyl group (e.g., phenylsulfinyl) optionally substituted by 1 to 3 halogen atoms (e.g., fluorine atom),
(j) a $C_{6-14}$ aryl-sulfonyl group (e.g., phenylsulfonyl) optionally substituted by 1 to 3 halogen atoms (e.g., fluorine atom),
(k) a $C_{1-6}$ alkoxy-carbonyl group (e.g., ethoxycarbonyl),
(l) a $C_{3-8}$ cycloalkyl group (e.g., cyclopropyl),
(m) a heterocyclic group (e.g., dihydrobenzofuranyl, benzofuranyl, pyridyl, thiazolyl, benzothiazolyl, imidazo[1,2-a]pyridyl, oxodihydropyridinyl, oxo-5H-thiazolo[3,2-a]pyrimidinyl, oxodihydrothieno[3,2-d]pyrimidinyl, imidazolyl, oxazolyl, morpholinyl, oxodihydrothieno[2,3-d]pyrimidinyl, imidazo[1,2-a]pyrimidinyl, dioxodihydroindolyl, oxadiazolyl) optionally substituted by substituent(s) selected from
  (i) a $C_{7-16}$ aralkyloxy group (e.g., benzyloxy),
  (ii) a $C_{1-6}$ alkyl group (e.g., methyl, propyl) optionally substituted by 1 to 3 $C_{3-8}$ cycloalkyl groups (e.g., cyclopropyl),
  (iii) a $C_{2-6}$ alkynyl group (e.g., 2-propynyl),
  (iv) a $C_{2-6}$ alkenyl group (e.g., vinyl) optionally substituted by a $C_{6-14}$ aryl group (e.g., phenyl) optionally substituted by 1 to 3 halogen atoms (e.g., fluorine atom),
  (v) a $C_{1-6}$ alkoxy group (e.g., methoxy),
  (vi) a heterocyclic group (e.g., thienyl), and
  (vii) a $C_{6-14}$ aryl group (e.g., phenyl) optionally substituted by 1 to 3 $C_{1-6}$ alkoxy groups (e.g., methoxy),
(n) a carbamoyl group,
(o) a mono- or di-$C_{1-6}$ alkyl-carbamoyl group (e.g., diethylcarbamoyl), and
(p) a $C_{6-14}$ aryl group (e.g., $C_{6-10}$ aryl group such as phenyl, 1-naphthyl, 2-naphthyl and the like) optionally substituted by substituent(s) selected from
  (i) a halogen atom (e.g., fluorine atom, chlorine atom),
  (ii) a cyano group,
  (iii) a heterocyclic group (e.g., 1-pyrrolyl),
  (iv) a $C_{1-6}$ alkyl group (e.g., methyl, tert-butyl) optionally substituted by 1 to 3 substituents selected from a halogen atom (e.g., fluorine atom) and a hydroxy group,
  (v) a $C_{1-6}$ alkoxy group (e.g., methoxy) optionally substituted by 1 to 3 halogen atoms (e.g., fluorine atom) etc.,
  (vi) a mono- or di-($C_{1-7}$ alkanoyl)-amino group (e.g., acetylamino),
  (vii) a $C_{1-6}$ alkylsulfonyl group (e.g., methylsulfonyl),
  (viii) a carboxyl group,
  (ix) a $C_{1-6}$ alkoxy-carbonyl group (e.g., methoxycarbonyl),
  (x) a heterocyclyl-carbonyl group (e.g., piperazinylcarbonyl, morpholinocarbonyl) optionally substituted by 1 to 3 $C_{1-6}$ alkyl groups (e.g., methyl), and
  (xi) a $C_{1-7}$ alkanoyl group (e.g., acetyl)
  (xii) a $C_{1-6}$ alkylthio group (e.g., methylthio),
  (xiii) a $C_{1-6}$ alkylsulfinyl group (e.g., methylsulfinyl);
(q) a $C_{1-7}$ alkanoyloxy group (e.g., acetyloxy),
(r) a hydroxy group,
(s) a $C_{1-6}$ alkylthio group (e.g., methylthio),
(t) a $C_{1-6}$ alkylsulfinyl group (e.g., methylsulfinyl),
(u) a $C_{1-6}$ alkylsulfonyl group (e.g., methylsulfonyl),
(v) a $C_{1-6}$ alkoxy group (e.g., methoxy), and
(w) a group represented by the formula:

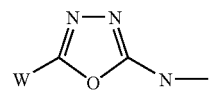

wherein each symbol is as defined above, or
(3') a cyano group; and
$W^a$ is a group represented by the formula:

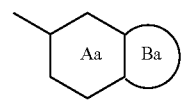

wherein
ring Aa is benzene or pyridine, and
ring Ba is

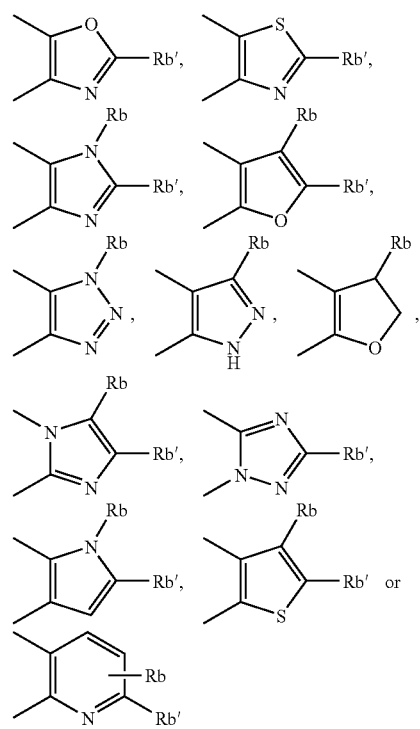

wherein Rb is
(1) a hydrogen atom;
(2) a $C_{1-6}$ alkyl group (e.g., methyl) optionally substituted by a hydroxy group;
(3) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group,
    (iii) a $C_{1-6}$ alkoxy group (e.g., methoxy), and
    (iv) a $C_{1-6}$ alkylsulfonyl group (e.g., methylsulfonyl), etc.,
  (d) a di-$C_{1-6}$ alkyl-amino group (e.g., dimethylamino),
  (e) a $C_{1-6}$ alkoxy group (e.g., methoxy, ethoxy) optionally substituted by 1 to 3 substituents selected from
    (i) a halogen atom,
    (ii) a $C_{1-6}$ alkylthio group (e.g., methylthio),
    (iii) a $C_{1-6}$ alkylsulfinyl group (e.g., methylsulfinyl),
    (iv) a $C_{1-6}$ alkylsulfonyl group (e.g., methylsulfonyl), and
    (v) a $C_{6-14}$ aryl group (e.g., phenyl),
  (f) a $C_{1-6}$ alkylthio group (e.g., methylthio, ethylthio, propylthio, isopropylthio) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (g) a $C_{1-6}$ alkylsulfinyl group (e.g., methylsulfinyl, ethylsulfinyl, propylsulfinyl, isopropylsulfinyl) optionally substituted by 1 to 3 substituents selected from
    (i) a halogen atom (e.g., fluorine atom),
    (ii) a $C_{6-14}$ aryl group (e.g., phenyl) optionally substituted by a cyano group, etc.,
  (h) a $C_{1-6}$ alkylsulfonyl group (e.g., methylsulfonyl, ethylsulfonyl, propylsulfonyl, isopropylsulfonyl) optionally substituted by 1 to 3 substituents selected from
    (i) a halogen atom (e.g., fluorine atom), and
    (ii) a $C_{6-14}$ aryl group (e.g., phenyl) optionally substituted by a cyano group, etc.,
  (i) a carboxyl group,
  (j) a $C_{1-6}$ alkoxy-carbonyl group (e.g., methoxycarbonyl),
  (k) a group represented by —CO—NR$^s$R$^t$ wherein R$^a$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., carbamoyl, methylcarbamoyl, dimethylcarbamoyl, morpholinocarbonyl, 1-pyrrolidinylcarbonyl),
  (l) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocycle optionally further having 1 or 2 hetero atoms selected from a nitrogen atom, an oxygen atom and a sulfur atom (e.g., methylaminosulfonyl, dimethylaminosulfonyl),
  (m) a $C_{1-6}$ alkylsulfonyloxy group (e.g., sulfonyloxy) optionally substituted by 1 to 3 halogen atoms (e.g., fluorine atom),
  (n) a $C_{1-6}$ alkylsulfonylamino group (e.g., methylsulfonylamino),
  (o) a di-$C_{1-6}$ alkoxyphosphoryl group (e.g., dimethoxyphosphoryl),
  (p) a $C_{1-6}$ alkoxy-carbonyl group (e.g., methoxycarbonyl),
  (q) a $C_{1-7}$ alkanoyl group (e.g., formyl group, $C_{1-6}$ alkyl-carbonyl group (e.g., acetyl),
  (r) a hydroxy group,
  etc., and optionally fused with a 5- or 6-membered heterocyclic group (e.g., thiophene, dimethyldihydrothiophene, dimethyltetrahydrothiophene 1-oxide, dimethyldihydrothiophene 1,1-dioxide) optionally substituted by 1 to 4 substituents selected from a $C_{1-6}$ alkyl group (e.g., methyl) and an oxo group [examples of such "$C_{6-14}$ aryl group fused with substituted 5- or 6-membered heterocyclic group" include dimethyldihydrothiophene, dimethyltetrahydrothiophene 1-oxide, and dimethyldihydrothiophene 1,1-dioxide];
(4) a heterocyclic group (e.g., 5- or 6-membered heterocyclic group such as pyridyl, piperidyl, oxazolyl, pyrazolyl and the like) optionally substituted by 1 to 3 substituents selected from
  (a) a halogen atom (e.g., fluorine atom, chlorine atom),
  (b) a $C_{1-6}$ alkyl group (e.g., methyl) optionally substituted by a $C_{1-6}$ alkoxy group (e.g., methoxy),
  (c) a carboxyl group,
  (d) a $C_{1-6}$ alkoxy-carbonyl group (e.g., ethoxycarbonyl),
  (e) a group represented by —CO—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., carbamoyl, morpholinocarbonyl, 1-pyrrolidinylcarbonyl),
  (f) a group represented by —SO$_2$—NR$^s$R$^t$ wherein R$^s$ and R$^t$ are each hydrogen or a $C_{1-6}$ alkyl group, or show, together with the adjacent nitrogen atom, a 5- or 6-membered nitrogen-containing heterocyclic group optionally further having 1 or 2 hetero atoms selected from a nitrogen atom, an oxygen atom and a sulfur atom (e.g., methylaminosulfonyl, dimethylaminosulfonyl),
  (g) a $C_{6-14}$ aryl-carbonyl group (e.g., benzoyl),
  (h) a $C_{1-6}$ alkylsulfonyl group (e.g., methylsulfonyl),
  (i) a $C_{1-6}$ alkylsulfonylamino group,
  (j) a $C_{7-10}$ aralkyl group (e.g., benzyl) optionally substituted by cyano, an optionally halogenated $C_{1-6}$ alkyl group (e.g., trifluoromethyl) or a halogen atom (e.g., fluorine),
  (k) a $C_{1-7}$ alkanoyl group (e.g., acetyl),
  (l) a 5- or 6-membered heterocyclyl-$C_{1-6}$ alkyl group (e.g., pyridylmethyl), etc.;
(5) a carboxyl group;
(6) a $C_{1-6}$ alkoxy-carbonyl group (e.g., ethoxycarbonyl);
(7) a heterocyclyl-carbonyl group (e.g., morpholinocarbonyl); or
(8) a $C_{1-6}$ alkyl-carbamoyl group (e.g., ethylcarbamoyl) optionally substituted by 1 to 3 carbamoyl groups;
(9) a cyano group; or
(10) a $C_{1-7}$ alkanoyl group (e.g., formyl), and Rb' is
(1) a hydrogen atom; or
(2) an amino group, excluding
(2) a group represented by the formula:

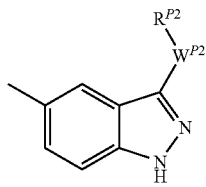

wherein each symbol is as defined above, or
a group represented by the formula:

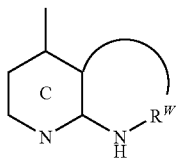

wherein
ring C is pyridine, and
$R^W$ is
(1) a hydrogen atom;
(2) a $C_{1-7}$ alkanoyl group (e.g., propionyl) optionally substituted by 1 to 3 substituents selected from
  (a) a heterocyclic group (e.g., morpholino, pyrrolidinyl),
  (b) a $C_{3-8}$ cycloalkylamino group (e.g., cyclopropylamino), and
  (c) a $C_{6-14}$ aryl group (e.g., phenyl):
(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl);
(6) a $C_{7-16}$ aralkyl group (e.g., 3-phenylpropionyl); or
(7) a $C_{6-10}$ aryl group (e.g., phenyl) optionally substituted by 1 to 3 substituents selected from
  (a) optionally halogenated $C_{1-6}$ alkyl (e.g., trifluoromethyl),
  (b) a $C_{1-6}$ alkoxy group (e.g., methoxy),
  (c) a $C_{1-6}$ alkylthio group (e.g., methylthio)
  (d) a $C_{1-6}$ alkylsulfinyl group (e.g., methylsulfinyl),
  (e) a $C_{1-6}$ alkylsulfonyl group (e.g., methylsulfonyl), etc.;
(8) a $C_{1-6}$ alkyl-carbamoyl group (e.g., methylcarbamoyl) optionally substituted by a heterocyclic group (e.g., pyridyl);
(9) a heterocyclic group (e.g., pyridyl), and the like, or optionally forms, together with the adjacent —NH— and a carbon atom on ring C, a nitrogen-containing 5- to 7-membered ring (e.g., pyrrole) optionally substituted by a $C_{7-16}$ aralkyl group (e.g., phenethyl) etc.
[Compound (II)-A']
A compound wherein $R^1$ is
(1) a hydrogen atom;
(2) a $C_{3-8}$ cycloalkyl group (e.g., cyclopropyl);
(3) a $C_{1-10}$ alkoxy group (e.g., methoxy) optionally substituted by a substituent selected from
  (a) a carboxyl group,
  (b) a $C_{1-6}$ alkoxy-carbonyl group (e.g., ethoxycarbonyl), and
  (c) a N—$C_{1-6}$ alkyl-N—$C_{1-6}$ alkoxy-carbamoyl group (e.g., N-methyl-N-methoxycarbamoyl);
(4) a $C_{7-16}$ aralkyloxy group (e.g., benzyloxy) optionally substituted by 1 to 3 halogen atoms (e.g., fluorine atom);
(5) a $C_{1-6}$ alkylsulfonyl group (e.g., methylsulfonyl); or
(6) a group of the formula: $R^{1a}$—Y—
wherein
Y is a bond, a sulfur atom, or —NH—, and
$R^{1a}$ is
(1') a hydrogen atom, or
(2') a $C_{1-6}$ alkyl group (e.g., a $C_{1-3}$ alkyl group such as methyl, ethyl, propyl and the like (preferably $C_{1-2}$ alkyl group)) optionally substituted by 1 to 3 substituents selected from
  (a) a halogen atom (e.g., fluorine atom),
  (b) a carboxyl group,
  (c) a $C_{1-6}$ alkoxy-carbonyl group (e.g., ethoxycarbonyl),
  (d) a N—$C_{1-6}$ alkyl-N—$C_{1-6}$ alkoxy-carbamoyl group (e.g., N-methyl-N-methoxycarbamoyl),
  (e) a $C_{6-14}$ aryloxy group (e.g., phenoxy) optionally substituted by 1 to 3 substituents selected from
    (i) a halogen atom (e.g., fluorine atom),
    (ii) a cyano group, and
    (iii) a $C_{1-6}$ alkoxy-carbonyl group (e.g., methoxycarbonyl),
  (f) a mono- or di-$C_{6-14}$ aryl-amino group (e.g., phenylamino) optionally substituted by 1 to 3 halogen atoms (e.g., fluorine atom),
  (g) a heterocyclyl-carbonyl group (e.g., thienylcarbonyl, tetrahydrobenzo[c]azepinylcarbonyl, tetrahydroisoquinolinylcarbonyl) optionally substituted by 1 to 3 $C_{1-6}$ alkyl groups (e.g., methyl),
  (h) a $C_{6-14}$ arylthio group (e.g., phenylthio, 2-naphthylthio) optionally substituted by 1 to 3 substituents selected from a halogen atom (e.g., fluorine atom, chlorine atom) and a cyano group,
  (i) a $C_{6-14}$ aryl-sulfinyl group (e.g., phenylsulfinyl) optionally substituted by 1 to 3 halogen atoms (e.g., fluorine atom),
  (j) a $C_{6-14}$ aryl-sulfonyl group (e.g., phenylsulfonyl) optionally substituted by 1 to 3 halogen atoms (e.g., fluorine atom),
  (k) a $C_{1-6}$ alkoxy-carbonyl group (e.g., ethoxycarbonyl),
  (l) a $C_{3-8}$ cycloalkyl group (e.g., cyclopropyl),
  (m) a heterocyclic group (e.g., dihydrobenzofuranyl, benzofuranyl, pyridyl, thiazolyl, benzothiazolyl, imidazo[1,2-a]pyridyl, oxodihydropyridinyl, oxo-5H-thiazolo[3,2-a]pyrimidinyl, oxodihydrothieno[3,2-d]pyrimidinyl, imidazolyl, oxazolyl, morpholinyl, oxodihydrothieno[2,3-d]pyrimidinyl, imidazo[1,2-a]pyrimidinyl, dioxodihydroindolyl, oxadiazolyl) optionally substituted by substituent(s) selected from
    (i) a $C_{7-16}$ aralkyloxy group (e.g., benzyloxy),
    (ii) a $C_{1-6}$ alkyl group (e.g., methyl, propyl) optionally substituted by 1 to 3 $C_{3-8}$ cycloalkyl groups (e.g., cyclopropyl),
    (iii) a $C_{2-6}$ alkynyl group (e.g., 2-propynyl),
    (iv) a $C_{2-6}$ alkenyl group (e.g., vinyl) optionally substituted by a $C_{6-14}$ aryl group (e.g., phenyl) optionally substituted by 1 to 3 halogen atoms (e.g., fluorine atom),
    (v) a $C_{1-6}$ alkoxy group (e.g., methoxy),
    (vi) a heterocyclic group (e.g., thienyl), and
    (vii) a $C_{6-14}$ aryl group (e.g., phenyl) optionally substituted by 1 to 3 $C_{1-6}$ alkoxy groups (e.g., methoxy),
  (n) a carbamoyl group,
  (o) a mono- or di-$C_{1-6}$ alkyl-carbamoyl group (e.g., diethylcarbamoyl), and (p) a $C_{6-14}$ aryl group (e.g., $C_{6-10}$ aryl group such as phenyl, 1-naphthyl, 2-naphthyl and the like) optionally substituted by substituent(s) selected from
  (i) a halogen atom (e.g., fluorine atom, chlorine atom),
  (ii) a cyano group,
  (iii) a heterocyclic group (e.g., 1-pyrrolyl),
  (iv) a $C_{1-6}$ alkyl group (e.g., methyl, tert-butyl) optionally substituted by 1 to 3 substituents selected from a halogen atom (e.g., fluorine atom) and a hydroxy group,
  (v) a $C_{1-6}$ alkoxy group (e.g., methoxy) optionally substituted by 1 to 3 halogen atoms (e.g., fluorine atom) etc.,
  (vi) a mono- or di-($C_{1-6}$ alkyl-carbonyl)-amino group (e.g., acetylamino),
  (vii) a $C_{1-6}$ alkylsulfonyl group (e.g., methylsulfonyl),
  (viii) a carboxyl group,
  (iv) a $C_{1-6}$ alkoxy-carbonyl group (e.g., methoxycarbonyl),
  (x) a heterocyclyl-carbonyl group (e.g., piperazinylcarbonyl, morpholinocarbonyl) optionally substituted by 1 to 3 $C_{1-6}$ alkyl groups (e.g., methyl), and
  (xi) a $C_{1-6}$ alkyl-carbonyl group (e.g., acetyl); and
$W^a$ is a group represented by the formula:

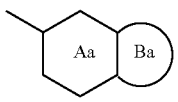

wherein
ring Aa is benzene or pyridine, and
ring Ba is

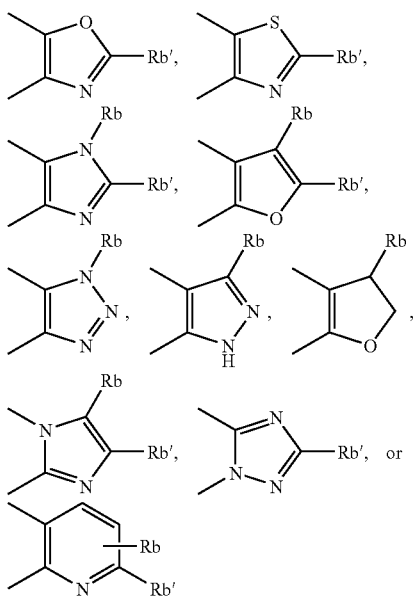

wherein Rb is
(1) a hydrogen atom;
(2) a $C_{1-6}$ alkyl group (e.g., methyl);
(3) a $C_{6-14}$ aryl group (e.g., phenyl) optionally substituted by 1 to 3 substituents selected from
  (a) a halogen atom (e.g., fluorine atom, chlorine atom),
  (b) a cyano group,
  (c) a $C_{1-6}$ alkyl group (e.g., methyl) optionally substituted by 1 to 3 substituents selected from
    (i) a halogen atom (e.g., fluorine atom),
    (ii) a hydroxy group, and
    (iii) a $C_{1-6}$ alkoxy group (e.g., methoxy),
  (d) a di-$C_{1-6}$ alkyl-amino group (e.g., dimethylamino),
  (e) a $C_{1-6}$ alkoxy group (e.g., methoxy) optionally substituted by 1 to 3 halogen atoms,
  (f) a $C_{1-6}$ alkylthio group (e.g., methylthio),
  (g) a $C_{1-6}$ alkylsulfinyl group (e.g., methylsulfinyl),
  (h) a $C_{1-6}$ alkylsulfonyl group (e.g., methylsulfonyl),
  (i) a carboxyl group,
  (j) a $C_{1-6}$ alkoxy-carbonyl group (e.g., methoxycarbonyl),
  (k) a carbamoyl group, and
  (l) a formyl group;
(4) a heterocyclic group (e.g., pyridyl);
(5) a carboxyl group;
(6) a $C_{1-6}$ alkoxy-carbonyl group (e.g., ethoxycarbonyl);
(7) a heterocyclyl-carbonyl group (e.g., morpholinocarbonyl); or
(8) a $C_{1-6}$ alkyl-carbamoyl group (e.g., ethylcarbamoyl) optionally substituted by 1 to 3 carbamoyl groups; and Rb' is
(1) a hydrogen atom; or
(2) an amino group,
excluding
(2) a group represented by the formula:

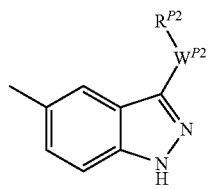

wherein each symbol is as defined above, or
a group represented by the formula:

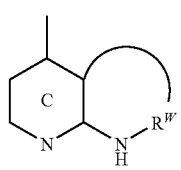

wherein
ring C is pyridine, and
$R^W$ is
(1) a hydrogen atom;
(2) a $C_{1-6}$ alkyl-carbonyl group (e.g., propionyl) optionally substituted by 1 to 3 substituents selected from
  (a) a heterocyclic group (e.g., morpholino, pyrrolidinyl),
  (b) a $C_{3-8}$ cycloalkylamino group (e.g., cyclopropylamino), and
  (c) a $C_{6-14}$ aryl group (e.g., phenyl);
(3) a $C_{1-6}$ alkoxy-carbonyl group (e.g., tert-butoxycarbonyl);
(4) a $C_{7-16}$ aralkyloxy-carbonyl group (e.g., benzyloxycarbonyl);
(5) a $C_{7-16}$ aralkyl-carbamoyl group (e.g., benzylcarbamoyl); or
(6) a $C_{7-16}$ aralkyl group (e.g., 3-phenylpropionyl); or optionally forms, together with the adjacent —NH— and a carbon atom on ring C, a nitrogen-containing 5- to 7-membered ring (e.g., pyrrole).

Among the compound (I), the following compounds are known; however, the GSK-3 inhibitory action possessed by these compounds has not been known heretofore.

(1) A compound wherein $R^1$ is an optionally substituted mercapto group, and $W^a$ is 1H-benzimidazol-6-yl, for example, the following compounds:

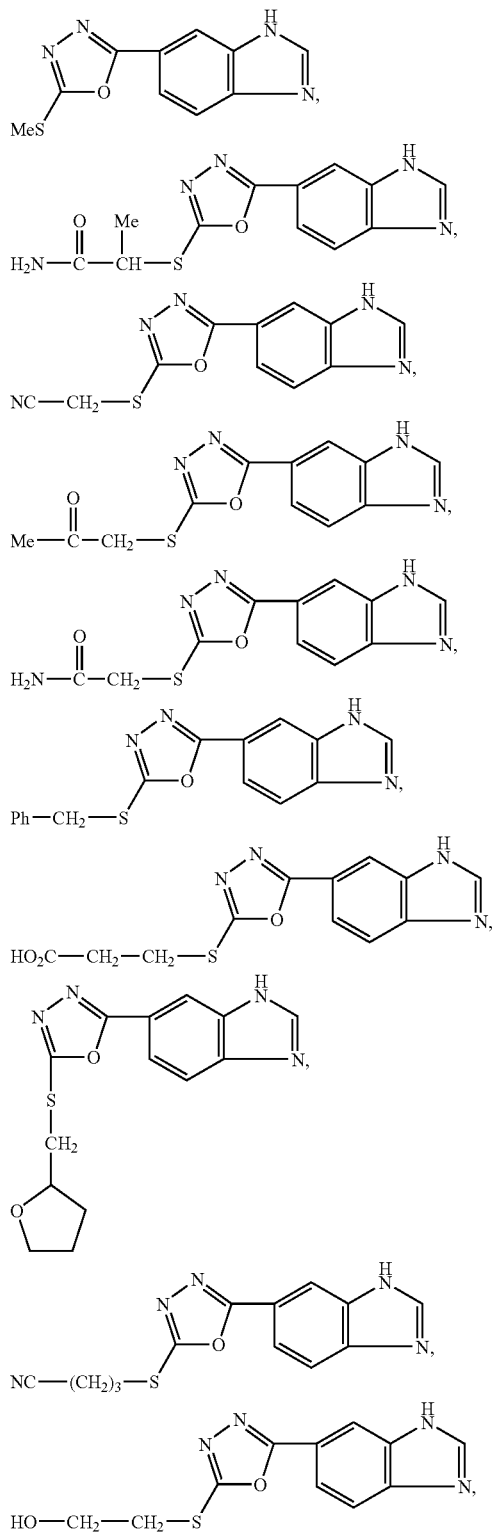

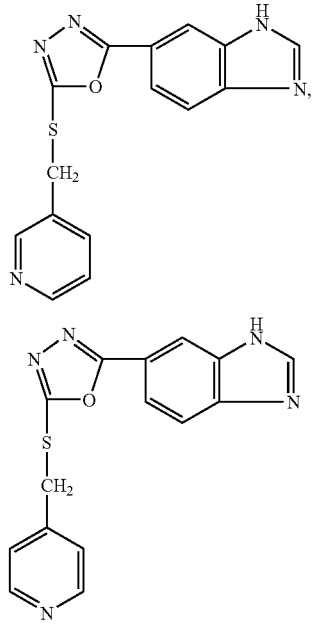

(2) A compound wherein $R^1$ is an optionally substituted phenyl group or a phenyl group optionally condensed with a heterocycle, and $W^a$ is 1H-benzotriazol-6-yl, for example, the following compounds:

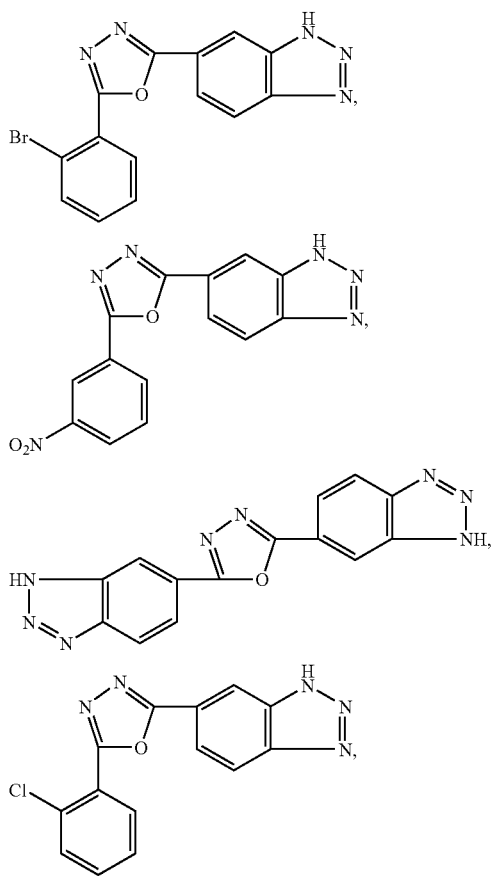

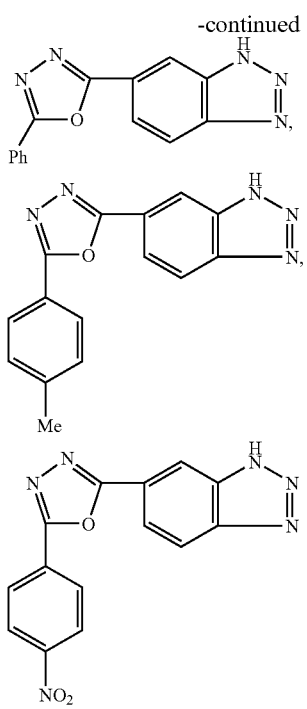

(3)
(a) 2,5-bis(3-phenyl-2,1-benzisoxazol-5-yl)-1,3,4-oxadiazole,
(b) N-ethyl-N'-[6-(5-methyl-1,3,4-oxadiazol-2-yl)-1H-benzimidazol-2-yl]urea,
(c) N-ethyl-N'-[6-(1,3,4-oxadiazol-2-yl)-1H-benzimidazol-2-yl]urea,
(d) N,N'-diethyl-N''-[5-(5-quinoxalin-6-yl-[1,3,4]oxadiazol-2-ylsulfanylmethyl)-pyrimidin-4-yl]guanidine,
(e) phenyl-(5-quinolin-6-yl-[1,3,4]oxadiazol-2-yl)amine,
(f) cyclohexyl-(5-quinolin-6-yl-[1,3,4]oxadiazol-2-yl)amine,
(g) ethyl-(5-quinolin-6-yl-[1,3,4]oxadiazol-2-yl)amine, and
(h) (5-quinolin-6-yl-[1,3,4]oxadiazol-2-yl)-4-tolylamine.

Examples of salts of compound (I) and compound (II) of the present invention (unless otherwise specified, these are collectively referred to as compound A) include metal salt, ammonium salt, salt with organic base, salt with inorganic acid, salt with organic acid, salt with basic or acidic amino acid and the like.

Here, preferable examples of the metal salt include alkali metal salt such as sodium salt, potassium salt and the like; alkaline earth metal salts such as calcium salt, magnesium salt, barium salt and the like, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like, and preferable examples of the salt with acidic amino acid include salts with aspartic acid, glutamic acid and the like.

Of these salts, a pharmaceutically acceptable salt is preferable. For example, when compound A has an acidic functional group, metal salts such as alkali metal salt, alkaline earth metal salt and the like; ammonium salt and the like are preferable, and when compound A has a basic functional group, for example, a salt with inorganic acid or organic acid is preferable.

A prodrug of the compound A or a salt thereof means a compound which is converted to the compound A with a reaction due to an enzyme, an gastric acid, etc. under the physiological condition in the living body, that is, a compound which is converted to the compound A by enzymatic oxidation, reduction, hydrolysis, etc.; a compound which is converted to the compound A by hydrolysis etc. due to gastric acid, etc.

A prodrug of compound A may be a compound obtained by subjecting an amino group in compound A to an acylation, alkylation or phosphorylation (e.g., a compound obtained by subjecting an amino group in compound A to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound A to an acylation, alkylation, phosphorylation or boration (e.g., a compound obtained by subjecting a hydroxy group in compound A to an acetylation, palmitoylation, propanoylation, pivaloylation, succinylation, fumarylation, alanylation, dimethylaminomethylcarbonylation, etc.); a compound obtained by subjecting a carboxyl group in compound A to an esterification or amidation (e.g., a compound obtained by subjecting a carboxy group in compound A to an $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Of these, a compound wherein the carboxy group in the compound A is esterified with a $C_{1-6}$ alkyl group such as methyl, ethyl, tert-butyl and the like is preferably used. Any of these compounds can be produced from compound A by a method known per se.

A prodrug of the compound A may be a compound that converts to the compound A under physiological conditions as described in Development of Pharmaceutical Products, vol. 7, Molecule Design, 163-198, Hirokawa Shoten (1990).

Hereinafter, the production methods of the compound of the present invention are explained.

Compound (I) can be produced according to a method known per se, for example, the production methods of compound (II) explained below or a method analogous thereto.

Compound (II) can be produced according to a method known per se, for example, the production methods explained in Reaction Scheme 1 to Reaction Scheme 5 described in detail in the following or a method analogous thereto.

Each starting material compound in the following production method may form a salt, and examples thereof include those similar to the salts of compound A.

The solvent, acid and base used for the production methods of the compound of the present invention are explained below.

As the "alcohols", for example, methanol, ethanol, 1-propanol, 2-propanol, tert-butyl alcohol and the like can be used.

As the "ethers", for example, diethyl ether, diisopropyl ether, diphenyl ether, tetrahydrofuran, 1,4-dioxane, 1,2-dimethoxyethane and the like can be used.

As the "hydrocarbons", for example, benzene, toluene, cyclohexane, hexane and the like can be used.

As the "amides", for example, N,N-dimethylformamide, N,N-dimethylacetamide, N-methylpyrrolidine, hexamethylphosphoric triamide and the like can be used.

As the "halogenated hydrocarbons", for example, dichloromethane, chloroform, carbon tetrachloride, 1,2-dichloroethane, chlorobenzene and the like can be used.

As the "nitriles", for example, acetonitrile, propionitrile and the like can be used.

As the "ketones", for example, acetone, ethylmethylketone and the like can be used.

As the "esters", for example, ethyl acetate and the like can be used.

As the "sulfoxides", for example, dimethyl sulfoxide and the like can be used.

As the "organic acids", for example, formic acid, acetic acid, propionic acid, trifluoroacetic acid, citric acid, methanesulfonic acid, p-toluenesulfonic acid and the like can be used.

As the "mineral acids", for example, hydrochloric acid, sulfuric acid and the like can be used.

hexyldimethylamine, 4-dimethylaminopyridine, N,N-diethylaniline, N-methylpiperidine, N-methylpyrrolidine, N-methylmorpholine, 1,8-diazabicyclo[5,4,0]undec-7-ene and the like can be used.

As the "alkali metal hydrides", for example, sodium hydride, potassium hydride and the like can be used.

As the "alkali metals", for example, sodium, lithium, potassium and the like can be used.

As the "metal amides", for example, sodium amide, lithium diisopropylamide, lithium hexamethyldisilazide and the like can be used.

As the "alkyl metals", for example, butyllithium, sec-butyllithium, tert-butyllithium and the like can be used.

As the "aryl metals", for example, phenyllithium and the like can be used.

As the "metal alkoxides", sodium methoxide, sodium ethoxide, sodium tert-butoxide, potassium tert-butoxide and the like can be used.

Compounds (II-a), (II-b), (II-c), (II-d) and (II-e) can be produced according to the method shown in the following Reaction Scheme 1 or a method analogous thereto.

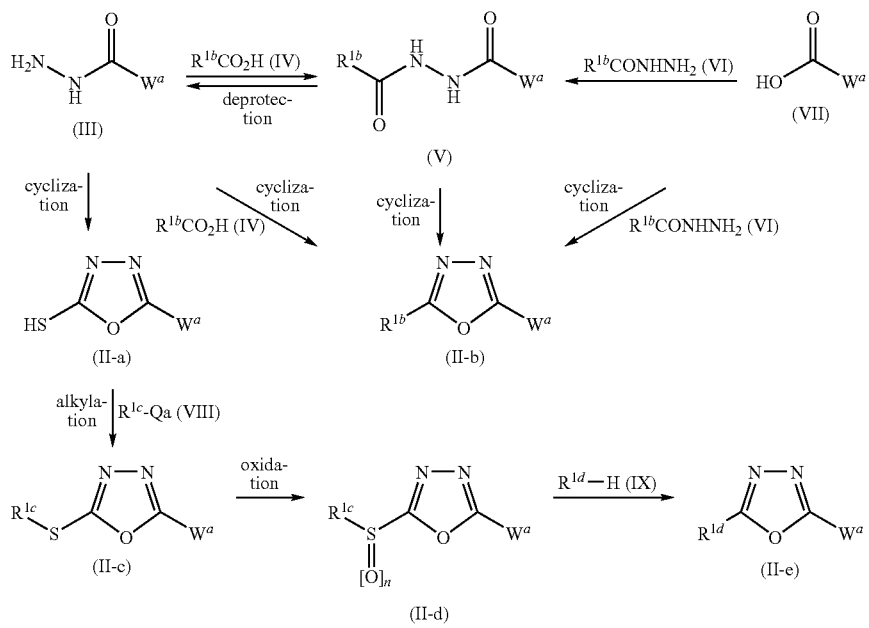

As the "Lewis acids", for example, boron trichloride, boron tribromide and the like can be used.

As the "inorganic bases", for example, sodium hydroxide, potassium hydroxide, lithium hydroxide, barium hydroxide and the like can be used.

As the "basic salts", for example, sodium carbonate, potassium carbonate, cesium carbonate, sodium hydrogen carbonate, sodium acetate, ammonium acetate and the like can be used.

As the "aromatic amines", for example, pyridine, lutidine and the like can be used.

As the "tertiary amines", for example, triethylamine, tripropylamine, tributylamine, diisopropylethylamine, cyclowherein $R^{1b}$ is a hydrogen atom, an optionally substituted hydrocarbon group or an optionally substituted heterocyclic group, $R^{1c}$ is an optionally substituted hydrocarbon group or an optionally substituted heterocyclic group, $R^{1d}$ is an optionally substituted hydrocarbon group, an optionally substituted heterocyclic group, an optionally substituted hydroxy group or an optionally substituted amino group, Qa is a leaving group, n is 1 or 2, and other symbols are as defined above.

Examples of the leaving group for Qa include a halogen atom (e.g., chlorine, bromine, iodine), an optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group optionally substituted by a $C_{1-6}$ alkyl group (e.g., benzenesulfonyloxy, 4-toluenesulfonyloxy), methanesulfonyl group and the like, with preference given to a halogen atom.

Compounds (III), (IV), (VI), (VII), (VIII) and (IX) are commercially easily available, or can be produced according to a method known per se or a method analogous thereto.

Compound (III) can also be produced by subjecting compound (V) to deprotection.

This reaction can be carried out according to a method known per se, for example, the methods described in Protective Groups in Organic Synthesis, vol. 3, 1999, "Protection for the Amino Group" and the like, or a method analogous thereto. The deprotection carried out, for example, by a method using an acid, a base, ultraviolet rays, hydrazine, phenylhydrazine, sodium N-methyldithiocarbamate, tetrabutylammonium fluoride, palladium acetate, a trialkylsilylhalide (e.g., trimethylsilyl iodide, trimethylsilyl bromide) and the like, a reduction method, and the like.

Compound (V) can be produced by reacting compound (III) with compound (IV) or a reactive derivative.

Examples of the reactive derivative of compound (IV) include acid halides (e.g., acid chlorides, acid bromides), acid amides (e.g., an acid amide with pyrazole, imidazole, benzotriazole and the like), acid anhydrides (e.g., an acid anhydride with a $C_{1-6}$ aliphatic carboxylic acid such as acetic acid, propionic acid, butyric acid and the like), acid azides, activated esters (e.g., diethoxyphosphate, diphenoxyphosphate, p-nitrophenyl ester, 2,4-dinitrophenyl ester, cyanomethyl ester, pentachlorophenyl ester, an ester with N-hydroxysuccinimide, an ester with N-hydroxyphthalimide, an ester with 1-hydroxybenzotriazole, an ester with 6-chloro-1-hydroxybenzotriazole, an ester with 1-hydroxy-1H-2-pyridone), activated thioesters (e.g., 2-pyridyl thioester, 2-benzothiazolyl thioester) and the like.

Compound (IV) or a reactive derivative is used generally in an amount of 1 to 10 mol, preferably 1 to 3 mol, per 1 mol of compound (III).

When an acid halide is used as a reactive derivative of compound (IV), the reaction can be carried out in the presence of a deoxidizing agent for the purpose of removing generated halogenated hydrogen from the reaction system. Preferable examples of the deoxidizing agent include basic salts, aromatic amines, tertiary amines and the like. The deoxidizing agent is used generally in an amount of 1 to 50 mol, preferably 1 to 10 mol, per 1 mol of compound (IV).

Alternatively, compound (V) can also be produced by directly reacting compound (III) with compound (IV) in the presence of a suitable condensation agent. Examples of the condensation agent include N,N'-disubstituted carbodiimides such as N,N'-dicyclohexylcarbodiimide, N,N'-diisopropylcarbodiimide, 3-(3-dimethylaminopropyl)-1-ethylcarbodiimide or a hydrochloride thereof and the like; azolides such as N,N'-carbonyldiimidazole and the like; dehydrating agents such as 2-ethoxy-N-ethoxycarbonyl-1,2-dihydroquinoline, phosphorus oxychloride, alkoxyacetylene and the like; 2-halogenopyridinium salts such as 2-chloromethylpyridinium iodide, 2-fluoro-1-methylpyridinium iodide and the like; phosphates such as diethyl cyanophosphate, diphenylphosphoryl azide and the like; and the like. It is considered that when the condensation agent is used, the reaction progresses via the reactive derivative of compound (IV). The amount of the condensation agent to be used is generally 1 to 20 mol, preferably 1 to 5 mol, per 1 mol of compound (III).

When the aforementioned N,N'-disubstituted carbodiimide is used as a condensation agent, the reaction efficiency can be improved by using as necessary suitable condensation promoter (e.g., 1-hydroxy-7-azabenzotriazole, 1-hydroxybenzotriazole, N-hydroxysuccinimide, N-hydroxyphthalimide). In addition, when the aforementioned phosphate is used as a condensation agent, the reaction efficiency can be generally improved by adding aromatic amines, tertiary amines and the like. The amount of the condensation promoter, aromatic amine, tertiary amine and the like to be used is generally 0.1 to 10 mol, preferably 0.3 to 3 mol, per 1 mol of compound (III).

The reaction of compound (III) with compound (IV) or a reactive derivative is advantageously carried out using a solvent inert to the reaction. The solvent is not particularly limited as long as the reaction proceeds, and preferable examples thereof include solvents such as ethers, hydrocarbons, amides, halogenated hydrocarbons, nitriles, ketones, esters, water and the like, mixed solvents thereof and the like.

While the reaction time varies depending on the reagent and solvent to be used, it is generally 30 min to 72 hr, preferably 30 min to 24 hr.

The reaction temperature is generally 0 to 100° C., preferably 0 to 70° C.

Compound (V) can be produced by reacting compound (VI) with compound (VII) or a reactive derivative. This reaction is carried out in the same manner as in the reaction of compound (III) with compound (IV) or a reactive derivative.

Compound (II-a) can be produced by reacting compound (III) with carbon disulfide.

This reaction is generally carried out in the presence of a base. Examples of the base include inorganic bases, basic salts, aromatic amines, tertiary amines, alkali metal hydrides, metal amides, alkyl metals, aryl metals, metal alkoxides and the like. The base is used generally in an amount of 1 to 10 mol, preferably 1 to 3 mol, per 1 mol of compound (III).

The carbon disulfide is used generally in an amount of 1 to 10 mol, preferably 1 to 3 mol, per 1 mol of compound (III).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, esters, sulfoxides, water and the like, mixed solvents thereof and the like.

While the reaction time varies depending on the reagent and solvent to be used, it is generally 30 min to 24 hr, preferably 1 hr to 12 hr.

The reaction temperature is generally 0 to 150° C., preferably 20 to 100° C.

Compound (II-b) can be produced by subjecting compound (V) to dehydrating cyclization reaction.

This reaction is carried out in the presence of a dehydrating agent. Examples of the dehydrating agent include thionyl chloride, phosphoryl chloride, phosphorus pentachloride, phosphorus tribromide, p-toluenesulfonyl chloride, methanesulfonyl chloride, diphosphorus pentoxide and the like. The dehydrating agent is used generally in an amount of 1 to 10 mol, preferably 2 to 5 mol, per 1 mol of compound (V).

This reaction is advantageously carried out using a solvent inert to the reaction. The solvent is not particularly limited as long as the reaction proceeds, and preferable examples thereof include solvents such as ethers, hydrocarbons, amides, halogenated hydrocarbons, nitriles, esters, organic acids, aromatic amines and the like, mixed solvents thereof and the like.

While the reaction time varies depending on the reagent and solvent to be used, it is generally 30 min to 72 hr, preferably 1 hr to 24 hr.

The reaction temperature is generally 0 to 150° C., preferably 20 to 100° C.

Alternatively, this reaction can also be carried out using a halogenated reagent as a solvent. Examples of the halogenated reagent include thionyl chloride, phosphoryl chloride, phosphorus pentachloride, phosphorus tribromide and the like.

While the reaction time varies depending on the solvent to be used, it is generally 30 min to 24 hr, preferably 1 hr to 6 hr.

The reaction temperature is generally 0 to 150° C., preferably 20 to 100° C.

Compound (II-b) can also be produced by directly reacting compound (III) with compound (IV).

Compound (IV) is used generally in an amount of 0.1 to 10 mol, preferably 0.5 to 2, per 1 mol of compound (III).

This reaction is carried out using a halogenated reagent as a solvent. Examples of the halogenated reagent include thionyl chloride, phosphoryl chloride, phosphorus pentachloride, phosphorus tribromide and the like.

While the reaction time varies depending on the solvent to be used, it is generally 30 min to 24 hr, preferably 1 hr to 6 hr.

The reaction temperature is generally 0 to 150° C., preferably 20 to 100° C.

Compound (II-b) can also be produced by directly reacting compound (VI) with compound (VII). This reaction is carried out in the same manner as in the reaction of compound (III) with compound (IV).

Compound (II-c) can be produced by reacting compound (II-a) with compound (VIII).

This reaction is generally carried out in the presence of a base. Examples of the base include inorganic bases, basic salts, aromatic amines, tertiary amines, alkali metal hydrides, metal amides, alkyl metals, aryl metals, metal alkoxides and the like. The base is used generally in an amount of about 1 to 10 mol, preferably 1 to 3 mol, per 1 mol of compound (II-a).

Compound (VIII) is used generally in an amount of 1 to 10 mol, preferably 1 to 3 mol, per 1 mol of compound (II-a).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, ketones, esters, sulfoxides, water and the like, mixed solvents thereof and the like.

While the reaction time varies depending on the reagent and solvent to be used, it is generally 5 min to 48 hr, preferably 10 min to 24 hr.

The reaction temperature is generally −20 to 150° C., preferably 0 to 50° C.

Compound (II-d) can be produced by reacting compound (II-c) with an oxidant.

Examples of the oxidant include hydrogen peroxide, peracetic acid, hydroperoxide, metaperiodic acid salt, metachloroperbenzoic acid, iodosobenzene chloride, iodosobenzene acetate, oxone and the like. When n=1, the oxidant is used generally in an amount of about 0.1 to 1.5 mol, preferably about 0.5 to 1 mol, per 1 mol of compound (II-c), and when n=2, it is used generally in an amount of about 1.5 to 10 mol, preferably about 1.5 to 3 mol, per 1 mol of compound (II-c).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, ketones, esters, water and the like, mixed solvents thereof and the like.

While the reaction time varies depending on the reagent and solvent to be used, it is generally 5 min to 24 hr, preferably 10 min to 24 hr.

The reaction temperature is generally −20 to 100° C., preferably 0 to 50° C.

Compound (II-e) can be produced by reacting compound (II-d) with compound (IX).

This reaction can be carried out in the presence of a base, if desired. Examples of the base include inorganic bases, basic salts, aromatic amines, tertiary amines, alkali metal hydrides, metal amides, alkyl metals, aryl metals, metal alkoxides and the like. The base is used generally in an amount of 1 to 10 mol, preferably 1 to 3 mol, per 1 mol of compound (II-d).

Compound (IX) is used generally in an amount of about 1 to 10 mol, preferably about 1 to 3 mol, per 1 mol of compound (II-d).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, ketones, esters, sulfoxides, water and the like, mixed solvents thereof and the like.

While the reaction time varies depending on the reagent and solvent to be used, it is generally 1 hr to 48 hr, preferably 3 hr to 24 hr.

The reaction temperature is generally −20 to 100° C., preferably 0 to 50° C.

Compound (II-g), which is compound (II) wherein ring Ba is

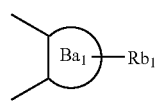

wherein ring $Ba_1$ is a 5- or 6-membered heterocycle optionally substituted and represented by

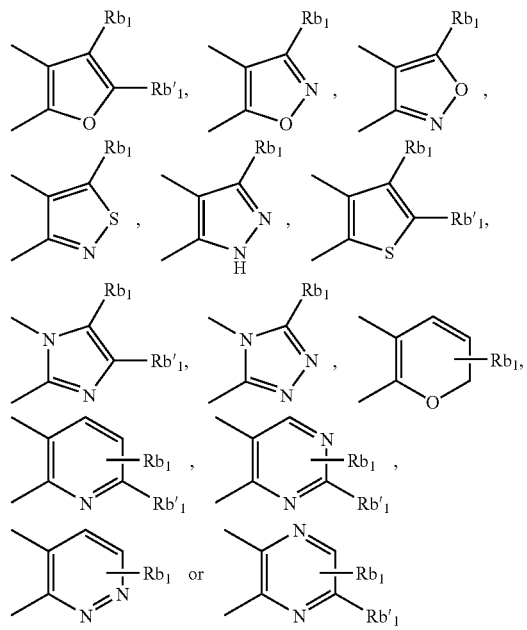

wherein $Rb_1$ is an optionally substituted hydrocarbon group or an optionally substituted heterocyclic group, and $Rb'_1$ is a hydrogen atom, an amino group or a mono-substituted amino group, can also be produced, for example, according to the method shown in the following Reaction Scheme 2 or a method analogous thereto.

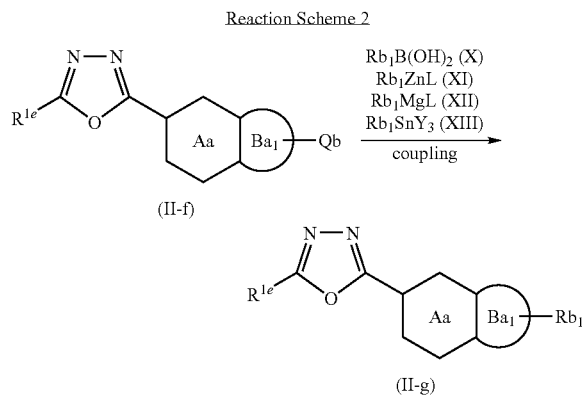

wherein $R^{1e}$ is a hydrogen atom, an optionally substituted hydrocarbon group, an optionally substituted heterocyclic group, an optionally substituted hydroxy group, an optionally substituted amino group or an optionally substituted mercapto group, Qb is a leaving group, L is a halogen atom, Y is an optionally substituted hydrocarbon group, and other symbols are as defined above.

Examples of the leaving group for Qb include a halogen atom (e.g., chlorine, bromine, iodine), an optionally halogenated $C_{1-6}$ alkylsulfonyloxy group (e.g., methylsulfonyloxy, ethylsulfonyloxy, trifluoromethylsulfonyloxy) and the like.

Compound (II-f) can be produced according to the method shown in Reaction Scheme 1 or a method analogous thereto.

Compound (X), compound (XI), compound (XII) and compound (XIII) are commercially easily available, or can be produced according to a method known per se or a method analogous thereto.

Compound (II-g) can be produced by subjecting compound (II-f) to a coupling reaction with compound (X), compound (XI), compound (XII) or compound (XIII).

This reaction is generally carried out in the presence of a catalyst and a base. Examples of the catalyst include palladium(II)acetate, dichlorobis(triphenylphosphine)palladium(II), tetrakis(triphenylphosphine)palladium(0) and the like. The catalyst is used generally in an amount of 0.01 to 1 mol, preferably 0.02 to 0.1 mol, per 1 mol of compound (II-f). Examples of the base include inorganic bases, basic salts, metal alkoxides and the like. The base is used generally in an amount of 2 to 10 mol, preferably 2 to 5 mol, per 1 mol of compound (II-f).

This reaction can be carried out by adding a phosphine ligand, if desired. Examples of the phosphine ligand include tri-tert-butylphosphine, 2-(di-tert-butylphosphino)biphenyl, 2-(dicyclohexylphosphino)biphenyl, triphenylphosphine and the like. The phosphine ligand is used generally in an amount of 2 mol, per 1 mol of the catalyst.

Compound (X), compound (XI), compound (XII) or compound (XIII) is used generally in an amount of 1 to 10 mol, preferably 1 to 3 mol, per 1 mol of compound (II-f).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, ketones, esters, sulfoxides, water and the like, mixed solvents thereof and the like.

While the reaction time varies depending on the reagent and solvent to be used, it is generally 30 min to 72 hr, preferably 1 hr to 48 hr.

The reaction temperature is generally 20 to 200° C., preferably 50 to 120° C.

The following compound (II-h), compound (II-i) or compound (II-j), which is compound (II) wherein ring Ba is a 5- or 6-membered heterocycle optionally substituted and represented by

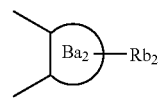

wherein ring $Ba_2$ is

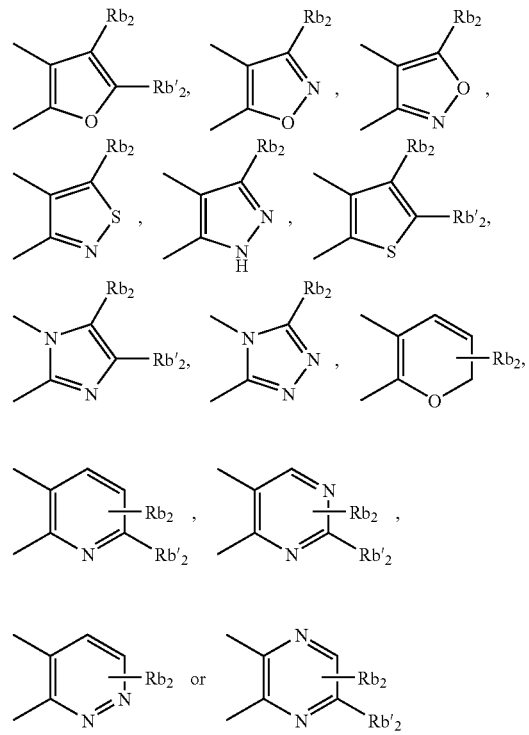

wherein $Rb_2$ is an optionally substituted carboxyl group or an optionally substituted carbamoyl group, and $Rb'_2$ is a hydrogen atom, an amino group, or a mono-substituted amino group, can also be produced, for example, according to the method shown in the following Reaction Scheme 3 or a method analogous thereto.

Reaction Scheme 3

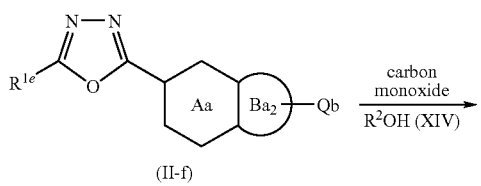

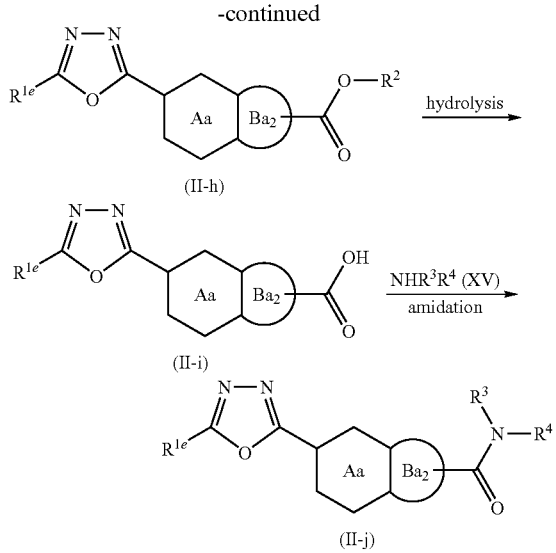

wherein R² is an optionally substituted hydrocarbon group, R³ and R⁴ are the same or different and each is a hydrogen atom, an optionally substituted hydrocarbon group, an optionally substituted heterocyclic group, an optionally substituted hydroxy group or an optionally substituted amino group, and other symbols are as defined above.

Compound (II-f) can be produced according to the method shown in Reaction Scheme 1 or a method analogous thereto.

Compound (XIV) and (XV) are commercially easily available, or can be produced according to a method known per se or a method analogous thereto.

Compound (II-h) can be produced by subjecting compound (II-f) to carbonylation reaction using compound (XIV) as a solvent.

This reaction is generally carried out in the presence of a catalyst and a base under carbon monoxide atmosphere. Examples of the catalyst include palladium(II)acetate, dichlorobis(triphenylphosphine)palladium(II), tetrakis (triphenylphosphine)palladium(0) and the like. The catalyst is used generally in an amount of 0.01 to 1 mol, preferably 0.02 to 0.1 mol, per 1 mol of compound (II-f). Examples of the base include tertiary amines and the like. The base is used generally in an amount of 2 to 10 mol, preferably 2 to 5 mol, per 1 mol of compound (II-f).

This reaction can be carried out by adding a phosphine ligand, if desired. Examples of the phosphine ligand include tri-tert-butylphosphine, 2-(di-tert-butylphosphino)biphenyl, 2-(dicyclohexylphosphino)biphenyl, triphenylphosphine and the like. The phosphine ligand is used generally in an amount of 2 mol, per 1 mol of the catalyst.

This reaction is carried out using compound (XIV) as a solvent. If desired, this reaction can also be carried out using a mixed solvent of compound (XIV) and ether, hydrocarbon, amide, halogenated hydrocarbon, nitrile or the like as a solvent.

While the reaction time varies depending on the reagent and solvent to be used, it is generally 1 hr to 72 hr, preferably 6 hr to 24 hr.

The reaction temperature is generally 20 to 200° C., preferably 50 to 150° C.

Compound (II-i) can be produced by subjecting compound (II-h) to hydrolysis using an acid or a base.

Examples of the acid include organic acids, mineral acids, Lewis acids and the like. Examples of the base include inorganic bases, basic salts, metal alkoxides, aromatic amines, tertiary amines and the like. The acid or base is used generally in an amount of 0.5 to 50 mol, preferably 0.5 to 10 mol, per 1 mol of compound (II-h).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, ketones, organic acids, water and the like, mixed solvents thereof and the like.

The reaction time is generally 10 min to 60 hr, preferably 10 min to 12 hr. The reaction temperature is generally −10 to 200° C., preferably 0 to 120° C.

Compound (II-j) can be produced by reacting compound (II-i) or a reactive derivative with compound (XV) or a salt thereof.

This reaction is carried out in the same manner as in the reaction of compound (III) with compound (IV) or a reactive derivative, as shown in Reaction Scheme 1.

The following compound (II-k), compound (II-l) or compound (II-m), which is compound (II) wherein ring Ba is a 5- or 6-membered heterocycle optionally substituted and represented by

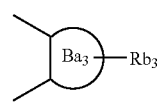

wherein ring Ba₃ is

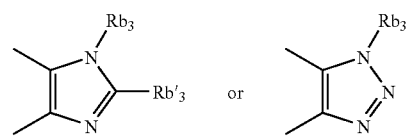

wherein Rb₃ is a hydrogen atom, an optionally substituted hydrocarbon group or an optionally substituted heterocyclic group, and Rb'₃ is a hydrogen atom, an amino group or a mono-substituted amino group,
can also be produced, for example, according to the method shown in the following Reaction Scheme 4 or a method analogous thereto.

Reaction Scheme 4

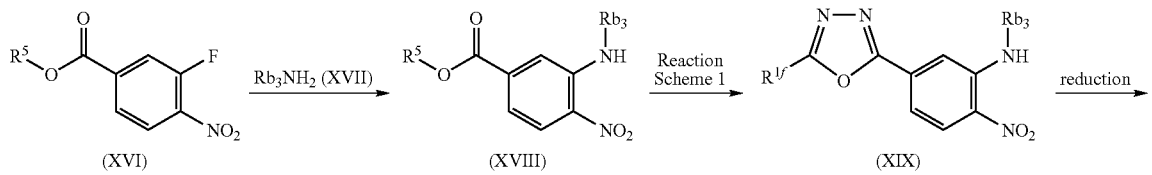

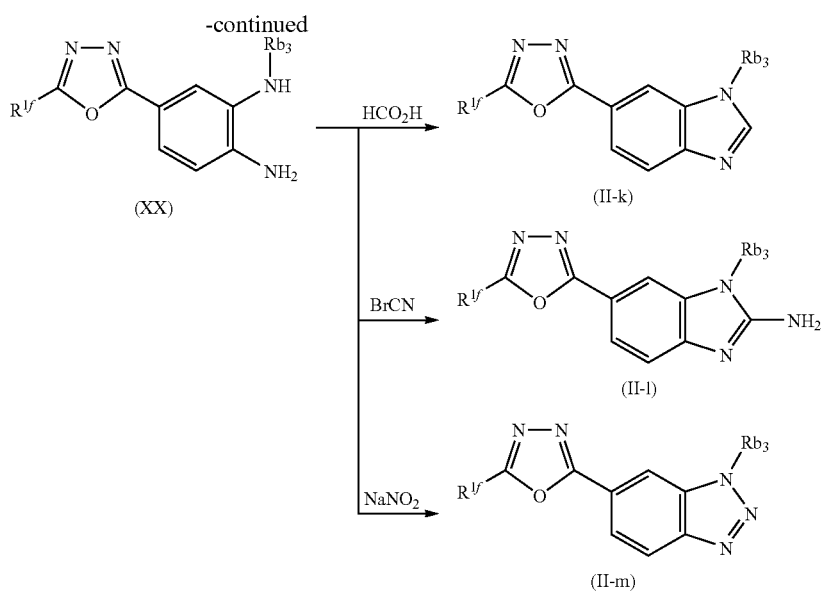

wherein $R^{1f}$ is a hydrogen atom, an optionally substituted hydrocarbon group, an optionally substituted heterocyclic group, an optionally substituted hydroxy group, an optionally substituted amino group or an optionally substituted mercapto group, $R^5$ is a hydrogen atom, an optionally substituted hydrocarbon group or an optionally substituted heterocyclic group, and other symbols are as defined above.

Compound (XVI) and compound (XVII) are commercially easily available, or can be produced according to a method known per se or a method analogous thereto.

Compound (XVIII) can be produced by reacting compound (XVI) with compound (XVII).

This reaction can be carried out in the presence of a base, if desired. Examples of the base include inorganic bases, basic salts, aromatic amines, tertiary amines, alkali metal hydrides and the like. The base is used generally in an amount of 1 to 10 mol, preferably 1 to 3 mol, per 1 mol of compound (XVI). Compound (XVII) is used generally in an amount of 1 to 10 mol, preferably 1 to 3 mol, per 1 mol of compound (XVI).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, esters, sulfoxides, water and the like, mixed solvents thereof and the like.

While the reaction time varies depending on the reagent and solvent to be used, it is generally 1 hr to 48 hr, preferably 3 hr to 24 hr.

The reaction temperature is generally −20 to 150° C., preferably 0 to 100° C.

Compound (XIX) can be produced from compound (XVIII), according to the method shown in Reaction Scheme 1 or a method analogous thereto.

Compound (XX) can be produced by subjecting compound (XIX) to reduction.

When hydrogen source is used as a reducing agent, this reaction is carried out in the presence of a catalyst. Examples of the hydrogen source include hydrogen, hydrazine, formic acid, ammonium formate, 1,4-cyclohexadiene and the like. When hydrogen is used as a hydrogen source, the pressure is generally 1 to 10 atm, preferably 1 to 3 atm. When hydrazine, formic acid or ammonium formate is used as a hydrogen source, the hydrogen source is used generally in an amount of 1 to 500 g, preferably 5 to 100 g, per 1 g of compound (XIX). Examples of the catalyst include platinum oxide, palladium; palladium which is supported by activated carbon, barium sulfate, calcium carbonate and the like, ruthenium, rhodium, iridium, Raney-nickel, and the like. The catalyst is used generally in an amount of 0.01 to 1 g, preferably 0.1 to 0.5 g, per 1 g of compound (XIX).

This reaction is advantageously carried out using a solvent inert to the reaction. The solvent is not particularly limited as long as the reaction proceeds, and preferable examples thereof include solvents such as alcohols, ethers, hydrocarbons, amides, nitriles, esters, organic acids, water and the like, mixed solvents thereof and the like.

The reaction temperature is generally 0 to 100° C., preferably 20 to 60° C.

The reaction time is generally 30 min to 100 hr, preferably 1 to 24 hr.

When metal is used as a reducing agent, this reaction is carried out in the presence of an acid. Examples of the metal include iron, zinc and the like. The metal is used generally in an amount of 1 to 100 mol, preferably 1 to 20 mol, per 1 mol of compound (XIX). Examples of the acid include organic acids, mineral acids and the like. The acid is used generally in an amount of 1 to 100 g, preferably 5 to 30 g, per 1 g of compound (XIX).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, esters, water and the like, mixed solvents thereof and the like.

The reaction temperature is generally 0 to 100° C., preferably 20 to 60° C.

The reaction time is generally 30 min to 100 hr, preferably 1 to 24 hr.

When sodium hydrosulfite is used as a reducing agent, it is used generally in an amount of 1 to 100 mol, preferably 10 to 30 mol, per 1 mol of compound (XIX).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, esters, water and the like, mixed solvents thereof and the like.

The reaction temperature is generally 0 to 100° C., preferably 20 to 60° C.

The reaction time is generally 30 min to 100 hr, preferably 1 to 24 hr.

Compound (II-k) can be produced by reacting compound (XX) with formic acid.

This reaction is generally carried out without solvent, and can also be carried out using a solvent inert to the reaction. The solvent is not particularly limited as long as the reaction proceeds, and preferable examples thereof include solvents such as alcohols, ethers, hydrocarbons, halogenated hydrocarbons, water and the like, mixed solvents thereof and the like.

The formic acid is used generally in an amount of 5 to 100 g, preferably 5 to 20 g, per 1 g of compound (XX).

The reaction time is generally 1 to 48 hr, preferably 6 to 24 hr.

The reaction temperature is generally 40 to 100° C., preferably 80 to 100° C.

Compound (II-l) can be produced by reacting compound (XX) with cyanogen bromide.

The cyanogen bromide is used generally in an amount of 1 to 10 mol, preferably 1 to 3 mol, per 1 mol of compound (XX).

While the reaction time varies depending on the reagent and solvent to be used, it is generally 30 min to 24 hr, preferably 1 hr to 6 hr.

The reaction temperature is generally 0 to 120° C., preferably 40 to 80° C.

Compound (II-m) can be produced by reacting compound (XX) with sodium nitrite.

This reaction is generally carried out in the presence of an acid. Examples of the acid include organic acids, mineral acids and the like. The acid is used generally in an amount of 5 to 100 mol, preferably 10 to 50 mol, per 1 mol of compound (XX).

The sodium nitrite is used generally in an amount of 1 to mol, preferably 1 to 3 mol, per 1 mol of compound (XX).

This reaction is advantageously carried out using a solvent inert to the reaction. The solvent is not particularly limited as long as the reaction proceeds, and preferable examples thereof include solvents such as alcohols, ethers, hydrocarbons, amides, halogenated hydrocarbons, nitriles, organic acids, water and the like, mixed solvents thereof and the like.

While the reaction time varies depending on the reagent and solvent to be used, it is generally 30 min to 48 hr, preferably 1 hr to 24 hr.

The reaction temperature is generally −20 to 100° C., preferably 20 to 60° C.

Compound (II-n), compound (II-o), compound (II-p) and compound (II-q) can also be produced, for example, according to the method shown in the following Reaction Scheme 5 or a method analogous thereto.

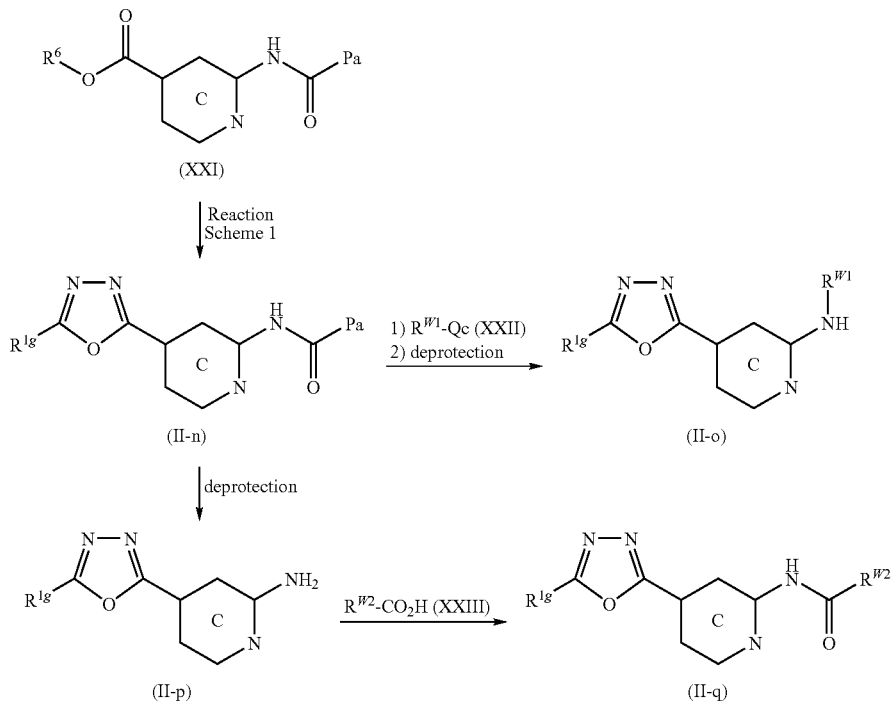

Reaction Scheme 5

This reaction is advantageously carried out using a solvent inert to the reaction. The solvent is not particularly limited as long as the reaction proceeds, and preferable examples thereof include solvents such as ethers, hydrocarbons, amides, halogenated hydrocarbons, nitriles and the like, mixed solvents thereof and the like.

wherein $R^{1g}$ is a hydrogen atom, an optionally substituted hydrocarbon group, an optionally substituted heterocyclic group, an optionally substituted hydroxy group, an optionally substituted amino group or an optionally substituted mercapto group, $R^6$ is a hydrogen atom, an optionally substituted hydrocarbon group or an optionally substituted heterocyclic group, Pa is an optionally substituted hydrocarbon group, an optionally substituted heterocyclic group, a substituted hydroxy group or an optionally substituted amino group, $R^{W1}$ is an optionally substituted hydrocarbon group or an optionally substituted heterocyclic group, $R^{W2}$ is an optionally substituted hydrocarbon group or an optionally substituted heterocyclic group, Qc is a leaving group, and other symbols are as defined above.

Examples of the substituted hydroxy group for Pa include an optionally substituted $C_{1-10}$ alkoxy group, an optionally substituted heterocyclyloxy group, an optionally substituted $C_{6-14}$ aryloxy group, an optionally substituted $C_{7-16}$ aralkyloxy group, a tri-$C_{1-6}$ alkyl-silyloxy group, an optionally substituted $C_{1-6}$ alkylsulfonyloxy group, an optionally substituted heterocyclylsulfonyloxy group and the like.

Examples of the leaving group for Qc include those exemplified as the aforementioned Qa.

Compound (XXI), compound (XXII) and compound (XXIII) are commercially easily available, or can be produced according to a method known per se or a method analogous thereto.

Compound (II-n) can be produced from compound (XXI), according to the method shown in Reaction Scheme 1 or a method analogous thereto.

Compound (II-o) can also be produced by reacting compound (II-n) with compound (XXII), and subjecting the obtained compound to deprotection.

The reaction of compound (II-n) with compound (XXII) is carried out in the same manner as in the reaction of compound (II-a) with compound (VII), as shown in Reaction Scheme 1.

The deprotection is carried out in the same manner as in the deprotection of compound (V), as shown in Reaction Scheme 1.

Compound (II-p) can be produced by subjecting compound (II-n) to deprotection.

This reaction is carried out in the same manner as in the deprotection of compound (V), as shown in Reaction Scheme 1.

Compound (II-q) can be produced by reacting compound (II-p) with compound (XXIII) or a reactive derivative.

This reaction is carried out in the same manner as in the reaction of compound (III) with compound (IV) or a reactive derivative, as shown in Reaction Scheme 1.

Compound (II-s) can also be produced, for example, according to the following Reaction Scheme 6 or a method analogous thereto.

Reaction Scheme 6

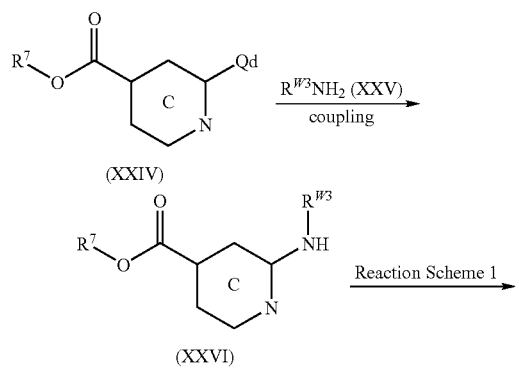

(XXIV)

(XXVI)

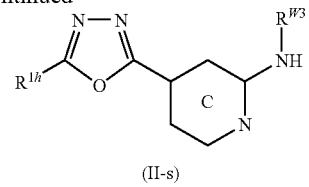

(II-s)

wherein $R^{1h}$ is a hydrogen atom, an optionally substituted hydrocarbon group, an optionally substituted heterocyclic group, an optionally substituted hydroxy group, an optionally substituted amino group, or an optionally substituted mercapto group, $R^7$ is a hydrogen atom, an optionally substituted hydrocarbon group or an optionally substituted heterocyclic group, $R^{W3}$ is an acyl group, an optionally substituted hydrocarbon group or an optionally substituted heterocyclic group, Qd is a leaving group, and other symbols are as defined above.

Examples of the leaving group for Qd include a halogen atom (e.g., chlorine, bromine, iodine), an optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group optionally substituted by $C_{1-6}$ alkyl (e.g., benzenesulfonyloxy, 4-toluenesulfonyloxy) and the like, with preference given to a halogen atom.

Compound (XXIV) and compound (XXV) are commercially easily available, or can be produced according to a method known per se or a method analogous thereto.

Compound (XXVI) can be produced by subjecting, compound (XXIV) to a coupling reaction with compound (XXV).

This reaction is generally carried out in the presence of a catalyst and a base. Examples of the catalyst include palladium(II)acetate, tris(dibenzylideneacetone)dipalladium(0), copper iodide(I) and the like. The catalyst is used generally in an amount of 0.01 to 1 mol, preferably 0.02 to 0.1 mol, per 1 mol of compound (XXIV). Examples of the base include basic salts, metal alkoxides and the like. The base is used generally in an amount of 1 to 10 mol, preferably 1 to 3 mol, per 1 mol of compound (XXIV).

When palladium catalyst is used as a catalyst, this reaction can be carried out by adding a phosphine ligand, if desired. Examples of the phosphine ligand include tri-tert-butylphosphine, 2,2'-bis(diphenylphosphino)-1,1'-binaphthyl, 2-(dicyclohexylphosphino)biphenyl, triphenylphosphine and the like. The phosphine ligand is used generally in an amount of 2 mol, per 1 mol of the catalyst.

When copper iodide(I) is used as a catalyst, this reaction is carried out in the presence of a diamine ligand. Examples of the diamine ligand include (±)-trans-1,2-diaminocyclohexane, N,N'-dimethylethylenediamine and the like. The diamine ligand is used generally in an amount of 2 mol, per 1 mol of the catalyst.

Compound (XXV) is used generally in an amount of 1 to 10 mol, preferably 1 to 3 mol, per 1 mol of compound (XXIV).

This reaction is advantageously carried out using a solvent inert to the reaction. The solvent is not particularly limited as long as the reaction proceeds, and preferable examples thereof include solvents such as alcohols, ethers, hydrocarbons, amides, nitriles, sulfoxides and the like, mixed solvents thereof and the like.

While the reaction time varies depending on the reagent and solvent to be used, it is generally 30 min to 72 hr, preferably 1 hr to 48 hr.

The reaction temperature is generally 20 to 200° C., preferably 50 to 120° C.

compound (II-s) can be produced from compound (XXVI), according to the method shown in Reaction Scheme 1 or a method analogous thereto.

Compound (II-t) can also be produced, for example, according to the following Reaction Scheme 7 or a method analogous thereto.

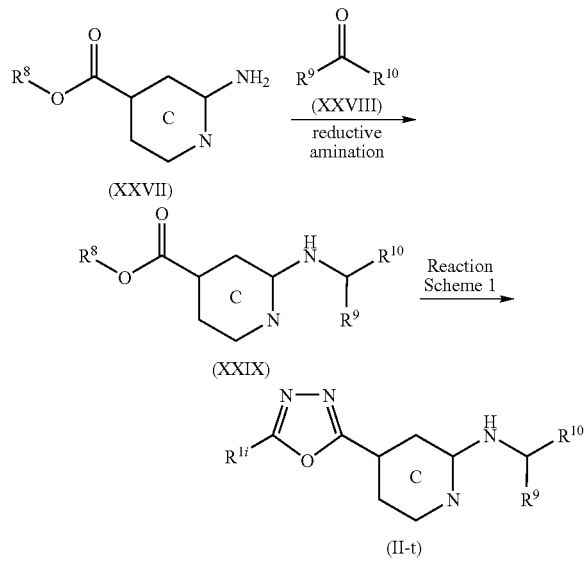

wherein $R^{1i}$ is a hydrogen atom, an optionally substituted hydrocarbon group, an optionally substituted heterocyclic group, an optionally substituted hydroxy group, an optionally substituted amino group, or an optionally substituted mercapto group, $R^8$ is a hydrogen atom, an optionally substituted hydrocarbon group or an optionally substituted heterocyclic group, $R^9$ and $R^{10}$ are the same or different and each is a hydrogen atom, an optionally substituted hydrocarbon group or an optionally substituted heterocyclic group, and other symbols are as defined above.

Compound (XXVII) and compound (XXVIII) are commercially easily available, or can be produced according to a method known per se or a method analogous thereto.

Compound (XXIX) can be produced by subjecting compound (XXVII) to a reductive amination reaction with compound (XXVIII).

This reaction is generally carried out in the presence of an acid. Examples of the acid include organic acids, mineral acids and the like. The acid is used generally in an amount of 0.5 to 50 mol, preferably 0.5 to 10 mol, per 1 mol of compound (XXVII).

Examples of the reducing agent include sodium borohydride, sodium cyanoborohydride, sodium triacetoxyborohydride and the like. The reducing agent is used generally in an amount of 1 to 50 mol, preferably 1 to 10 mol, per 1 mol of compound (XXVII).

This reaction is advantageously carried out using a solvent inert to the reaction. The solvent is not particularly limited as long as the reaction proceeds, and preferable examples thereof include solvents such as alcohols, ethers, halogenated hydrocarbons, nitriles, esters and the like, mixed solvents thereof and the like.

The reaction temperature is generally 0 to 100° C., preferably 20 to 60° C.

The reaction time is generally 30 min to 100 hr, preferably 1 to 24 hr.

Alternatively, this reaction can also be carried out using a hydrogen source as a reducing agent. In this case, this reaction is carried out in the presence of a catalyst. Examples of the hydrogen source include hydrogen, formic acid, 1,4-cyclohexadiene and the like. When hydrogen is used as a hydrogen source, the pressure is generally 1 to 10 atm, preferably 1 to 3 atm. When formic acid is used as a hydrogen source, the hydrogen source is used generally in an amount of 1 to 500 g, preferably 5 to 100 g, per 1 g of compound (XXVII). Examples of the catalyst include platinum oxide, palladium; palladium which is supported on activated carbon, barium sulfate, calcium carbonate and the like, ruthenium, rhodium, iridium, Raney-nickel, and the like. The catalyst is used generally in an amount of 0.01 to 1 g, preferably 0.1 to 0.5 g, per 1 g of compound (XXVII).

This reaction is advantageously carried out using a solvent inert to the reaction. The solvent is not particularly limited as long as the reaction proceeds, and preferable examples thereof include solvents such as alcohols, ethers, hydrocarbons, amides, nitriles, esters, organic acids and the like, mixed solvents thereof and the like.

The reaction temperature is generally 0 to 100° C., preferably 20 to 60° C.

The reaction time is generally 30 min to 100 hr, preferably 1 to 24 hr.

Compound (II-t) can be produced from compound (XXIX), according to the method shown in Reaction Scheme 1 or a method analogous thereto.

When a substituent that compound A has contains a convertible functional group (e.g., carboxyl group, amino group, hydroxy group, carbonyl group, mercapto group, $C_{1-6}$ alkoxy-carbonyl group, $C_{6-14}$ aryloxy-carbonyl group, $C_{7-16}$ aralkyloxy-carbonyl group, sulfo group, halogen atom etc.), various compounds can be produced by converting such functional groups by a method known per se or a method according thereto.

In the case of a carboxyl group, for example, conversion is possible by a reaction such as esterification, reduction, amidation, conversion reaction to an optionally protected amino group, and the like.

In the case of an amino group, for example, conversion is possible by a reaction such as amidation, sulfonylation, nitrosation, alkylation, arylation, imidation and the like.

In the case of a hydroxy group, for example, conversion is possible by a reaction such as esterification, carbamoylation, sulfonylation, alkylation, arylation, oxidation, halogenation and the like.

In the case of a carbonyl group, for example, conversion is possible by a reaction such as reduction, oxidation, imination (including oximation, hydrazonation), (thio)ketalation, alkylidenation, thiocarbonylation and the like.

In the case of a mercapto group, for example, conversion is possible by a reaction such as alkylation, oxidation and the like.

In the case of a $C_{1-6}$ alkoxy-carbonyl group, a $C_{6-19}$ aryloxy-carbonyl group or a $C_{7-16}$ aralkyloxy-carbonyl group, for example, conversion is possible by a reaction such as reduction, hydrolysis and the like.

In the case of a sulfo group, for example, conversion is possible by a reaction such as sulfonamidation, reduction and the like.

In the case of a halogen atom, for example, conversion is possible by a reaction such as various nucleophilic substitution reactions, various coupling reactions and the like.

In each of the aforementioned reactions, when the compound is obtained in a free form, it may be converted to a salt according to a conventional method, and when the compound is obtained as a salt, it can also be converted to a free form or other salt according to a conventional method.

In each reaction of the aforementioned production methods of compound A and each reaction of starting material compound syntheses, when a starting material compound has an amino group, a carboxyl group or a hydroxy group as a substituent, a protecting group generally used in peptide chemistry and the like may be introduced into these groups. By removal of the protecting group as necessary after the reaction, the objective compound can be obtained.

As the amino-protecting group, for example, formyl group; $C_{1-6}$ alkyl-carbonyl group (e.g., acetyl, ethylcarbonyl etc.), phenylcarbonyl group, $C_{1-6}$ alkyl-oxycarbonyl group (e.g., methoxycarbonyl, ethoxycarbonyl, tert-butoxycarbonyl (Boc) etc.), allyloxycarbonyl (Alloc) group, phenyloxycarbonyl group, fluorenylmethoxycarbonyl (Fmoc) group, $C_{7-10}$ aralkyl-carbonyl group (e.g., benzylcarbonyl etc.), $C_{7-10}$ aralkyl-oxycarbonyl group (e.g., benzyloxycarbonyl(Z) etc.), $C_{7-10}$ aralkyl group (e.g., benzyl etc.), trityl group, phthaloyl group, N,N-dimethylaminomethylene group etc., each optionally having substituent(s), and the like can be used. As these substituents, phenyl group, halogen atom (e.g., fluorine, chlorine, bromine, iodine etc.), $C_{1-6}$ alkyl-carbonyl group (e.g., methylcarbonyl, ethylcarbonyl, butylcarbonyl etc.), nitro group etc. can be used. The number of the substituent(s) is about 1 to 3.

As the carboxyl-protecting group, for example, $C_{1-6}$ alkyl group (e.g., methyl, ethyl, n-propyl, isopropyl, n-butyl, tert-butyl etc.), allyl group, benzyl group, phenyl group, trityl group, trialkylsilyl group, each optionally having substituent(s), and the like can be used. As these substituents, halogen atom (e.g., fluorine, chlorine, bromine, iodine etc.), formyl group, $C_{1-6}$ alkyl-carbonyl group (e.g., acetyl, ethylcarbonyl, butylcarbonyl etc.), nitro group and the like can be used. The number of the substituent(s) is about 1 to 3.

As the hydroxyl-protecting group, for example, $C_{1-6}$ alkyl group (e.g., methyl, ethyl, n-propyl, isopropyl, n-butyl, tert-butyl etc.), $C_{7-10}$ aralkyl group (e.g., benzyl etc.), formyl group, $C_{1-6}$ alkyl-carbonyl group (e.g., acetyl, ethylcarbonyl etc.), benzoyl group, $C_{7-10}$ aralkyl-carbonyl group (e.g., benzylcarbonyl etc.), tetrahydropyranyl group, furanyl group, silyl group, each optionally having substituent(s), and the like can be used. As these substituents, halogen atom (e.g., fluorine, chlorine, bromine, iodine etc.), $C_{1-6}$ alkyl group (e.g., methyl, ethyl, n-propyl etc.), phenyl group, $C_{7-10}$ aralkyl group (e.g., benzyl etc.), $C_{1-6}$ alkoxy group (e.g., methoxy, ethoxy, n-propoxy etc.), nitro group and the like can be used. The number of the substituent(s) is about 1 to 4.

The thus-obtained compound A can be isolated and purified by a known means, for example, solvent extraction, liquid conversion, phase transfer, crystallization, recrystallization, chromatography and the like.

Each starting material compound used for the production of compound A can also be isolated and purified by a known means such as those mentioned above and the like. It may also be used as a starting material in the form of a reaction mixture in the next step without isolation.

The solvent to be used for the above-mentioned recrystallization may be, for example, water, alcohols, ethers, hydrocarbons, amides, halogenated hydrocarbons, nitriles, ketones, esters, sulfoxides, organic acids and the like. These solvents may be used alone, or two or more kinds of solvents may be mixed at a suitable ratio, for example, 1:1-1:10, and used.

When compound A is present as a configurational isomer (stereoisomer), diastereomer, conformer or the like, they can be respectively isolated by a known means. When compound A is an optically active form, a racemate can be separated into a (+) form and a (−) form by a general optical resolution means.

When compound A contains optical isomer, stereoisomer, positional isomer, rotamer or tautomer, each of these can also be contained as compound A, as well as can be obtained as a single product by a synthesis method and a separation method known per se.

For example, the method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENALTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound A contains hydroxy group, or primary or secondary amino group in a molecule, the compound and an optically active organic acid (e.g., MTPA [α-methoxy-α-(trifluoromethyl) phenylacetic acid], (−)-menthoxyacetic acid, etc.) and the like are subjected to condensation reaction to give diastereomers in the ester form or in the amide form, respectively. When compound A has a carboxyl group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

A salt of compound A can be produced by a method known per se. For example, when compound A is a basic compound, it can be produced by adding an inorganic acid or organic acid, or when compound A is an acidic compound, by adding an organic base or inorganic base.

Compound A may be a hydrate, and both hydrate and non-hydrate are encompassed in the scope of the present invention. Compound A may be labeled with an isotope (e.g., $^{3}H$, $^{14}C$, $^{35}S$, $^{125}I$ and the like) or the like.

Since the GSK-3 inhibitor of the present invention selectively inhibits GSK-3 and shows low toxicity and a fewer side effects, it is useful as a safe pharmaceutical product. The GSK-3 inhibitor of the present invention shows a superior GSK-3 selective inhibitory action for a mammal (e.g., mouse, rat, hamster, rabbit, cat, dog, bovine, sheep, monkey, human etc.) and is superior in (oral) absorbability, (metabolic) stability and the like. Therefore, it can be used as an agent for the prophylaxis or treatment of GSK-3 related pathology or diseases, for example, metabolic diseases (e.g., diabetes (type 1 diabetes, type 2 diabetes, gestational diabetes etc.), impaired glucose tolerance, obesity, diabetic neuropathy, diabetic retinopathy, diabetic nephropathy, lipid metabolism abnormalities (hypertriglyceridemia, hypercholesterolemia, hypo-HDL-emia, postprandial hyperlipemia etc.) and the like), circulatory diseases (e.g., hypertension, cardiac hypertrophy, angina pectoris, arteriosclerosis and the like), inflammatory diseases (e.g., allergy, asthma, rheumatism, sepsis, psoriasis, colitis, Crohn's disease, COPD etc.), osteoarthritis, liver cirrhosis, alcoholic hepatitis, osteoporosis, cancer and alopecia, and an agent for preventing the progress from impaired glucose tolerance to diabetes.

In the area of neurological diseases, the GSK-3 inhibitor has a neural stem cell differentiation-promoting action. Accordingly, the GSK-3 inhibitor can be used as an agent for the prophylaxis, or treatment of neurodegenerative diseases such as Alzheimer's disease, mild cognitive impairment (MCI), Huntington's chorea, Parkinson's disease, epilepsy, amyotrophic lateral sclerosis (ALS), multiple sclerosis, cerebellum spinal cord denaturation, Pick disease, peripheral nerve disorders and the like and mental diseases such as schizophrenia, depression, anxiety, bipolar disorder, PTSD (posttraumatic stress disorder; hereinafter sometimes to be abbreviated to PTSD) and the like. Based on cell protection action and/or function regeneration action, it can be used as an agent for the prophylaxis or treatment of ischemic diseases such as cerebral infarction, myocardial infarction and the like. Particularly preferred is an agent for the prophylaxis or treatment of diabetes or neurodegenerative disease.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

Compound A of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

When compound A of the present invention is applied to each of the above-mentioned diseases, it can be used in an appropriate combination with a pharmaceutical agent or a treatment method generally employed for the disease. For example, acetylcholine esterase inhibitors (e.g., donepezil, rivastigmine, galanthamine, zanapezil (TAK-147) etc.), anti-dementia agents (memantine etc.), inhibitors of β amyloid protein production, secretion, accumulation, coagulation and/or deposition, β secretase inhibitors (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl) methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline etc.), other therapeutic drug for Parkinson's disease [(e.g., dopamine receptor agonists (L-DOPA, bromocriptine, pergolide, talipexole, pramipexole, Cabergoline, adamantadine etc.), monoamine oxidase (MAO) inhibitors (deprenyl, Selgiline (selegiline), remacemide, riluzole etc.), anticholinergic agents (e.g., trihexyphenidyl, biperiden etc.), COMT inhibitors (e.g., entacapone etc.)], therapeutic drug for amyotropic lateral sclerosis (e.g., riluzole etc., neurotrophic factor etc.), therapeutic drug for abnormal behavior, wandering and the like due to the progress of dementia (e.g., sedative drug, antianxiety drug etc.), apoptosis inhibitors (e.g., CPI-1189, IDN-6556, CEP-1347 etc.), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates, etc. thereof), antidepressants (e.g., desipramine, amitriptyline, imipramine, tramadol etc.), anticonvulsants (e.g., lamotrigine etc.), antianxiety drugs (e.g., benzodiazepine etc.), non-steroidal anti-inflammatory drugs (e.g., meloxicam, tenoxicam, indomethacin, ibuprofen, celecoxib, rofecoxib, aspirin, indomethacin etc.), disease-modifying anti-rheumatic drugs (DMARDs), anti-cytokine drugs (TNF inhibitor, MAP kinase inhibitor and the like), steroidal drugs (e.g., dexamethasone, hexestrol, cortisone acetate etc.), therapeutic agents for incontinence or frequent urination (e.g., flavoxate hydrochloride, oxybutynin hydrochloride, propiverine hydrochloride etc.), phosphodiesterase inhibitors (e.g., sildenafil (citrate) etc.), dopamine agonists (e.g., apomorphine etc.), antiarrhythmics (e.g., mexiletine etc.), sex hormones or derivatives thereof (e.g., progesterone, estradiol, estradiol benzoate etc.), therapeutic agents for osteoporosis (e.g., alfacalcidol, calcitriol, elcatonin, calcitonin salmon, estriol, ipriflavone, disodium pamidronate, sodium alendronate hydrate, disodium incadronate etc.), parathyroid hormone (PTH), calcium receptor antagonists and the like can be mentioned. Particularly, a combined use with a β secretase inhibitory agent such as 6-(4-biphenylyl)methoxy-2-[2-(N, N-dimethylamino)ethyl]tetralin hydrochloride.monohydrate etc., and the like is preferable.

In addition, a combined use with a transplantation method of neural stem cell or neural precursor cell, or fetal neural tissue prepared from embryonic stem cell or nervous tissue, and a combined use with a pharmaceutical agent such as an immunosuppressant after the transplantation and the like can be mentioned.

Examples of therapeutic agent for diabetes include insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1 etc.) and the like), insulin sensitizers [e.g., pioglitazone hydrochloride, troglitazone, rosiglitazone or maleate thereof, GI-262570, JTT-501, MCC-555, YM-440, KRP-297, CS-011, FK-614, compounds described in WO99/58510 (e.g., (E)-4-[4-(5-methyl-2-phenyl-4-oxazolyl-methoxy)benzyloxylmino]-4-phenylbutyric acid), NN-622, AZ-242, BMS-298585, ONO-5816, LM-4156, BM-13-1258, MBX-102, GW-1536 etc.], α-glucosidase inhibitors (e.g., voglibose, acarbose, miglitol, emiglitate etc.), biguanides (e.g., phenformin, metformin, buformin etc.), insulin secretagogues [sulfonylurea (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or calcium salt hydrate thereof, GLP-1 etc.], dipeptidyl-peptidase IV inhibitors (e.g., NVP-DPP-278, PT-100, NVP-DPP-728, LAF237 etc.), β3 agonists (e.g., CL-316243, SR-58611-A, UL-TG-307, SB-226552, AJ-9677, BMS-196085, AZ-40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitor, glucose-6-phosphatase inhibitor, glucagon antagonist etc.), SGLUT (sodium-glucose cotransporter) inhibitors (e.g., T-1095 etc.) and the like.

Examples of the therapeutic agents for diabetic complications include aldose reductase inhibitors (e.g., tolrestat, epalrestat, zenarestat, zopolrestat, minalrestat, fidarestat (SNK-860), CT-112 etc.), neurotrophic factors (e.g., NGF, NT-3, BDNF etc.), neurotrophic factor production-secretion promoters [e.g., neurotrophin production-secretion promoters described in WO01/14372 (e.g., 4-(4-chlorophenyl)-2-(2-methyl-1-imidazolyl)-5-[3-(2-methylphenoxy)propyl]oxazole and the like)], PKC inhibitors (e.g., LY-333531 etc.), AGE inhibitors (e.g., ALT946, pimagedine, pyratoxanthine, N-phenacylthiazolium bromide (ALT766), EXO-226 etc.), active oxygen scavengers (e.g., thioctic acid etc.), and cerebral vasodilators (e.g., tiapuride, mexiletine etc.).

Examples of the therapeutic agents for hyperlipidemia include HMG-CoA reductase inhibitors (e.g., pravastatin, simvastatin, lovastatin, atorvastatin, fluvastatin, lipantil, cerivastatin, itavastatin, ZD-4522 or a salt thereof (e.g., sodium salt etc.) and the like), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate and the like), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), ACAT inhibitors (e.g., avasimibe, eflucimibe and the like), anion exchange resins (e.g., colestyramine and the like), probucol, nicotinic acid drugs (e.g., nicomol, niceritrol and the like), ethyl icosapentate, phytosterol (e.g., soysterol, γ oryzanol and the like) and the like.

Examples of the antihypertensive agent include angiotensin converting enzyme inhibitors (e.g., captopril, enalapril, delapril etc.), angiotensin II antagonist (e.g., candesartan cilexetil, losartan, eprosartan, valsartan, telmisartan, irbesartan, tasosartan etc.), calcium antagonists (e.g., manidipine, nifedipine, nicardipine, amlodipine, efonidipine etc.), potassium channel openers (e.g., levcromakalim, L-27152, AL 0671, NIP-121 and the like), clonidine and the like.

Examples of the antiobesity agents include antiobesity agents acting on the central nervous system (e.g., dexfenfluramine, fenfluramine, phentermine, sibutramine, anfepramone, dexamphetamine, mazindol, phenylpropanolamine, clobenzorex etc.), pancreatic lipase inhibitors (e.g., orlistat etc.), β3 agonists (e.g., CL-316243; SR-58611-A, UL-TG-307, SB-226552, AJ-9677, BMS-196085, AZ-40140 etc.), anorectic peptides (e.g., leptin, CNTF (ciliary neurotrophic factor) etc.), cholecystokinin agonists (e.g., lintitript, FPL-15849 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agents include alkylating agents (e.g., cyclophosphamide, ifosfamide etc.), metabolic antagonists (e.g., methotrexate, 5-fluorouracil or derivative thereof etc.), antitumor antibiotics (e.g., mitomycin, adriamycin etc.), plant-derived antitumor agents (e.g., vincristine, vindesine, Taxol etc.), cisplatin, carboplatin, etoposide and the like. Of these, Furtulon and NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the cachexia improving pharmaceutical agent include cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-$\alpha$, LIF, IL-6, oncostatin M and the like.

It is also possible to apply compound A of the present invention to each of the above-mentioned diseases in combination with a biologic (e.g., antibody, vaccine preparation and the like), or as a combination therapy in combination with gene therapy method and the like. Examples of the antibody and vaccine preparation include vaccine preparation to angiotensin II, vaccine preparation to CETP, CETP antibody, TNF$\alpha$ antibody and antibody to other cytokine, amyloid $\beta$ vaccine preparation, type 1 diabetes vaccine (DIAPEP-277 manufactured by Peptor Ltd. and the like), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like. In addition, a combined use with a biological preparation involved in a growth factor such as GH, IGF and the like is possible. Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NF$\kappa$B decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid and the like), a treatment method using a gene relating to an enzyme or protein involved in angiogenesis therapy targeting obstruction of peripheral vessel and the like (e.g., growth factors such as HGF, VEGF etc., and the like), a treatment method using a gene relating to a protein involved in saccharometabolism or insulin resistance, an antisense to cytokine such as TNF and the like, and the like. In addition, it is possible to use compound A in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell and the like) or an artificial organ utilizing tissue engineering (artificial blood vessel and cardiac muscle cell sheet).

Compound A of the present invention or a salt thereof can be administered orally or parenterally as it is or after mixing with a pharmacologically acceptable carrier. As pharmacologically acceptable carriers, various organic or inorganic carrier substances conventionally used as preparation materials can be used, and added as excipient, lubricant, binder and disintegrant for solid preparations; or solvent, solubilizing agents, suspending agent, isotonicity agent, buffer, soothing agent and the like for liquid preparation. Where necessary, preparation additive such as preservative, antioxidant, colorant, sweetening agent and the like can be used.

For the pharmaceutical agent of the present invention containing compound A or a salt thereof, the dosage form for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, drip infusion, suppository and the like. In addition, it is effective to make a sustained release preparation by combining with a suitable base (e.g., polymer of butyric acid, polymer of glycolic acid, copolymer of butyric acid-glycolic acid, a mixture of polymer of butyric acid and polymer of glycolic acid, polyglycerol fatty acid ester etc.).

While the content of compound A or a salt thereof in the pharmaceutical agent of the present invention varies depending on the form of the pharmaceutical preparation, it is generally about 2 to 85 wt %, preferably about 5 to 70 wt %, relative to the whole preparation.

As a method for forming compound A or a salt thereof in the above-mentioned dosage form, a known production method generally used in the pertinent field can be applied. When the above-mentioned dosage form is produced, various preparation additives such as carrier (e.g., excipient, binder, disintegrant, lubricant and the like), sweetening agent, surfactant, suspending agent, emulsifier and the like generally used in the field of preparation are appropriately added in suitable amounts as necessary for production.

When the compound A or a salt thereof is prepared in to a tablet, for example, it can be produced by adding an excipient, a binder, a disintegrant, a lubricant and the like, and when a pill and a granule are to be prepared, they can be produced by adding an excipient, a binder, a disintegrant and the like. When a powder and a capsule are to be prepared, they can be produced by adding an excipient and the like, and when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, crystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound A or a salt thereof is produced in the above-mentioned dosage form, a suitable amount of a colorant, a preservative, an aromatic, a corrigent, a stabilizer, viscous agents and the like typically used in the field of preparation can be added on demand.

The pharmaceutical agent of the present invention containing compound A or a salt thereof is stable and low toxic, and can be used safely. The daily dose varies depending on the condition and body weight of patients, the kind of compound, administration route and the like. For example, in the case of oral administration to patients with diabetes, neurodegenerative disease and the like, the daily dose to an adult (body weight about 60 kg) is about 1 to 1000 mg, preferably about 3 to 300 mg, more preferably about 10 to 200 mg, as an active ingredient (the compound A or a salt thereof), which can be given in a single administration or administered in 2 or 3 portions a day.

When the compound A of the present invention or a salt thereof is administered parenterally, it is generally administered in the form of a liquid (e.g., injection). While the dose varies depending on the subject of administration, target organ, symptom, administration method and the like, it is, for example, about 0.01 mg-about 100 mg, preferably about 0.01-about 50 mg, more preferably about 0.01-about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, i.e., by dissolving, suspending or emulsifying the compound A of the present invention or a salt thereof in a sterilized aqueous solution or oily liquid. As an aqueous solution for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents (e.g., benzyl benzoate, benzyl alcohol and the like) and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like may be added. A prepared injection is generally filled in an ampoule.

When the compound of the present invention is used in combination with other pharmaceutical agent, the administration mode of the compound of the present invention and a combination drug is not particularly limited, and the compound of the present invention and a combination drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

The present invention is explained in detail in the following by referring to Reference Examples, Examples, Preparation Examples and Experimental Examples, which are not to be construed as limitative.

In the following Reference Examples and Examples, "%" means weight %, unless otherwise specified.

The $^1$H-NMR spectrum was determined using tetramethylsilane as an internal standard and represented as δ values in ppm.

Other abbreviations used in the specification mean the following.

s: singlet
d: doublet
t: triplet
q: quartet
m: multiplet
brs: broad singlet
J: coupling constant
Hz: Hertz
$CDCl_3$: deuterated chloroform
$DMSO-d_6$: dimethyl sulfoxide-$d_6$ Room temperature generally means the range of about 10° C.-35° C., but is not particularly limited.

In the present specification, the melting point is measured using, for example, a trace melting point measurement apparatus (YANAKO MP-500D or Buchi B-545) or a DSC (Differential Scanning Calorimetry analysis) apparatus (SEIKO EXSTAR6000) and the like.

In general, the melting point sometimes varies depending on the measurement device, measurement condition and the like. In the present specification, the crystal may show a melting point different from that described in the present specification, as long as it is within the general error range.

REFERENCE EXAMPLE 1 tert-butyl
2-(benzothiazol-6-ylcarbonyl)hydrazinecarboxylate

A solution of benzothiazole-6-carboxylic acid (4.48 g, 25.0 mmol), tert-butyl carbazate (3.63 g, 27.5 mmol), 3-(3-dimethylaminopropyl)-1-ethylcarbodiimide hydrochloride (5.75 g, 30.0 mmol) and 1-hydroxybenzotriazole (4.05 g, 30.0 mmol) in N,N-dimethylformamide (50 mL) was stirred overnight at room temperature. The reaction mixture was diluted with ethyl acetate, washed twice with water and once with saturated brine, dried over anhydrous magnesium sulfate and concentrated under reduced pressure. The residue was purified by basic silica gel column chromatography (ethyl acetate/tetrahydrofuran=2/1), and crystallized from hexane/acetone to give the title compound (5.51 g, yield 75%) as colorless crystals.

melting point 128-129° C.

$^1$NMR (CDCl$_3$) δ 1.52 (9H, s), 6.81 (1H, brs), 7.89 (1H, dd, J=1.7, 8.7 Hz), 8.12 (1H, d, J=8.7 Hz), 8.40 (1H, brs), 8.47 (1H, dd, J=0.6, 1.7 Hz), 9.12 (1H, s).

Elemental analysis (for $C_{13}H_{15}N_3O_3S$)

Calculated (%): C, 53.23; H, 5.15; N, 14.32.

Found (%): C, 53.10; H, 5.13; N, 14.38.

REFERENCE EXAMPLE 2 benzothiazole-6-carbohydrazide trifluoroacetate

A mixture of tert-butyl 2-(benzothiazol-6-ylcarbonyl)hydrazinecarboxylate (5.28 g, 18.0 mmol) and trifluoroacetic acid (20 mL) was stirred at room temperature for 1 hr. Trifluoroacetic acid was evaporated under reduced pressure, and the residue was recrystallized from ethanol to give the title compound (5.18 g, yield 94%) as colorless crystals.

melting point 154-155° C.

$^1$H NMR (DMSO-d$_6$) δ 8.01 (1H, dd, J=1.7, 8.7 Hz), 8.22 (1H, d, J=0.6, 8.7 Hz), 8.74 (1H, dd, J=0.6, 1.7 Hz), 9.60 (1H, s), 11.24 (1H, brs).

Elemental analysis (for $C_{10}H_8F_3N_3O_3S$)

Calculated (%): C, 39.09; H, 2.62; N, 13.68.

Found (%): C, 39.10; H, 2.50; N, 13.75.

REFERENCE EXAMPLE 3

5-(benzothiazol-6-yl)-1,3,4-oxadiazole-2-thiol

A suspension of benzothiazole-6-carbohydrazide trifluoroacetate (4.92 g, 16.0 mmol), carbon disulfide (2.41 mL, 40.0 mmol) and triethylamine (5.58 mL, 40.0 mmol) in ethanol (60 mL) was heated under reflux for 1.5 hr. After cooling, the reaction mixture was diluted with ethyl acetate/tetrahydrofuran, washed with 1M hydrochloric acid and water, and concentrated under reduced pressure. The residue was recrystallized from tetrahydrofuran to give the title compound (3.11 g, yield 83%) as pale-yellow crystals.

melting point 274-275° C.

$^1$H NMR (DMSO-d$_6$) δ 8.03 (1H, dd, J=1.7, 8.7 Hz), 8.26 (1H, dd, J=0.6, 8.7 Hz), 8.81 (1H, dd, J=0.6, 1.7 Hz), 9.59 (1H, s), 14.78 (1H, brs).

Elemental analysis (for $C_9H_5N_3OS$)

Calculated (%): C, 45.94; H, 2.14; N, 17.86.

Found (%): C, 45.81; H, 2.13; N, 17.72.

REFERENCE EXAMPLE 4

3-[3-(trifluoromethyl)phenyl]propanohydrazide

A solution of ethyl 3-[3-(trifluoromethyl)phenyl]propionate (9.85 g, 40.0 mmol) and hydrazine monohydrate (9.70 mL, 200 mmol) in ethanol (50 mL) was heated under reflux overnight. After cooling, the reaction mixture was concentrated under reduced pressure. The residue was diluted with ethyl acetate, washed with saturated brine, dried over anhydrous sodium sulfate, and concentrated under reduced pressure. The residue was purified by basic silica gel column chromatography (ethyl acetate) and recrystallized from hexane/ethyl acetate to give the title compound (7.51 g, yield 81%) as colorless crystals.

melting point 80-81° C.

$^1$NMR (CDCl$_3$) δ 2.44-2.49 (2H, m), 3.02-3.07 (2H, m), 3.87 (2H, d, J=4.0 Hz), 6.65 (1H, brs), 7.36-7.51 (4H, m).

Elemental analysis (for $C_{10}H_{11}F_3N_2O$)

Calculated (%): C, 51.73; H, 4.77; N, 12.06.

Found (%): C, 51.70; H, 4.65; N, 12.26.

REFERENCE EXAMPLE 5

N'-[3-[3-(trifluoromethyl)phenyl]propionyl]benzothiazole-6-carbohydrazide

To a solution of benzothiazole-6-carboxylic acid (358 mg, 2.00 mmol) in tetrahydrofuran (10 mL) was added N,N'-carbonyldiimidazole (341 mg, 2.10 mmol) at room temperature, and the resulting mixture was stirred for 1 hr. To this reaction mixture was added 3-[3-(trifluoromethyl)phenyl]propanohydrazide (557 mg, 2.40 mmol), and the mixture was further stirred at room temperature for 24 hr. The reaction mixture was concentrated under reduced pressure, and ethyl acetate was added to the residue. The precipitate was collected by filtration, purified by basic silica gel column chromatography (tetrahydrofuran) and recrystallized from hexane/tetrahydrofuran to give the title compound (524 mg, yield 67%) as colorless crystals.

melting point 206-207° C.

$^1$H NMR (CDCl$_3$) δ 2.66-2.71 (2H, m), 3.07-3.12 (2H, m), 7.39-7.49 (4H, m), 7.90 (1H, dd, J=1.7, 8.7 Hz), 8.15 (1H, d, J=8.7 Hz), 8.46 (1H, d, J=1.7 Hz), 8.81 (1H, brs), 9.14 (1H, s), 9.27 (1H, brs).

Elemental analysis (for $C_{18}H_{14}F_3N_3O_2S$)

Calculated (%): C, 54.96; H, 3.59; N, 10.68.

Found (%): C, 54.96; H, 3.48; N, 10.65.

REFERENCE EXAMPLE 6

3-[4-methoxy-3-(trifluoromethyl)phenyl]propionic acid

A mixture of 3-[4-methoxy-3-(trifluoromethyl)phenyl] acrylic acid (2.90 g, 11.8 mmol), 10% palladium on carbon (250 mg), ethanol (60 mL) and tetrahydrofuran (40 mL) was stirred under a hydrogen atmosphere (1 kg/cm$^2$) at room temperature overnight. The reaction mixture was filtered, and the filtrate was concentrated under reduced pressure. The residue was purified by silica gel column chromatography (hexane/ethyl acetate=10/1-0/1) to give the title compound (2.40 g, yield 83%) as colorless crystals.

$^1$NMR (CDCl$_3$) δ 2.66 (2H, t, J=7.5 Hz), 2.94 (2H, t, J=7.5 Hz), 3.88 (3H, s), 6.93 (1H, d, J=8.4 Hz), 7.32-7.41 (2H, m).

REFERENCE EXAMPLE 7

N'-[3-[4-methoxy-3-(trifluoromethyl)phenyl]propionyl]benzothiazole-6-carbohydrazide In the same manner as in Reference Example 5 and using 3-[4-methoxy-3-(trifluoromethyl)phenyl]propanohydrazide instead of 3-[3-(trifluoromethyl)phenyl]propanohydrazide, the title compound (yield 81%) was obtained as colorless crystals.

melting point 208-209° C. (recrystallized from hexane/tetrahydrofuran).

$^1$NMR (DMSO-d$_6$) δ 2.45-2.56 (2H, m), 2.81-2.93 (2H, m), 3.82 (0.3H, s), 3.86 (2.7H, s), 7.13 (0.1H, d, J=8.3 Hz), 7.19 (0.9H, d, J=8.3 Hz), 7.45-7.56 (2H, m), 8.02 (1H, dd, J=1.7, 8.5 Hz), 8.14-8.19 (1H, m), 8.67-8.69 (1H, m), 9.53 (0.1H, s), 9.56 (0.9H, s), 9.99 (1H, brs), 10.47 (1H, brs).

Elemental analysis (for C$_{19}$H$_{16}$F$_3$N$_3$O$_3$S)
Calculated (%): C, 53.90; H, 3.81; N, 9.92.
Found (%): C, 53.85; H, 3.89; N, 9.95.

REFERENCE EXAMPLE 8

N'-[3-[3-(trifluoromethyl)phenyl]propanoyl]benzoxazole-6-carbohydrazide

In the same manner as in Reference Example 5 and using benzoxazole-6-carboxylic acid instead of benzothiazole-6-carboxylic acid, the title compound (yield 50%) was obtained as colorless crystals.

$^1$NMR (DMSO-d$_6$) δ 2.59 (2H, t, J=7.8 Hz), 3.00 (2H, t, J=7.8 Hz), 7.51-7.65 (4H, m), 7.89-7.97 (2H, m), 8.26 (1H, s), 8.91 (1H, s), 9.99 (1H, s), 10.47 (1H, s).

Elemental analysis (for C$_{18}$H$_{14}$F$_3$N$_3$O$_3$)
Calculated (%): C, 57.30; H, 3.74; N, 11.14.
Found (%): C, 57.14; H, 3.69; N, 11.20.

REFERENCE EXAMPLE 9

1H-indazole-5-carbohydrazide

A solution of methyl 1H-indazole-5-carboxylate (5.02 g, 28.5 mmol) and hydrazine monohydrate (6.94 mL, 143 mmol) in methanol (50 mL) was heated under reflux for 48 hr. After cooling, the precipitate was collected by filtration, and washed with methanol to give the title compound (4.69 g, yield 93%) as colorless crystals.

melting point 251-252° C.
$^1$H NMR (DMSO-d$_6$) δ 4.48 (2H, s), 7.56 (1H, ddd, J=0.8, 0.9, 8.9 Hz), 7.83 (1H, dd, J=1.5, 8.9 Hz), 8.19 (1H, d, J=0.8 Hz), 8.29 (1H, dd, J=0.9, 1.5 Hz), 9.74 (1H, s), 13.27 (1H, s).

Elemental analysis (for C$_8$H$_8$N$_4$O)
Calculated (%): C, 54.54; H, 4.58; N, 31.80.
Found (%): C, 54.50; H, 4.52; N, 31.85.

REFERENCE EXAMPLE 10

5-(1H-indazol-5-yl)-1,3,4-oxadiazole-2-thiol

A suspension of 1H-indazole-5-carbohydrazide (4.40 g, 25.0 mmol), carbon disulfide (3.76 mL, 62.5 mmol) and triethylamine (4.18 mL, 30.0 mmol) in ethanol (100 mL) was heated under reflux for 7 hr. After cooling, the reaction mixture was poured into water, and acidified with 1M hydrochloric acid. The precipitate was collected by filtration, dried and recrystallized from tetrahydrofuran to give the title compound (5.27 g, yield 97%) as colorless crystals.

melting point 283-284° C.
$^1$H NMR (DMSO-d$_6$) δ 7.71 (1H, m), 7.84 (1H, dd, J=1.5, 8.9 Hz), 8.27 (1H, s), 8.37 (1H, dd, J=0.9, 1.5 Hz), 13.48 (1H, brs), 14.67 (1H, brs).

Elemental analysis (for C$_9$H$_6$N$_4$OS)
Calculated (%): C, 49.53; H, 2.77; N, 25.67.
Found (%): C, 49.43; H, 2.85; N, 25.49.

REFERENCE EXAMPLE 11

N'-[3-[3-(trifluoromethyl)phenyl]propionyl]-1H-indazole-5-carbohydrazide

To a solution of 3-[3-(trifluoromethyl)phenyl]propionic acid (437 mg, 2.00 mmol) and N,N-dimethylformamide (1 drop) in tetrahydrofuran (4 mL) was added oxalyl chloride (0.183 mL, 2.10 mmol) at room temperature, and the resulting mixture was stirred for 30 min. The reaction mixture was added dropwise to a mixture of 1H-indazole-5-carbohydrazide (352 mg, 2.00 mmol), tetrahydrofuran (10 mL) and saturated aqueous sodium hydrogen carbonate solution (10 mL) at room temperature, and the resulting mixture was stirred for 2 hr. The reaction mixture was diluted with ethyl acetate, washed with water and saturated brine, dried over anhydrous magnesium sulfate and concentrated under reduced pressure. The residue was recrystallized from hexane/ethanol to give the title compound (383 mg, yield 51%) as colorless crystals.

melting point 227-228° C.
$^1$NMR (DMSO-d$_6$) δ 2.55-2.60 (2H, m), 2.90-3.02 (2H, m), 7.47-7.65 (5H, m), 7.86 (1H, dd, J=1.7, 8.9 Hz), 8.22-8.23 (1H, m), 8.36-8.38 (1H, m), 9.93 (1H, brs), 10.30 (1H, brs), 13.33 (1H, brs).

Elemental analysis (for C$_{18}$H$_{15}$F$_3$N$_4$O$_2$)
Calculated (%): C, 57.45; H, 4.02; N, 14.89.
Found (%): C, 57.46; H, 4.02; N, 14.88.

REFERENCE EXAMPLE 12

N'-[3-[4-methoxy-3-(trifluoromethyl)phenyl]propionyl]-1H-indazole-5-carbohydrazide In the same manner as in Reference Example 11 and using 3-[4-methoxy-3-(trifluoromethyl)phenyl]propionic acid instead of 3-[3-(trifluoromethyl)phenyl]propionic acid, the title compound (yield 60%) was obtained as colorless crystals.

melting point 224-225° C. (recrystallized from ethanol/water).
$^1$H NMR (DMSO-d$_6$) δ 2.49-2.54 (2H, m), 2.80-2.92 (2H, m), 3.82 (0.3H, s), 3.86 (2.7H, s), 7.12-7.20 (1H, m), 7.44-7.56 (2H, m), 7.59-7.62 (1H, m), 7.83-7.88 (1H, m), 8.22-8.23 (1H, m), 8.35-8.37 (1H, m), 9.92 (1H, brs), 10.29 (1H, brs), 13.34 (1H, brs).

Elemental analysis (for C$_{19}$H$_{17}$F$_3$N$_4$O$_3$)
Calculated (%): C, 56.16; H, 4.22; N, 13.79.
Found (%): C, 56.27; H, 4.21; N, 13.80.

REFERENCE EXAMPLE 13 methyl 1-(methoxymethyl)-1H-indazole-5-carboxylate

To a solution of methyl 1H-indazole-5-carboxylate (5.02 g, 28.5 mmol) in N,N-dimethylformamide (60 mL) was added sodium hydride (60% in oil, 1.26 g, 31.5 mmol) at room temperature, and the resulting mixture was stirred for 10 min. To this reaction mixture was added dropwise a solution of (chloromethyl)methylether (2.39 mL, 31.5 mmol) in tetrahydrofuran (20 mL) at −20° C. over 10 min, and the resulting mixture was allowed to warm to room temperature over 2 hr. The reaction mixture was diluted with ethyl acetate, washed twice with water and once with saturated brine, dried over anhydrous magnesium sulfate and concentrated under reduced pressure. The residue was purified by silica gel column chromatography (hexane/ethyl acetate=2/1), and crystallized from hexane/ethyl acetate to give the title compound (3.62 g, yield 58%) as colorless crystals.

melting point 73-74° C.
$^1$H NMR (CDCl$_3$) δ 3.32 (3H, s), 3.96 (3H, s), 5.73 (2H, s), 7.59 (1H, td, J=0.9, 8.9 Hz), 8.10-8.14 (2H, m), 8.53 (1H, dd, J=0.9, 1.5 Hz).
Elemental analysis (for C$_{11}$H$_{12}$N$_2$O$_3$)
Calculated (%): C, 59.99; H, 5.49; N, 12.72.
Found (%): C, 59.91; H, 5.45; N, 12.82.

REFERENCE EXAMPLE 14

1-(methoxymethyl)-1H-indazole-5-carbohydrazide

In the same manner as in Reference Example 9 and using methyl 1-(methoxymethyl)-1H-indazole-5-carboxylate instead of methyl 1H-indazole-5-carboxylate, the title compound (yield 76%) was obtained as colorless crystals.

melting point 141-142° C. (recrystallized from methanol).
$^1$H NMR (DMSO-d$_6$) δ 3.31 (3H, s), 4.50 (2H, brs), 5.75 (2H, s), 7.80 (1H, td, J=0.8, 8.9 Hz), 7.91 (1H, td, J=1.5, 8.9 Hz), 8.28 (1H, d, J=0.8 Hz), 8.32 (1H, dd, J=0.8, 1.5 Hz), 9.80 (1H, brs).
Elemental analysis (for C$_{10}$H$_{12}$N$_4$O$_2$)
Calculated (%): C, 54.54; H, 5.49; N, 25.44.
Found (%): C, 54.50; H, 5.47; N, 25.48.

REFERENCE EXAMPLE 15

5-[1-(methoxymethyl)-1H-indazol-5-yl]-1,3,4-oxadiazole-2-thiol

In the same manner as in Reference Example 10 and using 1-(methoxymethyl)-1H-indazole-5-carbohydrazide instead of 1H-indazole-5-carbohydrazide, the title compound (yield 96%) was obtained as pale-yellow crystals.

melting point >300° C. (recrystallized from tetrahydrofuran).
$^1$H NMR (DMSO-d$_6$) δ 3.23 (3H, s), 5.79 (2H, s), 7.92 (1H, td, J=1.5, 8.9 Hz), 7.97 (1H, td, J=0.8, 8.9 Hz), 8.35 (1H, d, J=0.8 Hz), 8.40 (1H, dd, J=0.8, 1.5 Hz), 14.72 (1H, brs).
Elemental analysis (for C$_{11}$H$_{10}$N$_4$O$_2$S)
Calculated (%): C, 50.37; H, 3.84; N, 21.36.
Found (%): C, 50.43; H, 3.79; N, 21.37.

REFERENCE EXAMPLE 16

1-(methoxymethyl)-5-[5-[[3-(trifluoromethyl)benzyl]thio]-1,3,4-oxadiazol-2-yl]-1H-indazole A suspension of 5-[1-(methoxymethyl)-1H-indazol-5-yl]-1,3,4-oxadiazole-2-thiol (525 mg, 2.00 mmol), 3-(trifluoromethyl)benzyl chloride (0.372 mL, 2.40 mmol), and potassium carbonate (415 mg, 3.00 mmol) in N,N-dimethylformamide (10 mL) was stirred at room temperature for 5 hr. The reaction mixture was poured into water, the precipitate was collected by filtration, purified by basic silica gel column chromatography (tetrahydrofuran) and recrystallized from hexane/tetrahydrofuran to give the title compound (821 mg, yield 98%) as colorless crystals.

melting point 159-160° C.
$^1$NMR (CDCl$_3$) δ 3.34 (3H, s), 4.57 (2H, s), 5.74 (2H, s), 7.48 (1H, t, J=7.7 Hz), 7.57 (1H, d, J=7.7 Hz), 7.66-7.75 (3H, m) 8.08 (1H, dd, J=1.5, 8.9 Hz), 8.13 (1H, d, J=0.9 Hz), 8.38 (1H, dd, J=0.8, 1.5 Hz).

Elemental analysis (for C$_{19}$H$_{15}$F$_3$N$_4$O$_2$S)
Calculated (%): C, 54.28; H, 3.60; N, 13.33.
Found (%): C, 54.27; H, 3.49; N, 13.44.

REFERENCE EXAMPLE 17

1-(methoxymethyl)-5-[5-[[4-methoxy-3-(trifluoromethyl)benzyl]thio]-1,3,4-oxadiazol-2-yl]-1H-indazole In the same manner as in Reference Example 16 and using 4-methoxy-3-(trifluoromethyl)benzyl bromide instead of 3-(trifluoromethyl)benzyl chloride, the title compound (yield 95%) was obtained as colorless crystals.

melting point 158-159° C. (recrystallized from hexane/tetrahydrofuran).
$^1$NMR (CDCl$_3$) δ 3.34 (3H, s), 3.89 (3H, s), 4.50 (2H, s), 5.74 (2H, s), 6.97 (1H, d, J=8.3 Hz), 7.63-7.69 (3H, m), 8.09 (1H, dd, J=1.5, 8.9 Hz), 8.13 (1H, d, J=0.9 Hz), 8.34 (1H, dd, J=0.8, 1.5 Hz).
Elemental analysis (for C$_{20}$H$_{17}$F$_3$N$_4$O$_3$S)
Calculated (%): C, 53.33; H, 3.80; N, 12.44.
Found (%): C, 53.40; H, 3.79; N, 12.49.

REFERENCE EXAMPLE 18

1H-benzotriazole-5-carbohydrazide

In the same manner as in Reference Example 9 and using ethyl 1H-benzotriazole-5-carboxylate instead of methyl 1H-indazole-5-carboxylate and ethanol instead of methanol, the title compound (yield 95%) was obtained as pale-brown crystals.

melting point 295-296° C. (crystallized from ethanol).
$^1$H NMR (DMSO-d$_6$) δ 4.56 (2H, brs), 7.89-7.96 (2H, m), 8.40 (1H, t, J=1.1 Hz), 9.95 (1H, brs).
Elemental analysis (for C$_7$H$_7$N$_5$O)
Calculated (%): C, 47.46; H, 3.98; N, 39.53.
Found (%): C, 47.20; H, 3.93; N, 39.41.

REFERENCE EXAMPLE 19 methyl 3-(4-methoxyphenyl)imidazo[1,2-a]pyridine-6-carboxylate

A mixture of methyl 3-iodoimidazo[1,2-a]pyridine-6-carboxylate (1.40 g, 4.63 mmol), (4-methoxyphenyl)boronic acid (845 mg, 5.56 mmol), tetrakis(triphenylphosphine)palladium(0) (268 mg, 0.232 mmol), 2 M aqueous sodium carbonate solution (4.63 mL) and 1,2-dimethoxyethane (50 mL) was heated under reflux under an argon atmosphere overnight. After cooling, the reaction mixture was diluted with ethyl acetate, washed with saturated aqueous sodium hydrogen carbonate solution and saturated brine, dried over anhydrous magnesium sulfate and concentrated under reduced pressure. The residue was purified by silica gel column chromatography (hexane/ethyl acetate=1/1-0/1) to give the title compound (730 mg, yield 56%) as colorless crystals.

$^1$H NMR (DMSO-d$_6$) δ 3.85 (3H, s), 3.87 (3H, s), 7.17 (2H, d, J=8.7 Hz), 7.58-7.64 (2H, m), 7.65-7.75 (2H, m), 7.80 (1H, s), 8.90 (1H, t, J=1.2 Hz).

REFERENCE EXAMPLE 20

3-(4-methoxyphenyl)imidazo[1,2-a]pyridine-6-carbohydrazide

In the same manner as in Reference Example 4 and using methyl 3-(4-methoxyphenyl)imidazo[1,2-a]pyridine-6-carboxylate instead of ethyl 3-[3-(trifluoromethyl)phenyl]propionate, the title compound (yield 100%) was obtained as colorless crystals.

$^1$H NMR (DMSO-d$_6$) δ 3.85 (3H, s), 4.78 (2H, brs), 7.15 (2H, d, J=9.0 Hz), 7.60-7.67 (4H, m), 7.74 (1H, s), 8.85 (1H, s), 9.96 (1H, s).

REFERENCE EXAMPLE 21 methyl 3-(2-pyridyl)imidazo[1,2-a]pyridine-6-carboxylate

A mixture of methyl 3-iodoimidazo[1,2-a]pyridine-6-carboxylate (1.00 g, 3.30 mmol), 2-(tri-n-butylstannyl)pyridine (2.44 mg, 6.62 mmol), tetrakis(triphenylphosphine)palladium(0) (381 mg, 0.33 mmol) and toluene (50 mL) was heated under reflux overnight. After cooling, the reaction mixture was diluted with ethyl acetate, washed with saturated aqueous sodium hydrogen carbonate solution and saturated brine, dried over anhydrous magnesium sulfate and concentrated under reduced pressure. The residue was purified by basic silica gel column chromatography (hexane/ethyl acetate=4/1-1/1) to give the title compound (630 mg, yield 75%) as colorless crystals.

$^1$H NMR (DMSO-d$_6$) δ 3.93 (3H, s), 7.34-7.38 (1H, m), 7.80 (2H, d), 7.94 (1H, dt, J=2.1, 6.0 Hz), 8.07-8.10 (1H, m), 8.55 (1H, s), 8.73-8.75 (1H, m), 10.63 (1H, t, J=1.5 Hz).

REFERENCE EXAMPLE 22

3-(2-pyridyl)imidazo[1,2-a]pyridine-6-carbohydrazide

In the same manner as in Reference Example 4 and using methyl 3-(2-pyridyl)imidazo[1,2-a]pyridine-6-carboxylate instead of ethyl 3-[3-(trifluoromethyl)phenyl]propionate, the title compound (yield 57%) was obtained as colorless crystals.

$^1$NMR (DMSO-d$_6$) δ 4.59 (2H, s), 7.35 (1H, brs), 7.76 (2H, s), 7.93-7.95 (1H, m), 8.03-8.06 (1H, m), 8.47 (1H, s), 8.75 (1H, d, J=3.3 Hz), 9.97 (1H, s), 10.39 (1H, s).

REFERENCE EXAMPLE 23 methyl 1,2,4-triazolo[1,5-a]pyridine-7-carboxylate

A mixture of ethyl 2-aminoisonicotinate (2.35 g, 14.14 mmol), N,N-dimethylformamide dimethyl acetal (10 mL) and N,N-dimethylformamide (10 mL) was stirred at 130° C. overnight. After cooling, the reaction mixture was concentrated under reduced pressure, and the residue and pyridine (2.3 mL, 29 mmol) were dissolved in methanol (20 mL). Hydroxyamine-O-sulfonic acid (2.26 g, 20 mmol) was added to this solution at 0° C., and the resulting mixture was stirred at room temperature for 64 hr. The reaction mixture was diluted with ethyl acetate, washed with saturated aqueous sodium hydrogen carbonate solution, water and saturated brine, dried over anhydrous magnesium sulfate and concentrated under reduced pressure.

To a solution of the obtained residue in tetrahydrofuran (70 mL) was added trifluoroacetic anhydride (2.82 g, 13.41 mmol) at 0° C., and the resulting mixture was stirred at room temperature for 30 min, and at 60° C. for 16 hr. The reaction mixture was diluted with ethyl acetate, washed with saturated aqueous sodium hydrogen carbonate solution and saturated brine, dried over anhydrous magnesium sulfate and concentrated under reduced pressure. The residue was purified by silica gel column chromatography (hexane/ethyl acetate=95/5-0/100) and basic silica gel column chromatography (hexane/ethyl acetate=95/5-0/100) and recrystallized from hexane/ethyl acetate to give the title compound (1.01 g, yield 47%) as colorless crystals.

melting point 125-126° C.

$^1$H NMR (CDCl$_3$) δ 4.03 (3H, s), 7.67 (1H, dd, J=1.8, 7.2 Hz), 8.49 (1H, s), 8.50 (1H, dd, J=1.8, 0.9 Hz), 8.67 (1H, dd, J=0.9, 7.2 Hz).

REFERENCE EXAMPLE 24

1,2,4-triazolo[1,5-a]pyridine-7-carbohydrazide

In the same manner as in Reference Example 4 and using methyl 1,2,4-triazolo[1,5-a]pyridine-7-carboxylate instead of ethyl 3-[3-(trifluoromethyl)phenyl]propionate, the title compound (yield 80%) was obtained as pale-yellow crystals.

melting point 244-245° C. (recrystallized from ethanol).

$^1$NMR (DMSO-d$_6$) δ 4.66 (2H, brs), 7.58 (1H, dd, J=1.8, 7.2 Hz), 8.28 (1H, s), 8.61 (1H, s), 9.05 (1H, d, J=7.2 Hz), 10.24 (1H, brs).

REFERENCE EXAMPLE 25

5-(1,2,4-triazolo[1,5-a]pyridine-7-yl)-1,3,4-oxadiazole-2-thiol triethylamine salt A mixture of 1,2,4-triazolo[1,5-a]pyridine-7-carbohydrazide (450 mg, 2.54 mmol), carbon disulfide (0.38 mL, 6.35 mmol), triethylamine (0.44 mL, 3.18 mmol) and ethanol (30 mL) was stirred at 90° C. for 18 hr. The reaction mixture was concentrated under reduced pressure to give the title compound (814 mg, yield 100%) as brown crystals.

$^1$NMR (DMSO-d$_6$) δ 1.18 (9H, t, J=7.2 Hz), 3.11 (6H, q, J=7.2 Hz), 7.57 (1H, dd, J=1.5, 7.2 Hz), 8.03 (1H, dd, J=0.9, 1.5 Hz), 8.58 (1H, s), 9.02 (1H, dd, J=0.9, 7.2 Hz).

REFERENCE EXAMPLE 26

2,3-dihydro-1-benzofuran-5-carbohydrazide

In the same manner as in Reference Example 9 and using methyl 2,3-dihydro-1-benzofuran-5-carboxylate instead of methyl 1H-indazole-5-carboxylate, the title compound (yield 85%) was obtained as colorless crystals.

melting point 148-149° C. (crystallized from methanol).

$^1$H NMR (CDCl$_3$) δ 3.24 (2H, t, J=8.7 Hz), 4.06 (2H, d, J=4.1 Hz), 4.64 (2H, t, J=8.7 Hz), 6.79 (1H, d, J=8.3 Hz), 7.19 (1H, brs), 7.50-7.53 (1H, m), 7.64-7.65 (1H, m).

Elemental analysis (for C$_9$H$_{10}$N$_2$O$_2$)

Calculated (%): C, 60.66; H, 5.66; N, 15.72.

Found (%): C, 60.64; H, 5.71; N, 15.78.

REFERENCE EXAMPLE 27

2-(chloromethyl)-5-(2,3-dihydro-1-benzofuran-5-yl)-1,3,4-oxadiazole

A mixture of 2,3-dihydro-1-benzofuran-5-carbohydrazide (2.02 g, 11.3 mmol) and 2-chloro-1,1,1-trimethoxyethane (7.92 ml, 56.7 mmol) was tightly sealed in a vial, and microwave was irradiated thereon at 160° C. for 5 min. The reaction mixture was recrystallized from hexane to give the title compound (2.01 g, yield 75%) as colorless crystals.

¹H NMR (CDCl₃) δ 3.29 (2H, t, J=8.9 Hz), 4.68 (2H, t, J=8.9 Hz), 4.75 (2H, s), 6.89 (1H, d, J=8.7 Hz), 7.81-7.88 (1H, m), 7.90-7.94 (1H, m).

REFERENCE EXAMPLE 28

2-(2,3-dihydro-1-benzofuran-5-ylcarbonyl)-N-(3-fluorobenzyl)hydrazinecarboxamide A solution of 2,3-dihydro-1-benzofuran-5-carbohydrazide (0.50 g, 2.81 mmol) and 3-fluorobenzyl isocyanate (0.85 g, 5.61 mmol) in pyridine (5 mL) was stirred at room temperature for 3 days. The reaction mixture was diluted with ethyl acetate, washed with water and saturated brine, dried over anhydrous magnesium sulfate and concentrated under reduced pressure. The residue was washed with ethyl acetate to give the title compound (0.60 g, yield 65%) as colorless crystals.
melting point 200-201° C.
¹H NMR (DMSO-d₆) δ 3.21 (2H, t, J=8.7 Hz), 4.25 (2H, d, J=6.0 Hz), 4.60 (2H, t, J=8.7 Hz), 6.83 (1H, d, J=8.3 Hz), 6.96-7.17 (4H, m), 7.27-7.40 (1H, m), 7.68-7.76 (1H, m), 7.81 (1H, s), 7.96 (1H, s), 9.99 (1H, s).
Elemental analysis (for $C_{17}H_{16}FN_3O_3$)
Calculated (%): C, 62.00; H, 4.90; N, 12.76.
Found (%): C, 61.92; H, 4.84; N, 12.69.

REFERENCE EXAMPLE 29

5-(2,3-dihydro-1-benzofuran-5-yl)-1H-tetrazole

A mixture of 2,3-dihydro-1-benzofuran-5-carbonitrile (1.29 g, 8.89 mmol), sodium azide (1.16 g, 17.78 mmol), zinc bromide (1.00 g, 4.45 mmol), 2-propanol (15 mL) and water (30 mL) was stirred at 80° C. for 48 hr. The reaction mixture was basified with an aqueous sodium hydroxide solution, and washed with ethyl acetate. The aqueous layer was acidified with hydrochloric acid, and extracted with ethyl acetate/tetrahydrofuran. The organic layer was washed with saturated brine, dried over anhydrous magnesium sulfate and concentrated under reduced pressure to give the title compound (1.10 g, yield 66%) as colorless crystals.
melting point 199-200° C.
¹H NMR (DMSO-d₆) δ 3.28 (2H, t, J=8.7 Hz), 4.64 (2H, t, J=8.7 Hz), 6.97 (1H, d, J=8.1 Hz), 7.80 (1H, d, J=8.1 Hz), 7.90 (1H, s).

REFERENCE EXAMPLE 30

1-benzofuran-5-carbohydrazide

In the same manner as in Reference Example 9 and using methyl 1-benzofuran-5-carboxylate instead of methyl 1H-indazole-5-carboxylate, the title compound (yield 96%) was obtained as colorless crystals.
¹H NMR (DMSO-d₆) δ4.47 (2H, brs), 7.05 (1H, dd, J=1.1, 2.3 Hz), 7.65 (1H, d, J=8.7 Hz), 7.80 (1H, dd, J=1.5, 8.7 Hz), 8.07 (1H, d, J=2.3 Hz), 8.15 (1H, d, J=1.5 Hz), 9.76 (1H, brs).

REFERENCE EXAMPLE 31

5-(1-benzofuran-5-yl)-1,3,4-oxadiazole-2-thiol

To a solution of 1-benzofuran-5-carbohydrazide (1.50 g, 8.51 mmol) in ethanol (60 mL) were added potassium hydroxide (0.72 g, 12.8 mmol) and carbon disulfide (15.3 mL, 25.5 mmol), and the resulting mixture was stirred at room temperature for 5 hr. The reaction mixture was concentrated under reduced pressure, a mixture of the residue and N,N-dimethylformamide (30 mL) was tightly sealed in a vial, and the microwave was irradiated at 150° C. for 1 min. After cooling, the reaction mixture was acidified with 1M hydrochloric acid, and the mixture was extracted with ethyl acetate. The organic layer was washed with saturated brine, dried over anhydrous magnesium sulfate and concentrated under reduced pressure. The residue was recrystallized from hexane/ethyl acetate to give the title compound (0.66 g, yield 36%) as colorless crystals.
¹H NMR (CDCl₃) δ 6.88 (1H, dd, J=0.9, 2.3 Hz), 7.62 (1H, d, J=8.7 Hz), 7.74 (1H, d, J=2.3 Hz), 7.90 (1H, dd, J=1.7, 8.7 Hz), 8.22 (1H, d, J=1.7 Hz), 10.34 (1H, brs).

REFERENCE EXAMPLE 32

3-(4-methoxyphenyl)-1-benzofuran-5-carbohydrazide

In the same manner as in Reference Example 9 and using methyl 3-(4-methoxyphenyl)-1-benzofuran-5-carboxylate instead of methyl 1H-indazole-5-carboxylate, the title compound (yield 92%) was obtained as colorless crystals.
melting point 184-185° C. (recrystallized from tetrahydrofuran).
¹NMR (DMSO-d₆) δ 3.83 (3H, s), 4.51 (2H, s), 7.07-7.12 (2H, m), 7.69-7.75 (3H, m), 7.88 (1H, dd, J=1.5, 8.7 Hz), 8.35 (1H, d, J=1.5 Hz), 8.36 (1H, s), 9.90 (1H, brs).
Elemental analysis (for $C_{16}H_{14}N_2O_3$)
Calculated (%): C, 68.07; H, 5.00; N, 9.92.
Found (%): C, 68.22; H, 5.16; N, 9.86.

REFERENCE EXAMPLE 33

N'-acetyl-3-(4-methoxyphenyl)-1-benzofuran-5-carbohydrazide

To a solution of 3-(4-methoxyphenyl)-1-benzofuran-5-carbohydrazide (565 mg, 2.00 mmol) and triethylamine (0.418 mL, 3.00 mmol) in tetrahydrofuran (30 mL) was added acetyl chloride (0.213 mL, 3.00 mmol) at room temperature, and the resulting mixture was stirred for 30 min. The reaction mixture was diluted with ethyl acetate, washed with saturated brine, dried over anhydrous magnesium sulfate and concentrated under reduced pressure. The residue was washed with hexane/ethyl acetate (1/1) to give the title compound (613 mg, yield 94%) as colorless crystals.
melting point 219-220° C.
¹H NMR (DMSO-d₆) δ 1.85 (0.3H, s), 1.94 (2.7H, s), 3.83 (3H, s), 7.08-7.13 (2H, m), 7.70-7.80 (3H, m), 7.89-7.95 (1H, m), 8.39 (1H, s), 8.41 (1H, d, J=1.9 Hz), 9.15 (0.1H, s), 9.90 (0.9H, d, J=1.1 Hz), 10.43 (0.9H, d, J=1.1 Hz), 10.73 (0.1H, s).
Elemental analysis (for $C_{18}H_{16}N_2O_4$)
Calculated (%): C, 66.66; H, 4.97; N, 8.64.
Found (%): C, 66.51; H, 5.12; N, 8.61.

REFERENCE EXAMPLE 34

N'-acetyl-1-benzofuran-5-carbohydrazide

In the same manner as in Reference Example 5 and using 1-benzofuran-5-carboxylic acid instead of benzothiazole-6-carboxylic acid and acetohydrazide instead of 3-[3-(trifluoromethyl)phenyl]propanohydrazide, the title compound (yield 85%) was obtained as colorless crystals.

melting point 145-146° C. (recrystallized from ethyl acetate).

$^1$H NMR (DMSO-d$_6$) δ 1.85 (0.3H, s), 1.93 (2.7H, s), 7.09 (1H, dd, J=0.9, 2.3 Hz), 7.69-7.74 (1H, m), 7.84 (1H, dd, J=1.9, 8.7 Hz), 8.11 (0.9H, d, J=2.3 Hz), 8.12 (0.1H, d, J=2.3 Hz), 8.21-8.23 (1H, m), 9.14 (0.9H, brs), 9.89 (0.1H, brs), 10.31 (1H, brs).

Elemental analysis (for C$_{11}$H$_{10}$N$_2$O$_3$)

Calculated (%): C, 60.55; H, 4.62; N, 12.84.

Found (%): C, 60.53; H, 4.58; N, 12.97.

REFERENCE EXAMPLE 35

2-(1-benzofuran-5-yl)-5-methyl-1,3,4-oxadiazole

A solution of N'-acetyl-1-benzofuran-5-carbohydrazide (20.7 g, 36.2 mmol) and p-toluenesulfonyl chloride (36.2 g, 190 mmol) in pyridine (200 mL) was stirred under an argon atmosphere at 80° C. for 16 hr. After cooling, the reaction mixture was diluted with ethyl acetate, washed water, 2 M hydrochloric acid, saturated aqueous sodium hydrogen carbonate solution and saturated brine, dried over anhydrous magnesium sulfate and concentrated under reduced pressure. The residue was purified by basic silica gel column chromatography (tetrahydrofuran) and recrystallized from tetrahydrofuran to give the title compound (16.0 g, yield 84%) as colorless crystals.

melting point 159-160° C.

$^1$H NMR (CDCl$_3$) δ 2.63 (3H, s), 6.86 (1H, dd, J=0.9, 2.3 Hz), 7.61 (1H, td, J=0.8, 8.7 Hz), 7.71 (1H, d, J=2.3 Hz), 8.01 (1H, dd, J=1.7, 8:7 Hz), 8.30 (1H, dd, J=0.6, 1.7 Hz).

Elemental analysis (for C$_{11}$H$_8$N$_2$O$_2$)

Calculated (%): C, 66.00; H, 4.03; N, 13.99.

Found (%): C, 66.07; H, 4.00; N, 13.99.

REFERENCE EXAMPLE 36

2-(3-bromo-1-benzofuran-5-yl)-5-methyl-1,3,4-oxadiazole

To a solution of 2-(1-benzofuran-5-yl)-5-methyl-1,3,4-oxadiazole (14.8 g, 74.0 mmol) in dichloromethane (200 mL) was added dropwise bromine (7.58 mL, 148 mmol) at room temperature, and the resulting mixture was stirred for 15 min. The reaction mixture was washed with 1 M aqueous sodium sulfite solution and saturated brine, dried over anhydrous magnesium sulfate and concentrated under reduced pressure.

To a solution of the obtained residue in tetrahydrofuran (400 mL) was added a solution of potassium hydroxide (85%, 4.88 g, 74.0 mmol) in methanol (40 mL) at room temperature, and the resulting mixture was stirred for 15 min. The reaction mixture was concentrated under reduced pressure, water was added to the residue, and the mixture was extracted with chloroform. The organic layer was washed with saturated brine, dried over anhydrous magnesium sulfate and concentrated under reduced pressure. The residue was recrystallized from tetrahydrofuran to give the title compound (15.6 g, yield 76%) as colorless crystals.

melting point 215-216° C.

$^1$H NMR (CDCl$_3$) δ 2.65 (3H, s), 7.62 (1H, dd, J=0.6, 8.9 Hz), 7.75 (1H, s), 8.09 (1H, dd, J=1.7, 8.9 Hz), 8.24 (1H, dd, J=0.6, 1.7 Hz).

Elemental analysis (for C$_{11}$H$_7$BrN$_2$O$_2$)

Calculated (%): C, 47.34; H, 2.53; N, 10.04.

Found (%): C, 47.39; H, 2.53; N, 10.06.

REFERENCE EXAMPLE 37 methyl 1-(4-methoxyphenyl)-1H-benzimidazole-6-carboxylate

A suspension of methyl 1H-benzimidazole-5-carboxylate (10.4 g, 58.8 mmol), (4-methoxyphenyl)boronic acid (17.9 g, 118 mmol), copper(II) acetate (16.0 g, 88.2 mmol), pyridine (9.54 mL, 118 mmol) and molecular sieves 4A (24.0 g) in dichloromethane (240 mL) was stirred at room temperature for 6 hr. The reaction mixture was filtered, and the filtrate was washed with 5% aqueous ammonia and saturated brine, dried over anhydrous magnesium sulfate and concentrated under reduced pressure. The residue was purified by silica gel column chromatography (dichloromethane/ethyl acetate=5/1) and recrystallized from hexane/ethyl acetate to give the title compound (2.15 g, yield 13%) as colorless crystals.

melting point 112-113° C.

$^1$H NMR (CDCl$_3$) δ 3.91 (3H, s), 3.93 (3H, s), 7.08-7.13 (2H, m), 7.40-7.45 (2H, m), 7.88 (1H, d, J=8.7 Hz), 8.04 (1H, dd, J=1.5, 8.7 Hz), 8.17 (2H, s).

Elemental analysis (for C$_{16}$H$_{14}$N$_2$O$_3$)

Calculated (%): C, 68.07; H, 5.00: N, 9.92.

Found (%): C, 68.04; H, 5.05: N, 9.79.

REFERENCE EXAMPLE 38

1-(4-methoxyphenyl)-1H-benzimidazole-6-carbohydrazide

In the same manner as in Reference Example 9 and using methyl 1-(4-methoxyphenyl)-1H-benzimidazole-6-carboxylate instead of methyl 1H-indazole-5-carboxylate, the title compound (yield 30%) was obtained as colorless crystals.

melting point 196-197° C. (recrystallized from methanol).

$^1$H NMR (CDCl$_3$) δ 3.91 (3H, s), 4.12 (2H, brs), 7.06-7.11 (2H, m), 7.38-7.44 (2H, m), 7.45 (1H, brs), 7.63 (1H, dd, J=1.9, 8.7 Hz), 7.89 (1H, dd, J=0.8, 8.7 Hz), 7.97 (1H, dd, J=0.8, 1.9 Hz), 8.15 (1H, s).

Elemental analysis (for C$_{15}$H$_{14}$N$_4$O$_2$.H$_2$O)

Calculated (%): C, 59.99; H, 5.37; N, 18.66.

Found (%): C, 59.96; H, 5.37; N, 18.61.

REFERENCE EXAMPLE 39

5-[1-(4-methoxyphenyl)-1H-benzimidazol-6-yl]-1,3,4-oxadiazole-2-thiol

A mixture of 1-(4-methoxyphenyl)-1H-benzimidazole-6-carbohydrazide (1.09 g, 3.86 mmol), potassium hydroxide (0.32 g, 5.79 mmol), carbon disulfide (2.31 mL, 38.6 mmol) and ethanol (20 mL) was stirred overnight at room temperature. The reaction mixture was concentrated under reduced pressure, N,N-dimethylformamide (15 ml) was added to the residue, and the resulting mixture was stirred at 100° C. overnight. The reaction mixture was acidified with 1M hydrochloric acid, and the mixture was extracted with ethyl acetate. The organic layer was washed with saturated brine, dried over anhydrous magnesium sulfate and concentrated under reduced pressure. The residue was washed with water to give the title compound (0.66 g, yield 53%) as colorless crystals.

¹H NMR (DMSO-d₆) δ 3.87 (3H, s), 7.22 (2H, d, J=8.9 Hz), 7.65 (2H, d, J=8.9 Hz), 7.77-7.86 (2H, m), 7.89-7.95 (1H, m), 8.66 (1H, s).

REFERENCE EXAMPLE 40 methyl 3-[(4-methoxyphenyl)amino]-4-nitrobenzoate

A solution of methyl 3-fluoro-4-nitrobenzoate (10.0 g, 54.0 mmol) and p-anisidine (13.3 g, 108 mmol) in dimethylsulfoxide (300 mL) was stirred at 70° C. for 3.5 hr. The reaction mixture was diluted with ethyl acetate, washed with water and saturated brine, dried over anhydrous magnesium sulfate and concentrated under reduced pressure. The residue was recrystallized from hexane/tetrahydrofuran to give the title compound (12.9 g, yield 79%) as red crystals.
¹H NMR (DMSO-d₆) δ 3.80 (6H, s), 7.04 (2H, d, J=8.9 Hz), 7.23-7.31 (3H, m), 7.49-7.53 (1H, m), 8.21 (1H, d, J=8.9 Hz), 9.39 (1H, s).

REFERENCE EXAMPLE 41

3-[(4-methoxyphenyl)amino]-4-nitrobenzohydrazide

In the same manner as in Reference Example 9 and using methyl 3-[(4-methoxyphenyl)amino]-4-nitrobenzoate instead of methyl 1H-indazole-5-carboxylate, the title compound (1.92 g, yield 64%) was obtained as dark red crystals.
¹H NMR (DMSO-d₆) δ 3.80 (3H, s), 4.52 (2H, s), 7.02 (2H, d, J=9.0 Hz), 7.11 (1H, dd, J=1.7, 8.9 Hz), 7.28 (2H, d, J=9.0 Hz), 7.39 (1H, d, J=1.7 Hz), 8.14 (1H, d, J=8.9 Hz), 9.40 (1H, s), 9.93 (1H, s).

REFERENCE EXAMPLE 42

5-[5-[2-(3-fluorophenyl)ethyl]-1,3,4-oxadiazol-2-yl]-N-(4-methoxyphenyl)-2-nitroaniline A mixture of 3-[(4-methoxyphenyl)amino]-4-nitrobenzohydrazide (1.60 g, 5.29 mmol), 3-(3-fluorophenyl)propionic acid (0.89 g, 5.29 mmol) and phosphorus oxychloride (5.29 mL) was stirred at 100° C. for 2 hr. The reaction mixture was cooled to 0° C., neutralized with saturated aqueous sodium hydrogen carbonate solution, and extracted with ethyl acetate. The organic layer was washed with saturated brine, dried over anhydrous magnesium sulfate and concentrated. The residue was purified by basic silica gel column chromatography (hexane/ethyl acetate=3/1) to give the title compound (1.51 g, yield 69%) as orange crystals.
¹H NMR (DMSO-d₆) δ 3.16 (2H, t, J=7.3 Hz), 3.30 (2H, t, J=7.3 Hz), 3.81 (3H, s), 7.06 (2H, d, J=9.0 Hz), 7.25-7.30 (1H, m), 7.31 (2H, d, J=9.0 Hz), 7.47 (1H, d, J=1.7 Hz), 7.48-7.61 (3H, m), 7.65 (1H, s), 8.29 (1H, d, J=8.9 Hz), 9.51 (1H, s).

REFERENCE EXAMPLE 43

4-[5-[2-(3-fluorophenyl)ethyl]-1,3,4-oxadiazol-2-yl]-N²-(4-methoxyphenyl)benzene-1,2-diamine To an aqueous solution (5.1 mL) of sodium hydrosulfite (1.15 g, 6.61 mmol) was added a mixed solution of 5-[5-[2-(3-fluorophenyl)ethyl]-1,3,4-oxadiazol-2-yl]-N-(4-methoxyphenyl)-2-nitroaniline (0.20 g, 0.41 mmol), tetrahydrofuran (4.1 mL) and ethanol (2.1 mL) at 0° C., and the resulting mixture was stirred at room temperature for 30 min. A saturated aqueous sodium hydrogen carbonate solution was added to the reaction mixture, and the mixture was extracted with ethyl acetate. The organic layer was washed with saturated brine, dried over anhydrous magnesium sulfate and concentrated. The residue was purified by basic silica gel column chromatography (hexane/ethyl acetate=1/2) to give the title compound (0.12 g, yield 71%) as a yellow oil.
¹H NMR (DMSO-d₆) δ 3.03-3.10 (2H, m), 3.15-3.22 (2H, m), 3.71 (3H, s), 5.50 (2H, s), 6.78 (1H, d, J=8.3 Hz), 6.86 (4H, s), 6.91 (1H, s), 6.96-7.05 (1H, m), 7.07-7.18 (2H, m), 7.25-7.34 (2H, m), 7.43 (1H, d, J=1.9 Hz).

REFERENCE EXAMPLE 44

1-methyl-1H-benzimidazole-6-carbohydrazide

In the same manner as in Reference Example 9 and using methyl 1-methyl-1H-benzimidazole-6-carboxylate instead of methyl 1H-indazole-5-carboxylate, the title compound (yield 65%) was obtained as colorless crystals.
¹H NMR (DMSO-d₆) δ 3.88 (3H, s), 4.52 (2H, brs), 7.65-7.69 (1H, m), 7.70-7.76 (1H, m), 8.09-8.13 (1H, m), 8.30 (1H, s), 9.76 (1H, s).

REFERENCE EXAMPLE 45 methyl 3-[[4-(methylthio)phenyl]amino]-4-nitrobenzoate

In the same manner as in Reference Example 40 and using 4-methylthioaniline instead of p-anisidine, the title compound (yield 100%) was obtained as brown crystals.
¹H NMR (CDCl₃) δ 2.53 (3H, s), 3.89 (3H, s), 7.21 (2H, d, J=8.7 Hz), 7.31-7.34 (3H, m), 7.85 (1H, d, J=1.5 Hz), 8.25 (1H, d, J=8.7 Hz), 9.42 (1H, s).

REFERENCE EXAMPLE 46 methyl 4-amino-3-[[4-(methylthio)phenyl]amino]benzoate

In the same manner as in Reference Example 43 and using methyl 3-[[4-(methylthio)phenyl]amino]-4-nitrobenzoate instead of 5-[5-[2-(3-fluorophenyl)ethyl]-1,3,4-oxadiazol-2-yl]-N-(4-methoxyphenyl)-2-nitroaniline, the title compound (yield 100%) was obtained as a brown oil.
¹H NMR (CDCl₃) δ 2.43 (3H, s), 3.83 (3H, s), 4.22 (2H, s), 5.15 (1H, s), 6.66 (2H, d, J=8.7 Hz), 6.76 (1H, d, J=8.4 Hz), 7.22 (2H, d, J=8.7 Hz), 7.73-7.79 (2H, m).

REFERENCE EXAMPLE 47 methyl 1-[4-(methylthio)phenyl]-1H-benzimidazole-6-carboxylate

A solution of methyl 4-amino-3-[[4-(methylthio)phenyl]amino]benzoate (5.78 g, 20.0 mmol) in formic acid (50 mL) was stirred at 100° C. overnight. After cooling, the reaction mixture was concentrated under reduced pressure. The residue was diluted with ethyl acetate, washed with saturated aqueous sodium hydrogen carbonate solution and saturated brine, dried over anhydrous magnesium sulfate, and concentrated under reduced pressure. The residue was recrystallized from hexane/ethyl acetate to give the title compound (4.44 g, yield 74%) as colorless crystals.
¹H NMR (CDCl₃) δ 2.58 (3H, s), 3.94 (3H, s), 7.42-7.48 (4H, m), 7.88 (1H, d, J=8.4 Hz), 8.05 (1H, dd, J=1.2, 7.2 Hz), 8.20 (2H, d, J=5.2 Hz).

REFERENCE EXAMPLE 48 methyl 1-[4-(methylsulfinyl)phenyl]-1H-benzimidazole-6-carboxylate

To a solution of methyl 1-[4-(methylthio)phenyl]-1H-benzimidazole-6-carboxylate (4.44 g, 14.88 mmol) in dichloromethane (50 mL) was added m-chloroperbenzoic acid (3.07 g, 12.40 mmol) at 0° C., and the resulting mixture was stirred at room temperature for 30 min. Saturated aqueous sodium thiosulfate solution was added to the reaction mixture, and the mixture was stirred at room temperature for 15 min. The organic layer was separated, washed with saturated aqueous sodium hydrogen carbonate solution and saturated brine, dried over anhydrous magnesium sulfate, and concentrated under reduced pressure. The residue was purified by basic silica gel column chromatography (hexane/ethyl acetate=2/1-0/1) to give the title compound (3.89 g, yield 83%) as colorless crystals.

$^1$H NMR (CDCl$_3$) δ 2.85 (3H, s), 3.59 (3H, s), 7.74 (2H, d, J=8.7 Hz), 7.93 (3H, d, J=8.7 Hz), 8.08 (1H, dd, J=1.5, 7.2 Hz), 8.27 (2H, s).

REFERENCE EXAMPLE 49

1-[4-(methylsulfinyl)phenyl]-1H-benzimidazole-6-carbohydrazide

In the same manner as in Reference Example 9 and using methyl 1-[4-(methylsulfinyl)phenyl]-1H-benzimidazole-6-carboxylate instead of methyl 1H-indazole-5-carboxylate, the title compound (yield 100%) was obtained as colorless crystals.

$^1$H NMR (DMSO-d$_6$) δ 2.86 (3H, s), 4.49 (2H, s), 7.83 (2H, s), 7.98 (4H, s), 8.14 (1H, s), 8.77 (1H, s), 9.87 (1H, s).

REFERENCE EXAMPLE 50

1-[4-(methylthio)phenyl]-1H-benzimidazole-6-carbohydrazide

In the same manner as in Reference Example 9 and using methyl 1-[4-(methylthio)phenyl]-1H-benzimidazole-6-carboxylate instead of methyl 1H-indazole-5-carboxylate, the title compound (yield 86%) was obtained as colorless crystals.

$^1$H NMR (DMSO-d$_6$) δ 2.58 (3H, s), 4.47 (2H, s), 7.53 (2H, d, J=8.7 Hz), 7.67 (2H, d, J=8.7 Hz), 7.80 (2H, s), 8.06 (1H, s), 8.65 (1H, s), 9.83 (1H, s).

REFERENCE EXAMPLE 51

N'-acetyl-1-[4-(methylthio)phenyl]-1H-benzimidazole-6-carbohydrazide

To a solution of 1-[4-(methylthio)phenyl]-1H-benzimidazole-6-carbohydrazide (1.0 g, 3.35 mmol) in N,N-dimethylacetamide (5 mL) was added acetyl chloride (262 µL, 3.69 mmol) at 0° C., and the resulting mixture was stirred at room temperature for 1 hr. Ethyl acetate was added to the reaction mixture, the precipitate was collected by filtration and washed with ethyl acetate to give the title compound (1.14 g, yield 100%) as colorless crystals.

$^1$H NMR (DMSO-d$_6$) δ 1.92 (3H, s), 2.58 (3H, s), 7.53 (2H, d, J=8.7 Hz), 7.69 (2H, d, J=8.7 Hz), 7.87 (2H, s), 8.12 (1H, s), 8.82 (1H, s), 9.89 (1H, s), 10.38 (1H, s).

REFERENCE EXAMPLE 52

N'-(cyclopropylcarbonyl)-1-[4-(methylthio)phenyl]-1H-benzimidazole-6-carbohydrazide In the same manner as in Reference Example 51 and using cyclopropylcarbonyl chloride instead of acetyl chloride, the title compound (yield 97%) was obtained as colorless crystals.

$^1$H NMR (DMSO-d$_6$) δ 0.72-0.81 (4H, m), 1.67-1.73 (1H, m), 2.57 (3H, s), 7.53 (2H, d, J=8.7 Hz), 7.67 (2H, d, J=8.7 Hz), 7.85 (2H, s), 8.11 (1H, s), 8.68 (1H, s), 10.11 (1H, s), 10.38 (1H, s).

REFERENCE EXAMPLE 53

1-[4-(methylthio)phenyl]-N'-(3,3,3-trifluoropropanoyl)-1H-benzimidazole-6-carbohydrazide In the same manner as in Reference Example 51 and using 3,3,3-trifluoropropionyl chloride instead of acetyl chloride, the title compound (yield 100%) was obtained as colorless crystals.

$^1$H NMR (DMSO-d$_6$) δ 2.58 (3H, s), 3.41-3.54 (2H, m), 7.53 (2H, d, J=8.7 Hz), 7.68 (2H, d, J=8.7 Hz), 7.87 (2H, s), 8.13 (1H, s), 8.73 (1H, s), 10.37 (1H, s), 10.63 (1H, s).

REFERENCE EXAMPLE 54 quinoline-6-carbohydrazide

In the same manner as in Reference Example 9 and using ethyl quinoline-6-carboxylate instead of methyl 1H-indazole-5-carboxylate and ethanol instead of methanol, the title compound (yield 97%) was obtained as colorless crystals.

melting point 193-194° C. (recrystallized from ethanol).

$^1$H NMR (DMSO-d$_6$) δ 4.60 (2H, brs), 7.61 (1H, dd, J=4.1, 8.3 Hz), 8.06 (1H, d, J=8.9 Hz), 8.15 (1H, dd, J=1.9, 8.9 Hz), 8.45-8.49 (2H, m), 8.98 (1H, dd, J=1.7, 4.1 Hz), 10.01 (1H, brs).

Elemental analysis (for C$_{10}$H$_9$N$_3$O)

Calculated (%): C, 64.16; H, 4.85; N, 22.45.

Found (%): C, 64.16; H, 4.93; N, 22.46.

REFERENCE EXAMPLE 55

5-(6-quinolyl)-1,3,4-oxadiazole-2-thiol

A solution of quinoline-6-carbohydrazide (2.00 g, 10.7 mmol), carbon disulfide (1.61 mL, 26.8 mmol) and triethylamine (1.78 mL, 12.8 mmol) in ethanol (40 mL) was heated under reflux for 4 hr. After cooling, the reaction mixture was poured into water, a saturated aqueous ammonium chloride solution (100 mL) was added, and the mixture was saturated with sodium chloride. The precipitate was collected by filtration and recrystallized from methanol to give the title compound (1.24 g, yield 51%) as pale-yellow crystals.

$^1$H NMR (DMSO-d$_6$) δ 7.67 (1H, dd, J=4.1, 8.3 Hz), 8.18 (2H, d, J=1.1 Hz), 8.60-8.63 (2H, m), 9.03 (1H, dd, J=1.7, 4.1 Hz), 14.92 (1H, brs).

REFERENCE EXAMPLE 56 ethyl 2-[bis(tert-butoxycarbonyl)amino]isonicotinate

To a solution of ethyl 2-aminoisonicotinate (15.45 g, 92.97 mmol) in tetrahydrofuran (300 mL) were added triethylamine (32.22 mL, 232.43 mmol), di-tert-butyl bicarbonate (50.73 g, 232.43 mmol) and 4-dimethylaminopyridine (1.14 g, 9.30 mmol), and the resulting mixture was stirred at room temperature for 15 hr. The reaction mixture was concentrated under reduced pressure, water was added to the residue, and the mixture was extracted with ethyl acetate. The organic layer was washed with saturated brine, dried over anhydrous magnesium sulfate and concentrated under reduced pressure. The residue was purified by silica gel column chromatography (hexane/ethyl acetate=95/5-0/100) to give the title compound (20.35 g, yield 60%) as colorless crystals.

$^1$H NMR (CDCl$_3$) δ 1.42 (3H, t, J=7.2 Hz), 1.45 (18H, s), 4.42 (2H, q, J=7.2 Hz), 7.77 (1H, d, J=5.1 Hz), 7.81 (1H, s), 8.61 (1H, d, J=5.1 Hz).

REFERENCE EXAMPLE 57 tert-butyl[4-(hydrazinocarbonyl)-2-pyridyl]carbamate

In the same manner as in Reference Example 4 and using ethyl 2-[bis(tert-butoxycarbonyl)amino]isonicotinate instead of ethyl 3-[3-(trifluoromethyl)phenyl]propionate, the title compound (yield 88%) was obtained as pale-yellow crystals.
melting point 289-290° C. (recrystallized from ethanol).
$^1$H NMR (DMSO-d$_6$) δ 1.48 (9H, s), 4.58 (2H, s), 7.32 (1H, d, J=5.1 Hz), 8.15 (1H, s), 8.32 (1H, d, J=5.1 Hz), 9.91 (1H, s), 9.98 (1H, s).

REFERENCE EXAMPLE 58 tert-butyl[4-(5-mercapto-1,3,4-oxadiazol-2-yl)-2-pyridyl]carbamate triethylamine salt In the same manner as in Reference Example 25 and using tert-butyl[4-(hydrazinocarbonyl)-2-pyridyl]carbamate instead of 1,2,4-triazolo[1,5-a]pyridine-7-carbohydrazide, the title compound (yield 89%) was obtained as pale-yellow crystals.
$^1$H NMR (DMSO-d$_6$) δ 1.17 (9H, t, J=7.2 Hz), 1.49 (9H, s), 3.08 (6H, q, J=7.2 Hz), 7.33 (1H, dd, J=1.5, 5.1 Hz), 8.19 (1H, s), 8.30 (1H, dd, J=0.6, 5.1 Hz), 8.90 (1H, brs), 9.94 (1H, s).

REFERENCE EXAMPLE 59 tert-butyl[4-[[2-[3-(3-fluorophenyl)propanoyl]hydrazino]carbonyl]-2-pyridyl]carbamate In the same manner as in Reference Example 1 and using 3-(3-fluorophenyl)propionic acid instead of benzothiazole-6-carboxylic acid and tert-butyl[4-(hydrazinocarbonyl)-2-pyridyl]carbamate instead of tert-butyl carbazate, the title compound (yield 60%) was obtained as colorless crystals.
$^1$H NMR (DMSO-d$_6$) δ 1.49 (9H, s), 2.53 (2H, t, J=7.5 Hz), 2.91 (2H, t, J=7.5 Hz), 6.95-7.15 (3H, m), 7.28-7.40 (2H, m), 8.20 (1H, s), 8.38 (1H, d, J=5.1 Hz), 10.01 (2H, brs), 10.58 (1H, brs).

REFERENCE EXAMPLE 60 tert-butyl[4-[[2-[3-[3-(trifluoromethyl)phenyl]propanoyl]hydrazino]carbonyl]-2-pyridyl]carbamate In the same manner as in Reference Example 1 and using 3-[3-(trifluoromethyl)phenyl]propionic acid instead of benzothiazole-6-carboxylic acid and tert-butyl[4-(hydrazinocarbonyl)-2-pyridyl]carbamate instead of tert-butyl carbazate, the title compound (yield 80%) was obtained as colorless crystals.
$^1$H NMR (CDCl$_3$) δ 1.55 (9H, s), 2.68 (2H, t, J=7.5 Hz), 3.12 (2H, t, J=7.5 Hz), 7.30-7.55 (6H, m), 8.29 (1H, s), 8.37 (1H, d, J=4.8 Hz), 8.42 (1H, brs), 9.10 (1H, brs).

REFERENCE EXAMPLE 61 ethyl 2-[(3-phenylpropanoyl)amino]isonicotinate

To a solution of ethyl 2-aminoisonicotinate (4.50 g, 27.08 mmol) and triethylamine (9.0 mL, 64.93 mmol) in tetrahydrofuran (100 mL) was added 3-phenylpropanoyl chloride (8.3 mL, 56.11 mmol) at 0° C., and the resulting mixture was stirred at room temperature for 1 hr. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=95/5-0/100) and recrystallized from hexane/ethyl acetate to give the title compound (6.85 g, yield 85%) as colorless crystals.
melting point 107-108° C.
$^1$H NMR (CDCl$_3$) δ 1.43 (3H, t, J=7.2 Hz), 2.75 (2H, t, J=7.8 Hz), 3.10 (2H, t, J=7.8 Hz), 4.44 (2H, q, J=7.2 Hz), 7.20-7.35 (5H, m), 7.62 (1H, dd, J=1.5, 5.1 Hz), 8.07 (1H, brs), 8.38 (1H, dd, J=0.9, 5.1 Hz), 8.76 (1H, brs).

REFERENCE EXAMPLE 62

2-[(3-phenylpropanoyl)amino]isonicotinic acid

A mixture of ethyl 2-[(3-phenylpropanoyl)amino]isonicotinate (3.41 g, 11.43 mmol), 1 M aqueous sodium hydroxide solution (15 mL), ethanol (20 mL) and tetrahydrofuran (20 mL) was stirred at room temperature for 1 hr. The reaction mixture was neutralized with hydrochloric acid, and the precipitate was collected by filtration and washed with water to give the title compound (3.09 g, yield 100%) as colorless crystals.
melting point 266-267° C.
$^1$H NMR (DMSO-d$_6$) δ 2.74 (2H, t, J=7.5 Hz), 2.92 (2H, t, J=7.5 Hz), 7.12-7.32 (5H, m), 7.50 (1H, dd, J=1.5, 5.1 Hz), 8.46 (1H, dd, J=0.9, 5.1 Hz), 8.58 (1H, s), 10.72 (1H, s).

REFERENCE EXAMPLE 63 benzyl 2-[2-[(3-phenylpropanoyl)amino]isonicotinoyl]hydrazinecarboxylate

In the same manner as in Reference Example 1 and using 2-[(3-phenylpropanoyl)amino]isonicotinic acid instead of benzothiazole-6-carboxylic acid and benzyl carbazate instead of tert-butyl carbazate, the title compound (yield 53%) was obtained as colorless amorphous.
$^1$H NMR (CDCl$_3$) δ 2.74 (2H, t, J=7.5 Hz), 3.04 (2H, t, J=7.5 Hz), 5.22 (2H, s), 7.20-7.45 (12H, m), 8.29 (1H, d, J=5.1 Hz), 8.37 (1H, s), 8.64 (1H, brs), 8.91 (1H, brs).

REFERENCE EXAMPLE 64

N-[4-(hydrazinocarbonyl)-2-pyridyl]-3-phenylpropionamide

A mixture of benzyl 2-[2-[(3-phenylpropanoyl)amino]isonicotinoyl]hydrazinecarboxylate (1.10 g, 2.63 mmol), 10% palladium on carbon (50 mg), methanol (20 mL) and tetrahydrofuran (20 mL) was stirred under a hydrogen atmosphere at room temperature 18 hr. The reaction mixture was filtered, and the filtrate was concentrated to give the title compound (748 mg, yield 100%) as colorless crystals.

$^1$H NMR (DMSO-$d_6$) δ 2.73 (2H, t, J=7.5 Hz), 2.92 (2H, t, J=7.5 Hz), 4.64 (2H, brs), 7.10-7.35 (5H, m), 7.39 (1H, dd, J=1.5, 5.1 Hz), 8.38 (1H, dd, J=0.9, 5.1 Hz), 8.45 (1H, s), 10.02 (1H, brs), 10.63 (1H, s).

REFERENCE EXAMPLE 65

N-[4-(5-mercapto-1,3,4-oxadiazol-2-yl)-2-pyridyl]-3-phenylpropionamide

In the same manner as in Reference Example 3 and using benzyl 2-[2-[(3-phenylpropanoyl)amino]isonicotinoyl]hydrazinecarboxylate instead of benzothiazole-6-carbohydrazide trifluoroacetate, the title compound (yield 64%) was obtained as colorless crystals.

$^1$H NMR (DMSO-$d_6$) δ 2.76 (2H, t, J=7.5 Hz), 2.93 (2H, t, J=7.5 Hz), 7.10-7.30 (5H, m), 7.50 (1H, dd, J=1.5, 5.1 Hz), 8.51 (1H, dd, J=0.9, 5.1 Hz), 8.57 (1H, s), 10.84 (1H, s).

REFERENCE EXAMPLE 66

1H-pyrrolo[2,3-b]pyridine-4-carboxylic acid

A mixture of 1-acetyl-1H-pyrrolo[2,3-b]pyridine-4-carbonitrile (1.80 g, 11.10 mmol), 2 M aqueous sodium hydroxide solution (25 mL) and ethanol (25 mL) was stirred at 90° C. for 16 hr. The reaction mixture was neutralized with hydrochloric acid and diluted with water. The precipitate was collected by filtration, and washed with water and diethyl ether to give the title compound (1.51 g, yield 84%) as pale-yellow crystals.

melting point >300° C.

$^1$H NMR (DMSO-$d_6$) δ 6.87 (1H, dd, J=1.8, 3.3 Hz), 7.56 (1H, d, J=4.8 Hz), 7.65 (1H, t, J=3.3 Hz), 8.34 (1H, d, J=4.8 Hz), 11.95 (1H, brs), 13.31 (1H, brs).

REFERENCE EXAMPLE 67 benzyl 2-(1H-pyrrolo[2,3-b]pyridin-4-ylcarbonyl)hydrazinecarboxylate

In the same manner as in Reference Example 1 and using 1H-pyrrolo[2,3-b]pyridine-4-carboxylic acid instead of benzothiazole-6-carboxylic acid and benzyl carbazate instead of tert-butyl carbazate, the title compound (yield 67%) was obtained as pale-yellow crystals.

melting point 203-204° C. (recrystallized from methanol/diethyl ether).

$^1$H NMR (DMSO-$d_6$) δ 5.15 (2H, s), 6.70-6.85 (1H, m), 7.25-7.50 (6H, m), 7.61 (1H, s), 8.33 (1H, d, J=4.8 Hz), 9.08 (0.2H, brs), 9.46 (0.8H, brs), 10.40 (1H, brs), 11.91 (1H, brs).

REFERENCE EXAMPLE 68

1H-pyrrolo[2,3-b]pyridine-4-carbohydrazide

In the same manner as in Reference Example 64 and using benzyl 2-(1H-pyrrolo[2,3-b]pyridin-4-ylcarbonyl)hydrazinecarboxylate instead of benzyl 2-[2-[(3-phenylpropanoyl)amino]isonicotinoyl]hydrazinecarboxylate, the title compound (yield 72%) was obtained as pale-brown crystals.

melting point 239-240° C. (recrystallized from methanol/tetrahydrofuran/diethyl ether).

$^1$H NMR (DMSO-$d_6$) δ 4.59 (2H, brs), 6.78 (1H, d, J=2.7 Hz), 7.32 (1H, d, J=5.1 Hz), 7.57 (1H, m), 8.27 (1H, d, J=5.1 Hz), 9.82 (1H, brs), 11.82 (1H, brs).

REFERENCE EXAMPLE 69

5-(1H-pyrrolo[2,3-b]pyridin-4-yl)-1,3,4-oxadiazole-2-thiol 5/6 triethylamine salt In the same manner as in Reference Example 25 and using 1H-pyrrolo[2,3-b]pyridine-4-carbohydrazide instead of 1,2,4-triazolo[1,5-a]pyridine-7-carbohydrazide, the title compound (yield 100%) was obtained as brown crystals.

$^1$H NMR (DMSO-$d_6$) δ 1.18 (7.5H, t, J=7.2 Hz), 3.10 (5H, q, J=7.2 Hz), 6.92 (1H, dd, J=2.1, 3.3 Hz), 7.40 (1H, d, J=4.8 Hz), 7.61 (1H, t, J=3.3 Hz), 8.30 (1H, d, J=4.8 Hz), 11.88 (1H, brs).

REFERENCE EXAMPLE 70

3-(3-fluorophenyl)propanohydrazide

In the same manner as in Reference Example 4 and using methyl 3-(3-fluorophenyl)propionate instead of ethyl 3-[3-(trifluoromethyl)phenyl]propionate, the title compound (yield 81%) was obtained as colorless crystals.

melting point 109-110° C. (recrystallized from hexane/ethyl acetate).

$^1$H NMR (CDCl$_3$) δ 2.46 (2H, t, J=7.5 Hz), 3.00 (2H, t, J=7.5 Hz), 3.89 (2H, brs), 6.68 (1H, brs), 6.85-7.00 (3H, m), 7.20-7.35 (1H, m).

REFERENCE EXAMPLE 71

2-(1,3-benzodioxol-5-yl)-5-[(3-fluoro-4-methoxybenzyl)thio]-1,3,4-oxadiazole

Purchased from INTERMED.

REFERENCE EXAMPLE 72

2-[[5-(1,3-benzodioxol-5-yl)-1,3,4-oxadiazol-2-yl]thio]-N-[4-(diethylamino)phenyl]acetamide Purchased from UkrOrgSynthesis.

REFERENCE EXAMPLE 73 tert-butyl[4-(5-methyl-1,3,4-oxadiazol-2-yl)-2-pyridyl]carbamate

To a solution of tert-butyl[4-(hydrazinocarbonyl)-2-pyridyl]carbamate (1.01 g, 4.0 mmol) and triethylamine (0.832 mL, 6.0 mmol) in tetrahydrofuran (20 mL) was added acetyl chloride (0.341 mL, 4.8 mmol) under ice-cooling, and the resulting mixture was stirred at room temperature for 1 hr. To this reaction mixture were added triethylamine (2.77 mL, 20 mmol) and p-toluenesulfonyl chloride (1.53 g, 8.0 mmol), and the resulting mixture was heated under reflux for 20 hr. Water was added to the reaction mixture, and the mixture was extracted with ethyl acetate/tetrahydrofuran. The organic layer was washed with saturated brine, dried over anhydrous magnesium sulfate and concentrated under reduced pressure. The residue was purified by basic silica gel column chromatography (tetrahydrofuran), and washed with diethyl ether/methanol to give the title compound (448 mg, yield 41%) as pale-brown crystals.

melting point 290-291° C.

$^1$H NMR (DMSO-$d_6$) δ 1.50 (9H, s), 2.63 (3H, s), 7.54 (1H, dd, J=1.5, 5.1 Hz), 8.39 (1H, dd, J=0.6, 1.5 Hz), 8.46 (1H, dd, J=0.6, 5.1 Hz), 10.16 (1H, s).

REFERENCE EXAMPLE 74

4-(5-methyl-1,3,4-oxadiazol-2-yl)pyridin-2-amine

A mixture of tert-butyl[4-(5-methyl-1,3,4-oxadiazol-2-yl)pyridin-2-yl]carbamate (440 mg, 1.59 mmol) and trifluoroacetic acid (10 mL) was stirred at room temperature for 1.5 hr. The reaction mixture was concentrated under reduced pressure, and the residue was neutralized with saturated aqueous sodium hydrogen carbonate solution, and extracted with ethyl acetate/tetrahydrofuran. The organic layer was washed with saturated brine, dried over anhydrous magnesium sulfate and concentrated under reduced pressure to give the title compound (257 mg, yield 92%) as pale-yellow crystals.

melting point 216-217° C.

$^1$H NMR (DMSO-$d_6$) δ 2.59 (3H, s), 6.36 (2H, s), 6.90-7.00 (2H, m), 8.10 (1H, d, J=5.4 Hz).

REFERENCE EXAMPLE 75 diethyl[[2-[(3-phenylpropionyl)amino]-3-pyridyl]methyl]phosphonate

To a solution of diethyl[(2-amino-3-pyridyl)methyl]phosphonate (9.65 g, 39.51 mmol) in pyridine (60 mL) was added 3-phenylpropionyl chloride (7.00 mL, 47.41 mmol) under ice-cooling, and the resulting mixture was stirred at room temperature for 20 hrs. The reaction mixture was concentrated under reduced pressure, a saturated aqueous sodium hydrogen carbonate solution was added to the residue, and the mixture was extracted with ethyl acetate. The organic layer was washed with saturated brine, dried over anhydrous magnesium sulfate and concentrated under reduced pressure. The residue was purified by silica gel column chromatography (hexane/ethyl acetate=4/1-0/1, ethyl acetate/hexane=9/1) to give the title compound (13.56 g, yield 91%) as a brown oil.

$^1$H NMR (CDCl$_3$) δ 1.26 (6H, t, J=7.2 Hz), 2.81 (2H, t, J=7.8 Hz), 2.93 (2H, d, J=21.3 Hz), 3.12 (2H, t, J=7.8 Hz), 3.92-4.10 (4H, m), 7.10 (1H, ddd, J=0.6, 4.8, 7.5 Hz), 7.17-7.32 (5H, m), 7.52 (1H, td, J=2.1, 7.5 Hz), 8.43-8.50 (1H, m), 9.38 (1H, brs).

REFERENCE EXAMPLE 76

2-(2-phenylethyl)-1H-pyrrolo[2,3-b]pyridine

To a solution of diethyl[[2-[(3-phenylpropionyl)amino]-3-pyridyl]methyl]phosphonate (13.56 g, 36.03 mmol) in toluene (150 mL) was added a suspension of tert-butoxy potassium (11.41 g, 86.47 mmol) in tetrahydrofuran (86.47 mL), and the resulting mixture was stirred at 90° C. for 1 hr. The reaction mixture was concentrated under reduced pressure, water was added to the residue, and the mixture was extracted with ethyl acetate. The organic layer was washed with saturated brine, dried over anhydrous magnesium sulfate and concentrated under reduced pressure. The residue was purified by silica gel column chromatography (hexane/ethyl acetate=9/1-0/1) and recrystallized from hexane/ethyl acetate to give the title compound (2.02 g, yield 25%) as colorless crystals.

melting point 157-158° C.

$^1$H NMR (CDCl$_3$) δ 3.10-3.23 (4H, m), 6.21 (1H, m), 7.03 (1H, dd, J=4.8, 7.8 Hz), 7.19-7.35 (5H, m), 7.82 (1H, dd, J=1.5, 7.8 Hz), 8.22 (1H, dd, J=1.5, 4.8 Hz), 10.60 (1H, brs).

REFERENCE EXAMPLE 77

2-(2-phenylethyl)-1H-pyrrolo[2,3-b]pyridine 7-oxide

To a solution of 2-(2-phenylethyl)-1H-pyrrolo[2,3-b]pyridine (1.97 g, 8.86 mmol) in acetonitrile (100 mL) was added m-chloroperbenzoic acid (2.82 g, 10.63 mmol) under ice-cooling, and the resulting mixture was stirred at room temperature for 20 hrs. The reaction mixture was concentrated under reduced pressure, and the residue was purified by basic silica gel column chromatography (hexane/ethyl acetate=9/1-0/1) to give the title compound (1.17 g, yield 55%) as a yellow amorphous form.

$^1$H NMR (CDCl$_3$) δ 3.02-3.22 (4H, m), 6.24 (1H, s), 6.98 (1H, dd, J=6.3, 7.8 Hz), 7.15-7.30 (5H, m), 7.54 (1H, dd, J=0.6, 7.8 Hz), 8.11 (1H, dd, J=0.6, 6.3 Hz), 13.20 (1H, brs).

REFERENCE EXAMPLE 78

4-chloro-2-(2-phenylethyl)-1H-pyrrolo[2,3-b]pyridine

A mixture of 2-(2-phenylethyl)-1H-pyrrolo[2,3-b]pyridine 7-oxide (1.17 g, 4.91 mmol) and phosphorus oxychloride (9.73 g) was heated under reflux for 2 hr. The reaction mixture was poured into ice water, and the mixture was neutralized with sodium hydroxide and extracted with ethyl acetate. The organic layer was washed with saturated brine, dried over anhydrous magnesium sulfate and concentrated under reduced pressure. The residue was purified by silica gel column chromatography (hexane/ethyl acetate=9/1-0/1) and washed with hexane to give the title compound (0.71 g, yield 56%) as colorless crystals.

melting point 159-160° C.

$^1$H NMR (CDCl$_3$) δ 3.05-3.20 (4H, m), 6.34 (1H, d, J=2.1 Hz), 7.06 (1H, d, J=5.1 Hz), 7.29-7.35 (5H, m), 8.08 (1H, d, J=5.1 Hz), 9.45 (1H, brs).

REFERENCE EXAMPLE 79

1-acetyl-4-iodo-2-(2-phenylethyl)-1H-pyrrolo[2,3-b]pyridine

A mixture of 4-chloro-2-(2-phenylethyl)-1H-pyrrolo[2,3-b]pyridine (0.71 g, 2.77 mmol), acetyl chloride (0.59 mL, 8.31 mmol), sodium iodide (2.08 g, 13.85 mmol) and acetonitrile (20 mL) was stirred at 80° C. for 2 hr. The reaction mixture was diluted with ethyl acetate, washed with saturated aqueous sodium thiosulfate solution and saturated brine, dried over anhydrous magnesium sulfate and concentrated under reduced pressure.

Acetic anhydride (30 mL) and acetic acid (3 mL) were added to the residue, and the resulting mixture was heated under reflux for 16 hr. The reaction mixture was concentrated under reduced pressure, and the residue was purified by silica gel column chromatography (hexane/ethyl acetate=9/1-1/4), and crystallized from hexane to give the title compound (1.05 g, yield 97%) as colorless crystals.

melting point 109-110° C.

$^1$H NMR (CDCl$_3$) δ 3.02 (2H, t, J=8.1 Hz), 3.07 (3H, s), 3.39 (2H, t, J=8.1 Hz), 6.30 (1H, t, J=0.9 Hz), 7.18-7.33 (5H, m), 7.56 (1H, d, J=5.1 Hz), 7.91 (1H, d, J=5.1 Hz).

REFERENCE EXAMPLE 80

1-acetyl-2-(2-phenylethyl)-1H-pyrrolo[2,3-b]pyridine-4-carbonitrile

A mixture of 1-acetyl-4-iodo-2-(2-phenylethyl)-1H-pyrrolo[2,3-b]pyridine (1.00 g, 2.56 mmol), zinc cyanide (246 mg, 1.41 mmol), tetrakis(triphenylphosphine)palladium(0) (148 mg, 0.128 mmol) and N,N-dimethylformamide (20 mL) was stirred under an argon atmosphere at 80° C. for 2 hr. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=9/1-0/1), and crystallized from hexane to give the title compound (472 mg, yield 64%) as colorless crystals.

melting point 102-103° C.

$^1$H NMR (CDCl$_3$) δ 3.06 (2H, t, J=7.8 Hz), 3.10 (3H, s), 3.48 (2H, t, J=7.8 Hz), 6.63 (1H, s), 7.20-7.38 (5H, m), 7.42 (1H, d, J=5.1 Hz), 8.42 (1H, d, J=5.1 Hz).

REFERENCE EXAMPLE 81

2-(2-phenylethyl)-1H-pyrrolo[2,3-b]pyridine-4-carboxylic acid

In the same manner as in Reference Example 66 and using 1-acetyl-2-(2-phenylethyl)-1H-pyrrolo[2,3-b]pyridine-4-carbonitrile instead of 1-acetyl-1H-pyrrolo[2,3-b]pyridine-4-carbonitrile, the title compound (yield 90%) was obtained as yellow crystals.

melting point >300° C.

$^1$H NMR (DMSO-d$_6$) δ 3.00-3.15 (4H, m), 6.63 (1H, d, J=1.8 Hz), 7.11-7.30 (5H, m), 7.48 (1H, d, J=5.1 Hz), 8.22 (1H, d, J=5.1 Hz), 11.88 (1H, s).

REFERENCE EXAMPLE 82 tert-butyl 2-[[2-(2-phenylethyl)-1H-pyrrolo[2,3-b]pyridin-4-yl]carbonyl]hydrazinecarboxylate In the same manner as in Reference Example 1 and using 2-(2-phenylethyl)-1H-pyrrolo[2,3-b]pyridine-4-carboxylic acid instead of benzothiazole-6-carboxylic acid, the title compound (yield 85%) was obtained as colorless crystals.

melting point 187-188° C. (recrystallized from hexane/ethyl acetate).

$^1$H NMR (CDCl$_3$) δ 1.55 (9H, s), 3.05-3.25 (4H, m), 6.64 (1H, s), 6.88 (1H, brs), 7.20-7.38 (5H, m), 7.39 (1H, d, J=5.1 Hz), 8.06 (1H, brs), 8.27 (1H, d, J=5.1 Hz), 8.93 (1H, brs).

REFERENCE EXAMPLE 83

2-(2-phenylethyl)-1H-pyrrolo[2,3-b]pyridine-4-carbohydrazide

In the same manner as in Reference Example 74 and using tert-butyl 2-[[2-(2-phenylethyl)-1H-pyrrolo[2,3-b]pyridin-4-yl]carbonyl]hydrazinecarboxylate instead of tert-butyl[4-(5-methyl-1,3,4-oxadiazol-2-yl)pyridin-2-yl]carbamate, the title compound (yield 100%) was obtained as pale-yellow crystals.

melting point 233-234° C.

$^1$H NMR (DMSO-d$_6$) δ 2.98-3.10 (4H, m), 4.61 (2H, brs), 6.55 (1H, d, J=1.8 Hz), 7.15-7.30 (6H, m), 8.16 (1H, d, J=5.1 Hz), 9.74 (1H, s), 11.75 (1H, s).

REFERENCE EXAMPLE 84 methyl 2-[[4-(methylthio)phenyl]amino]isonicotinate

To a solution of 2-fluoroisonicotinic acid (620 mg, 4.95 mmol) and 4-(methylthio)aniline (0.984 mL, 8.42 mmol) in N,N-dimethylformamide (20 mL) was added sodium hydride (792 mg, 19.8 mmol), and the resulting mixture was stirred under an argon atmosphere at 85° C. for 5 hr. After cooling, acetic acid (1.2 mL) was added to the reaction mixture, and the mixture was concentrated under reduced pressure. Ethyl acetate and water were added to the residue, the mixture was stirred for 20 min, and the precipitate was collected by filtration to give crude 2-[[4-(methylthio)phenyl]amino]isonicotinic acid.

A suspension of the obtained crude 2-[[4-(methylthio)phenyl]amino]isonicotinic acid, iodomethane (0.134 mL, 2.15 mmol) and potassium carbonate (297 mg, 2.15 mmol) in N,N-dimethylformamide (10 mL) was stirred overnight. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=10/1-1/1) and recrystallized from hexane/ethyl acetate to give the title compound (324 mg, yield 24%) as yellow crystals.

melting point 142° C.

$^1$H NMR (DMSO-d$_6$) δ 2.44 (3H, s), 3.88 (3H, s), 7.12 (1H, dd, J=1.5, 5.3 Hz), 7.24 (2H, d, J=8.7 Hz), 7.35 (1H, s), 7.66 (2H, d, J=8.7 Hz), 8.30 (1H, d, J=5.3 Hz), 9.38 (1H, s).

REFERENCE EXAMPLE 85

2-[[4-(methylthio)phenyl]amino]isonicotinohydrazide

In the same manner as in Reference Example 9 and using methyl 2-[[4-(methylthio)phenyl]amino]isonicotinate instead of methyl 1H-indazole-5-carboxylate, the title compound (yield 100%) was obtained as yellow crystals.

$^1$H NMR (DMSO-d$_6$) δ 2.43 (3H, s), 4.58 (2H, brs), 7.05 (1H, dd, J=1.3, 5.3 Hz), 7.11-7.32 (3H, m), 7.65 (2H, d, J=8.9 Hz), 8.20 (1H, d, J=5.3 Hz), 9.25 (1H, s), 9.94 (1H, s).

REFERENCE EXAMPLE 86 methyl 2-[[3-methoxy-5-(trifluoromethyl)phenyl]amino]isonicotinate

In the same manner as in Reference Example 84 and using 3-methoxy-5-(trifluoromethyl)aniline instead of 4-(methylthio)aniline, the title compound (yield 26%) was obtained as colorless crystals.

melting point 178-179° C. (recrystallized from hexane/ethyl acetate).

$^1$H NMR (CDCl$_3$) δ 3.86 (3H, s), 3.94 (3H, s), 6.70 (1H, s), 6.82 (1H, s), 7.20-7.29 (1H, m), 7.33 (2H, d, J=4.9 Hz), 7.38 (1H, s), 8.37 (1H, d, J=5.3 Hz).

REFERENCE EXAMPLE 87

2-[[3-methoxy-5-(trifluoromethyl)phenyl]amino]isonicotinohydrazide

In the same manner as in Reference Example 9 and using methyl 2-[[3-methoxy-5-(trifluoromethyl)phenyl]amino]isonicotinate instead of methyl 1H-indazole-5-carboxylate, the title compound (yield 90%) was obtained as colorless crystals.

melting point 229-230° C. (recrystallized from ethanol).

$^1$H NMR (DMSO-d$_6$) δ 3.81 (3H, s), 4.60 (2H, brs), 6.76 (1H, s), 7.15 (1H, dd, J=1.5, 5.3 Hz), 7.25 (1H, s), 7.63 (1H, s), 7.71 (1H, s), 8.30 (1H, d, J=5.3 Hz), 9.61 (1H, s), 10.00 (1H, brs).

REFERENCE EXAMPLE 88

1,1-dimethyl-2-[2-[2-[[4-(methylthio)phenyl]amino]
isonicotinoyl]hydrazino]-2-oxoethyl acetate To a solution of 2-[[4-(methylthio)phenyl]amino]isonicotinohydrazide (513 mg, 1.87 mmol) in N,N-dimethylacetamide (5 mL) was added dropwise 2-chloro-1,1-dimethyl-2-oxoethyl acetate (0.294 mL, 2.06 mmol) under ice-cooling, and the resulting mixture was stirred at room temperature for 2 hr. The reaction mixture was diluted with ethyl acetate, washed with water and saturated brine, dried over anhydrous sodium sulfate, and concentrated under reduced pressure. The residue was recrystallized from hexane/ethyl acetate to give the title compound (624 mg, yield 83%) as colorless crystals.
$^1$H NMR (DMSO-$d_6$) δ 1.57 (6H, s), 2.04 (3H, s), 2.44 (3H, s), 7.11 (1H, dd, J=1.2, 5.2 Hz), 7.16-7.28 (3H, m), 7.65 (2H, d, J=8.7 Hz), 8.26 (1H, d, J=5.3 Hz), 9.31 (1H, s), 9.91 (1H, s), 10.52 (1H, s).

REFERENCE EXAMPLE 89 methyl 2-(2-pyridylamino)isonicotinate

A suspension of methyl 2-chloroisonicotinate (1.00 g, 5.83 mmol), 2-aminopyridine (658 mg, 6.99 mmol), tris(dibenzylideneacetone)dipalladium(0) (107 mg, 0.17 mmol), dicyclohexyl(2',4',6'-triisopropylbiphenyl-2-yl)phosphine (139 mg, 0.29 mmol) and tripotassium phosphate (3.09 g, 14.6 mmol) in toluene (30 mL) was heated under reflux under an argon atmosphere overnight. After cooling, the reaction mixture was diluted with ethyl acetate, washed with saturated aqueous sodium hydrogen carbonate solution and saturated brine, dried over anhydrous sodium sulfate, and concentrated under reduced pressure. The residue was purified by basic silica gel column chromatography (hexane/ethyl acetate=9/1-2/3) and recrystallized from hexane/ethyl acetate to give the title compound (866 mg, yield 65%) as colorless crystals.
$^1$H NMR (DMSO-$d_6$) δ 3.89 (3H, s), 6.83-6.97 (1H, m), 7.29 (1H, d, J=4.9 Hz), 7.61-7.75 (2H, m), 8.26 (1H, d, J=4.9 Hz), 8.31 (1H, s), 8.39 (1H, d, J=5.3 Hz), 9.98 (1H, s).

REFERENCE EXAMPLE 90

2-(2-pyridylamino)isonicotinohydrazide

In the same manner as in Reference Example 9 and using methyl 2-(2-pyridylamino)isonicotinate instead of methyl 1H-indazole-5-carboxylate, the title compound (yield 90%) was obtained as colorless crystals.
$^1$H NMR (DMSO-$d_6$) δ 4.57 (2H, brs), 6.83-6.93 (1H, m), 7.15 (1H, dd, J=1.3, 5.3 Hz), 7.61-7.77 (2H, m), 8.07 (1H, s), 8.19-8.36 (2H, m), 9.82 (1H, s), 9.92 (1H, s).

REFERENCE EXAMPLE 91

7-acetyl-4-iodo-7H-pyrrolo[2,3-d]pyrimidine

In the same manner as in Reference Example 79 and using 7-acetyl-4-chloro-7H-pyrrolo[2,3-d]pyrimidine instead of 4-chloro-2-(2-phenylethyl)-1H-pyrrolo[2,3-b]pyridine, the title compound (yield 51%) was obtained as pale-yellow crystals.
melting point 123-124° C. (recrystallized from hexane/ethyl acetate).
$^1$H NMR (CDCl$_3$) δ 3.05 (3H, s), 6.53 (1H, d, J=3.9 Hz), 8.03 (1H, d, J=3.9 Hz), 8.83 (1H, s).

REFERENCE EXAMPLE 92

7H-pyrrolo[2,3-d]pyrimidine-4-carbonitrile

A mixture of 7-acetyl-4-iodo-7H-pyrrolo[2,3-d]pyrimidine (1.28 g, 4.46 mmol), zinc cyanide (427 mg, 2.45 mmol), tetrakis(triphenylphosphine)palladium(0) (258 mg, 0.223 mmol) and N,N-dimethylformamide (10 mL) was tightly sealed in a vial, and the microwave was irradiated at 150° C. for 20 min. After cooling, the reaction mixture was diluted with ethyl acetate, washed with water and saturated brine, dried over anhydrous magnesium sulfate and concentrated under reduced pressure. The residue was purified by silica gel column chromatography (hexane/ethyl acetate=9/1-0/1) to give the title compound (520 mg, yield 80%) as pale-yellow crystals.
melting point 237-238° C.
$^1$H NMR (CDCl$_3$) δ 6.83 (1H, dd, J=2.1, 3.6 Hz), 7.57 (1H, d, J=3.6 Hz), 8.99 (1H, s), 9.34 (1H, brs).

REFERENCE EXAMPLE 93

7H-pyrrolo[2,3-d]pyrimidine-4-carboxylic acid

In the same manner as in Reference Example 66 and using 7H-pyrrolo[2,3-d]pyrimidine-4-carbonitrile instead of 1-acetyl-1H-pyrrolo[2,3-b]pyridine-4-carbonitrile, the title compound (350 mg, yield 61%) was obtained as pale-yellow crystals.
melting point 214-215° C.
$^1$H NMR (DMSO-$d_6$) δ 6.90 (1H, dd, J=1.5, 3.3 Hz), 7.77 (1H, dd, J=2.1, 3.3 Hz), 8.89 (1H, s), 12.44 (1H, brs).

REFERENCE EXAMPLE 94 benzyl 2-(7H-pyrrolo[2,3-d]pyrimidin-4-ylcarbonyl)
hydrazinecarboxylate

In the same manner as in Reference Example 1 and using 7H-pyrrolo[2,3-d]pyrimidine-4-carboxylic acid instead of benzothiazole-6-carboxylic acid and benzyl carbazate instead of tert-butyl carbazate, the title compound (yield 83%) was obtained as colorless crystals.
melting point 187-188° C. (recrystallized from diethyl ether/methanol).
$^1$H NMR (DMSO-$d_6$) δ 5.13 (2H, s), 6.99 (1H, d, J=3.6 Hz), 7.20-7.45 (5H, m), 7.76 (1H, d, J=3.6 Hz), 8.86 (1H, s).

REFERENCE EXAMPLE 95

7H-pyrrolo[2,3-d]pyrimidine-4-carbohydrazide

In the same manner as in Reference Example 64 and using benzyl 2-(7H-pyrrolo[2,3-d]pyrimidin-4-ylcarbonyl)hydrazinecarboxylate instead of benzyl 2-[2-[(3-phenylpropanoyl)amino]isonicotinoyl]hydrazinecarboxylate, the title compound (yield 100%) was obtained as colorless crystals.
melting point 252-254° C. (recrystallized from tetrahydrofuran/methanol).
$^1$H NMR (DMSO-$d_6$) δ 4.66 (2H, brs), 7.02 (1H, d, J=3.3 Hz), 7.71 (1H, d, J=3.3 Hz), 8.80 (1H, s), 10.08 (1H, brs), 12.32 (1H, brs).

REFERENCE EXAMPLE 96 methyl 4-(methylthio)-3-(trifluoromethyl)benzoate

To a solution of methyl 4-fluoro-3-(trifluoromethyl)benzoate (9.60 g, 43.2 mmol) in N,N-dimethylformamide (100 mL) was added mercaptan sodium (3.33 g, 47.5 mmol) at 0° C. by small portions, and the resulting mixture was stirred at room temperature for 2 hr. The reaction mixture was diluted with ethyl acetate, washed twice with water and once with saturated brine, dried over anhydrous magnesium sulfate and concentrated under reduced pressure. The residue was recrystallized from hexane to give the title compound (10.1 g, yield 93%) as colorless crystals.

melting point 76-77° C.
$^1$H NMR (CDCl$_3$) δ 2.57 (3H, s), 3.94 (3H, s), 7.36 (1H, d, J=8.3 Hz), 8.11 (1H, dd, J=1.9, 8.3 Hz), 8.27 (1H, d, J=1.9 Hz).
Elemental analysis (for C$_{10}$H$_9$F$_3$O$_2$S)
Calculated (%): C, 48.00; H, 3.63.
Found (%): C, 47.97; H, 3.62.

REFERENCE EXAMPLE 97

4-(methylthio)-3-(trifluoromethyl)benzyl alcohol

To a solution of methyl 4-(methylthio)-3-(trifluoromethyl)benzoate (10.0 g, 40.0 mmol) in tetrahydrofuran (100 mL) was added lithium aluminum hydride (1.52 g, 40.0 mmol) at 0° C. by small portions, and the resulting mixture was stirred for 15 min. Sodium sulfate decahydrate (12.9 g, 40.0 mmol) was added to the reaction mixture by small portions, and the obtained mixture was further stirred at room temperature for 1 hr. Insoluble material was filtered off, and the filtrate was concentrated under reduced pressure. The residue was purified by basic silica gel column chromatography (hexane/ethyl acetate=1/1), and crystallized from hexane/ethyl acetate to give the title compound (8.46 g, yield 95%) as colorless crystals.

melting point 168-169° C.
$^1$H NMR (CDCl$_3$) δ 1.77 (1H, t, J=5.8 Hz), 2.52 (3H, s), 4.71 (2H, d, J=5.8 Hz), 7.37 (1H, d, J=8.1 Hz), 7.47-7.51 (1H, m), 7.63-7.64 (1H, m).
Elemental analysis (for C$_9$H$_9$F$_3$OS)
Calculated (%): C, 48.64; H, 4.08.
Found (%): C, 48.73; H, 4.10.

REFERENCE EXAMPLE 98

4-(methylthio)-3-(trifluoromethyl)benzyl chloride

To a solution of 4-(methylthio)-3-(trifluoromethyl)benzyl alcohol (3.00 g, 13.5 mmol) in toluene (15 mL) was added thionyl chloride (1.18 mL, 16.2 mmol) at room temperature, and the resulting mixture was stirred for 1 hr. The reaction mixture was concentrated under reduced pressure. The residue was purified by basic silica gel column chromatography (hexane/ethyl acetate=10/1), and crystallized from hexane to give the title compound (2.54 g, yield 78%) as colorless crystals.

melting point 65-66° C.
$^1$H NMR (CDCl$_3$) δ 2.53 (3H, s), 4.58 (2H, s), 7.35 (1H, d, J=8.3 Hz), 7.50 (1H, dd, J=1.7, 8.3 Hz), 7.64 (1H, d, J=1.7 Hz).
Elemental analysis (for C$_9$H$_8$ClF$_3$S)
Calculated (%): C, 44.91; H, 3.35.
Found (%): C, 45.12; H, 3.36.

REFERENCE EXAMPLE 99 methyl 3-[4-(methylthio)phenyl]-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and 4-(methylthio)phenylboronic acid instead of (4-methoxyphenyl)boronic acid, the title compound (yield 92%) was obtained as colorless crystals.

melting point 95-96° C. (recrystallized from hexane/ethyl acetate).
$^1$H NMR (CDCl$_3$) δ 2.55 (3H, s), 3.95 (3H, s), 7.37-7.41 (2H, m), 7.55-7.60 (3H, m), 7.83 (1H, s), 8.08 (1H, dd, J=1.7, 8.7 Hz), 8.53 (1H, dd, J-=0.6, 1.7 Hz).
Elemental analysis (for C$_{17}$H$_{14}$O$_3$S)
Calculated (%): C, 68.44; H, 4.73.
Found (%): C, 68.57; H, 4.73.

REFERENCE EXAMPLE 100 methyl 3-[4-(methylsulfinyl)phenyl]-1-benzofuran-5-carboxylate

In the same manner as in Reference Example 48 and using methyl 3-[4-(methylthio)phenyl]-1-benzofuran-5-carboxylate instead of methyl 1-[4-(methylthio)phenyl]-1H-benzimidazole-6-carboxylate, the title compound (yield 93%) was obtained as colorless crystals.

melting point 145-146° C. (recrystallized from hexane/tetrahydrofuran).
$^1$H NMR (CDCl$_3$) δ 2.80 (3H, s), 3.96 (3H, s), 7.61 (1H, dd, J=0.6, 8.9 Hz), 7.77-7.84 (4H, m), 7.92 (1H, s), 8.12 (1H, dd, J=1.7, 8.9 Hz), 8.54 (1H, dd, J-=0.6, 1.7 Hz).
Elemental analysis (for C$_{17}$H$_{14}$O$_4$S)
Calculated (%): C, 64.95; H, 4.49.
Found (%): C, 64.98; H, 4.53.

REFERENCE EXAMPLE 101

4,4,5,5-tetramethyl-2-[4-[(trifluoromethyl)thio]phenyl]-1,3,2-dioxaborolane

A suspension of 1-bromo-4-[(trifluoromethyl)thio]benzene (5.74 mL, 38.2 mmol), bis(pinacolate)diboron (9.70 g, 38.2 mmol), [1,1'-bis(diphenylphosphino)ferrocene]palladium(II) chloride dichloromethane complex (0.934 g, 1.15 mmol) and potassium acetate (11.3 g, 115 mmol) in N,N-dimethylformamide (100 mL) was stirred under an argon atmosphere at 90° C. for 3.5 hr. After cooling, the reaction mixture was diluted with ethyl acetate, washed twice with water and once with saturated brine, dried over anhydrous magnesium sulfate and concentrated under reduced pressure. The residue was purified by silica gel column chromatography (hexane/ethyl acetate=3/1) and recrystallized from hexane to give the title compound (7.38 g, yield 64%) as colorless crystals.

melting point 118-119° C.
$^1$H NMR (CDCl$_3$) δ 1.35 (12H, s), 7.62-7.66 (2H, m), 7.82-7.86 (2H, m).
Elemental analysis (for C$_{13}$H$_{16}$BF$_3$O$_2$S)
Calculated (%): C, 51.34; H, 5.30.
Found (%): C, 51.42; H, 5.25.

REFERENCE EXAMPLE 102

[4-[(2-cyanobenzyl)thio]phenyl]boronic acid

A suspension of (4-mercaptophenyl)boronic acid (0.847 g, 5.50 mmol), 2-(bromomethyl)benzonitrile (1.62 g, 8.25 mmol) and potassium carbonate (2.28 g, 16.5 mmol) in N,N-dimethylformamide (10 mL) was stirred at room temperature for 30 min. The reaction mixture was diluted with ethyl acetate, washed twice with water and once with saturated brine, dried over anhydrous magnesium sulfate and concentrated under reduced pressure. The residue was washed with hexane/ethyl acetate (2/1) and recrystallized from hexane/ethyl acetate to give the title compound (903 mg, yield 61%) as colorless crystals.
$^1$H NMR (CDCl$_3$) δ 4.33 (0.6H, s), 4.39 (1.4H, s), 4.61 (0.6H, s), 7.30-7.55 (5H, m), 7.60-7.66 (1.6H, m), 8.06-8.10 (1.4H, m).

REFERENCE EXAMPLE 103

4-bromo-1-(methylthio)-2-(trifluoromethoxy)benzene

To a solution of 4-bromo-2-(trifluoromethoxy)benzenesulfonyl chloride (10.2 g, 30.0 mmol) in tetrahydrofuran (100 mL) was added triphenylphosphine (23.6 g, 90.0 mmol) at 0° C. by small portions, and the resulting mixture was stirred for 30 min. To this reaction mixture was added water (3 mL), and the mixture was further stirred at room temperature for 7 hrs. The reaction mixture was concentrated under reduced pressure, and the residue was diluted with dichloromethane and extracted with 1 M aqueous sodium hydroxide solution. The aqueous layer was acidified with 6 M hydrochloric acid, and the mixture was extracted with ethyl acetate. The organic layer was washed with saturated brine, dried over anhydrous magnesium sulfate and concentrated under reduced pressure.

A suspension of the obtained residue, iodomethane (2.80 mL, 45.0 mmol) and potassium carbonate (8.29 g, 60.0 mmol) in N,N-dimethylformamide (50 mL) was stirred at room temperature for 1 hr. The reaction mixture was diluted with ethyl acetate, washed twice with water and once with saturated brine, dried over anhydrous magnesium sulfate and concentrated under reduced pressure. The residue was purified by silica gel column chromatography (hexane/ethyl acetate=10/0-10/1) to give the title compound (6.63 g, yield 77%) as a colorless oil.
$^1$H NMR (CDCl$_3$) δ 2.45 (3H, s), 7.11 (1H, d, J=8.3 Hz), 7.37-7.41 (2H, m).

REFERENCE EXAMPLE 104

[4-(methylthio)-3-(trifluoromethoxy)phenyl]boronic acid

To a solution of 4-bromo-1-(methylthio)-2-(trifluoromethoxy)benzene (6.63 g, 23.1 mmol) and triisopropyl borate (6.92 mL, 30.0 mmol) in tetrahydrofuran (50 mL) was added dropwise 1.6 M n-butyllithium-hexane solution (25.0 mL, 40.0 mmol) at −78° C., and the resulting mixture was stirred for 30 min. The reaction mixture was warmed to 0° C., 2 M hydrochloric acid (150 mL) was added, and the mixture was extracted with ethyl acetate. The organic layer was washed with saturated brine, dried over anhydrous magnesium sulfate and concentrated under reduced pressure. The residue was washed with hexane/ethyl acetate (5/1) and recrystallized from hexane/tetrahydrofuran to give the title compound (4.13 g, yield 71%) as colorless crystals.
$^1$H NMR (CDCl$_3$) δ 2.48 (0.3H, s), 2.53 (2.7H, s), 4.57 (0.2H, s), 7.24 (0.1H, d, J=7.9 Hz), 7.33 (0.9H, d, J=7.9 Hz), 7.55-7.57 (0.1H, m), 7.61 (0.1H, dd, J=1.1, 7.9 Hz), 7.93-7.95 (0.9H, m), 8.04 (0.9H, dd, J=1.1, 7.9 Hz).

REFERENCE EXAMPLE 105

4-bromo-1-(ethylthio)-2-fluorobenzene

In the same manner as in Reference Example 103 and using 4-bromo-2-fluorobenzenesulfonyl chloride instead of 4-bromo-2-(trifluoromethoxy)benzenesulfonyl chloride, the title compound (yield 48%) was obtained as colorless oil.
$^1$H NMR (CDCl$_3$) δ 1.29 (3H, t, J=7.4 Hz), 2.91 (2H, q, J=7.4 Hz), 7.19-7.26 (3H, m).

REFERENCE EXAMPLE 106

[4-(ethylthio)-3-fluorophenyl]boronic acid

In the same manner as in Reference Example 104 and using 4-bromo-1-(ethylthio)-2-fluorobenzene instead of 4-bromo-1-(methylthio)-2-(trifluoromethoxy)benzene, the title compound (yield 38%) was obtained as colorless crystals.
$^2$H NMR (CDCl$_3$) δ 1.31-1.41 (3H, m), 2.94-3.08 (2H, m), 4.53 (0.2H, s), 7.30-7.44 (1.2H, m), 7.78 (0.9H, dd, J=0.8, 10.2 Hz), 7.89 (0.9H, dd, J=1.1, 7.6 Hz).

REFERENCE EXAMPLE 107 methyl 3-[3-chloro-4-(methylthio)phenyl]-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and [3-chloro-4-(methylthio)phenyl]boronic acid instead of (4-methoxyphenyl)boronic acid, the title compound (yield 84%) was obtained as colorless crystals.
melting point 115-116° C. (crystallized from hexane/ethyl acetate).
$^1$H NMR (CDCl$_3$) δ 2.55 (3H, s), 3.96 (3H, s), 7.30 (1H, d, J=8.3 Hz), 7.56 (1H, dd, J=1.9, 8.3 Hz), 7.58 (1H, dd, J=0.6, 8.7 Hz), 7.62 (1H, d, J=1.9 Hz), 7.84 (1H, s), 8.10 (1H, dd, J=1.7, 8.7 Hz), 8.50 (1H, dd, J=0.6, 1.7 Hz).
Elemental analysis (for C$_{17}$H$_{13}$ClO$_3$S)
Calculated (%): C, 61.35; H, 3.94.
Found (%): C, 61.37; H, 4.07.

REFERENCE EXAMPLE 108

3-[3-chloro-4-(methylthio)phenyl]-1-benzofuran-5-carbohydrazide

In the same manner as in Reference Example 9 and using methyl 3-[3-chloro-4-(methylthio)phenyl]-1-benzofuran-5-carboxylate instead of methyl 1H-indazole-5-carboxylate, the title compound (yield 91%) was obtained as colorless crystals.
melting point 207-208° C. (crystallized from methanol).
$^1$H NMR (DMSO-d$_6$) δ 2.57 (3H, s), 4.53 (2H, brs), 7.45 (1H, d, J=8.3 Hz), 7.74 (1H, d, J=8.7 Hz), 7.82 (1H, dd, J=1.9, 8.3 Hz), 7.88 (1H, d, J=1.9 Hz), 7.90 (1H, dd, J=1.7, 8.7 Hz), 8.37 (1H, d, J=1.7 Hz), 8.54 (1H, s), 9.94 (1H, brs).
Elemental analysis (for C$_{16}$H$_{13}$ClN$_2$O$_2$S)
Calculated (%): C, 57.74; H, 3.94; N, 8.42.
Found (%): C, 57.51; H, 3.97; N, 8.27.

REFERENCE EXAMPLE 109

1-bromo-2-chloro-4-(ethylthio)benzene

To a solution of 1-bromo-2-chloro-4-fluorobenzene (24.8 g, 119 mmol) and ethanethiol (10.6 mL, 143 mmol) in N,N-dimethylformamide (150 mL) was added sodium hydride (60% in oil, 6.00 g, 150 mmol) at room temperature by small portions, and the resulting mixture was stirred for 4 hr. The reaction mixture was diluted with ethyl acetate, washed twice with water and once with saturated brine, dried over anhydrous magnesium sulfate and concentrated under reduced pressure. The residue was purified by silica gel column chromatography (hexane) to give the title compound (19.4 g, yield 65%) as a colorless oil.

$^1$H NMR (CDCl$_3$) δ 1.32 (3H, t, J=7.2 Hz), 2.94 (2H, q, J=7.2 Hz), 7.04 (1H, dd, J=2.3, 8.3 Hz), 7.37 (1H, d, J=2.3 Hz), 7.49 (1H, d, J=8.3 Hz).

REFERENCE EXAMPLE 110

[2-chloro-4-(ethylthio)phenyl]boronic acid

In the same manner as in Reference Example 104 and using 1-bromo-2-chloro-4-(ethylthio)benzene instead of 4-bromo-1-(methylthio)-2-(trifluoromethoxy)benzene, the title compound (yield 47%) was obtained as colorless crystals.

$^1$H NMR (CDCl$_3$) δ 1.33-1.42 (3H, m), 2.95-3.07 (2H, m), 5.23 (0.6H, s), 7.16-7.25 (1.3H, m), 7.31 (0.7H, d, J=1.7 Hz), 7.83 (0.3H, d, J=7.9 Hz), 8.13 (0.7H, d, J=7.9 Hz).

REFERENCE EXAMPLE 111

1-[(4-bromophenyl)thio]-2-methylpropan-2-ol

To a solution of 4-bromothiophenol (9.45 g, 50.0 mmol) in tetrahydrofuran (150 mL) was added sodium hydride (60% in oil, 2.20 g, 55.0 mmol) at 0° C. by small portions, and the resulting mixture was stirred for 1 hr. To this reaction mixture was added isobutylene oxide (4.91 mL, 55.0 mmol), and the resulting mixture was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=1/1) to give the title compound (11.6 g, yield 89%) as a colorless oil.

$^1$H NMR (CDCl$_3$) δ 1.30 (6H, s), 2.09 (1H, s), 3.09 (2H, s), 7.25-7.30 (2H, m), 7.37-7.42 (2H, m).

REFERENCE EXAMPLE 112

5-bromo-3,3-dimethyl-2,3-dihydro-1-benzothiophene

To a suspension of aluminum chloride (10.7 g, 80.0 mmol) in carbon disulfide (80 mL) was added dropwise a solution of 1-[(4-bromophenyl)thio]-2-methylpropan-2-ol (5.22 g, 20.0 mmol) in carbon disulfide (20 mL) at 0° C., and the resulting mixture was stirred at room temperature for 30 min, and heated under reflux for 3 hr. After cooling, the reaction mixture was poured into ice water, and the mixture was extracted with ethyl acetate. The organic layer was washed with saturated aqueous sodium hydrogen carbonate solution and saturated brine, dried over anhydrous magnesium sulfate and concentrated under reduced pressure. The residue was purified by basic silica gel column chromatography (hexane) to give the title compound (1.64 g, yield 34%) as a colorless oil.

$^1$H NMR (CDCl$_3$) δ 1.36 (6H, s), 3.18 (2H, s), 7.03 (1H, d, J=8.3 Hz), 7.13 (1H, d, J=1.9 Hz), 7.22 (1H, dd, J=1.9, 8.3 Hz).

REFERENCE EXAMPLE 113

(3,3-dimethyl-2,3-dihydro-1-benzothien-5-yl)boronic acid

In the same manner as in Reference Example 104 and using 5-bromo-3,3-dimethyl-2,3-dihydro-1-benzothiophene instead of 4-bromo-1-(methylthio)-2-(trifluoromethoxy)benzene, the title compound (yield 32%) was obtained as colorless crystals.

$^1$H NMR (CDCl$_3$) δ 1.48 (6H, s), 3.24 (2H, s), 7.34 (1H, d, J=7.7 Hz), 7.83 (1H, d, J=1.1 Hz), 7.99 (1H, dd, J=1.1, 7.7 Hz).

REFERENCE EXAMPLE 114

[2-chloro-4-(methoxycarbonyl)phenyl]boronic acid

To a mixture of 3-chloro-4-(dihydroxyboryl)benzoic acid (1.00 g, 5.10 mmol), N,N-dimethylformamide (10 mL) and diethyl ether (1 ml) was added dropwise a 0.6 M trimethylsilylazide-hexane solution (10.2 mL, 6.12 mmol), and the resulting mixture was stirred overnight at room temperature. Acetic acid was added to the reaction mixture, and the mixture was concentrated under reduced pressure. Water was added to the residue, and the precipitate was collected by filtration and recrystallized from water to give the title compound (0.46 g, yield 42%) as colorless crystals.

$^1$H NMR (CDCl$_3$) δ 3.94 (3H, s), 5.41 (2H, brs), 7.94 (1H, dd, J=1.5, 7.9 Hz), 7.98-8.06 (2H, m).

REFERENCE EXAMPLE 115

N-methyl-2-[[3-[4-(methylthio)phenyl]-1-benzofuran-5-yl]carbonyl]hydrazinecarbothioamide A mixture of 3-[4-(methylthio)phenyl]-1-benzofuran-5-carbohydrazide (0.60 g, 2.01 mmol), methyl isothiocyanate (97%, 0.21 g, 2.82 mmol) and ethanol (15 mL) was tightly sealed in a vial, and the microwave was irradiated at 100° C. for 30 min. After cooling, the precipitate was collected by filtration, and washed with ethanol to give the title compound (0.70 g, yield 94%) as colorless crystals.

$^1$H NMR (DMSO-d$_6$) δ 2.54 (3H, s), 2.89 (3H, d, J=4.3 Hz), 7.43 (2H, d, J=8.7 Hz), 7.73-7.80 (3H, m), 7.96 (1H, dd, J=1.6, 8.7 Hz), 8.08 (1H, brs), 8.48 (1H, s), 8.51 (1H, d, J=1.6 Hz), 9.35 (1H, s), 10.49 (1H, brs).

REFERENCE EXAMPLE 116 methyl 3-[4-(trifluoromethoxy)phenyl]-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and [4-(trifluoromethoxy)phenyl]boronic acid instead of (4-methoxyphenyl)boronic acid, the title compound (yield 74%) was obtained as colorless crystals.

$^1$H NMR (CDCl$_3$) δ 3.96 (3H, s), 7.36 (2H, d, J=8.8 Hz), 7.58 (1H, d, J=8.9 Hz), 7.67 (2H, d, J=8.8 Hz), 7.84 (1H, s), 8.10 (1H, dd, J=1.6, 8.9 Hz), 8.51 (1H, d, J=1.6 Hz).

REFERENCE EXAMPLE 117

3-[4-(trifluoromethoxy)phenyl]-1-benzofuran-5-carbohydrazide

In the same manner as in Reference Example 9 and using methyl 3-[4-(trifluoromethoxy)phenyl]-1-benzofuran-5-carboxylate instead of methyl 1H-indazole-5-carboxylate, the title compound (yield 86%) was obtained as colorless crystals.
$^1$H NMR (DMSO-d$_6$) δ 2.02 (2H, s), 7.54 (2H, dd, J=0.8, 8.8 Hz), 7.73-7.81 (1H, m), 7.87-7.97 (3H, m), 8.33-8.41 (1H, m), 8.50-8.56 (1H, m), 10.57 (1H, brs).

REFERENCE EXAMPLE 118 methyl 3-[3-(trifluoromethoxy)phenyl]-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and [3-(trifluoromethoxy)phenyl]boronic acid instead of (4-methoxyphenyl)boronic acid, the title compound (yield 80%) was obtained as colorless crystals.
melting point 93-94° C. (recrystallized from hexane/ethyl acetate).
$^1$H NMR (CDCl$_3$) δ 3.96 (3H, s), 7.24-7.29 (1H, m), 7.47-7.49 (1H, m), 7.54 (1H, dd, J=7.6, 8.0 Hz), 7.58-7.67 (2H, m), 7.88 (1H, s), 8.11 (1H, dd, J=1.9, 8.7 Hz), 8.52 (1H, dd, J=0.8, 1.9 Hz).
Elemental analysis (for C$_{17}$H$_{11}$F$_3$O$_4$)
Calculated (%): C, 60.72; H, 3.30.
Found (%): C, 60.69; H, 3.17.

REFERENCE EXAMPLE 119

3-[3-(trifluoromethoxy)phenyl]-1-benzofuran-5-carbohydrazide

In the same manner as in Reference Example 9 and using methyl 3-[3-(trifluoromethoxy)phenyl]-1-benzofuran-5-carboxylate instead of methyl 1H-indazole-5-carboxylate, the title compound (yield 86%) was obtained as colorless crystals.
melting point 137-138° C. (recrystallized from hexane/ethyl acetate).
$^1$H NMR (CDCl$_3$) δ 4.14 (2H, s), 7.25-7.29 (1H, m), 7.42 (1H, brs), 7.45-7.47 (1H, m), 7.52 (1H, dd, J=7.7, 7.9 Hz), 7.56-7.62 (2H, m), 7.76 (1H, dd, J=1.7, 8.7 Hz), 7.88 (1H, s), 8.23 (1H, d, J=1.7 Hz).
Elemental analysis (for C$_{16}$H$_{11}$F$_3$N$_2$O$_3$)
Calculated (%): C, 57.15; H, 3.30; N, 8.33.
Found (%): C, 57.10; H, 3.10; N, 8.37.

REFERENCE EXAMPLE 120

2-(methylsulfonyl)-5-[3-[3-(trifluoromethoxy)phenyl]-1-benzofuran-5-yl]-1,3,4-oxadiazole To a solution of 2-(methylthio)-5-[3-[3-(trifluoromethoxy)phenyl]-1-benzofuran-5-yl]-1,3,4-oxadiazole (2.38 g, 6.07 mmol) in acetonitrile (25 mL) was added m-chloroperbenzoic acid (70%, 3.20 g, 13.3 mmol) at 0° C., and the resulting mixture was stirred overnight at room temperature. A saturated aqueous sodium thiosulfate solution was added to the reaction mixture, and the mixture was extracted with ethyl acetate. The organic layer was washed with water and saturated brine, dried over magnesium sulfate, and concentrated under reduced pressure. The residue was purified by silica gel column chromatography (hexane/ethyl acetate=4/1) to give the title compound (0.87 g, yield 34%) as colorless crystals.
$^1$H NMR (CDCl$_3$) δ 3.55 (3H, s), 7.27-7.33 (1H, m), 7.46 (1H, s), 7.53-7.65 (2H, m), 7.73 (1H, d, J=8.7 Hz), 7.93 (1H, s), 8.17 (1H, dd, J=1.7, 8.7 Hz), 8.55 (1H, d, J=1.7 Hz).

REFERENCE EXAMPLE 121 methyl 3-(2-chlorophenyl)-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and (2-chlorophenyl)boronic acid instead of (4-methoxyphenyl)boronic acid, the title compound (yield 92%) was obtained as colorless crystals.
$^1$H NMR (CDCl$_3$) δ 3.92 (3H, s), 7.31-7.45 (2H, m), 7.49-7.64 (3H, m), 7.90 (1H, s), 8.08 (1H, dd, J=1.7, 8.7 Hz), 8.30 (1H, d, J=1.7 Hz).

REFERENCE EXAMPLE 122

3-(2-chlorophenyl)-1-benzofuran-5-carbohydrazide

In the same manner as in Reference Example 9 and using methyl 3-(2-chlorophenyl)-1-benzofuran-5-carboxylate instead of methyl 1H-indazole-5-carboxylate, the title compound (yield 66%) was obtained as colorless crystals.
$^1$H NMR (DMSO-d$_6$) δ 4.43-4.51 (2H, m), 7.47-7.54 (2H, m), 7.62-7.70 (2H, m), 7.75 (1H, dd, J=0.4, 8.7 Hz), 7.88 (1H, dd, J=1.7, 8.7 Hz), 8.03 (1H, d, J=1.7 Hz), 8.34 (1H, s), 9.82 (1H, brs).

REFERENCE EXAMPLE 123

2-[3-(2-chlorophenyl)-1-benzofuran-5-yl]-5-(methylsulfonyl)-1,3,4-oxadiazole

In the same manner as in Reference Example 120 and using 2-[3-(2-chlorophenyl)-1-benzofuran-5-yl]-5-(methylthio)-1,3,4-oxadiazole instead of 2-(methylthio)-5-[3-[3-(trifluoromethoxy)phenyl]-1-benzofuran-5-yl]-1,3,4-oxadiazole, the title compound (yield 66%) was obtained as colorless crystals.
$^1$H NMR (CDCl$_3$) δ 3.53 (3H, s), 7.36-7.45 (2H, m), 7.49-7.54 (1H, m), 7.55-7.61 (1H, m), 7.72 (1H, dd, J=0.5, 8.7 Hz), 7.94 (1H, s), 8.16 (1H, dd, J=1.7, 8.7 Hz), 8.33 (1H, d, J=1.7 Hz).

REFERENCE EXAMPLE 124 methyl 3-(2,5-difluorophenyl)-1-benzofuran-5-carboxylate

In the same manner as in Reference Example 19 and using methyl 3-bromo-1-benzofuran-5-carboxylate instead of methyl 3-iodoimidazo[1,2-a]pyridine-6-carboxylate and (2,5-difluorophenyl)boronic acid instead of (4-methoxyphenyl)boronic acid, the title compound (yield 70%) was obtained as colorless crystals.

melting point 161-162° C. (recrystallized from hexane/tetrahydrofuran).

$^1$H NMR (CDCl$_3$) δ 3.96 (3H, s), 7.02-7.10 (1H, m), 7.20 (1H, dt, J=4.5, 9.5 Hz), 7.42 (1H, ddd, J=3.4, 5.7, 8.7 Hz), 7.60 (1H, d, J=8.7 Hz), 8.00 (1H, d, J=2.3 Hz), 8.11 (1H, dd, J=1.5, 8.7 Hz), 8.49 (1H, s).

Elemental analysis (for C$_{16}$H$_{10}$F$_2$O$_3$)

Calculated (%): C, 66.67; H, 3.50.

Found (%): C, 66.76; H, 3.58.

REFERENCE EXAMPLE 125

3-(2,5-difluorophenyl)-1-benzofuran-5-carbohydrazide

In the same manner as in Reference Example 9 and using methyl 3-(2,5-difluorophenyl)-1-benzofuran-5-carboxylate instead of methyl 1H-indazole-5-carboxylate, the title compound (yield 83%) was obtained as colorless crystals.

melting point 198-199° C. (recrystallized from methanol).

$^1$H NMR (DMSO-d$_6$) δ 4.52 (2H, brs), 7.31-7.39 (1H, m), 7.49 (1H, ddd, J=4.7, 9.2, 9.8 Hz), 7.70-7.79 (2H, m), 7.92 (1H, dd, J=1.7, 8.7 Hz), 8.26-8.27 (1H, m), 8.46 (1H, d, J=2.1 Hz), 9.92 (1H, brs).

REFERENCE EXAMPLE 126

2-(chloromethyl)-5-[3-[3-(trifluoromethoxy)phenyl]-1-benzofuran-5-yl]-1,3,4-oxadiazole A mixture of 3-[3-(trifluoromethoxy)phenyl]-1-benzofuran-5-carbohydrazide (3.00 g, 8.92 mmol) and 2-chloro-1,1,1-trimethoxyethane (4.70 mL, 24.4 mmol) was stirred at 80° C. for 3 hr. The reaction mixture was purified by silica gel column chromatography (hexane/ethyl acetate=1/1) and recrystallized from hexane/ethyl acetate to give the title compound (2.39 g, yield 68%) as colorless crystals.

$^1$H NMR (CDCl$_3$) δ 4.81 (2H, s), 7.27-7.33 (1H, m), 7.48 (1H, s), 7.53-7.64 (2H, m), 7.70 (1H, d, J=8.7 Hz), 7.91 (1H, s), 8.13 (1H, dd, J=1.7, 8.7 Hz), 8.50 (1H, d, J=1.7 Hz).

REFERENCE EXAMPLE 127

2-oxo-2-[2-[[3-[3-(trifluoromethoxy)phenyl]-1-benzofuran-5-yl]carbonyl]hydrazino]ethyl acetate In the same manner as in Reference Example 61 and using 3-[3-(trifluoromethoxy)phenyl]-1-benzofuran-5-carbohydrazide instead of ethyl 2-aminoisonicotinate and acetoxyacetyl chloride instead of 3-phenylpropanoyl chloride, the title compound (yield 94%) was obtained as colorless crystals.

melting point 161-162° C. (crystallized from hexane/ethyl acetate).

$^1$H NMR (CDCl$_3$) δ 2.19 (3H, s), 4.70 (2H, s), 7.22-7.27 (1H, m), 7.41 (1H, s), 7.47-7.57 (3H, m), 7.81 (1H, dd, J=1.7, 8.7 Hz), 7.84 (1H, s), 8.26 (1H, d, J=1.7 Hz), 9.13 (1H, d, J=4.0 Hz), 9.27 (1H, d, J=4.0 Hz).

Elemental analysis (for C$_{20}$H$_{15}$F$_3$N$_2$O$_6$)

Calculated (%): C, 55.05; H, 3.46; N, 6.42.

Found (%): C, 55.08; H, 3.37; N, 6.37.

REFERENCE EXAMPLE 128

1-methyl-2-oxo-2-[2-[[3-[3-(trifluoromethoxy)phenyl]-1-benzofuran-5-yl]carbonyl]hydrazino]ethyl acetate In the same manner as in Reference Example 1 and using (±)-2-acetoxypropionic acid instead of benzothiazole-6-carboxylic acid and 3-[3-(trifluoromethoxy)phenyl]-1-benzofuran-5-carbohydrazide instead of tert-butyl carbazate, the title compound (yield 48%) was obtained as colorless crystals.

$^1$H NMR (DMSO-d$_6$) δ 1.44 (3H, d, J=6.8 Hz), 2.10 (3H, s), 5.10 (1H, q, J=6.8 Hz), 7.41-7.47 (1H, m), 7.69 (1H, t, J=8.0 Hz), 7.78 (1H, s), 7.81 (1H, d, J=8.7 Hz), 7.90 (1H, d, J=8.0 Hz), 7.96 (1H, dd, J=1.5, 8.7 Hz), 8.46 (1H, d, J=1.5 Hz), 8.63 (1H, s), 10.17 (1H, brs), 10.59 (1H, brs).

REFERENCE EXAMPLE 129

(1S)-2-[2-[(3-bromo-1-benzofuran-5-yl)carbonyl]hydrazino]-1-methyl-2-oxoethyl acetate To a solution of 3-bromo-1-benzofuran-5-carbohydrazide (2.64 g, 10.35 mmol) in N,N-dimethylacetamide (10 mL) was added dropwise (1S)-2-chloro-1-methyl-2-oxoethyl acetate (1.44 mL, 11.38 mmol) at 0° C., and the resulting mixture was stirred overnight at room temperature. The reaction mixture was diluted with ethyl acetate, washed with water and saturated brine, dried over anhydrous sodium sulfate, and concentrated under reduced pressure. The residue was recrystallized from hexane/ethyl acetate to give the title compound (3.41 g, yield 89%) as colorless crystals.

$^1$H NMR (DMSO-d$_6$) δ 1.44 (3H, d, J=6.8 Hz), 2.10 (3H, s), 4.99-5.18 (1H, m), 7.80 (1H, d, J=8.7 Hz), 7.97 (1H, dd, J=1.5, 8.7 Hz), 8.16 (1H, d, J=1.5 Hz), 8.43 (1H, s), 10.18 (1H, brs), 10.60 (1H, brs).

REFERENCE EXAMPLE 130

(1S)-1-[5-(3-bromo-1-benzofuran-5-yl)-1,3,4-oxadiazol-2-yl]ethyl acetate

In the same manner as in Reference Example 35 and using (1S)-2-[2-[(3-bromo-1-benzofuran-5-yl)carbonyl]hydrazino]-1-methyl-2-oxoethyl acetate instead of N'-acetyl-1-benzofuran-5-carbohydrazide, the title compound (yield 85%) was obtained as colorless crystals.

$^1$H NMR (CDCl$_3$) δ 1.80 (3H, d, J=6.8 Hz), 2.17 (3H, s), 6.19 (1H, q, J=6.7 Hz), 7.63 (1H, d, J=9.2 Hz), 7.76 (1H, s), 8.12 (1H, dd, J=1.7, 8.7 Hz), 8.26 (1H, d, J=1.3 Hz).

REFERENCE EXAMPLE 131

(1S)-1-[5-[3-[3-(trifluoromethoxy)phenyl]-1-benzofuran-5-yl]-1,3,4-oxadiazol-2-yl]ethyl acetate In the same manner as in Reference Example 19 and using (1S)-1-[5-(3-bromo-1-benzofuran-5-yl)-1,3,4-oxadiazol-2-yl]ethyl acetate instead of methyl 3-iodoimidazo[1,2-a]pyridine-6-carboxylate and [3-(trifluoromethoxy)phenyl]boronic acid instead of (4-methoxyphenyl)boronic acid, the title compound (yield 75%) was obtained as colorless crystals.

$^1$H NMR (CDCl$_3$) δ 1.78 (3H, d, J=6.8 Hz), 2.17 (3H, s), 6.19 (1H, q, J=6.8 Hz), 7.23-7.36 (1H, m), 7.49 (1H, s), 7.51-7.64 (2H, m), 7.69 (1H, d, J=8.7 Hz), 7.91 (1H, s), 8.11 (1H, dd, J=1.7, 8.7 Hz), 8.48 (1H, d, J=1.5 Hz).

REFERENCE EXAMPLE 132

(1S)-1-[5-[3-[4-(methylthio)phenyl]-1-benzofuran-5-yl]-1,3,4-oxadiazol-2-yl]ethyl acetate In the same manner as in Reference Example 19 and using (1S)-1-[5-(3-bromo-1-benzofuran-5-yl)-1,3,4-oxadiazol-2-yl]ethyl acetate instead of methyl 3-iodoimidazo[1,2-a]pyridine-6-carboxylate and [4-(methylthio)phenyl]boronic acid instead of (4-methoxyphenyl)boronic acid, the title compound (yield 64%) was obtained as colorless crystals.
$^1$H NMR (CDCl$_3$) δ 1.78 (3H, d, J=6.8 Hz), 2.17 (3H, s), 2.56 (3H, s), 6.10-6.26 (1H, m), 7.36-7.45 (2H, m), 7.59 (2H, d, J=8.1 Hz), 7.66 (1H, d, J=8.7 Hz), 7.86 (1H, s), 8.08 (1H, dd, J=1.3, 8.7 Hz), 8.50 (1H, s).

REFERENCE EXAMPLE 133

(1R)-1-[5-[3-[3-(trifluoromethoxy)phenyl]-1-benzofuran-5-yl]-1,3,4-oxadiazol-2-yl]ethyl acetate To a solution of (1S)-1-[5-[3-[3-(trifluoromethoxy)phenyl]-1-benzofuran-5-yl]-1,3,4-oxadiazol-2-yl]ethanol (390 mg, 1.00 mmol), acetic acid (0.114 mL, 2.00 mmol) and triphenylphosphine (394 mg, 1.50 mmol) in tetrahydrofuran (5 mL) was added dropwise 40% diethyl azodicarboxylate-toluene solution (0.653 mL, 1.50 mmol) at 0° C., and the resulting mixture was stirred overnight at room temperature. The reaction mixture was diluted with ethyl acetate, washed with saturated aqueous sodium hydrogen carbonate solution and saturated brine, dried over anhydrous magnesium sulfate and concentrated under reduced pressure. The residue was purified by basic silica gel column chromatography (hexane/ethyl acetate=10/1-0/1) to give the title compound (406 mg, yield 94%) as a colorless oil.
$^1$H NMR (CDCl$_3$) δ 1.78 (3H, d, J=6.8 Hz), 2.17 (3H, s), 6.19 (1H, q, J=6.8 Hz), 7.23-7.36 (1H, m), 7.49 (1H, s), 7.51-7.64 (2H, m), 7.69 (1H, d, J=8.7 Hz), 7.91 (1H, s), 8.11 (1H, dd, J=1.7, 8.7 Hz), 8.48 (1H, d, J=1.5 Hz).

REFERENCE EXAMPLE 134

(1S)-1-[5-[3-(2-chloro-5-fluorophenyl)-1-benzofuran-5-yl]-1,3,4-oxadiazol-2-yl]ethyl acetate In the same manner as in Reference Example 19 and using (1S)-1-[5-(3-bromo-1-benzofuran-5-yl)-1,3,4-oxadiazol-2-yl]ethyl acetate instead of methyl 3-iodoimidazo[1,2-a]pyridine-6-carboxylate and (2-chloro-5-fluorophenyl)boronic acid instead of (4-methoxyphenyl)boronic acid, the title compound (yield 66%) was obtained as colorless crystals.
$^1$H NMR (CDCl$_3$) δ 1.77 (3H, d, J=6.8 Hz), 2.16 (3H, s), 6.14-6.20 (1H, m), 7.04-7.18 (1H, m), 7.21-7.32 (1H, m), 7.54 (1H, dd, J=5.2, 8.9 Hz), 7.69 (1H, d, J=8.7 Hz), 7.93 (1H, s), 8.09 (1H, dd, J=1.7, 8.7 Hz), 8.26 (1H, d, J=1.7 Hz).

REFERENCE EXAMPLE 135

2-[2-[[3-(2,5-difluorophenyl)-1-benzofuran-5-yl]carbonyl]hydrazino]-1,1-dimethyl-2-oxoethyl acetate In the same manner as in Reference Example 129 and using 3-(2,5-difluorophenyl)-1-benzofuran-5-carbohydrazide instead of 3-bromo-1-benzofuran-5-carbohydrazide and 2-chloro-1,1-dimethyl-2-oxoethyl acetate instead of (1S)-2-chloro-1-methyl-2-oxoethyl acetate, the title compound (yield 85%) was obtained as colorless crystals.
$^1$H NMR (CDCl$_3$) δ 1.74 (6H, s), 2.14 (3H, s), 7.00-7.12 (1H, m), 7.14-7.25 (1H, m), 7.32-7.43 (1H, m), 7.58-7.69 (1H, m), 7.85 (1H, dd, J=1.8, 8.6 Hz), 7.94-8.04 (1H, m), 8.25 (1H, s), 8.91 (2H, brs).

REFERENCE EXAMPLE 136 methyl 3-[(1-benzylpiperidin-4-yl)amino]-4-nitrobenzoate

In the same manner as in Reference Example 40 and using 4-amino-1-benzylpiperidine instead of p-anisidine, the title compound (yield 96%) was obtained as orange crystals.
$^1$H NMR (DMSO-d$_6$) δ 1.53-1.70 (2H, m), 1.90-2.03 (2H, m), 2.13-2.33 (2H, m), 2.66-2.79 (2H, m), 3.50 (2H, s), 3.64-3.81 (1H, m), 3.88 (3H, m), 7.15 (1H, dd, J=1.5, 8.9 Hz), 7.21-7.28 (1H, m), 7.29-7.37 (4H, m), 7.54 (1H, d, J=1.5 Hz), 7.93 (1H, d, J=7.5 Hz), 8.18 (1H, d, J=8.9 Hz).

REFERENCE EXAMPLE 137 methyl 4-amino-3-[(1-benzylpiperidin-4-yl)amino]benzoate

A mixture of methyl 3-[(1-benzylpiperidin-4-yl)amino]-4-nitrobenzoate (17.1 g, 46.3 mmol), 5% platinum carbon (5.13 g), tetrahydrofuran (115 mL) and methanol (115 mL) was stirred under a hydrogen atmosphere at room temperature overnight. The m reaction mixture was filtered, and the filtrate was concentrated under reduced pressure. The residue was purified by basic silica gel column chromatography (hexane/ethyl acetate=2/1) and recrystallized from diisopropyl ether/ethyl acetate to give the title compound (8.40 g, yield 53%) as pale-red crystals.
$^1$H NMR (DMSO-d$_6$) δ 1.34-1.51 (2H, m), 1.87-1.97 (2H, m), 2.03-2.15 (2H, m), 2.75-2.87 (2H, m), 3.13-3.28 (1H, m), 3.48 (2H, s), 3.71 (3H, s), 4.37 (1H, d, J=7.3 Hz), 5.43 (2H, s), 6.53 (1H, d, J=8.1 Hz), 6.99 (1H, d, J=1.7 Hz), 7.12 (1H, dd, J=1.9, 8.1 Hz), 7.18-7.27 (1H, m), 7.28-7.36 (4H, m).

REFERENCE EXAMPLE 138 methyl 1-(1-benzylpiperidin-4-yl)-1H-benzimidazole-6-carboxylate

In the same manner as in Reference Example 47 and using methyl 4-amino-3-[(1-benzylpiperidin-4-yl)amino]benzoate instead of methyl 4-amino-3-[[4-(methylthio)phenyl]amino]benzoate, the title compound (11.2 g, yield 91%) was obtained as pale-red crystals.
$^1$H NMR (DMSO-d$_6$) δ 1.94-2.17 (4H, m), 2.19-2.33 (2H, m), 2.88-3.00 (2H, m), 3.57 (2H, s), 3.89 (3H, s), 4.49-4.62 (1H, m), 7.23-7.31 (1H, m), 7.33-7.38 (4H, m), 7.74 (1H, d, J=8.5 Hz), 7.84 (1H, dd, J=1.5, 8.5 Hz), 8.30 (1H, d, J=1.5 Hz), 8.61 (1H, s).

REFERENCE EXAMPLE 139

1-(1-benzylpiperidin-4-yl)-1H-benzimidazole-6-carbohydrazide

In the same manner as in Reference Example 4 and using methyl 1-(1-benzylpiperidin-4-yl)-1H-benzimidazole-6-carboxylate instead of ethyl 3-[3-(trifluoromethyl)phenyl]propionate, the title compound (9.14 g, yield 83%) was obtained as pale-red crystals.

$^1$H NMR (DMSO-d$_6$) δ 1.99-2.30 (6H, m), 2.93-3.04 (2H, m), 3.57 (2H, s), 4.33-4.44 (1H, m), 4.49 (2H, brs), 7.23-7.32 (1H, m), 7.33-7.39 (4H, m), 7.63-7.69 (1H, m), 7.69-7.75 (1H, m), 8.16 (1H, s), 8.48 (1H, s), 9.75 (1H, brs).

REFERENCE EXAMPLE 140

6-(5-methyl-1,3,4-oxadiazol-2-yl)-1-(4-piperidinyl)-1H-benzimidazole

A suspension of 1-benzyl-4-[5-(5-methyl-1,3,4-oxadiazol-2-yl)-1-benzofuran-3-yl]piperidine (6.81 g, 18.2 mmol), 5% palladium on carbon (6.81 g) and ammonium formate (3.45 g, 54.7 mmol) in methanol (200 mL) was heated under reflux for 5.5 hr. The reaction mixture was filtered, and the filtrate was concentrated under reduced pressure. The residue was purified by basic silica gel column chromatography (ethyl acetate/methanol=1/9) to give the title compound (1.24 g, yield 24%) as colorless crystals.

$^1$H NMR (DMSO-d$_6$) δ 1.87-2.04 (5H, m), 2.61 (3H, s), 2.66-2.77 (2H, m), 3.04-3.14 (2H, m), 4.54-4.68 (1H, m), 7.82-7.86 (2H, m), 8.27-8.31 (1H, m), 8.53 (1H, brs).

REFERENCE EXAMPLE 141 methyl 4-nitro-3-[[4-(trifluoromethoxy)phenyl]amino]benzoate

In the same manner as in Reference Example 40 and using 4-(trifluoromethoxy)aniline instead of p-anisidine, the title compound (yield 83%) was obtained as yellow crystals.

$^1$H NMR (CDCl$_3$) δ 3.90 (3H, s), 7.31 (4H, s), 7.39-7.43 (1H, dd, J=1.5, 7.2 Hz), 7.88 (1H, d, J=1.5 Hz), 8.25-8.28 (1H, d, J=8.7 Hz), 9.41 (1H, s).

REFERENCE EXAMPLE 142 methyl 4-amino-3-[[4-(trifluoromethoxy)phenyl]amino]benzoate

In the same manner as in Reference Example 43 and using methyl 4-nitro-3-[[4-(trifluoromethoxy)phenyl]amino]benzoate instead of 5-[5-[2-(3-fluorophenyl)ethyl]-1,3,4-oxadiazol-2-yl]-N-(4-methoxyphenyl)-2-nitroaniline, the title compound (yield 100%) was obtained as a brown oil.

$^1$H NMR (DMSO-d$_6$) δ 3.73 (3H, s), 5.78 (2H, s), 6.74-6.79 (3H, m), 7.13 (2H, d, J=8.1 Hz), 7.51 (1H, dd, J=1.8, 6.6 Hz), 7.59 (1H, d, J=1.8 Hz), 7.65 (1H, s).

REFERENCE EXAMPLE 143 methyl 1-[4-(trifluoromethoxy)phenyl]-1H-benzimidazole-6-carboxylate

In the same manner as in Reference Example 47 and using methyl 4-amino-3-[[4-(trifluoromethoxy)phenyl]amino]benzoate instead of methyl 4-amino-3-[[4-(methylthio)phenyl]amino]benzoate, the title compound (yield 70%) was obtained as colorless crystals.

$^1$H NMR (CDCl$_3$) δ 3.95 (3H, s), 7.48 (2H, d, J=8.7 Hz), 7.58 (2H, d, J=8.4 Hz), 7.91 (1H, d, J=8.4 Hz), 8.07 (1H, dd, J=1.5, 6.9 Hz), 8.21 (2H, s).

REFERENCE EXAMPLE 144

1-[4-(trifluoromethoxy)phenyl]-1H-benzimidazole-6-carbohydrazide

In the same manner as in Reference Example 9 and using methyl 1-[4-(trifluoromethoxy)phenyl]-1H-benzimidazole-6-carboxylate instead of methyl 1H-indazole-5-carboxylate, the title compound (yield 86%) was obtained as colorless crystals.

$^1$H NMR (DMSO-d$_6$) δ 4.51 (2H, s), 7.67 (2H, d, J=8.1 Hz), 7.82 (2H, s), 7.85-7.94 (2H, m), 8.09 (1H, t, J=1.2 Hz), 8.72 (1H, s), 9.85 (1H, s).

REFERENCE EXAMPLE 145

N'-acetyl-1-[4-(trifluoromethoxy)phenyl]-1H-benzimidazole-6-carbohydrazide

A mixture of N-acetylimidazole (264 mg, 2.4 mmol), 1-[4-(trifluoromethoxy)phenyl]-1H-benzimidazole-6-carbohydrazide (672 mg, 2.0 mmol) and tetrahydrofuran (20 mL) was stirred overnight at room temperature, and at 50° C. for 4 hr. The reaction mixture was concentrated under reduced pressure, ethyl acetate was added to the residue, and the precipitate was collected by filtration to give the title compound (614 mg, yield 81%) as colorless crystals.

$^1$H NMR (DMSO-d$_6$) δ 2.51 (3H, s), 7.68 (2H, d, J=8.4 Hz), 7.82-7.92 (4H, m), 8.14 (1H, s), 8.75 (1H, s), 9.89 (1H, s), 10.38 (1H, s).

REFERENCE EXAMPLE 146

N-methyl-2-[[1-[4-(methylthio)phenyl]-1H-benzimidazol-6-yl]carbonyl]hydrazinecarbothioamide In the same manner as in Reference Example 115 and using 1-[4-(methylthio)phenyl]-1H-benzimidazole-6-carbohydrazide instead of 3-[4-(methylthio)phenyl]-1-benzofuran-5-carbohydrazide, the title compound (yield 95%) was obtained as colorless crystals.

$^1$H NMR (DMSO-d$_6$) δ 2.58 (3H, s), 2.87 (3H, d, J=4.2 Hz), 7.54 (2H, d, J=8.4 Hz), 7.67 (2H, d, J=8.4 Hz), 7.83-7.90 (2H, m), 8.03 (1H, m), 8.19 (1H, s), 8.69 (1H, s), 9.32 (1H, s), 10.41 (1H, s).

REFERENCE EXAMPLE 147

N-ethyl-2-[[1-[4-(methylthio)phenyl]-1H-benzimidazol-6-yl]carbonyl]hydrazinecarbothioamide In the same manner as in Reference Example 115 and using 1-[4-(methylthio)phenyl]-1H-benzimidazole-6-carbohydrazide instead of 3-[4-(methylthio)phenyl]-1-benzofuran-5-carbohydrazide and ethyl isothiocyanate instead of methyl isothiocyanate, the title compound (yield 90%) was obtained as colorless crystals.

$^1$H NMR (DMSO-d$_6$) δ 1.05 (3H, t, J=6.9 Hz), 2.58 (3H, s), 3.44-3.48 (2H, m), 7.54 (2H, d, J=8.7 Hz), 7.67 (2H, d, J=8.7 Hz), 7.83-7.91 (2H, m), 8.07 (1H, m), 8.19 (1H, s), 8.69 (1H, s), 9.24 (1H, s), 10.39 (1H, s).

REFERENCE EXAMPLE 148

6-[5-(methylsulfonyl)-1,3,4-oxadiazol-2-yl]-1-[4-(trifluoromethoxy)phenyl]-1H-benzimidazole To a mixture of 6-[5-(methylthio)-1,3,4-oxadiazol-2-yl]-1-[4-(trifluoromethoxy)phenyl]-1H-benzimidazole (898 mg, 2.29 mmol), acetonitrile (10 mL) and N,N-dimethylacetamide (20 mL) was added m-chloroperbenzoic acid (1.21 g, 5.03 mmol) at room temperature, and the resulting mixture was stirred for 3 days. m-Chloroperbenzoic acid (605 mg, 2.52 mmol) was added to this mixture, and the mixture was further stirred at room temperature for 1 day. A saturated aqueous sodium thiosulfate solution was added to the reaction mixture, and the mixture was stirred for 30 min and extracted with ethyl acetate. The organic layer was washed with saturated aqueous sodium hydrogen carbonate solution and saturated brine, dried over anhydrous magnesium sulfate and concentrated under reduced pressure. The residue was purified by silica gel column chromatography (hexane/ethyl acetate=10/1-0/1) and recrystallized from hexane/ethyl acetate to give the title compound (590 mg, yield 61%) as colorless crystals.

$^1$H NMR (CDCl$_3$) δ 3.72 (3H, s), 7.43-7.52 (2H, m), 7.58 (1H, s), 7.61 (1H, s), 7.92-8.04 (2H, m), 8.16 (1H, s), 8.20 (1H, s).

REFERENCE EXAMPLE 149 methyl 4-nitro-3-[[3-(trifluoromethoxy)phenyl]amino]benzoate

A solution of methyl 3-fluoro-4-nitrobenzoate (4.66 g, 23.4 mmol), 3-trifluoromethoxyaniline (4.98 g, 28.1 mmol) and N,N-diisopropylethylamine (4.84 mL, 28.1 mmol) in dimethyl sulfoxide (30 mL) was stirred at 120° C. overnight. The reaction mixture was diluted with ethyl acetate, washed with water and saturated brine, dried over anhydrous magnesium sulfate and concentrated under reduced pressure. The residue was recrystallized from hexane/tetrahydrofuran to give the title compound (2.90 g, yield 35%) as red crystals.

$^1$H NMR (CDCl$_3$) δ 3.90 (3H, s), 7.00-7.28 (3H, m), 7.40-7.52 (2H, m), 7.99 (1H, s), 8.27 (1H, d, J=9.1 Hz), 9.41 (1H, brs).

REFERENCE EXAMPLE 150 methyl 1-[3-(trifluoromethoxy)phenyl]-1H-benzimidazole-6-carboxylate

To a solution of sodium hydrosulfite (22.6 g, 130 mmol) in water (65 mL) was added a mixed solution of methyl 4-nitro-3-[[3-(trifluoromethoxy)phenyl]amino]benzoate (2.90 g, 8.14 mmol), tetrahydrofuran (40 mL) and ethanol (20 mL) at 0° C., and the resulting mixture was stirred at room temperature for 30 min. A saturated aqueous sodium hydrogen carbonate solution was added to the reaction mixture, and the mixture was extracted with ethyl acetate. The organic layer was washed with saturated brine, dried over anhydrous magnesium sulfate and concentrated.

A mixture of the obtained residue and formic acid (30 mL) was stirred at 100° C. overnight. After cooling, the reaction mixture was concentrated under reduced pressure. The residue was diluted with ethyl acetate, washed with saturated aqueous sodium hydrogen carbonate solution and saturated brine, dried over anhydrous magnesium sulfate, and concentrated under reduced pressure. The residue was recrystallized from hexane/ethyl acetate to give the title compound (2.14 g, yield 78%) as colorless crystals.

$^1$H NMR (CDCl$_3$) δ 3.95 (3H, s), 7.32-7.45 (2H, m), 7.51 (1H, d, J=8.3 Hz), 7.67 (1H, t, J=8.3 Hz), 7.91 (1H, d, J=8.3 Hz), 8.03-8.12 (1H, m), 8.18-8.30 (2H, m).

REFERENCE EXAMPLE 151

1-[3-(trifluoromethoxy)phenyl]-1H-benzimidazole-6-carbohydrazide

In the same manner as in Reference Example 9 and using methyl 1-[3-(trifluoromethoxy)phenyl]-1H-benzimidazole-6-carboxylate instead of methyl 1H-indazole-5-carboxylate, the title compound (yield 83%) was obtained as colorless crystals.

$^1$H NMR (DMSO-d$_6$) δ 4.50 (2H, brs), 7.56 (1H, d, J=8.3 Hz), 7.73-7.90 (5H, m), 8.10 (1H, s), 8.74 (1H, s), 9.86 (1H, brs).

REFERENCE EXAMPLE 152 methyl 3-[[4-(difluoromethoxy)phenyl]amino]-4-nitrobenzoate

In the same manner as in Reference Example 40 and using 4-(difluoromethoxy)aniline instead of p-anisidine, the title compound (yield 98%) was obtained as yellow crystals.

$^1$H NMR (CDCl$_3$) δ 3.88 (3H, s), 6.55 (1H, t, J=73.6 Hz), 7.14-7.32 (4H, m), 7.38 (1H, dd, J=1.5, 8.7 Hz), 7.82 (1H, d, J=1.5 Hz), 8.26 (1H, d, J=8.7 Hz), 9.39 (1H, s).

REFERENCE EXAMPLE 153 methyl 1-[4-(difluoromethoxy)phenyl]-1H-benzimidazole-6-carboxylate

In the same manner as in Reference Example 150 and using methyl 3-[[4-(difluoromethoxy)phenyl]amino]-4-nitrobenzoate instead of methyl 4-nitro-3-[[3-(trifluoromethoxy)phenyl]amino]benzoate, the title compound (yield 82%) was obtained as colorless crystals.

$^1$H NMR (CDCl$_3$) δ 3.94 (3H, s), 6.62 (1H, t, J=73.1 Hz), 7.38 (2H, d, J=8.7 Hz), 7.54 (2H, d, J=8.7 Hz), 7.90 (1H, d, J=9.1 Hz), 8.01-8.10 (1H, m), 8.20 (2H, s).

REFERENCE EXAMPLE 154

1-[4-(difluoromethoxy)phenyl]-1H-benzimidazole-6-carbohydrazide

In the same manner as in Reference Example 9 and using methyl 1-[4-(difluoromethoxy)phenyl]-1H-benzimidazole-6-carboxylate instead of methyl 1H-indazole-5-carboxylate, the title compound (yield 82%) was obtained as colorless crystals.

$^1$H NMR (DMSO-d$_6$) δ 4.49 (2H, brs), 7.37 (1H, d, J=100.0 Hz), 7.47 (2H, d, J=8.7 Hz), 7.68-7.88 (4H, m), 8.05 (1H, s), 8.67 (1H, s), 9.83 (1H, s).

REFERENCE EXAMPLE 155

1-[4-(difluoromethoxy)phenyl]-6-[5-(methylsulfonyl)-1,3,4-oxadiazol-2-yl]-1H-benzimidazole To a mixture of 1-[4-(difluoromethoxy)phenyl]-6-[5-(methylthio)-1,3,4-oxadiazol-2-yl]-1H-benzimidazole (3.22 g, 8.60 mmol), dichloromethane (24 mL) and N,N-dimethylacetamide (24 mL) was added m-chloroperbenzoic acid (5.15 g, 21.5 mmol), and the resulting mixture was stirred at 50° C. overnight. A saturated aqueous sodium thiosulfate solution was added to the reaction mixture, and the mixture was stirred for 30 min and extracted with ethyl acetate. The organic layer was washed with saturated aqueous sodium hydrogen carbonate solution and saturated brine, dried over anhydrous magnesium sulfate and concentrated under reduced pressure. The residue was purified by silica gel column chromatography (hexane/ethyl acetate=2/1-0/1) and recrystallized from hexane/ethyl acetate to give the title compound (2.23 g, yield 64%) as colorless crystals.

$^1$H NMR (DMSO-d$_6$) δ 3.72 (3H, s), 7.40 (1H, d, J=72.0 Hz), 7.50 (2H, d, J=8.9 Hz), 7.77-7.90 (2H, m), 7.97-8.12 (2H, m), 8.17 (1H, s), 8.81 (1H, s).

REFERENCE EXAMPLE 156

6-[5-(methylsulfonyl)-1,3,4-oxadiazol-2-yl]-1-[3-(trifluoromethoxy)phenyl]-1H-benzimidazole In the same manner as in Reference Example 155 and using 6-[5-(methylthio)-1,3,4-oxadiazol-2-yl]-1-[3-(trifluoromethoxy)phenyl]-1H-benzimidazole instead of 1-[4-(difluoromethoxy)phenyl]-6-[5-(methylthio)-1,3,4-oxadiazol-2-yl]-1H-benzimidazole, the title compound (yield 63%) was obtained as colorless crystals.

$^1$H NMR (DMSO-d$_6$) δ 3.72 (3H, s), 7.60 (1H, brs), 7.77-7.91 (3H, m), 7.91-8.04 (2H, m), 8.11 (1H, s), 8.81 (1H, s).

REFERENCE EXAMPLE 157 methyl 4-nitro-3-[[3-(trifluoromethyl)phenyl]amino]benzoate

In the same manner as in Reference Example 40 and using 3-(trifluoromethyl)aniline instead of p-anisidine, the title compound (yield 35%) was obtained as yellow crystals.

$^1$H NMR (CDCl$_3$) δ 3.90 (3H, s), 7.35-7.64 (5H, m), 7.93 (1H, d, J=1.5 Hz), 8.28 (1H, d, J=8.7 Hz), 9.44 (1H, s).

REFERENCE EXAMPLE 158 methyl 1-[3-(trifluoromethyl)phenyl]-1H-benzimidazole-6-carboxylate

In the same manner as in Reference Example 150 and using methyl 4-nitro-3-[[3-(trifluoromethyl)phenyl]amino]benzoate instead of methyl 4-nitro-3-[[3-(trifluoromethoxy)phenyl]amino]benzoate, the title compound (yield 86%) was obtained as colorless crystals.

$^1$H NMR (CDCl$_3$) δ 3.95 (3H, s), 7.73-7.84 (4H, m), 7.92 (1H, d, J=7.9 Hz), 8.09 (1H, dd, J=1.5, 8.5 Hz), 8.22 (1H, d, J=0.8 Hz), 8.25 (1H, s).

REFERENCE EXAMPLE 159

1-[3-(trifluoromethyl)phenyl]-1H-benzimidazole-6-carbohydrazide

In the same manner as in Reference Example 9 and using methyl 1-[3-(trifluoromethyl)phenyl]-1H-benzimidazole-6-carboxylate instead of methyl 1H-indazole-5-carboxylate, the title compound (yield 95%) was obtained as colorless crystals.

$^1$H NMR (DMSO-d$_6$) δ 4.60 (2H, brs), 7.83 (2H, s), 7.91 (2H, d, J=4.9 Hz), 7.98-8.18 (3H, m), 8.78 (1H, s), 9.85 (1H, s).

REFERENCE EXAMPLE 160 methyl 1-[2-chloro-5-(trifluoromethyl)phenyl]-1H-benzimidazole-6-carboxylate

To a solution of 2-chloro-5-(trifluoromethyl)aniline (2.15 g, 11.00 mmol) in diethylene glycol dimethyl ether (20 mL) was added sodium hydride (60% in oil, 440 mg, 11.00 mmol), and the resulting mixture was stirred at 80° C. for 30 min. To this reaction mixture was added methyl 3-fluoro-4-nitrobenzoate (1.99 g, 10.00 mmol), and the resulting mixture was stirred at 80° C. for 1 hr. After cooling, 1 M hydrochloric acid was added to the reaction mixture, and the mixture was extracted with ethyl acetate. The organic layer was washed with 1M hydrochloric acid and saturated brine, dried over anhydrous magnesium sulfate and concentrated under reduced pressure. The residue was purified by basic silica gel column chromatography (hexane/ethyl acetate=20/1) and recrystallized from hexane/ethyl acetate to give crude methyl 3-[[2-chloro-5-(trifluoromethyl)phenyl]amino]-4-nitrobenzoate (1.92 g).

To a solution of sodium hydrosulfite (18.46 g, 106 mmol) in water (60 mL) was added a mixed solution of the obtained crude methyl 3-[[2-chloro-5-(trifluoromethyl)phenyl]amino]-4-nitrobenzoate, tetrahydrofuran (40 mL) and ethanol (20 mL) at 0° C., and the resulting mixture was stirred at room temperature for 30 min. A saturated aqueous sodium hydrogen carbonate solution was added to the reaction mixture, and the mixture was extracted with ethyl acetate. The organic layer was washed with saturated brine, dried over anhydrous magnesium sulfate and concentrated under reduced pressure.

A mixture of the obtained residue and formic acid (10 mL) was stirred at 100° C. overnight. After cooling, the reaction mixture was concentrated under reduced pressure. The residue was diluted with ethyl acetate, washed with saturated aqueous sodium hydrogen carbonate solution and saturated brine, dried over anhydrous magnesium sulfate, and concentrated under reduced pressure. The residue was recrystallized from hexane/ethyl acetate to give the title compound (1.10 g, yield 31%) as colorless crystals.

$^1$H NMR (CDCl$_3$) δ 3.93 (3H, s), 7.77 (1H, s), 7.80-7.84 (2H, m), 7.89-7.92 (1H, m), 7.94 (1H, s), 8.09 (1H, dd, J=1.7, 8.5 Hz), 8.16 (1H, s).

REFERENCE EXAMPLE 161

1-[2-chloro-5-(trifluoromethyl)phenyl]-1H-benzimidazole-6-carbohydrazide

In the same manner as in Reference Example 9 and using methyl 1-[2-chloro-5-(trifluoromethyl)phenyl]-1H-benzimidazole-6-carboxylate instead of methyl 1H-indazole-5-carboxylate, the title compound (yield 93%) was obtained as colorless crystals.

$^1$H NMR (DMSO-d$_6$) δ 4.46 (2H, brs), 7.75 (1H, s), 7.84 (2H, s), 8.01-8.15 (2H, m), 8.27 (1H, d, J=1.9 Hz), 8.63 (1H, s), 9.76 (1H, brs).

REFERENCE EXAMPLE 162 methyl 3-[[3-chloro-4-(trifluoromethoxy)phenyl]amino]-4-nitrobenzoate

A solution of methyl 3-fluoro-4-nitrobenzoate (1.99 g, 10 mmol) and 3-chloro-4-(trifluoromethoxy)aniline (4.23 g, 20 mmol) in dimethylsulfoxide (10 mL) was stirred at 160° C.

for 2 days. After cooling, the reaction mixture was diluted with ethyl acetate, washed with water and saturated brine, dried over anhydrous magnesium sulfate and concentrated under reduced pressure. The residue was purified by silica gel column chromatography (hexane/ethyl acetate=4/1) and recrystallized from hexane/ethyl acetate to give the title compound (1.47 g, yield 38%) as orange crystals.

$^1$H NMR (CDCl$_3$) δ 3.92 (3H, s), 7.22 (1H, dd, J=2.7, 8.7 Hz), 7.35-7.43 (2H, m), 7.47 (1H, dd, J=1.9, 8.7 Hz), 7.91 (1H, d, J=1.5 Hz), 8.27 (1H, d, J=8.7 Hz), 9.33 (1H, s).

REFERENCE EXAMPLE 163 methyl 1-[3-chloro-4-(trifluoromethoxy)phenyl]-1H-benzimidazole-6-carboxylate

In the same manner as in Reference Example 150 and using methyl 3-[[3-chloro-4-(trifluoromethoxy)phenyl]amino]-4-nitrobenzoate instead of methyl 4-nitro-3-[[3-(trifluoromethoxy)phenyl]amino]benzoate, the title compound (yield 82%) was obtained as colorless crystals.

$^1$H NMR (CDCl$_3$) δ 3.96 (3H, s), 7.45-7.63 (2H, m), 7.69 (1H, d, J=2.7 Hz), 7.91 (1H, d, J=8.7 Hz), 8.00-8.14 (1H, m), 8.15-8.27 (2H, m).

REFERENCE EXAMPLE 164

1-[3-chloro-4-(trifluoromethoxy)phenyl]-1H-benzimidazole-6-carbohydrazide

In the same manner as in Reference Example 9 and using methyl 1-[3-chloro-4-(trifluoromethoxy)phenyl]-1H-benzimidazole-6-carboxylate instead of methyl 1H-indazole-5-carboxylate, the title compound (yield 84%) was obtained as colorless crystals.

$^1$NMR (DMSO-d$_6$) δ 4.51 (2H, brs), 7.74-8.00 (4H, m), 8.02-8.38 (2H, m), 8.74 (1H, s), 9.87 (1H, brs).

REFERENCE EXAMPLE 165

1,1-dimethyl-2-oxo-2-[2-[[1-[4-(trifluoromethoxy)phenyl]-1H-benzimidazol-6-yl]carbonyl]hydrazino] ethyl acetate In the same manner as in Reference Example 129 and using 1-[4-(trifluoromethoxy)phenyl]-1H-benzimidazole-6-carbohydrazide instead of 3-bromo-1-benzofuran-5-carbohydrazide and 2-chloro-1,1-dimethyl-2-oxoethyl acetate instead of (1S)-2-chloro-1-methyl-2-oxoethyl acetate, the title compound (yield 66%) was obtained as colorless crystals.

$^1$H NMR (CDCl$_3$) δ 1.72 (6H, s), 2.12 (3H, s), 7.39-7.48 (2H, m), 7.49-7.58 (2H, m), 7.70-7.93 (2H, m), 8.05 (1H, s), 8.20 (1H, s), 8.93 (1H, brs), 9.19 (1H, brs).

REFERENCE EXAMPLE 166 methyl 1-(2-chlorophenyl)-1H-benzimidazole-6-carboxylate

In the same manner as in Reference Example 37 and using (2-chlorophenyl)boronic acid instead of (4-methoxyphenyl)boronic acid, the title compound (yield 7%) was obtained as colorless crystals.

$^1$H NMR (CDCl$_3$) δ 3.92 (3H, s), 7.44-7.58 (3H, m), 7.62-7.72 (1H, m), 7.86-7.97 (2H, m), 8.06 (1H, dd, J=1.7, 8.5 Hz), 8.17 (1H, s).

REFERENCE EXAMPLE 167

1-(2-chlorophenyl)-1H-benzimidazole-6-carbohydrazide

In the same manner as in Reference Example 9 and using methyl 1-(2-chlorophenyl)-1H-benzimidazole-6-carboxylate instead of methyl 1H-indazole-5-carboxylate, the title compound (yield 41%) was obtained as colorless crystals.

$^1$H NMR (DMSO-d$_6$) δ 4.46 (2H, brs), 7.61-7.69 (2H, m), 7.70-7.79 (2H, m), 7.79-7.83 (3H, m), 8.59 (1H, s), 9.78 (1H, brs).

REFERENCE EXAMPLE 168 methyl 3-bromo-1-benzothiophene-5-carboxylate

To a solution of methyl 1-benzothiophene-5-carboxylate (5.15 g, 26.8 mmol) in acetic acid (50 mL) was added dropwise bromine (2.06 mL, 40.2 mmol) at room temperature, and the resulting mixture was stirred for 2 hr. The reaction mixture was diluted with ethyl acetate, washed with 1 M aqueous sodium sulfite solution, saturated aqueous sodium hydrogen carbonate solution and saturated brine, dried over anhydrous magnesium sulfate and concentrated under reduced pressure. The residue was purified by silica gel column chromatography (hexane/ethyl acetate=5/1), and crystallized from hexane/ethyl acetate to give the title compound (6.20 g, yield 85%) as colorless crystals.

melting point 93-94° C.

$^1$H NMR (CDCl$_3$) δ 3.99 (3H, s), 7.52 (1H, s), 7.90 (1H, dd, J=0.6, 8.5 Hz), 8.08 (1H, ddd, J=0.4, 1.5, 8.5 Hz), 8.53 (1H, dd, J=0.6, 1.5 Hz).

Elemental analysis (for C$_{10}$H$_7$BrO$_2$S)

Calculated (%): C, 44.30; H, 2.60.

Found (%): C, 44.40; H, 2.54.

REFERENCE EXAMPLE 169 methyl 3-[4-(methylthio)phenyl]-1-benzothiophene-5-carboxylate

In the same manner as in Reference Example 19 and using methyl 3-bromo-1-benzothiophene-5-carboxylate instead of methyl 3-iodoimidazo[1,2-a]pyridine-6-carboxylate and [4-(methylthio)phenyl]boronic acid instead of (4-methoxyphenyl)boronic acid, the title compound (yield 76%) was obtained as colorless crystals.

melting point 135-136° C. (recrystallized from hexane/ethyl acetate).

$^1$H NMR (CDCl$_3$) δ 2.56 (3H, s), 3.94 (3H, s), 7.38-7.42 (2H, m), 7.44 (1H, s), 7.49-7.53 (2H, m), 7.95 (1H, dd, J=0.6, 8.5 Hz), 8.05 (1H, dd, J=1.5, 8.5 Hz), 8.56 (1H, dd, J=0.6, 1.5 Hz).

Elemental analysis (for C$_{17}$H$_{14}$O$_2$S$_2$)

Calculated (%): C, 64.94; H, 4.49.

Found (%): C, 64.99; H, 4.42.

REFERENCE EXAMPLE 170

3-[4-(methylthio)phenyl]-1-benzothiophene-5-carbohydrazide

In the same manner as in Reference Example 9 and using methyl 3-[4-(methylthio)phenyl]-1-benzothiophene-5-carboxylate instead of methyl 1H-indazole-5-carboxylate, the title compound (yield 95%) was obtained as colorless crystals.

melting point 195-196° C. (recrystallized from hexane/ethyl acetate).

$^1$H NMR (DMSO-d$_6$) δ 2.56 (3H, s), 4.51 (2H, brs), 7.41-7.46 (2H, m), 7.59-7.63 (2H, m), 7.85 (1H, dd, J=1.5, 8.5 Hz), 7.89 (1H, s), 8.14 (1H, d, J=8.5 Hz), 8.31 (1H, d, J=1.5 Hz), 9.91 (1H, brs).

Elemental analysis (for C$_{16}$H$_{14}$N$_2$OS$_2$)
Calculated (%): C, 61.12; H, 4.49; N, 8.91.
Found (%): C, 61.09; H, 4.45; N, 8.92.

REFERENCE EXAMPLE 171 methyl 1-[4-(methylthio)phenyl]-1H-indole-6-carboxylate

In the same manner as in Reference Example 89 and using 1-bromo-4-(methylthio)benzene instead of methyl 2-chloroisonicotinate and methyl 1H-indole-6-carboxylate instead of 2-aminopyridine, the title compound (yield 47%) was obtained as colorless crystals.

$^1$H NMR (CDCl$_3$) δ 2.57 (3H, s), 3.91 (3H, s), 6.71 (1H, d, J=2.3 Hz), 7.38-7.50 (5H, m), 7.69 (1H, d, J=8.3 Hz), 7.86 (1H, dd, J=1.5, 8.3 Hz), 8.21 (1H, s).

REFERENCE EXAMPLE 172 methyl 3-bromofuro[2,3-b]pyridine-5-carboxylate

To a solution of ethyl furo[2,3-b]pyridine-5-carboxylate (438 mg, 2.29 mmol) in dichloromethane (2 mL) was added dropwise a solution of bromine (0.129 mL, 2.52 mmol) in dichloromethane (2 mL) at 0° C., and the obtained mixture was stirred at room temperature for 2 hr. A saturated aqueous sodium sulfite solution was added to the reaction mixture, and the mixture was stirred for 5 min and extracted with ethyl acetate. The organic layer was washed with saturated aqueous sodium sulfite solution and saturated brine, dried over anhydrous sodium sulfate, and concentrated under reduced pressure.

To a solution of the resulting residue in tetrahydrofuran (10 mL) was added dropwise a solution of potassium hydroxide (85%, 151 mg, 2.29 mmol) in methanol (2 mL) at 0° C., and the obtained mixture was stirred at room temperature for 1 hr. The reaction mixture was diluted with ethyl acetate, washed with water and saturated brine, dried over anhydrous sodium sulfate, and concentrated under reduced pressure. The residue was purified by silica gel column chromatography (hexane/ethyl acetate=50/1-1/1) and recrystallized from hexane/ethyl acetate to give the title compound (194 mg, yield 31%) as colorless crystals.

$^1$H NMR (CDCl$_3$) δ 4.00 (3H, s), 7.84 (1H, s), 8.57 (1H, d, J=2.3 Hz), 9.06 (1H, d, J=1.9 Hz).

REFERENCE EXAMPLE 173 methyl 3-(2-chlorophenyl)furo[2,3-b]pyridine-5-carboxylate

In the same manner as in Reference Example 19 and using methyl 3-bromofuro[2,3-b]pyridine-5-carboxylate instead of methyl 3-iodoimidazo[1,2-a]pyridine-6-carboxylate and (2-chlorophenyl)boronic acid instead of (4-methoxyphenyl)boronic acid, the title compound (yield 77%) was obtained as colorless crystals.

$^1$H NMR (CDCl$_3$) δ 3.97 (3H, s), 7.35-7.46 (2H, m), 7.46-7.53 (1H, m), 7.54-7.62 (1H, m), 7.99 (1H, s), 8.59 (1H, d, J=2.1 Hz), 9.07 (1H, d, J=1.9 Hz).

REFERENCE EXAMPLE 174

3-(2-chlorophenyl)furo[2,3-b]pyridine-5-carbohydrazide

In the same manner as in Reference Example 9 and using methyl 3-(2-chlorophenyl)furo[2,3-b]pyridine-5-carboxylate instead of methyl 1H-indazole-5-carboxylate, the title compound (yield 66%) was obtained as colorless crystals.

$^1$H NMR (DMSO-d$_6$) δ 4.55 (2H, d, J=4.1 Hz), 7.43-7.58 (2H, m), 7.61-7.75 (2H, m), 8.46 (1H, d, J=2.1 Hz), 8.51 (1H, s), 8.83 (1H, d, J=2.1 Hz), 9.99 (1H, brs).

REFERENCE EXAMPLE 175 ethyl 3-bromofuro[2,3-b]pyridine-5-carboxylate

In the same manner as in Reference Example 172 and using ethanol instead of methanol, the title compound (yield 30%) was obtained as colorless crystals.

melting point 107-108° C. (recrystallized from hexane/ethyl acetate).

$^1$H NMR (CDCl$_3$) δ 1.45 (3H, t, J=7.2 Hz), 4.47 (2H, q, J=7.2 Hz), 7.83 (1H, s), 8.56 (1H, d, J=2.1 Hz), 9.06 (1H, d, J=2.1 Hz).

Elemental analysis (for C$_{10}$H$_8$BrNO$_3$)
Calculated (%): C, 44.47; H, 2.19; N, 5.19.
Found (%): C, 44.42; H, 2.44; N, 5.19.

REFERENCE EXAMPLE 176 ethyl 3-[4-(methylthio)phenyl]furo[2,3-b]pyridine-5-carboxylate

In the same manner as in Reference Example 19 and using ethyl 3-bromofuro[2,3-b]pyridine-5-carboxylate instead of methyl 3-iodoimidazo[1,2-a]pyridine-6-carboxylate and [4-(methylthio)phenyl]boronic acid instead of (4-methoxyphenyl)boronic acid, the title compound (yield 95%) was obtained as colorless crystals.

$^1$H NMR (CDCl$_3$) δ 1.44 (3H, t, J=7.2 Hz), 2.55 (3H, s), 4.46 (2H, q, J=7.2 Hz), 7.39 (2H, d, J=8.7 Hz), 7.58 (2H, d, J=8.7 Hz), 7.94 (1H, s), 8.79 (1H, d, J=1.9 Hz), 9.07 (1H, d, J=2.3 Hz).

REFERENCE EXAMPLE 177

3-[4-(methylthio)phenyl]furo[2,3-b]pyridine-5-carbohydrazide

In the same manner as in Reference Example 9 and using ethyl 3-[4-(methylthio)phenyl]furo[2,3-b]pyridine-5-carboxylate instead of methyl 1H-indazole-5-carboxylate, the title compound (yield 49%) was obtained as colorless crystals.

$^1$H NMR (DMSO-d$_6$) δ 2.54 (3H, s), 4.60 (2H, brs), 7.43 (2H, d, J=8.5 Hz), 7.78 (2H, d, J=8.5 Hz), 8.63 (1H, s), 8.76-8.84 (2H, m), 10.06 (1H, brs).

REFERENCE EXAMPLE 178

N'-acetyl-3-bromofuro[2,3-c]pyridine-5-carbohydrazide

In the same manner as in Reference Example 1 and using 3-bromofuro[2,3-c]pyridine-5-carboxylic acid instead of benzothiazole-6-carboxylic acid and acetohydrazide instead of tert-butyl carbazate, the title compound (yield 95%) was obtained as colorless amorphous.

$^1$H NMR (CDCl$_3$) δ 1.93 (3H, s), 8.20 (1H, d, J=0.9 Hz), 8.70 (1H, s), 9.12 (1H, d, J=0.9 Hz), 10.06 (1H, s), 10.46 (1H, s).

REFERENCE EXAMPLE 179

3-bromo-5-(5-methyl-1,3,4-oxadiazol-2-yl)furo[2,3-c]pyridine

In the same manner as in Reference Example 35 and using N'-acetyl-3-bromofuro[2,3-c]pyridine-5-carbohydrazide instead of N'-acetyl-1-benzofuran-5-carbohydrazide, the title compound (yield 42%) was obtained as colorless crystals.

$^1$H NMR (CDCl$_3$) δ 2.69 (3H, s), 7.90 (1H, s), 8.51 (1H, d, J=0.9 Hz), 9.00 (1H, d, J=0.9 Hz).

REFERENCE EXAMPLE 180 ethyl 3-bromofuro[3,2-b]pyridine-5-carboxylate

To a solution of ethyl furo[3,2-b]pyridine-5-carboxylate (0.30 g, 1.57 mmol) in dichloromethane (5 mL) was added dropwise bromine (7.82 mL, 157 mmol) at room temperature, and the resulting mixture was stirred for 3.5 hr. The reaction mixture was concentrated under reduced pressure, and the residue was dissolved in tetrahydrofuran (5 mL). To this solution was added dropwise a 1 M potassium hydroxide ethanol solution (10 mL) at 0° C., and the resulting mixture was stirred at room temperature for 5 min. The reaction mixture was diluted with ethyl acetate, washed with water and saturated brine, dried over anhydrous sodium sulfate, and concentrated under reduced pressure. The residue was purified by silica gel column chromatography (hexane/ethyl acetate=17/3-1/1) to give the title compound (0.15 g, yield 36%) as colorless crystals.

$^1$H NMR (CDCl$_3$) δ 1.48 (3H, t, J=7.2 Hz), 4.51 (2H, q, J=7.2 Hz), 7.89 (1H, d, J=8.7 Hz), 8.00 (1H, s), 8.22 (1H, d, J=8.7 Hz).

REFERENCE EXAMPLE 181 ethyl 3-[4-(methylthio)phenyl]furo[3,2-b]pyridine-5-carboxylate

In the same manner as in Reference Example 19 and using ethyl 3-bromofuro[3,2-b]pyridine-5-carboxylate instead of methyl 3-iodoimidazo[1,2-a]pyridine-6-carboxylate and [4-(methylthio)phenyl]boronic acid instead of (4-methoxyphenyl)boronic acid, the title compound (yield 32%) was obtained as colorless crystals.

melting point 88-89° C. (crystallized from hexane).

$^1$H NMR (CDCl$_3$) δ 1.48 (3H, t, J=7.2 Hz), 2.54 (3H, s), 4.51 (2H, q, J=7.2 Hz), 7.38 (2H, d, J=8.7 Hz), 7.88 (1H, d, J=8.7 Hz), 8.09 (2H, d, J=8.7 Hz), 8.18 (1H, d, J=8.7 Hz), 8.21 (1H, s).

Elemental analysis (for C$_{17}$H$_{15}$NO$_3$S)

Calculated (%): C, 65.16; H, 4.82; N, 4.47.

Found (%): C, 65.15; H, 4.78; N, 4.47.

REFERENCE EXAMPLE 182

3-[4-(methylthio)phenyl]furo[3,2-b]pyridine-5-carbohydrazide

In the same manner as in Reference Example 9 and using ethyl 3-[4-(methylthio)phenyl]furo[3,2-b]pyridine-5-carboxylate instead of methyl 1H-indazole-5-carboxylate, the title compound (yield 82%) was obtained as colorless crystals.

melting point 240-241° C. (recrystallized from ethanol).

$^1$H NMR (DMSO-d$_6$) δ 2.54 (3H, s), 4.64 (2H, d, J=4.3 Hz), 7.38 (2H, d, J=8.5 Hz), 8.07 (1H, d, J=8.7 Hz), 8.23 (1H, d, J=8.7 Hz), 8.32 (2H, d, J=8.5 Hz), 8.97 (1H, s), 9.93 (1H, brs).

Elemental analysis (for C$_5$H$_{13}$N$_3$O$_2$S)

Calculated (%): C, 60.18; H, 4.38; N, 14.04.

Found (%): C, 59.88; H, 4.35; N, 13.80.

REFERENCE EXAMPLE 183

3-bromofuro[3,2-b]pyridine-5-carbohydrazide

In the same manner as in Reference Example 9 and using ethyl 3-bromofuro[3,2-b]pyridine-5-carboxylate instead of methyl 1H-indazole-5-carboxylate and ethanol instead of methanol, the title compound (yield 81%) was obtained as colorless crystals.

$^1$H NMR (CDCl$_3$) δ 4.62 (2H, d, J=4.1 Hz), 8.06 (1H, d, J=8.7 Hz), 8.27 (1H, d, J=8.7 Hz), 8.74 (1H, s), 9.72 (1H, brs).

Elemental analysis (for C$_8$H$_6$BrN$_3$O$_2$)

Calculated (%): C, 37.53; H, 2.36; N, 16.41.

Found (%): C, 37.60; H, 2.35; N, 16.46.

REFERENCE EXAMPLE 184

3-bromo-5-(5-methyl-1,3,4-oxadiazol-2-yl)furo[3,2-b]pyridine

A solution of 3-bromofuro[3,2-b]pyridine-5-carbohydrazide (0.16 g, 0.64 mmol) and triethyl orthoacetate (0.26 mL, 1.40 mmol) in n-butanol (3 mL) was heated under reflux for 1 hr. 1,8-Diazabicyclo[5.4.0]undec-7-ene (0.096 mL, 0.64 mmol) was added to the reaction mixture, and the resulting mixture was heated under reflux overnight. After cooling, the precipitate was collected by filtration, purified by silica gel column chromatography (hexane/ethyl acetate=3/1), and recrystallized from hexane/ethyl acetate to give the title compound (41 mg, yield 23%) as colorless crystals.

$^1$H NMR (CDCl$_3$) δ 2.70 (3H, s), 7.96 (1H, d, J=8.9 Hz), 8.02 (1H, s), 8.33 (1H, d, J=8.9 Hz).

REFERENCE EXAMPLE 185 methyl 2-[(3-methoxyphenyl)amino]isonicotinate

In the same manner as in Reference Example 89 and using 3-methoxyaniline instead of 2-aminopyridine, the title compound (yield 36%) was obtained as colorless crystals.

$^1$H NMR (CDCl$_3$) δ 3.82 (3H, s), 3.92 (3H, s), 6.54-6.71 (2H, m), 6.92 (1H, dd, J=1.5, 7.9 Hz), 7.01 (1H, t, J=2.3 Hz), 7.16-7.33 (2H, m), 7.43 (1H, s), 8.32 (1H, dd, J=0.8, 5.1 Hz).

Elemental analysis (for C$_4$H$_{14}$N$_2$O$_3$)

Calculated (%): C, 65.11; H, 5.46; N, 10.85.

Found (%): C, 65.04; H, 5.42; N, 10.76.

REFERENCE EXAMPLE 186

2-[(3-methoxyphenyl)amino]isonicotinohydrazide

In the same manner as in Reference Example 9 and using methyl 2-[(3-methoxyphenyl)amino]isonicotinate instead of methyl 1H-indazole-5-carboxylate, the title compound (yield 89%) was obtained as colorless crystals.

$^1$H NMR (DMSO-d$_6$) δ 3.73 (3H, s), 4.58 (2H, brs), 6.41-6.55 (1H, m), 7.06 (1H, dd, J=1.3, 5.3 Hz), 7.12-7.28 (3H, m), 7.40 (1H, d, J=2.1 Hz), 8.22 (1H, d, J=5.3 Hz), 9.23 (1H, s), 9.94 (1H, brs).
Elemental analysis (for C$_{13}$H$_4$N$_4$O$_2$)
Calculated (%): C, 60.45; H, 5.46; N, 21.69.
Found (%): C, 60.23; H, 5.38; N, 21.68.

REFERENCE EXAMPLE 187 methyl 2-[(2,5-difluorophenyl)amino]isonicotinate

In the same manner as in Reference Example 89 and using 2,5-difluoroaniline instead of 2-aminopyridine, the title compound (yield 40%) was obtained as colorless crystals.
$^1$H NMR (CDCl$_3$) δ 3.95 (3H, s), 6.54-6.69 (1H, m), 6.78 (1H, brs), 6.96-7.11 (1H, m), 7.31-7.41 (2H, m), 8.14-8.28 (1H, m), 8.33-8.43 (1H, m).
Elemental analysis (for C$_{13}$H$_{10}$F$_2$N$_2$O$_2$)
Calculated (%): C, 59.09; H, 3.81; N, 10.60.
Found (%): C, 59.07; H, 3.76; N, 10.60.

REFERENCE EXAMPLE 188

2-[(2,5-difluorophenyl)amino]isonicotinohydrazide

In the same manner as in Reference Example 9 and using methyl 2-[(2,5-difluorophenyl)amino]isonicotinate instead of methyl 1H-indazole-5-carboxylate, the title compound (yield 92%) was obtained as colorless crystals.
$^1$H NMR (DMSO-d$_6$) δ 4.59 (2H, brs), 6.66-6.86 (1H, m), 7.15 (1H, dd, J=1.2, 5.4 Hz), 7.18-7.32 (1H, m), 7.48 (1H, s), 8.12-8.34 (2H, m), 9.13 (1H, s), 9.95 (1H, brs).
Elemental analysis (for C$_{12}$H$_{10}$F$_2$N$_4$O)
Calculated (%): C, 54.55; H, 3.81; N, 21.20.
Found (%): C, 54.62; H, 3.69; N, 21.33.

REFERENCE EXAMPLE 189 methyl 2-[[3-(trifluoromethyl)phenyl]amino]isonicotinate

In the same manner as in Reference Example 89 and using 3-(trifluoromethyl)aniline instead of 2-aminopyridine, the title compound (yield 34%) was obtained as colorless crystals.
$^1$H NMR (CDCl$_3$) δ 3.94 (3H, s), 6.70 (1H, s), 7.27-7.39 (3H, m), 7.45 (1H, t, J=7.9 Hz), 7.58-7.69 (1H, m), 7.75 (1H, s), 8.37 (1H, dd, J=0.8, 5.1 Hz).
Elemental analysis (for C$_{14}$H$_{11}$F$_3$N$_2$O$_2$)
Calculated (%): C, 56.76; H, 3.74; N, 9.46.
Found (%): C, 56.77; H, 3.67; N, 9.58.

REFERENCE EXAMPLE 190

2-[[3-(trifluoromethyl)phenyl]amino]isonicotinohydrazide

In the same manner as in Reference Example 9 and using methyl 2-[[3-(trifluoromethyl)phenyl]amino]isonicotinate instead of methyl 1H-indazole-5-carboxylate, the title compound (yield 92%) was obtained as colorless crystals.
$^1$H NMR (DMSO-d$_6$) δ 4.61 (2H, brs), 7.15 (1H, dd, J=1.2, 5.4 Hz), 7.22 (1H, d, J=7.5 Hz), 7.27 (1H, s), 7.50 (1H, t, J=7.9 Hz), 7.89 (1H, d, J=9.4 Hz), 8.23 (1H, s), 8.29 (1H, d, J=5.5 Hz), 9.62 (1H, s), 10.00 (1H, s).

REFERENCE EXAMPLE 191 methyl 2-[[3-(trifluoromethyl)benzyl]amino]isonicotinate

A solution of methyl 2-aminoisonicotinate (1.52 g, 10.00 mmol), 3-(trifluoromethyl)benzaldehyde (2.09 g, 12.00 mmol) and acetic acid (0.572 mL, 10.00 mmol) in tetrahydrofuran (30 mL) was stirred at room temperature for 30 min. To this reaction mixture was added sodium triacetoxyhydroborate (4.46 g, 20.00 mmol), and the resulting mixture was stirred overnight at room temperature. The reaction mixture was diluted with ethyl acetate, washed with saturated aqueous sodium hydrogen carbonate solution and saturated brine, dried over anhydrous magnesium sulfate and concentrated under reduced pressure. The residue was purified by silica gel column chromatography (hexane/ethyl acetate=20/1-9/1) to give the title compound (1.06 g, yield 34%) as a colorless oil.
$^1$H NMR (CDCl$_3$) δ 3.90 (3H, s), 4.65 (2H, d, J=6.0 Hz), 5.04 (1H, brs), 7.00 (1H, s), 7.14 (1H, d, J=5.1 Hz), 7.38-7.60 (2H, m), 7.63 (2H, d, J=8.5 Hz), 8.22 (1H, d, J=5.3 Hz).

REFERENCE EXAMPLE 192

2-[[3-(trifluoromethyl)benzyl]amino]isonicotinohydrazide

In the same manner as in Reference Example 9 and using methyl 2-[[3-(trifluoromethyl)benzyl]amino]isonicotinate instead of methyl 1H-indazole-5-carboxylate, the title compound (yield 50%) was obtained as colorless crystals.
$^1$H NMR (DMSO-d$_6$) δ 4.52 (2H, brs), 4.59 (2H, d, J=6.0 Hz), 6.83 (1H, dd, J=1.3, 5.3 Hz), 6.91 (1H, s), 7.41 (1H, t, J=6.2 Hz), 7.47-7.72 (4H, m), 8.01 (1H, d, J=5.3 Hz), 9.82 (1H, brs).
Elemental analysis (for C$_{14}$H$_{13}$F$_3$N$_4$O)
Calculated (%): C, 54.19; H, 4.22; N, 18.06.
Found (%): C, 54.15; H, 4.18; N, 18.06.

REFERENCE EXAMPLE 193 methyl 2-[(2-pyridylmethyl)amino]isonicotinate

In the same manner as in Reference Example 191 and using pyridine-2-carbaldehyde instead of 3-(trifluoromethyl)benzaldehyde and trifluoroacetic acid instead of acetic acid, the title compound (yield 65%) was obtained as colorless crystals.
$^1$H NMR (CDCl$_3$) δ 3.91 (3H, s), 4.70 (2H, d, J=5.3 Hz), 5.88 (1H, brs), 7.06-7.12 (2H, m), 7.19 (1H, dd, J=1.3, 6.2 Hz), 7.32 (1H, d, J=7.7 Hz), 7.66 (1H, td, J=1.8, 7.7 Hz), 8.23 (1H, dd, J=0.8, 5.2 Hz), 8.57 (1H, d, J=0.9 Hz).

REFERENCE EXAMPLE 194

2-[(2-pyridylmethyl)amino]isonicotinohydrazide

In the same manner as in Reference Example 9 and using methyl 2-[(2-pyridylmethyl)amino]isonicotinate instead of methyl 1H-indazole-5-carboxylate, the title compound (yield 81%) was obtained as colorless crystals.
$^1$H NMR (DMSO-d$_6$) δ 4.58 (4H, d, J=6.0 Hz), 6.81 (1H, dd, J=1.4, 5.4 Hz), 6.94 (1H, s), 7.23 (1H, dd, J=5.5, 7.0 Hz), 7.28 (1H, d, J=7.7 Hz), 7.37 (1H, t, J=6.1 Hz), 7.71 (1H, td, J=1.9, 7.6 Hz), 8.00 (1H, d, J=5.3 Hz), 8.50 (1H, d, J=4.0 Hz), 9.82 (1H, brs).

REFERENCE EXAMPLE 195 methyl 2-[(3-pyridylmethyl)amino]isonicotinate

In the same manner as in Reference Example 191 and using nicotinaldehyde instead of 3-(trifluoromethyl)benzaldehyde and trifluoroacetic acid instead of acetic acid, the title compound (yield 47%) was obtained as colorless crystals.

$^1$H NMR (CDCl$_3$) δ 3.91 (3H, s), 4.62 (2H, d, J=6.0 Hz), 5.02 (1H, brs), 7.00 (1H, s), 7.14 (1H, dd, J=1.3, 5.3 Hz), 7.22?7.30 (1H, m), 7.69 (1H, d, J=7.9 Hz), 8.23 (1H, d, J=5.1 Hz), 8.53 (1H, dd, J=1.5, 4.7 Hz), 8.63 (1H, d, J=1.7 Hz).

REFERENCE EXAMPLE 196

2-[(3-pyridylmethyl)amino]isonicotinohydrazide

In the same manner as in Reference Example 9 and using methyl 2-[(3-pyridylmethyl)amino]isonicotinate instead of methyl 1H-indazole-5-carboxylate, the title compound (yield 81%) was obtained as colorless crystals.

$^1$H NMR (DMSO-d$_6$) δ 4.52 (4H, d, J=5.8 Hz), 6.82 (1H, dd, J=1.3, 5.3 Hz), 6.89 (1H, s), 7.25-7.41 (2H, m), 7.65-7.75 (1H, m), 8.02 (1H, d, J=5.3 Hz), 8.42 (1H, dd, J=1.5, 4.7 Hz), 8.54 (1H, d, J=1.9 Hz), 9.82 (1H, brs).

EXAMPLE 1

6-[5-[[3-(trifluoromethyl)benzyl]thio]-1,3,4-oxadiazol-2-yl]benzothiazole

A suspension of 5-(benzothiazol-6-yl)-1,3,4-oxadiazole-2-thiol (235 mg, 1.00 mmol), 3-(trifluoromethyl)benzyl chloride (0.186 mL, 1.20 mmol), and potassium carbonate (207 mg, 1.50 mmol) in N,N-dimethylformamide (5 mL) was stirred at room temperature for 5 hr. The reaction mixture was diluted with ethyl acetate, washed with water and saturated brine, dried over anhydrous magnesium sulfate and concentrated under reduced pressure. The residue was purified by basic silica gel column chromatography (tetrahydrofuran) and recrystallized from hexane/tetrahydrofuran to give the title compound (321 mg, yield 82%) as colorless crystals.

melting point 112-113° C.

$^1$H NMR (CDCl$_3$) δ 4.59 (2H, s), 7.48 (1H, t, J=7.7 Hz), 7.58 (1H, d, J=8.1 Hz), 7.70-7.75 (2H, m), 8.15 (1H, dd, J=1.7, 8.7 Hz), 8.24 (1H, dd, J=0.6, 8.7 Hz), 8.62 (1H, dd, J=0.6, 1.7 Hz), 9.14 (1H, s).

Elemental analysis (for C$_{17}$H$_{10}$F$_3$N$_3$OS$_2$)

Calculated (%): C, 51.90; H, 2.56; N, 10.68.

Found (%): C, 51.72; H, 2.49; N, 10.84.

EXAMPLE 2

6-[5-[(4-methoxybenzyl)thio]-1,3,4-oxadiazol-2-yl]benzothiazole

In the same manner as in Example 1 and using 4-methoxybenzyl chloride instead of 3-(trifluoromethyl)benzyl chloride, the title compound (yield 86%) was obtained as colorless crystals.

melting point 134-135° C. (recrystallized from hexane/ethyl acetate).

$^1$H NMR (CDCl$_3$) δ 3.80 (3H, s), 4.52 (2H, s), 6.85-6.90 (2H, m), 7.37-7.42 (2H, m), 8.16 (1H, dd, J=1.7, 8.7 Hz), 8.24 (1H, dd, J=0.6, 8.7 Hz), 8.62 (1H, dd, J=0.6, 1.7 Hz), 9.13 (1H, s).

Elemental analysis (for C$_{17}$H$_{13}$N$_3$O$_2$S$_2$)

Calculated (%): C, 57.45; H, 3.69; N, 11.82.

Found (%): C, 57.56; H, 3.84; N, 12.09.

EXAMPLE 3

6-[5-[[4-methoxy-3-(trifluoromethyl)benzyl]thio]-1,3,4-oxadiazol-2-yl]benzothiazole In the same manner as in Example 1 and using 4-methoxy-3-(trifluoromethyl)benzyl bromide instead of 3-(trifluoromethyl)benzyl chloride, the title compound (yield 82%) was obtained as colorless crystals.

melting point 145-146° C. (recrystallized from hexane/tetrahydrofuran).

$^1$H NMR (CDCl$_3$) δ 3.89 (3H, s), 4.52 (2H, s), 6.97 (1H, d, J=8.5 Hz), 7.63-7.68 (2H, m), 8.16 (1H, dd, J=1.7, 8.5 Hz), 8.24 (1H, dd, J=0.6, 8.5 Hz), 8.62 (1H, dd, J=0.6, 1.7 Hz), 9.13 (1H, s).

Elemental analysis (for C$_{18}$H$_{12}$F$_3$N$_3$O$_2$S$_2$)

Calculated (%): C, 51.06; H, 2.86; N, 9.92.

Found (%): C, 50.84; H, 2.89; N, 9.93.

EXAMPLE 4

5-[[[5-(benzothiazol-6-yl)-1,3,4-oxadiazol-2-yl]thio]methyl]-2-methoxybenzonitrile In the same manner as in Example 1 and using 5-(chloromethyl)-2-methoxybenzonitrile instead of 3-(trifluoromethyl)benzyl chloride, the title compound (yield 87%) was obtained as colorless crystals.

melting point 181-182° C. (recrystallized from hexane/ethyl acetate).

$^1$H NMR (CDCl$_3$) δ 3.92 (3H, s), 4.48 (2H, s), 6.93-6.96 (1H, m), 7.68-7.72 (2H, m), 8.16 (1H, dd, J=1.7, 8.7° Hz), 8.25 (1H, dd, J=0.6, 8.7 Hz), 8.62 (1H, dd, J=0.6, 1.7 Hz), 9.14 (1H, s).

Elemental analysis (for C$_{18}$H$_{12}$N$_4$O$_2$S$_2$)

Calculated (%): C, 56.83; H, 3.18; N, 14.73.

Found (%): C, 56.89; H, 3.11; N, 14.70.

EXAMPLE 5

6-[5-[2-[3-(trifluoromethyl)phenyl]ethyl]-1,3,4-oxadiazol-2-yl]benzothiazole A solution of N'-[3-[3-(trifluoromethyl)phenyl]propionyl]benzothiazole-6-carbohydrazide (433 mg, 1.10 mmol) and p-toluenesulfonyl chloride (419 mg, 2.20 mmol) in pyridine (5 mL) was stirred under an argon atmosphere at 80° C. for 16 hr. After cooling, the reaction mixture was diluted with ethyl acetate, washed with 0.1M hydrochloric acid and saturated brine, dried over anhydrous magnesium sulfate and concentrated under reduced pressure. The residue was purified by basic silica gel column chromatography (hexane/ethyl acetate=1/1) and recrystallized from hexane/ethyl acetate to give the title compound (308 mg, yield 75%) as colorless crystals.

melting point 126-127° C.

$^1$H NMR (CDCl$_3$) δ 3.24-3.35 (4H, m), 7.42-7.55 (4H, m), 8.17 (1H, dd, J=1.7, 8.7 Hz), 8.25 (1H, dd, J=0.6, 8.7 Hz), 8.64 (1H, dd, J=0.6, 1.7 Hz), 9.14 (1H, s).

Elemental analysis (for C$_{18}$H$_{12}$F$_3$N$_3$OS)

Calculated (%): C, 57.59; H, 3.22; N, 11.19.

Found (%): C, 57.59; H, 3.12; N, 11.29.

EXAMPLE 6

6-[5-[2-[3-(trifluoromethyl)phenyl]ethyl]-1,3,4-oxadiazol-2-yl]benzoxazole

In the same manner as in Example 5 and using N'-[3-[3-(trifluoromethyl)phenyl]propionyl]benzoxazole-6-carbohydrazide instead of N'-[3-[3-(trifluoromethyl)phenyl]propionyl]benzothiazole-6-carbohydrazide, the title compound (yield 11%) was obtained as colorless crystals.

melting point 117-118° C. (recrystallized from hexane/ethyl acetate).

$^1$H NMR (DMSO-$d_6$) δ 3.23-3.35 (4H, m), 7.51-7.60 (2H, m), 7.65 (1H, d, J=6.9 Hz), 7.72 (1H, s), 8.01 (2H, d, J=1.2 Hz), 8.34 (1H, s), 8.95 (1H, s).

LC-MS (ESI) m/z360 [M+H]$^+$.

EXAMPLE 7

5-[5-[[3-(trifluoromethyl)benzyl]thio]-1,3,4-oxadiazol-2-yl]-1H-indazole

To a solution of 5-(1H-indazol-5-yl)-1,3,4-oxadiazole-2-thiol (218 mg, 1.00 mmol) and 1 M aqueous sodium hydroxide solution (1.00 mL, 1.00 mmol) in N,N-dimethylformamide (5 mL) was added 3-(trifluoromethyl)benzyl chloride (0.155 mL, 1.00 mmol) at room temperature, and the resulting mixture was stirred overnight. The reaction mixture was diluted with ethyl acetate, washed with water and saturated brine, dried over anhydrous magnesium sulfate and concentrated under reduced pressure. The residue was purified by basic silica gel column chromatography (tetrahydrofuran) and recrystallized from methanol to give the title compound (279 mg, yield 74%) as colorless crystals.

melting point 159-160° C.

$^1$H NMR (CDCl$_3$) δ 4.57 (2H, s), 7.45-7.50 (1H, m), 7.55-7.63 (2H, m), 7.69-7.76 (2H, m), 8.07 (1H, dd, J=1.5, 8.7 Hz), 8.19 (1H, d, J=1.1 Hz), 8.39 (1H, dd, J=0.9, 1.5 Hz), 10.36 (1H, brs).

Elemental analysis (for C$_{17}$H$_{11}$F$_3$N$_4$OS)

Calculated (%): C, 54.25; H, 2.95; N, 14.89.

Found (%): C, 54.18; H, 2.83; N, 15.04.

EXAMPLE 8

3-[[[5-(1H-indazol-5-yl)-1,3,4-oxadiazol-2-yl]thio]methyl]benzonitrile

In the same manner as in Example 7 and using 3-(bromomethyl)benzonitrile instead of 3-(trifluoromethyl)benzyl chloride, the title compound (yield 85%) was obtained as colorless crystals.

melting point 172-173° C. (recrystallized from ethanol/water).

$^1$H NMR (CDCl$_3$) δ 4.53 (2H, s), 7.47 (1H, dt, J=0.4, 7.7 Hz), 7.58-7.64 (2H, m), 7.75-7.79 (1H, m), 7.81-7.82 (1H, m), 8.07 (1H, dd, J=1.5, 8.9 Hz), 8.20 (1H, d, J=0.9 Hz), 8.40 (1H, dd, J=0.8, 1.5 Hz), 10.32 (1H, brs).

Elemental analysis (for C$_{17}$H$_{11}$N$_5$OS)

Calculated (%): C, 61.25; H, 3.33; N, 21.01.

Found (%): C, 61.12; H, 3.32; N, 20.95.

EXAMPLE 9

5-[5-[(4-methoxybenzyl)thio]-1,3,4-oxadiazol-2-yl]-1H-indazole

In the same manner as in Example 7 and using 4-methoxybenzyl chloride instead of 3-(trifluoromethyl)benzyl chloride, the title compound (yield 85%) was obtained as colorless crystals.

melting point 204-205° C. (recrystallized from hexane/tetrahydrofuran).

$^1$H NMR (CDCl$_3$) δ 3.79 (3H, s), 4.51 (2H, s), 6.85-6.90 (2H, m), 7.37-7.40 (2H, m), 7.61 (1H, td, J=0.9, 8.9 Hz), 8.08 (1H, dd, J=1.5, 8.9 Hz), 8.19 (1H, d, J=0.8 Hz), 8.40 (1H, dd, J=0.8, 1.5 Hz), 10.37 (1H, brs).

Elemental analysis (for C$_{17}$H$_{14}$N$_4$O$_2$S)

Calculated (%): C, 60.34; H, 4.17; N, 16.56.

Found (%): C, 60.34; H, 4.11; N, 16.63.

EXAMPLE 10

5-[5-[[4-methoxy-3-(trifluoromethyl)benzyl]thio]-1,3,4-oxadiazol-2-yl]-1H-indazole In the same manner as in Example 7 and using 4-methoxy-3-(trifluoromethyl)benzyl bromide instead of 3-(trifluoromethyl)benzyl chloride, the title compound (yield 76%) was obtained as colorless crystals.

melting point 136-137° C. (recrystallized from methanol/water).

$^1$H NMR (CDCl$_3$) δ 3.89 (3H, s), 4.50 (2H, s), 6.97 (1H, d, J=8.3 Hz), 7.60-7.68 (3H, m), 8.07 (1H, dd, J=1.5, 8.9 Hz), 8.19 (1H, d, J=0.8 Hz), 8.40 (1H, dd, J=0.8, 1.5 Hz), 10.32 (1H, brs).

Elemental analysis (for C$_{18}$H$_{13}$F$_3$N$_4$O$_2$S.H$_2$O)

Calculated (%): C, 52.05; H, 3.40; N, 13.49.

Found (%): C, 52.13; H, 3.57; N, 13.46.

EXAMPLE 11

5-[[[5-(1H-indazol-5-yl)-1,3,4-oxadiazol-2-yl]thio]methyl]-2-methoxybenzonitrile In the same manner as in Example 7 and using 5-(chloromethyl)-2-methoxybenzonitrile instead of 3-(trifluoromethyl)benzyl chloride, the title compound (yield 85%) was obtained as colorless crystals.

melting point 192-193° C. (recrystallized from ethanol/water).

$^1$H NMR (CDCl$_3$) δ 3.92 (3H, s), 4.47 (2H, s), 6.93-6.96 (1H, m), 7.62 (1H, td, J=0.9, 8.9 Hz), 7.68-7.72 (2H, m), 8.07 (1H, dd, J=1.5, 8.9 Hz), 8.20 (1H, d, J=0.9 Hz), 8.40 (1H, dd, J=0.8, 1.5 Hz), 10.35 (1H, brs).

Elemental analysis (for C$_{18}$H$_{13}$N$_5$O$_2$S)

Calculated (%): C, 59.49; H, 3.61; N, 19.27.

Found (%): C, 59.10; H, 3.64; N, 19.13.

EXAMPLE 12

5-[5-[2-[3-(trifluoromethyl)phenyl]ethyl]-1,3,4-oxadiazol-2-yl]-1H-indazole

A solution of N'-[3-[3-(trifluoromethyl)phenyl]propionyl]-1H-indazole-5-carbohydrazide (320 mg, 0.850 mmol) and p-toluenesulfonyl chloride (486 mg, 2.55 mmol) in pyridine (3 mL) was stirred under an argon atmosphere at 80° C. for 24 hr. After cooling, the reaction mixture was diluted with ethyl acetate, washed with 1M hydrochloric acid, saturated aqueous sodium hydrogen carbonate solution and saturated brine, dried over anhydrous magnesium sulfate and concentrated under reduced pressure.

A mixture of the obtained residue, 1 M aqueous sodium hydroxide solution (5 mL), tetrahydrofuran (10 mL) and ethanol (5 mL) was heated under reflux for 30 min. After cooling, the reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=1/1-0/1), and recrystallized from ethanol/water to give the title compound (103 mg, yield 34%) as colorless crystals.

melting point 175-176° C.

$^1$H NMR (CDCl$_3$) δ 3.23-3.34 (4H, m), 7.42-7.55 (4H, m), 7.62 (1H, td, J=0.9, 8.9 Hz), 8.09 (1H, dd, J=1.5, 8.9 Hz), 8.20 (1H, d, J=1.1 Hz), 8.41 (1H, dd, J=0.8, 1.5 Hz), 10.40 (1H, brs).

Elemental analysis (for C$_{18}$H$_{13}$F$_3$N$_4$O)
Calculated (%): C, 60.34; H, 3.66; N, 15.64.
Found (%): C, 60.35; H, 3.66; N, 15.61.

EXAMPLE 13

5-[5-[2-[4-methoxy-3-(trifluoromethyl)phenyl] ethyl]-1,3,4-oxadiazol-2-yl]-1H-indazole In the same manner as in Example 12 and using N'-[3-[4-methoxy-3-(trifluoromethyl)phenyl]propionyl]-1H-indazole-5-carbohydrazide instead of N'-[3-[3-(trifluoromethyl)phenyl]propionyl]-1H-indazole-5-carbohydrazide, the title compound (yield 52%) was obtained as colorless crystals.

melting point 192-193° C. (recrystallized from ethanol/water).

$^1$H NMR (CDCl$_3$) δ 3.15-3.21 (2H, m), 3.23-3.28 (2H, m), 3.88 (3H, s), 6.95 (1H, d, J=8.5 Hz), 7.39 (1H, dd, J=2.1, 8.5 Hz), 7.48 (1H, d, J=2.1 Hz), 7.62 (1H, td, J=0.9, 8.9 Hz), 8.10 (1H, dd, J=1.5, 8.9 Hz), 8.20 (1H, d, J=1.1 Hz), 8.41 (1H, dd, J=0.8, 1.5 Hz), 10.38 (1H, brs).

Elemental analysis (for C$_{19}$H$_{15}$F$_3$N$_4$O$_2$)
Calculated (%): C, 58.76; H, 3.89; N, 14.43.
Found (%): C, 58.65; H, 3.90; N, 14.46.

EXAMPLE 14

3-[2-[5-(1H-benzotriazol-5-yl)-1,3,4-oxadiazol-2-yl] ethyl]benzonitrile

A mixture of 1H-benzotriazole-5-carbohydrazide (354 mg, 2.00 mmol), 3-(3-cyanophenyl)propionic acid (350 mg, 2.00 mmol) and phosphorus oxychloride (5 mL) was stirred at 100° C. for 4 hr. After cooling, the reaction mixture was poured into water and neutralized with sodium hydrogen carbonate, and the mixture was extracted with ethyl acetate. The organic layer was washed with saturated brine, dried over anhydrous magnesium sulfate and concentrated under reduced pressure. The residue was purified by silica gel column chromatography (ethyl acetate), and recrystallized from methanol/water to give the title compound (104 mg, yield 16%) as colorless crystals.

melting point 186-187° C.

$^1$H NMR (DMSO-d$_6$) δ 3.19-3.24 (2H, m), 3.33-3.38 (2H, m), 7.53 (1H, t, J=7.7 Hz), 7.69-7.72 (2H, m), 7.85-7.86 (1H, m), 8.04 (1H, dd, J=1.3, 8.7 Hz), 8.10 (1H, dd, J=0.8, 8.7 Hz), 8.50 (1H, dd, J=0.8, 1.3 Hz), 16.11 (1H, brs).

Elemental analysis (for C$_{17}$H$_{12}$N$_6$O.0.75H$_2$O)
Calculated (%): C, 61.91; H, 4.13; N, 25.48.
Found (%): C, 61.83; H, 4.13; N, 25.44.

EXAMPLE 15

5-[5-[2-[4-methoxy-3-(trifluoromethyl)phenyl] ethyl]-1,3,4-oxadiazol-2-yl]-1H-benzotriazole In the same manner as in Example 14 and using 3-[4-methoxy-3-(trifluoromethyl)phenyl]propionic acid instead of 3-(3-cyanophenyl)propionic acid, the title compound (yield 24%) was obtained as colorless crystals.

melting point 154-155° C. (recrystallized from methanol/water).

$^1$H NMR (DMSO-d$_6$) δ 3.13-3.18 (2H, m), 3.28-3.33 (2H, m), 3.85 (3H, s), 7.18-7.21 (1H, m), 7.56-7.60 (2H, m), 8.04 (1H, dd, J=1.5, 8.7 Hz), 8.10 (1H, dd, J=0.8, 8.7 Hz), 8.51 (1H, dd, J=0.8, 1.5 Hz), 16.10 (1H, brs).

Elemental analysis (for C$_{18}$H$_{14}$F$_3$N$_5$O$_2$.0.5H$_2$O)
Calculated (%): C, 54.27; H, 3.80; N, 17.58.
Found (%): C, 54.11; H, 3.84; N, 17.43.

EXAMPLE 16

6-[5-[[4-methoxy-3-(trifluoromethyl)benzyl]thio]-1,3,4-oxadiazol-2-yl]imidazo[1,2-a]pyridine A solution of imidazo[1,2-a]pyridine-6-carbohydrazide (1.00 g, 5.67 mmol), carbon disulfide (0.85 mL, 14.2 mmol) and triethylamine (0.97 mL, 7.09 mmol) in ethanol (50 mL) was heated under reflux overnight. After cooling, the reaction mixture was concentrated under reduced pressure.

A suspension of the obtained residue and 4-methoxy-3-(trifluoromethyl)benzyl bromide (1.83 g, 6.00 mmol) in N,N-dimethylformamide (10 mL) was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=4/1-1/1) and recrystallized from hexane/ethyl acetate to give the title compound (1.67 g, yield 71%) as colorless crystals.

melting point 146-147° C.

$^1$H NMR (DMSO-d$_6$) δ 3.86 (3H, s), 4.62 (2H, s), 7.25 (2H, d, J=8.4 Hz), 7.67-7.79 (4H, m), 8.11 (1H, s), 9.37 (1H, t, J=1.2 Hz).

Elemental analysis (for C$_{18}$H$_{13}$F$_3$N$_4$O$_2$S.0.1H$_2$O)
Calculated (%): C, 52.96; H, 3.26; N, 13.72.
Found (%): C, 52.94; H, 3.28; N, 13.42.

EXAMPLE 17

6-[5-[[3-(trifluoromethyl)benzyl]thio]-1,3,4-oxadiazol-2-yl]imidazo[1,2-a]pyridine In the same manner as in Example 16 and using 3-(trifluoromethyl)benzyl chloride instead of 4-methoxy-3-(trifluoromethyl)benzyl bromide, the title compound (yield 32%) was obtained as colorless crystals.

melting point 147-148° C. (recrystallized from hexane/ethyl acetate).

$^1$H NMR (DMSO-d$_6$) δ 4.69 (2H, s), 7.58-7.76 (5H, m), 7.83 (1H, d, J=7.8 Hz), 7.91 (1H, s), 8.11 (1H, s), 9.36 (1H, t, J=0.6 Hz).

Elemental analysis (for C$_{17}$H$_{11}$F$_3$N$_2$OS)
Calculated (%): C, 54.25; H, 2.95; N, 14.89.
Found (%): C, 54.26; H, 3.01; N, 15.10.

EXAMPLE 18

6-[5-[(3-fluorobenzyl)thio]-1,3,4-oxadiazol-2-yl]imidazo[1,2-a]pyridine

In the same manner as in Example 16 and using 3-fluorobenzyl bromide instead of 4-methoxy-3-(trifluoromethyl)benzyl bromide, the title compound (yield 61%) was obtained as colorless crystals.

melting point 173-174° C. (recrystallized from hexane/ethyl acetate).

$^1$H NMR (DMSO-$d_6$) δ 4.62 (2H, s), 7.10-7.17 (1H, m), 7.33-7.44 (3H, m), 7.67-7.77 (3H, m), 8.11 (1H, s), 9.36 (1H, s).

Elemental analysis (for $C_{16}H_{11}FN_4OS$)
Calculated (%): C, 58.89; H, 3.40; N, 17.17.
Found (%): C, 58.60; H, 3.32; N, 17.17.

EXAMPLE 19

3-[[[5-(imidazo[1,2-a]pyridin-6-yl)-1,3,4-oxadiazol-2-yl]thio]methyl]benzonitrile In the same manner as in Example 16 and using 3-(bromomethyl)benzonitrile instead of 4-methoxy-3-(trifluoromethyl)benzyl bromide, the title compound (yield 71%) was obtained as colorless crystals.

melting point 175-176° C. (recrystallized from hexane/ethyl acetate).

$^1$H NMR (DMSO-$d_6$) δ 4.64 (2H, s), 7.58 (1H, t, J=7.8 Hz), 7.67-7.79 (4H, m), 7.86 (1H, d, J=7.8 Hz), 7.99 (1H, s), 8.11 (1H, s), 9.35 (1H, s).

EXAMPLE 20

6-[5-[(4-methoxybenzyl)thio]-1,3,4-oxadiazol-2-yl]imidazo[1,2-a]pyridine

In the same manner as in Example 16 and using 4-methoxybenzyl chloride instead of 4-methoxy-3-(trifluoromethyl)benzyl bromide, the title compound (yield 57%) was obtained as colorless crystals.

melting point 155-156° C. (recrystallized from hexane/ethyl acetate).

$^1$H NMR (DMSO-$d_6$) δ 3.73 (3H, s), 4.56 (2H, s), 6.91 (2H, d, J=8.4 Hz), 7.42 (2H, d, J=8.4 Hz), 7.68-7.77 (3H, m), 8.12 (1H, s), 9.37 (1H, s).

Elemental analysis (for $C_{17}H_{14}N_4O_2S$)
Calculated (%): C, 60.34; H, 4.17; N, 16.56.
Found (%): C, 60.04; H, 4.13; N, 16.47.

EXAMPLE 21

3-(4-methoxyphenyl)-6-[5-[[3-(trifluoromethyl)benzyl]thio]-1,3,4-oxadiazol-2-yl]imidazo[1,2-a]pyridine In the same manner as in Example 16 and using 3-(4-methoxyphenyl)imidazo[1,2-a]pyridine-6-carbohydrazide instead of imidazo[1,2-a]pyridine-6-carbohydrazide and 3-(trifluoromethyl)benzyl chloride instead of 4-methoxy-3-(trifluoromethyl)benzyl bromide, the title compound (yield 9.2%) was obtained as colorless crystals.

melting point 104-105° C. (recrystallized from hexane/ethyl acetate).

$^1$H NMR (DMSO-$d_6$) δ 3.85 (3H, s), 4.66 (2H, s), 7.19 (2H, d, J=2.7 Hz), 7.52 (1H, t, J=7.8 Hz), 7.60-7.66 (3H, m), 7.73 (1H, dd, J=1.8, 7.8 Hz), 7.79-7.87 (4H, m), 8.82 (1H, t, J=1.8 Hz).

Elemental analysis (for $C_{24}H_{17}F_3N_4O_2S$)
Calculated (%): C, 59.75; H, 3.55; N, 11.61.
Found (%): C, 59.50; H, 3.55; N, 11.71.

EXAMPLE 22

3-[[[5-[3-(4-methoxyphenyl)imidazo[1,2-a]pyridin-6-yl]-1,3,4-oxadiazol-2-yl]thio]methyl]benzonitrile In the same manner as in Example 16 and using 3-(4-methoxyphenyl)imidazo[1,2-a]pyridine-6-carbohydrazide instead of imidazo[1,2-a]pyridine-6-carbohydrazide and 3-(bromomethyl)benzonitrile instead of 4-methoxy-3-(trifluoromethyl)benzyl bromide, the title compound (yield 11%) was obtained as colorless crystals.

melting point 143-144° C. (recrystallized from hexane/ethyl acetate).

$^1$H NMR (DMSO-$d_6$) δ 3.85 (3H, s), 4.66 (2H, s), 7.18 (2H, d, J=9.0 Hz), 7.52 (1H, t, J=7.8 Hz), 7.64 (2H, d, J=9.0 Hz), 7.73 (2H, dd, J=1.5, 7.8 Hz), 7.81-7.85 (3H, m), 7.95 (1H, s), 8.82 (1H, s).

EXAMPLE 23

3-(2-pyridyl)-6-[5-[[3-(trifluoromethyl)benzyl]thio]-1,3,4-oxadiazol-2-yl]imidazo[1,2-a]pyridine In the same manner as in Example 16 and using 3-(2-pyridyl)imidazo[1,2-a]pyridine-6-carbohydrazide instead of imidazo[1,2-a]pyridine-6-carbohydrazide and 3-(trifluoromethyl)benzyl chloride instead of 4-methoxy-3-(trifluoromethyl)benzyl bromide, the title compound (yield 50%) was obtained as colorless crystals.

melting point 181-182° C. (recrystallized from hexane/ethyl acetate).

$^1$H NMR (DMSO-$d_6$) δ 4.71 (2H, s), 7.34-7.39 (1H, m), 7.56-7.66 (2H, m), 7.82-7.98 (5H, m), 8.11 (1H, d, J=8.1 Hz), 8.57 (1H, s), 8.76 (1H, d, J=4.8 Hz), 10.60 (1H, s).

Elemental analysis (for $C_{22}H_{14}F_3N_5OS$)
Calculated (%): C, 58.27; H, 3.11; N, 15.44.
Found (%): C, 58.21; H, 3.13; N, 15.26.

EXAMPLE 24

3-[[[5-[3-(2-pyridyl)imidazo[1,2-a]pyridin-6-yl]-1,3,4-oxadiazol-2-yl]thio]methyl]benzonitrile In the same manner as in Example 16 and using 3-(2-pyridyl)imidazo[1,2-a]pyridine-6-carbohydrazide instead of imidazo[1,2-a]pyridine-6-carbohydrazide and 3-(bromomethyl)benzonitrile instead of 4-methoxy-3-(trifluoromethyl)benzyl bromide, the title compound (yield 56%) was obtained as colorless crystals.

melting point 192-193° C. (recrystallized from hexane/ethyl acetate).

$^1$H NMR (DMSO-$d_6$) δ 4.67 (2H, s), 7.35-7.39 (1H, m), 7.57 (1H, t, J=7.8 Hz), 7.74-7.78 (1H, m), 7.82-8.00 (5H, m), 8.11 (1H, d, J=8.4 Hz), 8.57 (1H, s), 8.75-8.77 (1H, m), 10.60 (1H, s).

Elemental analysis (for $C_{22}H_{14}N_6OS$)
Calculated (%): C, 64.38; H, 3.44; N, 20.48.
Found (%): C, 64.49; H, 3.46; N, 20.45.

EXAMPLE 25

5-[[[5-(imidazo[1,2-a]pyridin-6-yl)-1,3,4-oxadiazol-2-yl]thio]methyl]-2-methoxybenzonitrile In the same manner as in Example 16 and using 5-(chloromethyl)-2-methoxybenzonitrile instead of 4-methoxy-3-(trifluoromethyl)benzyl bromide, the title compound (yield 58%) was obtained as colorless crystals.
melting point 211-212° C. (recrystallized from hexane/tetrahydrofuran).
$^1$H NMR (DMSO-d$_6$) δ 3.89 (3H, s), 4.57 (2H, s), 7.24 (1H, d, J=8.7 Hz), 7.67-7.74 (3H, m), 7.77-7.83 (1H, m), 7.88 (1H, d, J=2.1 Hz), 8.11 (1H, s), 9.35 (1H, s).
Elemental analysis (for C$_{18}$H$_{13}$N$_5$O$_2$S)
Calculated (%): C, 59.49; H, 3.61; N, 19.27.
Found (%): C, 59.30; H, 3.53; N, 19.13.

EXAMPLE 26

3-[2-(5-imidazo[1,2-a]pyridin-6-yl-1,3,4-oxadiazol-2-yl)ethyl]benzonitrile

In the same manner as in Example 14 and using imidazo[1,2-a]pyridine-6-carbohydrazide instead of 1H-benzotriazole-5-carbohydrazide, the title compound (yield 62%) was obtained as colorless crystals.
melting point 168-169° C. (recrystallized from diisopropyl ether/ethanol).
$^1$H NMR (DMSO-d$_6$) δ 3.20 (2H, t, J=7.2 Hz), 3.31-3.36 (2H, m), 7.53 (1H, t, J=7.5 Hz), 7.67-7.78 (5H, m), 7.85 (1H, s), 8.14 (1H, s), 9.35 (1H, t, J=1.2 Hz).
Elemental analysis (for C$_{18}$H$_{13}$N$_5$O)
Calculated (%): C, 68.56; H, 4.16; N, 22.21.
Found (%): C, 68.53; H, 4.18; N, 22.19.

EXAMPLE 27

6-[5-[2-[3-(trifluoromethyl)phenyl]ethyl]-1,3,4-oxadiazol-2-yl]imidazo[1,2-a]pyridine In the same manner as in Example 14 and using imidazo[1,2-a]pyridine-6-carbohydrazide instead of 1H-benzotriazole-5-carbohydrazide and 3-[3-(trifluoromethyl)phenyl]propionic acid instead of 3-(3-cyanophenyl)propionic acid, the title compound (yield 58%) was obtained as colorless crystals.
melting point 152-153° C. (recrystallized from hexane/ethyl acetate).
$^1$H NMR (DMSO-d$_6$) δ 3.21-3.26 (2H, m), 3.32 (2H, m), 7.52-7.77 (7H, m), 8.14 (1H, s), 9.35 (1H, t, J=1.5 Hz).
Elemental analysis (for C$_{18}$H$_{13}$F$_3$N$_4$O)
Calculated (%): C, 60.34; H, 3.66; N, 15.64.
Found (%): C, 60.30; H, 3.66; N, 15.74.

EXAMPLE 28

6-[5-[2-[4-methoxy-3-(trifluoromethyl)phenyl]ethyl]-1,3,4-oxadiazol-2-yl]imidazo[1,2-a]pyridine In the same manner as in Example 14 and using imidazo[1,2-a]pyridine-6-carbohydrazide instead of 1H-benzotriazole-5-carbohydrazide and 3-[4-methoxy-3-(trifluoromethyl)phenyl]propionic acid instead of 3-(3-cyanophenyl)propionic acid, the title compound (yield 38%) was obtained as colorless crystals.
melting point 150-151° C. (recrystallized from hexane/ethyl acetate).
$^1$H NMR (DMSO-d$_6$) δ 3.14 (2H, t, J=7.2 Hz), 3.26 (2H, t, J=7.2 Hz), 3.85 (3H, s), 7.20 (1H, t, J=4.5 Hz), 7.55-7.57 (2H, m), 7.68-7.77 (3H, m), 8.13 (1H, s), 9.35 (1H, t, J=1.2 Hz).
Elemental analysis (for C$_{19}$H$_{15}$F$_3$N$_4$O$_2$)
Calculated (%): C, 58.76; H, 3.89; N, 14.43.
Found (%): C, 58.76; H, 3.84; N, 14.48.

EXAMPLE 29

7-[5-[[3-(trifluoromethyl)benzyl]thio]-1,3,4-oxadiazol-2-yl]-1,2,4-triazolo[1,5-a]pyridine In the same manner as in Example 1 and using 5-(1,2,4-triazolo[1,5-a]pyridin-7-yl)-1,3,4-oxadiazole-2-thiol triethylamine salt instead of 5-(benzothiazol-6-yl)-1,3,4-oxadiazole-2-thiol, the title compound (yield 66%) was obtained as colorless crystals.
melting point 147-148° C. (recrystallized from hexane/ethyl acetate).
$^1$H NMR (CDCl$_3$) δ 4.62 (2H, s), 7.51 (1H, t, J=7.8 Hz), 7.60 (1H, d, J=7.8 Hz), 7.70-7.79 (3H, m), 8.33 (1H, dd, J=0.9, 1.5 Hz), 8.48 (1H, s), 8.72 (1H, dd, J=0.9, 7.2 Hz).
Elemental analysis (for C$_{16}$H$_{10}$F$_3$N$_5$OS)
Calculated (%): C, 50.93; H, 2.67; N, 18.56.
Found (%): C, 50.94; H, 2.59; N, 18.64.

EXAMPLE 30

7-[5-[[4-methoxy-3-(trifluoromethyl)benzyl]thio]-1,3,4-oxadiazol-2-yl]-1,2,4-triazolo[1,5-a]pyridine In the same manner as in Example 1 and using 5-(1,2,4-triazolo[1,5-a]pyridin-7-yl)-1,3,4-oxadiazole-2-thiol triethylamine salt instead of 5-(benzothiazol-6-yl)-1,3,4-oxadiazole-2-thiol and 4-methoxy-3-(trifluoromethyl)benzyl bromide instead of 3-(trifluoromethyl)benzyl chloride, the title compound (yield 62%) was obtained as colorless crystals.
melting point 178-179° C. (recrystallized from methanol).
$^1$H NMR (CDCl$_3$) δ 3.92 (3H, s), 4.56 (2H, s), 7.00 (1H, d, J=8.1 Hz), 7.64-7.71 (2H, m), 7.74 (1H, dd, J=1.5, 7.2 Hz), 8.34 (1H, dd, J=0.9, 1.5 Hz), 8.48 (1H, s), 8.73 (1H, dd, J=0.9, 7.2 Hz).
Elemental analysis (for C$_{17}$H$_{12}$F$_3$N$_5$O$_2$S)
Calculated (%): C, 50.12; H, 2.97; N, 17.19.
Found (%): C, 50.21; H, 2.96; N, 17.18.

EXAMPLE 31

2-methoxy-5-[[[5-(1,2,4-triazolo[1,5-a]pyridin-7-yl)-1,3,4-oxadiazol-2-yl]thio]methyl]benzonitrile In the same manner as in Example 1 and using 5-(1,2,4-triazolo[1,5-a]pyridin-7-yl)-1,3,4-oxadiazole-2-thiol triethylamine salt instead of 5-(benzothiazol-6-yl)-1,3,4-oxadiazole-2-thiol and 5-(chloromethyl)-2-methoxybenzonitrile instead of 3-(trifluoromethyl)benzyl chloride, the title compound (yield 56%) was obtained as pale-brown crystals.
melting point 247-248° C. (recrystallized from N,N-dimethylformamide/water).
$^1$H NMR (DMSO-d$_6$) δ 3.90 (3H, s), 4.62 (2H, s), 7.25 (1H, d, J=8.7 Hz), 7.70 (1H, dd, J=1.8, 7.2 Hz), 7.83 (1H, dd, J=1.8, 8.7 Hz), 7.89 (1H, d, J=1.8 Hz), 8.45 (1H, dd, J=0.9, 1.8 Hz), 8.69 (1H, s), 9.15 (1H, dd, J=0.9, 7.2 Hz).
Elemental analysis (for $C_{17}H_{12}N_6O_2S$)
Calculated (%): C, 56.04; H, 3.32; N, 23.06.
Found (%): C, 55.85; H, 3.26; N, 23.04.

EXAMPLE 32

7-[5-[(3-fluorobenzyl)thio]-1,3,4-oxadiazol-2-yl]-1, 2,4-triazolo[1,5-a]pyridine In the same manner as in Example 1 and using 5-(1,2,4-triazolo[1,5-a]pyridin-7-yl)-1,3,4-oxadiazole-2-thiol triethylamine salt instead of 5-(benzothiazol-6-yl)-1,3,4-oxadiazole-2-thiol and 3-fluorobenzyl chloride instead of 3-(trifluoromethyl)benzyl chloride, the title compound (yield 27%) was obtained as colorless crystals.
melting point 153-154° C. (recrystallized from hexane/ethyl acetate).
$^1$H NMR (CDCl$_3$) δ 4.57 (2H, s), 7.05 (1H, m), 7.20-7.40 (3H, m), 7.74 (1H, dd, J=1.8, 7.2 Hz), 8.33 (1H, dd, J=0.9, 1.8 Hz), 8.48 (1H, s), 8.73 (1H, dd, J=0.9, 7.2 Hz).
Elemental analysis (for $C_{15}H_{10}FN_5OS$)
Calculated (%): C, 55.04; H, 3.08; N, 21.39.
Found (%): C, 54.99; H, 3.11; N, 21.39.

EXAMPLE 33

3-[[[5-(1,2,4-triazolo[1,5-a]pyridin-7-yl)-1,3,4-oxadiazol-2-yl]thio]methyl]benzonitrile In the same manner as in Example 1 and using 5-(1,2,4-triazolo[1,5-a]pyridin-7-yl)-1,3,4-oxadiazole-2-thiol triethylamine salt instead of 5-(benzothiazol-6-yl)-1,3,4-oxadiazole-2-thiol and 3-(bromomethyl)benzonitrile instead of 3-(trifluoromethyl)benzyl chloride, the title compound (yield 20%) was obtained as colorless crystals.
melting point 196-197° C. (recrystallized from ethyl acetate).
$^1$H NMR (CDCl$_3$) δ 4.59 (2H, s), 7.50 (1H, t, J=7.5 Hz), 7.63 (1H, dt, J=1.5, 7.5 Hz), 7.74 (1H, dd, J=1.8, 7.2 Hz), 7.79 (1H, dt, J=1.5, 7.5 Hz), 7.84 (1H, t, J=1.5 Hz), 8.33 (1H, dd, J=0.9, 1.8 Hz), 8.48 (1H, s), 8.73 (1H, dd, J=0.9, 7.2 Hz).
Elemental analysis (for $C_{16}H_{10}N_6OS$)
Calculated (%): C, 57.48; H, 3.01; N, 25.14.
Found (%): C, 57.36; H, 3.05; N, 25.05.

EXAMPLE 34

5-(2,3-dihydro-1-benzofuran-5-yl)-1,3,4-oxadiazole-2-thiol

A solution of 2,3-dihydro-1-benzofuran-5-carbohydrazide (535 mg, 3.00 mmol), carbon disulfide (0.397 mL, 6.60 mmol) and triethylamine (0.460 mL, 3.30 mmol) in ethanol (5 mL) was heated under reflux for 24 hr. After cooling, the reaction mixture was diluted with ethyl acetate, washed with 0.1M hydrochloric acid and saturated brine, dried over anhydrous magnesium sulfate and concentrated under reduced pressure. The residue was recrystallized from hexane/tetrahydrofuran to give the title compound (529 mg, yield 80%) as pale-yellow crystals.
melting point 219-221° C.
$^1$H NMR (CDCl$_3$) δ 3.28 (2H, t, J=8.9 Hz), 4.28 (2H, t, J=8.9 Hz), 6.88 (1H, d, J=8.3 Hz), 7.71-7.75 (1H, m), 7.76-7.77 (1H, m), 10.85 (1H, brs).
Elemental analysis (for $C_{10}H_8N_2O_2S$)
Calculated (%): C, 54.53; H, 3.66; N, 12.72.
Found (%): C, 54.62; H, 3.70; N, 12.73.

EXAMPLE 35

2-(2,3-dihydro-1-benzofuran-5-yl)-5-(methylthio)-1, 3,4-oxadiazole

A mixture of 2,3-dihydro-1-benzofuran-5-carbohydrazide (2.00 g, 11.2 mmol), carbon disulfide (6.71 mL, 112 mmol), potassium hydroxide (0.94 g, 16.8 mmol) and ethanol (50 mL) was stirred at room temperature for 1 hr. The reaction mixture was concentrated under reduced pressure, N,N-dimethylformamide (50 mL) was added to the residue, and the resulting mixture was stirred at 100° C. overnight. 5 M Hydrochloric acid was added to the reaction mixture, and the mixture was extracted with ethyl acetate. The organic layer was washed with saturated brine, dried over anhydrous magnesium sulfate and concentrated under reduced pressure.
Potassium carbonate (2.32 g, 16.8 mmol), iodomethane (1.39 mL, 22.4 mmol) and N,N-dimethylformamide (50 mL) were added to the obtained residue, and the resulting mixture was stirred overnight at room temperature. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=2/1) and recrystallized from hexane/ethyl acetate to give the title compound (1.75 g, yield 45%) as colorless crystals.
$^1$H NMR (CDCl$_3$) δ 2.76 (3H, s), 3.27 (2H, t, J=8.8 Hz), 4.66 (2H, t, J=8.8 Hz), 6.86 (1H, d, J=8.3 Hz), 7.77 (1H, m), 7.83-7.87 (1H, m).

EXAMPLE 36

2-(2,3-dihydro-1-benzofuran-5-yl)-5-(methylsulfonyl)-1,3,4-oxadiazole

To a solution of 2-(2,3-dihydro-1-benzofuran-5-yl)-5-(methylthio)-1,3,4-oxadiazole (0.50 g, 2.13 mmol) in acetonitrile (10 mL) was added m-chloroperbenzoic acid (70%, 1.51 g, 6.40 mmol) at 0° C., and the obtained mixture was stirred at room temperature for 2 days. A saturated aqueous sodium thiosulfate solution was added to the reaction mixture, and the mixture was extracted with ethyl acetate. The organic layer was washed with saturated brine, dried over anhydrous magnesium sulfate and concentrated under reduced pressure. The residue was purified by silica gel column chromatography (hexane/ethyl acetate=2/1) to give the title compound (0.44 g, yield 78%) as colorless crystals.
melting point 144-145° C.
$^1$H NMR (CDCl$_3$) δ 3.31 (2H, t, J=8.7 Hz), 3.51 (3H, s), 4.71 (2H, t, J=8.7 Hz), 6.91 (1H, d, J=8.3 Hz), 7.90-7.95 (1H, m), 7.96-7.98 (1H, m).

EXAMPLE 37 ethyl[[5-(2,3-dihydro-1-benzofuran-5-yl)-1,3,4-oxadiazol-2-yl]thio]acetate

In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and ethyl bromoacetate instead of 3-(trifluoromethyl)benzyl chloride, the title compound (yield 54%) was obtained as colorless crystals.

melting point 92-93° C. (recrystallized from hexane/ethyl acetate).

$^1$H NMR (CDCl$_3$) δ 1.30 (3H, t, J=7.2 Hz), 3.28 (2H, t, J=8.9 Hz), 4.09 (2H, s), 4.26 (2H, q, J=7.2 Hz), 4.67 (2H, t, J=8.9 Hz), 6.86 (1H, d, J=8.3 Hz), 7.77 (1H, d, J=8.3 Hz), 7.85 (1H, s).

EXAMPLE 38

2-[(cyclopropylmethyl)thio]-5-(2,3-dihydro-1-benzofuran-5-yl)-1,3,4-oxadiazole

In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and (chloromethyl)cyclopropane instead of 3-(trifluoromethyl)benzyl chloride, the title compound (yield 56%) was obtained as colorless crystals.

melting point 57-58° C. (recrystallized from hexane/ethyl acetate).

$^1$H NMR (CDCl$_3$) δ 0.34-0.41 (2H, m), 0.63-0.73 (2H, m), 1.19-1.36 (1H, m), 3.18-3.33 (4H, m), 4.66 (2H, t, J=8.9 Hz), 6.86 (1H, d, J=8.3 Hz), 7.71-7.81 (1H, m), 7.83-7.88 (1H, m).
Elemental analysis (for C$_{14}$H$_{14}$N$_2$O$_2$S)
Calculated (%): C, 61.29; H, 5.14; N, 10.21.
Found (%): C, 61.33; H, 5.26; N, 10.27.

EXAMPLE 39

2-(2,3-dihydro-1-benzofuran-5-yl)-5-[(3-fluorobenzyl)thio]-1,3,4-oxadiazole

A mixture of 5-(2,3-dihydro-1-benzofuran-5-yl)-1,3,4-oxadiazole-2-thiol (0.20 g, 0.91 mmol), 3-fluorobenzyl chloride (0.11 mL, 0.91 mmol), 1 M aqueous sodium hydroxide solution (1.00 mL, 1.00 mmol) and water (4 mL) was stirred overnight at room temperature. The precipitate was collected by filtration and recrystallized from hexane/ethyl acetate to give the title compound (0.21 g, yield 74%) as colorless crystals.

melting point 128-129° C. (recrystallized from hexane/ethyl acetate).

$^1$H NMR (CDCl$_3$) δ 3.27 (2H, t, J=8.8 Hz), 4.48 (2H, s), 4.66 (2H, t, J=8.8 Hz), 6.86 (1H, d, J=8.3 Hz), 6.95-7.03 (1H, m), 7.15-7.35 (3H, m), 7.72-7.78 (1H, m), 7.82-7.85 (1H, m).
Elemental analysis (for C$_{17}$H$_{13}$FN$_2$O$_2$S)
Calculated (%): C, 61.18; H, 3.99; N, 8.53.
Found (%): C, 62.04; H, 3.96; N, 8.55.

EXAMPLE 40

2-[(2-chlorobenzyl)thio]-5-(2,3-dihydro-1-benzofuran-5-yl)-1,3,4-oxadiazole

In the same manner as in Example 39 and using 2-chlorobenzyl chloride instead of 3-fluorobenzyl chloride, the title compound (yield 48%) was obtained as pale-red crystals.

melting point 140-141° C. (recrystallized from hexane/ethyl acetate).

$^1$H NMR (CDCl$_3$) δ 3.27 (2H, t, J=8.9 Hz), 4.61 (2H, s), 4.66 (2H, t, J=8.9 Hz), 6.85 (1H, d, J=8.7 Hz), 7.19-7.29 (2H, m), 7.38-7.43 (1H, m), 7.59-7.64 (1H, m), 7.73-7.77 (1H, m), 7.82-7.85 (1H, m).
Elemental analysis (for C$_{17}$H$_{13}$ClN$_2$O$_2$S)
Calculated (%): C, 59.21; H, 3.80; N, 8.12.
Found (%): C, 59.09; H, 3.68; N, 8.12.

EXAMPLE 41

2-(2,3-dihydro-1-benzofuran-5-yl)-5-[(3-methoxybenzyl)thio]-1,3,4-oxadiazole

In the same manner as in Example 39 and using 3-methoxybenzyl chloride instead of 3-fluorobenzyl chloride, the title compound (yield 55%) was obtained as pale-red crystals.

melting point 91-93° C. (recrystallized from hexane/ethyl acetate).

$^1$H NMR (CDCl$_3$) δ 3.27 (2H, t, J=8.8 Hz), 3.80 (3H, s), 4.48 (2H, s), 4.66 (2H, t, J=8.8 Hz), 6.80-6.89 (2H, m), 6.97-7.06 (2H, m), 7.20-7.30 (1H, m), 7.76 (1H, d, J=8.7 Hz), 7.84 (1H, s).
Elemental analysis (for C$_{18}$H$_{16}$N$_2$O$_3$S)
Calculated (%): C, 63.51; H, 4.74; N, 8.23.
Found (%): C, 63.53; H, 4.65; N, 8.25.

EXAMPLE 42

2-(2,3-dihydro-1-benzofuran-5-yl)-5-[(4-methoxybenzyl)thio]-1,3,4-oxadiazole

In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and 4-methoxybenzyl chloride instead of 3-(trifluoromethyl)benzyl chloride, the title compound (yield 56%) was obtained as colorless crystals.

melting point 121-124° C. (recrystallized from hexane/ethyl acetate).

$^1$H NMR (CDCl$_3$) δ 3.27 (2H, t, J=8.8 Hz), 3.79 (3H, s), 4.46 (2H, s), 4.66 (2H, t, J=8.8 Hz), 6.83-6.90 (3H, m), 7.37 (2H, d, J=8.7 Hz), 7.72-7.79 (1H, m), 7.81-7.85 (1H, m).
Elemental analysis (for C$_{18}$H$_{16}$N$_2$O$_3$S)
Calculated (%): C, 63.51; H, 4.74; N, 8.23.
Found (%): C, 63.45; H, 4.71; N, 8.19.

EXAMPLE 43

2-(2,3-dihydro-1-benzofuran-5-yl)-5-[[3-(trifluoromethyl)benzyl]thio]-1,3,4-oxadiazole In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol, the title compound (yield 85%) was obtained as colorless crystals.

melting point 88-90° C. (recrystallized from hexane/ethyl acetate).

$^1$H NMR (CDCl$_3$) δ 3.27 (2H, t, J=8.8 Hz), 4.53 (2H, s), 4.66 (2H, t, J=8.8 Hz), 6.85 (1H, d, J=8.7 Hz), 7.42-7.50 (1H, m), 7.52-7.59 (1H, m), 7.66-7.77 (3H, m), 7.80-7.84 (1H, m).
Elemental analysis (for C$_{18}$H$_{13}$F$_3$N$_2$O$_2$S)
Calculated (%): C, 57.14; H, 3.46; N, 7.40.
Found (%): C, 57.17; H, 3.34; N, 7.41.

EXAMPLE 44 methyl 4-[[[5-(2,3-dihydro-1-benzofuran-5-yl)-1,3,4-oxadiazol-2-yl]thio]methyl]benzoate In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and methyl 4-(bromomethyl)benzoate instead of 3-(trifluoromethyl)benzyl chloride, the title compound (yield 36%) was obtained as colorless crystals.

melting point 125-126° C. (recrystallized from hexane/ethyl acetate).

$^1$H NMR (CDCl$_3$) δ 3.27 (2H, t, J=8.8 Hz), 3.91 (3H, s), 4.52 (2H, s), 4.66 (2H, t, J=8.8 Hz), 6.85 (1H, d, J=8.5 Hz), 7.54 (2H, d, J=8.5 Hz), 7.72-7.77 (1H, m), 7.80-7.84 (2H, m), 8.01 (1H, d, J=8.5 Hz).

Elemental analysis (for C$_{19}$H$_{16}$N$_2$O$_4$S)

Calculated (%): C, 61.94; H, 4.38; N, 7.60.

Found (%): C, 61.75; H, 4.08; N, 7.57.

EXAMPLE 45

4-[[[5-(2,3-dihydro-1-benzofuran-5-yl)-1,3,4-oxadiazol-2-yl]thio]methyl]benzoic acid In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and 4-(chloromethyl)benzoic acid instead of 3-(trifluoromethyl)benzyl chloride, the title compound (yield 100%) was obtained as colorless crystals.

melting point 203-205° C. (recrystallized from ethyl acetate).

$^1$H NMR (DMSO-d$_6$) δ 3.26 (2H, t, J=8.8 Hz), 4.59-4.68 (4H, m), 6.94 (1H, d, J=8.3 Hz), 7.59 (2H, d, J=8.5 Hz), 7.71 (1H, dd, J=1.6, 8.3 Hz), 7.79 (1H, d, J=1.6 Hz), 7.91 (2H, d, J=8.5 Hz), 12.99 (1H, s).

Elemental analysis (for C$_{18}$H$_{34}$N$_2$O$_4$S)

Calculated (%): C, 61.01; H, 3.98; N, 7.90.

Found (%): C, 61.00; H, 4.14; N, 7.61.

EXAMPLE 46

2-(2,3-dihydro-1-benzofuran-5-yl)-5-[(4-methylbenzyl)thio]-1,3,4-oxadiazole

In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and 4-methylbenzyl bromide instead of 3-(trifluoromethyl)benzyl chloride, the title compound (yield 75%) was obtained as colorless crystals.

melting point 190-191° C. (recrystallized from hexane/ethyl acetate).

$^1$H NMR (CDCl$_3$) δ 2.33 (3H, s), 3.27 (2H, t, J=8.8 Hz), 4.47 (2H, s), 4.66 (2H, t, J=8.8 Hz), 6.85 (1H, d, J=8.3 Hz), 7.14 (2H, d, J=8.0 Hz), 7.33 (2H, d, J=8.0 Hz), 7.71-7.78 (1H, m), 7.80-7.86 (1H, m).

Elemental analysis (for C$_{18}$H$_{16}$N$_2$O$_2$S)

Calculated (%): C, 66.64; H, 4.97; N, 8.64.

Found (%): C, 66.52; H, 4.84; N, 8.68.

EXAMPLE 47

2-(2,3-dihydro-1-benzofuran-5-yl)-5-[(3-fluoro-4-methoxybenzyl)thio]-1,3,4-oxadiazole To a solution of 2,3-dihydro-1-benzofuran-5-carbohydrazide (356 mg, 2.00 mmol) and potassium hydroxide (85%, 198 mg, 3.00 mmol) in ethanol (15 mL) was added carbon disulfide (0.180 mL, 3.00 mmol), and the resulting mixture was stirred at room temperature for 1 hr. The reaction mixture was concentrated under reduced pressure. A mixture of the obtained residue and N,N-dimethylformamide (10 mL) was tightly sealed in a vial, and the microwave was irradiated at 150° C. for 30 sec. After cooling to room temperature, 3-fluoro-4-methoxybenzyl chloride (698 mg, 4.00 mmol) was added, and the resulting mixture was stirred for 2 hr. The reaction mixture was diluted with ethyl acetate, washed twice with water and once with saturated brine, dried over anhydrous magnesium sulfate and concentrated under reduced pressure. The residue was crystallized from hexane/ethyl acetate to give the title compound (478 mg, yield 67%) as colorless crystals.

melting point 121-122° C.

$^1$H NMR (CDCl$_3$) δ 3.27 (2H, t, J=8.9 Hz), 3.87 (3H, s), 4.43 (2H, s), 4.66 (2H, t, J=8.9 Hz), 6.84-6.93 (2H, m), 7.15-7.22 (2H, m), 7.74-7.77 (1H, m), 7.83-7.84 (1H, m).

Elemental analysis (for C$_{18}$H$_{15}$FN$_2$O$_3$S)

Calculated (%): C, 60.32; H, 4.22; N, 7.82.

Found (%): C, 60.50; H, 4.47; N, 7.92.

EXAMPLE 48

2-[(3-chloro-4-methoxybenzyl)thio]-5-(2,3-dihydro-1-benzofuran-5-yl)-1,3,4-oxadiazole In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and 3-chloro-4-methoxybenzyl bromide instead of 3-(trifluoromethyl)benzyl chloride, the title compound (yield 87%) was obtained as colorless crystals.

melting point 136-137° C. (recrystallized from hexane/ethyl acetate).

$^1$H NMR (CDCl$_3$) δ 3.27 (2H, t, J=8.9 Hz), 3.89 (3H, s), 4.42 (2H, s), 4.66 (2H, t, J=8.9 Hz), 6.84-6.89 (2H, m), 7.33 (1H, dd, J=2.3, 8.5 Hz), 7.47 (1H, d, J=2.3 Hz), 7.74-7.77 (1H, m), 7.82-7.84 (1H, m).

Elemental analysis (for C$_{18}$H$_{15}$ClN$_2$O$_3$S)

Calculated (%): C, 57.68; H, 4.03; N, 7.47.

Found (%): C, 57.66; H, 4.00; N, 7.44.

EXAMPLE 49

5-[[[5-(2,3-dihydro-1-benzofuran-5-yl)-1,3,4-oxadiazol-2-yl]thio]methyl]-2-methoxybenzonitrile In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and 5-(chloromethyl)-2-methoxybenzonitrile instead of 3-(trifluoromethyl)benzyl chloride, the title compound (yield 72%) was obtained as colorless crystals.

melting point 176-177° C. (recrystallized from hexane/tetrahydrofuran).

$^1$H NMR (CDCl$_3$) δ 3.28 (2H, t, J=8.8 Hz), 3.92 (3H, s), 4.43 (2H, s), 4.67 (2H, t, J=8.8 Hz), 6.86 (1H, d, J=8.3 Hz), 6.93 (1H, d, J=9.4 Hz), 7.66-7.70 (2H, m), 7.73-7.78 (1H, m), 7.80-7.85 (1H, m).

Elemental analysis (for C$_{19}$H$_{15}$N$_3$O$_3$S)

Calculated (%): C, 62.45; H, 4.14; N, 11.50.

Found (%): C, 62.45; H, 4.08; N, 11.71.

EXAMPLE 50

2-[(3,4-difluorobenzyl)thio]-5-(2,3-dihydro-1-benzofuran-5-yl)-1,3,4-oxadiazole

In the same manner as in Example 39 and using 3,4-difluorobenzyl bromide instead of 3-fluorobenzyl chloride, the title compound (yield 44%) was obtained as colorless crystals.

melting point 138-139° C. (recrystallized from ethyl acetate).

$^1$H NMR (CDCl$_3$) δ 3.27 (2H, t, J=8.8 Hz), 4.44 (2H, s), 4.66 (2H, t, J=8.8 Hz), 6.86 (1H, d, J=8.3 Hz), 7.06-7.16 (1H, m), 7.16-7.23 (1H, m), 7.27-7.36 (1H, m), 7.71-7.79 (1H, m), 7.80-7.85 (1H, m).

Elemental analysis (for C$_{17}$H$_{12}$F$_2$N$_2$O$_2$S)
Calculated (%): C, 58.95; H, 3.49; N, 8.09.
Found (%): C, 58.94; H, 3.36; N, 8.10.

EXAMPLE 51

2-(2,3-dihydro-1-benzofuran-5-yl)-5-[[4-fluoro-3-(trifluoromethyl)benzyl]thio]-1,3,4-oxadiazole In the same manner as in Example 1 and using 5-(2,3-dihydro-1-benzofuran-5-yl)-1,3,4-oxadiazole-2-thiol instead of 5-(benzothiazol-6-yl)-1,3,4-oxadiazole-2-thiol and [4-fluoro-3-(trifluoromethyl)]benzyl chloride instead of 3-(trifluoromethyl)benzyl chloride, the title compound (yield 45%) was obtained as colorless crystals.

melting point 94-95° C. (recrystallized from hexane/ethyl acetate).

$^1$H NMR (CDCl$_3$) δ 3.27 (2H, t, J=8.8 Hz), 4.49 (2H, s), 4.66 (2H, t, J=8.8 Hz), 6.85 (1H, d, J=8.5 Hz), 7.17 (1H, t, J=9.1 Hz), 7.66-7.78 (3H, m), 7.80-7.84 (1H, m).

Elemental analysis (for C$_{18}$H$_{12}$F$_4$N$_2$O$_2$S)
Calculated (%): C, 54.54; H, 3.05; N, 7.07.
Found (%): C, 54.58; H, 2.99; N, 6.96.

EXAMPLE 52

2-(2,3-dihydro-1-benzofuran-5-yl)-5-[(2,3-dihydro-1-benzofuran-5-ylmethyl)thio]-1,3,4-oxadiazole In the same manner as in Example 47 and using 5-(chloromethyl)-2,3-dihydro-1-benzofuran instead of 3-fluoro-4-methoxybenzyl chloride, the title compound (yield 56%) was obtained as colorless crystals.

melting point 130-132° C. (recrystallized from ethyl acetate).

$^1$H NMR (CDCl$_3$) δ 3.19 (2H, t, J=8.7 Hz), 3.27 (2H, t, J=8.7 Hz), 4.45 (2H, s), 4.56 (2H, t, J=8.7 Hz), 4.66 (2H, t, J=8.7 Hz), 6.73 (1H, d, J=8.3 Hz), 6.85 (1H, d, J=8.3 Hz), 7.17 (1H, dd, J=1.9, 8.3 Hz), 7.29 (1H, d, J=1.9 Hz), 7.74-7.78 (1H, m), 7.83-7.85 (1H, m).

Elemental analysis (for C$_{19}$H$_{16}$N$_2$O$_3$S)
Calculated (%): C, 64.76; H, 4.58; N, 7.95.
Found (%): C, 64.65; H, 4.73; N, 7.74.

EXAMPLE 53

2-[(1-benzofuran-5-ylmethyl)thio]-5-(2,3-dihydro-1-benzofuran-5-yl)-1,3,4-oxadiazole In the same manner as in Example 47 and using 5-(chloromethyl)-1-benzofuran instead of 3-fluoro-4-methoxybenzyl chloride, the title compound (yield 50%) was obtained as colorless crystals.

melting point 145-147° C. (recrystallized from ethyl acetate).

$^1$H NMR (CDCl$_3$) δ 3.27 (2H, t, J=8.7 Hz), 4.61 (2H, s), 4.66 (2H, t, J=8.7 Hz), 6.74 (1H, dd, J=1.1, 2.3 Hz), 6.85 (1H, d, J=8.3 Hz), 7.38 (1H, dd, J=1.9, 8.3 Hz), 7.47 (1H, d, J=8.3 Hz), 7.63 (1H, d, J=2.3 Hz), 7.70 (1H, d, J=1.9 Hz), 7.73-7.76 (1H, m), 7.82-7.83 (1H, m).

Elemental analysis (for C$_{19}$H$_{14}$N$_2$O$_3$S)
Calculated (%): C, 65.13; H, 4.03; N, 7.99.
Found (%): C, 65.19; H, 4.08; N, 7.75.

EXAMPLE 54

3-[[[5-(2,3-dihydro-1-benzofuran-5-yl)-1,3,4-oxadiazol-2-yl]thio]methyl]pyridine In the same manner as in Example 39 and using 3-(chloromethyl)pyridine hydrochloride instead of 3-fluorobenzyl chloride, the title compound (yield 81%) was obtained as colorless crystals.

melting point 118-122° C. (recrystallized from ethyl acetate).

$^1$H NMR (CDCl$_3$) δ 3.27 (2H, t, J=8.8 Hz), 4.49 (2H, s), 4.66 (2H, t, J=8.8 Hz), 6.85 (1H, d, J=8.3 Hz), 7.24-7.30 (1H, m), 7.72-7.77 (1H, m), 7.81-7.87 (2H, m), 8.54 (1H, dd, J=1.7, 4.7 Hz), 8.71 (1H, d, J=2.3 Hz).

Elemental analysis (for C$_{16}$H$_{13}$N$_3$O$_2$S)
Calculated (%): C, 61.72; H, 4.21; N, 13.50.
Found (%): C, 61.76; H, 4.16; N, 13.44.

EXAMPLE 55

2-(benzylthio)-5-(2,3-dihydro-1-benzofuran-5-yl)-1,3,4-oxadiazole

In the same manner as in Example 39 and using benzyl bromide instead of 3-fluorobenzyl chloride, the title compound (yield 51%) was obtained as colorless crystals.

melting point 148-149° C. (recrystallized from hexane/ethyl acetate).

$^1$H NMR (CDCl$_3$) δ 3.27 (2H, t, J=8.8 Hz), 4.50 (2H, s), 4.66 (2H, t, J=8.8 Hz), 6.85 (1H, d, J=8.7 Hz), 7.28-7.38 (3H, m), 7.42-7.48 (2H, m), 7.75 (1H, dd, J=1.7, 8.3 Hz), 7.84 (1H, d, J=1.7 Hz).

Elemental analysis (for C$_{17}$H$_{14}$N$_2$O$_2$S)
Calculated (%): C, 65.79; H, 4.55; N, 9.03.
Found (%): C, 65.49; H, 4.44; N, 8.93.

EXAMPLES 56-106

To a solution of 5-(2,3-dihydro-1-benzofuran-5-yl)-1,3,4-oxadiazole-2-thiol (50 μmol) in N,N-dimethylformamide (0.5 mL) were added solutions of various halide reagents (62.5 μmol) in N,N-dimethylformamide (0.5 mL) and potassium carbonate (50 mg), and the resulting mixture was stirred at 60° C. for 24 hr. The reaction mixture was filtered, and the filtrate was purified by preparative HPLC to give the title compound.

HPLC and LC-MS analysis of Examples 56-107 was performed under the following conditions.

measurement device: LC-MS system, Waters
HPLC unit: Agilent HP1100
MS unit: Micromass Quattro micro API
column: CAPCELL PAK c18UG120 S-3 μm, 1.5×35 mm (manufactured by Shiseido)
solvent: SOLUTION A; 5 mM ammonium acetate-containing 2% aqueous acetonitrile solution, SOLUTION B; 5 mM ammonium acetate-containing 95% aqueous acetonitrile solution
gradient cycle: 0.00 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.30 min (SOLUTION A/SOLUTION B=100/0)
injection volume: 2 μL, flow rate: 0.5 mL/min, detection method: UV 220 nm
MS conditions: ionization method (ESI)

Purification by preparative HLPC in Examples 56-106 was performed under the following conditions.
equipment: GILSON, High-Throughput purification system
column: YMC CombiPrep ODS-A S-5 μm, 50×20 mm
solvent: SOLUTION A; 0.1% aqueous trifluoroacetic acid solution, SOLUTION B; 0.1% trifluoroacetic acid-acetonitrile solution
gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)
flow rate: 25 mL/min, detection method: UV 220 nm

EXAMPLE 56

3-[[[5-(2,3-dihydro-1-benzofuran-5-yl)-1,3,4-oxadiazol-2-yl]thio]methyl]benzonitrile yield 13.7 mg
HPLC purity 100% (retention time 1.96 min)
LC-MS (ESI) m/z 336 [M+H]$^+$

EXAMPLE 57

2-(2,3-dihydro-1-benzofuran-5-yl)-5-[(1-naphthylmethyl)thio]-1,3,4-oxadiazole yield 14.4 mg
HPLC purity 94% (retention time 2.20 min)
LC-MS (ESI) m/z 361 [M+H]$^+$

EXAMPLE 58

2-[(3-chlorobenzyl)thio]-5-(2,3-dihydro-1-benzofuran-5-yl)-1,3,4-oxadiazole yield 13.4 mg
HPLC purity 100% (retention time 2.13 min)
LC-MS (ESI) m/z 345 [M+H]$^+$

EXAMPLE 59

2-[(4-chlorobenzyl)thio]-5-(2,3-dihydro-1-benzofuran-5-yl)-1,3,4-oxadiazole yield 12.8 mg
HPLC purity 100% (retention time 2.15 min)
LC-MS (ESI) m/z 345 [M+H]$^+$

EXAMPLE 60

2-(2,3-dihydro-1-benzofuran-5-yl)-5-[(2-methoxybenzyl)thio]-1,3,4-oxadiazole yield 12.8 mg
HPLC purity 100% (retention time 2.08 min)
LC-MS (ESI) m/z 341 [M+H]$^+$

EXAMPLE 61

2-(2,3-dihydro-1-benzofuran-5-yl)-5-[(1-phenylethyl)thio]-1,3,4-oxadiazole yield 13.3 mg
HPLC purity 100% (retention time 2.10 min)
LC-MS (ESI) m/z 325 [M+H]$^+$

EXAMPLE 62

2-(2,3-dihydro-1-benzofuran-5-yl)-5-[(2-naphthylmethyl)thio]-1,3,4-oxadiazole yield 12.9 mg
HPLC purity 85% (retention time 2.18 min)
LC-MS (ESI) m/z 361 [M+H]$^+$

EXAMPLE 63

2-(2,3-dihydro-1-benzofuran-5-yl)-5-[(3-methylbenzyl)thio]-1,3,4-oxadiazole yield 11.7 mg
HPLC purity 97% (retention time 2.13 min)
LC-MS (ESI) m/z 325 [M+H]$^+$

EXAMPLE 64 methyl 3-[[[5-(2,3-dihydro-1-benzofuran-5-yl)-1,3,4-oxadiazol-2-yl]thio]methyl]benzoate yield 14.6 mg
HPLC purity 97% (retention time 2.02 min)
LC-MS (ESI) m/z 369 [M+H]$^+$

EXAMPLE 65

2-(2,3-dihydro-1-benzofuran-5-yl)-5-[[3-(trifluoromethoxy)benzyl]thio]-1,3,4-oxadiazole yield 14.9 mg
HPLC purity 100% (retention time 2.18 min)
LC-MS (ESI) m/z 395 [M+H]$^+$

EXAMPLE 66

N-[4-[[[5-(2,3-dihydro-1-benzofuran-5-yl)-1,3,4-oxadiazol-2-yl]thio]methyl]phenyl]acetamide yield 15.7 mg
HPLC purity 100% (retention time 1.79 min)
LC-MS (ESI) m/z 368 [M+H]$^+$

EXAMPLE 67

2-[(4-tert-butylbenzyl)thio]-5-(2,3-dihydro-1-benzofuran-5-yl)-1,3,4-oxadiazole yield 13.2 mg
HPLC purity 95% (retention time 2.33 min)
LC-MS (ESI) m/z 367 [M+H]$^+$

EXAMPLE 68

2-[[3,5-bis(trifluoromethyl)benzyl]thio]-5-(2,3-dihydro-1-benzofuran-5-yl)-1,3,4-oxadiazole yield 19.0 mg
HPLC purity 95% (retention time 2.26 min)
LC-MS (ESI) m/z 447 [M+H]$^+$

EXAMPLE 69

2-(2,3-dihydro-1-benzofuran-5-yl)-5-[(3,5-dimethylbenzyl)thio]-1,3,4-oxadiazole yield 14.7 mg
HPLC purity 100% (retention time 2.22 min)
LC-MS (ESI) m/z 339 [M+H]$^+$

EXAMPLE 70

2-(2,3-dihydro-1-benzofuran-5-yl)-5-[(4-thiazolylmethyl)thio]-1,3,4-oxadiazole yield 9.7 mg
HPLC purity 100% (retention time 1.77 min)
LC-MS (ESI) m/z 318 [M+H]$^+$

EXAMPLE 71

2-[(2,4-difluorobenzyl)thio]-5-(2,3-dihydro-1-benzofuran-5-yl)-1,3,4-oxadiazole yield 13.5 mg
HPLC purity 100% (retention time 2.08 min)
LC-MS (ESI) m/z 347 [M+H]$^+$

EXAMPLE 72

2-[(2,6-difluorobenzyl)thio]-5-(2,3-dihydro-1-benzofuran-5-yl)-1,3,4-oxadiazole yield 12.7 mg
HPLC purity 96% (retention time 2.05 min)
LC-MS (ESI) m/z 347 [M+H]$^+$

EXAMPLE 73

2-[(2,3-dichlorobenzyl)thio]-5-(2,3-dihydro-1-benzofuran-5-yl)-1,3,4-oxadiazole yield 8.9 mg
HPLC purity 100% (retention time 2.23 min)
LC-MS (ESI) m/z 379 [M+H]$^+$

EXAMPLE 74

2-[(2,5-dichlorobenzyl)thio]-5-(2,3-dihydro-1-benzofuran-5-yl)-1,3,4-oxadiazole yield 14.0 mg
HPLC purity 100% (retention time 2.23 min)
LC-MS (ESI) m/z 379 [M+H]$^+$

EXAMPLE 75

2-[(3,4-dichlorobenzyl)thio]-5-(2,3-dihydro-1-benzofuran-5-yl)-1,3,4-oxadiazole yield 11.1 mg
HPLC purity 100% (retention time 2.21 min)
LC-MS (ESI) m/z 379 [M+H]$^+$

EXAMPLE 76

2-(2,3-dihydro-1-benzofuran-5-yl)-5-[(2,5-dimethoxybenzyl)thio]-1,3,4-oxadiazole yield 12.0 mg
HPLC purity 96% (retention time 2.06 min)
LC-MS (ESI) m/z 371 [M+H]$^+$

EXAMPLE 77 methyl 4-[[[5-(2,3-dihydro-1-benzofuran-5-yl)-1,3,4-oxadiazol-2-yl]thio]methyl]-3-methoxybenzoate yield 15.5 mg
HPLC purity 100% (retention time 2.06 min)
LC-MS (ESI) m/z 399 [M+H]$^+$

EXAMPLE 78

2-(2,3-dihydro-1-benzofuran-5-yl)-5-[[4-methoxy-3-(trifluoromethyl)benzyl]thio]-1,3,4-oxadiazole yield 15.0 mg
HPLC purity 95% (retention time 2.14 min)
LC-MS (ESI) m/z 409 [M+H]$^+$

EXAMPLE 79

[4-[[[5-(2,3-dihydro-1-benzofuran-5-yl)-1,3,4-oxadiazol-2-yl]thio]methyl]phenyl]methanol yield 14.8 mg
HPLC purity 94% (retention time 1.80 min)
LC-MS (ESI) m/z 341 [M+H]$^+$

EXAMPLE 80

2-(2,3-dihydro-1-benzofuran-5-yl)-5-[[4-(methylsulfonyl)benzyl]thio]-1,3,4-oxadiazole yield 12.2 mg
HPLC purity 95% (retention time 1.82 min)
LC-MS (ESI) m/z 389 [M+H]$^+$

EXAMPLE 81

2-(2,3-dihydro-1-benzofuran-5-yl)-5-[[4-(1H-pyrrol-1-yl)benzyl]thio]-1,3,4-oxadiazole yield 3.5 mg
HPLC purity 88% (retention time 2.15 min)
LC-MS (ESI) m/z 376 [M+H]$^+$

EXAMPLE 82

2-[[[5-(2,3-dihydro-1-benzofuran-5-yl)-1,3,4-oxadiazol-2-yl]thio]methyl]benzothiazole yield 4.3 mg
HPLC purity 96% (retention time 2.00 min)
LC-MS (ESI) m/z 368 [M+H]$^+$

EXAMPLE 83

5-[[[5-(2,3-dihydro-1-benzofuran-5-yl)-1,3,4-oxadiazol-2-yl]thio]methyl]imidazo[1,2-a]pyridine yield 13.1 mg
HPLC purity 90% (retention time 1.73 min)
LC-MS (ESI) m/z 351 [M+H]$^+$

EXAMPLE 84

5-(benzyloxy)-2-[[[5-(2,3-dihydro-1-benzofuran-5-yl)-1,3,4-oxadiazol-2-yl]thio]methyl]pyridin-4(1H)-one yield 17.7 mg
HPLC purity 91% (retention time 1.70 min)
LC-MS (ESI) m/z 434 [M+H]$^+$

EXAMPLE 85

1-[4-[[[5-(2,3-dihydro-1-benzofuran-5-yl)-1,3,4-oxadiazol-2-yl]thio]methyl]benzoyl]-4-methylpiperazine yield 10.9 mg
HPLC purity 100% (retention time 1.73 min)
LC-MS (ESI) m/z 437 [M+H]$^+$

EXAMPLE 86

2-[[5-(2,3-dihydro-1-benzofuran-5-yl)-1,3,4-oxadiazol-2-yl]thio]-N,N-diethylacetamide yield 18.8 mg
HPLC purity 89% (retention time 1.65 min)
LC-MS (ESI) m/z 334 [M+H]$^+$

EXAMPLE 87

2-[[5-(2,3-dihydro-1-benzofuran-5-yl)-1,3,4-oxadiazol-2-yl]thio]-2-phenylacetamide yield 1.9 mg
HPLC purity 100% (retention time 1.76 min)
LC-MS (ESI) m/z 354 [M+H]$^+$

EXAMPLE 88

7-[[[5-(2,3-dihydro-1-benzofuran-5-yl)-1,3,4-oxadiazol-2-yl]thio]methyl]-5H-thiazolo[3,2-a]pyrimidin-5-one yield 4.8 mg
HPLC purity 100% (retention time 1.71 min)
LC-MS (ESI) m/z 385 [M+H]$^+$

EXAMPLE 89

2-[[[5-(2,3-dihydro-1-benzofuran-5-yl)-1,3,4-oxadiazol-2-yl]thio]methyl]thieno[3,2-d]pyrimidin-4(3H)-one yield 0.9 mg
HPLC purity 100% (retention time 1.68 min)
LC-MS (ESI) m/z 385 [M+H]$^+$

EXAMPLE 90

2-(2,3-dihydro-1-benzofuran-5-yl)-5-[[[1-(2-propyn-1-yl)-1H-imidazol-5-yl]methyl]thio]-1,3,4-oxadiazole yield 13.9 mg
HPLC purity 80% (retention time 1.71 min)
LC-MS (ESI) m/z 339 [M+H]$^+$

EXAMPLE 91

2-[[[1-(cyclopropylmethyl)-1H-imidazol-5-yl]methyl]thio]-5-(2,3-dihydro-1-benzofuran-5-yl)-1,3,4-oxadiazole yield 14.5 mg
HPLC purity 95% (retention time 1.78 min)
LC-MS (ESI) m/z 355 [M+H]$^+$

EXAMPLE 92

2-(2,3-dihydro-1-benzofuran-5-yl)-5-[[(5-methyl-1-propyl-1H-imidazol-4-yl)methyl]thio]-1,3,4-oxadiazole yield 10.8 mg
HPLC purity 80% (retention time 1.79 min)
LC-MS (ESI) m/z 357 [M+H]$^+$

EXAMPLE 93

2-[[[2-[(E)-2-(3,4-difluorophenyl)vinyl]oxazol-4-yl]methyl]thio]-5-(2,3-dihydro-1-benzofuran-5-yl)-1,3,4-oxadiazole yield 15.9 mg
HPLC purity 100% (retention time 2.14 min)
LC-MS (ESI) m/z 440 [M+H]$^+$

EXAMPLE 94

2-[[[5-(2,3-dihydro-1-benzofuran-5-yl)-1,3,4-oxadiazol-2-yl]thio]acetyl]-5,5-dimethyl-2,3,4,5-tetrahydro-1H-2-benzazepine yield 17.7 mg
HPLC purity 100% (retention time 2.04 min)
LC-MS (ESI) m/z 436 [M+H]$^+$

EXAMPLE 95

2-[[[5-(2,3-dihydro-1-benzofuran-5-yl)-1,3,4-oxadiazol-2-yl]thio]acetyl]-1-methyl-1,2,3,4-tetrahydroisoquinoline yield 15.7 mg
HPLC purity 97% (retention time 1.96 min)
LC-MS (ESI) m/z 408 [M+H]$^+$

EXAMPLE 96 methyl 4-[2-[[5-(2,3-dihydro-1-benzofuran-5-yl)-1,3,4-oxadiazol-2-yl]thio]ethoxy]benzoate yield 1.0 mg
HPLC purity 100% (retention time 2.00 min)
LC-MS (ESI) m/z 399 [M+H]$^+$

EXAMPLE 97

4-[3-[[5-(2,3-dihydro-1-benzofuran-5-yl)-1,3,4-oxadiazol-2-yl]thio]propyl]morpholine yield 19.6 mg
HPLC purity 92% (retention time 1.74 min)
LC-MS (ESI) m/z 348 [M+H]$^+$

EXAMPLE 98

4-[4-[[[5-(2,3-dihydro-1-benzofuran-5-yl)-1,3,4-oxadiazol-2-yl]thio]methyl]benzoyl]morpholine yield 15.5 mg
HPLC purity 95% (retention time 1.78 min)
LC-MS (ESI) m/z 424 [M+H]$^+$

EXAMPLE 99

2-[[2-[(6-chloro-2-naphthyl)thio]ethyl]thio]-5-(2,3-dihydro-1-benzofuran-5-yl)-1,3,4-oxadiazole yield 14.7 mg
HPLC purity 98% (retention time 2.40 min)
LC-MS (ESI) m/z 441 [M+H]$^+$

EXAMPLE 100

4-[2-[[5-(2,3-dihydro-1-benzofuran-5-yl)-1,3,4-oxadiazol-2-yl]thio]ethoxy]benzonitrile yield 12.5 mg
HPLC purity 95% (retention time 1.95 min)
LC-MS (ESI) m/z 366 [M+H]$^+$

EXAMPLE 101

2-[[[5-(2,3-dihydro-1-benzofuran-5-yl)-1,3,4-oxadiazol-2-yl]thio]methyl]-5-methylthieno[2,3-d]pyrimidin-4(3H)-one yield 1.6 mg
HPLC purity 100% (retention time 1.80 min)
LC-MS (ESI) m/z 399 [M+H]$^+$

EXAMPLE 102

2-[[[5-(2,3-dihydro-1-benzofuran-5-yl)-1,3,4-oxadiazol-2-yl]thio]methyl]-5,7-dimethylimidazo[1,2-a]pyrimidine yield 4.2 mg
HPLC purity 80% (retention time 1.68 min)
LC-MS (ESI) m/z 380 [M+H]$^+$

EXAMPLE 103

1-[3-[[5-(2,3-dihydro-1-benzofuran-5-yl)-1,3,4-oxadiazol-2-yl]thio]propyl]-5-methoxy-1H-indole-2,3-dione yield 6.6 mg
HPLC purity 85% (retention time 1.90 min)
LC-MS (ESI) m/z 438 [M+H]$^+$

EXAMPLE 104

3-[[[5-(2,3-dihydro-1-benzofuran-5-yl)-1,3,4-oxadiazol-2-yl]thio]methyl]-5-(3-thienyl)-1,2,4-oxadiazole yield 10.1 mg
HPLC purity 100% (retention time 1.95 min)
LC-MS (ESI) m/z 385 [M+H]$^+$

EXAMPLE 105

3-[[[5-(2,3-dihydro-1-benzofuran-5-yl)-1,3,4-oxadiazol-2-yl]thio]methyl]-5-(2-methoxyphenyl)-1,2,4-oxadiazole yield 17.0 mg
HPLC purity 89% (retention time 1.96 min)
LC-MS (ESI) m/z 409 [M+H]$^+$

EXAMPLE 106

1-[3-[[[5-(2,3-dihydro-1-benzofuran-5-yl)-1,3,4-oxadiazol-2-yl]thio]methyl]-4-methoxyphenyl]ethanone yield 15.2 mg
HPLC purity 90% (retention time 1.94 min)
LC-MS (ESI) m/z 383 [M+H]$^+$

EXAMPLE 107

2-(2,3-dihydro-1-benzofuran-5-yl)-5-[2-(3-fluorophenyl)ethyl]-1,3,4-oxadiazole

In the same manner as in Example 14 and using 2,3-dihydro-1-benzofuran-5-carbohydrazide instead of 1H-benzotriazole-5-carbohydrazide and 3-(3-fluorophenyl)propionic acid instead of 3-(3-cyanophenyl)propionic acid, the title compound (yield 59%) was obtained as colorless crystals.
melting point 85-86° C. (recrystallized from hexane/ethyl acetate).
$^1$H NMR (CDCl$_3$) δ 3.07-3.22 (4H, m), 3.28 (2H, t, J=8.8 Hz), 4.66 (2H, t, J=8.8 Hz), 6.86 (1H, d, J=8.7 Hz), 6.89-7.06 (3H, m), 7.19-7.32 (1H, m), 7.77 (1H, dd, J=1.7, 8.3 Hz), 7.86 (1H, d, J=1.7 Hz).
Elemental analysis (for C$_{18}$H$_{15}$FN$_2$O$_2$)
Calculated (%): C, 69.67; H, 4.87; N, 9.03.
Found (%): C, 69.66; H, 4.98; N, 9.01.

EXAMPLE 108

2-(2,3-dihydro-1-benzofuran-5-yl)-5-[[(3-fluorophenyl)thio]methyl]-1,3,4-oxadiazole A solution of 2-(chloromethyl)-5-(2,3-dihydro-1-benzofuran-5-yl)-1,3,4-oxadiazole (0.16 g, 0.68 mmol), 3-fluorothiophenol (57 µL, 0.68 mmol) and potassium carbonate (0.10 g, 0.75 mmol) in N,N-dimethylformamide (5 mL) was stirred overnight at room temperature. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=2/1) and recrystallized from hexane/ethyl acetate to give the title compound (32 mg, yield 14%) as colorless crystals.
melting point 55-56° C.
$^1$H NMR (CDCl$_3$) δ 3.28 (2H, t, J=8.8 Hz), 4.30 (2H, s), 4.67 (2H, t, J=8.8 Hz), 6.86 (1H, d, J=8.3 Hz), 6.92-7.01 (1H, m), 7.16-7.33 (3H, m), 7.73-7.78 (1H, m), 7.83-7.86 (1H, m).
Elemental analysis (for C$_{17}$H$_{13}$FN$_2$O$_2$S)
Calculated (%): C, 62.18; H, 3.99; N, 8.53.
Found (%): C, 62.17; H, 3.82; N, 8.54.

EXAMPLE 109

5-(2,3-dihydro-1-benzofuran-5-yl)-N-(3-fluorobenzyl)-1,3,4-oxadiazol-2-amine

A solution of 2-(2,3-dihydro-1-benzofuran-5-ylcarbonyl)-N-(3-fluorobenzyl)hydrazinecarboxamide (0.50 g, 2.81 mmol), polystyrene resin-immobilized triphenylphosphine (2.15 mmol/g, 0.76 g, 1.64 mmol), triethylamine (0.17 mL, 1.22 mmol) and carbon tetrachloride (0.12 mL, 1.22 mmol) in tetrahydrofuran (5 mL) was stirred at 80° C. for 4 hr. The reaction mixture was filtered, water was added to the filtrate, and the mixture was extracted with ethyl acetate. The organic layer was washed with saturated brine, dried over anhydrous magnesium sulfate and concentrated under reduced pressure. The residue was recrystallized from hexane/ethyl acetate to give the title compound (97 mg, yield 51%) as colorless crystals.
melting point 180-181° C.

¹H NMR (CDCl₃) δ 3.25 (2H, t, J=8.9 Hz), 4.56-4.68 (4H, m), 5.36 (1H, brs), 6.82 (1H, d, J=8.3 Hz), 6.95-7.05 (1H, m), 7.07-7.22 (2H, m), 7.27-7.38 (1H, m), 7.59-7.66 (1H, m), 7.75 (1H, brs).
Elemental analysis (for $C_{17}H_{14}FN_3O_2$)
Calculated (%): C, 65.59; H, 4.53; N, 13.50.
Found (%): C, 65.35; H, 4.56; N, 13.40.

EXAMPLE 110

2-(2,3-dihydro-1-benzofuran-5-yl)-5-[(3-fluorobenzyl)oxy]-1,3,4-oxadiazole

A solution of 2-(2,3-dihydro-1-benzofuran-5-yl)-5-(methylsulfonyl)-1,3,4-oxadiazole (0.15 g, 0.56 mmol), potassium carbonate (111 mg, 0.80 mmol) and 3-fluorobenzyl alcohol (91 μL, 0.83 mmol) in N,N-dimethylformamide (5 mL) was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=3/1) and recrystallized from hexane/ethyl acetate to give the title compound (84 mg, yield 48%) as colorless crystals.
melting point 91-92° C.
¹H NMR (CDCl₃) δ 3.27 (2H, t, J=8.9 Hz), 4.65 (2H, t, J=8.9 Hz), 5.51 (2H, s), 6.84 (1H, d, J=8.3 Hz), 7.04-7.13 (1H, m), 7.19-7.30 (2H, m), 7.34-7.44 (1H, m), 7.66-7.73 (1H, m), 7.76-7.81 (1H, m).
Elemental analysis (for $C_{17}H_{13}FN_2O_3$)
Calculated (%): C, 59.29; H, 3.81; N, 8.13.
Found (%): C, 59.24; H, 3.85; N, 8.15.

EXAMPLE 111

N-[[5-(2,3-dihydro-1-benzofuran-5-yl)-1,3,4-oxadiazol-2-yl]methyl]-3-fluoroaniline In the same manner as in Example 108 and using 3-fluoroaniline instead of 3-fluorothiophenol, the title compound (yield 30%) was obtained as colorless crystals.
melting point 166-167° C. (recrystallized from ethyl acetate).
¹H NMR (CDCl₃) δ 3.27 (2H, t, J=8.9 Hz), 4.40-4.50 (1H, m), 4.56-4.62 (2H, m), 4.66 (2H, t, J=8.9 Hz), 6.41-6.56 (3H, m), 6.86 (1H, d, J=8.3 Hz), 7.09-7.20 (1H, m), 7.78 (1H, dd, J=1.9, 8.3 Hz), 7.85-7.89 (1H, m).
Elemental analysis (for $C_{17}H_{14}FN_3O_2$)
Calculated (%): C, 65.59; H, 4.53; N, 13.50.
Found (%): C, 65.59; H, 4.47; N, 13.46.

EXAMPLE 112

2-(2,3-dihydro-1-benzofuran-5-yl)-5-[(3-fluorophenoxy)methyl]-1,3,4-oxadiazole

In the same manner as in Example 108 and using 3-fluorophenol instead of 3-fluorothiophenol, the title compound (yield 93%) was obtained as colorless crystals.
melting point 91-93° C. (recrystallized from hexane/ethyl acetate).
¹H NMR (CDCl₃) δ 3.28 (2H, t, J=8.9 Hz), 4.67 (2H, t, J=8.9 Hz), 5.29 (2H, s), 6.69-6.85 (3H, m), 6.88 (1H, d, J=8.7 Hz), 7.21-7.32 (1H, m), 7.84 (1H, dd, J=1.7, 8.3 Hz), 7.92 (1H, d, J=1.7 Hz).
Elemental analysis (for $C_{17}H_{13}FN_2O_3$)
Calculated (%): C, 65.38; H, 4.20; N, 8.97.
Found (%): C, 65.52; H, 4.16; N, 9.01.

EXAMPLE 113

2-(2,3-dihydro-1-benzofuran-5-yl)-5-[[(3-fluorophenyl)sulfinyl]methyl]-1,3,4-oxadiazole To a solution of 2-(2,3-dihydro-1-benzofuran-5-yl)-5-[[(3-fluorophenyl)thio]methyl]-1,3,4-oxadiazole (0.25 g, 0.76 mmol) in acetonitrile (5 mL) was added m-chloroperbenzoic acid (70%, 0.18 g, 0.76 mmol) at 0° C., and the resulting mixture was stirred overnight at room temperature. A saturated aqueous sodium thiosulfate solution was added to the reaction mixture, and the mixture was extracted with ethyl acetate. The organic layer was washed with saturated brine, dried over anhydrous magnesium sulfate and concentrated under reduced pressure. The residue was purified by silica gel column chromatography (hexane/ethyl acetate=3/1-2/1) and recrystallized from hexane/ethyl acetate to give the title compound (0.12 g, yield 46%) as colorless crystals.
melting point 131-132° C.
¹H NMR (CDCl₃) δ 3.28 (2H, t, J=8.9 Hz), 4.38 (2H, s), 4.68 (2H, t, J=8.9 Hz), 6.86 (1H, d, J=8.7 Hz), 7.18-7.26 (1H, m), 7.30-7.35 (1H, m), 7.38-7.44 (1H, m), 7.45-7.54 (1H, m), 7.69-7.75 (1H, m), 7.81-7.85 (1H, m).
Elemental analysis (for $C_{17}H_{13}FN_2O_3S$)
Calculated (%): C, 59.29; H, 3.81; N, 8.13.
Found (%): C, 59.24; H, 3.85; N, 8.15.

EXAMPLE 114

2-(2,3-dihydro-1-benzofuran-5-yl)-5-[[(3-fluorophenyl)sulfonyl]methyl]-1,3,4-oxadiazole In the same manner as in Example 113 and using m-chloroperbenzoic acid (2 mol) per 1 mol of 2-(2,3-dihydro-1-benzofuran-5-yl)-5-[[(3-fluorophenyl)thio]methyl]-1,3,4-oxadiazole, the title compound (yield 71%) was obtained as colorless crystals.
melting point 93-94° C. (recrystallized from hexane/ethyl acetate).
¹H NMR (CDCl₃) δ 3.29 (2H, t, J=8.9 Hz), 4.69 (2H, t, J=8.9 Hz), 4.73 (2H, s), 6.88 (1H, d, J=8.3 Hz), 7.37-7.45 (1H, m), 7.52-7.66 (3H, m), 7.76-7.81 (1H, m), 7.86-7.89 (1H, m).
Elemental analysis (for $C_{17}H_{13}FN_2O_4S$)
Calculated (%): C, 56.66; H, 3.64; N, 7.77.
Found (%): C, 56.70; H, 3.75; N, 7.74.

EXAMPLE 115 ethyl 3-[5-(2,3-dihydro-1-benzofuran-5-yl)-1,3,4-oxadiazol-2-yl]propionate

To a solution of 5-(2,3-dihydro-1-benzofuran-5-yl)-1H-tetrazole (4.40 g, 23.38 mmol) in pyridine (50 mL) was added ethyl 4-chloro-4-oxobutyrate (4.62 g, 28.06 mmol), and the resulting mixture was stirred at room temperature for 30 min and at 100° C. for 3.5 hr. After cooling, the reaction mixture was diluted with ethyl acetate, washed with water, 1M hydrochloric acid, 1M aqueous sodium hydroxide solution and saturated brine, dried over anhydrous magnesium sulfate and concentrated under reduced pressure. The residue was purified by basic silica gel column chromatography (hexane/ethyl acetate=95/5-0/100) and recrystallized from hexane/ethyl acetate to give the title compound (5.27 g, yield 78%) as pale-yellow crystals.

melting point 81-82° C.
$^1$H NMR (CDCl$_3$) δ 1.29 (3H, t, J=7.2 Hz), 2.92 (2H, t, J=7.2 Hz), 3.24 (2H, t, J=7.2 Hz), 3.30 (2H, t, J=9.0 Hz), 4.21 (2H, q, J=7.2 Hz), 4.69 (2H, t, J=9.0 Hz), 6.88 (1H, d, J=8.4 Hz), 7.80 (1H, dd, J=1.8, 8.4 Hz), 7.90 (1H, d, J=1.8 Hz).
Elemental analysis (for C$_{15}$H$_{16}$N$_2$O$_4$)
Calculated (%): C, 62.49; H, 5.59; N, 9.72.
Found (%): C, 62.29; H, 5.50; N, 9.70.

EXAMPLE 116

3-[5-(2,3-dihydro-1-benzofuran-5-yl)-1,3,4-oxadiazol-2-yl]propionic acid

To a mixture of ethyl 3-[5-(2,3-dihydro-1-benzofuran-5-yl)-1,3,4-oxadiazol-2-yl]propionate (5.20 g, 18.04 mmol), ethanol (30 mL) and tetrahydrofuran (15 mL) was added 1 M aqueous sodium hydroxide solution (20 mL), and the resulting mixture was stirred at room temperature for 3 hr. The reaction mixture was neutralized with 5 M hydrochloric acid, and extracted with ethyl acetate/tetrahydrofuran. The organic layer was washed with saturated brine, dried over anhydrous magnesium sulfate and concentrated under reduced pressure. The residue was recrystallized from methanol/diethyl ether to give the title compound (3.63 g, yield 77%) as colorless crystals.

melting point 181-182° C.
$^1$H NMR (DMSO-d$_6$) δ 2.79 (2H, t, J=7.2 Hz), 3.10 (2H, t, J=7.2 Hz), 3.27 (2H, t, J=9.0 Hz), 4.64 (2H, t, J=9.0 Hz), 6.95 (1H, d, J=8.4 Hz), 7.73 (1H, dd, J=1.5, 8.4 Hz), 7.84 (1H, d, J=1.5 Hz), 12.43 (1H, brs).
Elemental analysis (for C$_{13}$H$_{12}$N$_2$O$_4$)
Calculated (%): C, 60.00; H, 4.65; N, 10.76.
Found (%): C, 59.97; H, 4.50; N, 10.87.

EXAMPLE 117

3-[5-(2,3-dihydro-1-benzofuran-5-yl)-1,3,4-oxadiazol-2-yl]-N-methoxy-N-methylpropionamide A suspension of 3-[5-(2,3-dihydro-1-benzofuran-5-yl)-1,3,4-oxadiazol-2-yl]propionic acid (3.00 g, 11.53 mmol), N,O-dimethylhydroxyamine hydrochloride (2.25 g, 23.06 mmol), triethylamine (4.0 mL, 28.83 mmol), 3-(3-dimethylaminopropyl)-1-ethylcarbodiimide hydrochloride (3.32 g, 17.30 mmol) and 1-hydroxybenzotriazole (2.34 g, 17.30 mmol) in N,N-dimethylformamide (50 mL) was stirred at room temperature for 16 hr. The reaction mixture was diluted with ethyl acetate, washed with water, aqueous sodium hydroxide solution, hydrochloric acid and saturated brine, dried over anhydrous magnesium sulfate and concentrated under reduced pressure. The residue was recrystallized from hexane/ethyl acetate to give the title compound (2.75 g, yield 79%) as colorless crystals.

melting point 112-113° C.
$^1$H NMR (CDCl$_3$) δ 3.07 (2H, t, J=7.2 Hz), 3.20-3.35 (7H, m), 3.77 (3H, s), 4.68 (2H, t, J=9.0 Hz), 6.88 (1H, d, J=8.4 Hz), 7.81 (1H, dd, J=1.8, 8.4 Hz), 7.90 (1H, d, J=1.8 Hz).
Elemental analysis (for C$_{15}$H$_{17}$N$_3$O$_4$)
Calculated (%): C, 59.40; H, 5.65; N, 13.85.
Found (%): C, 59.36; H, 5.61; N, 13.84.

EXAMPLE 118

3-[5-(2,3-dihydro-1-benzofuran-5-yl)-1,3,4-oxadiazol-2-yl]-1-(2-thienyl)propan-1-one To a solution of 3-[5-(2,3-dihydro-1-benzofuran-5-yl)-1,3,4-oxadiazol-2-yl]-N-methoxy-N-methylpropionamide (2.50 g, 8.24 mmol) in tetrahydrofuran (50 mL) was added 1 M (2-thienyl)magnesium bromide-tetrahydrofuran solution (9.9 mL, 9.9 mmol), and the resulting mixture was stirred at room temperature for 1 hr. A saturated aqueous ammonium chloride solution (50 mL) and water were added to the reaction mixture, and the mixture was extracted with ethyl acetate. The organic layer was washed with saturated brine, dried over anhydrous magnesium sulfate and concentrated under reduced pressure. The residue was recrystallized from hexane/ethyl acetate to give the title compound (1.10 g, yield 41%) as colorless crystals.

melting point 151-152° C.
$^1$H NMR (CDCl$_3$) δ 3.25-3.40 (4H, m), 3.52-3.60 (2H, m), 4.68 (2H, t, J=8.7 Hz), 6.88 (1H, d, J=8.4 Hz), 7.18 (1H, dd, J=3.6, 5.1 Hz), 7.70 (1H, dd, J=1.2, 5.1 Hz), 7.78-7.85 (2H, m), 7.89 (1H, d, J=1.2 Hz).
Elemental analysis (for C$_{17}$H$_{14}$N$_2$O$_3$S)
Calculated (%): C, 62.56; H, 4.32; N, 8.58.
Found (%): C, 62.54; H, 4.27; N, 8.70.

EXAMPLE 119 ethyl[[5-(2,3-dihydro-1-benzofuran-5-yl)-1,3,4-oxadiazol-2-yl]oxy]acetate

In the same manner as in Example 108 and using ethyl glycolate instead of 3-fluorothiophenol, the title compound (yield 100%) was obtained as pale-pink crystals.

melting point 103-104° C. (recrystallized from hexane/ethyl acetate).
$^1$H NMR (CDCl$_3$) δ 1.34 (3H, t, J=7.2 Hz), 3.29 (2H, t, J=8.7 Hz), 4.32 (2H, q, J=7.2 Hz), 4.68 (2H, t, J=8.7 Hz), 5.04 (2H, s), 6.87 (1H, d, J=8.4 Hz), 7.73 (1H, dd, J=1.5, 8.4 Hz), 7.81 (1H, d, J=1.5 Hz).
Elemental analysis (for C$_{14}$H$_{14}$N$_2$O$_5$)
Calculated (%): C, 57.93; H, 4.86; N, 9.65.
Found (%): C, 57.84; H, 4.78; N, 9.72.

EXAMPLE 120

[[5-(2,3-dihydro-1-benzofuran-5-yl)-1,3,4-oxadiazol-2-yl]oxy]acetic acid

In the same manner as in Example 116 and using ethyl[[5-(2,3-dihydro-1-benzofuran-5-yl)-1,3,4-oxadiazol-2-yl]oxy]acetate instead of ethyl 3-[5-(2,3-dihydro-1-benzofuran-5-yl)-1,3,4-oxadiazol-2-yl]propionate, the title compound (yield 34%) was obtained as colorless crystals.

melting point 151-153° C. (recrystallized from methanol/diethyl ether).
$^1$H NMR (DMSO-d$_6$) δ 3.26 (2H, t, J=8.7 Hz), 4.63 (2H, t, J=8.7 Hz), 5.04 (2H, s), 6.93 (1H, d, J=8.4 Hz), 7.65 (1H, dd, J=1.5, 8.4 Hz), 7.77 (1H, d, J=1.5 Hz), 13.56 (1H, brs).
Elemental analysis (for C$_{12}$H$_{10}$N$_2$O$_5$)
Calculated (%): C, 54.97; H, 3.84; N, 10.68.
Found (%): C, 54.73; H, 3.85; N, 10.81.

EXAMPLE 121

2-[[5-(2,3-dihydro-1-benzofuran-5-yl)-1,3,4-oxadiazol-2-yl]oxy]-N-methoxy-N-methylacetamide In the same manner as in Example 117 and using [[5-(2,3-dihydro-1-benzofuran-5-yl)-1,3,4-oxadiazol-2-yl]oxy]acetic acid instead of 3-[5-(2,3-dihydro-1-benzofuran-5-yl)-1,3,4-oxadiazol-2-yl]propionic acid, the title compound (yield 72%) was obtained as colorless crystals.

melting point 139-140° C. (recrystallized from hexane/ethyl acetate).

$^1$H NMR (CDCl$_3$) δ 3.27 (3H, s), 3.28 (2H, t, J=8.7 Hz), 3.82 (3H, s), 4.67 (2H, t, J=8.7 Hz), 5.26 (2H, s), 6.86 (1H, d, J=8.4 Hz), 7.73 (1H, dd, J=1.5, 8.4 Hz), 7.80 (1H, d, J=1.5 Hz).

Elemental analysis (for C$_{14}$H$_{15}$N$_3$O$_5$)
Calculated (%): C, 55.08; H, 4.95; N, 13.76.
Found (%): C, 55.16; H, 4.86; N, 13.89.

EXAMPLE 122

2-(1-benzofuran-5-yl)-5-[(3-fluorobenzyl)thio]-1,3,4-oxadiazole

In the same manner as in Example 1 and using 5-(1-benzofuran-5-yl)-1,3,4-oxadiazole-2-thiol instead of 5-(benzothiazol-6-yl)-1,3,4-oxadiazole-2-thiol and 3-fluorobenzyl chloride instead of 3-(trifluoromethyl)benzyl chloride, the title compound (yield 84%) was obtained as colorless crystals.

melting point 112-113° C. (recrystallized from hexane/ethyl acetate).

$^1$H NMR (CDCl$_3$) δ 4.51 (2H, s), 6.85 (1H, dd, J=0.8, 2.3 Hz), 6.96-7.04 (1H, m), 7.17-7.36 (3H, m), 7.57-7.62 (1H, m), 7.71 (1H, d, J=2.1 Hz), 7.96 (1H, dd, J=2.1, 8.7 Hz), 8.23-8.25 (1H, m).

Elemental analysis (for C$_{17}$H$_{11}$FN$_2$O$_2$S)
Calculated (%): C, 62.57; H, 3.40; N, 8.58.
Found (%): C, 62.57; H, 3.48; N, 8.59.

EXAMPLE 123

2-(1-benzofuran-5-yl)-5-[(3-chlorobenzyl)thio]-1,3,4-oxadiazole

In the same manner as in Example 1 and using 5-(1-benzofuran-5-yl)-1,3,4-oxadiazole-2-thiol instead of 5-(benzothiazol-6-yl)-1,3,4-oxadiazole-2-thiol and 3-chlorobenzyl chloride instead of 3-(trifluoromethyl)benzyl chloride, the title compound (yield 89%) was obtained as colorless crystals.

melting point 125-126° C. (recrystallized from hexane/ethyl acetate).

$^1$H NMR (CDCl$_3$) δ 4.48 (2H, s), 6.84-6.86 (1H, m), 7.24-7.30 (2H, m), 7.33-7.40 (1H, m), 7.48 (1H, brs), 7.60 (1H, d, J=8.7 Hz), 7.71 (1H, d, J=2.3 Hz), 7.96 (1H, dd, J=1.3, 8.7 Hz), 8.24 (1H, d, J=1.3 Hz).

Elemental analysis (for C$_{17}$H$_{11}$ClN$_2$O$_2$S)
Calculated (%): C, 59.56; H, 3.23; N, 8.17.
Found (%): C, 59.52; H, 3.37; N, 8.18.

EXAMPLE 124

2-(1-benzofuran-5-yl)-5-[(4-chlorobenzyl)thio]-1,3,4-oxadiazole

In the same manner as in Example 1 and using 5-(1-benzofuran-5-yl)-1,3,4-oxadiazole-2-thiol instead of 5-(benzothiazol-6-yl)-1,3,4-oxadiazole-2-thiol and 4-chlorobenzyl chloride instead of 3-(trifluoromethyl)benzyl chloride, the title compound (yield 89%) was obtained as colorless crystals.

melting point 162-163° C. (recrystallized from hexane/ethyl acetate).

$^1$H NMR (CDCl$_3$) δ 4.48 (2H, s), 6.83-6.87 (1H, m), 7.29-7.34 (2H, m), 7.39-7.44 (2H, m), 7.60 (1H, d, J=8.9 Hz), 7.71 (1H, d, J=2.3 Hz), 7.96 (1H, dd, J=1.7, 8.9 Hz), 8.23 (1H, d, J=1.7 Hz).

Elemental analysis (for C$_{17}$H$_{11}$ClN$_2$O$_2$S)
Calculated (%): C, 59.56; H, 3.23; N, 8.17.
Found (%): C, 59.63; H, 3.35; N, 8.20.

EXAMPLE 125

2-(1-benzofuran-5-yl)-5-[(4-methoxybenzyl)thio]-1,3,4-oxadiazole

In the same manner as in Example 1 and using 5-(1-benzofuran-5-yl)-1,3,4-oxadiazole-2-thiol instead of 5-(benzothiazol-6-yl)-1,3,4-oxadiazole-2-thiol and 4-methoxybenzyl chloride instead of 3-(trifluoromethyl)benzyl chloride, the title compound (yield 87%) was obtained as colorless crystals.

melting point 124-125° C. (recrystallized from hexane/ethyl acetate).

$^1$H NMR (CDCl$_3$) δ 3.79 (3H, s), 4.50 (2H, s), 6.84-6.91 (3H, m), 7.39 (2H, d, J=8.7 Hz), 7.59 (1H, d, J=8.7 Hz), 7.70 (1H, d, J=1.9 Hz), 7.96 (1H, dd, J=1.5, 8.7 Hz), 8.24 (1H, d, J=1.5 Hz)

Elemental analysis (for C$_{18}$H$_{14}$N$_2$O$_3$S)
Calculated (%): C, 63.89; H, 4.17; N, 8.28.
Found (%): C, 64.05; H, 4.38; N, 8.19.

EXAMPLE 126

2-(1-benzofuran-5-yl)-5-[(3-fluoro-4-methoxybenzyl)thio]-1,3,4-oxadiazole

In the same manner as in Example 47 and using 1-benzofuran-5-carbohydrazide instead of 2,3-dihydro-1-benzofuran-5-carbohydrazide, the title compound (yield 53%) was obtained as colorless crystals.

melting point 134-136° C. (recrystallized from hexane/ethyl acetate).

$^1$H NMR (CDCl$_3$) δ 3.87 (3H, s), 4.46 (2H, s), 6.85-6.87 (1H, m), 6.87-6.94 (1H, m), 7.16-7.25 (2H, m), 7.60 (1H, d, J=8.7 Hz), 7.71 (1H, d, J=2.3 Hz), 7.97 (1H, dd, J=1.7, 8.7 Hz), 8.25 (1H, d, J=1.7 Hz).

Elemental analysis (for C$_{18}$H$_{13}$FN$_2$O$_3$S)
Calculated (%): C, 60.67; H, 3.68; N, 7.86.
Found (%): C, 60.68; H, 3.74; N, 7.85.

EXAMPLE 127

2-(1-benzofuran-5-yl)-5-[[4-methoxy-3-(trifluoromethyl)benzyl]thio]-1,3,4-oxadiazole In the same manner as in Example 1 and using 5-(1-benzofuran-5-yl)-1,3,4-oxadiazole-2-thiol instead of 5-(benzothiazol-6-yl)-1,3,4-oxadiazole-2-thiol and 4-methoxy-3-(trifluoromethyl)benzyl chloride instead of 3-(trifluoromethyl)benzyl chloride, the title compound (yield 100%) was obtained as colorless crystals.

melting point 135-136° C. (recrystallized from hexane/ethyl acetate).

¹H NMR (CDCl₃) δ 3.89 (3H, s), 4.49 (2H, s), 6.86 (1H, dd, J=0.8, 2.2 Hz), 6.96 (1H, d, J=8.3 Hz), 7.58-7.68 (3H, m), 7.71 (1H, d, J=2.2 Hz), 7.96 (1H, dd, J=1.6, 8.7 Hz), 8.24 (1H, d, J=1.6 Hz).
Elemental analysis (for $C_{19}H_{13}F_3N_2O_3S$)
Calculated (%): C, 56.16; H, 3.22; N, 6.89.
Found (%): C, 56.12; H, 3.31; N, 6.78.

EXAMPLE 128

2-(1-benzofuran-5-yl)-5-(4-methoxybenzyl)-1,3,4-oxadiazole

In the same manner as in Example 14 and using 1-benzofuran-5-carbohydrazide instead of 1H-benzotriazole-5-carbohydrazide and (4-methoxyphenyl)acetic acid instead of 3-(3-cyanophenyl)propionic acid, the title compound (yield 58%) was obtained as colorless crystals.
melting point 108-109° C. (recrystallized from hexane/ethyl acetate).
¹H NMR (CDCl₃) δ 3.79 (3H, s), 4.22 (2H, s), 6.82-6.84 (1H, m), 6.89 (2H, d, J=8.7 Hz), 7.30 (2H, d, J=8.7 Hz), 7.58 (1H, d, J=8.7 Hz), 7.69 (1H, d, J=2.3 Hz), 7.97 (1H, dd, J=1.7, 8.7 Hz), 8.25 (1H, d, J=1.7 Hz).
Elemental analysis (for $C_{18}H_{14}N_2O_3$)
Calculated (%): C, 70.58; H, 4.61; N, 9.15.
Found (%): C, 70.60; H, 4.81; N, 9.20.

EXAMPLE 129

2-(1-benzofuran-5-yl)-5-[2-(4-methoxyphenyl)ethyl]-1,3,4-oxadiazole

In the same manner as in Example 14 and using 1-benzofuran-5-carbohydrazide instead of 1H-benzotriazole-5-carbohydrazide and 3-(4-methoxyphenyl)propionic acid instead of 3-(3-cyanophenyl)propionic acid, the title compound (yield 53%) was obtained as colorless crystals.
melting point 127-128° C. (recrystallized from hexane/ethyl acetate).
¹H NMR (CDCl₃) δ 3.08-3.26 (4H, m), 3.79 (3H, s), 6.83-6.88 (3H, m), 7.18 (2H, d, J=8.7 Hz), 7.60 (1H, d, J=8.7 Hz), 7.71 (1H, d, J=2.3 Hz), 7.99 (1H, dd, J=1.7, 8.7 Hz), 8.27 (1H, d, J=1.7 Hz).
Elemental analysis (for $C_{19}H_{16}N_2O_3$)
Calculated (%): C, 71.24; H, 5.03; N, 8.74.
Found (%): C, 71.24; H, 5.07; N, 8.80.

EXAMPLE 130

2-(1-benzofuran-5-yl)-5-[3-(4-methoxyphenyl)propyl]-1,3,4-oxadiazole

In the same manner as in Example 14 and using 1-benzofuran-5-carbohydrazide instead of 1H-benzotriazole-5-carbohydrazide and 4-(4-methoxyphenyl)butyric acid instead of 3-(3-cyanophenyl)propionic acid, the title compound (yield 15%) was obtained as colorless crystals.
melting point 116-117° C. (recrystallized from ethyl acetate).
¹H NMR (CDCl₃) δ 2.17 (2H, t, J=7.5 Hz), 2.73 (2H, t, J=7.5 Hz), 2.94 (2H, t, J=7.5 Hz), 3.77 (3H, s), 6.81-6.88 (3H, m), 7.14 (2H, d, J=8.7 Hz), 7.61 (1H, d, J=8.7 Hz), 7.71 (1H, d, J=2.3 Hz), 8.00 (1H, dd, J=1.6, 8.5 Hz), 8.28 (1H, d, J=1.6 Hz).
Elemental analysis (for $C_{20}H_{18}N_2O_3$)
Calculated (%): C, 71.84; H, 5.43; N, 8.38.
Found (%): C, 71.72; H, 5.33; N, 8.25.

EXAMPLE 131

2-[3-(4-methoxyphenyl)-1-benzofuran-5-yl]-5-methyl-1,3,4-oxadiazole

In the same manner as in Example 5 and using N'-acetyl-3-(4-methoxyphenyl)-1-benzofuran-5-carbohydrazide instead of N'-[3-[3-(trifluoromethyl)phenyl]propionyl]benzothiazole-6-carbohydrazide, the title compound (yield 66%) was obtained as colorless crystals.
melting point 175-176° C.
¹H NMR (CDCl₃) δ 2.63 (3H, s), 3.88 (3H, s), 7.03-7.07 (2H, m), 7.56-7.61 (2H, m), 7.64 (1H, d, J=8.7 Hz), 7.80 (1H, s), 8.04 (1H, dd, J=1.9, 8.7 Hz), 8.48 (1H, d, J=1.9 Hz).
Elemental analysis (for $C_{18}H_{14}N_2O_3$)
Calculated (%): C, 70.58; H, 4.61; N, 9.15.
Found (%): C, 70.42; H, 4.72; N, 9.05.

EXAMPLE 132

2-[3-(4-fluorophenyl)-1-benzofuran-5-yl]-5-methyl-1,3,4-oxadiazole

A mixture of 2-(3-bromo-1-benzofuran-5-yl)-5-methyl-1,3,4-oxadiazole (251 mg, 0.900 mmol), (4-fluorophenyl)boronic acid (140 mg, 1.00 mmol), tetrakis(triphenylphosphine)palladium(0) (31.2 mg, 0.0270 mmol), sodium carbonate (212 mg, 2.00 mmol), 1,2-dimethoxyethane (5 mL) and water (1 mL) was heated overnight under reflux under an argon atmosphere. After cooling, the reaction mixture was diluted with ethyl acetate, washed with water and saturated brine, dried over anhydrous magnesium sulfate and concentrated under reduced pressure. The residue was purified by silica gel column chromatography (hexane/ethyl acetate=1/1) and recrystallized from hexane/ethyl acetate to give the title compound (182 mg, yield 69%) as colorless crystals.
melting point 130-131° C.
¹H NMR (CDCl₃) δ 2.64 (3H, s), 7.17-7.35 (2H, m), 7.59-7.67 (3H, m), 7.83 (1H, s), 8.06 (1H, dd, J=1.7, 8.7 Hz), 8.45 (1H, dd, J=0.6, 1.7 Hz).
Elemental analysis (for $C_{17}H_{11}FN_2O_2$)
Calculated (%): C, 69.38; H, 3.77; N, 9.52.
Found (%): C, 69.38; H, 3.75; N, 9.60.

EXAMPLE 133 methyl 4-[5-(5-methyl-1,3,4-oxadiazol-2-yl)-1-benzofuran-3-yl]benzoate

In the same manner as in Example 132 and using [4-(methoxycarbonyl)phenyl]boronic acid instead of (4-fluorophenyl)boronic acid, the title compound (yield 64%) was obtained as colorless crystals.
melting point 208-209° C. (recrystallized from tetrahydrofuran).
¹H NMR (CDCl₃) δ 2.65 (3H, s), 3.97 (3H, s), 7.68 (1H, dd, J=0.6, 8.7 Hz), 7.73-7.77 (2H, m), 7.95 (1H, s), 8.09 (1H, dd, J=1.7, 8.7 Hz), 8.16-8.20 (2H, m), 8.51 (1H, dd, J=0.6, 1.7 Hz).
Elemental analysis (for $C_{19}H_{14}N_2O_4$)
Calculated (%): C, 68.26; H, 4.22; N, 8.38.
Found (%): C, 68.32; H, 4.13; N, 8.28.

EXAMPLE 134

4-[5-(5-methyl-1,3,4-oxadiazol-2-yl)-1-benzofuran-3-yl]benzoic acid

A mixture of methyl 4-[5-(5-methyl-1,3,4-oxadiazol-2-yl)-1-benzofuran-3-yl]benzoate (204 mg, 0.610 mmol), 1 M aqueous sodium hydroxide solution (3 mL), tetrahydrofuran (6 mL) and methanol (6 mL) was stirred at 60° C. for 24 hr. After cooling, the reaction mixture was poured into water, and acidified with 1M hydrochloric acid. The precipitate was collected by filtration, dried, and recrystallized from ethanol to give the title compound (163 mg, yield 83%) as colorless crystals.

melting point >300° C.
$^1$H NMR (DMSO-$d_6$) δ 2.61 (3H, s), 7.89-7.94 (3H, m), 8.05 (1H, dd, J=1.7, 8.7 Hz), 8.10-8.14 (2H, m), 8.46 (1H, dd, J=0.6, 1.7 Hz), 8.67 (1H, s), 13.08 (1H, brs).
Elemental analysis (for $C_{18}H_{12}N_2O_4$)
Calculated (%): C, 67.50; H, 3.78; N, 8.75.
Found (%): C, 67.37; H, 3.72; N, 8.73.

EXAMPLE 135

[4-[5-(5-methyl-1,3,4-oxadiazol-2-yl)-1-benzofuran-3-yl]phenyl]methanol

To a solution of methyl 4-[5-(5-methyl-1,3,4-oxadiazol-2-yl)-1-benzofuran-3-yl]benzoate (408 mg, 1.22 mmol) in tetrahydrofuran (35 mL) was added lithium aluminum hydride (46.3 mg, 1.22 mmol) at room temperature, and the resulting mixture was stirred for 10 min. Sodium sulfate decahydrate (393 mg, 1.22 mmol) was added to the reaction mixture, and the mixture was further stirred at room temperature for 1 hr. Insoluble material was removed by filtration, and the filtrate was concentrated under reduced pressure. The residue was purified by basic silica gel column chromatography (tetrahydrofuran) and recrystallized from hexane/tetrahydrofuran to give the title compound (321 mg, yield 86%) as colorless crystals.

melting point 157-158° C.
$^1$H NMR (CDCl$_3$) δ 1.83 (1H, t, J=5.8 Hz), 2.64 (3H, s), 4.79 (2H, d, J=5.8 Hz), 7.50-7.54 (2H, m), 7.64-7.69 (3H, m), 7.87 (1H, s), 8.06 (1H, dd, J=1.7, 8.7 Hz), 8.50 (1H, dd, J=0.6, 1.7 Hz).
Elemental analysis (for $C_{18}H_{14}N_2O_3$)
Calculated (%): C, 70.58; H, 4.61; N, 9.15.
Found (%): C, 70.62; H, 4.55; N, 9.17.

EXAMPLE 136

2-[3-[4-(methoxymethyl)phenyl]-1-benzofuran-5-yl]-5-methyl-1,3,4-oxadiazole

To a mixture of [4-[5-(5-methyl-1,3,4-oxadiazol-2-yl)-1-benzofuran-3-yl]phenyl]methanol (193 mg, 0.630 mmol), tetrahydrofuran (3 mL) and N,N-dimethylformamide (3 mL) was added sodium hydride (60% in oil, 37.8 mg, 0.945 mmol) at room temperature, and the resulting mixture was stirred for 10 min. Iodomethane (0.0588 mL, 0.945 mmol) was added to the reaction mixture, and the mixture was further stirred at room temperature for 1 hr. The reaction mixture was diluted with ethyl acetate, washed with water and saturated brine, dried over anhydrous magnesium sulfate and concentrated under reduced pressure. The residue was purified by basic silica gel column chromatography (hexane/tetrahydrofuran=2/1), and crystallized from hexane/tetrahydrofuran to give the title compound (146 mg, yield 73%) as colorless crystals.

melting point 158-159° C.
$^1$H NMR (CDCl$_3$) δ 2.64 (3H, s), 3.45 (3H, s), 4.54 (2H, s), 7.47-7.51 (2H, m), 7.63-7.67 (3H, m), 7.87 (1H, s), 8.06 (1H, dd, J=1.7, 8.7 Hz), 8.49 (1H, dd, J=0.6, 1.7 Hz).
Elemental analysis (for $C_{19}H_{16}N_2O_3$)
Calculated (%): C, 71.24; H, 5.03; N, 8.74.
Found (%): C, 71.16; H, 4.93; N, 8.73.

EXAMPLE 137

4-[5-(5-methyl-1,3,4-oxadiazol-2-yl)-1-benzofuran-3-yl]benzamide

In the same manner as in Example 132 and using (4-carbamoylphenyl)boronic acid instead of (4-fluorophenyl)boronic acid, the title compound (yield 65%) was obtained as colorless crystals.

melting point 250-251° C. (recrystallized from methanol).
$^1$H NMR (DMSO-$d_6$) δ 2.61 (3H, s), 7.46 (1H, brs), 7.84-7.88 (2H, m), 7.92 (1H, dd, J=0.6, 8.7 Hz), 8.03-8.08 (4H, m), 8.44 (1H, dd, J=0.6, 1.7 Hz), 8.63 (1H, s).
Elemental analysis (for $C_{18}H_{13}FN_3O_3$)
Calculated (%): C, 67.71; H, 4.10; N, 13.16.
Found (%): C, 67.69; H, 4.03; N, 13.23.

EXAMPLE 138

N,N-dimethyl-4-[5-(5-methyl-1,3,4-oxadiazol-2-yl)-1-benzofuran-3-yl]aniline

In the same manner as in Example 132 and using [4-(dimethylamino)phenyl]boronic acid instead of (4-fluorophenyl)boronic acid, the title compound (yield 33%) was obtained as colorless crystals.

melting point 205-206° C. (recrystallized from hexane/tetrahydrofuran).
$^1$H NMR (CDCl$_3$) δ 2.63 (3H, s), 3.03 (6H, s), 6.84-6.89 (2H, m), 7.52-7.57 (2H, m), 7.62 (1H, dd, J=0.6, 8.7 Hz), 7.78 (1H, s), 8.03 (1H, dd, J=1.7, 8.7 Hz), 8.50 (1H, dd, J=0.6, 1.7 Hz).
Elemental analysis (for $C_{19}H_{17}N_3O_2$)
Calculated (%): C, 71.46; H, 5.37; N, 13.16.
Found (%): C, 71.49; H, 5.28; N, 13.22.

EXAMPLE 139

2-methyl-5-[3-[4-(methylthio)phenyl]-1-benzofuran-5-yl]-1,3,4-oxadiazole

In the same manner as in Example 132 and using [4-(methylthio)phenyl]boronic acid instead of (4-fluorophenyl)boronic acid, the title compound (yield 71%) was obtained as colorless crystals.

melting point 173-174° C. (recrystallized from hexane/tetrahydrofuran).
$^1$H NMR (CDCl$_3$) δ 2.55 (3H, s), 2.64 (3H, s), 7.37-7.42 (2H, m), 7.57-7.61 (2H, m), 7.65 (1H, dd, J=0.8, 8.7 Hz), 7.85 (1H, s), 8.06 (1H, dd, J=1.7, 8.7 Hz), 8.48 (1H, dd, J=0.6, 1.7 Hz).
Elemental analysis (for $C_{18}H_{14}N_2O_2S$)
Calculated (%): C, 67.06; H, 4.38; N, 8.69.
Found (%): C, 66.96; H, 4.38; N, 8.63.

EXAMPLE 140

2-methyl-5-[3-[4-(methylsulfinyl)phenyl]-1-benzofuran-5-yl]-1,3,4-oxadiazole

To a solution of 2-methyl-5-[3-[4-(methylthio)phenyl]-1-benzofuran-5-yl]-1,3,4-oxadiazole (322 mg, 1.00 mmol) in dichloromethane (10 mL) was added m-chloroperbenzoic acid (70%, 259 mg, 1.05 mmol) at room temperature, and the resulting mixture was stirred for 5 min. The reaction mixture was concentrated under reduced pressure, and the residue was purified by basic silica gel column chromatography (ethyl acetate) and recrystallized from tetrahydrofuran to give the title compound (284 mg, yield 84%) as colorless crystals.
melting point 183-184° C.
$^1$H NMR (CDCl$_3$) δ 2.65 (3H, s), 2.81 (3H, s), 7.69 (1H, dd, J=0.6, 8.7 Hz), 7.78-7.85 (4H, m), 7.94 (1H, s), 8.08 (1H, dd, J=1.7, 8.7 Hz), 8.50 (1H, dd, J=0.6, 1.7 Hz).
Elemental analysis (for C$_{18}$H$_{14}$N$_2$O$_3$S)
Calculated (%): C, 63.89; H, 4.17; N, 8.28.
Found (%): C, 63.82; H, 4.26; N, 8.14.

EXAMPLE 141

2-methyl-5-[3-[4-(methylsulfonyl)phenyl]-1-benzofuran-5-yl]-1,3,4-oxadiazole

In the same manner as in Example 132 and using [4-(methylsulfonyl)phenyl]boronic acid instead of (4-fluorophenyl)boronic acid, the title compound (yield 85%) was obtained as colorless crystals.
melting point 212-213° C. (recrystallized from tetrahydrofuran).
$^1$H NMR (CDCl$_3$) δ 2.65 (3H, s), 3.13 (3H, s), 7.70 (1H, dd, J=0.6, 8.7 Hz), 7.85-7.89 (2H, m), 7.98 (1H, s), 8.08-8.12 (3H, m), 8.50 (1H, dd, J=0.6, 1.7 Hz).
Elemental analysis (for C$_{18}$H$_{14}$N$_2$O$_4$S)
Calculated (%): C, 61.01; H, 3.98; N, 7.90.
Found (%): C, 60.79; H, 3.88; N, 7.96.

EXAMPLE 142

2-[3-(3-fluorophenyl)-1-benzofuran-5-yl]-5-methyl-1,3,4-oxadiazole

In the same manner as in Example 132 and using (3-fluorophenyl)boronic acid instead of (4-fluorophenyl)boronic acid, the title compound (yield 68%) was obtained as colorless crystals.
melting point 138-139° C. (recrystallized from hexane/ethyl acetate).
$^1$H NMR (CDCl$_3$) δ 2.65 (3H, s), 7.08-7.15 (1H, m), 7.33-7.38 (1H, m), 7.43-7.52 (2H, m), 7.67 (1H, dd, J=0.6, 8.7 Hz), 7.88 (1H, s), 8.08 (1H, dd, J=1.7, 8.7 Hz), 8.48 (1H, dd, J=0.6, 1.7 Hz).
Elemental analysis (for C$_{17}$H$_{11}$FN$_2$O$_2$)
Calculated (%): C, 69.38; H, 3.77; N, 9.52.
Found (%): C, 69.42; H, 3.77; N, 9.50.

EXAMPLE 143

2-[3-(3-methoxyphenyl)-1-benzofuran-5-yl]-5-methyl-1,3,4-oxadiazole

In the same manner as in Example 132 and using (3-methoxyphenyl)boronic acid instead of (4-fluorophenyl)boronic acid, the title compound (yield 77%) was obtained as colorless crystals.
melting point 127-128° C. (recrystallized from hexane/ethyl acetate).
$^1$H NMR (CDCl$_3$) δ 2.64 (3H, s), 3.90 (3H, s), 6.97 (1H, ddd, J=0.9, 2.6, 8.3 Hz), 7.18 (1H, dd, J=1.5, 2.6 Hz), 7.26 (1H, ddd, J=0.9, 1.5, 7.5 Hz), 7.44 (1H, dd, J=7.5, 8.3 Hz), 7.65 (1H, dd, J=0.6, 8.7 Hz), 7.86 (1H, s), 8.07 (1H, dd, J=1.7, 8.7 Hz), 8.50 (1H, dd, J=0.6, 1.7 Hz).
Elemental analysis (for C$_{18}$H$_{14}$N$_2$O$_3$)
Calculated (%): C, 70.58; H, 4.61; N, 9.15.
Found (%): C, 70.55; H, 4.57; N, 9.11.

EXAMPLE 144

[3-[5-(5-methyl-1,3,4-oxadiazol-2-yl)-1-benzofuran-3-yl]phenyl]methanol

In the same manner as in Example 132 and using [3-(hydroxymethyl)phenyl]boronic acid instead of (4-fluorophenyl)boronic acid, the title compound (yield 82%) was obtained as colorless crystals.
melting point 115-116° C. (crystallized from hexane/ethyl acetate).
$^1$H NMR (CDCl$_3$) δ 2.09 (1H, t, J=5.8 Hz), 2.63 (3H, s), 4.81 (2H, d, J=5.8 Hz), 7.39-7.43 (1H, m), 7.50 (1H, t, J=7.5 Hz), 7.57-7.61 (1H, m), 7.63-7.66 (2H, m), 7.86 (1H, s), 8.04 (1H, dd, J=1.7, 8.7 Hz), 8.49 (1H, dd, J=0.6, 1.7 Hz).
Elemental analysis (for C$_{18}$H$_{14}$N$_2$O$_3$)
Calculated (%): C, 70.58; H, 4.61; N, 9.15.
Found (%): C, 70.41; H, 4.55; N, 9.02.

EXAMPLE 145

2-[3-[3-(methoxymethyl)phenyl]-1-benzofuran-5-yl]-5-methyl-1,3,4-oxadiazole

In the same manner as in Example 136 and using [3-[5-(5-methyl-1,3,4-oxadiazol-2-yl)-1-benzofuran-3-yl]phenyl]methanol instead of [4-[5-(5-methyl-1,3,4-oxadiazol-2-yl)-1-benzofuran-3-yl]phenyl]methanol, the title compound (yield 71%) was obtained as colorless crystals.
melting point 111-112° C. (crystallized from hexane/ethyl acetate).
$^1$H NMR (CDCl$_3$) δ 2.64 (3H, s), 3.46 (3H, s), 4.56 (2H, s), 7.37-7.41 (1H, m), 7.48-7.53 (1H, m), 7.59-7.63 (2H, m), 7.65 (1H, dd, J=0.6, 8.7 Hz), 7.87 (1H, s), 8.06 (1H, dd, J=1.7, 8.7 Hz), 8.49 (1H, dd, J=0.6, 1.7 Hz).
Elemental analysis (for C$_{19}$H$_{16}$N$_2$O$_3$)
Calculated (%): C, 71.24; H, 5.03; N, 8.74.
Found (%): C, 71.02; H, 4.93; N, 8.62.

EXAMPLE 146

2-methyl-5-[3-[3-(trifluoromethyl)phenyl]-1-benzofuran-5-yl]-1,3,4-oxadiazole

In the same manner as in Example 132 and using [3-(trifluoromethyl)phenyl]boronic acid instead of (4-fluorophenyl)boronic acid, the title compound (yield 56%) was obtained as colorless crystals.
melting point 126-127° C. (crystallized from hexane/tetrahydrofuran).
$^1$H NMR (CDCl$_3$) δ 2.64 (3H, s), 7.63-7.70 (3H, m), 7.84-7.89 (2H, m), 7.93 (1H, s), 8.09 (1H, dd, J=1.7, 8.7 Hz), 8.45 (1H, dd, J=0.6, 1.7 Hz).
Elemental analysis (for C$_{18}$H$_{11}$F$_3$N$_2$O$_2$)
Calculated (%): C, 62.79; H, 3.22; N, 8.14.
Found (%): C, 62.81; H, 3.31; N, 8.14.

EXAMPLE 147

2-methyl-5-[3-[3-(trifluoromethoxy)phenyl]-1-benzofuran-5-yl]-1,3,4-oxadiazole

In the same manner as in Example 132 and using [3-(trifluoromethoxy)phenyl]boronic acid instead of (4-fluorophenyl)boronic acid, the title compound (yield 56%) was obtained as colorless crystals.

melting point 110-111° C. (recrystallized from hexane/tetrahydrofuran).

$^1$H NMR (CDCl$_3$) δ 2.65 (3H, s), 7.26-7.31 (1H, m), 7.47-7.49 (1H, m), 7.55 (1H, t, J=7.9 Hz), 7.62 (1H, td, J=1.3, 7.7 Hz), 7.68 (1H, dd, J=0.6, 8.7 Hz), 7.90 (1H, s), 8.09 (1H, dd, J=1.7, 8.7 Hz), 8.46 (1H, dd, J=0.6, 1.7 Hz).

Elemental analysis (for C$_{18}$H$_{11}$F$_3$N$_2$O$_3$)
Calculated (%): C, 60.01; H, 3.08; N, 7.78.
Found (%): C, 60.00; H, 2.94; N, 7.80.

EXAMPLE 148

2-[3-(3-chlorophenyl)-1-benzofuran-5-yl]-5-methyl-1,3,4-oxadiazole

In the same manner as in Example 132 and using (3-chlorophenyl)boronic acid instead of (4-fluorophenyl)boronic acid, the title compound (yield 73%) was obtained as colorless crystals.

melting point 145-146° C. (recrystallized from hexane/ethyl acetate).

$^1$H NMR (CDCl$_3$) δ 2.65 (3H, s), 7.39 (1H, ddd, J=1.5, 1.9, 7.9 Hz), 7.45 (1H, ddd, J=0.6, 7.4, 7.9 Hz), 7.56 (1H, td, J=1.5, 7.4 Hz), 7.62 (1H, ddd, J=0.6, 1.5, 1.9 Hz), 7.67 (1H, dd, J=0.6, 8.7 Hz), 7.87 (1H, s), 8.08 (1H, dd, J=1.7, 8.7 Hz), 8.46 (1H, dd, J=0.6, 1.7 Hz).

Elemental analysis (for C$_{17}$H$_{11}$ClN$_2$O$_2$)
Calculated (%): C, 65.71; H, 3.57; N, 9.02.
Found (%): C, 65.58; H, 3.53; N, 8.99.

EXAMPLE 149

3-[5-(5-methyl-1,3,4-oxadiazol-2-yl)-1-benzofuran-3-yl]benzonitrile

In the same manner as in Example 132 and using (3-cyanophenyl)boronic acid instead of (4-fluorophenyl)boronic acid, the title compound (yield 77%) was obtained as colorless crystals.

melting point 204-205° C. (recrystallized from tetrahydrofuran).

$^1$H NMR (CDCl$_3$) δ 2.66 (3H, s), 7.62-7.67 (1H, m), 7.68-7.74 (2H, m), 7.89-7.93 (3H, s), 8.11 (1H, dd, J=1.7, 8.7 Hz), 8.42 (1H, dd, J=0.6, 1.7 Hz).

Elemental analysis (for C$_{18}$H$_{11}$N$_3$O$_2$)
Calculated (%): C, 71.75; H, 3.68; N, 13.95.
Found (%): C, 71.66; H, 3.65; N, 13.97.

EXAMPLE 150

2-methyl-5-[3-[3-(methylthio)phenyl]-1-benzofuran-5-yl]-1,3,4-oxadiazole

In the same manner as in Example 132 and using [3-(methylthio)phenyl]boronic acid instead of (4-fluorophenyl)boronic acid, the title compound (yield 88%) was obtained as colorless crystals.

melting point 99-100° C. (crystallized from hexane/ethyl acetate).

$^1$H NMR (CDCl$_3$) δ 2.56 (3H, s), 2.64 (3H, s), 7.27-7.34 (1H, m), 7.42-7.46 (2H, m), 7.50-7.51 (1H, m), 7.66 (1H, dd, J=0.8, 8.7 Hz), 7.86 (1H, s), 8.07 (1H, dd, J=1.7, 8.7 Hz), 8.46 (1H, dd, J=0.6, 1.7 Hz).

Elemental analysis (for C$_{18}$H$_{14}$N$_2$O$_2$S)
Calculated (%): C, 67.06; H, 4.38; N, 8.69.
Found (%): C, 66.97; H, 4.30; N, 8.70.

EXAMPLE 151

2-methyl-5-[3-[3-(methylsulfonyl)phenyl]-1-benzofuran-5-yl]-1,3,4-oxadiazole

To a solution of 2-methyl-5-[3-[3-(methylthio)phenyl]-1-benzofuran-5-yl]-1,3,4-oxadiazole (774 mg, 2.40 mmol) in dichloromethane (15 mL) was added m-chloroperbenzoic acid (70%, 888 mg, 3.60 mmol) at room temperature, and the resulting mixture was stirred for 5 min. The reaction mixture was concentrated under reduced pressure, and the residue was purified by basic silica gel column chromatography (ethyl acetate), and recrystallized from dichloromethane/methanol to give the title compound (503 mg, yield 59%) as colorless crystals.

melting point 212-213° C.

$^1$H NMR (CDCl$_3$) δ 2.65 (3H, s), 3.14 (3H, s), 7.70 (1H, dd, J=0.6, 8.7 Hz), 7.73-7.78 (1H, m), 7.97-8.01 (3H, m), 8.10 (1H, dd, J=1.7, 8.7 Hz), 8.18-8.19 (1H, m), 8.46 (1H, dd, J=0.6, 1.7 Hz).

Elemental analysis (for C$_{18}$H$_{14}$N$_2$O$_4$S)
Calculated (%): C, 61.01; H, 3.98; N, 7.90.
Found (%): C, 60.69; H, 4.02; N, 8.02.

EXAMPLE 152

2-methyl-5-[3-[3-(methylsulfinyl)phenyl]-1-benzofuran-5-yl]-1,3,4-oxadiazole

In the column purification in Example 151, an eluate obtained by elution of 2-methyl-5-[3-[3-(methylsulfonyl)phenyl]-1-benzofuran-5-yl]-1,3,4-oxadiazole was recrystallized from hexane/acetone to give the title compound (243 mg, yield 30%) as colorless crystals.

melting point 166-167° C.

$^1$H NMR (CDCl$_3$) δ 2.64 (3H, s), 2.82 (3H, s), 7.63-7.72 (3H, m), 7.84 (1H, td, J=1.7, 7.0 Hz), 7.92-7.93 (1H, m), 7.96 (1H, s), 8.08 (1H, dd, J=1.7, 8.7 Hz), 8.48 (1H, dd, J=0.6, 1.7 Hz).

Elemental analysis (for C$_{18}$H$_{14}$N$_2$O$_3$S)
Calculated (%): C, 63.89; H, 4.17; N, 8.28.
Found (%): C, 63.69; H, 3.94; N, 8.30.

EXAMPLE 153

2-[3-(3-fluoro-4-methoxyphenyl)-1-benzofuran-5-yl]-5-methyl-1,3,4-oxadiazole

In the same manner as in Example 132 and using (3-fluoro-4-methoxyphenyl)boronic acid instead of (4-fluorophenyl)boronic acid, the title compound (yield 80%) was obtained as colorless crystals.

melting point 159-160° C. (recrystallized from hexane/tetrahydrofuran).

$^1$H NMR (CDCl$_3$) δ 2.65 (3H, s), 3.97 (3H, s), 7.07-7.13 (1H, m), 7.35-7.41 (2H, m), 7.65 (1H, dd, J=0.6, 8.7 Hz), 7.81 (1H, s), 8.06 (1H, dd, J=1.7, 8.7 Hz), 8.45 (1H, dd, J=0.6, 1.7 Hz).

Elemental analysis (for C$_{18}$H$_{13}$FN$_2$O$_3$)
Calculated (%): C, 66.66; H, 4.04; N, 8.64.
Found (%): C, 66.74; H, 4.04; N, 8.69.

EXAMPLE 154

2-fluoro-4-[5-(5-methyl-1,3,4-oxadiazol-2-yl)-1-benzofuran-3-yl]benzaldehyde

In the same manner as in Example 132 and using (3-fluoro-4-formylphenyl)boronic acid instead of (4-fluorophenyl)boronic acid, the title compound (yield 71%) was obtained as colorless crystals.
melting point 207-208° C. (recrystallized from tetrahydrofuran).
$^1$H NMR (CDCl$_3$) δ 2.66 (3H, s), 7.50 (1H, dd, J=1.5, 11.1 Hz), 7.58-7.61 (1H, m), 7.70 (1H, dd, J=0.6, 8.7 Hz), 8.00-8.05 (2H, m), 8.12 (1H, dd, J=1.7, 8.7 Hz), 8.51 (1H, dd, J=0.6, 1.7 Hz), 10.42 (1H, d, J=0.4 Hz).
Elemental analysis (for C$_{18}$H$_{13}$FN$_2$O$_3$)
Calculated (%): C, 67.08; H, 3.44; N, 8.69.
Found (%): C, 67.10; H, 3.27; N, 8.72.

EXAMPLE 155

2-fluoro-4-[5-(5-methyl-1,3,4-oxadiazol-2-yl)-1-benzofuran-3-yl]benzoic acid

A suspension of 2-fluoro-4-[5-(5-methyl-1,3,4-oxadiazol-2-yl)-1-benzofuran-3-yl]benzaldehyde (0.693 g, 2.15 mmol) and oxone (registered trade mark) (1.99 g, 3.23 mmol) in N,N-dimethylformamide (25 mL) was stirred overnight at room temperature. The reaction mixture was poured into water, and the precipitate was collected by filtration, dried and recrystallized from tetrahydrofuran to give the title compound (555 mg, yield 76%) as colorless crystals.
melting point 282-283° C.
$^1$H NMR (DMSO-d$_6$) δ 2.62 (3H, s), 7.73 (1H, dd, J=1.3, 3.0 Hz), 7.76 (1H, s), 7.93 (1H, dd, J=0.4, 8.7 Hz), 8.02-8.08 (2H, m), 8.47 (1H, dd, J=0.4, 1.7 Hz), 8.73 (1H, s), 13.34 (1H, brs).
Elemental analysis (for C$_{18}$H$_{11}$FN$_2$O$_4$)
Calculated (%): C, 63.91; H, 3.28; N, 8.28.
Found (%): C, 63.91; H, 3.23; N, 8.26.

EXAMPLE 156

2-methyl-5-(3-phenyl-1-benzofuran-5-yl)-1,3,4-oxadiazole

In the same manner as in Example 132 and using phenylboronic acid instead of (4-fluorophenyl)boronic acid, the title compound (yield 85%) was obtained as colorless crystals.
melting point 117-118° C. (crystallized from hexane/ethyl acetate).
$^1$H NMR (CDCl$_3$) δ 2.64 (3H, s), 7.39-7.45 (1H, m), 7.49-7.55 (2H, m), 7.64-7.68 (3H, m), 7.87 (1H, s), 8.06 (1H, dd, J=1.7, 8.7 Hz), 8.51 (1H, dd, J=0.6, 1.7 Hz).
Elemental analysis (for C$_{17}$H$_{12}$N$_2$O$_2$)
Calculated (%): C, 73.90; H, 4.38; N, 10.14.
Found (%): C, 73.90; H, 4.33; N, 10.23.

EXAMPLE 157

2-[5-(5-methyl-1,3,4-oxadiazol-2-yl)-1-benzofuran-3-yl]pyridine

A solution of 2-(3-bromo-1-benzofuran-5-yl)-5-methyl-1,3,4-oxadiazole (279 mg, 1.00 mmol), 2-(tri-n-butylstannyl)pyridine (0.384 mL, 1.20 mmol) and tetrakis(triphenylphosphine)palladium(0) (34.7 mg, 0.0300 mmol) in tetrahydrofuran (5 mL) was heated under reflux under an argon atmosphere for 85 hr. After cooling, the reaction mixture was concentrated under reduced pressure, and the residue was purified by basic silica gel column chromatography (hexane/tetrahydrofuran=1/1) and recrystallized from hexane/tetrahydrofuran to give the title compound (113 mg, yield 41%) as colorless crystals.
melting point 148-149° C.
$^1$H NMR (CDCl$_3$) δ 2.66 (3H, s), 7.27 (1H, ddd, J=1.3, 4.9, 7.4 Hz), 7.66 (1H, dd, J=0.6, 8.7 Hz), 7.72 (1H, ddd, J=0.9, 1.3, 7.9 Hz), 7.79 (1H, ddd, J=1.9, 7.4, 7.9 Hz), 8.09 (1H, dd, J=1.7, 8.7 Hz), 8.23 (1H, s), 8.76 (1H, ddd, J=0.9, 1.9, 4.9 Hz), 8.98 (1H, dd, J=0.6, 1.7 Hz).
Elemental analysis (for C$_{16}$H$_{11}$N$_3$O$_2$)
Calculated (%): C, 69.31; H, 4.00; N, 15.15.
Found (%): C, 69.40; H, 3.85; N, 15.19.

EXAMPLE 158

3-[5-(5-methyl-1,3,4-oxadiazol-2-yl)-1-benzofuran-3-yl]pyridine

In the same manner as in Example 132 and using (3-pyridine)boronic acid instead of (4-fluorophenyl)boronic acid, the title compound (yield 84%) was obtained as colorless crystals.
melting point 139-140° C. (recrystallized from hexane/ethyl acetate).
$^1$H NMR (CDCl$_3$) δ 2.64 (3H, s), 7.46 (1H, ddd, J=0.8, 4.9, 7.9 Hz), 7.69 (1H, dd, J=0.6, 8.7 Hz), 7.94 (1H, s), 7.99 (1H, ddd, J=1.7, 2.3, 7.9 Hz), 8.11 (1H, dd, J=1.7, 8.7 Hz), 8.46 (1H, dd, J=0.6, 1.7 Hz), 8.67 (1H, dd, J=1.7, 4.9 Hz), 8.94 (1H, dd, J=0.8, 2.3 Hz).
Elemental analysis (for C$_{16}$H$_{11}$N$_3$O$_2$)
Calculated (%): C, 69.31; H, 4.00; N, 15.15.
Found (%): C, 69.17; H, 4.00; N, 15.19.

EXAMPLE 159

4-[5-(5-methyl-1,3,4-oxadiazol-2-yl)-1-benzofuran-3-yl]pyridine

In the same manner as in Example 132 and using (4-pyridine)boronic acid instead of (4-fluorophenyl)boronic acid, the title compound (yield 42%) was obtained as colorless crystals.
melting point 166-167° C. (recrystallized from hexane/tetrahydrofuran).
$^1$H NMR (CDCl$_3$) δ 2.66 (3H, s), 7.60 (2H, dd, J=1.5, 4.5 Hz), 7.70 (1H, dd, J=0.6, 8.7 Hz), 8.03 (1H, s), 8.11 (1H, dd, J=1.7, 8.7 Hz), 8.54 (1H, dd, J=0.6, 1.7 Hz), 8.75 (2H, d, J=5.1 Hz).
Elemental analysis (for C$_{16}$H$_{11}$N$_3$O$_2$)
Calculated (%): C, 69.31; H, 4.00; N, 15.15.
Found (%): C, 69.28; H, 3.90; N, 15.14.

EXAMPLE 160 ethyl 5-(5-methyl-1,3,4-oxadiazol-2-yl)-1-benzofuran-3-carboxylate

A mixture of 2-(3-bromo-1-benzofuran-5-yl)-5-methyl-1,3,4-oxadiazole (837 mg, 3.00 mmol), [1,1'-bis(diphenylphosphino)ferrocene]palladium(II) chloride dichloromethane complex (245 mg, 0.300 mmol), triethylamine (0.836 mL, 6.00 mmol), dimethyl sulfoxide (6 mL) and ethanol (3 mL) was stirred under a carbon monoxide atmosphere at 100° C. for 10 hr. After cooling, the reaction mixture was diluted with ethyl acetate, and insoluble material was removed by filtration. The filtrate was washed with 1M hydrochloric acid, water and saturated brine, dried over anhydrous magnesium sulfate and concentrated under reduced pressure. The residue was purified by silica gel column chromatography (ethyl acetate), and recrystallized from ethyl acetate to give the title compound (379 mg, yield 46%) as colorless crystals.

melting point 135-136° C.

$^1$H NMR (CDCl$_3$) δ 1.45 (3H, t, J=7.2 Hz), 2.65 (3H, s), 4.46 (2H, q, J=7.2 Hz), 7.65 (1H, dd, J=0.6, 8.7 Hz), 8.13 (1H, dd, J=1.9, 8.7 Hz), 8.33 (1H, s), 8.71 (1H, dd, J=0.6, 1.9 Hz).

Elemental analysis (for C$_{14}$H$_{12}$N$_2$O$_4$)

Calculated (%): C, 61.76; H, 4.44; N, 10.29.

Found (%): C, 61.80; H, 4.44; N, 10.41.

EXAMPLE 161

5-(5-methyl-1,3,4-oxadiazol-2-yl)-1-benzofuran-3-carboxylic acid

In the same manner as in Example 134 and using ethyl 5-(5-methyl-1,3,4-oxadiazol-2-yl)-1-benzofuran-3-carboxylate instead of methyl 4-[5-(5-methyl-1,3,4-oxadiazol-2-yl)-1-benzofuran-3-yl]benzoate and ethanol instead of methanol, the title compound (yield 32%) was obtained as pale-yellow crystals.

melting point 252-253° C. (recrystallized from methanol).

$^1$H NMR (DMSO-d$_6$) δ 2.61 (3H, s), 7.92 (1H, dd, J=0.6, 8.7 Hz), 8.04 (1H, dd, J=1.9, 8.7 Hz), 8.56 (1H, dd, J=0.6, 1.9 Hz), 8.83 (1H, s), 13.29 (1H, brs).

Elemental analysis (for C$_{12}$H$_8$N$_2$O$_4$·0.25H$_2$O)

Calculated (%): C, 57.95; H, 3.44; N, 11.26.

Found (%): C, 57.91; H, 3.75; N, 11.33.

EXAMPLE 162

4-[[5-(5-methyl-1,3,4-oxadiazol-2-yl)-1-benzofuran-3-yl]carbonyl]morpholine

To a suspension of 5-(5-methyl-1,3,4-oxadiazol-2-yl)-1-benzofuran-3-carboxylic acid (97.7 mg, 0.400 mmol) and N,N-dimethylformamide (1 drop) in tetrahydrofuran (5 mL) was added oxalyl chloride (0.0698 mL, 0.800 mmol) at room temperature, and the resulting mixture was stirred for 15 min. The reaction mixture was added dropwise to a mixture of morpholine (0.105 mL, 1.20 mmol) and saturated aqueous sodium hydrogen carbonate solution (5 mL) at room temperature, and the resulting mixture was stirred for 1 hr. The reaction mixture was diluted with ethyl acetate, washed with saturated brine, dried over anhydrous magnesium sulfate and concentrated under reduced pressure. The residue was purified by basic silica gel column chromatography (ethyl acetate), and recrystallized from methanol/water to give the title compound (33.8 mg, yield 27%) as colorless crystals.

melting point 168-169° C.

$^1$H NMR (CDCl$_3$) δ 2.64 (3H, s), 3.77 (8H, brs), 7.65 (1H, dd, J=0.6, 8.7 Hz), 7.94 (1H, s), 8.11 (1H, dd, J=1.7, 8.7 Hz), 8.37 (1H, dd, J=0.6, 1.7 Hz).

Elemental analysis (for C$_{16}$H$_{15}$N$_3$O$_4$·0.25H$_2$O)

Calculated (%): C, 60.47; H, 4.92; N, 13.22.

Found (%): C, 60.49; H, 4.92; N, 13.37.

EXAMPLE 163

N-(3-amino-3-oxopropyl)-5-(5-methyl-1,3,4-oxadiazol-2-yl)-1-benzofuran-3-carboxamide In the same manner as in Example 162 and using β-alaninamide hydrochloride instead of morpholine, the title compound (yield 46%) was obtained as colorless crystals.

melting point 242-243° C. (recrystallized from methanol).

$^1$H NMR (DMSO-d$_6$) δ 2.39 (2H, t, J=7.0 Hz), 2.61 (3H, s), 3.47 (2H, dt, J=5.7, 7.0 Hz), 6.86 (1H, brs), 7.39 (1H, brs), 7.87 (1H, dd, J=0.6, 8.7 Hz), 8.01 (1H, dd, J=1.7, 8.7 Hz), 8.57 (1H, t, J=5.7 Hz), 8.68 (1H, s), 8.70 (1H, dd, J=0.6, 1.7 Hz).

Elemental analysis (for C$_{15}$H$_{14}$N$_4$O$_4$·H$_2$O)

Calculated (%): C, 54.21; H, 4.85; N, 16.86.

Found (%): C, 54.99; H, 4.76; N, 17.21.

EXAMPLE 164

5-[3-(4-methoxyphenyl)-1-benzofuran-5-yl]-1,3,4-oxadiazole-2-thiol

In the same manner as in Example 34 and using 3-(4-methoxyphenyl)-1-benzofuran-5-carbohydrazide instead of 2,3-dihydro-1-benzofuran-5-carbohydrazide, the title compound (yield 87%) was obtained as pale-yellow crystals.

melting point 204-205° C. (recrystallized from ethyl acetate).

$^1$H NMR (CDCl$_3$) δ 3.89 (3H, s), 7.03-7.08 (2H, m), 7.53-7.58 (2H, m), 7.65 (1H, dd, J=0.8, 8.7 Hz), 7.82 (1H, s), 8.95 (1H, dd, J=1.7, 8.7 Hz), 8.37 (1H, dd, J=0.4, 1.7 Hz), 10.63 (1H, brs).

Elemental analysis (for C$_{17}$H$_{12}$N$_2$O$_3$S)

Calculated (%): C, 62.95; H, 3.73; N, 8.64.

Found (%): C, 62.90; H, 3.82; N, 8.52.

EXAMPLE 165

2-[3-(4-methoxyphenyl)-1-benzofuran-5-yl]-5-(methylthio)-1,3,4-oxadiazole

In the same manner as in Example 47 and using 3-(4-methoxyphenyl)-1-benzofuran-5-carbohydrazide instead of 2,3-dihydro-1-benzofuran-5-carbohydrazide and iodomethane instead of 3-fluoro-4-methoxybenzyl chloride, the title compound (yield 73%) was obtained as colorless crystals.

melting point 156-157° C. (recrystallized from ethyl acetate).

$^1$H NMR (CDCl$_3$) δ 2.79 (3H, s), 3.89 (3H, s), 7.03-7.08 (2H, m), 7.56-7.61 (2H, m), 7.63 (1H, d, J=8.7 Hz), 7.80 (1H, s), 8.03 (1H, dd, J=1.9, 8.7 Hz), 8.43 (1H, d, J=1.9 Hz).

Elemental analysis (for C$_{18}$H$_{14}$N$_2$O$_3$S)

Calculated (%): C, 63.89; H, 4.17; N, 8.28.

Found (%): C, 63.73; H, 4.12; N, 8.20.

EXAMPLE 166

2-[(3-fluorobenzyl)thio]-5-[3-(4-methoxyphenyl)-1-benzofuran-5-yl]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2- thiol and 3-fluorobenzyl bromide instead of 3-(trifluoromethyl)benzyl chloride, the title compound (yield 85%) was obtained as colorless crystals.

melting point 146-147° C. (crystallized from hexane/acetone).

$^1$H NMR (CDCl$_3$) δ 3.88 (3H, s), 4.51 (2H, s), 6.96-7.08 (3H, m), 7.18-7.34 (3H, m), 7.55-7.60 (2H, m), 7.63 (1H, dd, J=0.6, 8.7 Hz), 7.80 (1H, s), 8.00 (1H, dd, J=1.7, 8.7 Hz), 8.42 (1H, dd, J=0.6, 1.7 Hz).

Elemental analysis (for C$_{24}$H$_{17}$FN$_2$O$_3$S)
Calculated (%): C, 66.65; H, 3.96; N, 6.48.
Found (%): C, 66.65; H, 3.93; N, 6.45.

EXAMPLE 167

2-[(3-chlorobenzyl)thio]-5-[3-(4-methoxyphenyl)-1-benzofuran-5-yl]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 3-chlorobenzyl chloride instead of 3-(trifluoromethyl)benzyl chloride, the title compound (yield 88%) was obtained as colorless crystals.

melting point 155-156° C. (recrystallized from hexane/tetrahydrofuran).

$^1$H NMR (CDCl$_3$) δ 3.88 (3H, s), 4.49 (2H, s), 7.03-7.07 (2H, m), 7.26-7.29 (2H, m), 7.34-7.39 (1H, m), 7.47-7.49 (1H, m), 7.55-7.60 (2H, m), 7.63 (1H, dd, J=0.6, 8.7 Hz), 7.80 (1H, s), 8.00 (1H, dd, J=1.7, 8.7 Hz), 8.42 (1H, dd, J=0.6, 1.7 Hz).

Elemental analysis (for C$_{24}$H$_{17}$ClN$_2$O$_3$S)
Calculated (%): C, 64.21; H, 3.82; N, 6.24.
Found (%): C, 64.28; H, 3.88; N, 6.18.

EXAMPLE 168

2-[3-(4-methoxyphenyl)-1-benzofuran-5-yl]-5-[[3-(trifluoromethyl)benzyl]thio]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol, the title compound (yield 94%) was obtained as colorless crystals.

melting point 119-120° C. (recrystallized from hexane/ethyl acetate).

$^1$H NMR (CDCl$_3$) δ 3.88 (3H, s), 4.56 (2H, s), 7.02-7.07 (2H, m), 7.46 (1H, t, J=7.7 Hz), 7.54-7.59 (3H, m), 7.63 (1H, dd, J=0.6, 8.7 Hz), 7.69-7.74 (2H, m), 7.80 (1H, s), 7.99 (1H, dd, J=1.7, 8.7 Hz), 8.42 (1H, dd, J=0.6, 1.7 Hz).

Elemental analysis (for C$_{25}$H$_{17}$F$_3$N$_2$O$_3$S)
Calculated (%): C, 62.23; H, 3.55; N, 5.81.
Found (%): C, 62.23; H, 3.66; N, 5.77.

EXAMPLE 169

3-[[[5-[3-(4-methoxyphenyl)-1-benzofuran-5-yl]-1,3,4-oxadiazol-2-yl]thio]methyl]benzonitrile In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 3-(bromomethyl)benzonitrile instead of 3-(trifluoromethyl)benzyl chloride, the title compound (yield 87%) was obtained as colorless crystals.

melting point 145-146° C. (recrystallized from methanol).

$^1$H NMR (CDCl$_3$) δ 3.88 (3H, s), 4.52 (2H, s), 7.03-7.07 (2H, m), 7.45 (1H, dt, J=0.4, 7.7 Hz), 7.54-7.60 (3H, m), 7.63 (1H, dd, J=0.6, 8.7 Hz), 7.74-7.81 (3H, m), 7.99 (1H, dd, J=1.7, 8.7 Hz), 8.41 (1H, dd, J=0.6, 1.7 Hz).

Elemental analysis (for C$_{25}$H$_{17}$N$_3$O$_3$S)
Calculated (%): C, 68.32; H, 3.90; N, 9.56.
Found (%): C, 68.36; H, 3.87; N, 9.56.

EXAMPLE 170

2-[3-(4-methoxyphenyl)-1-benzofuran-5-yl]-5-[(3-methylbenzyl)thio]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 3-methylbenzyl bromide instead of 3-(trifluoromethyl)benzyl chloride, the title compound (yield 80%) was obtained as colorless crystals.

melting point 123-124° C. (recrystallized from hexane/ethyl acetate).

$^1$H NMR (CDCl$_3$) δ 2.34 (3H, s), 3.88 (3H, s), 4.50 (2H, s), 7.03-7.07 (2H, m), 7.09-7.12 (1H, m), 7.20-7.28 (3H, m), 7.55-7.60 (2H, m), 7.63 (1H, dd, J=0.6, 8.7 Hz), 7.80 (1H, s), 8.01 (1H, dd, J=1.7, 8.7 Hz), 8.42 (1H, dd, J=0.6, 1.7 Hz).

Elemental analysis (for C$_{25}$H$_{20}$N$_2$O$_3$S)
Calculated (%): C, 70.07; H, 4.70; N, 6.54.
Found (%): C, 69.98; H, 4.53; N, 6.46.

EXAMPLE 171

2-[(3-methoxybenzyl)thio]-5-[3-(4-methoxyphenyl)-1-benzofuran-5-yl]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 3-methoxybenzyl chloride instead of 3-(trifluoromethyl)benzyl chloride, the title compound (yield 87%) was obtained as colorless crystals.

melting point 118-119° C. (recrystallized from hexane/ethyl acetate).

$^1$H NMR (CDCl$_3$) δ 3.80 (3H, s), 3.88 (3H, s), 4.51 (2H, s), 6.84 (1H, ddd, J=0.9, 2.5, 8.3 Hz), 7.01-7.08 (4H, m), 7.25 (1H, dd, J=7.4, 8.3 Hz), 7.55-7.60 (2H, m), 7.63 (1H, dd, J=0.6, 8.7 Hz), 7.80 (1H, s), 8.01 (1H, dd, J=1.9, 8.7 Hz), 8.42 (1H, dd, J=0.6, 1.9 Hz).

Elemental analysis (for C$_{25}$H$_{20}$N$_2$O$_4$S)
Calculated (%): C, 67.55; H, 4.54: N, 6.30.
Found (%): C, 67.38; H, 4.54: N, 6.08.

EXAMPLE 172

2-[(4-methoxybenzyl)thio]-5-[3-(4-methoxyphenyl)-1-benzofuran-5-yl]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 4-methoxybenzyl chloride instead of 3-(trifluoromethyl)benzyl chloride, the title compound (yield 80%) was obtained as colorless crystals.

melting point 162-163° C. (recrystallized from methanol).
$^1$H NMR (CDCl$_3$) δ 3.78 (3H, s), 3.88 (3H, s), 4.50 (2H, s), 6.84-6.89 (2H, m), 7.03-7.07 (2H, m), 7.37-7.42 (2H, m), 7.55-7.60 (2H, m), 7.63 (1H, dd, J=0.6, 8.7 Hz), 7.80 (1H, s), 8.01 (1H, dd, J=1.9, 8.7 Hz), 8.42 (1H, dd, J=0.6, 1.9 Hz).

Elemental analysis (for C$_{25}$H$_{20}$N$_2$O$_4$S)
Calculated (%): C, 67.55; H, 4.54: N, 6.30.
Found (%): C, 67.44; H, 4.55: N, 6.19.

EXAMPLE 173

2-[(3-fluoro-4-methoxybenzyl)thio]-5-[3-(4-methoxyphenyl)-1-benzofuran-5-yl]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 3-fluoro-4-methoxybenzyl chloride instead of 3-(trifluoromethyl)benzyl chloride, the title compound (yield 86%) was obtained as colorless crystals.

melting point 162-163° C. (recrystallized from hexane/tetrahydrofuran). $^1$H NMR (CDCl$_3$) δ 3.86 (3H, s), 3.88 (3H, s), 4.46 (2H, s), 6.87-6.92 (1H, m), 7.03-7.08 (2H, m), 7.17-7.24 (2H, m), 7.55-7.60 (2H, m), 7.63 (1H, dd, J=0.6, 8.7 Hz), 7.80 (1H, s), 8.01 (1H, dd, J=1.7, 8.7 Hz), 8.42 (1H, dd, J=0.6, 1.7 Hz).

Elemental analysis (for $C_{25}H_{19}FN_2O_4S$)
Calculated (%): C, 64.92; H, 4.14; N, 6.06.
Found (%): C, 64.96; H, 4.15; N, 5.98.

EXAMPLE 174

2-[3-(4-methoxyphenyl)-1-benzofuran-5-yl]-5-[[4-methoxy-3-(trifluoromethyl)benzyl]thio]-1,3,4-oxadiazole In the same manner as in Example 1 and using 5-[3-(4-methoxyphenyl)-1-benzofuran-5-yl]-1,3,4-oxadiazole-2-thiol instead of 5-(benzothiazol-6-yl)-1,3,4-oxadiazole-2-thiol and 4-methoxy-3-(trifluoromethyl)benzyl bromide instead of 3-(trifluoromethyl)benzyl chloride, the title compound (yield 91%) was obtained as colorless crystals.

melting point 162-163° C. (recrystallized from hexane/tetrahydrofuran).
$^1$H NMR (CDCl$_3$) δ 3.88 (6H, s), 4.50 (2H, s), 6.96 (1H, d, J=8.1 Hz), 7.02-7.07 (2H, m), 7.55-7.60 (2H, m), 7.61-7.66 (3H, m), 7.80 (1H, s), 8.00 (1H, dd, J=1.7, 8.7 Hz), 8.43 (1H, dd, J=0.6, 1.7 Hz).

Elemental analysis (for $C_{26}H_{19}F_3N_2O_4S$)
Calculated (%): C, 60.93; H, 3.74; N, 5.47.
Found (%): C, 60.95; H, 3.95; N, 5.36.

EXAMPLE 175

1-(4-methoxyphenyl)-6-[5-(methylthio)-1,3,4-oxadiazol-2-yl]-1H-benzimidazole

In the same manner as in Example 47 and using 1-(4-methoxyphenyl)-1H-benzimidazole-6-carbohydrazide instead of 2,3-dihydro-1-benzofuran-5-carbohydrazide and iodomethane instead of 3-fluoro-4-methoxybenzyl chloride, the title compound (yield 71%) was obtained as colorless crystals.

melting point 187-188° C. (recrystallized from ethyl acetate).
$^1$H NMR (CDCl$_3$) δ 2.78 (3H, s), 3.92 (3H, s), 7.09-7.14 (2H, m), 7.41-7.46 (2H, m), 7.95 (1H, d, J=8.7 Hz), 7.99 (1H, dd, J=1.5, 8.7 Hz), 8.10 (1H, s), 8.16 (1H, s).

Elemental analysis (for $C_{17}H_{14}N_4O_2S$)
Calculated (%): C, 60.34; H, 4.17; N, 16.56.
Found (%): C, 60.28; H, 4.15; N, 16.48.

EXAMPLE 176

1-(4-methoxyphenyl)-6-[5-[[4-methoxy-3-(trifluoromethyl)benzyl]thio]-1,3,4-oxadiazol-2-yl]-1H-benzimidazole In the same manner as in Example 1 and using 5-[1-(4-methoxyphenyl)-1H-benzimidazol-6-yl]-1,3,4-oxadiazole-2-thiol instead of 5-(benzothiazol-6-yl)-1,3,4-oxadiazole-2-thiol and 4-methoxy-3-(trifluoromethyl)benzyl bromide instead of 3-(trifluoromethyl)benzyl chloride, the title compound (yield 34%) was obtained as colorless crystals.

melting point 163-164° C. (recrystallized from hexane/ethyl acetate).
$^1$H NMR (CDCl$_3$) δ 3.88 (3H, s), 3.91 (3H, s), 4.49 (2H, s), 6.95 (1H, d, J=8.3 Hz), 7.11 (2H, d, J=9.0 Hz), 7.43 (2H, d, J=9.0 Hz), 7.59-7.67 (2H, m), 7.95 (2H, d, J=1.0 Hz), 8.09 (1H, t, J=1.0 Hz), 8.16 (1H, s).

Elemental analysis (for $C_{25}H_{19}F_3N_4O_3S$)
Calculated (%): C, 58.59; H, 3.74; N, 10.93.
Found (%): C, 58.38; H, 3.87; N, 10.69.

EXAMPLE 177

6-[5-[(3-fluorobenzyl)thio]-1,3,4-oxadiazol-2-yl]-1-(4-methoxyphenyl)-1H-benzimidazole In the same manner as in Example 1 and using 5-[1-(4-methoxyphenyl)-1H-benzimidazol-6-yl]-1,3,4-oxadiazole-2-thiol instead of 5-(benzothiazol-6-yl)-1,3,4-oxadiazole-2-thiol and 3-fluorobenzyl chloride instead of 3-(trifluoromethyl)benzyl chloride, the title compound (yield 26%) was obtained as colorless crystals.

melting point 155-156° C. (recrystallized from hexane/ethyl acetate).
$^1$H NMR (CDCl$_3$) δ 3.92 (3H, s), 4.50 (2H, s), 6.94-7.03 (1H, m), 7.11 (2H, d, J=9.0 Hz), 7.16-7.34 (4H, m), 7.43 (2H, d, J=9.0 Hz), 7.95 (1H, s), 8.08 (1H, s), 8.16 (1H, s).

Elemental analysis (for $C_{23}H_{17}FN_4O_2S$)
Calculated (%): C, 63.88; H, 3.96; N, 12.96.
Found (%): C, 63.69; H, 4.03; N, 12.67.

EXAMPLE 178

1-(4-methoxyphenyl)-6-[5-[[3-(trifluoromethyl)benzyl]thio]-1,3,4-oxadiazol-2-yl]-1H-benzimidazole In the same manner as in Example 1 and using 5-[1-(4-methoxyphenyl)-1H-benzimidazol-6-yl]-1,3,4-oxadiazole-2-thiol instead of 5-(benzothiazol-6-yl)-1,3,4-oxadiazole-2-thiol, the title compound (yield 61%) was obtained as colorless crystals.

melting point 174-175° C. (recrystallized from hexane/ethyl acetate).
$^1$H NMR (CDCl$_3$) δ 3.92 (3H, s), 4.55 (2H, s), 7.11 (2H, d, J=8.9 Hz), 7.40-7.49 (3H, m), 7.52-7.58 (1H, m), 7.66-7.74 (2H, m), 7.95 (2H, d, J=0.9 Hz), 8.08 (1H, t, J=0.9 Hz), 8.16 (1H, s).

Elemental analysis (for $C_{24}H_{17}F_3N_4O_2S$)
Calculated (%): C, 59.75; H, 3.55; N, 11.61.
Found (%): C, 59.73; H, 3.52; N, 11.54.

EXAMPLE 179

3-[[[5-[1-(4-methoxyphenyl)-1H-benzimidazol-6-yl]-1,3,4-oxadiazol-2-yl]thio]methyl]benzonitrile In the same manner as in Example 1 and using 5-[1-(4-methoxyphenyl)-1H-benzimidazol-6-yl]-1,3,4-oxadiazole-2-thiol instead of 5-(benzothiazol-6-yl)-1,3,4-oxadiazole-2-thiol and 3-(bromomethyl)benzonitrile instead of 3-(trifluoromethyl)benzyl chloride, the title compound (yield 24%) was obtained as colorless crystals.

melting point 157-158° C. (recrystallized from hexane/ethyl acetate).

$^1$H NMR (CDCl$_3$) δ 3.92 (3H, s), 4.51 (2H, s), 7.11 (2H, d, J=8.9 Hz), 7.39-7.48 (3H, m), 7.55-7.61 (1H, m), 7.71-7.80 (2H, m), 7.95 (2H, s), 8.05-8.09 (1H, m), 8.16 (1H, s).

Elemental analysis (for C$_{24}$H$_{17}$N$_5$O$_2$S)

Calculated (%): C, 65.59; H, 3.90; N, 15.94.

Found (%): C, 65.34; H, 3.66; N, 16.04.

EXAMPLE 180

3-[[[5-[1-(4-methoxyphenyl)-1H-benzimidazol-6-yl]-1,3,4-oxadiazol-2-yl]thio]methyl]benzoic acid In the same manner as in Example 1 and using 5-[1-(4-methoxyphenyl)-1H-benzimidazol-6-yl]-1,3,4-oxadiazole-2-thiol instead of 5-(benzothiazol-6-yl)-1,3,4-oxadiazole-2-thiol and 3-(chloromethyl)benzoic acid instead of 3-(trifluoromethyl)benzyl chloride, the title compound (yield 31%) was obtained as colorless crystals.

$^1$H NMR (DMSO-d$_6$) δ 3.87 (3H, s), 4.61 (2H, s), 7.22 (2H, d, J=8.9 Hz), 7.33 (1H, t, J=7.5 Hz), 7.59 (1H, d, J=7.5 Hz), 7.65 (2H, d, J=8.9 Hz), 7.82 (1H, d, J=7.5 Hz), 7.88-7.97 (3H, m), 8.06 (1H, s), 8.67 (1H, s).

EXAMPLE 181

6-[5-[2-(3-fluorophenyl)ethyl]-1,3,4-oxadiazol-2-yl]-1-(4-methoxyphenyl)-1H-benzimidazole A mixture of 4-[5-[2-(3-fluorophenyl)ethyl]-1,3,4-oxadiazol-2-yl]-N$^2$-(4-methoxyphenyl)benzene-1,2-diamine (0.20 g, 0.49 mmol) and formic acid (1.4 mL) was stirred at 100° C. overnight. After cooling, saturated aqueous sodium hydrogen carbonate solution was added to the reaction mixture, and the mixture was extracted with ethyl acetate. The organic layer was washed with saturated brine, dried over anhydrous magnesium sulfate and concentrated under reduced pressure. The residue was purified by basic silica gel column chromatography (hexane/ethyl acetate=1/1) to give the title compound (0.10 g, yield 49%) as colorless crystals.

melting point 145-147° C.

$^1$H NMR (DMSO-d$_6$) δ 3.12 (2H, t, J=7.4 Hz), 3.28 (2H, t, J=7.4 Hz), 3.88 (3H, s), 6.95-7.04 (1H, m), 7.09-7.20 (2H, m), 7.23 (2H, d, J=9.0 Hz), 7.26-7.35 (1H, m), 7.64 (2H, d, J=9.0 Hz), 7.88-7.99 (3H, m), 8.67 (1H, s).

Elemental analysis (for C$_{24}$H$_{19}$FN$_4$O$_2$)

Calculated (%): C, 69.55; H, 4.62; N, 13.52.

Found (%): C, 69.41; H, 4.61; N, 13.54.

EXAMPLE 182

6-[5-[2-(3-fluorophenyl)ethyl]-1,3,4-oxadiazol-2-yl]-1-(4-methoxyphenyl)-1H-1,2,3-benzotriazole To a mixture of 4-[5-[2-(3-fluorophenyl)ethyl]-1,3,4-oxadiazol-2-yl]-N$^2$-(4-methoxyphenyl)benzene-1,2-diamine (0.20 g, 0.49 mmol), 6 M hydrochloric acid (2.5 mL) and acetic acid (2.5 mL) was added an aqueous solution (0.25 mL) of sodium nitrite (41 mg, 0.59 mmol) at 0° C., and the obtained mixture was stirred at 0° C. for 30 min and at room temperature overnight. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=1/1) and recrystallized from hexane/ethyl acetate to give the title compound (51.2 mg, yield 25%) as colorless crystals.

melting point 125-126° C.

$^1$H NMR (DMSO-d$_6$) δ 3.14 (2H, t, J=7.4 Hz), 3.32 (2H, t, J=7.4 Hz), 3.91 (3H, s), 6.96-7.04 (1H, m), 7.11-7.22 (2H, m), 7.25-7.36 (1H, m), 7.29 (2H, d, J=9.0 Hz), 7.82 (2H, d, J=9.0 Hz), 8.09 (1H, dd, J=1.4, 8.8 Hz), 8.15-8.21 (1H, m), 8.34-8.42 (1H, m).

Elemental analysis (for C$_{23}$H$_{18}$FN$_5$O$_2$)

Calculated (%): C, 66.50; H, 4.37; N, 16.86.

Found (%): C, 66.20; H, 4.41; N, 16.84.

EXAMPLE 183

6-[5-[2-(3-fluorophenyl)ethyl]-1,3,4-oxadiazol-2-yl]-1-(4-methoxyphenyl)-1H-benzimidazol-2-amine A solution of 4-[5-[2-(3-fluorophenyl)ethyl]-1,3,4-oxadiazol-2-yl]-N$^2$-(4-methoxyphenyl)benzene-1,2-diamine (0.20 g, 0.49 mmol) and cyanogen bromide (0.11 g, 1.03 mmol) in ethanol (5 mL) was stirred at 60° C. for 4 hr. After cooling, saturated aqueous sodium hydrogen carbonate solution was added to the reaction mixture, and the mixture was extracted with ethyl acetate. The organic layer was washed with saturated brine, dried over anhydrous magnesium sulfate and concentrated under reduced pressure. The residue was purified by basic silica gel column chromatography (hexane/ethyl acetate=1/2-1/3) to give the title compound (0.13 g, yield 62%) as colorless crystals.

melting point 241-242° C.

$^1$H NMR (DMSO-d$_6$) δ 3.03-3.11 (2H, m), 3.17-3.25 (2H, m), 3.87 (3H, s), 6.64 (2H, brs), 6.94-7.02 (1H, m), 7.07-7.18 (3H, m), 7.20 (2H, d, J=9.0 Hz), 7.24-7.32 (1H, m), 7.33 (1H, d, J=8.1 Hz), 7.43 (2H, d, J=9.0 Hz), 7.63 (1H, dd, J=1.7, 8.3 Hz).

Elemental analysis (for C$_{24}$H$_{20}$FN$_5$O$_2$)

Calculated (%): C, 67.12; H, 4.69; N, 16.31.

Found (%): C, 67.04; H, 4.68; N, 16.33.

EXAMPLE 184

1-(4-methoxyphenyl)-6-[5-[2-[3-(trifluoromethyl)phenyl]ethyl]-1,3,4-oxadiazol-2-yl]-1H-benzimidazole In the same manner as in Example 14 and using 1-(4-methoxyphenyl)-1H-benzimidazole-6-carbohydrazide instead of 1H-benzotriazole-5-carbohydrazide and 3-[3-(trifluoromethyl)phenyl]propionic acid instead of 3-(3-cyanophenyl)propionic acid, the title compound (yield 50%) was obtained as colorless crystals.

melting point 159-160° C. (recrystallized from hexane/ethyl acetate).

$^1$H NMR (CDCl$_3$) δ 3.26 (4H, s), 3.92 (3H, s), 7.12 (2H, d, J=8.9 Hz), 7.40-7.55 (6H, m), 7.93-7.97 (2H, m), 8.10-8.13 (1H, m), 8.16 (1H, s).

Elemental analysis (for C$_{25}$H$_{19}$F$_3$N$_4$O$_2$)

Calculated (%): C, 64.65; H, 4.12; N, 12.06.

Found (%): C, 64.68; H, 4.12; N, 12.12.

EXAMPLE 185

3-[2-[5-[1-(4-methoxyphenyl)-1H-benzimidazol-6-yl]-1,3,4-oxadiazol-2-yl]ethyl]benzonitrile In the same manner as in Example 14 and using 1-(4-methoxyphenyl)-1H-benzimidazole-6-carbohydrazide instead of 1H-benzotriazole-5-carbohydrazide, the title compound (yield 29%) was obtained as colorless crystals.

melting point 125-127° C. (recrystallized from hexane/ethyl acetate).

$^1$H NMR (CDCl$_3$) δ 3.25 (4H, s), 3.92 (3H, s), 7.12 (2H, d, J=8.9 Hz), 7.37-7.47 (3H, m), 7.48-7.55 (2H, m), 7.57 (1H, brs), 7.96 (2H, brs), 8.11 (1H, brs), 8.17 (1H, s).

Elemental analysis (for C$_{25}$H$_{19}$N$_5$O$_2$.0.2H$_2$O)
Calculated (%): C, 70.64; H, 4.60; N, 16.48.
Found (%): C, 70.64; H, 4.57; N, 16.49.

EXAMPLE 186

N-(3-fluorobenzyl)-5-[1-(4-methoxyphenyl)-1H-benzimidazol-6-yl]-1,3,4-oxadiazol-2-amine In the same manner as in Example 109 and using N-(3-fluorobenzyl)-2-[[1-(4-methoxyphenyl)-1H-benzimidazol-6-yl]carbonyl]hydrazinecarboxamide instead of 2-(2,3-dihydro-1-benzofuran-5-ylcarbonyl)-N-(3-fluorobenzyl)hydrazinecarboxamide, the title compound (yield 9%) was obtained as colorless crystals.

melting point 164-166° C. (recrystallized from hexane/ethyl acetate).

$^1$H NMR (DMSO-d$_6$) δ 3.91 (3H, s), 4.62 (2H, d, J=5.7 Hz), 5.07-5.16 (1H, m), 6.96-7.05 (1H, m), 7.09 (2H, d, J=9.0 Hz), 7.06-7.21 (2H, m), 7.28-7.38 (1H, m), 7.42 (2H, d, J=9.0 Hz), 7.85 (1H, dd, 1.5, 8.5 Hz), 7.89-7.93 (1H, m), 8.00-8.02 (1H, m), 8.13 (1H, s).

EXAMPLE 187

1-methyl-6-[5-[[3-(trifluoromethyl)benzyl]thio]-1,3,4-oxadiazol-2-yl]-1H-benzimidazole A solution (5 mL) of 1-methyl-1H-benzimidazole-6-carbohydrazide (0.20 g, 1.05 mmol), triethylamine (0.18 mL, 1.26 mmol) and carbon disulfide (0.16 mL, 2.63 mmol) in ethanol was heated under reflux overnight. The reaction mixture was cooled to 0° C., potassium hydroxide (58.9 mg, 1.05 mmol) and 3-(trifluoromethyl)benzyl chloride were added, and the resulting mixture was stirred overnight at room temperature. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=1/3) to give the title compound (49.9 mg, yield 12%) as colorless crystals.

melting point 126-127° C.

$^1$H NMR (CDCl$_3$) δ 3.92 (3H, s), 4.57 (2H, s), 7.44-7.51 (1H, m), 7.54-7.60 (1H, m), 7.68-7.77 (2H, m), 7.85-7.93 (2H, m), 7.99 (1H, brs), 8.09 (1H, brs).

Elemental analysis (for C$_{18}$H$_{13}$F$_3$N$_4$OS)
Calculated (%): C, 55.38; H, 3.86; N, 14.35.
Found (%): C, 55.18; H, 3.45; N, 14.11.

EXAMPLE 188

6-[5-[2-(3-fluorophenyl)ethyl]-1,3,4-oxadiazol-2-yl]-1-methyl-1H-benzimidazole

In the same manner as in Example 14 and using 1-methyl-1H-benzimidazole-6-carbohydrazide instead of 1H-benzotriazole-5-carbohydrazide and 3-(3-fluorophenyl)propionic acid instead of 3-(3-cyanophenyl)propionic acid, the title compound (yield 66%) was obtained as colorless crystals.

melting point 145-146° C. (recrystallized from hexane/ethyl acetate).

$^1$H NMR (CDCl$_3$) δ 3.16-3.33 (4H, m), 3.93 (3H; s), 6.89-7.07 (3H, m), 7.23-7.33 (1H, m), 7.86-7.90 (1H, m), 7.90-7.94 (1H, m), 7.99 (1H, s), 8.12-8.14 (1H, m).

Elemental analysis (for C$_{18}$H$_{15}$FN$_4$O)
Calculated (%): C, 67.07; H, 4.69; N, 17.38
Found (%): C, 67.04; H, 4.50; N, 17.42.

EXAMPLE 189

1-[4-(methylsulfinyl)phenyl]-6-(1,3,4-oxadiazol-2-yl)-1H-benzimidazole

A solution of acetic acid (57 μl, 1.00 mmol) and N,N'-carbonyldiimidazole (195 mg, 1.20 mmol) in tetrahydrofuran (20 mL) was stirred at room temperature for 1 hr. To this reaction mixture were added 1-[4-(methylsulfinyl)phenyl]-1H-benzimidazole-6-carbohydrazide (314 mg, 1.00 mmol) and N,N-dimethylformamide (5 mL), and the resulting mixture was stirred overnight. To this reaction mixture was added a solution of p-toluenesulfonyl chloride (381 mg, 2.00 mmol) in pyridine (5 mL), and the resulting mixture was stirred at 80° C. for 24 hr. After cooling, the reaction mixture was diluted with chloroform, washed with 1M hydrochloric acid, saturated aqueous sodium hydrogen carbonate solution and saturated brine, dried over anhydrous magnesium sulfate and concentrated under reduced pressure. The residue was purified by basic silica gel column chromatography (hexane/ethyl acetate=4/1-0/1) and recrystallized from hexane/ethyl acetate to give the title compound (12 mg, yield 3.8%) as colorless crystals.

melting point 224° C.

$^1$H NMR (CDCl$_3$) δ 2.85 (3H, s), 7.75 (2H, d, J=8.7 Hz), 7.94 (2H, d, J=8.7 Hz), 8.01-8.10 (2H, m), 8.28 (1H, s), 8.34 (1H, s), 8.49 (1H, s).

EXAMPLE 190

5-[1-[4-(methylsulfinyl)phenyl]-1H-benzimidazol-6-yl]-1,3,4-oxadiazole-2-thiol

A solution of 1-[4-(methylsulfinyl)phenyl]-1H-benzimidazole-6-carbohydrazide (1.26 g, 4.00 mmol), carbon disulfide (0.601 mL, 10.0 mmol) and triethylamine (0.669 mL, 4.80 mmol) in ethanol (20 mL) was heated under reflux for 3 hr. After cooling, the reaction mixture was poured into water, and alkalified with 1 M aqueous sodium hydroxide solution. The obtained aqueous solution was filtered, and the filtrate was neutralized with 1M hydrochloric acid. The precipitate was collected by filtration, and washed with ethanol to give the title compound (0.955 g, yield 67%) as colorless crystals.

melting point 299-300° C.

$^1$H NMR (DMSO-d$_6$) δ 2.87 (3H, s), 7.86 (1H, dd, J=1.5, 8.5 Hz), 7.98-8.01 (5H, m), 8.04 (1H, dd, J=0.6, 1.5 Hz), 8.85 (1H, s), 14.75 (1H, brs).

Elemental analysis (for C$_{16}$H$_{12}$N$_4$O$_2$S$_2$.0.2H$_2$O)
Calculated (%): C, 53.38; H, 3.47; N, 15.56.
Found (%): C, 53.35; H, 3.38; N, 15.57.

EXAMPLE 191

6-[5-[(3-fluorobenzyl)thio]-1,3,4-oxadiazol-2-yl]-1-[4-(methylsulfinyl)phenyl]-1H-benzimidazole In the same manner as in Example 7 and using 5-[1-[4-(methylsulfinyl)phenyl]-1H-benzimidazol-6-yl]-1,3,4-oxadiazole-2-thiol instead of 5-(1H-indazol-5-yl)-1,3,4-oxadiazole-2-thiol and 3-fluorobenzyl bromide instead of 3-(trifluoromethyl)benzyl chloride, the title compound (yield 77%) was obtained as colorless crystals.

melting point 137-138° C. (crystallized from hexane/ethyl acetate).

$^1$H NMR (CDCl$_3$) δ 2.85 (3H, s), 4.51 (2H, s), 6.95-7.02 (1H, m), 7.17-7.22 (1H, m), 7.23-7.34 (2H, m), 7.71-7.76 (2H, m), 7.91-7.95 (2H, m), 7.99 (2H, d, J=1.1 Hz), 8.20 (1H, t, J=1.1 Hz), 8.26 (1H, s).

Elemental analysis (for C$_{23}$H$_{17}$FN$_4$O$_2$S$_2$)
Calculated (%): C, 59.47; H, 3.69; N, 12.06.
Found (%): C, 59.22; H, 3.81; N, 11.89.

EXAMPLE 192

3-[[[5-[1-[4-(methylsulfinyl)phenyl]-1H-benzimidazol-6-yl]-1,3,4-oxadiazol-2-yl]thio]methyl]benzonitrile In the same manner as in Example 7 and using 5-[1-[4-(methylsulfinyl)phenyl]-1H-benzimidazol-6-yl]-1,3,4-oxadiazole-2-thiol instead of 5-(1H-indazol-5-yl)-1,3,4-oxadiazole-2-thiol and 3-(bromomethyl)benzonitrile instead of 3-(trifluoromethyl)benzyl chloride, the title compound (yield 67%) was obtained as colorless crystals.

melting point 152-153° C. (crystallized from hexane/ethyl acetate).

$^1$H NMR (CDCl$_3$) δ 2.85 (3H, s), 4.53 (2H, s), 7.45 (1H, dt, J=0.4, 7.7 Hz), 7.59 (1H, td, J=1.5, 7.7 Hz), 7.71-7.77 (3H, m), 7.79-7.80 (1H, m), 7.91-7.95 (2H, m), 7.99 (2H, d, J=0.9 Hz), 8.20 (1H, t, J=0.9 Hz), 8.26 (1H, s).

Elemental analysis (for C$_{24}$H$_{17}$N$_5$O$_2$S$_2$)
Calculated (%): C, 61.13; H, 3.63; N, 14.85.
Found (%): C, 61.03; H, 3.69; N, 14.67.

EXAMPLE 193

1-[4-(methylsulfinyl)phenyl]-6-[5-[[3-(trifluoromethyl)benzyl]thio]-1,3,4-oxadiazol-2-yl]-1H-benzimidazole In the same manner as in Example 7 and using 5-[1-[4-(methylsulfinyl)phenyl]-1H-benzimidazol-6-yl]-1,3,4-oxadiazole-2-thiol instead of 5-(1H-indazol-5-yl)-1,3,4-oxadiazole-2-thiol, the title compound (yield 55%) was obtained as colorless crystals.

melting point 88-91° C. (crystallized from diisopropyl ether/ethyl acetate).

$^1$H NMR (CDCl$_3$) δ 2.85 (3H, s), 4.56 (2H, s), 7.43-7.50 (1H, m), 7.53-7.59 (1H, m), 7.66-7.76 (2H, m), 7.73 (2H, d, J=8.6 Hz), 7.93 (2H, d, J=8.6 Hz), 7.99 (2H, m), 8.19-8.21 (1H, m), 8.26 (1H, s).

Elemental analysis (for C$_{24}$H$_{17}$F$_3$N$_4$O$_2$S$_2$)
Calculated (%): C, 56.02; H, 3.33; N, 10.89.
Found (%): C, 55.78; H, 3.53; N, 10.70.

EXAMPLE 194

6-(5-methyl-1,3,4-oxadiazol-2-yl)-1-[4-(methylthio)phenyl]-1H-benzimidazole

In the same manner as in Example 5 and using N'-acetyl-1-[4-(methylthio)phenyl]-1H-benzimidazole-6-carbohydrazide instead of N'-[3-[3-(trifluoromethyl)phenyl]propionyl]benzothiazole-6-carbohydrazide, the title compound (yield 66%) was obtained as colorless crystals.

melting point 202-204° C. (recrystallized from hexane/tetrahydrofuran).

$^1$H NMR (CDCl$_3$) δ 2.58 (3H, s), 2.63 (3H, s), 7.43-7.49 (4H, m), 7.95-8.02 (2H, m), 8.19 (2H, s).

Elemental analysis (for C$_{17}$H$_{14}$N$_4$OS.0.3H$_2$O)
Calculated (%): C, 62.29; H, 4.48; N, 17.09.
Found (%): C, 62.24; H, 4.37; N, 16.97.

EXAMPLE 195

6-(5-cyclopropyl-1,3,4-oxadiazol-2-yl)-1-[4-(methylthio)phenyl]-1H-benzimidazole In the same manner as in Example 5 and using N'-(cyclopropylcarbonyl)-1-[4-(methylthio)phenyl]-1H-benzimidazole-6-carbohydrazide instead of N'-[3-[3-(trifluoromethyl)phenyl]propionyl]benzothiazole-6-carbohydrazide, the title compound (yield 67%) was obtained as colorless crystals.

melting point 198-199° C. (crystallized from hexane/chloroform).

$^1$H NMR (CDCl$_3$) δ 0.86-1.20 (4H, m), 2.26-2.35 (1H, m), 2.58 (3H, s), 7.54 (2H, d, J=8.7 Hz), 7.69 (2H, d, J=8.7 Hz), 7.90-7.97 (2H, m), 8.05 (1H, s), 8.71 (1H, s).

Elemental analysis (for C$_{19}$H$_{16}$N$_4$OS.0.5H$_2$O)
Calculated (%): C, 63.85; H, 4.79; N, 15.67.
Found (%): C, 63.71; H, 4.55; N, 15.45.

EXAMPLE 196

1-[4-(methylthio)phenyl]-6-[5-(2,2,2-trifluoroethyl)-1,3,4-oxadiazol-2-yl]-1H-benzimidazole In the same manner as in Example 5 and using 1-[4-(methylthio)phenyl]-N'-(3,3,3-trifluoropropanoyl)-1H-benzimidazole-6-carbohydrazide instead of N'-[3-[3-(trifluoromethyl)phenyl]propionyl]benzothiazole-6-carbohydrazide, the title compound (yield 44%) was obtained as colorless crystals.

melting point 190-192° C. (crystallized from hexane/chloroform).

$^1$H NMR (CDCl$_3$) δ 2.58 (3H, s), 4.42 (2H, q, J=10.5 Hz), 7.56 (2H, d, J=8.7 Hz), 7.68 (2H, d, J=8.7 Hz), 7.93-8.02 (2H, m), 8.07 (1H, s), 8.75 (1H, s).

Elemental analysis (for C$_{18}$H$_{13}$F$_3$N$_4$OS)
Calculated (%): C, 55.38; H, 3.36; N, 14.35.
Found (%): C, 55.35; H, 3.34; N, 14.38.

EXAMPLE 197

6-(5-methyl-1,3,4-oxadiazol-2-yl)-1-[4-(methylsulfinyl)phenyl]-1H-benzimidazole

In the same manner as in Example 113 and using 6-(5-methyl-1,3,4-oxadiazol-2-yl)-1-[4-(methylthio)phenyl]-1H-benzimidazole instead of 2-(2,3-dihydro-1-benzofuran-5-yl)-5-[[(3-fluorophenyl)thio]methyl]-1,3,4-oxadiazole and dichloromethane instead of acetonitrile, the title compound (yield 85%) was obtained as colorless crystals.

melting point 246-247° C. (crystallized from hexane/chloroform).

$^1$H NMR (CDCl$_3$) δ 2.64 (3H, s), 2.85 (3H, s), 7.74 (2H, d, J=8.7 Hz), 7.94 (2H, d, J=8.7 Hz), 7.98-8.05 (2H, m), 8.26-8.28 (2H, m).

Elemental analysis (for C$_{17}$H$_{14}$N$_4$O$_2$S.0.5H$_2$O)
Calculated (%): C, 58.78; H, 4.35; N, 16.13.
Found (%): C, 59.03; H, 4.12; N, 16.11.

EXAMPLE 198

6-(5-cyclopropyl-1,3,4-oxadiazol-2-yl)-1-[4-(methylsulfinyl)phenyl]-1H-benzimidazole In the same manner as in Example 113 and using 6-(5-cyclopropyl-1,3,4-oxadiazol-2-yl)-1-[4-(methylthio)phenyl]-1H-benzimidazole instead of 2-(2,3-dihydro-1-benzofuran-5-yl)-5-[[(3-fluorophenyl)thio]methyl]-1,3,4-oxadiazole and dichloromethane instead of acetonitrile, the title compound (yield 91%) was obtained as colorless crystals.

melting point 243-245° C. (crystallized from hexane/chloroform).

$^1$H NMR (CDCl$_3$) δ 1.19-1.25 (4H, m), 2.19-2.28 (1H, m), 2.85 (3H, s), 7.73 (2H, d, J=8.7 Hz), 7.93 (2H, d, J=8.7 Hz), 7.98 (2H, m), 8.22-8.27 (2H, m).

Elemental analysis (for C$_{19}$H$_{16}$N$_4$O$_2$S.0.5H$_2$O)
Calculated (%): C, 61.11; H, 4.59; N, 15.00.
Found (%): C, 61.12; H, 4.40; N, 14.87.

EXAMPLE 199

1-[4-(methylsulfinyl)phenyl]-6-[5-(2,2,2-trifluoroethyl)-1,3,4-oxadiazol-2-yl]-1H-benzimidazole In the same manner as in Example 113 and using 1-[4-(methylthio)phenyl]-6-[5-(2,2,2-trifluoroethyl)-1,3,4-oxadiazol-2-yl]-1H-benzimidazole instead of 2-(2,3-dihydro-1-benzofuran-5-yl)-5-[[(3-fluorophenyl)thio]methyl]-1,3,4-oxadiazole and dichloromethane instead of acetonitrile, the title compound (yield 44%) was obtained as colorless crystals.

melting point 184-185° C. (crystallized from hexane/chloroform).

$^1$H NMR (CDCl$_3$) δ 2.86 (3H, s), 3.87 (2H, q, J=9.6 Hz), 7.75 (2H, d, J=8.7 Hz), 7.94 (2H, d, J=8.7 Hz), 8.00-8.07 (2H, m), 8.28-8.30 (2H, m).

Elemental analysis (for C$_{18}$H$_{13}$F$_3$N$_4$O$_2$S)
Calculated (%): C, 53.20; H, 3.22; N, 13.79.
Found (%): C, 53.30; H, 3.30; N, 13.66.

EXAMPLE 200

6-(5-methyl-1,3,4-oxadiazol-2-yl)-1-[4-(methylsulfonyl)phenyl]-1H-benzimidazole

To a solution of 6-(5-methyl-1,3,4-oxadiazol-2-yl)-1-[4-(methylthio)phenyl]-1H-benzimidazole (322 mg, 1.00 mmol) in dichloromethane (10 mL) was added m-chloroperbenzoic acid (479 mg, 2.00 mmol) at 0° C., and the resulting mixture was stirred at room temperature for 1 hr. A saturated aqueous sodium thiosulfate solution was added to the reaction mixture, and the mixture was stirred for 1 hr. The organic layer was separated, washed with saturated aqueous sodium hydrogen carbonate solution and saturated brine, dried over anhydrous sodium sulfate, and concentrated under reduced pressure. The residue was purified by basic silica gel column chromatography (hexane/ethyl acetate=4/1-0/1), and recrystallized from hexane/chloroform to give the title compound (302 mg, yield 85%) as colorless crystals.

melting point 223-225° C.

$^1$H NMR (CDCl$_3$) δ 2.65 (3H, s), 3.18 (3H, s), 7.80 (2H, d, J=8.7 Hz), 7.99-8.07 (2H, m), 8.23 (2H, d, J=8.7 Hz), 8.28-8.29 (2H, m).

Elemental analysis (for C$_{17}$H$_{14}$N$_4$O$_3$S)
Calculated (%): C, 57.62; H, 3.98; N, 15.81.
Found (%): C, 57.35; H, 3.95; N, 15.76.

EXAMPLE 201

6-(5-cyclopropyl-1,3,4-oxadiazol-2-yl)-1-[4-(methylsulfonyl)phenyl]-1H-benzimidazole In the same manner as in Example 200 and using 6-(5-cyclopropyl-1,3,4-oxadiazol-2-yl)-1-[4-(methylthio)phenyl]-1H-benzimidazole instead of 6-(5-methyl-1,3,4-oxadiazol-2-yl)-1-[4-(methylthio)phenyl]-1H-benzimidazole, the title compound (yield 78%) was obtained as colorless crystals.

melting point 215-216° C. (crystallized from hexane/chloroform).

$^1$H NMR (CDCl$_3$) δ 1.17-1.28 (4H, m), 2.20-2.29 (1H, m), 3.18 (3H, s), 7.80 (2H, d, J=8.7 Hz), 7.99 (2H, s), 8.22-8.27 (4H, m).

Elemental analysis (for C$_{19}$H$_{16}$N$_4$O$_3$S.0.5H$_2$O)
Calculated (%): C, 58.60; H, 4.40; N, 14.39.
Found (%): C, 58.39; H, 4.16; N, 14.21.

EXAMPLE 202

1-[4-(methylsulfonyl)phenyl]-6-[5-(2,2,2-trifluoroethyl)-1,3,4-oxadiazol-2-yl]-1H-benzimidazole In the same manner as in Example 200 and using 1-[4-(methylthio)phenyl]-6-[5-(2,2,2-trifluoroethyl)-1,3,4-oxadiazol-2-yl]-1H-benzimidazole instead of 6-(5-methyl-1,3,4-oxadiazol-2-yl)-1-[4-(methylthio)phenyl]-1H-benzimidazole, the title compound (yield 53%) was obtained as colorless crystals.

melting point 229-232° C. (crystallized from hexane/chloroform).

$^1$H NMR (CDCl$_3$) δ 3.18 (3H, s), 3.88 (2H, q, J=9.6 Hz), 7.81 (2H, d, J=8.7 Hz), 8.02-8.09 (2H, m), 8.24 (2H, d, J=8.7 Hz), 8.28-8.32 (2H, m).

Elemental analysis (for C$_{18}$H$_{13}$F$_3$N$_4$O$_3$S)
Calculated (%): C, 51.18; H, 3.10; N, 13.26.
Found (%): C, 50.91; H, 3.10; N, 13.13.

EXAMPLE 203

6-[5-[[3-(trifluoromethyl)benzyl]thio]-1,3,4-oxadiazol-2-yl]quinoline

In the same manner as in Example 7 and using 5-(6-quinolyl)-1,3,4-oxadiazole-2-thiol instead of 5-(1H-indazol-5-yl)-1,3,4-oxadiazole-2-thiol, the title compound (yield 78%) was obtained as colorless crystals.

melting point 158-159° C. (recrystallized from hexane/tetrahydrofuran).

$^1$H NMR (CDCl$_3$) δ 4.60 (2H, s), 7.46-7.52 (2H, m), 7.56-7.60 (1H, m), 7.70-7.74 (1H, m), 7.75-7.77 (1H, m), 8.20-8.27 (2H, m), 8.31 (1H, dd, J=2.1, 8.9 Hz), 8.46 (1H, d, J=1.9 Hz), 9.01 (1H, dd, J=1.7, 4.1 Hz).

Elemental analysis (for C$_{19}$H$_{12}$F$_3$N$_3$OS)
Calculated (%): C, 58.91; H, 3.12; N, 10.85.
Found (%): C, 58.89; H, 2.97; N, 10.99.

EXAMPLE 204

6-[5-[[4-methoxy-3-(trifluoromethyl)benzyl]thio]-1,3,4-oxadiazol-2-yl]quinoline

In the same manner as in Example 7 and using 5-(6-quinolyl)-1,3,4-oxadiazole-2-thiol instead of 5-(1H-indazol- 5-yl)-1,3,4-oxadiazole-2-thiol and 4-methoxy-3-(trifluoromethyl)benzyl bromide instead of 3-(trifluoromethyl)benzyl chloride, the title compound (yield 74%) was obtained as colorless crystals.

melting point 130-131° C. (recrystallized from ethanol/water).

$^1$H NMR (CDCl$_3$) δ 3.89 (3H, s), 4.53 (2H, s), 6.98 (1H, d, J=8.5 Hz), 7.50 (1H, dd, J=4.1, 8.3 Hz), 7.64-7.69 (2H, m), 8.20-8.27 (2H, m), 8.32 (1H, dd, J=1.9, 8.9 Hz), 8.46 (1H, d, J=1.9 Hz), 9.01 (1H, dd, J=1.7, 4.1 Hz).

Elemental analysis (for C$_{20}$H$_{14}$F$_3$N$_3$O$_2$S)
Calculated (%): C, 57.55; H, 3.38; N, 10.07.
Found (%): C, 57.44; H, 3.35; N, 10.11.

EXAMPLE 205 tert-butyl[4-[5-[(4-fluorobenzyl)thio]-1,3,4-oxadiazol-2-yl]-2-pyridyl]carbamate In the same manner as in Example 47 and using tert-butyl [4-(hydrazinocarbonyl)-2-pyridyl]carbamate instead of 2,3-dihydro-1-benzofuran-5-carbohydrazide and 4-fluorobenzyl chloride instead of 3-fluoro-4-methoxybenzyl chloride, the title compound (yield 39%) was obtained as colorless crystals.

melting point 176-177° C. (recrystallized from methanol).

$^1$H NMR (DMSO-d$_6$) δ 1.50 (9H, s), 4.60 (2H, s), 7.15-7.22 (2H, m), 7.50-7.60 (3H, m), 8.35 (1H, s), 8.46 (1H, d, J=5.1 Hz), 10.19 (1H, s).

Elemental analysis (for C$_{19}$H$_{19}$FN$_4$O$_3$S)
Calculated (%): C, 56.70; H, 4.76; N, 13.92.
Found (%): C, 56.76; H, 4.66; N, 13.92.

EXAMPLE 206

4-[5-[(4-fluorobenzyl)thio]-1,3,4-oxadiazol-2-yl]pyridin-2-amine

To a solution of tert-butyl[4-[5-[(4-fluorobenzyl)thio]-1,3,4-oxadiazol-2-yl]-2-pyridyl]carbamate (138 mg, 0.343 mmol) in dichloromethane (5 mL) was added trifluoroacetic acid (5 mL), and the resulting mixture was stirred at room temperature for 5 hr. The reaction mixture was alkalified with aqueous sodium hydroxide solution, and the mixture was extracted with chloroform. The organic layer was washed with saturated brine, dried over anhydrous magnesium sulfate and concentrated under reduced pressure. The residue was purified by silica gel column chromatography (hexane/ethyl acetate=95/5-0/100), and recrystallized from methanol/chloroform/diethyl ether to give the title compound (44 mg, yield 43%) as colorless crystals.

melting point 200-201° C.

$^1$H NMR (DMSO-d$_6$) δ 4.58 (2H, s), 6.37 (2H, s), 6.92-6.97 (2H, m), 7.19 (2H, m), 7.54 (2H, m), 8.10 (1H, d, J=5.4 Hz).

Elemental analysis (for C$_{14}$H$_{11}$FN$_4$OS)
Calculated (%): C, 55.62; H, 3.67; N, 18.53.
Found (%): C, 55.67; H, 3.78; N, 18.62.

EXAMPLE 207

4-[5-[(4-chlorobenzyl)thio]-1,3,4-oxadiazol-2-yl]pyridin-2-amine

In the same manner as in Example 47 and using tert-butyl [4-(hydrazinocarbonyl)-2-pyridyl]carbamate instead of 2,3-dihydro-1-benzofuran-5-carbohydrazide and 4-chlorobenzyl chloride instead of 3-fluoro-4-methoxybenzyl chloride, tert-butyl [4-[5-[(4-chlorobenzyl)thio]-1,3,4-oxadiazol-2-yl]-2-pyridyl]carbamate was obtained. Then, in the same manner as in Example 206 and using tert-butyl[4-[5-[(4-chlorobenzyl)thio]-1,3,4-oxadiazol-2-yl]-2-pyridyl]carbamate instead of tert-butyl [4-[5-[(4-fluorobenzyl)thio]-1,3,4-oxadiazol-2-yl]-2-pyridyl]carbamate, the title compound (yield 32%) was obtained as colorless crystals.

melting point 200-201° C. (crystallized from chloroform).

$^1$H NMR (DMSO-d$_6$) δ 4.58 (2H, s), 6.38 (2H, s), 6.92-6.97 (2H, m), 7.42 (2H, d, J=8.4 Hz), 7.52 (2H, d, J=8.4 Hz), 8.10 (1H, dd, J=0.6, 5.1 Hz).

Elemental analysis (for C$_{14}$H$_{11}$ClN$_4$OS)
Calculated (%): C, 52.75; H, 3.48; N, 17.58.
Found (%): C, 52.72; H, 3.46; N, 17.65.

EXAMPLE 208 tert-butyl[4-[5-[(3-fluoro-4-methoxybenzyl)thio]-1,3,4-oxadiazol-2-yl]-2-pyridyl]carbamate In the same manner as in Example 47 and using tert-butyl [4-(hydrazinocarbonyl)-2-pyridyl]carbamate instead of 2,3-dihydro-1-benzofuran-5-carbohydrazide, the title compound (yield 38%) was obtained as colorless crystals.

melting point 244-245° C. (recrystallized from hexane/ethyl acetate).

$^1$H NMR (DMSO-d$_6$) δ 1.50 (9H, s), 3.81 (3H, s), 4.56 (2H, s), 7.13 (1H, m), 7.29 (1H, d, J=8.4 Hz), 7.37 (1H, dd, J=1.5, 12.3 Hz), 7.52 (1H, dd, J=1.5, 5.4 Hz), 8.36 (1H, s), 8.46 (1H, d, J=5.4 Hz), 10.19 (1H, s).

Elemental analysis (for C$_{20}$H$_{21}$FN$_4$O$_4$S)
Calculated (%): C, 55.54; H, 4.89; N, 12.96.
Found (%): C, 55.49; H, 4.84; N, 12.97.

EXAMPLE 209

4-[5-[(3-fluoro-4-methoxybenzyl)thio]-1,3,4-oxadiazol-2-yl]pyridin-2-amine

In the same manner as in Example 206 and using tert-butyl [4-[5-[(3-fluoro-4-methoxybenzyl)thio]-1,3,4-oxadiazol-2-yl]-2-pyridyl]carbamate instead of tert-butyl[4-[5-[(4-fluorobenzyl)thio]-1,3,4-oxadiazol-2-yl]-2-pyridyl]carbamate, the title compound (yield 16%) was obtained as pale-yellow crystals.

melting point 166-167° C. (crystallized from chloroform/diethyl ether).

$^1$H NMR (DMSO-d$_6$) δ 3.81 (3H, s), 4.53 (2H, s), 6.37 (2H, s), 6.92-6.97 (2H, m), 7.13 (1H, m), 7.26 (1H, d, J=9.0 Hz), 7.36 (1H, dd, J=2.1, 12.6 Hz), 8.10 (1H, d, J=5.4 Hz).

Elemental analysis (for C$_{15}$H$_{13}$FN$_4$O$_2$S)
Calculated (%): C, 54.21; H, 3.94; N, 16.86.
Found (%): C, 54.09; H, 4.03; N, 16.77.

EXAMPLE 210

N-benzyl-N'-[4-[5-[(4-chlorobenzyl)thio]-1,3,4-oxadiazol-2-yl]-2-pyridyl]urea

A suspension of 4-[5-[(4-chlorobenzyl)thio]-1,3,4-oxadiazol-2-yl]pyridin-2-amine (90 mg, 0.282 mmol) and benzyl isocyanate (187 mg, 1.41 mmol) in tetrahydrofuran (5 mL) was stirred at 70° C. for 20 hr. The reaction mixture was concentrated under reduced pressure, and the residue was recrystallized from methanol/chloroform/diethyl ether to give the title compound (72 mg, yield 56%) as colorless crystals.

melting point 199-201° C.

$^1$H NMR (DMSO-d$_6$) δ 4.40 (2H, d, J=6.0 Hz), 4.59 (2H, s), 7.22-7.45 (8H, m), 7.54 (2H, d, J=8.4 Hz), 8.08 (1H, m), 8.14 (1H, s), 8.39 (1H, d, J=5.4 Hz), 9.56 (1H, s).

Elemental analysis (for C$_{22}$H$_{18}$ClN$_5$O$_2$S)

Calculated (%): C, 58.47; H, 4.01; N, 15.50.

Found (%): C, 58.46; H, 4.10; N, 15.58.

EXAMPLE 211 tert-butyl[4-[5-[(3-fluorobenzyl)thio]-1,3,4-oxadiazol-2-yl]-2-pyridyl]carbamate In the same manner as in Example 1 and using tert-butyl [4-(5-mercapto-1,3,4-oxadiazol-2-yl)-2-pyridyl]carbamate triethylamine salt instead of 5-(benzothiazol-6-yl)-1,3,4-oxadiazole-2-thiol and 3-fluorobenzyl bromide instead of 3-(trifluoromethyl)benzyl chloride, the title compound (yield 93%) was obtained as colorless crystals.

melting point 237-238° C. (recrystallized from methanol/tetrahydrofuran/chloroform).

$^1$H NMR (DMSO-d$_6$) δ 1.50 (9H, s), 4.62 (2H, s), 7.09-7.19 (1H, m), 7.30-7.45 (3H, m), 7.51 (1H, dd, J=1.5, 5.1 Hz), 8.35 (1H, s), 8.46 (1H, d, J=5.1 Hz), 10.21 (1H, s).

Elemental analysis (for C$_{19}$H$_{19}$FN$_4$O$_3$S)

Calculated (%): C, 56.70; H, 4.76; N, 13.92.

Found (%): C, 56.50; H, 4.54; N, 14.00.

EXAMPLE 212

4-[5-[(3-fluorobenzyl)thio]-1,3,4-oxadiazol-2-yl]pyridin-2-amine

In the same manner as in Example 206 and using tert-butyl [4-[5-[(3-fluorobenzyl)thio]-1,3,4-oxadiazol-2-yl]-2-pyridyl]carbamate instead of tert-butyl[4-[5-[(4-fluorobenzyl)thio]-1,3,4-oxadiazol-2-yl]-2-pyridyl]carbamate, the title compound (yield 95%) was obtained as colorless crystals.

melting point 175-176° C. (recrystallized from methanol/tetrahydrofuran/chloroform).

$^1$H NMR (DMSO-d$_6$) δ 4.52 (2H, s), 4.65 (2H, brs), 6.95-7.10 (2H, m) 7.15-7.35 (4H, m), 8.22 (1H, dd, J=0.6, 5.4 Hz).

Elemental analysis (for C$_{14}$H$_{11}$FN$_4$OS)

Calculated (%): C, 55.62; H, 3.67; N, 18.53.

Found (%): C, 55.50; H, 3.56; N, 18.49.

EXAMPLE 213

N-[4-[5-[(3-fluorobenzyl)thio]-1,3,4-oxadiazol-2-yl]pyridin-2-yl]-3-phenylpropionamide To a solution of 4-[5-[(3-fluorobenzyl)thio]-1,3,4-oxadiazol-2-yl]pyridin-2-amine (360 mg, 1.19 mmol) and triethylamine (290 mg, 2.86 mmol) in tetrahydrofuran (30 mL) was added 3-phenylpropionyl chloride (482 mg, 2.86 mmol) at 0° C., and the resulting mixture was stirred at room temperature for 15 hr. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=95/5-0/100) and recrystallized from hexane/ethyl acetate to give the title compound (205 mg, yield 40%) as colorless crystals.

melting point 162-163° C.

$^1$H NMR (CDCl$_3$) δ 2.77 (2H, t, J=7.8 Hz), 3.10 (2H, t, J=7.8 Hz), 4.55 (2H, s), 6.90-7.05 (1H, m), 7.15-7.38 (8H, m), 7.69 (1H, dd, J=1.5, 5.1 Hz), 8.03 (1H, brs), 8.40 (1H, dd, J=0.6, 5.1 Hz), 8.75 (1H, s).

Elemental analysis (for C$_{23}$H$_{19}$FN$_4$O$_2$S)

Calculated (%): C, 63.58; H, 4.41; N, 12.89.

Found (%): C, 63.41; H, 4.13; N, 12.94.

EXAMPLE 214

3-phenyl-N-[4-[5-[[3-(trifluoromethyl)benzyl]thio]-1,3,4-oxadiazol-2-yl]-2-pyridyl]propionamide In the same manner as in Example 1 and using N-[4-(5-mercapto-1,3,4-oxadiazol-2-yl)-2-pyridyl]-3-phenylpropionamide instead of 5-(benzothiazol-6-yl)-1,3,4-oxadiazole-2-thiol, the title compound (yield 68%) was obtained as colorless crystals.

melting point 159-160° C. (recrystallized from hexane/ethyl acetate).

$^1$H NMR (CDCl$_3$) δ 2.77 (2H, t, J=7.5 Hz), 3.10 (2H, t, J=7.5 Hz), 4.60 (2H, s), 7.20-7.35 (5H, m), 7.50 (1H, t, J=7.5 Hz), 7.59 (1H, d, J=7.5 Hz), 7.68 (1H, dd, J=1.5, 5.1 Hz), 7.70-7.78 (2H, m), 8.09 (1H, s), 8.40 (1H, dd, J=0.9, 5.1 Hz), 8.75 (1H, s).

Elemental analysis (for C$_{24}$H$_{19}$F$_3$N$_4$O$_2$S)

Calculated (%): C, 59.50; H, 3.95; N, 11.56.

Found (%): C, 59.43; H, 3.86; N, 11.66.

EXAMPLE 215

N-[4-[5-[(3-cyanobenzyl)thio]-1,3,4-oxadiazol-2-yl]-2-pyridyl]-3-phenylpropionamide In the same manner as in Example 1 and using N-[4-(5-mercapto-1,3,4-oxadiazol-2-yl)-2-pyridyl]-3-phenylpropionamide instead of 5-(benzothiazol-6-yl)-1,3,4-oxadiazole-2-thiol and 3-(bromomethyl)benzonitrile instead of 3-(trifluoromethyl)benzyl chloride, the title compound (yield 36%) was obtained as colorless crystals.

melting point 153-154° C. (recrystallized from ethyl acetate).

$^1$H NMR (CDCl$_3$) δ 2.77 (2H, t, J=7.5 Hz), 3.10 (2H, t, J=7.5 Hz), 4.56 (2H, s), 7.20-7.36 (5H, m), 7.49 (1H, t, J=7.8 Hz), 7.62 (1H, m), 7.68 (1H, dd, J=1.5, 5.1 Hz), 7.76-7.84 (2H, m), 8.04 (1H, brs), 8.41 (1H, dd, J=0.9, 5.1 Hz), 8.74 (1H, s).

Elemental analysis (for C$_{24}$H$_{19}$N$_5$O$_2$S)

Calculated (%): C, 65.29; H, 4.34; N, 15.86.

Found (%): C, 65.20; H, 4.28; N, 15.88.

EXAMPLE 216

N-[4-[5-[[4-methoxy-3-(trifluoromethyl)benzyl]thio]-1,3,4-oxadiazol-2-yl]-2-pyridyl]-3-phenylpropionamide In the same manner as in Example 1 and using N-[4-(5-mercapto-1,3,4-oxadiazol-2-yl)-2-pyridyl]-3-phenylpropionamide instead of 5-(benzothiazol-6-yl)-1,3,4-oxadiazole-2-thiol and 4-methoxy-3-(trifluoromethyl)benzyl bromide instead of 3-(trifluoromethyl)benzyl chloride, the title compound (yield 39%) was obtained as colorless crystals.

melting point 180-181° C. (recrystallized from hexane/ethyl acetate).

$^1$H NMR (CDCl$_3$) δ 2.77 (2H, t, J=7.5 Hz), 3.10 (2H, t, J=7.5 Hz), 3.92 (3H, s), 4.54 (2H, s), 7.00 (1H, d, J=9.3 Hz), 7.20-7.40 (5H, m), 7.65-7.70 (3H, m), 7.95 (1H, brs), 8.41 (1H, d, J=5.1 Hz), 8.75 (1H, s).

Elemental analysis (for $C_{25}H_{21}F_3N_4O_3S$)
Calculated (%): C, 58.36; H, 4.11; N, 10.89.
Found (%): C, 58.09; H, 3.99; N, 10.88.

EXAMPLE 217

N-[4-[5-[(3-cyano-4-methoxybenzyl)thio]-1,3,4-oxadiazol-2-yl]-2-pyridyl]-3-phenylpropionamide In the same manner as in Example 1 and using N-[4-(5-mercapto-1,3,4-oxadiazol-2-yl)-2-pyridyl]-3-phenylpropionamide instead of 5-(benzothiazol-6-yl)-1,3,4-oxadiazole-2-thiol and 5-(chloromethyl)-2-methoxybenzonitrile instead of 3-(trifluoromethyl)benzyl chloride, the title compound (yield 39%) was obtained as colorless crystals.

melting point 176-177° C. (recrystallized from hexane/ethyl acetate).

$^1$H NMR (CDCl$_3$) δ 2.77 (2H, t, J=7.5 Hz), 3.10 (2H, t, J=7.5 Hz), 3.95 (3H, s), 4.50 (2H, s), 6.98 (1H, dd, J=1.5, 7.8 Hz), 7.20-7.37 (5H, m), 7.67-7.75 (3H, m), 7.96 (1H, brs), 8.41 (1H, dd, J=0.9, 5.1 Hz), 8.74 (1H, s).

Elemental analysis (for $C_{25}H_{21}N_5O_3S$)
Calculated (%): C, 63.68; H, 4.49; N, 14.85.
Found (%): C, 63.60; H, 4.42; N, 14.89.

EXAMPLE 218

N-[4-[5-[(3-fluorobenzyl)thio]-1,3,4-oxadiazol-2-yl]-2-pyridyl]-3-morpholinopropionamide To a solution of 4-[5-[(3-fluorobenzyl)thio]-1,3,4-oxadiazol-2-yl]pyridin-2-amine (1.35 g, 4.75 mmol) and triethylamine (1.98 mL, 14.25 mmol) in tetrahydrofuran (100 mL) was added acryloyl chloride (0.97 mL, 11.88 mmol) at 0° C., and the resulting mixture was stirred for 30 min. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=95/5-0/100) to give a mixture (1/1, 1.08 g, yield 61%) of N-[4-[5-[(3-fluorobenzyl)thio]-1,3,4-oxadiazol-2-yl]-2-pyridyl]acrylamide and N-acryloyl-N-[4-[5-[(3-fluorobenzyl)thio]-1,3,4-oxadiazol-2-yl]-2-pyridyl]acrylamide as pale-yellow crystals.

A mixture of the obtained compound (262 mg, 0.7 mmol), morpholine (305 mg, 3.5 mmol), ethanol (5 mL) and tetrahydrofuran (5 mL) was stirred at 80° C. for 2.5 hr. After cooling, the reaction mixture was concentrated under reduced pressure. The residue was purified by basic silica gel column chromatography (hexane/ethyl acetate=95/5-0/100) and recrystallized from hexane/ethyl acetate to give the title compound (208 mg, yield 67%) as colorless crystals.

melting point 149-150° C.

$^1$H NMR (CDCl$_3$) δ 2.55-2.75 (6H, m), 2.80 (2H, t, J=6.0 Hz), 3.89 (4H, t, J=4.8 Hz), 4.54 (2H, s), 7.02 (1H, m), 7.18-7.38 (3H, m), 7.65 (1H, dd, J=1.5, 5.1 Hz), 8.44 (1H, dd, J=0.6, 5.1 Hz), 8.70 (1H, dd, J=0.6, 5.1 Hz), 11.42 (1H, brs).

Elemental analysis (for $C_{21}H_{22}FN_5O_3S$)
Calculated (%): C, 56.87; H, 5.00; N, 15.79.
Found (%): C, 56.81; H, 4.95; N, 15.72.

EXAMPLE 219

N-[4-[5-[(3-fluorobenzyl)thio]-1,3,4-oxadiazol-2-yl]-2-pyridyl]-3-(1-Pyrrolidinyl)propionamide In the same manner as in Example 218 and using pyrrolidine instead of morpholine, the title compound (yield 61%) was obtained as colorless crystals.

melting point 114-115° C. (recrystallized from hexane/ethyl acetate).

$^1$H NMR (CDCl$_3$) δ 1.93 (4H, m), 2.61 (2H, t, J=6.0 Hz), 2.72 (4H, m), 2.90 (2H, t, J=6.0 Hz), 4.54 (2H, s), 7.02 (1H, m), 7.21 (1H, m), 7.25-7.38 (2H, m), 7.63 (1H, dd, J=1.5, 5.1 Hz), 8.43 (1H, dd, J=0.9, 5.1 Hz), 8.72 (1H, dd, J=0.9, 1.5 Hz), 11.66 (1H, brs).

Elemental analysis (for $C_{21}H_{22}FN_5O_2S$)
Calculated (%): C, 59.00; H, 5.19; N, 16.38.
Found (%): C, 58.83; H, 5.18; N, 16.43.

EXAMPLE 220

$N^3$-cyclopropyl-N-[4-[5-[(3-fluorobenzyl)thio]-1,3,4-oxadiazol-2-yl]pyridin-2-yl]-β-alaninamide In the same manner as in Example 218 and using cyclopropylamine instead of morpholine, the title compound (yield 36%) was obtained as colorless crystals.

melting point 102-103° C. (recrystallized from hexane/ethyl acetate).

$^1$H NMR (CDCl$_3$) δ 0.55-0.60 (4H, m), 1.98 (1H, brs), 2.21 (1H, m), 2.60 (2H, t, J=5.7 Hz), 3.15 (2H, t, J=5.7 Hz), 4.54 (2H, s), 7.02 (1H, m), 7.18-7.38 (3H, m), 7.64 (1H, dd, J=1.5, 5.1 Hz), 8.43 (1H, dd, J=0.9, 5.1 Hz), 8.70 (1H, dd, J=0.9, 1.5 Hz), 10.77 (1H, brs).

Elemental analysis (for $C_{20}H_{20}FN_5O_2S$)
Calculated (%): C, 58.10; H, 4.88; N, 16.94.
Found (%): C, 57.88; H, 4.84; N, 17.00.

EXAMPLE 221 tert-butyl[4-[5-[2-(3-fluorophenyl)ethyl]-1,3,4-oxadiazol-2-yl]-2-pyridyl]carbamate A solution of tert-butyl[4-[[2-[3-(3-fluorophenyl)propanoyl]hydrazino]carbonyl]-2-pyridyl]carbamate (1.00 g, 2.48 mmol), p-toluenesulfonyl chloride (946 mg, 4.96 mmol) and triethylamine (1.72 mL, 12.4 mmol) in tetrahydrofuran (30 mL) was heated under reflux for 17 hr. After cooling, the reaction mixture was diluted with ethyl acetate, washed with water and saturated brine, dried over anhydrous magnesium sulfate and concentrated under reduced pressure. The residue was purified by silica gel column chromatography (hexane/ethyl acetate=95/5-0/100), and recrystallized from ethyl acetate to give the title compound (0.70 g, yield 73%) as colorless crystals.

melting point 256-257° C.

$^1$H NMR (DMSO-d$_6$) δ 1.51 (9H, s), 3.14 (2H, t, J=7.5 Hz), 3.33 (2H, t, J=7.5 Hz), 7.00-7.38 (4H, m), 7.53 (1H, dd, J=1.5, 5.1 Hz), 8.38 (1H, s), 8.47 (1H, d, J=5.1 Hz), 10.19 (1H, s).

Elemental analysis (for $C_{20}H_{21}FN_4O_3$)
Calculated (%): C, 62.49; H, 5.51; N, 14.57.
Found (%): C, 62.38; H, 5.44; N, 14.58.

EXAMPLE 222

4-[5-[2-(3-fluorophenyl)ethyl]-1,3,4-oxadiazol-2-yl]pyridin-2-amine

In the same manner as in Example 206 and using tert-butyl [4-[5-[2-(3-fluorophenyl)ethyl]-1,3,4-oxadiazol-2-yl]-2-pyridyl]carbamate instead of tert-butyl[4-[5-[(4-fluorobenzyl)thio]-1,3,4-oxadiazol-2-yl]-2-pyridyl]carbamate, the title compound (yield 74%) was obtained as colorless crystals.

melting point 165-166° C. (recrystallized from ethyl acetate).

$^1$H NMR (DMSO-$d_6$) δ 3.12 (2H, t, J=7.5 Hz), 3.29 (2H, t, J=7.5 Hz), 6.38 (2H, brs), 6.90-7.20 (5H, m), 7.35 (1H, m), 8.10 (1H, d, J=5.4 Hz).

Elemental analysis (for $C_{15}H_{13}FN_4O$)

Calculated (%): C, 63.37; H, 4.61; N, 19.71.

Found (%): C, 63.33; H, 4.58; N, 19.74.

EXAMPLE 223

N-[4-[5-[2-(3-fluorophenyl)ethyl]-1,3,4-oxadiazol-2-yl]-2-pyridyl]-3-phenylpropionamide In the same manner as in Example 213 and using 4-[5-[2-(3-fluorophenyl)ethyl]-1,3,4-oxadiazol-2-yl]pyridin-2-amine instead of 4-[5-[(3-fluorobenzyl)thio]-1,3,4-oxadiazol-2-yl]pyridin-2-amine, the title compound (yield 73%) was obtained as colorless crystals.

melting point 171-172° C. (recrystallized from hexane/ethyl acetate).

$^1$H NMR (CDCl$_3$) δ 2.78 (2H, t, J=7.3 Hz), 3.12 (2H, t, J=7.5 Hz), 3.18-3.33 (4H, m), 6.90-7.10 (3H, m), 7.20-7.35 (6H, m), 7.74 (1H, dd, J=1.5, 5.1 Hz), 7.99 (1H, brs), 8.42 (1H, dd, J=0.9, 5.1 Hz), 8.78 (1H, brs).

Elemental analysis (for $C_{24}H_{21}FN_4O_2$)

Calculated (%): C, 69.22; H, 5.08; N, 13.45.

Found (%): C, 69.07; H, 4.89; N, 13.48.

EXAMPLE 224 benzyl[4-[5-[2-(3-fluorophenyl)ethyl]-1,3,4-oxadiazol-2-yl]-2-pyridyl]carbamate

To a solution of 4-[5-[2-(3-fluorophenyl)ethyl]-1,3,4-oxadiazol-2-yl]pyridin-2-amine (280 mg, 0.985 mmol), triethylamine (0.82 mL, 5.92 mmol) and 4-dimethylaminopyridine (12 mg, 0.0985 mmol) in tetrahydrofuran (10 mL) was added benzyl chloroformate (0.70 mL, 4.92 mmol) at 0° C., and the resulting mixture was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=95/5-0/100) and recrystallized from hexane/ethyl acetate to give the title compound (30 mg, yield 7%) as colorless crystals.

melting point 172-173° C.

$^1$H NMR (CDCl$_3$) δ 3.15-3.30 (4H, m), 5.29 (2H, s), 6.90-7.08 (3H, m), 7.25-7.50 (6H, m), 7.64 (1H, dd, J=1.5, 5.1 Hz), 8.27 (1H, brs), 8.38 (1H, d, J=5.1 Hz), 8.56 (1H, brs).

Elemental analysis (for $C_{23}H_{19}FN_4O_3$)

Calculated (%): C, 66.02; H, 4.58; N, 13.39.

Found (%): C, 65.79; H, 4.56; N, 13.49.

EXAMPLE 225

4-[5-[2-(3-fluorophenyl)ethyl]-1,3,4-oxadiazol-2-yl]-N-(3-phenylpropyl)pyridin-2-amine To a suspension of tert-butyl[4-[5-[2-(3-fluorophenyl)ethyl]-1,3,4-oxadiazol-2-yl]-2-pyridyl]carbamate (270 mg, 0.70 mmol) in N,N-dimethylformamide (5 mL) was added sodium hydride (60% in oil, 34 mg, 0.84 mmol) at room temperature, and the resulting mixture was stirred for 10 min. To this reaction mixture were added 3-phenylpropyl bromide (167 mg, 0.84 mmol) and potassium iodide (10 mg), and the mixture was further stirred at room temperature for 5 hr. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=95/5-0/100) to give tert-butyl[4-[5-[2-(3-fluorophenyl)ethyl]-1,3,4-oxadiazol-2-yl]-2-pyridyl](3-phenylpropyl)carbamate (232 mg, yield 66%) as a colorless oil.

Then, in the same manner as in Example 206 and using tert-butyl[4-[5-[2-(3-fluorophenyl)ethyl]-1,3,4-oxadiazol-2-yl]-2-pyridyl](3-phenylpropyl)carbamate obtained in the above-mentioned reaction instead of tert-butyl[4-[5-[(4-fluorobenzyl)thio]-1,3,4-oxadiazol-2-yl]-2-pyridyl]carbamate, the title compound (yield 93%) was obtained as colorless crystals.

melting point 91-92° C. (recrystallized from hexane/diethyl ether).

$^1$H NMR (CDCl$_3$) δ 2.02 (2H, m), 2.78 (2H, t, J=7.5 Hz), 3.15-3.42 (6H, m), 4.76 (1H, t, J=5.4 Hz), 6.90-7.11 (5H, m), 7.15-7.35 (6H, m), 8.24 (1H, d, J=5.1 Hz).

Elemental analysis (for $C_{24}H_{23}FN_4O$)

Calculated (%): C, 71.62; H, 5.76; N, 13.92.

Found (%): C, 71.70; H, 5.80; N, 14.06.

EXAMPLE 226

N-[4-[5-[2-(3-fluorophenyl)ethyl]-1,3,4-oxadiazol-2-yl]-2-pyridyl]-3-morpholinopropionamide In the same manner as in Example 218 and using 4-[5-[2-(3-fluorophenyl)ethyl]-1,3,4-oxadiazol-2-yl]pyridin-2-amine instead of 4-[5-[(3-fluorobenzyl)thio]-1,3,4-oxadiazol-2-yl]pyridin-2-amine, the title compound (yield 11%) was obtained as colorless crystals.

melting point 149-150° C. (recrystallized from hexane/ethyl acetate).

$^1$H NMR (CDCl$_3$) δ 2.60-2.75 (6H, m), 2.80 (2H, t, J=6.0 Hz), 3.18-3.33 (4H, m), 3.90 (4H, m), 6.90-7.05 (3H, m), 7.25-7.35 (1H, m), 7.70 (1H, dd, J=1.5, 5.1 Hz), 8.45 (1H, dd, J=0.6, 5.1 Hz), 8.73 (1H, m), 11.43 (1H, brs).

Elemental analysis (for $C_{22}H_{24}FN_5O_3$)

Calculated (%): C, 62.11; H, 5.69; N, 16.46.

Found (%): C, 61.99; H, 5.62; N, 16.45.

EXAMPLE 227 tert-butyl[4-[5-[2-[3-(trifluoromethyl)phenyl]ethyl]-1,3,4-oxadiazol-2-yl]-2-pyridyl]carbamate In the same manner as in Example 221 and using tert-butyl [4-[[2-[3-[3-(trifluoromethyl)phenyl]propanoyl]hydrazino]carbonyl]-2-pyridyl]carbamate instead of tert-butyl[4-[[2-[3-

(3-fluorophenyl)propanoyl]hydrazino]carbonyl]-2-pyridyl] carbamate, the title compound (yield 92%) was obtained as colorless crystals.

melting point 256-257° C. (recrystallized from ethyl acetate).

$^1$H NMR (CDCl$_3$) δ 1.59 (9H, s), 3.31 (4H, m), 7.45-7.59 (4H, m), 7.64 (1H, dd, J=1.5, 5.1 Hz), 7.86 (1H, s), 8.43 (1H, dd, J=0.9, 5.1 Hz), 8.51 (1H, s).

Elemental analysis (for C$_{21}$H$_{21}$F$_3$N$_4$O$_3$)
Calculated (%): C, 58.06; H, 4.87; N, 12.90.
Found (%): C, 58.09; H, 4.83; N, 12.98.

EXAMPLE 228

4-[5-[2-[3-(trifluoromethyl)phenyl]ethyl]-1,3,4-oxadiazol-2-yl]pyridin-2-amine

In the same manner as in Example 206 and using tert-butyl [4-[5-[2-[3-(trifluoromethyl)phenyl]ethyl]-1,3,4-oxadiazol-2-yl]-2-pyridyl]carbamate instead of tert-butyl[4-[5-[(4-fluorobenzyl)thio]-1,3,4-oxadiazol-2-yl]-2-pyridyl]carbamate, the title compound (yield 76%) was obtained as pale-brown crystals.

melting point 161-163° C. (recrystallized from hexane/ethyl acetate).

$^1$H NMR (CDCl$_3$) δ 3.30 (4H, m), 4.66 (2H, brs), 7.09 (1H, s), 7.20 (1H, dd, J=1.5, 5.1 Hz), 7.42-7.60 (4H, m), 8.25 (1H, d, J=5.1 Hz).

Elemental analysis (for C$_{16}$H$_{13}$F$_3$N$_4$O)
Calculated (%): C, 57.49; H, 3.92; N, 16.76.
Found (%): C, 57.28; H, 3.83; N, 16.70.

EXAMPLE 229

3-phenyl-N-[4-[5-[2-[3-(trifluoromethyl)phenyl] ethyl]-1,3,4-oxadiazol-2-yl]-2-pyridyl]propionamide In the same manner as in Example 213 and using 4-[5-[2-[3-(trifluoromethyl)phenyl]ethyl]-1,3,4-oxadiazol-2-yl]pyridin-2-amine instead of 4-[5-[(3-fluorobenzyl)thio]-1,3,4-oxadiazol-2-yl]pyridin-2-amine, the title compound (yield 76%) was obtained as colorless crystals.

melting point 169-170° C. (recrystallized from hexane/ethyl acetate).

$^1$H NMR (CDCl$_3$) δ 2.78 (2H, t, J=7.5 Hz), 3.12 (2H, t, J=7.5 Hz), 3.30 (4H, m), 7.20-7.38 (5H, m), 7.42-7.57 (4H, m), 7.73 (1H, dd, J=1.5, 5.1 Hz), 8.00 (1H, brs), 8.42 (1H, d, J=5.1 Hz), 8.78 (1H, brs).

Elemental analysis (for C$_{25}$H$_{21}$F$_3$N$_4$O$_2$)
Calculated (%): C, 64.37; H, 4.53; N, 12.01.
Found (%): C, 64.30; H, 4.50; N, 12.03.

EXAMPLE 230

4-[5-[[3-(trifluoromethyl)benzyl]thio]-1,3,4-oxadiazol-2-yl]-1H-pyrrolo[2,3-b]pyridine In the same manner as in Example 1 and using 5-(1H-pyrrolo[2,3-b]pyridin-4-yl)-1,3,4-oxadiazole-2-thiol 5/6 triethylamine salt instead of 5-(benzothiazol-6-yl)-1,3,4-oxadiazole-2-thiol, the title compound (yield 40%) was obtained as pale-yellow crystals.

melting point 164-165° C. (recrystallized from hexane/ethyl acetate).

$^1$H NMR (CDCl$_3$) δ 4.64 (2H, s), 7.18 (1H, dd, J=2.1, 3.6 Hz), 7.47-7.62 (3H, m), 7.67 (1H, d, J=5.1 Hz), 7.72-7.80 (2H, m), 8.47 (1H, d, J=5.1 Hz), 9.59 (1H, brs).

Elemental analysis (for C$_{17}$H$_{11}$F$_3$N$_4$OS)
Calculated (%): C, 54.25; H, 2.95; N, 14.89.
Found (%): C, 53.96; H, 2.84; N, 15.00.

EXAMPLE 231

4-[5-[(3-fluorobenzyl)thio]-1,3,4-oxadiazol-2-yl]-1H-pyrrolo[2,3-b]pyridine

In the same manner as in Example 1 and using 5-(1H-pyrrolo[2,3-b]pyridin-4-yl)-1,3,4-oxadiazole-2-thiol 5/6 triethylamine salt instead of 5-(benzothiazol-6-yl)-1,3,4-oxadiazole-2-thiol and 3-fluorobenzyl bromide instead of 3-(trifluoromethyl)benzyl chloride, the title compound (yield 64%) was obtained as pale-yellow crystals.

melting point 190-191° C. (recrystallized from methanol).

$^1$H NMR (DMSO-d$_6$) δ 4.66 (2H, s), 6.91 (1H, d, J=3.6 Hz), 7.10-7.18 (1H, m), 7.33-7.45 (3H, m), 7.61 (1H, d, J=5.1 Hz), 7.74 (1H, d, J=3.6 Hz), 8.42 (1H, d, J=5.1 Hz), 12.15 (1H, brs).

Elemental analysis (for C$_{16}$H$_{11}$FN$_4$OS)
Calculated (%): C, 58.89; H, 3.40; N, 17.17.
Found (%): C, 58.77; H, 3.44; N, 17.14.

EXAMPLE 232

4-[5-[2-(3-fluorophenyl)ethyl]-1,3,4-oxadiazol-2-yl]-1H-pyrrolo[2,3-b]pyridine

In the same manner as in Example 14 and using 3-(3-fluorophenyl)propanohydrazide instead of 1H-benzotriazole-5-carbohydrazide and 1H-pyrrolo[2,3-b]pyridine-4-carboxylic acid instead of 3-(3-cyanophenyl)propionic acid, the title compound (yield 40%) was obtained as pale-yellow crystals.

melting point 147-148° C. (recrystallized from hexane/ethyl acetate).

$^1$H NMR (CDCl$_3$) δ 3.20-3.40 (4H, m), 6.92-7.10 (3H, m), 7.17 (1H, dd, J=2.1, 3.3 Hz), 7.26-7.35 (1H, m), 7.54 (1H, dd, J=2.7, 3.3 Hz), 7.71 (1H, d, J=5.1 Hz), 8.48 (1H, d, J=5.1 Hz), 9.49 (1H, brs).

Elemental analysis (for C$_{17}$H$_{13}$FN$_4$O)
Calculated (%): C, 66.23; H, 4.25; N, 18.17.
Found (%): C, 66.17; H, 4.24; N, 18.17.

EXAMPLE 233

4-[5-[2-[3-(trifluoromethyl)phenyl]ethyl]-1,3,4-oxadiazol-2-yl]-1H-pyrrolo[2,3-b]pyridine In the same manner as in Example 14 and using 3-[(3-trifluoromethyl)phenyl]propanohydrazide instead of 1H-benzotriazole-5-carbohydrazide and 1H-pyrrolo[2,3-b]pyridine-4-carboxylic acid instead of 3-(3-cyanophenyl)propionic acid, the title compound (yield 51%) was obtained as pale-yellow crystals.

melting point 176-177° C. (recrystallized from hexane/ethyl acetate).

$^1$H NMR (CDCl$_3$) δ 3.29-3.41 (4H, m), 7.14 (1H, dd, J=2.1, 3.3 Hz), 7.42-7.60 (5H, m), 7.70 (1H, d, J=5.1 Hz), 8.48 (1H, d, J=5.1 Hz), 9.59 (1H, brs).

Elemental analysis (for C$_{18}$H$_{13}$F$_3$N$_4$O)
Calculated (%): C, 60.34; H, 3.66; N, 15.64.
Found (%): C, 60.23; H, 3.70; N, 15.57.

EXAMPLE 234

N-[4-[5-[(3-fluorobenzyl)thio]-1,3,4-oxadiazol-2-yl]-2-pyridyl]-N'-(2-pyridylmethyl)urea To a solution of 4-[5-[(3-fluorobenzyl)thio]-1,3,4-oxadiazol-2-yl]pyridin-2-amine (408 mg, 1.35 mmol) and triethylamine (0.468 mL) in tetrahydrofuran (20 mL) was added 2,2,2-trichloroethyl chloroformate (0.558 mL, 4.05 mmol) under ice-cooling, and the resulting mixture was stirred for 30 min. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=9/1-0/10), and the obtained compound was dissolved in N,N-dimethylformamide (15 mL). To this solution were added potassium carbonate (383 mg, 2.77 mmol), water (3 mL) and 2-(aminomethyl)pyridine (300 mg, 2.77 mmol) under ice-cooling, and the resulting mixture was stirred at room temperature for 30 min and at 50° C. for 30 min. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=9/1-0/10, ethyl acetate/methanol=9/1), and recrystallized from diethyl ether/methanol to give the title compound (313 mg, yield 57%) as colorless crystals.

melting point 164-165° C.
$^1$H NMR (CDCl$_3$) δ 4.55 (2H, s), 4.76 (2H, d, J=5.7 Hz), 6.97-7.07 (1H, m), 7.16-7.50 (7H, m), 7.67 (1H, dt, J=1.8, 7.5 Hz), 8.32-8.40 (2H, m), 8.60 (1H, d, J=4.5 Hz), 9.74 (1H, brs).
Elemental analysis (for C$_{21}$H$_{17}$FN$_6$O$_2$S)
Calculated (%): C, 57.79; H, 3.93; N, 19.25.
Found (%): C, 57.67; H, 4.09; N, 19.29.

EXAMPLE 235

N-[4-(5-methyl-1,3,4-oxadiazol-2-yl)-2-pyridyl]-N'-(2-pyridylmethyl)urea

In the same manner as in Example 234 and using 4-(5-methyl-1,3,4-oxadiazol-2-yl)pyridin-2-amine instead of 4-[5-[(3-fluorobenzyl)thio]-1,3,4-oxadiazol-2-yl]pyridin-2-amine, the title compound (yield 48%) was obtained as colorless crystals.

melting point 202-203° C. (recrystallized from diethyl ether/methanol).
$^1$H NMR (CDCl$_3$) δ 2.65 (3H, s), 4.76 (2H, d, J=5.7 Hz), 7.18 (1H, m), 7.41 (1H, d, J=7.5 Hz), 7.48 (1H, s), 7.51 (1H, dd, J=1.5, 5.1 Hz), 7.66 (1H, dt, J=1.5, 7.5 Hz), 8.35 (1H, brs), 8.38 (1H, dd, J=0.9, 5.1 Hz), 8.58 (1H, m), 9.71 (1H, brs).
Elemental analysis (for C$_{15}$H$_{14}$N$_6$O$_2$)
Calculated (%): C, 58.06; H, 4.55; N, 27.08.
Found (%): C, 58.06; H, 4.60; N, 27.20.

EXAMPLE 236

5-[2-(2-phenylethyl)-1H-pyrrolo[2,3-b]pyridin-4-yl]-1,3,4-oxadiazol-2-amine

To a solution of 2-(2-phenylethyl)-1H-pyrrolo[2,3-b]pyridine-4-carbohydrazide (104 mg, 0.371 mmol) in N,N-dimethylacetamide (1 mL) was added a solution of cyanogen bromide (47 mg, 0.445 mmol) in N,N-dimethylacetamide (0.5 mL) at room temperature, and the resulting mixture was stirred overnight. The reaction mixture was diluted with ethyl acetate, washed with water and saturated brine, dried over anhydrous magnesium sulfate and concentrated under reduced pressure. The residue was purified by basic silica gel column chromatography (ethyl acetate), and recrystallized from N,N-dimethylformamide/water to give the title compound (50 mg, yield 44%) as pale-yellow crystals.

melting point 234-235° C.
$^1$H NMR (DMSO-d$_6$) δ 3.00-3.15 (4H, m), 6.69 (1H, s), 7.15-7.30 (5H, m), 7.34 (1H, d, J=5.1 Hz), 7.40 (2H, s), 8.23 (1H, d, J=5.1 Hz), 11.91 (1H, brs).

EXAMPLE 237

4-[5-[(3-fluorobenzyl)thio]-1,3,4-oxadiazol-2-yl]-2-(2-phenylethyl)-1H-pyrrolo[2,3-b]pyridine A solution of 2-(2-phenylethyl)-1H-pyrrolo[2,3-b]pyridine-4-carbohydrazide (126 mg, 0.449 mmol), triethylamine (0.156 mL, 1.122 mmol) and carbon disulfide (0.136 mL, 2.246 mmol) in ethanol (10 mL) was stirred at 90° C. for 20 hr. The reaction mixture was concentrated under reduced pressure, and the residue was dissolved in N,N-dimethylformamide (5 mL). To this solution were added potassium carbonate (93 mg, 0.674 mmol) and 3-fluorobenzyl chloride (0.065 mL, 0.539 mmol), and the resulting mixture was stirred at room temperature for 3 hr. The reaction mixture was diluted with ethyl acetate, washed with water and saturated brine, dried over anhydrous magnesium sulfate and concentrated under reduced pressure. The residue was purified by silica gel column chromatography (hexane/ethyl acetate=9/1-0/1) and basic silica gel column chromatography (hexane/ethyl acetate=9/1-0/1) and recrystallized from hexane/ethyl acetate to give the title compound (44 mg, yield 23%) as pale-yellow crystals.

melting point 212° C.
$^1$H NMR (CDCl$_3$) δ 3.10-3.28 (4H, m), 4.58 (2H, s), 6.93 (1H, s), 7.03 (1H, m), 7.20-7.38 (8H, m), 7.60 (1H, d, J=5.1 Hz), 8.33 (1H, d, J=5.1 Hz), 9.26 (1H, brs).
Elemental analysis (for C$_{24}$H$_{19}$FN$_4$OS)
Calculated (%): C, 66.96; H, 4.45; N, 13.01.
Found (%): C, 66.97; H, 4.47; N, 13.02.

EXAMPLE 238

4-(5-methyl-1,3,4-oxadiazol-2-yl)-2-(2-phenylethyl)-1H-pyrrolo[2,3-b]pyridine

A mixture of 2-(2-phenylethyl)-1H-pyrrolo[2,3-b]pyridine-4-carbohydrazide (104 mg, 0.371 mmol) and ethyl orthoacetate (5 mL) was stirred at 120° C. for 1 hr and at 140° C. for 1 hr. The reaction mixture was concentrated under reduced pressure, and the residue was purified by silica gel column chromatography (hexane/ethyl acetate=4/1-0/1) and basic silica gel column chromatography (hexane/ethyl acetate=4/1-0/1), and recrystallized from hexane/ethyl acetate to give the title compound (85 mg, yield 75%) as pale-yellow crystals.

melting point 210° C.
$^1$H NMR (CDCl$_3$) δ 2.70 (3H, s), 3.10-3.25 (4H, m), 6.96 (1H, d, J=2.1 Hz), 7.20-7.35 (5H, m), 7.63 (1H, d, J=5.1 Hz), 8.33 (1H, d, J=5.1 Hz), 9.34 (1H, brs).
Elemental analysis (for C$_{18}$H$_{16}$N$_4$O)
Calculated (%): C, 71.04; H, 5.30; N, 18.41.
Found (%): C, 70.85; H, 5.29; N, 18.36.

EXAMPLE 239

4-(5-methyl-1,3,4-oxadiazol-2-yl)-N-[4-(methylthio)phenyl]pyridin-2-amine

A mixture of 2-[[4-(methylthio)phenyl]amino]isonicotinohydrazide (511 mg, 1.86 mmol) and triethyl orthoacetate (10 mL) was stirred at 120° C. overnight. After cooling, the precipitate was collected by filtration and recrystallized from hexane/ethyl acetate to give the title compound (441 mg, yield 80%) as yellow crystals.

melting point 203-204° C.
$^1$H NMR (DMSO-d$_6$) δ 2.44 (3H, s), 2.61 (3H, s), 7.09-7.30 (3H, m), 7.38 (1H, s), 7.54-7.75 (2H, m), 8.34 (1H, d, J=5.3 Hz), 9.43 (1H, s).
Elemental analysis (for C$_{15}$H$_{14}$N$_4$OS)
Calculated (%): C, 60.38; H, 4.73; N, 18.78.
Found (%): C, 60.34; H, 4.58; N, 18.73.

EXAMPLE 240

N-[3-methoxy-5-(trifluoromethyl)phenyl]-4-(5-methyl-1,3,4-oxadiazol-2-yl)pyridin-2-amine In the same manner as in Example 239 and using 2-[[3-methoxy-5-(trifluoromethyl)phenyl]amino]isonicotinohydrazide instead of 2-[[4-(methylthio)phenyl]amino]isonicotinohydrazide, the title compound (yield 76%) was obtained as colorless crystals.

melting point 241-242° C. (recrystallized from hexane/ethyl acetate).
$^1$H NMR (DMSO-d$_6$) δ 2.62 (3H, s), 3.83 (3H, s), 6.80 (1H, s), 7.30 (1H, dd, J=1.5, 5.3 Hz), 7.42 (1H, s), 7.65 (1H, s), 7.72 (1H, s), 8.43 (1H, d, J=5.5 Hz), 9.78 (1H, s).
Elemental analysis (for C$_{16}$H$_{13}$F$_3$N$_4$O$_2$)
Calculated (%): C, 54.86; H, 3.74; N, 15.99.
Found (%): C, 54.90; H, 3.68; N, 16.03.

EXAMPLE 241

4-(5-methyl-1,3,4-oxadiazol-2-yl)-N-[4-(methylsulfonyl)phenyl]pyridin-2-amine To a solution of 4-(5-methyl-1,3,4-oxadiazol-2-yl)-N-[4-(methylthio)phenyl]pyridin-2-amine (441 mg, 1.48 mmol) in N,N-dimethylacetamide (5 mL) was added m-chloroperbenzoic acid (70%, 531 mg, 2.22 mmol) at room temperature, and the resulting mixture was stirred for 1 hr. A saturated aqueous sodium thiosulfate solution was added to the reaction mixture, and the mixture was stirred for 15 min and extracted with ethyl acetate. The organic layer was washed with water and saturated brine, dried over anhydrous magnesium sulfate and concentrated under reduced pressure. The residue was purified by basic silica gel column chromatography (ethyl acetate) and recrystallized from hexane/tetrahydrofuran to give the title compound (213 mg, yield 43%) as colorless crystals.

melting point 244-245° C.
$^1$H NMR (DMSO-d$_6$) δ 2.62 (3H, s), 3.15 (3H, s), 7.36 (1H, dd, J=1.5, 5.3 Hz), 7.51 (1H, s), 7.82 (2H, d, J=8.7 Hz), 7.96 (2H, d, J=8.7 Hz), 8.45 (1H, d, J=5.3 Hz), 9.99 (1H, s).
Elemental analysis (for C$_{15}$H$_{14}$N$_4$O$_3$S)
Calculated (%): C, 54.53; H, 4.27; N, 16.96.
Found (%): C, 54.63; H, 4.29; N, 16.88.

EXAMPLE 242

4-(5-methyl-1,3,4-oxadiazol-2-yl)-N-[4-(methylsulfinyl)phenyl]pyridin-2-amine The eluate obtained after elution of 4-(5-methyl-1,3,4-oxadiazol-2-yl)-N-[4-(methylsulfonyl)phenyl]pyridin-2-amine by column purification (basic silica gel, ethyl acetate) in Example 241 was recrystallized from hexane/tetrahydrofuran to give the title compound (118 mg, yield 25%) as colorless crystals.

melting point 214-215° C.
$^1$H NMR (DMSO-d$_6$) δ 2.62 (3H, s), 2.71 (3H, s), 7.25-7.33 (1H, m), 7.46 (1H, m), 7.62 (2H, d, J=8.7 Hz), 7.91 (2H, d, J=8.7 Hz), 8.41 (1H, d, J=5.3 Hz), 9.76 (1H, s).
Elemental analysis (for C$_{15}$H$_{14}$N$_4$O$_2$S)
Calculated (%): C, 57.31; H, 4.49; N, 17.82.
Found (%): C, 57.36; H, 4.49; N, 17.77.

EXAMPLE 243

1-methyl-1-[5-[2-[[4-(methylthio)phenyl]amino]-4-pyridyl]-1,3,4-oxadiazol-2-yl]ethyl acetate A solution of 1,1-dimethyl-2-[2-[2-[[4-(methylthio)phenyl]amino]isonicotinoyl]hydrazino]-2-oxoethyl acetate (624 mg, 1.55 mmol) and p-toluenesulfonyl chloride (888 mg, 4.66 mmol) in pyridine (15 mL) was stirred at 90-95° C. overnight. After cooling, the reaction mixture was concentrated under reduced pressure. The residue was diluted with ethyl acetate, washed with saturated aqueous sodium hydrogen carbonate solution and saturated brine, dried over anhydrous sodium sulfate, and concentrated under reduced pressure. The residue was purified by basic silica gel column chromatography (hexane/ethyl acetate=10/1-0/1) and recrystallized from hexane/ethyl acetate to give the title compound (240 mg, yield 40%) as yellow crystals.

melting point 142-143° C. $^1$H NMR (CDCl$_3$) δ 1.88 (6H, s), 2.08 (3H, s), 2.49 (3H, s), 6.61 (1H, s), 7.26-7.42 (6H, m), 8.34 (1H, d, J=5.3 Hz).
Elemental analysis (for C$_{19}$H$_{20}$N$_4$O$_3$S)
Calculated (%): C, 59.36; H, 5.24; N, 14.57.
Found (%): C, 59.39; H, 5.23; N, 14.54.

EXAMPLE 244

2-[5-[2-[[4-(methylthio)phenyl]amino]-4-pyridyl]-1,3,4-oxadiazol-2-yl]propan-2-ol A mixture of 1-methyl-1-[5-[2-[[4-(methylthio)phenyl]amino]-4-pyridyl]-1,3,4-oxadiazol-2-yl]ethyl acetate (192 mg, 4.99 mmol), 1 M aqueous sodium hydroxide solution (5 mL), tetrahydrofuran (5 mL) and methanol (5 mL) was stirred at room temperature for 1.5 hr. The reaction mixture was diluted with ethyl acetate, washed with water and saturated brine, dried over anhydrous sodium sulfate, and concentrated under reduced pressure. The residue was purified by basic silica gel column chromatography (hexane/ethyl acetate=10/1-0/1) and recrystallized from hexane/ethyl acetate to give the title compound (61.2 mg, yield 36%) as yellow crystals.

melting point 172-173° C.
$^1$H NMR (CDCl$_3$) δ 1.77 (6H, s), 2.50 (3H, s), 2.56 (1H, s), 6.67 (1H, s), 7.28-7.46 (6H, m), 8.35 (1H, d, J=5.1 Hz).
Elemental analysis (for C$_{17}$H$_{18}$N$_4$O$_2$S)
Calculated (%): C, 59.63; H, 5.30; N, 16.36.
Found (%): C, 59.42; H, 5.33; N, 16.06.

EXAMPLE 245

4-(5-methyl-1,3,4-oxadiazol-2-yl)-N-(2-pyridyl)pyridin-2-amine

In the same manner as in Example 239 and using 2-(2-pyridylamino)isonicotinohydrazide instead of 2-[[4-(methylthio)phenyl]amino]isonicotinohydrazide, the title compound (yield 70%) was obtained as colorless crystals.
melting point 196-197° C. (recrystallized from hexane/ethyl acetate).
$^1$H NMR (DMSO-$d_6$) δ 2.63 (3H, s), 6.84-6.99 (1H, m), 7.37 (1H, dd, J=1.7, 4.9 Hz), 7.59-7.74 (2H, m), 8.20-8.33 (1H, m), 8.35-8.48 (2H, m), 10.04 (1H, s).
Elemental analysis (for $C_{13}H_{11}N_5O$)
Calculated (%): C, 61.65; H, 4.38; N, 27.65.
Found (%): C, 61.55; H, 4.39; N, 27.46.

EXAMPLE 246

4-[5-[(3-fluorobenzyl)thio]-1,3,4-oxadiazol-2-yl]-N-(2-pyridyl)pyridin-2-amine

A solution of 2-(2-pyridylamino)isonicotinohydrazide (392 mg, 1.71 mmol), carbon disulfide (0.26 mL, 4.27 mmol) and triethylamine (0.30 mL, 2.14 mmol) in ethanol (15 mL) was heated under reflux overnight. After cooling, the reaction mixture was concentrated under reduced pressure.
To a suspension of the obtained residue in N,N-dimethylformamide (10 mL) were added 3-fluorobenzyl bromide (0.26 mL, 2.14 mmol) and potassium hydroxide (85%, 141 mg, 2.14 mmol) in an ice bath, and the resulting mixture was stirred at room temperature for 4 hr. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=9/1-2/1) and recrystallized from hexane/ethyl acetate to give the title compound (110 mg, yield 17%) as colorless crystals.
melting point 141-142° C. (recrystallized from hexane/ethyl acetate).
$^1$H NMR (DMSO-$d_6$) δ 4.63 (2H, s), 6.85-6.99 (1H, m), 7.05-7.19 (1H, m), 7.26-7.48 (4H, m), 7.57-7.77 (2H, m), 8.28 (1H, d, J=4.7 Hz), 8.36-8.50 (2H, m), 10.04 (1H, s).

EXAMPLE 247

4-[5-[(3-fluorobenzyl)thio]-1,3,4-oxadiazol-2-yl]-7H-pyrrolo[2,3-d]pyrimidine

In the same manner as in Example 237 and using 7H-pyrrolo[2,3-d]pyrimidine-4-carbohydrazide instead of 2-(2-phenylethyl)-1H-pyrrolo[2,3-b]pyridine-4-carbohydrazide, the title compound (yield 35%) was obtained as pale-yellow crystals.
melting point 182-183° C. (recrystallized from hexane/ethyl acetate).
$^1$H NMR (CDCl$_3$) δ 4.59 (2H, s), 6.95-7.05 (1H, m), 7.29-7.37 (4H, m), 7.56 (1H, dd, J=2.4, 3.6 Hz), 9.06 (1H, s), 10.00 (1H, brs).
Elemental analysis (for $C_{15}H_{10}FN_5OS$)
Calculated (%): C, 55.04; H, 3.08; N, 21.39.
Found (%): C, 55.17; H, 3.20; N, 21.13.

EXAMPLE 248

4-[5-[[3-(trifluoromethyl)benzyl]thio]-1,3,4-oxadiazol-2-yl]-7H-pyrrolo[2,3-d]pyrimidine In the same manner as in Example 237 and using 7H-pyrrolo[2,3-d]pyrimidine-4-carbohydrazide instead of 2-(2-phenylethyl)-1H-pyrrolo[2,3-b]pyridine-4-carbohydrazide and 3-(trifluoromethyl)benzyl chloride instead of 3-fluorobenzyl chloride, the title compound (yield 13%) was obtained as pale-yellow crystals.
melting point 199-200° C. (recrystallized from hexane/ethyl acetate).
$^1$H NMR (CDCl$_3$) δ 4.64 (2H, s), 7.29 (1H, dd, J=2.1, 3.6 Hz), 7.45-7.60 (3H, m), 7.70-7.88 (2H, m), 9.04 (1H, s), 9.58 (1H, brs).
Elemental analysis (for $C_{16}H_{10}F_3N_5OS$)
Calculated (%): C, 50.93; H, 2.67; N, 18.56.
Found (%): C, 51.20; H, 2.79; N, 18.35.

EXAMPLE 249

6-[5-[[4-(methylthio)-3-(trifluoromethyl)benzyl]thio]-1,3,4-oxadiazol-2-yl]benzothiazole In the same manner as in Example 7 and using 5-(benzothiazol-6-yl)-1,3,4-oxadiazole-2-thiol instead of 5-(1H-indazol-5-yl)-1,3,4-oxadiazole-2-thiol and 4-(methylthio)-3-(trifluoromethyl)benzyl chloride instead of 3-(trifluoromethyl)benzyl chloride, the title compound (yield 94%) was obtained as colorless crystals.
melting point 122-123° C. (crystallized from hexane/ethyl acetate).
$^1$H NMR (CDCl$_3$) δ 2.51 (3H, s), 4.53 (2H, s), 7.33 (1H, d, J=8.1 Hz), 7.64 (1H, dd, J=1.7, 8.1 Hz), 7.73 (1H, d, J=1.7 Hz), 8.15 (1H, dd, J=1.7, 8.7 Hz), 8.24 (1H, dd, J=0.6, 8.7 Hz), 8.61 (1H, dd, J=0.6, 1.7 Hz), 9.13 (1H, s).
Elemental analysis (for $C_{18}H_{12}F_3N_3OS_3$)
Calculated (%): C, 49.19; H, 2.75; N, 9.56.
Found (%): C, 49.27; H, 2.72; N, 9.58.

EXAMPLE 250

6-[5-[[4-(methylsulfinyl)-3-(trifluoromethyl)benzyl]thio]-1,3,4-oxadiazol-2-yl]benzothiazole In the same manner as in Example 140 and using 6-[5-[[4-(methylthio)-3-(trifluoromethyl)benzyl]thio]-1,3,4-oxadiazol-2-yl]benzothiazole instead of 2-methyl-5-[3-[4-(methylthio)phenyl]-1-benzofuran-5-yl]-1,3,4-oxadiazole, the title compound (yield 86%) was obtained as colorless crystals.
melting point 179-180° C. (recrystallized from methanol).
$^1$H NMR (CDCl$_3$) δ 2.74 (3H, s), 4.62 (2H, s), 7.85-7.86 (1H, m), 7.97-8.01 (1H, m), 8.15 (1H, dd, J=1.5, 8.7 Hz), 8.25 (1H, dd, J=0.6, 8.7 Hz), 8.30 (1H, d, J=8.1 Hz), 8.62 (1H, dd, J=0.6, 1.5 Hz), 9.14 (1H, s).
Elemental analysis (for $C_{18}H_{12}F_3N_3O_2S_3$)
Calculated (%): C, 47.46; H, 2.66; N, 9.23.
Found (%): C, 47.42; H, 2.59; N, 9.27.

EXAMPLE 251

5-[5-[[4-(methylthio)-3-(trifluoromethyl)benzyl]thio]-1,3,4-oxadiazol-2-yl]-1H-indazole In the same manner as in Example 7 and using 4-(methylthio)-3-(trifluoromethyl)benzyl chloride instead of 3-(trifluoromethyl)benzyl chloride, the title compound (yield 80%) was obtained as colorless crystals.

melting point 184-185° C. (recrystallized from methanol).

$^1$H NMR (CDCl$_3$) δ 2.50 (3H, s), 4.51 (2H, s), 7.32 (1H, d, J=8.1 Hz), 7.60-7.65 (2H, m), 7.73 (1H, d, J=1.9 Hz), 8.06 (1H, dd, J=1.5, 8.7 Hz), 8.19 (1H, d, J=0.9 Hz), 8.39 (1H, dd, J=0.9, 1.5 Hz), 10.38 (1H, brs).

Elemental analysis (for C$_{18}$H$_{13}$F$_3$N$_4$OS$_2$)

Calculated (%): C, 51.18; H, 3.10; N, 13.26.

Found (%): C, 50.94; H, 3.05; N, 13.22.

EXAMPLE 252

5-[5-[[4-(methylsulfinyl)-3-(trifluoromethyl)benzyl]thio]-1,3,4-oxadiazol-2-yl]-1H-indazole In the same manner as in Example 140 and using 5-[5-[[4-(methylthio)-3-(trifluoromethyl)benzyl]thio]-1,3,4-oxadiazol-2-yl]-1H-indazole instead of 2-methyl-5-[3-[4-(methylthio)phenyl]-1-benzofuran-5-yl]-1,3,4-oxadiazole, the title compound (yield 80%) was obtained as colorless crystals.

melting point 170-171° C. (recrystallized from methanol).

$^1$H NMR (CDCl$_3$) δ 2.75 (3H, s), 4.60 (2H, s), 7.62 (1H, td, J=0.9, 8.9 Hz), 7.86 (1H, d, J=1.3 Hz), 7.98 (1H, dd, J=1.3, 8.1 Hz), 8.06 (1H, dd, J=1.5, 8.9 Hz), 8.19 (1H, d, J=0.9 Hz), 8.30 (1H, d, J=8.1 Hz), 8.40 (1H, dd, J=0.8, 1.5 Hz), 10.54 (1H, brs).

Elemental analysis (for C$_{18}$H$_{13}$F$_3$N$_4$O$_2$S$_2$)

Calculated (%): C, 49.31; H, 2.99; N, 12.78.

Found (%): C, 49.14; H, 3.00; N, 12.77.

EXAMPLE 253

6-(5-methyl-1,3,4-oxadiazol-2-yl)-3-[4-(methylthio)phenyl]imidazo[1,2-a]pyridine To a solution of 3-[4-(methylthio)phenyl]imidazo[1,2-a]pyridine-6-carbohydrazide (505 mg, 1.69 mmol) in N,N-dimethylacetamide (4 mL) was added acetyl chloride (0.132 mL, 1.86 mmol) at room temperature, and the resulting mixture was stirred for 1.5 hr. Ethyl acetate was added to the reaction mixture, and the precipitate was collected by filtration to give N'-acetyl-3-[4-(methylthio)phenyl]imidazo[1,2-a]pyridine-6-carbohydrazide (425 mg) as colorless crystals.

A solution of the obtained crude N'-acetyl-3-[4-(methylthio)phenyl]imidazo[1,2-a]pyridine-6-carbohydrazide and p-toluenesulfonyl chloride (714 mg, 3.74 mmol) in pyridine (5 mL) was stirred under an argon atmosphere at 100° C. for 24 hr. After cooling, the reaction mixture was concentrated under reduced pressure. The residue was diluted with ethyl acetate, washed with saturated aqueous sodium hydrogen carbonate solution and saturated brine, dried over magnesium sulfate, and concentrated under reduced pressure. The residue was purified by basic silica gel column chromatography (hexane/ethyl acetate=4/1-1/1) and recrystallized from hexane/chloroform to give the title compound (160 mg, yield 40%) as yellow crystals.

melting point 180-181° C.

$^1$H NMR (CDCl$_3$) δ 2.57 (3H, s), 2.63 (3H, s), 7.42-7.52 (4H, m), 7.75-7.83 (3H, m), 8.95 (1H, s).

Elemental analysis (for C$_{17}$H$_{14}$N$_4$OS)

Calculated (%): C, 63.33; H, 4.38; N, 17.38.

Found (%): C, 63.10; H, 4.34; N, 17.28.

EXAMPLE 254

6-(5-methyl-1,3,4-oxadiazol-2-yl)-3-[4-(methylsulfinyl)phenyl]imidazo[1,2-a]pyridine In the same manner as in Example 140 and using 6-(5-methyl-1,3,4-oxadiazol-2-yl)-3-[4-(methylthio)phenyl]imidazo[1,2-a]pyridine instead of 2-methyl-5-[3-[4-(methylthio)phenyl]-1-benzofuran-5-yl]-1,3,4-oxadiazole, the title compound (yield 82%) was obtained as colorless crystals.

melting point 190° C. (recrystallized from hexane/ethyl acetate).

$^1$H NMR (CDCl$_3$) δ 2.65 (3H, s), 2.84 (3H, s), 7.75-7.81 (2H, m), 7.83-7.89 (5H, m), 9.02 (1H, t, J=1.5 Hz).

Elemental analysis (for C$_{17}$H$_{14}$N$_4$O$_2$S.H$_2$O)

Calculated (%): C, 57.29; H, 4.52; N, 15.72.

Found (%): C, 57.06; H, 4.52; N, 16.61.

EXAMPLE 255

2-[3-(4-methoxyphenyl)-2,3-dihydro-1-benzofuran-5-yl]-5-methyl-1,3,4-oxadiazole

A mixture of 2-[3-(4-methoxyphenyl)-1-benzofuran-5-yl]-5-methyl-1,3,4-oxadiazole (447 mg, 1.46 mmol), 10% palladium carbon (50% containing water, 450 mg), tetrahydrofuran (5 mL) and methanol (15 mL) was stirred at room temperature for 48 hr under 1 atm hydrogen atmosphere. Palladium on carbon was removed by filtration, and the filtrate was concentrated under reduced pressure. The residue was purified by basic silica gel column chromatography (ethyl acetate), and crystallized from hexane/ethyl acetate to give the title compound (335 mg, yield 74%) as colorless crystals.

melting point 117-118° C.

$^1$H NMR (CDCl$_3$) δ 2.55 (3H, s), 3.80 (3H, s), 4.48 (1H, dd, J=7.7, 8.9 Hz), 4.68 (1H, dd, J=7.7, 9.6 Hz), 4.99 (1H, dd, J=8.9, 9.6 Hz), 6.85-6.90 (2H, m), 6.96 (1H, d, J=8.3 Hz), 7.11-7.16 (2H, m), 7.66-7.67 (1H, m), 7.86 (1H, ddd, J=0.8, 1.9, 8.3 Hz).

Elemental analysis (for C$_{18}$H$_{16}$N$_2$O$_3$)

Calculated (%): C, 70.12; H, 5.23; N, 9.09.

Found (%): C, 70.10; H, 5.18; N, 9.08.

EXAMPLE 256

2-(2,3-dihydro-1-benzofuran-5-yl)-5-[[4-(methylthio)-3-(trifluoromethyl)benzyl]thio]-1,3,4-oxadiazole In the same manner as in Example 7 and using 5-(2,3-dihydro-1-benzofuran-5-yl)-1,3,4-oxadiazole-2-thiol instead of 5-(1H-indazol-5-yl)-1,3,4-oxadiazole-2-thiol and 4-(methylthio)-3-(trifluoromethyl)benzyl chloride instead of 3-(trifluoromethyl)benzyl chloride, the title compound (yield 89%) was obtained as colorless crystals.

melting point 108-109° C. (crystallized from hexane/ethyl acetate).

$^1$H NMR (CDCl$_3$) δ 2.50 (3H, s), 3.27 (2H, t, J=8.9 Hz), 4.47 (2H, s), 4.66 (2H, t, J=8.9 Hz), 6.85 (1H, d, J=8.5 Hz), 7.31 (1H, d, J=8.1 Hz), 7.61 (1H, dd, J=1.7, 8.1 Hz), 7.70 (1H, d, J=1.7 Hz), 7.73-7.76 (1H, m), 7.81-7.82 (1H, m).

Elemental analysis (for C$_{19}$H$_{15}$F$_3$N$_2$O$_2$S$_2$)

Calculated (%): C, 53.76; H, 3.56; N, 6.60.

Found (%): C, 53.75; H, 3.52; N, 6.67.

EXAMPLE 257

2-(2,3-dihydro-1-benzofuran-5-yl)-5-[[4-(methyl-sulfinyl)-3-(trifluoromethyl)benzyl]thio]-1,3,4-oxadiazole In the same manner as in Example 140 and using 2-(2,3-dihydro-1-benzofuran-5-yl)-5-[[4-(methylthio)-3-(trifluoromethyl)benzyl]thio]-1,3,4-oxadiazole instead of 2-methyl-5-[3-[4-(methylthio)phenyl]-1-benzofuran-5-yl]-1,3,4-oxadiazole, the title compound (yield 94%) was obtained as colorless crystals.

melting point 177-178° C. (recrystallized from methanol).
$^1$H NMR (CDCl$_3$) δ 2.74 (3H, s), 3.27 (2H, t, J=8.9 Hz), 4.56 (2H, s), 4.67 (2H, t, J=8.9 Hz), 6.87 (1H, d, J=8.3 Hz), 7.72-7.76 (1H, m), 7.82-7.83 (2H, m), 7.96 (1H, dd, J=1.3, 8.1 Hz), 8.28 (1H, d, J=8.1 Hz).
Elemental analysis (for C$_{19}$H$_{15}$F$_3$N$_2$O$_3$S$_2$)
Calculated (%): C, 51.81; H, 3.43; N, 6.36.
Found (%): C, 51.74; H, 3.42; N, 6.41.

EXAMPLE 258

5-[3-[4-(methylsulfinyl)phenyl]-1-benzofuran-5-yl]-1,3,4-oxadiazole-2-thiol

A solution of methyl 3-[4-(methylsulfinyl)phenyl]-1-benzofuran-5-carboxylate (2.23 g, 7.10 mmol) and hydrazine monohydrate (1.76 mL, 36.3 mmol) in methanol (25 mL) was heated under reflux for 4 days. After cooling, the reaction mixture was concentrated under reduced pressure, and a solution of the obtained residue, carbon disulfide (1.28 mL, 21.3 mmol) and triethylamine (1.19 mL, 8.52 mmol) in ethanol (30 mL) was heated under reflux for 4 hr. After cooling, the reaction mixture was poured into water, and the mixture was acidified with 1M hydrochloric acid and extracted with ethyl acetate. The organic layer was washed with saturated brine, dried over anhydrous magnesium sulfate and concentrated under reduced pressure. The residue was recrystallized from tetrahydrofuran to give the title compound (1.19 g, yield 47%) as pale-yellow crystals.

melting point 234-235° C.
$^1$H NMR (DMSO-d$_6$) δ 2.82 (3H, s), 7.85-7.89 (2H, m), 7.92 (1H, dd, J=0.8, 8.9 Hz), 7.94-8.00 (3H, m), 8.33 (1H, dd, J=0.8, 1.5 Hz), 8.65 (1H, s), 14.75 (1H, brs).

EXAMPLE 259

2-[(3-fluorobenzyl)thio]-5-[3-[4-(methylsulfinyl) phenyl]-1-benzofuran-5-yl]-1,3,4-oxadiazole In the same manner as in Example 7 and using 5-[3-[4-(methylsulfinyl)phenyl]-1-benzofuran-5-yl]-1,3,4-oxadiazole-2-thiol instead of 5-(1H-indazol-5-yl)-1,3,4-oxadiazole-2-thiol and 3-fluorobenzyl bromide instead of 3-(trifluoromethyl)benzyl chloride, the title compound (yield 87%) was obtained as colorless crystals.

melting point 135-136° C. (recrystallized from hexane/ethyl acetate).
$^1$H NMR (CDCl$_3$) δ 2.81 (3H, s), 4.52 (2H, s), 6.96-7.03 (1H, m), 7.18-7.34 (3H, m), 7.68 (1H, dd, J=0.6, 1.7 Hz), 7.78-7.84 (4H, m), 7.94 (1H, s), 8.04 (1H, dd, J=1.7, 8.7 Hz), 8.44 (1H, dd, J=0.6, 1.7 Hz).
Elemental analysis (for C$_{24}$H$_{17}$FN$_2$O$_3$S$_2$)
Calculated (%): C, 62.05; H, 3.69; N, 6.03.
Found (%): C, 62.02; H, 3.93; N, 5.99.

EXAMPLE 260

2-[(3-chlorobenzyl)thio]-5-[3-[4-(methylsulfinyl) phenyl]-1-benzofuran-5-yl]-1,3,4-oxadiazole In the same manner as in Example 7 and using 5-[3-[4-(methylsulfinyl)phenyl]-1-benzofuran-5-yl]-1,3,4-oxadiazole-2-thiol instead of 5-(1H-indazol-5-yl)-1,3,4-oxadiazole-2-thiol and 3-chlorobenzyl bromide instead of 3-(trifluoromethyl)benzyl chloride, the title compound (yield 84%) was obtained as colorless crystals.

melting point 176-177° C. (recrystallized from hexane/tetrahydrofuran).
$^1$H NMR (CDCl$_3$) δ 2.81 (3H, s), 4.49 (2H, s), 7.26-7.30 (2H, m), 7.34-7.39 (1H, m), 7.47-7.49 (1H, m), 7.68 (1H, dd, J=0.6, 8.7 Hz), 7.78-7.84 (4H, m), 7.94 (1H, s), 8.04 (1H, dd, J=1.7, 8.7 Hz), 8.44 (1H, dd, J=0.6, 1.7 Hz).
Elemental analysis (for C$_{24}$H$_{17}$ClN$_2$O$_3$S$_2$)
Calculated (%): C, 59.93; H, 3.56; N, 5.82.
Found (%): C, 60.02; H, 3.80; N, 5.87.

EXAMPLE 261

2-[3-[4-(methylsulfinyl)phenyl]-1-benzofuran-5-yl]-5-[[3-(trifluoromethyl)benzyl]thio]-1,3,4-oxadiazole In the same manner as in Example 7 and using 5-[3-[4-(methylsulfinyl)phenyl]-1-benzofuran-5-yl]-1,3,4-oxadiazole-2-thiol instead of 5-(1H-indazol-5-yl)-1,3,4-oxadiazole-2-thiol, the title compound (yield 76%) was obtained as colorless crystals.

melting point 176-177° C. (recrystallized from hexane/ethyl acetate).
$^1$H NMR (CDCl$_3$) δ 2.80 (3H, s), 4.57 (2H, s), 7.44-7.50 (1H, m), 7.54-7.58 (1H, m), 7.66-7.75 (3H, m), 7.78-7.84 (4H, m), 7.94 (1H, s), 8.03 (1H, dd, J=1.7, 8.7 Hz), 8.44 (1H, dd, J=0.6, 1.7 Hz).
Elemental analysis (for C$_{25}$H$_{17}$F$_3$N$_2$O$_3$S$_2$)
Calculated (%): C, 58.36; H, 3.33; N, 5.44.
Found (%): C, 58.42; H, 3.61; N, 5.48.

EXAMPLE 262

3-[[[5-[3-[4-(methylsulfinyl)phenyl]-1-benzofuran-5-yl]-1,3,4-oxadiazol-2-yl]thio]methyl]benzonitrile In the same manner as in Example 7 and using 5-[3-[4-(methylsulfinyl)phenyl]-1-benzofuran-5-yl]-1,3,4-oxadiazole-2-thiol instead of 5-(1H-indazol-5-yl)-1,3,4-oxadiazole-2-thiol and 3-(bromomethyl)benzonitrile instead of 3-(trifluoromethyl)benzyl chloride, the title compound (yield 76%) was obtained as colorless crystals.

melting point 186-187° C. (recrystallized from ethanol/water).
$^1$H NMR (CDCl$_3$) δ 2.81 (3H, s), 4.53 (2H, s), 7.46 (1H, dt, J=0.4, 7.7 Hz), 7.59 (1H, td, J=1.3, 7.7 Hz), 7.68 (1H, dd, J=0.6, 8.7 Hz), 7.74-7.84 (6H, m), 7.94 (1H, s), 8.03 (1H, dd, J=1.7, 8.7 Hz), 8.44 (1H, dd, J=0.6, 1.7 Hz).
Elemental analysis (for C$_{25}$H$_{17}$N$_3$O$_3$S$_2$)
Calculated (%): C, 63.68; H, 3.63; N, 8.91.
Found (%): C, 63.67; H, 3.81; N, 9.01.

EXAMPLE 263

2-[3-[4-(isopropylthio)phenyl]-1-benzofuran-5-yl]-5-methyl-1,3,4-oxadiazole

In the same manner as in Example 132 and using [4-(isopropylthio)phenyl]boronic acid instead of (4-fluorophenyl)boronic acid, the title compound (yield 78%) was obtained as colorless crystals.

melting point 96-97° C. (recrystallized from hexane/ethyl acetate).

$^1$H NMR (CDCl$_3$) δ 1.36 (6H, d, J=6.6 Hz), 2.64 (3H, s), 3.40-3.53 (1H, m), 7.50-7.54 (2H, m), 7.57-7.61 (2H, m), 7.65 (1H, dd, J=0.6, 8.7 Hz), 7.87 (1H, s), 8.05 (1H, dd, J=1.5, 8.7 Hz), 8.50 (1H, dd, J=0.6, 1.5 Hz).

Elemental analysis (for C$_{20}$H$_{18}$N$_2$O$_2$S)
Calculated (%): C, 68.55; H, 5.18; N, 7.99.
Found (%): C, 68.56; H, 5.18; N, 7.94.

EXAMPLE 264

2-[3-[4-(isopropylsulfinyl)phenyl]-1-benzofuran-5-yl]-5-methyl-1,3,4-oxadiazole

In the same manner as in Example 140 and using 2-[3-[4-(isopropylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 78%) was obtained as colorless crystals.

melting point 157-158° C. (recrystallized from hexane/ethyl acetate).

$^1$H NMR (CDCl$_3$) δ 1.21 (3H, d, J=6.8 Hz), 1.30 (3H, d, J=6.8 Hz), 2.65 (3H, s), 2.84-2.98 (1H, m), 7.68 (1H, dd, J=0.6, 8.7 Hz), 7.72-7.75 (2H, m), 7.79-7.83 (2H, m), 7.94 (1H, s), 8.07 (1H, dd, J=1.7, 8.7 Hz), 8.52 (1H, dd, J=0.6, 1.7 Hz).

Elemental analysis (for C$_{20}$H$_{18}$N$_2$O$_3$S)
Calculated (%): C, 65.55; H, 4.95; N, 7.64.
Found (%): C, 65.49; H, 4.86; N, 7.48.

EXAMPLE 265

2-[3-[4-(isopropylsulfonyl)phenyl]-1-benzofuran-5-yl]-5-methyl-1,3,4-oxadiazole

In the same manner as in Example 200 and using 2-[3-[4-(isopropylthio)phenyl]-1-benzofuran-5-yl]-5-methyl-1,3,4-oxadiazole instead of 6-(5-methyl-1,3,4-oxadiazol-2-yl)-1-[4-(methylthio)phenyl]-1H-benzimidazole, the title compound (yield 87%) was obtained as colorless crystals.

melting point 229-230° C. (recrystallized from hexane/tetrahydrofuran).

$^1$H NMR (CDCl$_3$) δ 1.37 (6H, d, J=6.8 Hz), 2.65 (3H, s), 3.20-3.34 (1H, m), 7.70 (1H, dd, J=0.6, 8.7 Hz), 7.84-7.88 (2H, m), 7.98 (1H, s), 8.01-8.05 (2H, m), 8.09 (1H, dd, J=1.7, 8.7 Hz), 8.51 (1H, dd, J=0.6, 1.7 Hz).

Elemental analysis (for C$_{20}$H$_{18}$N$_2$O$_4$S)
Calculated (%): C, 62.81; H, 4.74; N, 7.33.
Found (%): C, 62.74; H, 4.68; N, 7.24.

EXAMPLE 266

2-methyl-5-[3-[4-(propylthio)phenyl]-1-benzofuran-5-yl]-1,3,4-oxadiazole

In the same manner as in Example 132 and using [4-(propylthio)phenyl]boronic acid instead of (4-fluorophenyl)boronic acid, the title compound (yield 85%) was obtained as colorless crystals.

melting point 101-102° C. (recrystallized from hexane/ethyl acetate).

$^1$H NMR (CDCl$_3$) δ 1.07 (3H, t, J=7.4 Hz), 1.68-1.80 (2H, m), 2.64 (3H, s), 2.97 (2H, t, J=7.4 Hz), 7.43-7.47 (2H, m), 7.55-7.60 (2H, m), 7.65 (1H, dd, J=0.8, 8.7 Hz), 7.85 (1H, s), 8.05 (1H, dd, J=1.7, 8.7 Hz), 8.49 (1H, dd, J=0.8, 1.7 Hz).

Elemental analysis (for C$_{20}$H$_{18}$N$_2$O$_2$S)
Calculated (%): C, 68.55; H, 5.18; N, 7.99.
Found (%): C, 68.62; H, 5.24; N, 8.00.

EXAMPLE 267

2-methyl-5-[3-[4-(propylsulfinyl)phenyl]-1-benzofuran-5-yl]-1,3,4-oxadiazole

In the same manner as in Example 140 and using 2-methyl-5-[3-[4-(propylthio)phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 82%) was obtained as colorless crystals.

melting point 140-141° C. (crystallized from hexane/ethyl acetate).

$^1$H NMR (CDCl$_3$) δ 1.10 (3H, t, J=7.4 Hz), 1.67-1.79 (1H, m), 1.81-1.96 (1H, m), 2.65 (3H, s), 2.78-2.93 (2H, m), 7.68 (1H, dd, J=0.6, 8.7 Hz), 7.75-7.84 (4H, m), 7.94 (1H, s), 8.07 (1H, dd, J=1.9, 8.7 Hz), 8.51 (1H, dd, J=0.6, 1.9 Hz).

Elemental analysis (for C$_{20}$H$_{18}$N$_2$O$_3$S)
Calculated (%): C, 65.55; H, 4.95; N, 7.64.
Found (%): C, 65.57; H, 5.00; N, 7.51.

EXAMPLE 268

2-methyl-5-[3-[4-(propylsulfonyl)phenyl]-1-benzofuran-5-yl]-1,3,4-oxadiazole

In the same manner as in Example 200 and using 2-methyl-5-[3-[4-(propylthio)phenyl]-1-benzofuran-5-yl]-1,3,4-oxadiazole instead of 6-(5-methyl-1,3,4-oxadiazol-2-yl)-1-[4-(methylthio)phenyl]-1H-benzimidazole, the title compound (yield 93%) was obtained as colorless crystals.

melting point 182-183° C. (recrystallized from hexane/tetrahydrofuran).

$^1$H NMR (CDCl$_3$) δ 1.05 (3H, t, J=7.4 Hz), 1.75-1.88 (2H, m), 2.65 (3H, s), 3.12-3.17 (2H, m), 7.70 (1H, dd, J=0.6, 8.7 Hz), 7.84-7.88 (2H, m), 7.98 (1H, s), 8.03-8.07 (2H, m), 8.09 (1H, dd, J=1.7, 8.7 Hz), 8.51 (1H, dd, J=0.6, 1.7 Hz).

Elemental analysis (for C$_{20}$H$_{18}$N$_2$O$_4$S)
Calculated (%): C, 62.81; H, 4.74; N, 7.33.
Found (%): C, 62.87; H, 4.80; N, 7.26.

EXAMPLE 269

2-[3-[4-(ethylthio)phenyl]-1-benzofuran-5-yl]-5-methyl-1,3,4-oxadiazole

In the same manner as in Example 132 and using [4-(ethylthio)phenyl]boronic acid instead of (4-fluorophenyl)boronic acid, the title compound (yield 72%) was obtained as colorless crystals.

melting point 144-145° C. (recrystallized from hexane/ethyl acetate).

$^1$H NMR (CDCl$_3$) δ 1.38 (3H, t, J=7.3 Hz), 2.64 (3H, s), 3.02 (2H, q, J=7.3 Hz), 7.46 (2H, d, J=8.5 Hz), 7.58 (2H, d, J=8.5 Hz), 7.65 (1H, dd, J=0.8, 8.7 Hz), 7.86 (1H, s), 8.05 (1H, dd, J=1.7, 8.7 Hz), 8.49 (1H, d, J=1.7 Hz).

Elemental analysis (for C$_{19}$H$_{16}$N$_2$O$_2$S)
Calculated (%): C, 67.84; H, 4.79; N, 8.33.
Found (%): C, 67.90; H, 4.84; N, 8.29.

EXAMPLE 270

2-[3-[4-(ethylsulfinyl)phenyl]-1-benzofuran-5-yl]-5-methyl-1,3,4-oxadiazole

In the same manner as in Example 140 and using 2-[3-[4-(ethylthio)phenyl]-1-benzofuran-5-yl]-5-methyl-1,3,4-oxadiazole instead of 2-methyl-5-[3-[4-(methylthio)phenyl]-1- benzofuran-5-yl]-1,3,4-oxadiazole, the title compound (yield 82%) was obtained as colorless crystals.

melting point 156-157° C. (recrystallized from hexane/ethyl acetate).

$^1$H NMR (CDCl$_3$) δ 1.27 (3H, t, J=7.3 Hz), 2.65 (3H, s), 2.78-3.06 (2H, m), 7.68 (1H, d, J=8.7 Hz), 7.73-7.78 (2H, m), 7.79-7.85 (2H, m), 7.94 (1H, s), 8.08 (1H, dd, J=1.7, 8.7 Hz), 8.51 (1H, d, J=1.1 Hz).

Elemental analysis (for C$_{19}$H$_{16}$N$_2$O$_3$S)
Calculated (%): C, 64.76; H, 4.58; N, 7.95.
Found (%): C, 64.76; H, 4.69; N, 7.91.

EXAMPLE 271

2-[3-[4-(ethylsulfonyl)phenyl]-1-benzofuran-5-yl]-5-methyl-1,3,4-oxadiazole

In the same manner as in Example 200 and using 2-[3-[4-(ethylthio)phenyl]-1-benzofuran-5-yl]-5-methyl-1,3,4-oxadiazole instead of 6-(5-methyl-1,3,4-oxadiazol-2-yl)-1-[4-(methylthio)phenyl]-1H-benzimidazole, the title compound (yield 26%) was obtained as colorless crystals.

melting point 180-181° C. (recrystallized from hexane/ethyl acetate).

$^1$H NMR (CDCl$_3$) δ 1.35 (3H, t, J=7.4 Hz), 2.65 (3H, s), 3.19 (2H, q, J=7.3 Hz), 7.70 (1H, dd, J=0.6, 8.7 Hz), 7.87 (2H, d, J=8.5 Hz), 7.98 (1H, s), 8.05 (2H, d, J=8.5 Hz), 8.10 (1H, dd, J=1.7, 8.7 Hz), 8.49-8.51 (1H, m).

Elemental analysis (for C$_{19}$H$_{16}$N$_2$O$_4$S)
Calculated (%): C, 61.94; H, 4.38; N, 7.60.
Found (%): C, 61.89; H, 4.36; N, 7.53.

EXAMPLE 272

2-methyl-5-[3-[4-[(trifluoromethyl)thio]phenyl]-1-benzofuran-5-yl]-1,3,4-oxadiazole In the same manner as in Example 132 and using 4,4,5,5-tetramethyl-2-[4-[(trifluoromethyl)thio]phenyl]-1,3,2-dioxaborolane instead of (4-fluorophenyl)boronic acid and [1,1'-bis(diphenylphosphino)ferrocene]palladium(II) chloride dichloromethane complex instead of tetrakis(triphenylphosphine)palladium(0), the title compound (yield 61%) was obtained as colorless crystals.

melting point 170-171° C. (recrystallized from hexane/ethyl acetate).

$^1$H NMR (CDCl$_3$) δ 2.65 (3H, s), 7.68 (1H, dd, J=0.6, 8.7 Hz), 7.70-7.74 (2H, m), 7.78-7.82 (2H, m), 7.93 (1H, s), 8.08 (1H, dd, J=1.9, 8.7 Hz), 8.49 (1H, dd, J=0.6, 1.9 Hz).

Elemental analysis (for C$_{18}$H$_{11}$F$_3$N$_2$O$_2$S)
Calculated (%): C, 57.44; H, 2.95; N, 7.44.
Found (%): C, 57.45; H, 2.88; N, 7.41.

EXAMPLE 273

2-methyl-5-[3-[4-[(trifluoromethyl)sulfinyl]phenyl]-1-benzofuran-5-yl]-1,3,4-oxadiazole In the same manner as in Example 140 and using 2-methyl-5-[3-[4-[(trifluoromethyl)thio]phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 32%) was obtained as colorless crystals.

melting point 183-184° C. (recrystallized from hexane/ethyl acetate).

$^1$H NMR (CDCl$_3$) δ 2.65 (3H, s), 7.71 (1H, dd, J=0.6, 8.7 Hz), 7.90-7.97 (4H, m), 7.99 (1H, s), 8.10 (1H, dd, J=1.7, 8.7 Hz), 8.51 (1H, dd, J=0.6, 1.7 Hz).

Elemental analysis (for C$_{18}$H$_{11}$F$_3$N$_2$O$_3$S)
Calculated (%): C, 55.10; H, 2.83; N, 7.14.
Found (%): C, 55.07; H, 2.79; N, 7.10.

EXAMPLE 274

2-[3-[4-[(fluoromethyl)thio]phenyl]-1-benzofuran-5-yl]-5-methyl-1,3,4-oxadiazole To a solution of [bis(2-methoxyethyl)amino]sulfur trifluoride (1.38 mL, 7.50 mmol) in dichloromethane (10 mL) was added dropwise a solution of 2-methyl-5-[3-[4-(methylthio)phenyl]-1-benzofuran-5-yl]-1,3,4-oxadiazole (1.61 g, 5.00 mmol) in dichloromethane (15 mL) at room temperature. Antimony (III) chloride (0.0570 g, 0.250 mmol) was added to the solution, and the resulting mixture was stirred overnight at room temperature. The reaction mixture was diluted with ethyl acetate, washed with saturated aqueous sodium hydrogen carbonate solution and saturated brine, dried over anhydrous magnesium sulfate and concentrated under reduced pressure. The residue was purified by silica gel column chromatography (hexane/tetrahydrofuran=1/1) and recrystallized from hexane/ethyl acetate to give the title compound (517 mg, yield 30%) as pale-yellow crystals.

melting point 143-144° C.

$^1$H NMR (CDCl$_3$) δ 2.64 (3H, s), 5.79 (2H, d, J=52.8 Hz), 7.64 (4H, s), 7.66 (1H, dd, J=0.6, 8.7 Hz), 7.88 (1H, s), 8.07 (1H, dd, J=1.7, 8.7 Hz), 8.48 (1H, dd, J=0.6, 1.7 Hz).

Elemental analysis (for C$_{18}$H$_{13}$FN$_2$O$_2$S)
Calculated (%): C, 63.52; H, 3.85; N, 8.23.
Found (%): C, 63.37; H, 3.81; N, 8.30.

EXAMPLE 275

2-[3-[4-[(fluoromethyl)sulfinyl]phenyl]-1-benzofuran-5-yl]-5-methyl-1,3,4-oxadiazole In the same manner as in Example 140 and using 2-[3-[4-[(fluoromethyl)thio]phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 93%) was obtained as colorless crystals.

melting point 173-174° C. (crystallized from hexane/ethyl acetate).

$^1$H NMR (CDCl$_3$) δ 2.65 (3H, s), 5.14 (1H, dd, J=8.3, 47.5 Hz), 5.21 (1H, dd, J=8.3, 48.0 Hz), 7.70 (1H, dd, J=0.6, 8.7 Hz), 7.82-7.90 (4H, m), 7.96 (1H, s), 8.09 (1H, dd, J=1.5, 8.7 Hz), 8.50 (1H, dd, J=0.6, 1.5 Hz).

Elemental analysis (for C$_{18}$H$_{13}$FN$_2$O$_3$S)
Calculated (%): C, 60.67; H, 3.68; N, 7.86.
Found (%): C, 60.66; H, 3.64; N, 7.96.

EXAMPLE 276

2-[3-[4-[(fluoromethyl)sulfonyl]phenyl]-1-benzofuran-5-yl]-5-methyl-1,3,4-oxadiazole In the same manner as in Example 140 and using 2-[3-[4-[(fluoromethyl)sulfinyl]phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 92%) was obtained as colorless crystals.

melting point 191-192° C. (recrystallized from methanol).

$^1$H NMR (CDCl$_3$) δ 2.65 (3H, s), 5.21 (2H, d, J=47.1 Hz), 7.71 (1H, dd, J=0.6, 8.7 Hz), 7.89-7.93 (2H, m), 8.00 (1H, s), 8.09-8.13 (3H, m), 8.50 (1H, dd, J=0.6, 1.7 Hz).

Elemental analysis (for C$_{18}$H$_{13}$FN$_2$O$_4$S)
Calculated (%): C, 58.06; H, 3.52; N, 7.52.
Found (%): C, 57.97; H, 3.49; N, 7.65.

EXAMPLE 277

2-[3-[4-(benzylthio)phenyl]-1-benzofuran-5-yl]-5-methyl-1,3,4-oxadiazole

In the same manner as in Example 132 and using [4-(benzylthio)phenyl]boronic acid instead of (4-fluorophenyl)boronic acid, the title compound (yield 91%) was obtained as colorless crystals.

melting point 158-159° C. (recrystallized from hexane/tetrahydrofuran).

$^1$H NMR (CDCl$_3$) δ 2.64 (3H, s), 4.16 (2H, s), 7.24-7.38 (5H, m), 7.41-7.45 (2H, m), 7.53-7.57 (2H, m), 7.64 (1H, dd, J=0.6, 8.7 Hz), 7.85 (1H, s), 8.05 (1H, dd, J=1.7, 8.7 Hz), 8.47 (1H, dd, J=0.6, 1.7 Hz).

Elemental analysis (for C$_{24}$H$_{18}$N$_2$O$_2$S)
Calculated (%): C, 72.34; H, 4.55; N, 7.03.
Found (%): C, 72.41; H, 4.58; N, 7.24.

EXAMPLE 278

2-[3-[4-(benzylsulfinyl)phenyl]-1-benzofuran-5-yl]-5-methyl-1,3,4-oxadiazole

In the same manner as in Example 140 and using 2-[3-[4-(benzylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 91%) was obtained as colorless crystals.

melting point 183-184° C. (crystallized from ethyl acetate).

$^1$H NMR (CDCl$_3$) δ 2.65 (3H, s), 4.07 (1H, d, J=12.5 Hz), 4.17 (1H, d, J=12.5 Hz), 7.05-7.09 (2H, m), 7.25-7.36 (3H, m), 7.49-7.53 (2H, m), 7.68 (1H, dd, J=0.6, 8.7 Hz), 7.70-7.74 (2H, m), 7.93 (1H, s), 8.08 (1H, dd, J=1.7, 8.7 Hz), 8.48 (1H, dd, J=0.6, 1.7 Hz).

Elemental analysis (for C$_{24}$H$_{18}$N$_2$O$_3$S)
Calculated (%): C, 69.55; H, 4.38; N, 6.76.
Found (%): C, 69.49; H, 4.42; N, 6.81.

EXAMPLE 279

2-[3-[4-(benzylsulfonyl)phenyl]-1-benzofuran-5-yl]-5-methyl-1,3,4-oxadiazole

In the same manner as in Example 140 and using 2-[3-[4-(benzylsulfinyl)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 97%) was obtained as colorless crystals.

melting point 229-230° C. (recrystallized from tetrahydrofuran/methanol).

$^1$H NMR (CDCl$_3$) δ 2.66 (3H, s), 4.38 (2H, s), 7.15-7.19 (2H, m), 7.27-7.39 (3H, m), 7.69 (1H, dd, J=0.6, 8.7 Hz), 7.72-7.78 (4H, m), 7.96 (1H, s), 8.09 (1H, dd, J=1.5, 8.7 Hz), 8.47 (1H, dd, J=0.6, 1.5 Hz).

Elemental analysis (for C$_{24}$H$_{18}$N$_2$O$_4$S)
Calculated (%): C, 66.96; H, 4.21; N, 6.51.
Found (%): C, 66.80; H, 4.25; N, 6.56.

EXAMPLE 280

2-[[[4-[5-(5-methyl-1,3,4-oxadiazol-2-yl)-1-benzofuran-3-yl]phenyl]thio]methyl]benzonitrile In the same manner as in Example 132 and using [4-[(2-cyanobenzyl)thio]phenyl]boronic acid instead of (4-fluorophenyl)boronic acid, the title compound (yield 80%) was obtained as colorless crystals.

melting point 141-142° C. (recrystallized from methanol).

$^1$H NMR (CDCl$_3$) δ 2.64 (3H, s), 4.34 (2H, s), 7.36 (1H, dt, J=1.3, 7.5 Hz), 7.44-7.59 (6H, m), 7.63-7.67 (2H, m), 7.86 (1H, s), 8.06 (1H, dd, J=1.7, 8.7 Hz), 8.47 (1H, dd, J=0.6, 1.7 Hz).

Elemental analysis (for C$_{25}$H$_{17}$N$_3$O$_2$S)
Calculated (%): C, 70.90; H, 4.05; N, 9.92.
Found (%): C, 70.84; H, 4.00; N, 9.89.

EXAMPLE 281

2-[[[4-[5-(5-methyl-1,3,4-oxadiazol-2-yl)-1-benzofuran-3-yl]phenyl]sulfinyl]methyl]benzonitrile In the same manner as in Example 140 and using 2-[[[4-[5-(5-methyl-1,3,4-oxadiazol-2-yl)-1-benzofuran-3-yl]phenyl]thio]methyl]benzonitrile instead of 2-methyl-5-[3-[4-(methylthio)phenyl]-1-benzofuran-5-yl]-1,3,4-oxadiazole, the title compound (yield 94%) was obtained as colorless crystals.

melting point 171-172° C. (crystallized from methanol/water).

$^1$H NMR (CDCl$_3$) δ 2.65 (3H, s), 4.23 (1H, d, J=13.0 Hz), 4.39 (1H, d, J=13.0 Hz), 7.44-7.49 (2H, m), 7.60-7.65 (4H, m), 7.69 (1H, dd, J=0.6, 8.7 Hz), 7.75-7.79 (2H, m), 7.95 (1H, s), 8.09 (1H, dd, J=1.7, 8.7 Hz), 8.46 (1H, dd, J=0.6, 1.7 Hz).

Elemental analysis (for C$_{25}$H$_{17}$N$_3$O$_3$S)
Calculated (%): C, 68.32; H, 3.90; N, 9.56.
Found (%): C, 68.30; H, 3.80; N, 9.62.

EXAMPLE 282

2-[[[4-[5-(5-methyl-1,3,4-oxadiazol-2-yl)-1-benzofuran-3-yl]phenyl]sulfonyl]methyl]benzonitrile In the same manner as in Example 140 and using 2-[[[4-[5-(5-methyl-1,3,4-oxadiazol-2-yl)-1-benzofuran-3-yl]phenyl]sulfinyl]methyl]benzonitrile instead of 2-methyl-5-[3-[4-(methylthio)phenyl]-1-benzofuran-5-yl]-1,3,4-oxadiazole, the title compound (yield 96%) was obtained as colorless crystals.

melting point 223-224° C. (crystallized from tetrahydrofuran/water).

$^1$H NMR (CDCl$_3$) δ 2.65 (3H, s), 4.64 (2H, s), 7.48-7.53 (1H, m), 7.59-7.62 (1H, m), 7.65-7.71 (3H, m), 7.79-7.88 (4H, m), 7.99 (1H, s), 8.11 (1H, dd, J=1.7, 8.7 Hz), 8.46 (1H, dd, J=0.6, 1.7 Hz).

Elemental analysis (for C$_{25}$H$_{17}$N$_3$O$_4$S)
Calculated (%): C, 65.92; H, 3.76; N, 9.23.
Found (%): C, 66.06; H, 3.63; N, 9.30.

EXAMPLE 283

2-methyl-5-[3-[4-(methylthio)-3-(trifluoromethoxy)phenyl]-1-benzofuran-5-yl]-1,3,4-oxadiazole In the same manner as in Example 132 and using [4-(methylthio)-3-(trifluoromethoxy)phenyl]boronic acid instead of (4-fluorophenyl)boronic acid, the title compound (yield 86%) was obtained as colorless crystals.

melting point 185-186° C. (recrystallized from hexane/tetrahydrofuran).

$^1$H NMR (CDCl$_3$) δ 2.54 (3H, s), 2.64 (3H, s), 7.39 (1H, d, J=8.3 Hz), 7.47-7.49 (1H, m), 7.59 (1H, dd, J=1.7, 8.3 Hz), 7.67 (1H, dd, J=0.6, 8.7 Hz), 7.88 (1H, s), 8.09 (1H, dd, J=1.7, 8.7 Hz), 8.43 (1H, dd, J=0.6, 1.7 Hz).

Elemental analysis (for C$_{19}$H$_{13}$F$_3$N$_2$O$_3$S)
Calculated (%): C, 56.16; H, 3.22; N, 6.89.
Found (%): C, 56.16; H, 3.15; N, 6.82.

EXAMPLE 284

2-methyl-5-[3-[4-(methylsulfinyl)-3-(trifluoromethoxy)phenyl]-1-benzofuran-5-yl]-1,3,4-oxadiazole In the same manner as in Example 140 and using 2-methyl-5-[3-[4-(methylthio)-3-(trifluoromethoxy)phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 91%) was obtained as colorless crystals.

melting point 182-183° C. (recrystallized from hexane/acetone).

$^1$H NMR (CDCl$_3$) δ 2.65 (3H, s), 2.88 (3H, s), 7.55-7.57 (1H, m), 7.71 (1H, dd, J=0.6, 8.7 Hz), 7.85 (1H, dd, J=1.5, 8.1 Hz), 7.96 (1H, s), 8.12 (1H, dd, J=1.7, 8.7 Hz), 8.14 (1H, d, J=8.1 Hz), 8.44 (1H, dd, J=0.6, 1.7 Hz).

Elemental analysis (for C$_{19}$H$_{13}$F$_3$N$_2$O$_4$S)
Calculated (%): C, 54.03; H, 3.10; N, 6.63.
Found (%): C, 54.01; H, 3.02; N, 6.61.

EXAMPLE 285

2-methyl-5-[3-[4-(methylsulfonyl)-3-(trifluoromethoxy)phenyl]-1-benzofuran-5-yl]-1,3,4-oxadiazole In the same manner as in Example 140 and using 2-methyl-5-[3-[4-(methylsulfinyl)-3-(trifluoromethoxy)phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 89%) was obtained as colorless crystals.

melting point 218-219° C. (recrystallized from tetrahydrofuran/methanol). $^1$H NMR (CDCl$_3$) δ 2.65 (3H, s), 3.28 (3H, s), 7.68-7.70 (1H, m), 7.72 (1H, dd, J=0.6, 8.7 Hz), 7.78 (1H, dd, J=1.5, 8.3 Hz), 8.01 (1H, s), 8.14 (1H, dd, J=1.7, 8.7 Hz), 8.25 (1H, d, J=8.3 Hz), 8.44 (1H, dd, J=0.6, 1.7 Hz).

Elemental analysis (for C$_{19}$H$_{13}$F$_3$N$_2$O$_5$S)
Calculated (%): C, 52.06; H, 2.99; N, 6.39.
Found (%): C, 51.97; H, 2.93; N, 6.37.

EXAMPLE 286

2-[3-[3-fluoro-4-(methylthio)phenyl]-1-benzofuran-5-yl]-5-methyl-1,3,4-oxadiazole In the same manner as in Example 132 and using [3-fluoro-4-(methylthio)phenyl]boronic acid instead of (4-fluorophenyl)boronic acid, the title compound (yield 90%) was obtained as colorless crystals.

melting point 179-180° C. (recrystallized from hexane/tetrahydrofuran).

$^1$H NMR (CDCl$_3$) δ 2.54 (3H, s), 2.65 (3H, s), 7.32-7.45 (3H, m), 7.66 (1H, dd, J=0.6, 8.7 Hz), 7.87 (1H, s), 8.08 (1H, dd, J=1.7, 8.7 Hz), 8.46 (1H, dd, J=0.6, 1.7 Hz).

Elemental analysis (for C$_{18}$H$_{13}$FN$_2$O$_2$S)
Calculated (%): C, 63.52; H, 3.85; N, 8.23.
Found (%): C, 63.64; H, 3.80; N, 8.18.

EXAMPLE 287

2-[3-[3-fluoro-4-(methylsulfinyl)phenyl]-1-benzofuran-5-yl]-5-methyl-1,3,4-oxadiazole In the same manner as in Example 140 and using 2-[3-[3-fluoro-4-(methylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 90%) was obtained as colorless crystals.

melting point 168-169° C. (recrystallized from hexane/tetrahydrofuran).

$^1$H NMR (CDCl$_3$) δ 2.66 (3H, s), 2.91 (3H, s), 7.43 (1H, dd, J=1.5, 10.4 Hz), 7.68-7.71 (2H, m), 7.96 (1H, s), 8.00 (1H, dd, J=7.4, 7.9 Hz), 8.10 (1H, dd, J=1.7, 8.7 Hz), 8.48 (1H, dd, J=0.6, 1.7 Hz).

Elemental analysis (for C$_{18}$H$_{13}$FN$_2$O$_3$S)
Calculated (%): C, 60.67; H, 3.68; N, 7.86.
Found (%): C, 60.80; H, 3.66; N, 7.77.

EXAMPLE 288

2-[3-[3-fluoro-4-(methylsulfonyl)phenyl]-1-benzofuran-5-yl]-5-methyl-1,3,4-oxadiazole In the same manner as in Example 140 and using 2-[3-[3-fluoro-4-(methylsulfinyl)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 93%) was obtained as colorless crystals.

melting point 199-200° C. (recrystallized from methanol/water).

$^1$H NMR (CDCl$_3$) δ 2.66 (3H, s), 3.30 (3H, s), 7.56 (1H, dd, J=1.5, 10.7 Hz), 7.64 (1H, dd, J=1.5, 8.1 Hz), 7.71 (1H, dd, J=0.6, 8.7 Hz), 8.00 (1H, s), 8.08-8.14 (2H, m), 8.47 (1H, dd, J=0.6, 1.9 Hz).

Elemental analysis (for C$_{18}$H$_{13}$FN$_2$O$_4$S)
Calculated (%): C, 58.06; H, 3.52; N, 7.52.
Found (%): C, 58.06; H, 3.40; N, 7.52.

EXAMPLE 289

2-[3-[4-(ethylthio)-3-fluorophenyl]-1-benzofuran-5-yl]-5-methyl-1,3,4-oxadiazole In the same manner as in Example 132 and using [4-(ethylthio)-3-fluorophenyl]boronic acid instead of (4-fluorophenyl)boronic acid, the title compound (yield 94%) was obtained as colorless crystals.

melting point 115-116° C. (recrystallized from hexane/ethyl acetate).

$^1$H NMR (CDCl$_3$) δ 1.36 (3H, t, J=7.4 Hz), 2.65 (3H, s), 3.00 (2H, q, J=7.4 Hz), 7.35 (1H, dd, J=1.7, 10.4 Hz), 7.41 (1H, dd, J=1.7, 7.9 Hz), 7.49 (1H, t, J=7.7 Hz), 7.66 (1H, dd, J=0.6, 8.7 Hz), 7.88 (1H, s), 8.08 (1H, dd, J=1.7, 8.7 Hz), 8.47 (1H, dd, J=0.6, 1.7 Hz).

Elemental analysis (for C$_{19}$H$_{15}$FN$_2$O$_2$S)
Calculated (%): C, 64.39; H, 4.27; N, 7.90.
Found (%): C, 64.47; H, 4.24; N, 7.80.

EXAMPLE 290

2-[3-[4-(ethylsulfinyl)-3-fluorophenyl]-1-benzofuran-5-yl]-5-methyl-1,3,4-oxadiazole In the same manner as in Example 140 and using 2-[3-[4-(ethylthio)-3-fluorophenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 84%) was obtained as colorless crystals.

melting point 187-188° C. (recrystallized from methanol/water).

$^1$H NMR (CDCl$_3$) δ 1.31 (3H, t, J=7.2 Hz), 2.66 (3H, s), 2.88-3.00 (1H, m), 3.09-3.21 (1H, m), 7.42 (1H, dd, J=1.5, 10.4 Hz), 7.68 (1H, dd, J=1.5, 8.1 Hz), 7.69 (1H, dd, J=0.6, 8.7 Hz), 7.92-7.97 (2H, m), 8.10 (1H, dd, J=1.7, 8.7 Hz), 8.48 (1H, dd, J=0.6, 1.7 Hz).
Elemental analysis (for $C_{19}H_{15}FN_2O_3S$)
Calculated (%): C, 61.61; H, 4.08; N, 7.56.
Found (%): C, 61.71; H, 4.08; N, 7.56.

EXAMPLE 291

2-[3-[4-(ethylsulfonyl)-3-fluorophenyl]-1-benzofuran-5-yl]-5-methyl-1,3,4-oxadiazole In the same manner as in Example 140 and using 2-[3-[4-(ethylsulfinyl)-3-fluorophenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 89%) was obtained as colorless crystals.
melting point 200-201° C. (recrystallized from methanol/water).
$^1$H NMR (CDCl$_3$) δ 1.38 (3H, t, J=7.5 Hz), 2.66 (3H, s), 3.39 (2H, q, J=7.5 Hz), 7.75 (1H, dd, J=1.5, 10.6 Hz), 7.64 (1H, dd, J=1.5, 8.1 Hz), 7.71 (1H, dd, J=0.6, 8.7 Hz), 8.00 (1H, s), 8.08 (1H, dd, J=7.4, 8.1 Hz), 8.12 (1H, dd, J=1.7, 8.7 Hz), 8.48 (1H, dd, J=0.6, 1.7 Hz).
Elemental analysis (for $C_{19}H_{15}FN_2O_4S$)
Calculated (%): C, 59.06; H, 3.91; N, 7.25.
Found (%): C, 58.91; H, 3.78; N, 7.20.

EXAMPLE 292

2-[3-[3-chloro-4-(methylthio)phenyl]-1-benzofuran-5-yl]-5-methyl-1,3,4-oxadiazole In the same manner as in Example 239 and using 3-[3-chloro-4-(methylthio)phenyl]-1-benzofuran-5-carbohydrazide instead of 2-[[4-(methylthio)phenyl]amino]isonicotinohydrazide, the title compound (yield 80%) was obtained as colorless crystals.
melting point 200-201° C. (recrystallized from tetrahydrofuran).
$^1$H NMR (CDCl$_3$) δ 2.55 (3H, s), 2.64 (3H, s), 7.30 (1H, d, J=8.3 Hz), 7.57 (1H, dd, J=1.9, 8.3 Hz), 7.66 (1H, dd, J=0.6, 8.7 Hz), 7.63 (1H, d, J=1.9 Hz), 7.86 (1H, s), 8.07 (1H, dd, J=1.7, 8.7 Hz), 8.45 (1H, dd, J=0.6, 1.7 Hz).
Elemental analysis (for $C_{18}H_{13}ClN_2O_2S$)
Calculated (%): C, 60.59; H, 3.67; N, 7.85.
Found (%): C, 60.68; H, 3.76; N, 7.74.

EXAMPLE 293

2-[3-[3-chloro-4-(methylsulfinyl)phenyl]-1-benzofuran-5-yl]-5-methyl-1,3,4-oxadiazole In the same manner as in Example 140 and using 2-[3-[3-chloro-4-(methylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 86%) was obtained as colorless crystals.
melting point 196-197° C. (recrystallized from methanol).
$^1$H NMR (CDCl$_3$) δ 2.65 (3H, s), 2.90 (3H, s), 7.68-7.71 (2H, m), 7.82 (1H, dd, J=1.7, 8.1 Hz), 7.95 (1H, s), 8.09-8.12 (2H, m), 8.46 (1H, dd, J=0.6, 1.7 Hz).
Elemental analysis (for $C_{18}H_{13}ClN_2O_3S$)
Calculated (%): C, 57.99; H, 3.51; N, 7.51.
Found (%): C, 57.82; H, 3.68; N, 7.47.

EXAMPLE 294

2-[3-[3-chloro-4-(methylsulfonyl)phenyl]-1-benzofuran-5-yl]-5-methyl-1,3,4-oxadiazole In the same manner as in Example 200 and using 2-[3-[3-chloro-4-(methylthio)phenyl]-1-benzofuran-5-yl]-5-methyl-1,3,4-oxadiazole instead of 6-(5-methyl-1,3,4-oxadiazol-2-yl)-1-[4-(methylthio)phenyl]-1H-benzimidazole, the title compound (yield 81%) was obtained as colorless crystals.
melting point 204-205° C. (recrystallized from hexane/tetrahydrofuran).
$^1$H NMR (CDCl$_3$) δ 2.65 (3H, s), 2.90 (3H, s), 7.68-7.71 (2H, m), 7.82 (1H, dd, J=1.7, 8.1 Hz), 7.95 (1H, s), 8.09-8.12 (2H, m), 8.46 (1H, dd, J=0.6, 1.7 Hz).
Elemental analysis (for $C_{18}H_{13}ClN_2O_4S$)
Calculated (%): C, 55.60; H, 3.37; N, 7.20.
Found (%): C, 55.72 H, 3.45; N, 7.12.

EXAMPLE 295

2-methyl-5-[3-[3-methyl-4-(methylthio)phenyl]-1-benzofuran-5-yl]-1,3,4-oxadiazole In the same manner as in Example 132 and using [3-methyl-4-(methylthio)phenyl]boronic acid instead of (4-fluorophenyl)boronic acid, the title compound (yield 84%) was obtained as colorless crystals.
melting point 185-186° C. (recrystallized from tetrahydrofuran/methanol).
$^1$H NMR (CDCl$_3$) δ 2.43 (3H, s), 2.53 (3H, s), 2.64 (3H, s), 7.29 (1H, d, J=8.1 Hz), 7.41 (1H, d, J=1.9 Hz), 7.50 (1H, dd, J=1.9, 8.1 Hz), 7.64 (1H, d, J=8.7 Hz), 7.83 (1H, s), 8.05 (1H, dd, J=1.9, 8.7 Hz), 8.48 (1H, d, J=1.9 Hz).
Elemental analysis (for $C_{19}H_{16}N_2O_2S$)
Calculated (%): C, 67.84; H, 4.79; N, 8.33.
Found (%): C, 67.77; H, 4.74; N, 8.31.

EXAMPLE 296

2-methyl-5-[3-[3-methyl-4-(methylsulfinyl)phenyl]-1-benzofuran-5-yl]-1,3,4-oxadiazole In the same manner as in Example 140 and using 2-methyl-5-[3-[3-methyl-4-(methylthio)phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 89%) was obtained as colorless crystals.
melting point 195-196° C. (recrystallized from methanol/water).
$^1$H NMR (CDCl$_3$) δ 2.49 (3H, s), 2.65 (3H, s), 2.76 (3H, s), 7.49 (1H, d, J=1.5 Hz), 7.68 (1H, dd, J=0.6, 8.7 Hz), 7.73 (1H, dd, J=1.5, 8.1 Hz), 7.91 (1H, s), 8.07 (1H, dd, J=1.7, 8.7 Hz), 8.11 (1H, d, J=8.1 Hz), 8.49 (1H, dd, J=0.6, 1.7 Hz).
Elemental analysis (for $C_{19}H_{16}N_2O_3S$)
Calculated (%): C, 64.76; H, 4.58; N, 7.95.
Found (%): C, 64.69; H, 4.43; N, 7.90.

EXAMPLE 297

2-methyl-5-[3-[3-methyl-4-(methylsulfonyl)phenyl]-1-benzofuran-5-yl]-1,3,4-oxadiazole In the same manner as in Example 140 and using 2-methyl-5-[3-[3-methyl-4-(methylsulfinyl)phenyl]-1-benzofuran-5-yl]-1,3,4-oxadiazole instead of 2-methyl-5-[3-[4-(methylthio)phenyl]-1-benzofuran-5-yl]-1,3,4-oxadiazole, the title compound (yield 88%) was obtained as colorless crystals.

melting point 173-174° C. (recrystallized from methanol/water).

$^1$H NMR (CDCl$_3$) δ 2.65 (3H, s), 2.82 (3H, s), 3.15 (3H, s), 7.62 (1H, d, J=1.5 Hz), 7.66-7.71 (2H, m), 7.95 (1H, s), 8.09 (1H, dd, J=1.7, 8.7 Hz), 8.18 (1H, d, J=8.3 Hz), 8.48 (1H, dd, J=0.6, 1.7 Hz).

Elemental analysis (for C$_{19}$H$_{16}$N$_2$O$_4$S)
Calculated (%): C, 61.94; H, 4.38; N, 7.60.
Found (%): C, 61.89; H, 4.43; N, 7.75.

EXAMPLE 298

2-[3-[2-chloro-4-(methylthio)phenyl]-1-benzofuran-5-yl]-5-methyl-1,3,4-oxadiazole In the same manner as in Example 132 and using [2-chloro-4-(methylthio)phenyl]boronic acid instead of (4-fluorophenyl)boronic acid, the title compound (yield 93%) was obtained as colorless crystals.

melting point 153-154° C. (recrystallized from hexane/tetrahydrofuran).

$^1$H NMR (CDCl$_3$) δ 2.55 (3H, s), 2.62 (3H, s), 7.26 (1H, dd, J=1.9, 8.1 Hz), 7.42 (1H, d, J=1.9 Hz), 7.45 (1H, d, J=8.1 Hz), 7.66 (1H, dd, J=0.6, 8.7 Hz), 7.89 (1H, s), 8.06 (1H, dd, J=1.7, 8.7 Hz), 8.22 (1H, dd, J=0.6, 1.7 Hz).

Elemental analysis (for C$_{18}$H$_{13}$ClN$_2$O$_2$S)
Calculated (%): C, 60.59; H, 3.67; N, 7.85.
Found (%): C, 60.81; H, 3.68; N, 7.72.

EXAMPLE 299

2-[3-[2-chloro-4-(methylsulfinyl)phenyl]-1-benzofuran-5-yl]-5-methyl-1,3,4-oxadiazole In the same manner as in Example 140 and using 2-[3-[2-chloro-4-(methylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 84%) was obtained as colorless crystals.

melting point 175-176° C. (recrystallized from methanol/water).

$^1$H NMR (CDCl$_3$) δ 2.63 (3H, s), 2.84 (3H, s), 7.65 (1H, dd, J=1.9, 7.9 Hz), 7.68-7.74 (2H, m), 7.89 (1H, d, J=1.5 Hz), 7.98 (1H, s), 8.07 (1H, dd, J=1.7, 8.7 Hz), 8.25 (1H, dd, J=0.6, 1.7 Hz).

Elemental analysis (for C$_{18}$H$_{13}$ClN$_2$O$_3$S)
Calculated (%): C, 57.99; H, 3.51; N, 7.51.
Found (%): C, 57.90; H, 3.45; N, 7.42.

EXAMPLE 300

2-[3-[2-chloro-4-(methylsulfonyl)phenyl]-1-benzofuran-5-yl]-5-methyl-1,3,4-oxadiazole In the same manner as in Example 140 and using 2-[3-[2-chloro-4-(methylsulfinyl)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 93%) was obtained as colorless crystals.

melting point 198-199° C. (recrystallized from methanol/water).

$^1$H NMR (CDCl$_3$) δ 2.63 (3H, s), 3.16 (3H, s), 7.71 (1H, dd, J=0.6, 8.7 Hz), 7.78 (1H, d, J=8.1 Hz), 7.97 (1H, dd, J=1.9, 8:1 Hz), 8.02 (1H, s), 8.09 (1H, dd, J=1.7, 8.7 Hz), 8.16 (1H, d, J=1.9 Hz), 8.24 (1H, dd, J=0.6, 1.9 Hz).

Elemental analysis (for C$_{18}$H$_{13}$ClN$_2$O$_4$S)
Calculated (%): C, 55.60; H, 3.37; N, 7.20.
Found (%): C, 55.41; H, 3.32; N, 7.10.

EXAMPLE 301

2-[3-[2-chloro-4-(ethylthio)phenyl]-1-benzofuran-5-yl]-5-methyl-1,3,4-oxadiazole In the same manner as in Example 132 and using [2-chloro-4-(ethylthio)phenyl]boronic acid instead of (4-fluorophenyl)boronic acid, the title compound (yield 95%) was obtained as colorless crystals.

melting point 108-109° C. (recrystallized from hexane/ethyl acetate).

$^1$H NMR (CDCl$_3$) δ 1.40 (3H, t, J=7.4 Hz), 2.62 (3H, s), 3.03 (2H, q, J=7.4 Hz), 7.31 (1H, dd, J=1.9, 7.9 Hz), 7.44 (1H, d, J=7.9 Hz), 7.48 (1H, d, J=1.9 Hz), 7.66 (1H, dd, J=0.6, 8.7 Hz), 7.90 (1H, s), 8.05 (1H, dd, J=1.9, 8.7 Hz), 8.23 (1H, dd, J=0.6, 1.9 Hz).

Elemental analysis (for C$_{19}$H$_{15}$ClN$_2$O$_2$S)
Calculated (%): C, 61.53; H, 4.08; N, 7.55.
Found (%): C, 61.56; H, 4.00; N, 7.55.

EXAMPLE 302

2-[3-[2-chloro-4-(ethylsulfinyl)phenyl]-1-benzofuran-5-yl]-5-methyl-1,3,4-oxadiazole In the same manner as in Example 140 and using 2-[3-[2-chloro-4-(ethylthio)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 92%) was obtained as colorless crystals.

melting point 151-152° C. (crystallized from hexane/ethyl acetate).

$^1$H NMR (CDCl$_3$) δ 1.31 (3H, t, J=7.4 Hz), 2.63 (3H, s), 2.86 (1H, qd, J=7.4, 13.4 Hz), 3.03 (1H, qd, J=7.4, 13.4 Hz), 7.61 (1H, dd, J=1.7, 7.9 Hz), 7.70 (1H, dd, J=0.6, 8.7 Hz), 7.71 (1H, d, J=7.9 Hz), 7.84 (1H, d, J=1.7 Hz), 7.98 (1H, s), 8.07 (1H, dd, J=1.7, 8.7 Hz), 8.25 (1H, dd, J=0.6, 1.7 Hz).

Elemental analysis (for C$_{19}$H$_{15}$ClN$_2$O$_3$S)
Calculated (%): C, 58.99; H, 3.91; N, 7.24.
Found (%): C, 58.96; H, 3.92; N, 7.16.

EXAMPLE 303

2-[3-[2-chloro-4-(ethylsulfonyl)phenyl]-1-benzofuran-5-yl]-5-methyl-1,3,4-oxadiazole In the same manner as in Example 140 and using 2-[3-[2-chloro-4-(ethylsulfinyl)phenyl]-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 90%) was obtained as colorless crystals.

melting point 180-181° C. (recrystallized from methanol).

$^1$H NMR (CDCl$_3$) δ 1.39 (3H, t, J=7.5 Hz), 2.63 (3H, s), 3.23 (2H, q, J=7.5 Hz), 7.71 (1H, dd, J=0.6, 8.9 Hz), 7.78 (1H, d, J=8.1 Hz), 7.93 (1H, dd, J=1.9, 8.1 Hz), 8.02 (1H, s), 8.09 (1H, dd, J=1.9, 8.9 Hz), 8.12 (1H, d, J=1.9 Hz), 8.25 (1H, dd, J=0.6, 1.9 Hz).

Elemental analysis (for C$_{19}$H$_{15}$ClN$_2$O$_4$S)
Calculated (%): C, 56.65; H, 3.75; N, 6.95.
Found (%): C, 56.57; H, 3.71; N, 6.93.

EXAMPLE 304

2-[3-(3,3-dimethyl-2,3-dihydro-1-benzothien-5-yl)-1-benzofuran-5-yl]-5-methyl-1,3,4-oxadiazole In the same manner as in Example 132 and using (3,3-dimethyl-2,3-dihydro-1-benzothien-5-yl)boronic acid instead of (4-fluorophenyl)boronic acid, the title compound (yield 91%) was obtained as colorless crystals.

melting point 159-160° C. (recrystallized from hexane/tetrahydrofuran).

$^1$H NMR (CDCl$_3$) δ 1.45 (6H, s), 2.63 (3H, s), 3.26 (2H, s), 7.26 (1H, d, J=1.7 Hz), 7.33 (1H, d, J=7.9 Hz), 7.44 (1H, dd, J=1.7, 7.9 Hz), 7.64 (1H, dd, J=0.6, 8.7 Hz), 7.83 (1H, s), 8.06 (1H, dd, J=1.7, 8.7 Hz), 8.43 (1H, dd, J=0.6, 1.7 Hz).

Elemental analysis (for $C_{21}H_{18}N_2O_2S$)

Calculated (%): C, 69.59; H, 5.01; N, 7.73.

Found (%): C, 69.59; H, 4.95; N, 7.75.

EXAMPLE 305

2-[3-(3,3-dimethyl-1-oxido-2,3-dihydro-1-benzothien-5-yl)-1-benzofuran-5-yl]-5-methyl-1,3,4-oxadiazole In the same manner as in Example 140 and using 2-[3-(3,3-dimethyl-2,3-dihydro-1-benzothien-5-yl)-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 89%) was obtained as colorless crystals.

melting point 179-180° C. (crystallized from methanol).

$^1$H NMR (CDCl$_3$) δ 1.50 (3H, s), 1.70 (3H, s), 2.64 (3H, s), 3.23 (1H, d, J=13.4 Hz), 3.37 (1H, d, J=13.4 Hz), 7.57 (1H, d, J=1.5 Hz), 7.69 (1H, dd, J=0.6, 8.7 Hz), 7.76 (1H, dd, J=1.5, 7.9 Hz), 7.95 (1H, s), 7.97 (1H, d, J=7.9 Hz), 8.10 (1H, dd, J=1.7, 8.7 Hz), 8.43 (1H, dd, J=0.6, 1.7 Hz).

Elemental analysis (for $C_{21}H_{18}N_2O_3S \cdot 0.25H_2O$)

Calculated (%): C, 65.86; H, 4.87; N, 7.32.

Found (%): C, 65.76; H, 4.82; N, 7.43.

EXAMPLE 306

2-[3-(3,3-dimethyl-1,1-dioxido-2,3-dihydro-1-benzothien-5-yl)-1-benzofuran-5-yl]-5-methyl-1,3,4-oxadiazole In the same manner as in Example 140 and using 2-[3-(3,3-dimethyl-1-oxido-2,3-dihydro-1-benzothien-5-yl)-1-benzofuran-5-yl]-5-methyl-1,3,4-oxadiazole instead of 2-methyl-5-[3-[4-(methylthio)phenyl]-1-benzofuran-5-yl]-1,3,4-oxadiazole, the title compound (yield 92%) was obtained as colorless crystals.

melting point 242-243° C. (recrystallized from hexane/tetrahydrofuran).

$^1$H NMR (CDCl$_3$) δ 1.64 (6H, s), 2.64 (3H, s), 3.43 (2H, s), 7.66 (1H, dd, J=0.6, 1.3 Hz), 7.70 (1H, dd, J=0.6, 8.7 Hz), 7.78 (1H, dd, J=1.3, 8.1 Hz), 7.86 (1H, dd, J=0.6, 8.1 Hz), 7.96 (1H, s), 8.11 (1H, dd, J=1.7, 8.7 Hz), 8.41 (1H, dd, J=0.6, 1.7 Hz).

Elemental analysis (for $C_{21}H_{18}N_2O_4S$)

Calculated (%): C, 63.94; H, 4.60; N, 7.10.

Found (%): C, 63.99; H, 4.61; N, 7.02.

EXAMPLE 307 optically active form of 2-methyl-5-[3-[4-(methylsulfinyl)phenyl]-1-benzofuran-5-yl]-1,3,4-oxadiazole (short retention time)

EXAMPLE 308 optically active form of 2-methyl-5-[3-[4-(methylsulfinyl)phenyl]-1-benzofuran-5-yl]-1,3,4-oxadiazole (long retention time)

2-Methyl-5-[3-[4-(methylsulfinyl)phenyl]-1-benzofuran-5-yl]-1,3,4-oxadiazole (1 g) was optically resolved by preparative HPLC to give an optically active form (485 mg, recovery rate 97%) having a short retention time and an optically active form (488 mg, recovery rate 98%) having a long retention time.

The optical resolution by preparative HPLC was performed under the following conditions.

column: CHIRALPAK AS 50 mmID×500 mmL
mobile phase: ethanol
flow rate: 45 mL/min
temperature: 25° C.
detection: UV 254 nm
concentration: 4 mg/mL (ethanol)
injection volume: 50 mL The analysis conditions and analysis results of the separated fractions are as follows.

column: CHIRALPAK AS 4.6 mmID×250 mmL
mobile phase: ethanol
flow rate: 0.4 mL/min
temperature: 30° C.
detection: UV 254 nm
concentration: 0.2 mg/mL (ethanol)
injection volume: 10 µL
retention time: 17.9 min (short retention time), 25.4 min (long retention time)
enantiomer excess: >99.9% (short retention time), >99.9% (long retention time)

Each of the obtained optically active forms was purified by basic silica gel column chromatography (tetrahydrofuran) and crystallized from ethyl acetate to give an optically active form (471.2 mg) having a short retention time and an optically active form (467.7 mg) having a long retention time, both as colorless crystals.

melting point 170-171° C.

EXAMPLE 309 optically active form of 2-[3-[4-(ethylsulfinyl)phenyl]-5-methyl-1-benzofuran-5-yl]-1,3,4-oxadiazole (short retention time)

EXAMPLE 310 optically active form of 2-[3-[4-(ethylsulfinyl)phenyl]-5-methyl-1-benzofuran-5-yl]-1,3,4-oxadiazole (long retention time)

2-[3-[4-(Ethylsulfinyl)phenyl]-5-methyl-1-benzofuran-5-yl]-1,3,4-oxadiazole (530 mg) was optically resolved by preparative HPLC to give an optically active form (249 mg, recovery rate 94%) having a short retention time and an optically active form (245 mg, recovery rate 92%) having a long retention time.

The optical resolution by preparative HPLC was performed under the following conditions.
column: CHIRALCEL OJ 50 mmID×500 mmL
mobile phase: hexane/ethanol=50/50
flow rate: 80 mL/min
temperature: 30° C.
detection: UV 254 nm
concentration: 2.5 mg/mL (ethanol)
injection volume: 80 mL The analysis conditions and analysis results of the separated fractions are as follows.
column: CHIRALCEL OJ 4.6 mmID×250 mmL
mobile phase: hexane/ethanol=50/50
flow rate: 0.5 mL/min
temperature: 30° C.
detection: UV 254 nm
concentration: 0.5 mg/mL (hexane/ethanol=50/50)
injection volume: 10 μL
retention time: 19.8 min (short retention time), 30.5 min (long retention time)
enantiomer excess: >99.9% (short retention time), >99.9% (long retention time)

Each of the obtained optically active forms was purified by basic silica gel column chromatography (ethyl acetate) and recrystallized from hexane/ethyl acetate to give an optically active form (210 mg) having a short retention time and an optically active form (190 mg) having a long retention time, both as colorless crystals.
melting point 172-173° C.

EXAMPLE 311 optically active form of 2-[3-[2-chloro-4-(methylsulfinyl)phenyl]-1-benzofuran-5-yl]-5-methyl-1,3,4-oxadiazole (short retention time)

EXAMPLE 312 optically active form of 2-[3-[2-chloro-4-(methylsulfinyl)phenyl]-1-benzofuran-5-yl]-5-methyl-1,3,4-oxadiazole (long retention time)

2-[3-[2-Chloro-4-(methylsulfinyl)phenyl]-1-benzofuran-5-yl]-5-methyl-1,3,4-oxadiazole (240 mg) was optically resolved by preparative HPLC to give an optically active form (116.9 mg, recovery rate 97%) having a short retention time and an optically active form (119.0 mg, recovery rate 99%) having a long retention time.

The optical resolution by preparative HPLC was performed under the following conditions.
column: CHIRALPAK AS 50 mmID×500 mmL
mobile phase: ethanol
flow rate: 40 mL/min
temperature: 25° C.
detection: UV 220 nm
concentration: 4 mg/mL (ethanol)
injection volume: 15 mL The analysis conditions and analysis results of the separated fractions are as follows.
column: CHIRALPAK AS 4.6 mmID×250 mmL
mobile phase: ethanol
flow rate: 0.3 mL/min
temperature: 25° C.
detection: UV 220 nm
concentration: 0.5 mg/mL (ethanol)
injection volume: 10 μL
retention time: 27.6 min (short retention time), 37.0 min (long retention time)
enantiomer excess: 99.2% (short retention time), 99.7% (long retention time)

Each of the obtained optically active forms was purified by basic silica gel column chromatography (tetrahydrofuran) and recrystallized from methanol to give an optically active form (91.0 mg) having a short retention time and an optically active form (92.9 mg) having a long retention time, both as colorless crystals.
melting point 195-196° C.

EXAMPLE 313 optically active form of 2-[3-[2-chloro-4-(ethylsulfinyl)phenyl]-1-benzofuran-5-yl]-5-methyl-1,3,4-oxadiazole (short retention time)

EXAMPLE 314 optically active form of 2-[3-[2-chloro-4-(ethylsulfinyl)phenyl]-1-benzofuran-5-yl]-5-methyl-1,3,4-oxadiazole (long retention time)

2-[3-[2-Chloro-4-(ethylsulfinyl)phenyl]-1-benzofuran-5-yl]-5-methyl-1,3,4-oxadiazole (230 mg) was optically resolved by preparative HPLC to give an optically active form (enantiomer excess 94.5%) having a short retention time and an optically active form (enantiomer excess 83.2%) having a long retention time.

The optical resolution by preparative HPLC was performed under the following conditions.
column: CHIRALPAK AS 50 mmID×500 mmL
mobile phase: ethanol
flow rate: 40 mL/min
temperature: 25° C.
detection: UV 220 nm
concentration: 1 mg/mL (ethanol)
injection volume: 30 mL Each of the obtained optically active forms was purified again by preparative HPLC to give an optically active form (102.4 mg, recovery rate 89%) having a short retention time and an optically active form (86.6 mg, recovery rate 77%) having a long retention time.

The optically active form having a short retention time was purified by preparative HPLC under the conditions similar to the above.

The optically active form having a long retention time was purified by preparative HPLC under the following conditions.
column: CHIRALCEL OJ 50 mmID×500 mmL
mobile phase: hexane/ethanol=70/30
flow rate: 70 mL/min
temperature: 30° C.
detection: UV 220 nm
concentration: 0.5 mg/mL (ethanol)
injection volume: 65 mL The analysis conditions and analysis results of the separated fractions are as follows.
column: CHIRALPAK AS 4.6 mmID×250 mmL
mobile phase: ethanol
flow rate: 0.3 mL/min
temperature: 25° C.
detection: UV 220 nm
concentration: 0.1 mg/mL (ethanol)
injection volume: 10 μL
retention time: 23.4 min (short retention time), 30.0 min (long retention time)
enantiomer excess: 98.9% (short retention time), 99.3% (long retention time)

Each of the obtained optically active forms was purified by basic silica gel column chromatography (tetrahydrofuran) and recrystallized from hexane/ethyl acetate to give an optically active form (78.8 mg) having a short retention time and an optically active form (78.6 mg) having a long retention time, both as colorless crystals.

melting point 145-146° C.

EXAMPLE 315 optically active form of 2-[3-[3-fluoro-4-(methyl-sulfinyl)phenyl]-1-benzofuran-5-yl]-5-methyl-1,3,4-oxadiazole (short retention time)

EXAMPLE 316 optically active form of 2-[3-[3-fluoro-4-(methyl-sulfinyl)phenyl]-1-benzofuran-5-yl]-5-methyl-1,3,4-oxadiazole (long retention time)

2-[3-[3-Fluoro-4-(methylsulfinyl)phenyl]-1-benzofuran-5-yl]-5-methyl-1,3,4-oxadiazole (600 mg) was optically resolved by preparative HPLC to give an optically active form (295 mg, recovery rate 98%) having a short retention time and an optically active form (290 mg, recovery rate 97%) having a long retention time.

The optical resolution by preparative HPLC was performed under the following conditions.
column: CHIRALPAK AD 50 mmID×500 mmL
mobile phase: ethanol
flow rate: 40 mL/min
temperature: 40° C.
detection: UV 220 nm
concentration: 2 mg/mL (ethanol)
injection volume: 60 mL The analysis conditions and analysis results of the separated fractions are as follows.
column: CHIRALPAK AD-H 4.6 mmID×250 mmL
mobile phase: ethanol
flow rate: 0.5 mL/min
temperature: 35° C.
detection: UV 220 nm
concentration: 0.1 mg/mL (ethanol)
injection volume: 10 μL
retention time: 18.9 min (short retention time), 25.6 min (long retention time)
enantiomer excess: >99.9% (short retention time), >99.9% (long retention time)

Each of the obtained optically active forms was purified by basic silica gel column chromatography (tetrahydrofuran) and recrystallized from ethyl acetate to give an optically active form (262.7 mg) having a short retention time and an optically active form (283.7 mg) having a long retention time, both as colorless crystals.

melting point 168-169° C.

EXAMPLE 317 optically active form of 2-methyl-5-[3-[4-(methyl-sulfinyl)-3-(trifluoromethoxy)phenyl]-1-benzofuran-5-yl]-1,3,4-oxadiazole (short retention time)

EXAMPLE 318 optically active form of 2-methyl-5-[3-[4-(methyl-sulfinyl)-3-(trifluoromethoxy)phenyl]-1-benzofuran-5-yl]-1,3,4-oxadiazole (long retention time)

2-Methyl-5-[3-[4-(methylsulfinyl)-3-(trifluoromethoxy)phenyl]-1-benzofuran-5-yl]-1,3,4-oxadiazole (390 mg) was optically resolved by preparative HPLC to give an optically active form (168.1 mg, recovery rate 86%) having a short retention time and an optically active form (167.5 mg, recovery rate 86%) having a long retention time.

The optical resolution by preparative HPLC was performed under the following conditions.
column: CHIRALPAK AD 50 mmID×500 mmL
mobile phase: ethanol
flow rate: 40 mL/min
temperature: 30° C.
detection: UV 220 nm
concentration: 2 mg/mL (ethanol)
injection volume: 65 mL The analysis conditions and analysis results of the separated fractions are as follows.
column: CHIRALPAK AD 4.6 mmID×250 mmL
mobile phase: ethanol
flow rate: 0.3 mL/min
temperature: 30° C.
detection: UV 220 nm
concentration: 1.0 mg/mL (ethanol)
injection volume: 10 μL
retention time: 16.9 min (short retention time), 25.0 min (long retention time)
enantiomer excess: 99.9% (short retention time), 99.1% (long retention time)

Each of the obtained optically active forms was purified by basic silica gel column chromatography (ethyl acetate) and recrystallized from hexane/acetone to give an optically active form (158.2 mg) having a short retention time and an optically active form (140.5 mg) having a long retention time, both as colorless crystals.

melting point 200-201° C.

EXAMPLE 319

4-[5-(5-methyl-1,3,4-oxadiazol-2-yl)-1-benzofuran-3-yl]phenol

In the same manner as in Example 132 and using (4-hydroxyphenyl)boronic acid instead of (4-fluorophenyl)boronic acid, the title compound (yield 95%) was obtained as colorless crystals.

melting point 226-227° C. (recrystallized from hexane/tetrahydrofuran).

$^1$H NMR (DMSO-$d_6$) δ 2.60 (3H, s), 6.95 (2H, d, J=8.3 Hz), 7.56 (2H, d, J=8.3 Hz), 7.86 (1H, d, J=8.7 Hz), 8.00 (1H, dd, J=1.7, 8.7 Hz), 8.36 (2H, s).

Elemental analysis (for $C_{17}H_{12}N_2O_3 \cdot 0.2H_2O$)
Calculated (%): C, 69.01; H, 4.22; N, 9.47.
Found (%): C, 69.18; H, 4.16; N, 9.33.

EXAMPLE 320

4-[5-(5-methyl-1,3,4-oxadiazol-2-yl)-1-benzofuran-3-yl]phenyl methanesulfonate

A suspension of 4-[5-(5-methyl-1,3,4-oxadiazol-2-yl)-1-benzofuran-3-yl]phenol (351 mg, 1.20 mmol), methanesulfonyl chloride (0.111 mL, 1.44 mmol) and potassium carbonate (332 mg, 2.40 mmol) in N,N-dimethylformamide (5 mL) was stirred at room temperature for 2 hr and at 60° C. overnight. The reaction mixture was diluted with ethyl acetate. The mixture was washed with water and saturated brine, dried over anhydrous magnesium sulfate and concentrated under reduced pressure. The residue was purified by basic silica gel column chromatography (hexane/ethyl acetate=10/1-1/1)

and recrystallized from hexane/ethyl acetate to give the title compound (107 mg, yield 24%) as colorless crystals.

melting point 139-140° C.

$^1$H NMR (CDCl$_3$) δ 2.65 (3H, s), 3.22 (3H, s), 7.44 (2H, d, J=8.7 Hz), 7.59-7.77 (3H, m), 7.87 (1H, s), 8.08 (1H, dd, J=1.5, 8.7 Hz), 8.46 (1H, s).

Elemental analysis (for C$_{18}$H$_{14}$N$_2$O$_5$S)
Calculated (%): C, 58.37; H, 3.81; N, 7.56.
Found (%): C, 58.42; H, 3.77; N, 7.58.

EXAMPLE 321

2-methyl-5-[3-[4-[(methylthio)methoxy]phenyl]-1-benzofuran-5-yl]-1,3,4-oxadiazole To a solution of 4-[5-(5-methyl-1,3,4-oxadiazol-2-yl)-1-benzofuran-3-yl]phenol (1.17 g, 4.00 mmol) in N,N-dimethylformamide (15 mL) was added sodium hydride (60% in oil, 0.320 g, 8.00 mmol) at room temperature, and the resulting mixture was stirred for 15 min. (Chloromethyl) methyl sulfide (90%, 0.744 mL, 8.00 mmol) was added to the reaction mixture, and the resulting mixture was further stirred for 1 hr. The reaction mixture was diluted with ethyl acetate, washed twice with water and once with saturated brine, dried over anhydrous magnesium sulfate and concentrated under reduced pressure. The residue was purified by basic silica gel column chromatography (hexane/ethyl acetate=2/1) and recrystallized from methanol to give the title compound (1.22 g, yield 87%) as colorless crystals.

melting point 116-117° C.

$^1$H NMR (CDCl$_3$) δ 2.30 (3H, s), 2.63 (3H, s), 5.22 (2H, s), 7.08-7.13 (2H, m), 7.58-7.65 (3H, m), 7.81 (1H, s), 8.05 (1H, dd, J=1.7, 8.7 Hz), 8.17 (1H, dd, J=0.6, 1.7 Hz).

Elemental analysis (for C$_{19}$H$_{16}$N$_2$O$_3$S)
Calculated (%): C, 64.76; H, 4.58; N, 7.95.
Found (%): C, 64.40; H, 4.62; N, 7.87.

EXAMPLE 322

2-methyl-5-[3-[4-[(methylsulfonyl)methoxy]phenyl]-1-benzofuran-5-yl]-1,3,4-oxadiazole In the same manner as in Reference Example 151 and using 2-methyl-5-[3-[3-(methylthio)phenyl]-1-benzofuran-5-yl]-1,3,4-oxadiazole instead of 2-methyl-5-[3-[4-[(methylthio)methoxy]phenyl]-1-benzofuran-5-yl]-1,3,4-oxadiazole, the title compound (yield 29%) was obtained as colorless crystals.

melting point 198-199° C. (recrystallized from methanol).

$^1$H NMR (CDCl$_3$) δ 2.64 (3H, s), 3.07 (3H, s), 5.06 (2H, s), 7.19-7.24 (2H, m), 7.61-7.67 (3H, m), 7.83 (1H, s), 8.06 (1H, dd, J=1.7, 8.7 Hz), 8.45 (1H, dd, J=0.6, 1.7 Hz).

Elemental analysis (for C$_{19}$H$_{16}$N$_2$O$_5$S)
Calculated (%): C, 59.37; H, 4.20; N, 7.29.
Found (%): C, 59.23; H, 4.17; N, 7.29.

EXAMPLE 323

2-methyl-5-[3-[4-[(methylsulfinyl)methoxy]phenyl]-1-benzofuran-5-yl]-1,3,4-oxadiazole The eluate obtained after elution of 2-methyl-5-[3-[4-[(methylsulfonyl)methoxy]phenyl]-1-benzofuran-5-yl]-1,3,4-oxadiazole by column purification (basic silica gel, ethyl acetate) in Example 322 was recrystallized from methanol to give the title compound (yield 56%) as colorless crystals.

melting point 155-156° C. (recrystallized from methanol).

$^1$H NMR (CDCl$_3$) δ 2.64 (3H, s), 2.75 (3H, s), 4.98 (1H, d, J=10.4 Hz), 5.10 (1H, d, J=10.4 Hz), 7.19-7.24 (2H, m), 7.60-7.67 (3H, m), 7.82 (1H, s), 8.06 (1H, dd, J=1.7, 8.7 Hz), 8.45 (1H, dd, J=0.6, 1.7 Hz).

Elemental analysis (for C$_{19}$H$_{16}$N$_2$O$_4$S)
Calculated (%): C, 61.94; H, 4.38; N, 7.60.
Found (%): C, 61.68; H, 4.36; N, 7.59.

EXAMPLE 324

2-methyl-5-[3-[4-[2-(methylthio)ethoxy]phenyl]-1-benzofuran-5-yl]-1,3,4-oxadiazole A suspension of 4-[5-(5-methyl-1,3,4-oxadiazol-2-yl)-1-benzofuran-3-yl]phenol (693 mg, 2.37 mmol), 1-chloro-2-(methylthio)ethane (1.18 mL, 11.9 mmol), sodium iodide (355 mg, 2.37 mmol) and potassium carbonate (1.64 g, 11.9 mmol) in N,N-dimethylformamide (10 mL) was stirred at 90° C. overnight. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=10/1-1/1) and recrystallized from hexane/ethyl acetate to give the title compound (452 mg, yield 52%) as colorless crystals.

melting point 89-90° C.

$^1$H NMR (CDCl$_3$) δ 2.25 (3H, s), 2.64 (3H, s), 2.94 (2H, t, J=6.8 Hz), 4.24 (2H, t, J=6.8 Hz), 6.95-7.10 (2H, m), 7.51-7.61 (2H, m), 7.64 (1H, d, J=8.7 Hz), 7.81 (1H, s), 8.04 (1H, dd, J=1.5, 8.7 Hz), 8.48 (1H, d, J=1.5 Hz).

Elemental analysis (for C$_{20}$H$_{18}$N$_2$O$_3$S)
Calculated (%): C, 65.55; H, 4.95; N, 7.64.
Found (%): C, 65.46; H, 4.89; N, 7.65.

EXAMPLE 325

2-methyl-5-[3-[4-[2-(methylsulfinyl)ethoxy]phenyl]-1-benzofuran-5-yl]-1,3,4-oxadiazole To a mixture of 2-methyl-5-[3-[4-[2-(methylthio)ethoxy]phenyl]-1-benzofuran-5-yl]-1,3,4-oxadiazole (186 mg, 0.51 mmol), N,N-dimethylacetamide (2.5 mL) and acetonitrile (2.5 mL) was added m-chloroperbenzoic acid (122 mg, 0.51 mmol) at room temperature, and the resulting mixture was stirred for 2 hr. A saturated aqueous sodium thiosulfate solution was added to the reaction mixture, and the mixture was stirred for 30 min and extracted with ethyl acetate. The organic layer was washed with saturated aqueous sodium hydrogen carbonate solution and saturated brine, dried over anhydrous magnesium sulfate and concentrated under reduced pressure. The residue was purified by basic silica gel column chromatography (hexane/ethyl acetate=10/1-0/1) and recrystallized from hexane/ethyl acetate to give the title compound (53.0 mg, yield 27%) as colorless crystals.

melting point 163-164° C.

$^1$H NMR (CDCl$_3$) δ 2.64 (3H, s), 2.73 (3H, s), 3.00-3.36 (2H, m), 4.39 (2H, m), 7.07 (2H, d, J=8.7 Hz), 7.54-7.69 (3H, m), 7.81 (1H, s), 8.05 (1H, dd, J=1.9, 8.7 Hz), 8.47 (1H, s).

EXAMPLE 326

2-methyl-5-[3-[4-[2-(methylsulfonyl)ethoxy]phenyl]-1-benzofuran-5-yl]-1,3,4-oxadiazole In the same manner as in Example 200 and using 2-methyl-5-[3-[4-[2-(methylthio)ethoxy]phenyl]-1-benzofuran-5-yl]-1,3,4-oxadiazole instead of 6-(5-methyl-1,3,4-oxadiazol-2- yl)-1-[4-(methylthio)phenyl]-1H-benzimidazole, the title compound (yield 77%) was obtained as colorless crystals.

melting point 132-133° C. (recrystallized from hexane/ethyl acetate).

$^1$H NMR (CDCl$_3$) δ 2.64 (3H, s), 3.11 (3H, s), 3.50 (2H, t, J=5.3 Hz), 4.53 (2H, t, J=5.3 Hz), 7.06 (2H, d, J=8.7 Hz), 7.54-7.69 (3H, m), 7.82 (1H, s), 8.04 (1H, d, J=8.3 Hz), 8.47 (1H, s).

Elemental analysis (for C$_{20}$H$_{18}$N$_2$O$_5$S)
Calculated (%): C, 60.29; H, 4.55; N, 7.03.
Found (%): C, 60.10; H, 4.47; N, 6.95.

EXAMPLE 327

2-methyl-5-[3-[4-[(methylsulfonyl)methyl]phenyl]-1-benzofuran-5-yl]-1,3,4-oxadiazole To a solution of [4-[5-(5-methyl-1,3,4-oxadiazol-2-yl)-1-benzofuran-3-yl]phenyl]methanol (204 mg, 0.66 mmol) in 1,2-dichloroethane (5 mL) was added thionyl chloride (0.240 mL, 3.33 mmol), and the resulting mixture was heated under reflux for 1 hr. After cooling, the reaction mixture was concentrated under reduced pressure to give crude 2-[3-[4-(chloromethyl)phenyl]-1-benzofuran-5-yl]-5-methyl-1,3,4-oxadiazole as yellow crystals.

A mixture of the obtained crude 2-[3-[4-(chloromethyl)phenyl]-1-benzofuran-5-yl]-5-methyl-1,3,4-oxadiazole, sodium methanesulfinate (210 mg, 2.00 mmol), tetrahydrofuran (5 mL) and ethanol (20 mL) was heated under reflux for 4 hr. After cooling, the reaction mixture was diluted with chloroform, washed with water and saturated brine, is dried over anhydrous sodium sulfate, and concentrated under reduced pressure. The residue was purified by silica gel column chromatography (hexane/ethyl acetate=10/1-1/1) and recrystallized from hexane/ethyl acetate to give the title compound (136 mg, yield 56%) as colorless crystals.

melting point 250-251° C.

$^1$H NMR (DMSO-d$_6$) δ 2.61 (3H, s), 2.94 (3H, s), 4.58 (2H, s), 7.60 (2H, d, J=8.4 Hz), 7.81 (2H, d, J=8.4 Hz), 7.91 (1H, d, J=8.7 Hz), 8.04 (1H, dd, J=1.5, 7.2 Hz), 8.43 (1H, d, J=1.5 Hz), 8.56 (1H, s).

Elemental analysis (for C$_{19}$H$_{16}$N$_2$O$_4$S.0.5H$_2$O)
Calculated (%): C, 60.46; H, 4.54; N, 7.42.
Found (%): C, 60.76; H, 4.35; N, 7.28.

EXAMPLE 328

4-[5-(5-methyl-1,3,4-oxadiazol-2-yl)-1-benzofuran-3-yl]phenyl trifluoromethanesulfonate To a solution of 4-[5-(5-methyl-1,3,4-oxadiazol-2-yl)-1-benzofuran-3-yl]phenol (380 mg, 1.30 mmol) and N-phenylbis(trifluoromethanesulfonimide) (511 mg, 1.43 mmol) in tetrahydrofuran (15 mL) was added sodium hydride (60% in oil, 57.2 mg, 1.43 mmol) by small portions at room temperature, and the resulting mixture was stirred for 30 min. The reaction mixture was diluted with ethyl acetate, washed with water and saturated brine, dried over anhydrous magnesium sulfate and concentrated under reduced pressure. The residue was purified by basic silica gel column chromatography (hexane/tetrahydrofuran=1/2) and recrystallized from hexane/tetrahydrofuran to give the title compound (507 mg, yield 92%) as colorless crystals.

melting point 136-137° C.

$^1$H NMR (CDCl$_3$) δ 2.65 (3H, s), 7.41-7.46 (2H, m), 7.68 (1H, dd, J=0.6, 8.7 Hz), 7.72-7.77 (2H, m), 7.90 (1H, s), 8.09 (1H, dd, J=1.7, 8.7 Hz), 8.46 (1H, dd, J=0.6, 1.7 Hz).

Elemental analysis (for C$_{18}$H$_{11}$F$_3$N$_2$O$_5$S)
Calculated (%): C, 50.95; H, 2.61; N, 6.60.
Found (%): C, 51.04; H, 2.56; N, 6.63.

EXAMPLE 329 dimethyl[4-[5-(5-methyl-1,3,4-oxadiazol-2-yl)-1-benzofuran-3-yl]phenyl]phosphonate A solution of 4-[5-(5-methyl-1,3,4-oxadiazol-2-yl)-1-benzofuran-3-yl]phenyl trifluoromethanesulfonate (391 mg, 0.900 mmol), dimethyl phosphite (0.165 mL, 1.80 mmol), tetrakis(triphenylphosphine)palladium(0) (104 mg, 0.0900 mmol) and N,N-diisopropylethylamine (0.314 mL, 1.80 mmol) in toluene (5 mL) was stirred at 100° C. for 2 hr under an argon atmosphere. After cooling, the reaction mixture was diluted with ethyl acetate, washed with 1M hydrochloric acid and saturated brine, dried over anhydrous magnesium sulfate and concentrated under reduced pressure. The residue was purified by basic silica gel column chromatography (ethyl acetate) and recrystallized from hexane/ethyl acetate to give the title compound (190 mg, yield 55%) as colorless crystals.

melting point 168-169° C.

$^1$H NMR (CDCl$_3$) δ 2.65 (3H, s), 3.82 (6H, d, J=11.1 Hz), 7.68 (1H, dd, J=0.6, 8.7 Hz), 7.76-7.81 (2H, m), 7.91-7.99 (3H, m), 8.09 (1H, dd, J=1.7, 8.7 Hz), 8.50 (1H, dd, J=0.6, 1.7 Hz).

Elemental analysis (for C$_{19}$H$_{17}$N$_2$O$_5$P)
Calculated (%): C, 59.38; H, 4.46; N, 7.29.
Found (%): C, 59.40; H, 4.41; N, 7.26.

EXAMPLE 330

1-[4-[5-(5-methyl-1,3,4-oxadiazol-2-yl)-1-benzofuran-3-yl]phenyl]ethanone

In the same manner as in Example 132 and using (4-acetylphenyl)boronic acid instead of (4-fluorophenyl)boronic acid, the title compound (yield 79%) was obtained as colorless crystals.

melting point 197-198° C. (recrystallized from hexane/tetrahydrofuran).

$^1$H NMR (CDCl$_3$) δ 2.65 (3H, s), 2.67 (3H, s), 7.69 (1H, dd, J=0.6, 8.7 Hz), 7.75-7.80 (2H, m), 7.96 (1H, s), 8.06-8.14 (3H, m), 8.50-8.56 (1H, m).

Elemental analysis (for C$_{19}$H$_{14}$N$_2$O$_3$)
Calculated (%): C, 71.69; H, 4.43; N, 8.80.
Found (%): C, 71.62; H, 4.42; N, 8.74.

EXAMPLE 331

1-[4-[5-(5-methyl-1,3,4-oxadiazol-2-yl)-1-benzofuran-3-yl]phenyl]ethanol

To a solution of 1-[4-[5-(5-methyl-1,3,4-oxadiazol-2-yl)-1-benzofuran-3-yl]phenyl]ethanone (0.30 g, 0.94 mmol) in ethanol (3 mL) was added sodium borohydride (90%, 59 mg, 1.41 mmol) at 0° C., and the resulting mixture was stirred overnight at room temperature. The reaction mixture was concentrated under reduced pressure, water was added to the residue, and the mixture was extracted with ethyl acetate. The organic layer was washed with saturated brine, dried over anhydrous magnesium sulfate and concentrated under reduced pressure. The residue was purified by basic silica gel column chromatography (hexane/ethyl acetate=1/2-1/3) and recrystallized from hexane/ethyl acetate to give the title compound (0.23 g, yield 76%) as colorless crystals.

melting point 148-149° C.

¹H NMR (CDCl₃) δ 1.57 (3H, d, J=6.4 Hz), 1.86-1.94 (1H, m), 2.57-2.68 (3H, m), 4.94-5.05 (1H, m), 7.53 (2H, d, J=7.9 Hz), 7.61-7.69 (3H, m), 7.86 (1H, s), 8.05 (1H, dd, J=1.5, 8.7 Hz), 8.49 (1H, d, J=1.5 Hz).

Elemental analysis (for C₁₉H₁₆N₂O₃)

Calculated (%): C, 71.24; H, 5.03; N, 8.74.

Found (%): C, 71.26; H, 5.03; N, 8.72.

EXAMPLE 332

2-fluoro-N-methyl-4-[5-(5-methyl-1,3,4-oxadiazol-2-yl)-1-benzofuran-3-yl]benzamide In the same manner as in Example 117 and using 2-fluoro-4-[5-(5-methyl-1,3,4-oxadiazol-2-yl)-1-benzofuran-3-yl]benzoic acid instead of 3-[5-(2,3-dihydro-1-benzofuran-5-yl)-1,3,4-oxadiazol-2-yl]propionic acid and 2M methylamine-tetrahydrofuran solution instead of N,O-dimethylhydroxyamine hydrochloride, the title compound (yield 54%) was obtained as pale-yellow crystals.

melting point 183-184° C. (recrystallized from hexane/ethyl acetate).

¹H NMR (DMSO-d₆) δ 2.61 (3H, s), 2.82 (3H, d, J=4.3 Hz), 7.67-7.75 (2H, m), 7.82 (1H, t, J=7.9 Hz), 7.89-7.98 (1H, m), 8.00-8.10 (1H, m), 8.31 (1H, brs), 8.44 (1H, s), 8.68 (1H, s).

Elemental analysis (for C₁₉H₁₄FN₃O₃)

Calculated (%): C, 64.95; H, 4.02; N, 11.96.

Found (%): C, 64.83; H, 4.00; N, 11.97.

EXAMPLE 333

2-fluoro-N,N-dimethyl-4-[5-(5-methyl-1,3,4-oxadiazol-2-yl)-1-benzofuran-3-yl]benzamide In the same manner as in Example 117 and using 2-fluoro-4-[5-(5-methyl-1,3,4-oxadiazol-2-yl)-1-benzofuran-3-yl]benzoic acid instead of 3-[5-(2,3-dihydro-1-benzofuran-5-yl)-1,3,4-oxadiazol-2-yl]propionic acid and using 2.0M dimethylaminetetrahydrofuran solution instead of N,O-dimethylhydroxyamine hydrochloride, the title compound (yield 74%) was obtained as colorless crystals.

melting point 152-153° C. (recrystallized from hexane/ethyl acetate).

¹H NMR (DMSO-d₆) δ 2.61 (3H, s), 2.93 (3H, s), 3.05 (3H, s), 7.55-7.62 (1H, m), 7.69-7.75 (2H, m), 7.92 (1H, d, J=8.7 Hz), 8.05 (1H, dd, J=1.4, 8.7 Hz), 8.45 (1H, d, J=1.4 Hz), 8.66 (1H, s).

Elemental analysis (for C₂₀H₁₆FN₃O₃)

Calculated (%): C, 65.75; H, 4.41; N, 11.50.

Found (%): C, 65.70; H, 4.36; N, 11.55.

EXAMPLE 334

4-[2-fluoro-4-[5-(5-methyl-1,3,4-oxadiazol-2-yl)-1-benzofuran-3-yl]benzoyl]morpholine In the same manner as in Example 117 and using 2-fluoro-4-[5-(5-methyl-1,3,4-oxadiazol-2-yl)-1-benzofuran-3-yl]benzoic acid instead of 3-[5-(2,3-dihydro-1-benzofuran-5-yl)-1,3,4-oxadiazol-2-yl]propionic acid and using morpholine instead of N,O-dimethylhydroxyamine hydrochloride, the title compound (yield 78%) was obtained as colorless crystals.

melting point 167-168° C. (recrystallized from hexane/ethyl acetate).

¹H NMR (DMSO-d₆) δ 2.61 (3H, s), 3.29-3.37 (2H, m), 3.54-3.61 (2H, m), 3.69 (4H, brs), 7.56-7.65 (1H, m), 7.71 (1H, brs), 7.72-7.76 (1H, m), 7.92 (1H, d, J=8.7 Hz), 8.05 (1H, dd, J=1.7, 8.7 Hz), 8.45 (1H, d, J=1.7 Hz), 8.65 (1H, s).

Elemental analysis (for C₂₂H₁₈FN₃O₄)

Calculated (%): C, 64.86; H, 4.45; N, 10.31.

Found (%): C, 64.57; H, 4.51; N, 10.15.

EXAMPLE 335

N-[2-fluoro-4-[5-(5-methyl-1,3,4-oxadiazol-2-yl)-1-benzofuran-3-yl]phenyl]methanesulfonamide A solution of 2-fluoro-4-[5-(5-methyl-1,3,4-oxadiazol-2-yl)-1-benzofuran-3-yl]benzoic acid (1.00 g, 2.96 mmol), diphenylphosphoryl azide (0.65 mL, 2.96 mmol) and triethylamine (0.82 mL, 5.92 mmol) in tert-butanol (10 mL) was heated under reflux overnight. A saturated aqueous sodium hydrogen carbonate solution was added to the reaction mixture, insoluble material was removed by filtration, and the filtrate was extracted with ethyl acetate. The organic layer was washed with saturated brine, dried over anhydrous magnesium sulfate and concentrated under reduced pressure. The residue was purified by basic silica gel column chromatography (hexane/ethyl acetate=9/1-4/1) to give colorless crystals (0.40 g).

To a solution of the obtained crystals in ethyl acetate (5 mL) was added 4M hydrogen chloride-ethyl acetate solution (1.83 mL, 7.32 mmol), and the resulting mixture was stirred overnight at room temperature. The precipitate was collected by filtration and washed with ethyl acetate to give colorless crystals (0.30 g).

To a solution of the obtained crystals (0.20 g) in pyridine (5 mL) was added methanesulfonyl chloride (0.15 mL, 1.95 mmol), and the resulting mixture was stirred overnight at room temperature. Water was added to the reaction mixture, and the mixture was extracted with ethyl acetate. The organic layer was diluted with 4M hydrogen chloride-ethyl acetate solution, washed with water, dried over anhydrous sodium sulfate, and concentrated under reduced pressure. The residue was purified by silica gel column chromatography (hexane/ethyl acetate=7/3-3/2) and recrystallized from hexane/ethyl acetate to give the title compound (53.7 mg, yield 7%) as colorless crystals.

melting point 185-186° C.

¹H NMR (CDCl₃) δ 2.65 (3H, s), 3.11 (3H, s), 6.63 (1H, brs), 7.40-7.50 (2H, m), 7.67 (1H, d, J=8.7 Hz), 7.70-7.76 (1H, m), 7.87 (1H, s), 8.08 (1H, dd, J=1.7, 8.7 Hz), 8.46 (1H, d, J=1.7 Hz).

EXAMPLE 336

2-[3-[3-fluoro-4-(pyrrolidin-1-ylcarbonyl)phenyl]-1-benzofuran-5-yl]-5-methyl-1,3,4-oxadiazole In the same manner as in Example 117 and using 2-fluoro-4-[5-(5-methyl-1,3,4-oxadiazol-2-yl)-1-benzofuran-3-yl]benzoic acid instead of 3-[5-(2,3-dihydro-1-benzofuran-5-yl)-1,3,4-oxadiazol-2-yl]propionic acid and using pyrrolidine instead of N,O-dimethylhydroxyamine hydrochloride, the title compound (yield 53%) was obtained as colorless crystals.

melting point 195-196° C. (recrystallized from hexane/ethyl acetate).

¹H NMR (DMSO-d₆) δ 1.80-1.96 (4H, m), 2.61 (3H, s), 3.25-3.33 (2H, m), 3.51 (2H, t, J=6.8 Hz), 7.57-7.65 (1H, m), 7.67-7.75 (2H, m), 7.92 (1H, d, J=8.7 Hz), 8.04 (1H, dd, J=1.7, 8.7 Hz), 8.44 (1H, d, J=1.7 Hz), 8.65 (1H, s).
Elemental analysis (for $C_{22}H_{18}FN_3O_3$)
Calculated (%): C, 67.51; H, 4.64; N, 10.74.
Found (%): C, 67.42; H, 4.63; N, 10.85.

EXAMPLE 337 methyl 3-chloro-4-[5-(5-methyl-1,3,4-oxadiazol-2-yl)-1-benzofuran-3-yl]benzoate

In the same manner as in Example 132 and using [2-chloro-4-(methoxycarbonyl)phenyl]boronic acid instead of (4-fluorophenyl)boronic acid, the title compound (yield 10%) was obtained as colorless crystals.
melting point 171-172° C. (recrystallized from hexane/ethyl acetate).
$^1$H NMR (CDCl$_3$) δ 2.62 (3H, s), 3.98 (3H, s), 7.65 (1H, d, J=8.1 Hz), 7.67-7.72 (1H, m), 8.00 (1H, s), 8.04-8.12 (2H, m), 8.17-8.27 (2H, m).
Elemental analysis (for $C_{19}H_{13}ClN_2O_4$)
Calculated (%): C, 61.88; H, 3.55; N, 7.60.
Found (%): C, 61.80; H, 3.52; N, 7.58.

EXAMPLE 338

3-chloro-4-[5-(5-methyl-1,3,4-oxadiazol-2-yl)-1-benzofuran-3-yl]benzoic acid

In the same manner as in Example 134 and using methyl 3-chloro-4-[5-(5-methyl-1,3,4-oxadiazol-2-yl)-1-benzofuran-3-yl]benzoate instead of methyl 4-[5-(5-methyl-1,3,4-oxadiazol-2-yl)-1-benzofuran-3-yl]benzoate, the title compound (yield 73%) was obtained as colorless crystals.
melting point 267-268° C. (recrystallized from hexane/acetone).
$^1$H NMR (DMSO-d$_6$) δ 2.57 (3H, s), 7.79 (1H, d, J=7.9 Hz), 7.92-7.97 (1H, m), 8.03 (1H, d, J=1.7 Hz), 8.05-8.09 (2H, m), 8.14 (1H, d, J=1.5 Hz), 8.52 (1H, s), 13.49 (1H, brs).

EXAMPLE 339

3-chloro-N-methyl-4-[5-(5-methyl-1,3,4-oxadiazol-2-yl)-1-benzofuran-3-yl]benzamide In the same manner as in Example 117 and using 3-chloro-4-[5-(5-methyl-1,3,4-oxadiazol-2-yl)-1-benzofuran-3-yl]benzoic acid instead of 3-[5-(2,3-dihydro-1-benzofuran-5-yl)-1,3,4-oxadiazol-2-yl]propionic acid and using 2M methylamine-tetrahydrofuran solution instead of N,O-dimethylhydroxyamine hydrochloride, the title compound (yield 21%) was obtained as colorless crystals.
melting point 250-251° C. (recrystallized from hexane/ethyl acetate).
$^1$H NMR (CDCl$_3$) δ 2.62 (3H, s), 3.07 (3H, d, J=4.9 Hz), 6.18 (1H, brs), 7.63 (1H, d, J=7.9 Hz), 7.69 (1H, d, J=8.7 Hz), 7.77 (1H, dd, J=1.9, 7.9 Hz), 7.96-8.00 (2H, m), 8.08 (1H, dd, J=1.7, 8.7 Hz), 8.23 (1H, d, J=1.7 Hz).
Elemental analysis (for $C_{19}H_{14}ClN_3O_3$)
Calculated (%): C, 62.05; H, 3.84; N, 11.43.
Found (%): C, 61.76; H, 3.61; N, 11.36.

EXAMPLE 340

N-methyl-4-[5-(5-methyl-1,3,4-oxadiazol-2-yl)-1-benzofuran-3-yl]benzenesulfonamide In the same manner as in Example 132 and using [4-[(methylamino)sulfonyl]phenyl]boronic acid instead of (4-fluorophenyl)boronic acid, the title compound (yield 71%) was obtained as colorless crystals.
melting point 203-204° C. (recrystallized from ethyl acetate).
$^1$H NMR (DMSO-d$_6$) δ 2.48 (3H, s), 2.61 (3H, s), 7.55 (1H, s), 7.91-7.97 (3H, m), 8.00-8.04 (2H, m), 8.06 (1H, dd, J=1.7, 8.7 Hz), 8.47 (1H, d, J=1.7 Hz), 8.68 (1H, s).
Elemental analysis (for $C_{18}H_{15}N_3O_4S$)
Calculated (%): C, 58.53; H, 4.09; N, 11.38.
Found (%): C, 58.56; H, 4.09; N, 11.23.

EXAMPLE 341

N,N-dimethyl-4-[5-(5-methyl-1,3,4-oxadiazol-2-yl)-1-benzofuran-3-yl]benzenesulfonamide In the same manner as in Example 132 and using [4-[(dimethylamino)sulfonyl]phenyl]boronic acid instead of (4-fluorophenyl)boronic acid, the title compound (yield 37%) was obtained as colorless crystals.
melting point 246-247° C. (recrystallized from hexane/ethyl acetate).
$^1$H NMR (CDCl$_3$) δ 2.65 (3H, s), 2.80 (6H, s), 7.70 (1H, d, J=8.7 Hz), 7.84 (2H, d, J=8.5 Hz), 7.93 (2H, d, J=8.5 Hz), 7.97 (1H, s), 8.08 (1H, dd, J=1.7, 8.7 Hz), 8.53 (1H, d, J=1.7 Hz).
Elemental analysis (for $C_{19}H_{17}N_3O_4S$)
Calculated (%): C, 59.52; H, 4.47; N, 10.96.
Found (%): C, 59.41; H, 4.31; N, 11.09.

EXAMPLE 342

4-[5-(5-methyl-1,3,4-oxadiazol-2-yl)-1-benzofuran-3-yl]benzonitrile

In the same manner as in Example 132 and using (4-cyanophenyl)boronic acid instead of (4-fluorophenyl)boronic acid, the title compound (yield 68%) was obtained as colorless crystals.
melting point 201-202° C. (recrystallized from hexane/ethyl acetate).
$^1$H NMR (CDCl$_3$) δ 2.65 (3H, s), 7.70 (1H, dd, J=0.6, 8.7 Hz), 7.77-7.83 (4H, m), 7.96 (1H, s), 8.09 (1H, dd, J=1.7, 8.7 Hz), 8.49 (1H, dd, J=0.6, 1.7 Hz).
Elemental analysis (for $C_{18}H_{11}N_3O_2$)
Calculated (%): C, 71.75; H, 3.68; N, 13.95.
Found (%): C, 71.76; H, 3.50; N, 13.96.

EXAMPLE 343

2-methyl-5-[3-[4-(trifluoromethyl)phenyl]-1-benzofuran-5-yl]-1,3,4-oxadiazole

In the same manner as in Example 132 and using [4-(trifluoromethyl)phenyl]boronic acid instead of (4-cyanophenyl)boronic acid, the title compound (yield 82%) was obtained as colorless crystals.
melting point 190-191° C. (recrystallized from hexane/ethyl acetate).
$^1$H NMR (CDCl$_3$) δ 2.64 (3H, s), 7.69 (1H, dd, J=0.6, 8.7 Hz), 7.75-7.81 (4H, m), 7.94 (1H, s), 8.09 (1H, dd, J=1.7, 8.7 Hz), 8.48 (1H, dd, J=0.6, 1.7 Hz).
Elemental analysis (for $C_{18}H_{11}F_3N_2O_2$)
Calculated (%): C, 62.79; H, 3.22; N, 8.14.
Found (%): C, 62.84; H, 3.09; N, 8.11.

EXAMPLE 344

2-methyl-5-[3-[4-(trifluoromethoxy)phenyl]-1-benzofuran-5-yl]-1,3,4-oxadiazole

In the same manner as in Example 132 and using [4-(trifluoromethoxy)phenyl]boronic acid instead of (4-fluorophenyl)boronic acid, the title compound (yield 85%) was obtained as colorless crystals.

melting point 129-130° C. (recrystallized from hexane/ethyl acetate).

$^1$H NMR (CDCl$_3$) δ 2.64 (3H, s), 7.35-7.39 (2H, m), 7.65-7.71 (3H, m), 7.87 (1H, s), 8.07 (1H, dd, J=1.9, 8.7 Hz), 8.46 (1H, dd, J-=0.6, 1.9 Hz).

Elemental analysis (for C$_{18}$H$_{11}$F$_3$N$_2$O$_3$)

Calculated (%): C, 60.01; H, 3.08; N, 7.78.

Found (%): C, 60.12; H, 3.08; N, 7.69.

EXAMPLE 345

2-[3-[3-(benzyloxy)phenyl]-1-benzofuran-5-yl]-5-methyl-1,3,4-oxadiazole

In the same manner as in Example 132 and using [3-(benzyloxy)phenyl]boronic acid instead of (4-fluorophenyl)boronic acid, the title compound (yield 81%) was obtained as colorless crystals.

melting point 96-97° C. (crystallized from hexane/ethyl acetate).

$^1$H NMR (CDCl$_3$) δ 2.64 (3H, s), 5.15 (2H, s), 7.01-7.05 (1H, m), 7.25-7.29 (2H, m), 7.31-7.50 (6H, m), 7.65 (1H, dd, J=0.6, 8.7 Hz), 7.84 (1H, s), 8.06 (1H, dd, J=1.7, 8.7 Hz), 8.48 (1H, dd, J-=0.6, 1.7 Hz).

Elemental analysis (for C$_{24}$H$_{18}$N$_2$O$_3$)

Calculated (%): C, 75.38; H, 4.74; N, 7.33.

Found (%): C, 75.33; H, 4.76; N, 7.27.

EXAMPLE 346

2-[3-(2-chlorophenyl)-1-benzofuran-5-yl]-5-methyl-1,3,4-oxadiazole

In the same manner as in Example 132 and using (2-chlorophenyl)boronic acid instead of (4-fluorophenyl)boronic acid, the title compound (yield 59%) was obtained as colorless crystals.

melting point 83-84° C. (crystallized from hexane/ethyl acetate).

$^1$H NMR (CDCl$_3$) δ 2.61 (3H, s), 7.34-7.43 (2H, m), 7.50-7.61 (2H, m), 7.67 (1H, dd, J=0.6, 8.7 Hz), 7.91 (1H, s), 8.06 (1H, dd, J=1.7, 8.7 Hz), 8.24 (1H, dd, J=0.6, 1.7 Hz).

Elemental analysis (for C$_{17}$H$_{11}$ClN$_2$O$_2$)

Calculated (%): C, 65.71; H, 3.57; N, 9.02.

Found (%): C, 65.39; H, 3.57; N, 9.07.

EXAMPLE 347

2-methyl-5-[3-(2-methylphenyl)-1-benzofuran-5-yl]-1,3,4-oxadiazole

In the same manner as in Example 132 and using (2-methylphenyl)boronic acid instead of (4-fluorophenyl)boronic acid, the title compound (yield 73%) was obtained as colorless crystals.

melting point 83-84° C. (crystallized from hexane/ethyl acetate).

$^1$H NMR (CDCl$_3$) δ 2.32 (3H, s), 2.60 (3H, s), 7.28-7.40 (4H, m), 7.66 (1H, dd, J=0.4, 8.7 Hz), 7.70 (1H, s), 8.05 (1H, dd, J=1.7, 8.7 Hz), 8.12 (1H, dd, J=0.4, 1.7 Hz).

Elemental analysis (for C$_{18}$H$_{14}$N$_2$O$_2$)

Calculated (%): C, 74.47; H, 4.86; N, 9.65.

Found (%): C, 74.53; H, 4.84; N, 9.65.

EXAMPLE 348

2-methyl-5-[3-[2-(trifluoromethyl)phenyl]-1-benzofuran-5-yl]-1,3,4-oxadiazole

In the same manner as in Example 132 and using [2-(trifluoromethyl)phenyl]boronic acid instead of (4-fluorophenyl)boronic acid, the title compound (yield 81%) was obtained as colorless crystals.

melting point 159-160° C. (recrystallized from hexane/ethyl acetate).

$^1$H NMR (CDCl$_3$) δ 2.60 (3H, s), 7.54-7.60 (2H, m), 7.65-7.70 (2H, m), 7.77 (1H, s), 7.85 (1H, d, J=7.7 Hz), 8.05 (1H, dd, J=1.7, 8.7 Hz), 8.09 (1H, d, J=1.7 Hz).

Elemental analysis (for C$_{18}$H$_{11}$F$_3$N$_2$O$_2$)

Calculated (%): C, 62.79; H, 3.22; N, 8.14.

Found (%): C, 62.79; H, 3.24; N, 8.17.

EXAMPLE 349

2-[3-(2-chloro-5-fluorophenyl)-1-benzofuran-5-yl]-5-methyl-1,3,4-oxadiazole

In the same manner as in Example 132 and using (2-chloro-5-fluorophenyl)boronic acid instead of (4-fluorophenyl)boronic acid, the title compound (yield 75%) was obtained as colorless crystals.

melting point 130-131° C. (recrystallized from hexane/ethyl acetate).

$^1$H NMR (CDCl$_3$) δ 2.63 (3H, s), 7.10 (1H, ddd, J=3.0, 7.9, 8.9 Hz), 7.27 (1H, dd, J=3.0, 8.9 Hz), 7.53 (1H, dd, J=5.1, 8.9 Hz), 7.68 (1H, dd, J=0.6, 8.7 Hz), 7.93 (1H, s), 8.08 (1H, dd, J=1.7, 8.7 Hz), 8.23 (1H, dd, J=0.6, 1.7 Hz).

Elemental analysis (for C$_{17}$H$_{10}$ClFN$_2$O$_2$)

Calculated (%): C, 62.11; H, 3.07; N, 8.52.

Found (%): C, 62.11; H, 3.05; N, 8.60.

EXAMPLE 350

2-[3-(5-chloro-2-fluorophenyl)-1-benzofuran-5-yl]-5-methyl-1,3,4-oxadiazole

In the same manner as in Example 132 and using (5-chloro-2-fluorophenyl)boronic acid instead of (4-fluorophenyl)boronic acid, the title compound (yield 49%) was obtained as colorless crystals.

melting point 187-188° C. (recrystallized from hexane/tetrahydrofuran).

$^1$H NMR (CDCl$_3$) δ 2.64 (3H, s), 7.19 (1H, dd, J=9.1, 9.5 Hz), 7.35 (1H, ddd, J=2.7, 4.5, 9.1 Hz), 7.64-7.69 (2H, m), 7.97 (1H, d, J=1.5 Hz), 8.09 (1H, dd, J=1.5, 8.7 Hz), 8.38-8.39 (1H, m).

Elemental analysis (for C$_{17}$H$_{10}$ClFN$_2$O$_2$)

Calculated (%): C, 62.11; H, 3.07; N, 8.52.

Found (%): C, 62.12; H, 2.94; N, 8.52.

EXAMPLE 351

2-[3-[2-fluoro-5-(trifluoromethyl)phenyl]-1-benzofuran-5-yl]-5-methyl-1,3,4-oxadiazole In the same manner as in Example 132 and using [2-fluoro-5-(trifluoromethyl)phenyl]boronic acid instead of (4-fluorophenyl)boronic acid, the title compound (yield 80%) was obtained as colorless crystals.

melting point 178-179° C. (recrystallized from hexane/tetrahydrofuran).

$^1$H NMR (CDCl$_3$) δ 2.64 (3H, s), 7.35-7.41 (1H, m), 7.66-7.71 (2H, m), 7.93 (1H, dd, J=2.1, 6.6 Hz), 8.00 (1H, d, J=1.5 Hz), 8.11 (1H, dd, J=1.7, 8.7 Hz), 8.34-8.35 (1H, m).

Elemental analysis (for C$_{18}$H$_{10}$F$_4$N$_2$O$_2$)
Calculated (%): C, 59.68; H, 2.78; N, 7.73.
Found (%): C, 59.74; H, 2.88; N, 7.83.

EXAMPLE 352

2-[3-(2,5-dichlorophenyl)-1-benzofuran-5-yl]-5-methyl-1,3,4-oxadiazole

In the same manner as in Example 132 and using (2,5-dichlorophenyl)boronic acid instead of (4-fluorophenyl)boronic acid, the title compound (yield 83%) was obtained as colorless crystals.

melting point 185-186° C. (recrystallized from hexane/tetrahydrofuran).

$^1$H NMR (CDCl$_3$) δ 2.62 (3H, s), 7.36 (1H, dd, J=2.5, 8.7 Hz), 7.49-7.52 (2H, m), 7.68 (1H, dd, J=0.6, 8.7 Hz), 7.89 (1H, s), 8.08 (1H, dd, J=1.7, 8.7 Hz), 8.20 (1H, dd, J=0.6, 1.7 Hz).

Elemental analysis (for C$_{17}$H$_{10}$Cl$_2$N$_2$O$_2$)
Calculated (%): C, 59.15; H, 2.92; N, 8.12.
Found (%): C, 59.36; H, 3.07; N, 8.14.

EXAMPLE 353

2-[3-[2-chloro-5-(trifluoromethyl)phenyl]-1-benzofuran-5-yl]-5-methyl-1,3,4-oxadiazole In the same manner as in Example 132 and using [2-chloro-5-(trifluoromethyl)phenyl]boronic acid instead of (4-fluorophenyl)boronic acid, the title compound (yield 69%) was obtained as colorless crystals.

melting point 188-189° C. (recrystallized from hexane/ethyl acetate).

$^1$H NMR (CDCl$_3$) δ 2.62 (3H, s), 7.65 (1H, dd, J=2.1, 8.5 Hz), 7.68-7.72 (2H, m), 7.76-7.77 (1H, m), 7.91 (1H, s), 8.10 (1H, dd, J=1.7, 8.7 Hz), 8.17 (1H, dd, J=0.4, 1.7 Hz).

Elemental analysis (for C$_{18}$H$_{10}$ClF$_3$N$_2$O$_2$)
Calculated (%): C, 57.08; H, 2.66; N, 7.40.
Found (%): C, 57.15; H, 2.79; N, 7.49.

EXAMPLE 354

2-[3-(2-fluorophenyl)-1-benzofuran-5-yl]-5-methyl-1,3,4-oxadiazole

In the same manner as in Example 132 and using (2-fluorophenyl)boronic acid instead of (4-fluorophenyl)boronic acid, the title compound (yield 80%) was obtained as colorless crystals.

melting point 112-113° C. (crystallized from hexane/ethyl acetate).

$^1$H NMR (CDCl$_3$) δ 2.64 (3H, s), 7.21-7.33 (2H, m), 7.36-7.43 (1H, m), 7.67 (1H, d, J=8.7 Hz), 7.72 (1H, dt, J=1.9, 7.6 Hz), 7.99 (1H, d, J=1.9 Hz), 8.06 (1H, dd, J=1.9, 8.7 Hz), 8.45 (1H, s).

Elemental analysis (for C$_{17}$H$_{11}$FN$_2$O$_2$)
Calculated (%): C, 69.38; H, 3.77; N, 9.52.
Found (%): C, 69.42; H, 3.70; N, 9.61.

EXAMPLE 355

2-[3-(2,3-difluorophenyl)-1-benzofuran-5-yl]-5-methyl-1,3,4-oxadiazole

In the same manner as in Example 132 and using (2,3-difluorophenyl)boronic acid instead of (4-fluorophenyl)boronic acid, the title compound (yield 69%) was obtained as colorless crystals.

melting point 112-113° C. (recrystallized from hexane/ethyl acetate).

$^1$H NMR (CDCl$_3$) δ 2.64 (3H, s), 7.29-7.49 (3H, m), 7.67 (1H, d, J=8.7 Hz), 7.84 (1H, s), 8.08 (1H, dd, J=1.5, 8.7 Hz), 8.42 (1H, d, J=1.5 Hz).

Elemental analysis (for C$_{17}$H$_{10}$F$_2$N$_2$O$_2$)
Calculated (%): C, 65.39; H, 3.23; N, 8.97.
Found (%): C, 65.03; H, 3.24; N, 9.04.

EXAMPLE 356

2-[3-(2,5-difluorophenyl)-1-benzofuran-5-yl]-5-methyl-1,3,4-oxadiazole

In the same manner as in Example 132 and using (2,5-difluorophenyl)boronic acid instead of (4-fluorophenyl)boronic acid, the title compound (yield 59%) was obtained as colorless crystals.

melting point 143-144° C. (recrystallized from hexane/ethyl acetate).

$^1$H NMR (CDCl$_3$) δ 2.65 (3H, s), 7.03-7.11 (1H, m), 7.21 (1H, ddd, J=4.5, 9.1, 9.5 Hz), 7.42 (1H, ddd, J=3.4, 5.7, 9.1 Hz), 7.68 (1H, d, J=8.7 Hz), 8.01 (1H, d, J=8.3 Hz), 8.09 (1H, dd, J=1.9, 8.7 Hz), 8.42 (1H, s).

Elemental analysis (for C$_{17}$H$_{10}$F$_2$N$_2$O$_2$)
Calculated (%): C, 65.39; H, 3.23; N, 8.97.
Found (%): C, 65.13; H, 3.16; N, 9.01.

EXAMPLE 357

2-[3-(1-benzothien-5-yl)-1-benzofuran-5-yl]-5-methyl-1,3,4-oxadiazole

In the same manner as in Example 132 and using 2-(1-benzothien-5-yl)-4,4,5,5-tetramethyl-1,3,2-dioxaborolane instead of (4-fluorophenyl)boronic acid and using [1,1'-bis(diphenylphosphino)ferrocene]palladium(II)chloride dichloromethane complex instead of tetrakis(triphenylphosphine)palladium(0), the title compound (yield 78%) was obtained as colorless crystals.

melting point 159-160° C. (recrystallized from hexane/tetrahydrofuran).

$^1$H NMR (CDCl$_3$) δ 2.63 (3H, s), 7.44 (1H, dd, J=0.6, 5.5 Hz), 7.54 (1H, d, J=5.5 Hz), 7.62 (1H, dd, J=1.7, 8.3 Hz), 7.67 (1H, dd, J=0.6, 8.7 Hz), 7.91 (1H, s), 8.01 (1H, dd, J=0.6, 8.3 Hz), 8.07 (1H, dd, J=1.7, 8.7 Hz), 8.10 (1H, dd, J=0.6, 1.9 Hz), 8.54 (1H, dd, J=0.6, 1.9 Hz).

Elemental analysis (for C$_{19}$H$_{12}$N$_2$O$_2$S)
Calculated (%): C, 68.66; H, 3.64; N, 8.43.
Found (%): C, 68.67; H, 3.59; N, 8.46.

EXAMPLE 358

6-[5-(5-methyl-1,3,4-oxadiazol-2-yl)-1-benzofuran-3-yl]quinoline

In the same manner as in Example 132 and using 6-(4,4,5,5-tetramethyl-1,3,2-dioxaborolan-2-yl)quinoline instead of (4-fluorophenyl)boronic acid, the title compound (yield 83%) was obtained as colorless crystals.

melting point 212-213° C. (recrystallized from tetrahydrofuran).

$^1$H NMR (CDCl$_3$) δ 2.63 (3H, s), 7.49 (1H, dd, J=4.3, 8.3 Hz), 7.71 (1H, dd, J=0.6, 8.7 Hz), 7.98-8.02 (2H, m), 8.10 (1H, dd, J=1.7, 8.7 Hz), 8.13 (1H, d, J=1.9 Hz), 8.24-8.30 (2H, m), 8.61 (1H, dd, J-=0.6, 1.7 Hz), 8.97 (1H, d, J=1.7, 4.3 Hz).

Elemental analysis (for C$_{20}$H$_{13}$N$_3$O$_2$)
Calculated (%): C, 73.38; H, 4.00; N, 12.84.
Found (%): C, 73.19; H, 3.91; N, 12.84.

EXAMPLE 359

3-chloro-4-[5-(5-methyl-1,3,4-oxadiazol-2-yl)-1-benzofuran-3-yl]pyridine

In the same manner as in Example 132 and using 3-chloropyridine-4-boronic acid instead of (4-fluorophenyl)boronic acid, the title compound (yield 21%) was obtained as colorless crystals.

melting point 147-148° C. (recrystallized from hexane/ethyl acetate).

$^1$H NMR (CDCl$_3$) δ 2.64 (3H, s), 7.54 (1H, dd, J=0.4, 5.1 Hz), 7.71 (1H, dd, J=0.6, 8.7 Hz), 8.09-8.12 (2H, m), 8.30 (1H, dd, J-=0.6, 1.7 Hz), 8.63 (1H, d, J=5.1 Hz), 8.78 (1H, dd, J=0.4 Hz).

Elemental analysis (for C$_{16}$H$_{10}$ClN$_3$O$_2$.0.5H$_2$O)
Calculated (%): C, 59.92; H, 3.46; N, 13.10.
Found (%): C, 60.19; H, 3.37; N, 13.16.

EXAMPLE 360

2-methyl-4-[5-(5-methyl-1,3,4-oxadiazol-2-yl)-1-benzofuran-3-yl]pyridine

In the same manner as in Example 132 and using 2-methyl-4-(4,4,5,5-tetramethyl-1,3,2-dioxaborolan-2-yl)pyridine instead of (4-fluorophenyl)boronic acid, the title compound (yield 76%) was obtained as colorless crystals.

melting point 151-152° C. (recrystallized from hexane/ethyl acetate).

$^1$H NMR (CDCl$_3$) δ 2.66 (3H, s), 2.67 (3H, s), 7.40 (1H, dd, J=1.5, 5.1 Hz), 7.43 (1H, d, J=1.5 Hz), 7.69 (1H, dd, J=0.6, 8.7 Hz), 7.99 (1H, s), 8.09 (1H, dd, J=1.7, 8.7 Hz), 8.52 (1H, dd, J=0.6, 1.7 Hz), 8.63 (1H, d, J=5.1 Hz).

Elemental analysis (for C$_{17}$H$_{13}$N$_3$O$_2$)
Calculated (%): C, 70.09; H, 4.50; N, 14.42.
Found (%): C, 70.12; H, 4.43; N, 14.44.

EXAMPLE 361

5-(5-methyl-1,3,4-oxadiazol-2-yl)-1-benzofuran-3-carbonitrile

A suspension of 2-(3-bromo-1-benzofuran-5-yl)-5-methyl-1,3,4-oxadiazole (5.58 g, 20.0 mmol), zinc cyanide (1.41 g, 12.0 mmol) and tetrakis(triphenylphosphine)palladium (0) (1.16 g, 1.00 mmol) in N,N-dimethylformamide (50 mL) was stirred at 80° C. for 10 hr under an argon atmosphere. After cooling, the reaction mixture was diluted with ethyl acetate, washed twice with water and once with saturated brine, dried over anhydrous magnesium sulfate and concentrated under reduced pressure. The residue was purified by basic silica gel column chromatography (tetrahydrofuran) and recrystallized from hexane/tetrahydrofuran to give the title compound (3.74 g, yield 83%) as colorless crystals.

melting point 188-189° C.

$^1$H NMR (CDCl$_3$) δ 2.66 (3H, s), 7.73 (1H, dd, J=0.6, 8.7 Hz), 8.22 (1H, dd, J=1.7, 8.7 Hz), 8.25 (1H, s), 8.41 (1H, dd, J=0.6, 1.7 Hz).

Elemental analysis (for C$_{12}$H$_7$N$_3$O$_2$)
Calculated (%): C, 64.00; H, 3.13; N, 18.66.
Found (%): C, 64.06; H, 2.99; N, 18.66.

EXAMPLE 362

5-(5-methyl-1,3,4-oxadiazol-2-yl)-1-benzofuran-3-carbaldehyde

A mixture of 5-(5-methyl-1,3,4-oxadiazol-2-yl)-1-benzofuran-3-carbonitrile (1.00 g, 4.44 mmol), Raney-nickel (2.0 g), formic acid (16 mL) and water (4 mL) was heated under reflux for 30 min. After cooling, the reaction mixture was filtered, and the filtrate was concentrated under reduced pressure. The residue was diluted with ethyl acetate, washed with water, saturated aqueous sodium hydrogen carbonate solution and saturated brine, dried over anhydrous magnesium sulfate and concentrated under reduced pressure. The residue was purified by silica gel column chromatography (hexane/tetrahydrofuran=1/1) and recrystallized from hexane/tetrahydrofuran to give the title compound (558 mg, yield 55%) as colorless crystals.

melting point 182-183° C.

$^1$H NMR (CDCl$_3$) δ 2.65 (3H, s), 7.69 (1H, dd, J=0.6, 8.9 Hz), 8.21 (1H, dd, J=1.7, 8.9 Hz), 8.37 (1H, s), 8.81 (1H, dd, J=0.6, 1.7 Hz), 10.22 (1H, s).

Elemental analysis (for C$_{12}$H$_8$N$_2$O$_3$)
Calculated (%): C, 63.16; H, 3.53; N, 12.28.
Found (%): C, 63.12; H, 3.49; N, 12.45.

EXAMPLE 363

2-methyl-5-[3-(5-oxazolyl)-1-benzofuran-5-yl]-1,3,4-oxadiazole

A suspension of 5-(5-methyl-1,3,4-oxadiazol-2-yl)-1-benzofuran-3-carbaldehyde (500 mg, 2.19 mmol), p-toluenesulfonylmethyl isocyanide (471 mg, 2.41 mmol) and potassium carbonate (363 mg, 2.63 mmol) in methanol (10 mL) was heated under reflux for 7 hr. After cooling, the reaction mixture was diluted with ethyl acetate, washed with water and saturated brine, dried over anhydrous magnesium sulfate and concentrated under reduced pressure. The residue was purified by basic silica gel column chromatography (tetrahydrofuran) and recrystallized from methanol to give the title compound (118 mg, yield 20%) as colorless crystals.

melting point 184-185° C.

$^1$H NMR (CDCl$_3$) δ 2.67 (3H, s), 7.49 (1H, s), 7.67 (1H, dd, J=0.6, 8.7 Hz), 8.01 (1H, s), 8.07 (1H, s), 8.11 (1H, dd, J=1.7, 8.7 Hz), 8.49 (1H, dd, J=0.6, 1.7 Hz).

Elemental analysis (for C$_{14}$H$_9$N$_3$O$_3$)
Calculated (%): C, 62.92; H, 3.39; N, 15.72.
Found (%): C, 62.82; H, 3.33; N, 15.66.

EXAMPLE 364

2-ethyl-5-[3-[4-(methylthio)phenyl]-1-benzofuran-5-yl]-1,3,4-oxadiazole

In the same manner as in Example 239 and using 3-[4-(methylthio)phenyl]-1-benzofuran-5-carbohydrazide instead of 2-[[4-(methylthio)phenyl]amino]isonicotinohydrazide and using triethyl orthopropionate instead of triethyl orthoacetate, the title compound (yield 9%) was obtained as colorless crystals.

melting point 164-165° C. (recrystallized from hexane/ethyl acetate).

$^1$H NMR (CDCl$_3$) δ 1.46 (3H, t, J=7.5 Hz), 2.55 (3H, s), 2.98 (2H, q, J=7.5 Hz), 7.40 (2H, d, J=8.7 Hz), 7.59 (2H, d, J=8.5 Hz), 7.65 (1H, dd, J=0.6, 8.7 Hz), 7.85 (1H, s), 8.06 (1H, dd, J=1.7, 8.7 Hz), 8.48 (1H, dd, J=0.6, 1.7 Hz).

Elemental analysis (for C$_{19}$H$_{16}$N$_2$O$_2$S)
Calculated (%): C, 67.84; H, 4.79; N, 8.33.
Found (%): C, 67.62; H, 4.82; N, 8.46.

EXAMPLE 365

5-[3-[4-(methylthio)phenyl]-1-benzofuran-5-yl]-1,3,4-oxadiazol-2-amine

In the same manner as in Example 236 and using 3-[4-(methylthio)phenyl]-1-benzofuran-5-carbohydrazide instead of 2-(2-phenylethyl)-1H-pyrrolo[2,3-b]pyridine-4-carbohydrazide, the title compound (yield 79%) was obtained as colorless crystals.

melting point 255-256° C. (recrystallized from hexane/tetrahydrofuran).

$^1$H NMR (DMSO-d$_6$) δ 2.54 (3H, s), 7.23 (2H, brs), 7.44 (2H, d, J=8.3 Hz), 7.69 (2H, d, J=8.3 Hz), 7.80-7.90 (2H, m), 8.21 (1H, brs), 8.47 (1H, s).

Elemental analysis (for C$_{17}$H$_{13}$N$_3$O$_2$S)
Calculated (%): C, 63.14; H, 4.05; N, 12.99.
Found (%): C, 63.07; H, 4.26; N, 12.87.

EXAMPLE 366

5-[3-[4-(methylsulfinyl)phenyl]-1-benzofuran-5-yl]-1,3,4-oxadiazol-2-amine

To a solution of 5-[3-[4-(methylthio)phenyl]-1-benzofuran-5-yl]-1,3,4-oxadiazol-2-amine (0.25 g, 0.77 mmol) in tetrahydrofuran (10 mL) was added a solution of oxone (registered trade mark, 0.24 g, 0.77 mmol) in water (3 mL) at 0° C., and the mixture was stirred at 0° C. for 30 min and at room temperature for 1 hr. Water was added to the reaction mixture, and the precipitate was collected by filtration and purified by preparative HPLC to give the title compound (15.2 mg, yield 6%) as colorless crystals.

melting point 284-285° C.

$^1$H NMR (DMSO-d$_6$) δ 2.81 (3H, s), 7.24 (2H, s), 7.84-7.92 (4H, m), 7.93-7.98 (2H, m), 8.25 (1H, s), 8.59 (1H, s).

Elemental analysis (for C$_{17}$H$_{13}$N$_3$O$_3$S)
Calculated (%): C, 60.17; H, 3.86; N, 12.38.
Found (%): C, 60.02; H, 3.97; N, 12.32.

The purification by preparative HPLC was performed under the following conditions.
measurement device: GILSON semi-preparative system
column: YMC CombiPrep ODS-A 20×50 mm S-5 μm
mobile phase: SOLUTION A; distilled water (0.1% trifluoroacetic acid), SOLUTION B; acetonitrile (0.1% trifluoroacetic acid)
gradient: 0 min (SOLUTION A/SOLUTION B=95/5)-10 min (SOLUTION A/SOLUTION B=0/100)
flow rate: 25 mL/min
temperature: 25° C.
detection: UV 220 nm

EXAMPLE 367

5-[3-[4-(methylsulfonyl)phenyl]-1-benzofuran-5-yl]-1,3,4-oxadiazol-2-amine

In the same manner as in Example 366 and using oxone (registered trade mark, 3 mol) per 1 mol of 5-[3-[4-(methylthio)phenyl]-1-benzofuran-5-yl]-1,3,4-oxadiazol-2-amine, the title compound (yield 91%) was obtained as colorless crystals.

melting point 274-275° C.

$^1$H NMR (DMSO-d$_6$) δ 3.29 (3H, s), 7.24 (2H, brs), 7.86-7.93 (2H, m), 8.01-8.06 (2H, m), 8.07-8.12 (2H, m), 8.27 (1H, s), 8.67 (1H, s).

Elemental analysis (for C$_{17}$H$_{13}$N$_3$O$_4$S)
Calculated (%): C, 57.46; H, 3.69; N, 11.82.
Found (%): C, 57.38; H, 3.79; N, 11.75.

EXAMPLE 368

N-methyl-5-[3-[4-(methylthio)phenyl]-1-benzofuran-5-yl]-1,3,4-oxadiazol-2-amine

To a solution of N-methyl-2-[[3-[4-(methylthio)phenyl]-1-benzofuran-5-yl]carbonyl]hydrazinecarbothioamide (0.58 g, 1.56 mmol) in ethanol (10 mL) was added 2 M sodium hydroxide to adjust to pH 9 at 0° C., and 5% potassium iodide-iodine aqueous solution was added at room temperature until the color of iodine started to remain. N,N-Dimethylformamide (10 mL) was added to the mixture, and the resulting mixture was stirred overnight at room temperature. Ethyl acetate and water were added to the reaction mixture, and insoluble material was removed by filtration. The filtrate was diluted with ethyl acetate, washed with water and saturated brine, dried over anhydrous sodium sulfate, and concentrated under reduced pressure. The residue was purified by basic silica gel column chromatography (hexane/ethyl acetate=2/3-3/2) and recrystallized from hexane/tetrahydrofuran to give the title compound (0.13 g, yield 24%) as colorless crystals.

melting point 196-197° C.

$^1$H NMR (CDCl$_3$) δ 2.55 (3H, s), 3.12 (3H, d, J=5.1 Hz), 4.80 (1H, q, J=5.0 Hz), 7.38 (2H, d, J=8.5 Hz), 7.54-7.62 (3H, m), 7.82 (1H, s), 7.94 (1H, dd, J=1.7, 8.7 Hz), 8.33 (1H, d, J=1.1 Hz).

Elemental analysis (for C$_{18}$H$_{15}$N$_3$O$_2$S)
Calculated (%): C, 64.08; H, 4.48; N, 12.45.
Found (%): C, 63.86; H, 4.50; N, 12.42.

EXAMPLE 369

N-methyl-5-[3-[4-(methylsulfinyl)phenyl]-1-benzofuran-5-yl]-1,3,4-oxadiazol-2-amine In the same manner as in Example 36 and using N-methyl-5-[3-[4-(methylthio)phenyl]-1-benzofuran-5-yl]-1,3,4-oxadiazol-2-amine instead of 2-(2,3-dihydro-1-benzofuran-5-yl)-5-(methylthio)-1,3,4-oxadiazole, the title compound (yield 53%) was obtained as colorless crystals.

melting point 240-241° C. (recrystallized from hexane/ethyl acetate).

¹H NMR (DMSO-d₆) δ 2.82 (3H, s), 2.88 (3H, d, J=4.5 Hz), 7.64 (1H, q, J=4.5 Hz), 7.82-7.90 (4H, m), 7.90-7.99 (2H, m), 8.26 (1H, brs), 8.57-8.61 (1H, m).

EXAMPLE 370

5-[3-[3-chloro-4-(methylthio)phenyl]-1-benzofuran-5-yl]-1,3,4-oxadiazol-2-amine

In the same manner as in Example 236 and using 3-[3-chloro-4-(methylthio)phenyl]-1-benzofuran-5-carbohydrazide instead of 2-(2-phenylethyl)-1H-pyrrolo[2,3-b]pyridine-4-carbohydrazide, the title compound (yield 46%) was obtained as colorless crystals.

melting point 232-233° C. (recrystallized from methanol).

¹H NMR (DMSO-d₆) δ 2.57 (3H, s), 7.24 (2H, brs), 7.45 (1H, d, J=8.3 Hz), 7.75 (1H, dd, J=1.9, 8.3 Hz), 7.82 (1H, d, J=1.9 Hz), 7.85 (1H, s), 7.88 (1H, dd, J=1.5, 8.7 Hz), 8.20 (1H, d, J=0.8 Hz), 8.55 (1H, s).

Elemental analysis (for $C_{17}H_{12}ClN_3O_2S$)

Calculated (%): C, 57.06; H, 3.38; N, 11.74.

Found (%): C, 56.78; H, 3.37; N, 11.54.

EXAMPLE 371

5-[3-[3-chloro-4-(methylsulfinyl)phenyl]-1-benzofuran-5-yl]-1,3,4-oxadiazol-2-amine In the same manner as in Example 140 and using 5-[3-[3-chloro-4-(methylthio)phenyl]-1-benzofuran-5-yl]-1,3,4-oxadiazol-2-amine instead of 2-methyl-5-[3-[4-(methylthio)phenyl]-1-benzofuran-5-yl]-1,3,4-oxadiazole and using N,N-dimethylformamide instead of dichloromethane, the title compound (yield 84%) was obtained as colorless crystals.

melting point 266-267° C. (recrystallized from methanol).

¹H NMR (DMSO-d₆) δ 2.87 (3H, s), 7.27 (2H, brs), 7.86-7.93 (2H, m), 7.97-8.01 (2H, m), 8.07 (1H, dd, J=1.5, 8.1 Hz), 8.25-8.26 (1H, m), 8.67 (1H, s).

Elemental analysis (for $C_{17}H_{12}ClN_3O_3S \cdot 0.25H_2O$)

Calculated (%): C, 53.97; H, 3.33; N, 11.11.

Found (%): C, 53.97; H, 3.27; N, 11.00.

EXAMPLE 372

5-[3-[3-chloro-4-(methylsulfonyl)phenyl]-1-benzofuran-5-yl]-1,3,4-oxadiazol-2-amine In the same manner as in Example 140 and using 5-[3-[3-chloro-4-(methylsulfinyl)phenyl]-1-benzofuran-5-yl]-1,3,4-oxadiazol-2-amine instead of 2-methyl-5-[3-[4-(methylthio)phenyl]-1-benzofuran-5-yl]-1,3,4-oxadiazole and using N,N-dimethylformamide instead of dichloromethane, the title compound (yield 84%) was obtained as colorless crystals.

melting point 263-264° C. (recrystallized from methanol/water).

¹H NMR (DMSO-d₆) δ 3.43 (3H, s), 7.25 (2H, brs), 7.87-7.93 (2H, m), 8.04 (1H, dd, J=1.5, 8.3 Hz), 8.13 (1H, d, J=1.5 Hz), 8.20 (1H, d, J=8.3 Hz), 8.27-8.28 (1H, m), 8.75 (1H, s).

Elemental analysis (for $C_{17}H_{12}ClN_3O_4S$)

Calculated (%): C, 52.38; H, 3.10; N, 10.78.

Found (%): C, 52.19; H, 3.10; N, 10.59.

EXAMPLE 373

5-[3-[4-(trifluoromethoxy)phenyl]-1-benzofuran-5-yl]-1,3,4-oxadiazol-2-amine

In the same manner as in Example 183 and using 3-[4-(trifluoromethoxy)phenyl]-1-benzofuran-5-carbohydrazide instead of 4-[5-[2-(3-fluorophenyl)ethyl]-1,3,4-oxadiazol-2-yl]-N²-(4-methoxyphenyl)benzene-1,2-diamine, the title compound (yield 21%) was obtained as colorless crystals.

melting point 223-224° C. (recrystallized from hexane/ethyl acetate).

¹H NMR (CDCl₃) δ 4.95 (2H, s), 7.36 (2H, d, J=8.0 Hz), 7.61-7.70 (3H, m), 7.85 (1H, s), 7.97 (1H, dd, J=1.6, 8.5 Hz), 8.34 (1H, d, J=1.6 Hz).

Elemental analysis (for $C_{17}H_{10}F_3N_3O_3$)

Calculated (%): C, 56.52; H, 2.79; N, 11.63.

Found (%): C, 56.53; H, 2.78; N, 11.66.

EXAMPLE 374

5-[3-[4-(trifluoromethoxy)phenyl]-1-benzofuran-5-yl]-1,3,4-oxadiazole-2-thiol

In the same manner as in Example 34 and using 3-[4-(trifluoromethoxy)phenyl]-1-benzofuran-5-carbohydrazide instead of 2,3-dihydro-1-benzofuran-5-carbohydrazide, the title compound (yield 11%) was obtained as colorless crystals.

melting point 197-198° C. (recrystallized from hexane/ethyl acetate).

¹H NMR (CDCl₃) δ 7.38 (2H, d, J=7.9 Hz), 7.61-7.71 (3H, m), 7.89 (1H, s), 7.98 (1H, dd, J=1.7, 8.8 Hz), 8.36 (1H, d, J=1.7 Hz).

Elemental analysis (for $C_{17}H_9F_3N_2O_3S$)

Calculated (%): C, 53.97; H, 2.40; N, 7.40.

Found (%): C, 53.67; H, 2.48; N, 7.41.

EXAMPLE 375

2-(methylthio)-5-[3-[4-(trifluoromethoxy)phenyl]-1-benzofuran-5-yl]-1,3,4-oxadiazole In the same manner as in Example 1 and using 5-[3-[4-(trifluoromethoxy)phenyl]-1-benzofuran-5-yl]-1,3,4-oxadiazole-2-thiol instead of 5-(benzothiazol-6-yl)-1,3,4-oxadiazole-2-thiol and using iodomethane instead of 3-(trifluoromethyl)benzyl chloride, the title compound (yield 80%) was obtained as colorless crystals.

melting point 138-139° C. (recrystallized from hexane/ethyl acetate).

¹H NMR (CDCl₃) δ 2.80 (3H, s), 7.37 (2H, d, J=8.0 Hz), 7.63-7.71 (3H, m), 7.86 (1H, s), 8.05 (1H, dd, J=1.5, 8.7 Hz), 8.42 (1H, d, J=1.5 Hz).

Elemental analysis (for $C_{18}H_{11}F_3N_2O_3S$)

Calculated (%): C, 55.10; H, 2.83; N, 7.14.

Found (%): C, 55.15; H, 2.86; N, 7.18.

EXAMPLE 376

2-(methylsulfinyl)-5-[3-[4-(trifluoromethoxy)phenyl]-1-benzofuran-5-yl]-1,3,4-oxadiazole In the same manner as in Example 36 and using 2-(methylthio)-5-[3-[4-(trifluoromethoxy)phenyl]-1-benzofuran-5-yl]-1,3,4-oxadiazole instead of 2-(2,3-dihydro-1-benzofuran-5-yl)-5-(methylthio)-1,3,4-oxadiazole, the title compound (yield 77%) was obtained as colorless crystals.

melting point 134-135° C. (recrystallized from hexane/diethyl ether).

$^1$H NMR (CDCl$_3$) δ 3.31 (3H, s), 7.36-7.42 (2H, m), 7.68 (2H, d, J=8.7 Hz), 7.72 (1H, d, J=8.7 Hz), 7.90 (1H, s), 8.18 (1H, dd, J=1.7, 8.7 Hz), 8.55 (1H, d, J=1.7 Hz).
Elemental analysis (for C$_{18}$H$_{11}$F$_3$N$_2$O$_4$S)
Calculated (%): C, 52.94; H, 2.72; N, 6.86.
Found (%): C, 53.09; H, 2.66; N, 7.15.

EXAMPLE 377

2-(methylsulfonyl)-5-[3-[4-(trifluoromethoxy)phenyl]-1-benzofuran-5-yl]-1,3,4-oxadiazole In the same manner as in Example 200 and using 2-(methylthio)-5-[3-[4-(trifluoromethoxy)phenyl]-1-benzofuran-5-yl]-1,3,4-oxadiazole instead of 6-(5-methyl-1,3,4-oxadiazol-2-yl)-1-[4-(methylthio)phenyl]-1H-benzimidazole, the title compound (yield 3%) was obtained as colorless crystals.
melting point 196-197° C. (recrystallized from hexane/ethyl acetate).
$^1$H NMR (CDCl$_3$) δ 3.55 (3H, s), 7.37-7.44 (2H, m), 7.65-7.70 (2H, m), 7.73 (1H, d, J=8.7 Hz), 7.91 (1H, s), 8.18 (1H, dd, J=1.8, 8.7 Hz), 8.55 (1H, d, J=1.8 Hz).
Elemental analysis (for C$_{18}$H$_{11}$F$_3$N$_2$O$_5$S)
Calculated (%): C, 50.95; H, 2.61; N, 6.60.
Found (%): C, 50.90; H, 2.80; N, 6.79.

EXAMPLE 378

N-methyl-5-[3-[4-(trifluoromethoxy)phenyl]-1-benzofuran-5-yl]-1,3,4-oxadiazol-2-amine In the same manner as in Example 110 and using 2-(methylsulfonyl)-5-[3-[4-(trifluoromethoxy)phenyl]-1-benzofuran-5-yl]-1,3,4-oxadiazole instead of 2-(2,3-dihydro-1-benzofuran-5-yl)-5-(methylsulfonyl)-1,3,4-oxadiazole and using 2M methylamine-tetrahydrofuran solution instead of 3-fluorobenzylalcohol, the title compound (yield 33%) was obtained as colorless crystals.
melting point 184-185° C. (recrystallized from hexane/ethyl acetate).
$^1$H NMR (DMSO-d$_6$) δ 2.88 (3H, d, J=4.9 Hz), 7.56 (2H, d, J=7.9 Hz), 7.60-7.68 (1H, m), 7.82-7.95 (4H, m), 8.19-8.25 (1H, m), 8.54 (1H, s).
Elemental analysis (for C$_{18}$H$_{12}$F$_3$N$_3$O$_3$)
Calculated (%): C, 57.61; H, 3.22; N, 11.20.
Found (%): C, 57.57; H, 3.14; N, 11.29.

EXAMPLE 379

1-[5-[3-[4-(trifluoromethoxy)phenyl]-1-benzofuran-5-yl]-1,3,4-oxadiazol-2-yl]piperazine In the same manner as in Example 110 and using 2-(methylsulfonyl)-5-[3-[4-(trifluoromethoxy)phenyl]-1-benzofuran-5-yl]-1,3,4-oxadiazole instead of 2-(2,3-dihydro-1-benzofuran-5-yl)-5-(methylsulfonyl)-1,3,4-oxadiazole and using piperazine instead of 3-fluorobenzylalcohol, the title compound (yield 20%) was obtained as colorless crystals.
melting point 138-140° C. (recrystallized from hexane/ethyl acetate).
$^1$H NMR (CDCl$_3$) δ 2.96-3.08 (4H, m), 3.53-3.63 (4H, m), 7.36 (2H, d, J=8.7 Hz), 7.62 (1H, d, J=8.7 Hz), 7.67 (2H, d, J=8.7 Hz), 7.84 (1H, s), 7.96 (1H, dd, J=1.7, 8.7 Hz), 8.31 (1H, d, J=1.7 Hz).
Elemental analysis (for C$_{21}$H$_{17}$F$_3$N$_4$O$_3$.0.25H$_2$O)
Calculated (%): C, 58.00; H, 4.06; N, 12.88.
Found (%): C, 58.06; H, 4.00; N, 12.76.

EXAMPLE 380

5-[3-[3-(trifluoromethoxy)phenyl]-1-benzofuran-5-yl]-1,3,4-oxadiazol-2-amine

In the same manner as in Example 183 and using 3-[3-(trifluoromethoxy)phenyl]-1-benzofuran-5-carbohydrazide instead of 4-[5-[2-(3-fluorophenyl)ethyl]-1,3,4-oxadiazol-2-yl]-N$^2$-(4-methoxyphenyl)benzene-1,2-diamine, the title compound (yield 34%) was obtained as colorless crystals.
melting point 182-183° C. (recrystallized from hexane/ethyl acetate).
$^1$H NMR (CDCl$_3$) δ 5.20 (2H, s), 7.23-7.30 (1H, m), 7.47 (1H, s), 7.53 (1H, t, J=7.8 Hz), 7.60 (1H, dt, J=1.3, 7.8 Hz), 7.64 (1H, d, J=8.7 Hz), 7.88 (1H, s), 7.98 (1H, dd, J=1.7, 8.7 Hz), 8.33 (1H, d, J=1.7 Hz).
Elemental analysis (for C$_{17}$H$_{10}$F$_3$N$_3$O$_3$)
Calculated (%): C, 56.52; H, 2.79; N, 11.63.
Found (%): C, 56.45; H, 2.79; N, 11.68.

EXAMPLE 381

2-(methylthio)-5-[3-[3-(trifluoromethoxy)phenyl]-1-benzofuran-5-yl]-1,3,4-oxadiazole A solution of methyl 3-[3-(trifluoromethoxy)phenyl]-1-benzofuran-5-carboxylate (6.80 g, 20.2 mmol) and hydrazine monohydrate (9.92 mL, 202.2 mmol) in ethanol (70 mL) was heated under reflux overnight. After cooling, the precipitate was collected by filtration to give 3-[3-(trifluoromethoxy)phenyl]-1-benzofuran-5-carbohydrazide.
A mixture of the obtained 3-[3-(trifluoromethoxy)phenyl]-1-benzofuran-5-carbohydrazide, triethylamine (5.6 mL, 40.4 mmol), carbon disulfide (18.2 mL, 303 mmol) and ethanol (70 mL) was heated under reflux for 5 hr. After cooling, saturated aqueous ammonium chloride solution was added to the reaction mixture, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate=2/1-1/2) and recrystallized from hexane/ethyl acetate to give 5-[3-[3-(trifluoromethoxy)phenyl]-1-benzofuran-5-yl]-1,3,4-oxadiazole-2-thiol.
A suspension of the obtained 5-[3-[3-(trifluoromethoxy)phenyl]-1-benzofuran-5-yl]-1,3,4-oxadiazole-2-thiol, iodomethane (2.17 mL, 34.8 mmol) and potassium carbonate (3.61 g, 26.1 mmol) in N,N-dimethylformamide (70 mL) was stirred overnight at room temperature. The reaction mixture was diluted with ethyl acetate, washed twice with water and once with saturated brine, dried over anhydrous magnesium sulfate and concentrated under reduced pressure. The residue was purified by basic silica gel column chromatography (hexane/ethyl acetate=4/1) and recrystallized from hexane/ethyl acetate to give the title compound (1.01 g, yield 15%) as colorless crystals.
melting point 113-114° C.
$^1$H NMR (CDCl$_3$) δ 2.80 (3H, s), 7.26-7.31 (1H, m), 7.48 (1H, brs), 7.55 (1H, t, J=7.7 Hz), 7.61 (1H, dt, J=1.5, 7.7 Hz), 7.65-7.69 (1H, m), 7.90 (1H, s), 8.07 (1H, dd, J=1.7, 8.7 Hz), 8.42 (1H, d, J=1.7 Hz).
Elemental analysis (for C$_{18}$H$_{11}$F$_3$N$_2$O$_3$S)
Calculated (%): C, 55.10; H, 2.83; N, 7.14.
Found (%): C, 55.07; H, 2.76; N, 7.24.

EXAMPLE 382

2-(methylsulfinyl)-5-[3-[3-(trifluoromethoxy)phenyl]-1-benzofuran-5-yl]-1,3,4-oxadiazole In the same manner as in Example 36 and using 2-(methylthio)-5-[3-[3-(trifluoromethoxy)phenyl]-1-benzofuran-5-yl]-1,3,4-oxadiazole instead of 2-(2,3-dihydro-1-benzofuran-5-yl)-5-(methylthio)-1,3,4-oxadiazole, the title compound (yield 58%) was obtained as colorless crystals.

melting point 98-99° C. (recrystallized from hexane/ethyl acetate).

$^1$H NMR (CDCl$_3$) δ 3.30 (3H, s), 7.27-7.34 (1H, m), 7.47 (1H, s), 7.54-7.65 (2H, m), 7.73 (1H, d, J=8.7 Hz), 7.93 (1H, s), 8.18 (1H, dd, J=1.7, 8.7 Hz), 8.56 (1H, d, J=1.7 Hz).

Elemental analysis (for C$_{18}$H$_{11}$F$_3$N$_2$O$_4$S)

Calculated (%): C, 52.94; H, 2.72; N, 6.86.

Found (%): C, 52.95; H, 2.70; N, 6.82.

EXAMPLE 383

N-methyl-5-[3-[3-(trifluoromethoxy)phenyl]-1-benzofuran-5-yl]-1,3,4-oxadiazol-2-amine In the same manner as in Example 110 and using 2-(methylsulfonyl)-5-[3-[3-(trifluoromethoxy)phenyl]-1-benzofuran-5-yl]-1,3,4-oxadiazole instead of 2-(2,3-dihydro-1-benzofuran-5-yl)-5-(methylsulfonyl)-1,3,4-oxadiazole and using 2M methylamine-tetrahydrofuran solution instead of 3-fluorobenzylalcohol, the title compound (yield 67%) was obtained as colorless crystals.

melting point 169-170° C. (recrystallized from hexane/ethyl acetate).

$^1$H NMR (CDCl$_3$) δ 3.13 (3H, d, J=5.3 Hz), 4.62-4.72 (1H, m), 7.24-7.29 (1H, m), 7.48 (1H, s), 7.53 (1H, t, J=7.8 Hz), 7.57-7.66 (2H, m), 7.87 (1H, s), 7.99 (1H, dd, J=1.7, 8.7 Hz), 8.31 (1H, d, J=1.7 Hz).

Elemental analysis (for C$_{18}$H$_{12}$F$_3$N$_3$O$_3$)

Calculated (%): C, 57.61; H, 3.22; N, 11.20.

Found (%): C, 57.58; H, 3.19; N, 11.11.

EXAMPLE 384

[5-[3-[3-(trifluoromethoxy)phenyl]-1-benzofuran-5-yl]-1,3,4-oxadiazol-2-yl]cyanamide In the same manner as in Example 110 and using 2-(methylsulfonyl)-5-[3-[3-(trifluoromethoxy)phenyl]-1-benzofuran-5-yl]-1,3,4-oxadiazole instead of 2-(2,3-dihydro-1-benzofuran-5-yl)-5-(methylsulfonyl)-1,3,4-oxadiazole and using cyanamide instead of 3-fluorobenzylalcohol, the title compound (yield 24%) was obtained as colorless crystals.

melting point 237-238° C. (recrystallized from hexane/ethyl acetate).

$^1$H NMR (DMSO-d$_6$) δ 7.41-7.49 (1H, m), 7.68-7.76 (2H, m), 7.79-7.85 (1H, m), 7.88-7.98 (2H, m), 8.26 (1H, s), 8.66 (1H, s).

EXAMPLE 385

N,N-dimethyl-5-[3-[3-(trifluoromethoxy)phenyl]-1-benzofuran-5-yl]-1,3,4-oxadiazol-2-amine To a mixture of O-methylhydroxylamine hydrochloride (0.59 g, 7.07 mmol), N,N-dimethylformamide (0.7 mL) and tetrahydrofuran (1.4 mL) was added sodium hydride (60% in oil, 0.31 g, 12.8 mmol) at 0° C., and the resulting mixture was stirred for 15 min. 2-(Methylsulfonyl)-5-[3-[3-(trifluoromethoxy)phenyl]-1-benzofuran-5-yl]-1,3,4-oxadiazole (0.30 g, 0.71 mmol) was added to the mixture, and the resulting mixture was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=7/3) and recrystallized from hexane/diisopropyl ether to give the title compound (32.7 mg, yield 12%) as colorless crystals.

melting point 105-106° C.

$^1$H NMR (CDCl$_3$) δ 3.17 (6H, s), 7.23-7.29 (1H, m), 7.48-7.66 (4H, m), 7.87 (1H, s), 7.99 (1H, dd, J=1.7, 8.7 Hz), 8.30 (1H, d, J=1.7 Hz).

Elemental analysis (for C$_{19}$H$_{14}$F$_3$N$_3$O$_3$)

Calculated (%): C, 58.61; H, 3.62; N, 10.79.

Found (%): C, 58.66; H, 3.52; N, 10.79.

EXAMPLE 386

5-[3-(2-chlorophenyl)-1-benzofuran-5-yl]-1,3,4-oxadiazol-2-amine

In the same manner as in Example 236 and using 3-(2-chlorophenyl)-1-benzofuran-5-carbohydrazide instead of 2-(2-phenylethyl)-1H-pyrrolo[2,3-b]pyridine-4-carbohydrazide, the title compound (yield 30%) was obtained as colorless crystals.

melting point 220-221° C. (recrystallized from hexane/ethyl acetate).

$^1$H NMR (CDCl$_3$) δ 7.22 (2H, s), 7.48-7.55 (2H, m), 7.60-7.65 (1H, m), 7.67-7.72 (1H, m), 7.82-7.88 (3H, m), 8.38 (1H, s).

Elemental analysis (for C$_{16}$H$_{10}$ClN$_3$O$_2$)

Calculated (%): C, 61.65; H, 3.23; N, 13.48.

Found (%): C, 61.57; H, 3.16; N, 13.57.

EXAMPLE 387

2-[3-(2-chlorophenyl)-1-benzofuran-5-yl]-5-(methylthio)-1,3,4-oxadiazole

A solution of 3-(2-chlorophenyl)-1-benzofuran-5-carbohydrazide (2.22 g, 7.74 mmol), triethylamine (2.14 mL, 15.4 mmol) and carbon disulfide (6.96 g, 116.1 mmol) in ethanol (25 mL) was heated under reflux overnight. After cooling, iodomethane (0.96 mL, 15.4 mmol), potassium carbonate (1.60 g, 11.6 mmol) and N,N-dimethylformamide (25 mL) were added to the reaction mixture, and the resulting mixture was stirred overnight at room temperature. The reaction mixture was diluted with ethyl acetate, washed with water and saturated brine, dried over anhydrous sodium sulfate, and concentrated under reduced pressure. The residue was purified by silica gel column chromatography (hexane/ethyl acetate=6/1) and recrystallized from hexane/ethyl acetate to give the title compound (1.95 g, yield 73%) as colorless crystals.

melting point 137-138° C.

$^1$H NMR (CDCl$_3$) δ 2.77 (3H, s), 7.33-7.45 (2H, m), 7.50-7.61 (2H, m), 7.66 (1H, d, J=8.7 Hz), 7.91 (1H, s), 8.00-8.07 (1H, m), 8.17-8.21 (1H, m).

Elemental analysis (for C$_{17}$H$_{11}$ClN$_2$O$_2$S)

Calculated (%): C, 59.56; H, 3.23; N, 8.17.

Found (%): C, 59.53; H, 3.10; N, 8.10.

EXAMPLE 388

5-[3-(2-chlorophenyl)-1-benzofuran-5-yl]-N-methyl-1,3,4-oxadiazol-2-amine

In the same manner as in Example 110 and using 2-[3-(2-chlorophenyl)-1-benzofuran-5-yl]-5-(methylsulfonyl)-1,3,4-oxadiazole instead of 2-(2,3-dihydro-1-benzofuran-5-yl)-5-(methylsulfonyl)-1,3,4-oxadiazole and using 2M methylamine-tetrahydrofuran solution instead of 3-fluorobenzylalcohol, the title compound (yield 65%) was obtained as colorless crystals.

melting point 205-206° C. (recrystallized from hexane/ethyl acetate).

$^1$H NMR (CDCl$_3$) δ 3.11 (3H, d, J=5.1 Hz), 4.62-4.72 (1H, m), 7.32-7.43 (2H, m), 7.51-7.58 (2H, m), 7.62 (1H, d, J=8.7 Hz), 7.89 (1H, s), 7.95 (1H, dd, J=1.7, 8.7 Hz), 8.10 (1H, d, J=1.7 Hz).

Elemental analysis (for C$_{17}$H$_{12}$ClN$_3$O$_2$)
Calculated (%): C, 62.68; H, 3.71; N, 12.90.
Found (%): C, 62.66; H, 3.59; N, 12.96.

EXAMPLE 389

5-[3-(2,5-difluorophenyl)-1-benzofuran-5-yl]-1,3,4-oxadiazol-2-amine

In the same manner as in Example 236 and using 3-(2,5-difluorophenyl)-1-benzofuran-5-carbohydrazide instead of 2-(2-phenylethyl)-1H-pyrrolo[2,3-b]pyridine-4-carbohydrazide, the title compound (yield 36%) was obtained as colorless crystals.

melting point 245-246° C. (recrystallized from methanol).

$^1$H NMR (CDCl$_3$) δ 7.26 (2H, brs), 7.33-7.41 (1H, m), 7.52 (1H, ddd, J=4.7, 9.4, 9.6 Hz), 7.64 (1H, ddd, J=3.2, 5.8, 9.0 Hz), 7.87 (1H, dd, J=0.6, 8.7 Hz), 7.91 (1H, dd, J=1.5, 8.7 Hz), 8.04-8.06 (1H, m), 8.50 (1H, d, J=1.1 Hz).

Elemental analysis (for C$_{16}$H$_9$F$_2$N$_3$O$_2$.0.5H$_2$O)
Calculated (%): C, 59.63; H, 3.13; N, 13.04.
Found (%): C, 59.34; H, 3.00; N, 13.03.

EXAMPLE 390

5-[3-(2,5-difluorophenyl)-1-benzofuran-5-yl]-1,3,4-oxadiazole-2-thiol

In the same manner as in Example 34 and using 3-(2,5-difluorophenyl)-1-benzofuran-5-carbohydrazide instead of 2,3-dihydrobenzofuran-5-carbohydrazide, the title compound (yield 61%) was obtained as colorless crystals.

melting point 206-207° C. (recrystallized from methanol/water).

$^1$H NMR (DMSO-d$_6$) δ 7.34-7.42 (1H, m), 7.51 (1H, ddd, J=4.7, 9.4, 9.6 Hz), 7.66 (1H, ddd, J=3.2, 5.7, 9.0 Hz), 7.91-7.97 (2H, m), 8.15-8.16 (1H, m), 8.55 (1H, d, J=1.1 Hz), 14.76 (1H, brs).

Elemental analysis (for C$_{16}$H$_8$F$_2$N$_2$O$_2$S.0.2H$_2$O)
Calculated (%): C, 57.55; H, 2.54; N, 8.39.
Found (%): C, 57.55; H, 2.67; N, 8.40.

EXAMPLE 391

2-[3-(2,5-difluorophenyl)-1-benzofuran-5-yl]-5-(methylthio)-1,3,4-oxadiazole

In the same manner as in Example 7 and using 5-[3-(2,5-difluorophenyl)-1-benzofuran-5-yl]-1,3,4-oxadiazole-2-thiol instead of 5-(1H-indazol-5-yl)-1,3,4-oxadiazole-2-thiol and using iodomethane instead of 3-(trifluoromethyl)benzyl chloride, the title compound (yield 89%) was obtained as colorless crystals.

melting point 158-159° C. (recrystallized from hexane/tetrahydrofuran).

$^1$H NMR (CDCl$_3$) δ 2.80 (3H, s), 7.04-7.12 (1H, m), 7.21 (1H, dt, J=4.5, 9.2 Hz), 7.41 (1H, ddd, J=3.2, 5.7, 8.7 Hz), 7.67 (1H, d, J=8.7 Hz), 8.00 (1H, d, J=2.1 Hz), 8.07 (1H, dd, J=1.7, 8.7 Hz), 8.38 (1H, s).

Elemental analysis (for C$_{17}$H$_{10}$F$_2$N$_2$O$_2$S)
Calculated (%): C, 59.30; H, 2.93; N, 8.14.
Found (%): C, 59.33; H, 3.04; N, 8.21.

EXAMPLE 392

2-[3-(2,5-difluorophenyl)-1-benzofuran-5-yl]-5-(methylsulfinyl)-1,3,4-oxadiazole In the same manner as in Example 140 and using 2-[3-(2,5-difluorophenyl)-1-benzofuran-5-yl]-5-(methylthio)-1,3,4-oxadiazole instead of 2-methyl-5-[3-[4-(methylthio)phenyl]-1-benzofuran-5-yl]-1,3,4-oxadiazole, the title compound (yield 92%) was obtained as colorless crystals.

melting point 151-152° C. (recrystallized from hexane/ethyl acetate).

$^1$H NMR (CDCl$_3$) δ 3.31 (3H, s), 7.06-7.14 (1H, m), 7.23 (1H, dt, J=4.5, 9.2 Hz), 7.38 (1H, ddd, J=3.0, 5.7, 8.7 Hz), 7.73 (1H, d, J=8.7 Hz), 8.02 (1H, d, J=1.9 Hz), 8.18 (1H, dd, J=1.7, 8.7 Hz), 8.51 (1H, s).

Elemental analysis (for C$_{17}$H$_{10}$F$_2$N$_2$O$_3$S)
Calculated (%): C, 56.66; H, 2.80; N, 7.77.
Found (%): C, 56.72; H, 2.86; N, 7.89.

EXAMPLE 393

2-[(methylthio)methyl]-5-[3-[3-(trifluoromethoxy)phenyl]-1-benzofuran-5-yl]-1,3,4-oxadiazole A solution of 2-(chloromethyl)-5-[3-[3-(trifluoromethoxy)phenyl]-1-benzofuran-5-yl]-1,3,4-oxadiazole (1.40 g, 3.55 mmol) and sodium methyl mercaptan (95%, 0.42 g, 5.67 mmol) in tetrahydrofuran (15 mL) was stirred overnight at room temperature. The reaction mixture was diluted with ethyl acetate, washed with water and saturated brine, dried over anhydrous sodium sulfate, and concentrated under reduced pressure. The residue was purified by silica gel column chromatography (hexane/ethyl acetate=3/1) and recrystallized from hexane/diisopropyl ether to give the title compound (1.12 g, yield 78%) as colorless crystals.

melting point 84-85° C.

$^1$H NMR (CDCl$_3$) δ 2.25 (3H, s), 3.92 (2H, s), 7.26-7.32 (1H, m), 7.49 (1H, s), 7.55 (1H, t, J=7.8 Hz), 7.59-7.64 (1H, m), 7.69 (1H, dd, J=0.6, 8.7 Hz), 7.91 (1H, s), 8.11 (1H, dd, J=1.7, 8.7 Hz), 8.48 (1H, d, J=1.7 Hz).

Elemental analysis (for C$_{19}$H$_{13}$F$_3$N$_2$O$_3$S)
Calculated (%): C, 56.16; H, 3.22; N, 6.89.
Found (%): C, 56.24; H, 3.20; N, 6.92.

EXAMPLE 394

2-[(methylsulfinyl)methyl]-5-[3-[3-(trifluoromethoxy)phenyl]-1-benzofuran-5-yl]-1,3,4-oxadiazole In the same manner as in Example 140 and using 2-[(methylthio)methyl]-5-[3-[3-(trifluoromethoxy)phenyl]-1-benzofuran-5-yl]-1,3,4-oxadiazole instead of 2-methyl-5-[3-[4-

(methylthio)phenyl]-1-benzofuran-5-yl]-1,3,4-oxadiazole, the title compound (yield 68%) was obtained as colorless crystals.

melting point 138-139° C. (recrystallized from hexane/ethyl acetate).

$^1$H NMR (CDCl$_3$) δ 2.82 (3H, s), 4.25 (1H, d, J=14.0 Hz), 4.44 (1H, d, J=14.0 Hz), 7.26-7.32 (1H, m), 7.47 (1H, s), 7.52-7.59 (1H, m), 7.59-7.64 (1H, m), 7.69 (1H, d, J=8.7 Hz), 7.91 (1H, s), 8.12 (1H, dd, J=1.7, 8.7 Hz), 8.49 (1H, d, J=1.7 Hz).

Elemental analysis (for C$_{19}$H$_{13}$F$_3$N$_2$O$_4$S)
Calculated (%): C, 54.03; H, 3.10; N, 6.63.
Found (%): C, 53.97; H, 2.99; N, 6.62.

EXAMPLE 395

2-[(methylsulfonyl)methyl]-5-[3-[3-(trifluoromethoxy)phenyl]-1-benzofuran-5-yl]-1,3,4-oxadiazole In the same manner as in Example 200 and using 2-[(methylthio)methyl]-5-[3-[3-(trifluoromethoxy)phenyl]-1-benzofuran-5-yl]-1,3,4-oxadiazole instead of 6-(5-methyl-1,3,4-oxadiazol-2-yl)-1-[4-(methylthio)phenyl]-1H-benzimidazole, the title compound (yield 36%) was obtained as colorless crystals.

melting point 162-163° C. (recrystallized from hexane/ethyl acetate).

$^1$H NMR (CDCl$_3$) δ 3.18 (3H, s), 4.62-4.67 (2H, m), 7.27-7.33 (1H, m), 7.47 (1H, brs), 7.53-7.63 (2H, m), 7.71 (1H, dd, J=0.6, 8.7 Hz), 7.92 (1H, s), 8.13 (1H, dd, J=1.7, 8.7 Hz), 8.50 (1H, d, J=1.7 Hz).

Elemental analysis (for C$_{19}$H$_{13}$F$_3$N$_2$O$_5$S)
Calculated (%): C, 52.06; H, 2.99; N, 6.39.
Found (%): C, 52.03; H, 2.88; N, 6.33.

EXAMPLE 396

5-[3-[4-(methylthio)phenyl]-1-benzofuran-5-yl]-1,3,4-oxadiazol-2-ol

To a solution of 3-[4-(methylthio)phenyl]-1-benzofuran-5-carbohydrazide (0.25 g, 0.83 mmol) and triethylamine (0.17 mL, 1.25 mmol) in N,N-dimethylformamide (5 mL) was added N,N'-carbonyldiimidazole (0.27 g, 1.68 mmol) at 0° C., and the resulting mixture was stirred for 1 hr. Water was added to the reaction mixture, and the mixture was extracted with ethyl acetate/tetrahydrofuran. The organic layer was washed with saturated brine, dried over anhydrous magnesium sulfate and concentrated under reduced pressure. The residue was recrystallized from hexane/ethyl acetate to give the title compound (0.20 g, yield 74%) as colorless crystals.

melting point 211-212° C.

$^1$H NMR (DMSO-d$_6$) δ 2.54 (3H, s), 7.44 (2H, d, J=8.6 Hz), 7.70 (2H, d, J=8.6 Hz), 7.85 (2H, d, J=1.1 Hz), 8.20 (1H, t, J=1.1 Hz), 8.50 (1H, s), 12.59 (1H, brs).

Elemental analysis (for C$_{17}$H$_{12}$N$_2$O$_3$S)
Calculated (%): C, 62.95; H, 3.73; N, 8.64.
Found (%): C, 62.73; H, 3.90; N, 8.63.

EXAMPLE 397

5-[3-[4-(methylsulfinyl)phenyl]-1-benzofuran-5-yl]-1,3,4-oxadiazol-2-ol

In the same manner as in Example 140 and using 5-[3-[4-(methylthio)phenyl]-1-benzofuran-5-yl]-1,3,4-oxadiazol-2-ol instead of 2-methyl-5-[3-[4-(methylthio)phenyl]-1-benzofuran-5-yl]-1,3,4-oxadiazole, the title compound (yield 80%) was obtained as colorless crystals.

melting point 234-237° C. (recrystallized from hexane/ethyl acetate).

$^1$H NMR (DMSO-d$_6$) δ 2.81 (3H, s), 7.80-7.95 (4H, m), 7.96 (2H, d, J=8.4 Hz), 8.24 (1H, s), 8.62 (1H, s), 12.59 (1H, s).

Elemental analysis (for C$_{17}$H$_{12}$N$_2$O$_4$S)
Calculated (%): C, 59.99; H, 3.55; N, 8.23.
Found (%): C, 59.68; H, 3.52, N, 8.09.

EXAMPLE 398

5-[3-[4-(methylsulfonyl)phenyl]-1-benzofuran-5-yl]-1,3,4-oxadiazol-2-ol

In the same manner as in Example 140 and using 5-[3-[4-(methylsulfinyl)phenyl]-1-benzofuran-5-yl]-1,3,4-oxadiazol-2-ol instead of 2-methyl-5-[3-[4-(methylthio)phenyl]-1-benzofuran-5-yl]-1,3,4-oxadiazole, the title compound (yield 77%) was obtained as colorless crystals.

melting point 284-285° C. (recrystallized from tetrahydrofuran/diethyl ether).

$^1$H NMR (DMSO-d$_6$) δ 3.33 (3H, s), 7.90 (2H, s), 8.00-8.15 (4H, m), 8.28 (1H, s), 8.77 (1H, s), 12.62 (1H, brs).

Elemental analysis (for C$_{17}$H$_{12}$N$_2$O$_5$S)
Calculated (%): C, 57.30; H, 3.39; N, 7.86.
Found (%): C, 57.21; H, 3.30, N, 7.74.

EXAMPLE 399

2-methoxy-5-[3-[4-(trifluoromethoxy)phenyl]-1-benzofuran-5-yl]-1,3,4-oxadiazole

In the same manner as in Example 110 and using 2-(methylsulfonyl)-5-[3-[4-(trifluoromethoxy)phenyl]-1-benzofuran-5-yl]-1,3,4-oxadiazole instead of 2-(2,3-dihydro-1-benzofuran-5-yl)-5-(methylsulfonyl)-1,3,4-oxadiazole and using methanol instead of 3-fluorobenzyl alcohol, the title compound (yield 4%) was obtained as colorless crystals.

melting point 143-144° C. (recrystallized from hexane/ethyl acetate).

$^1$H NMR (CDCl$_3$) δ 3.52 (3H, s), 7.37 (2H, d, J=7.9 Hz), 7.62-7.68 (3H, m), 7.85-7.91 (2H, m), 8.25 (1H, d, J=1.6 Hz).

EXAMPLE 400

[5-[3-[3-(trifluoromethoxy)phenyl]-1-benzofuran-5-yl]-1,3,4-oxadiazol-2-yl]methyl acetate In the same manner as in Example 5 and using 2-oxo-2-[2-[[3-[3-(trifluoromethoxy)phenyl]-1-benzofuran-5-yl]carbonyl]hydrazino]ethyl acetate instead of N'-[3-[3-(trifluoromethyl)phenyl]propionyl]benzothiazole-6-carbohydrazide, the title compound (yield 29%) was obtained as colorless crystals.

melting point 93-94° C. (crystallized from hexane/ethyl acetate).

$^1$H NMR (CDCl$_3$) δ 2.20 (3H, s), 5.37 (2H, s), 7.27-7.31 (1H, m), 7.48-7.49 (1H, m), 7.56 (1H, dd, J=7.7, 7.9 Hz), 7.61 (1H, td, J=1.5, 7.7 Hz), 7.70 (1H, dd, J=0.6, 8.7 Hz), 7.91 (1H, s), 8.12 (1H, dd, J=1.7, 8.7 Hz), 8.50 (1H, dd, J=0.6, 1.7 Hz).

Elemental analysis (for C$_{20}$H$_{13}$F$_3$N$_2$O$_5$)
Calculated (%): C, 57.42; H, 3.13; N, 6.70.
Found (%): C, 57.40; H, 3.07; N, 6.71.

EXAMPLE 401

[5-[3-[3-(trifluoromethoxy)phenyl]-1-benzofuran-5-yl]-1,3,4-oxadiazol-2-yl]methanol A mixture of [5-[3-[3-(trifluoromethoxy)phenyl]-1-benzofuran-5-yl]-1,3,4-oxadiazol-2-yl]methyl acetate (230 mg, 0.550 mmol), 1M aqueous sodium hydroxide solution (1 mL) and methanol (4 mL) was stirred at room temperature for 20 min. The reaction mixture was diluted with ethyl acetate, washed with water and saturated brine, dried over anhydrous magnesium sulfate and concentrated under reduced pressure. The residue was recrystallized from hexane/ethyl acetate to give the title compound (yield 85%) as colorless crystals.

melting point 158-159° C.

$^1$H NMR (CDCl$_3$) δ 2.91 (1H, t, J=6.8 Hz), 4.98 (2H, d, J=6.8 Hz), 7.26-7.31 (1H, m), 7.45-7.47 (1H, m), 7.55 (1H, dd, J=7.7, 7.9 Hz), 7.60 (1H, td, J=1.5, 7.7 Hz), 7.67 (1H, dd, J=0.6, 8.7 Hz), 7.89 (1H, s), 8.11 (1H, dd, J=1.7, 8.7 Hz), 8.47 (1H, dd, J=0.6, 1.7 Hz).

Elemental analysis (for C$_{18}$H$_{11}$F$_3$N$_2$O$_4$)
Calculated (%): C, 57.45; H, 2.95; N, 7.44.
Found (%): C, 57.48; H, 2.85; N, 7.47.

EXAMPLE 402

1-[5-[3-[3-(trifluoromethoxy)phenyl]-1-benzofuran-5-yl]-1,3,4-oxadiazol-2-yl]ethyl acetate In the same manner as in Example 5 and using 1-methyl-2-oxo-2-[2-[[3-[3-(trifluoromethoxy)phenyl]-1-benzofuran-5-yl]carbonyl]hydrazino]ethyl acetate instead of N'-[3-[3-(trifluoromethyl)phenyl]propionyl]benzothiazole-6-carbohydrazide, the title compound (yield 29%) was obtained as colorless oil.

$^1$H NMR (CDCl$_3$) δ 1.79 (3H, d, J=6.8 Hz), 2.17 (3H, s), 6.18 (1H, q, J=6.8 Hz), 7.26-7.32 (1H, m), 7.50 (1H, s), 7.56 (1H, t, J=7.8 Hz), 7.61 (1H, dt, J=7.8, 1.5 Hz), 7.69 (1H, d, J=8.7 Hz), 7.91 (1H, s), 8.11 (1H, dd, J=1.7, 8.7 Hz), 8.48 (1H, d, J=1.7 Hz).

EXAMPLE 403

1-[5-[3-[3-(trifluoromethoxy)phenyl]-1-benzofuran-5-yl]-1,3,4-oxadiazol-2-yl]ethanol In the same manner as in Example 401 and using 1-[5-[3-[3-(trifluoromethoxy)phenyl]-1-benzofuran-5-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 64%) was obtained as colorless crystals.

melting point 131-132° C. (recrystallized from hexane/ethyl acetate).

$^1$H NMR (CDCl$_3$) δ 1.76 (3H, d, J=6.6 Hz), 2.72-2.80 (1H, m), 5.15-5.28 (1H, m), 7.26-7.32 (1H, m), 7.46-7.50 (1H, m), 7.52?7.64 (2H, m), 7.68 (1H, d, J=8.7 Hz), 7.90 (1H, s), 8.11 (1H, dd, J=1.7, 8.7 Hz), 8.47 (1H, d, J=1.7 Hz).

Elemental analysis (for C$_{19}$H$_{13}$F$_3$N$_2$O$_4$)
Calculated (%): C, 58.47; H, 3.36; N, 7.18.
Found (%): C, 58.62; H, 3.43; N, 7.29.

EXAMPLE 404

1-[5-[3-[3-(trifluoromethoxy)phenyl]-1-benzofuran-5-yl]-1,3,4-oxadiazol-2-yl]ethanone To a solution of 1-[5-[3-[3-(trifluoromethoxy)phenyl]-1-benzofuran-5-yl]-1,3,4-oxadiazol-2-yl]ethanol (0.30 g, 0.77 mmol) in dichloromethane (3 mL) was added a solution of 1,1,1-triacetoxy-1,1-dihydro-1,2-benziodoxol-3(1H)-one (0.65 g, 1.54 mmol) in dichloromethane (3 mL) at room temperature, and the resulting mixture was stirred overnight. A saturated aqueous sodium thiosulfate solution was added to the reaction mixture, and the mixture was extracted with ethyl acetate. The organic layer was washed with saturated aqueous sodium hydrogen carbonate solution and saturated brine, dried over anhydrous sodium sulfate, and concentrated under reduced pressure. The residue was purified by silica gel column chromatography (hexane/ethyl acetate=17/3) and recrystallized from hexane/ethyl acetate to give the title compound (0.17 g, yield 57%) as colorless crystals.

melting point 64-65° C.

$^1$H NMR (CDCl$_3$) δ 2.83 (3H, s), 7.27-7.33 (1H, m), 7.47 (1H, s), 7.53-7.65 (2H, m), 7.72 (1H, d, J=8.7 Hz), 7.92 (1H, s), 8.22 (1H, dd, J=1.7, 8.7 Hz), 8.60 (1H, d, J=1.7 Hz).

Elemental analysis (for C$_{19}$H$_{11}$F$_3$N$_2$O$_4$)
Calculated (%): C, 58.77; H, 2.86; N, 7.21.
Found (%): C, 58.92; H, 2.86; N, 7.36.

EXAMPLE 405

(1S)-1-[5-[3-[3-(trifluoromethoxy)phenyl]-1-benzofuran-5-yl]-1,3,4-oxadiazol-2-yl]ethanol In the same manner as in Example 401 and using (1S)-1-[5-[3-[3-(trifluoromethoxy)phenyl]-1-benzofuran-5-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 80%) was obtained as colorless crystals.

melting point 130-131° C. (recrystallized from hexane/ethyl acetate).

$^1$H NMR (CDCl$_3$) δ 1.76 (3H, d, J=6.8 Hz), 2.55 (1H, d, J=5.8 Hz), 5.15-5.27 (1H, m), 7.24-7.34 (1H, m), 7.48 (1H, s), 7.50-7.64 (2H, m), 7.69 (1H, d, J=8.7 Hz), 7.91 (1H, s), 8.12 (1H, dd, J=1.7, 8.7 Hz), 8.48 (1H, d, J=1.3 Hz).

Elemental analysis (for C$_{19}$H$_{13}$F$_3$N$_2$O$_4$)
Calculated (%): C, 58.47; H, 3.36; N, 7.18.
Found (%): C, 58.50; H, 3.25; N, 7.05.

EXAMPLE 406

(1S)-1-[5-[3-[4-(methylthio)phenyl]-1-benzofuran-5-yl]-1,3,4-oxadiazol-2-yl]ethanol In the same manner as in Example 401 and using (1S)-1-[5-[3-[4-(methylthio)phenyl]-1-benzofuran-5-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 88%) was obtained as colorless crystals.

melting point 164-165° C. (recrystallized from hexane/ethyl acetate).

$^1$H NMR (CDCl$_3$) δ 1.76 (3H, d, J=6.4 Hz), 2.53 (1H, d, J=5.7 Hz), 2.56 (3H, s), 5.14-5.26 (1H, m), 7.35-7.44 (2H, m), 7.54-7.61 (2H, m), 7.66 (1H, d, J=8.7 Hz), 7.85 (1H, s), 8.09 (1H, dd, J=1.9, 8.7 Hz), 8.49 (1H, s).

Elemental analysis (for C$_{19}$H$_{16}$N$_2$O$_3$S)
Calculated (%): C, 64.76; H, 4.58; N, 7.95.
Found (%): C, 64.75; H, 4.51; N, 7.88.

EXAMPLE 407

(1S)-1-[5-[3-[4-(methylsulfinyl)phenyl]-1-benzofuran-5-yl]-1,3,4-oxadiazol-2-yl]ethanol In the same manner as in Example 140 and using (1S)-1-[5-[3-[4-(methylthio)phenyl]-1-benzofuran-5-yl]-1,3,4-oxadiazol-2-yl]ethanol instead of 2-methyl-5-[3-[4-(methylthio)phenyl]-1-benzofuran-5-yl]-1,3,4-oxadiazole, the title compound (yield 80%) was obtained as colorless crystals.

melting point 163-164° C. (recrystallized from hexane/tetrahydrofuran).

$^1$H NMR (CDCl$_3$) δ 1.76 (3H, d, J=6.6 Hz), 2.74 (1H, d, J=5.7 Hz), 2.81 (3H, s), 5.13-5.32 (1H, m), 7.69 (1H, d, J=8.7 Hz), 7.80 (4H, s), 7.93 (1H, s), 8.11 (1H, dd, J=1.7, 8.7 Hz), 8.50 (1H, d, J=1.3 Hz)

Elemental analysis (for C$_{19}$H$_{16}$N$_2$O$_4$S)
Calculated (%): C, 61.94; H, 4.38; N, 7.60.
Found (%): C, 62.03; H, 4.38; N, 7.42.

EXAMPLE 408

(1S)-1-[5-[3-[4-(methylsulfonyl)phenyl]-1-benzofuran-5-yl]-1,3,4-oxadiazol-2-yl]ethanol In the same manner as in Example 200 and using (1S)-1-[5-[3-[4-(methylsulfinyl)phenyl]-1-benzofuran-5-yl]-1,3,4-oxadiazol-2-yl]ethanol instead of 6-(5-methyl-1,3,4-oxadiazol-2-yl)-1-[4-(methylthio)phenyl]-1H-benzimidazole, the title compound (yield 88%) was obtained as colorless crystals.

melting point 175-176° C. (recrystallized from hexane/ethyl acetate).

$^1$H NMR (CDCl$_3$) δ 1.77 (3H, d, J=6.8 Hz), 2.56 (1H, d, J=5.7 Hz), 3.14 (3H, s), 5.07-5.31 (1H, m), 7.71 (1H, d, J=8.7 Hz), 7.82-7.93 (2H, m), 7.98 (1H, s), 8.03-8.18 (3H, m), 8.51 (1H, d, J=1.3 Hz).

Elemental analysis (for C$_{19}$H$_{16}$N$_2$O$_5$S)
Calculated (%): C, 59.37; H, 4.20; N, 7.29.
Found (%): C, 59.33; H, 4.10; N, 6.99.

EXAMPLE 409

(1R)-1-[5-[3-[3-(trifluoromethoxy)phenyl]-1-benzofuran-5-yl]-1,3,4-oxadiazol-2-yl]ethanol In the same manner as in Example 401 and using (1R)-1-[5-[3-[3-(trifluoromethoxy)phenyl]-1-benzofuran-5-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 64%) was obtained as colorless crystals.

melting point 131-132° C. (recrystallized from hexane/ethyl acetate).

$^1$H NMR (CDCl$_3$) δ 1.76 (3H, d, J=6.8 Hz), 2.92 (1H, d, J=5.3 Hz), 5.14-5.30 (1H, m), 7.27-7.34 (1H, m), 7.40-7.78 (4H, m), 7.89 (1H, s), 8.10 (1H, dd, J=1.9, 8.7 Hz), 8.46 (1H, s).

Elemental analysis (for C$_{19}$H$_{13}$F$_3$N$_2$O$_4$)
Calculated (%): C, 58.47; H, 3.36; N, 7.18.
Found (%): C, 58.63; H, 3.40; N, 7.21.

EXAMPLE 410

(1S)-1-[5-[3-(2-chloro-5-fluorophenyl)-1-benzofuran-5-yl]-1,3,4-oxadiazol-2-yl]ethanol In the same manner as in Example 401 and using (1S)-1-[5-[3-(2-chloro-5-fluorophenyl)-1-benzofuran-5-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 88%) was obtained as colorless crystals.

melting point 204-205° C. (recrystallized from hexane/ethyl acetate).

$^1$H NMR (CDCl$_3$) δ 1.75 (3H, d, J=6.8 Hz), 2.47 (1H, d, J=5.7 Hz), 5.12-5.27 (1H, m), 7.02-7.17 (1H, m), 7.20-7.30 (1H, m), 7.53 (1H, dd, J=5.1, 8.9 Hz), 7.69 (1H, d, J=8.3 Hz), 7.93 (1H, s), 8.11 (1H, dd, J=1.7, 8.5 Hz), 8.25 (1H, d, J=1.9 Hz).

Elemental analysis (for C$_{18}$H$_{12}$ClFN$_2$O$_3$)
Calculated (%): C, 60.26; H, 3.37; N, 7.81.
Found (%): C, 60.25; H, 3.35; N, 7.85.

EXAMPLE 411

1-[5-[3-(2,5-difluorophenyl)-1-benzofuran-5-yl]-1,3,4-oxadiazol-2-yl]-1-methylethyl acetate In the same manner as in Example 5 and using 2-[2-[[3-(2,5-difluorophenyl)-1-benzofuran-5-yl]carbonyl]hydrazino]-1,1-dimethyl-2-oxoethyl acetate instead of N'-[3-[3-(trifluoromethyl)phenyl]propionyl]benzothiazole-6-carbohydrazide, the title compound (yield 71%) was obtained as colorless crystals.

melting point 125-126° C. (recrystallized from hexane/ethyl acetate).

$^1$H NMR (CDCl$_3$) δ 1.91 (6H, s), 2.10 (3H, s), 7.02-7.13 (1H, m), 7.16-7.25 (1H, m), 7.35-7.46 (1H, m), 7.68 (1H, d, J=8.7 Hz), 8.01 (1H, d, J=2.1 Hz), 8.07 (1H, dd, J=1.7, 8.7 Hz), 8.42 (1H, s).

Elemental analysis (for C$_{21}$H$_{16}$F$_2$N$_2$O$_4$)
Calculated (%): C, 63.32; H, 4.05; N, 7.03.
Found (%): C, 63.35; H, 4.06; N, 6.98.

EXAMPLE 412

2-[5-[3-(2,5-difluorophenyl)-1-benzofuran-5-yl]-1,3,4-oxadiazol-2-yl]propan-2-ol In the same manner as in Example 401 and using 1-[5-[3-(2,5-difluorophenyl)-1-benzofuran-5-yl]-1,3,4-oxadiazol-2-yl]-1-methylethyl acetate instead of [5-[3-[3-(trifluoromethoxy)phenyl]-1-benzofuran-5-yl]-1,3,4-oxadiazol-2-yl]methyl acetate, the title compound (yield 74%) was obtained as colorless crystals.

melting point 155-156° C. (recrystallized from hexane/ethyl acetate).

$^1$H NMR (CDCl$_3$) δ 1.80 (6H, s), 2.58 (1H, s), 7.02-7.13 (1H, m), 7.20 (1H, dd, J=4.5, 9.5 Hz), 7.36-7.45 (1H, m), 7.69 (1H, d, J=8.7 Hz), 8.00 (1H, d, J=1.9 Hz), 8.11 (1H, dd, J=1.9, 8.7 Hz), 8.43 (1H, s).

Elemental analysis (for C$_{19}$H$_{14}$F$_2$N$_2$O$_3$)
Calculated (%): C, 64.04; H, 3.96; N, 7.86.
Found (%): C, 64.01; H, 3.85; N, 7.75.

EXAMPLE 413

2-(methoxymethyl)-5-[3-[3-(trifluoromethoxy)phenyl]-1-benzofuran-5-yl]-1,3,4-oxadiazole A solution of 2-(chloromethyl)-5-[3-[3-(trifluoromethoxy)phenyl]-1-benzofuran-5-yl]-1,3,4-oxadiazole (0.30 g, 0.76 mmol) and potassium tert-butoxide (85%, 0.12 g, 0.91 mmol) in methanol (5 mL) was stirred overnight at room temperature. Potassium tert-butoxide (85%, 0.03 g, 0.23 mmol) was added to the reaction mixture, and the resulting mixture was stirred at 50° C. overnight. The reaction mixture was concentrated under reduced pressure, saturated aqueous ammonium chloride solution was added to the residue, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate=3/1) and recrystallized from hexane/ethyl acetate to give the title compound (0.20 g, yield 67%) as colorless crystals.

melting point 90-91° C.

$^1$H NMR (CDCl$_3$) δ 3.52 (3H, s), 4.75 (2H, s), 7.25-7.32 (1H, m), 7.48 (1H, brs), 7.56 (1H, t, J=7.8 Hz), 7.59-7.64 (1H, m), 7.69 (1H, d, J=8.7 Hz), 7.91 (1H, s), 8.14 (1H, dd, J=1.7, 8.7 Hz), 8.51 (1H, d, J=1.7 Hz).

Elemental analysis (for C$_{19}$H$_{13}$F$_3$N$_2$O$_4$)

Calculated (%): C, 58.47; H, 3.36; N, 7.18.

Found (%): C, 58.51; H, 3.26; N, 7.14.

EXAMPLE 414

N-methyl-1-[5-[3-[3-(trifluoromethoxy)phenyl]-1-benzofuran-5-yl]-1,3,4-oxadiazol-2-yl]methylamine A mixture of 2-(chloromethyl)-5-[3-[3-(trifluoromethoxy)phenyl]-1-benzofuran-5-yl]-1,3,4-oxadiazole (0.30 g, 0.76 mmol), potassium iodide (0.13 g, 0.76 mmol) and 2M methylamine-tetrahydrofuran solution (10 mL) was stirred overnight at room temperature. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=7/3) and recrystallized from hexane/diisopropyl ether to give the title compound (0.20 g, yield 67%) as colorless crystals.

melting point 65-66° C.

$^1$H NMR (DMSO-d$_6$) δ 2.35 (3H, s), 2.46 (1H, brs), 3.96 (2H, s), 7.42-7.50 (1H, m), 7.68-7.77 (2H, m), 7.81-7.87 (1H, m), 7.91-7.96 (1H, m), 8.07 (1H, dd, J=1.7, 8.7 Hz), 8.44 (1H, d, J=1.7 Hz), 8.66 (1H, s).

Elemental analysis (for C$_{19}$H$_{14}$F$_3$N$_3$O$_3$)

Calculated (%): C, 58.61; H, 3.62; N, 10.79.

Found (%): C, 58.59; H, 3.55; N, 10.81.

EXAMPLE 415

1-(1-benzylpiperidin-4-yl)-6-(5-methyl-1,3,4-oxadiazol-2-yl)-1H-benzimidazole

In the same manner as in Example 239 and using 1-(1-benzylpiperidin-4-yl)-1H-benzimidazole-6-carbohydrazide instead of 2-[[4-(methylthio)phenyl]amino]isonicotinohydrazide, the title compound (yield 45%) was obtained as colorless crystals.

melting point 173-174° C. (recrystallized from hexane/ethyl acetate).

$^1$H NMR (CDCl$_3$) δ 2.10-2.36 (6H, m), 2.65 (3H, s), 3.06-3.17 (2H, m), 3.62 (2H, s), 4.23-4.37 (1H, m), 7.28-7.33 (1H, m), 7.34-7.38 (4H, m), 7.88-7.91 (2H, m), 8.12 (1H, brs), 8.19-8.21 (1H, m).

Elemental analysis (for C$_{22}$H$_{23}$N$_5$O)

Calculated (%): C, 70.76; H, 6.21; N, 18.75.

Found (%): C, 70.58; H, 6.37; N, 18.70.

EXAMPLE 416

3-[2-[5-[1-[4-(methylthio)phenyl]-1H-benzimidazol-6-yl]-1,3,4-oxadiazol-2-yl]ethyl]benzonitrile In the same manner as in Example 14 and using 1-[4-(methylthio)phenyl]-1H-benzimidazole-6-carbohydrazide instead of 1H-benzotriazole-5-carbohydrazide, the title compound (yield 64%) was obtained as colorless crystals.

melting point 185-186° C. (recrystallized from hexane/ethyl acetate).

$^1$H NMR (CDCl$_3$) δ 2.59 (3H, s), 3.25 (4H, s), 7.38-7.57 (8H, m), 7.97 (2H, s), 8.15 (1H, s), 8.19 (1H, s).

Elemental analysis (for C$_{25}$H$_{19}$N$_5$OS.0.5H$_2$O)

Calculated (%): C, 67.25; H, 4.51; N, 15.68.

Found (%): C, 67.55; H, 4.37; N, 15.72.

EXAMPLE 417

3-[2-[5-[1-[4-(methylsulfinyl)phenyl]-1H-benzimidazol-6-yl]-1,3,4-oxadiazol-2-yl]ethyl]benzonitrile In the same manner as in Example 140 and using 3-[2-[5-[1-[4-(methylthio)phenyl]-1H-benzimidazol-6-yl]-1,3,4-oxadiazol-2-yl]ethyl]benzonitrile instead of 2-methyl-5-[3-[4-(methylthio)phenyl]-1-benzofuran-5-yl]-1,3,4-oxadiazole, the title compound (yield 82%) was obtained as colorless crystals.

melting point 194-195° C. (crystallized from hexane/chloroform).

$^1$H NMR (CDCl$_3$) δ 2.85 (3H, s), 3.27 (4H, s), 7.40-7.45 (1H, t, J=7.5 Hz), 7.50-7.57 (3H, m), 7.74 (2H, d, J=8.7 Hz), 7.93-8.00 (4H, m), 8.24-8.27 (2H, m).

Elemental analysis (for C$_{25}$H$_{19}$N$_5$O$_2$S.0.5H$_2$O)

Calculated (%): C, 64.92; H, 4.36; N, 15.14.

Found (%): C, 64.77; H, 4.27; N, 14.97.

EXAMPLE 418

3-[2-[5-[1-[4-(methylsulfonyl)phenyl]-1H-benzimidazol-6-yl]-1,3,4-oxadiazol-2-yl]ethyl]benzonitrile In the same manner as in Example 200 and using 3-[2-[5-[1-[4-(methylthio)phenyl]-1H-benzimidazol-6-yl]-1,3,4-oxadiazol-2-yl]ethyl]benzonitrile instead of 6-(5-methyl-1,3,4-oxadiazol-2-yl)-1-[4-(methylthio)phenyl]-1H-benzimidazole, the title compound (yield 77%) was obtained as colorless crystals.

melting point 225-226° C. (recrystallized from hexane/chloroform).

$^1$H NMR (CDCl$_3$) δ 3.18 (3H, s), 3.27 (4H, s), 7.40-7.56 (4H, m), 7.80 (2H, d, J=8.4 Hz), 8.01 (2H, s), 8.23-8.29 (4H, m).

Elemental analysis (for C$_{25}$H$_{19}$N$_5$O$_3$S.0.3H$_2$O)

Calculated (%): C, 63.22; H, 4.16; N, 14.74.

Found (%): C, 63.29; H, 4.14; N, 14.77.

EXAMPLE 419

1-[4-(methylthio)phenyl]-6-[5-[2-[3-(trifluoromethyl)phenyl]ethyl]-1,3,4-oxadiazol-2-yl]-1H-benzimidazole In the same manner as in Example 14 and using 1-[4-(methylthio)phenyl]-1H-benzimidazole-6-carbohydrazide instead of 1H-benzotriazole-5-carbohydrazide and using 3-[3-(trifluoromethyl)phenyl]propionic acid instead of 3-(3-cyanophenyl)propionic acid, the title compound (yield 70%) was obtained as colorless crystals.

melting point 167-168° C. (recrystallized from tetrahydrofuran/diisopropyl ether).

$^1$H NMR (CDCl$_3$) δ 2.59 (3H, s), 3.27 (4H, s), 7.39-7.53 (8H, m), 7.97 (2H, s), 8.15 (1H, t, J=1.2 Hz), 8.19 (1H, s).

Elemental analysis (for C$_{25}$H$_{19}$F$_3$N$_4$OS)

Calculated (%): C, 62.49; H, 3.99; N, 11.66.

Found (%): C, 62.36; H, 4.12; N, 11.50.

EXAMPLE 420

1-[4-(methylsulfinyl)phenyl]-6-[5-[2-[3-(trifluoromethyl)phenyl]ethyl]-1,3,4-oxadiazol-2-yl]-1H-benzimidazole In the same manner as in Example 140 and using 1-[4-(methylthio)phenyl]-6-[5-[2-[3-(trifluoromethyl)phenyl]ethyl]-1,3,4-oxadiazol-2-yl]-1H-benzimidazole instead of 2-methyl-5-[3-[4-(methylthio)phenyl]-1-benzofuran-5-yl]-1,3,4-oxadiazole, the title compound (yield 76%) was obtained as colorless crystals.
melting point 169-170° C. (recrystallized from hexane/chloroform).
$^1$H NMR (CDCl$_3$) δ 2.85 (3H, s), 3.28 (4H, s), 7.43-7.53 (4H, m), 7.74 (2H, d, J=8.4 Hz), 7.93 (2H, d, J=8.4 Hz), 7.99 (2H, s), 8.24 (1H, t, J=0.9 Hz), 8.26 (1H, s).
Elemental analysis (for C$_{25}$H$_{19}$F$_3$N$_4$O$_2$S)
Calculated (%): C, 60.48; H, 3.86; N, 11.28.
Found (%): C, 60.21; H, 4.05; N, 11.11.

EXAMPLE 421

1-[4-(methylsulfonyl)phenyl]-6-[5-[2-[3-(trifluoromethyl)phenyl]ethyl]-1,3,4-oxadiazol-2-yl]-1H-benzimidazole In the same manner as in Example 200 and using 1-[4-(methylthio)phenyl]-6-[5-[2-[3-(trifluoromethyl)phenyl]ethyl]-1,3,4-oxadiazol-2-yl]-1H-benzimidazole instead of 6-(5-methyl-1,3,4-oxadiazol-2-yl)-1-[4-(methylthio)phenyl]-1H-benzimidazole, the title compound (yield 77%) was obtained as colorless crystals.
melting point 204-205° C. (recrystallized from hexane/chloroform)
$^1$H NMR (CDCl$_3$) δ 3.18 (3H, s), 3.28 (4H, s), 7.43-7.52 (4H, m), 7.79 (2H, d, J=8.7 Hz), 8.00 (2H, s), 8.22-8.28 (4H, m).
Elemental analysis (for C$_{25}$H$_{19}$F$_3$N$_4$O$_3$S.0.2H$_2$O)
Calculated (%): C, 58.18; H, 3.79; N, 10.86.
Found (%): C, 58.04; H, 3.82; N, 10.79.

EXAMPLE 422

5-[1-[4-(methylthio)phenyl]-1H-benzimidazol-6-yl]-1,3,4-oxadiazol-2-amine

In the same manner as in Example 236 and using 1-[4-(methylthio)phenyl]-1H-benzimidazole-6-carbohydrazide instead of 2-(2-phenylethyl)-1H-pyrrolo[2,3-b]pyridine-4-carbohydrazide, the title compound (yield 75%) was obtained as colorless crystals.
melting point 254-255° C. (recrystallized from N,N-dimethylformamide/water).
$^1$H NMR (DMSO-d$_6$) δ 2.58 (3H, s), 7.21 (2H, s), 7.55 (2H, d, J=8.7 Hz), 7.67 (2H, d, J=8.7 Hz), 7.77-7.92 (3H, m), 8.67 (1H, s).
Elemental analysis (for C$_{16}$H$_{13}$N$_5$OS.0.4H$_2$O)
Calculated (%): C, 58.13; H, 4.21; N, 21.19.
Found (%): C, 58.33; H, 4.22; N, 20.99.

EXAMPLE 423

5-[1-[4-(methylsulfinyl)phenyl]-1H-benzimidazol-6-yl]-1,3,4-oxadiazol-2-amine

In the same manner as in Example 140 and using 5-[1-[4-(methylthio)phenyl]-1H-benzimidazol-6-yl]-1,3,4-oxadiazol-2-amine instead of 2-methyl-5-[3-[4-(methylthio)phenyl]-1-benzofuran-5-yl]-1,3,4-oxadiazole, the title compound (yield 44%) was obtained as colorless crystals.
melting point 290-291° C. (recrystallized from N,N-dimethylformamide/water).
$^1$H NMR (CDCl$_3$) δ 2.86 (3H, s), 7.23 (2H, s), 7.71 (1H, dd, J=1.5, 7.2 Hz), 7.92-7.98 (6H, m), 8.77 (1H, s).

EXAMPLE 424

6-(5-methyl-1,3,4-oxadiazol-2-yl)-1-[1-(methylsulfonyl)piperidin-4-yl]-1H-benzimidazole To a solution of 6-(5-methyl-1,3,4-oxadiazol-2-yl)-1-(4-piperidinyl)-1H-benzimidazole (0.25 g, 0.88 mmol) and triethylamine (0.24 mL, 1.76 mmol) in tetrahydrofuran (5 mL) was added methanesulfonyl chloride (0.10 mL, 1.32 mmol) at 0° C., and the resulting mixture was stirred at room temperature for 1 hr. The reaction solution was filtered, and the filtrate was concentrated under reduced pressure. The residue was purified by basic silica gel column chromatography (ethyl acetate/methanol=1/0-19/1) and recrystallized from diethyl ether/methanol to give the title compound (0.19 g, yield 60%) as colorless crystals.
melting point 233-234° C.
$^1$H NMR (DMSO-d$_6$) δ 2.06-2.24 (4H, m), 2.61 (3H, s), 2.97 (3H, s), 3.00-3.19 (2H, m), 3.69-3.82 (2H, m), 4.71-4.86 (1H, m), 7.82-7.89 (2H, m), 8.32 (1H, brs), 8.62 (1H, s).
Elemental analysis (for C$_{16}$H$_{19}$N$_5$O$_3$S)
Calculated (%): C, 53.17; H, 5.30; N, 19.38.
Found (%): C, 52.89; H, 5.45; N, 19.18.

EXAMPLE 425

1-(1-benzoylpiperidin-4-yl)-6-(5-methyl-1,3,4-oxadiazol-2-yl)-1H-benzimidazole

In the same manner as in Example 424 and using benzoyl chloride instead of methanesulfonyl chloride, the title compound (yield 41%) was obtained as colorless crystals.
melting point 158-159° C. (recrystallized from hexane/ethyl acetate).
$^1$H NMR (CDCl$_3$) δ 2.10 (2H, brs), 2.29 (2H, brs), 2.65 (3H, s), 3.17 (2H, brs), 4.11 (1H, brs), 4.50-4.64 (1H, m), 5.00 (1H, brs), 7.41-7.51 (5H, m), 7.90-7.96 (2H, m), 8.12 (1H, s), 8.19-8.23 (1H, m).
Elemental analysis (for C$_{22}$H$_{21}$N$_5$O$_2$.H$_2$O)
Calculated (%): C, 65.17; H, 5.72; N, 17.40.
Found (%): C, 65.22; H, 5.70; N, 17.40.

EXAMPLE 426

1-(1-acetylpiperidin-4-yl)-6-(5-methyl-1,3,4-oxadiazol-2-yl)-1H-benzimidazole

In the same manner as in Example 424 and using acetyl chloride instead of methanesulfonyl chloride, the title compound (yield 5%) was obtained as colorless crystals.
melting point 228-229° C. (recrystallized from hexane/ethyl acetate).
$^1$H NMR (CDCl$_3$) δ 1.91-2.11 (2H, m), 2.19 (3H, s), 2.22-2.37 (2H, m), 2.66 (3H, s), 2.72-2.85 (1H, m), 3.27-3.41 (1H, m), 4.03-4.13 (1H, m), 4.47-4.60 (1H, m), 4.90-5.01 (1H, m), 7.92 (2H, brs), 8.08 (1H, s), 8.21 (1H, brs).
Elemental analysis (for C$_{17}$H$_{19}$N$_5$O$_2$.0.25H$_2$O)
Calculated (%): C, 61.90; H, 5.96; N, 21.23.
Found (%): C, 61.98; H, 5.97; N, 21.13.

EXAMPLE 427 ethyl 4-[6-(5-methyl-1,3,4-oxadiazol-2-yl)-1H-benzimidazol-1-yl]piperidine-1-carboxylate In the same manner as in Example 424 and using ethyl chloroformate instead of methanesulfonyl chloride, the title compound (yield 48%) was obtained as colorless crystals.

melting point 179-180° C. (recrystallized from hexane/ethyl acetate).

$^1$H NMR (CDCl$_3$) δ 1.31 (3H, t, J=7.2 Hz), 1.96-2.12 (2H, m), 2.19-2.29 (2H, m), 2.66 (3H, s), 2.95-3.08 (2H, m), 4.20 (2H, q, J=7.2 Hz), 4.39-4.52 (3H, m), 7.90-7.92 (2H, m), 8.09 (1H, s), 8.17-8.21 (1H, m).

Elemental analysis (for C$_{18}$H$_{21}$N$_5$O$_3$)
Calculated (%): C, 60.83; H, 5.96; N, 19.71.
Found (%): C, 60.69; H, 5.97; N, 19.69.

EXAMPLE 428

6-(5-methyl-1,3,4-oxadiazol-2-yl)-1-[4-(trifluoromethoxy)phenyl]-1H-benzimidazole In the same manner as in Example 5 and using N'-acetyl-1-[4-(trifluoromethoxy)phenyl]-1H-benzimidazole-6-carbohydrazide instead of N'-[3-[3-(trifluoromethyl)phenyl]propionyl]benzothiazole-6-carbohydrazide, the title compound (yield 67%) was obtained as colorless crystals.

melting point 160-161° C. (recrystallized from hexane/ethyl acetate).

$^1$H NMR (CDCl$_3$) δ 2.63 (3H, s), 7.54 (2H, d, J=8.7 Hz), 7.60 (2H, d, J=8.7 Hz), 7.97-8.04 (2H, m), 8.21 (2H, d, J=1.5 Hz).

Elemental analysis (for C$_{17}$H$_{11}$F$_3$N$_4$O$_2$.0.1H$_2$O)
Calculated (%): C, 56.39; H, 3.12; N, 15.47.
Found (%): C, 56.21; H, 3.16; N, 15.48.

EXAMPLE 429

N-methyl-5-[1-[4-(methylthio)phenyl]-1H-benzimidazol-6-yl]-1,3,4-oxadiazol-2-amine In the same manner as in Example 368 and using N-methyl-2-[[1-[4-(methylthio)phenyl]-1H-benzimidazol-6-yl]carbonyl]hydrazinecarbothioamide instead of N-methyl-2-[[3-[4-(methylthio)phenyl]-1-benzofuran-5-yl]carbonyl]hydrazinecarbothioamide, the title compound (yield 10%) was obtained as colorless crystals.

melting point 224-225° C. (recrystallized from hexane/tetrahydrofuran).

$^1$H NMR (DMSO-d$_6$) δ 2.58 (3H, s), 2.86 (3H, d, J=5.1 Hz), 7.55 (2H, d, J=8.7 Hz), 7.59-7.64 (1H, m), 7.66 (2H, d, J=8.7 Hz), 7.79 (1H, dd, J=1.5, 6.9 Hz), 7.81-7.92 (2H, m), 8.66 (1H, s).

Elemental analysis (for C$_{17}$H$_{15}$N$_5$OS)
Calculated (%): C, 60.52; H, 4.48; N, 20.76.
Found (%): C, 60.36; H, 4.64; N, 20.56.

EXAMPLE 430

N-ethyl-5-[1-[4-(methylthio)phenyl]-1H-benzimidazol-6-yl]-1,3,4-oxadiazol-2-amine In the same manner as in Example 368 and using N-ethyl-2-[[1-[4-(methylthio)phenyl]-1H-benzimidazol-6-yl]carbonyl]hydrazinecarbothioamide instead of N-methyl-2-[[3-[4-(methylthio)phenyl]-1-benzofuran-5-yl]carbonyl]hydrazinecarbothioamide, the title compound (yield 27%) was obtained as colorless crystals.

melting point 226-227° C. (recrystallized from hexane/tetrahydrofuran).

$^1$H NMR (DMSO-d$_6$) δ 1.18 (3H, t, J=7.2 Hz), 2.58 (3H, s), 3.22-3.29 (2H, m), 7.54 (2H, d, J=8.4 Hz), 7.65-7.72 (3H, m), 7.79 (1H, dd, J=1.5, 6.9 Hz), 7.86-7.92 (2H, m), 8.66 (1H, s).

Elemental analysis (for C$_{18}$H$_{17}$N$_5$OS.0.1H$_2$O)
Calculated (%): C, 61.21; H, 4.91; N, 19.83.
Found (%): C, 61.08; H, 4.85; N, 19.79.

EXAMPLE 431

5-[1-[4-(trifluoromethoxy)phenyl]-1H-benzimidazol-6-yl]-1,3,4-oxadiazol-2-amine

In the same manner as in Example 236 and using 1-[4-(trifluoromethoxy)phenyl]-1H-benzimidazole-6-carbohydrazide instead of 2-(2-phenylethyl)-1H-pyrrolo[2,3-b]pyridine-4-carbohydrazide, the title compound (yield 50%) was obtained as colorless crystals.

melting point 231-232° C. (recrystallized from N,N-dimethylformamide/water).

$^1$H NMR (DMSO-d$_6$) δ 7.22 (2H, s), 7.70 (2H, d, J=8.4 Hz), 7.81 (1H, dd, J=1.5, 6.9 Hz), 7.89-7.94 (4H, m), 8.72 (1H, s).

Elemental analysis (for C$_{16}$H$_{10}$F$_3$N$_5$O$_2$.0.5H$_2$O)
Calculated (%): C, 51.90; H, 2.99; N, 18.91.
Found (%): C, 51.87; H, 2.96; N, 18.63.

EXAMPLE 432

6-[5-(methylthio)-1,3,4-oxadiazol-2-yl]-1-[4-(trifluoromethoxy)phenyl]-1H-benzimidazole In the same manner as in Example 387 and using 1-[4-(trifluoromethoxy)phenyl]-1H-benzimidazole-6-carbohydrazide instead of 3-(2-chlorophenyl)-1-benzofuran-5-carbohydrazide, the title compound (yield 41%) was obtained as colorless crystals.

melting point 200-201° C. (recrystallized from hexane/ethyl acetate).

$^1$H NMR (DMSO-d$_6$) δ 2.79 (3H, s), 7.43-7.52 (2H, m), 7.58 (1H, s), 7.61 (1H, s), 7.92-8.04 (2H, m), 8.16 (1H, s), 8.20 (1H, s).

Elemental analysis (for C$_{17}$H$_{11}$F$_3$N$_4$O$_2$S)
Calculated (%): C, 52.04; H, 2.83; N, 14.28.
Found (%): C, 52.04; H, 2.94; N, 14.38.

EXAMPLE 433

6-(5-methoxy-1,3,4-oxadiazol-2-yl)-1-[4-(trifluoromethoxy)phenyl]-1H-benzimidazole To a solution of 6-[5-(methylsulfonyl)-1,3,4-oxadiazol-2-yl]-1-[4-(trifluoromethyl)phenyl]-1H-benzimidazole (150 mg, 0.35 mmol) in N,N-dimethylformamide (3 mL) was added sodium methoxide (23 mg, 0.42 mmol) at room temperature, and the resulting mixture was stirred for 2 hr. The reaction mixture was diluted with ethyl acetate, washed with water and saturated brine, dried over anhydrous magnesium sulfate and concentrated under reduced pressure. The residue was purified by basic silica gel column chromatography (hexane/ethyl acetate=2/1-0/1) and recrystallized from hexane/ ethyl acetate to give the title compound (35.4 mg, yield 27%) as colorless crystals.

melting point 150-151° C.
$^1$H NMR (CDCl$_3$) δ 4.25 (3H, s), 7.48 (2H, d, J=8.7 Hz), 7.59 (2H, d, J=8.7 Hz), 7.93-7.98 (2H, m), 8.09 (1H, s), 8.19 (1H, s).

EXAMPLE 434

N,N-dimethyl-5-[1-[4-(trifluoromethoxy)phenyl]-1H-benzimidazol-6-yl]-1,3,4-oxadiazol-2-amine In the same manner as in Example 433 and using 2M dimethylamine-tetrahydrofuran solution instead of sodium methoxide and using 1-methyl-2-pyrrolidone instead of N,N-dimethylformamide, the title compound (yield 49%) was obtained as colorless crystals.

melting point 224-225° C. (recrystallized from hexane/ethyl acetate).
$^1$H NMR (CDCl$_3$) δ 3.16 (6H, s), 7.47 (2H, d, J=8.7 Hz), 7.59 (2H, d, J=8.7 Hz), 7.82-7.97 (2H, m), 8.09 (1H, s), 8.16 (1H, s).
Elemental analysis (for C$_{18}$H$_{14}$F$_3$N$_5$O$_2$)
Calculated (%): C, 55.53; H, 3.62; N, 17.99.
Found (%): C, 55.45; H, 3.65; N, 17.95.

EXAMPLE 435

N-methyl-5-[1-[4-(trifluoromethoxy)phenyl]-1H-benzimidazol-6-yl]-1,3,4-oxadiazol-2-amine In the same manner as in Example 433 and using 2M methylamine-tetrahydrofuran solution instead of sodium methoxide and using 1-methyl-2-pyrrolidone instead of N,N-dimethylformamide, the title compound (yield 43%) was obtained as colorless crystals.

melting point 183-184° C. (recrystallized from hexane/ethyl acetate).
$^1$H NMR (CDCl$_3$) δ 3.12 (3H, d, J=5.3 Hz), 4.66 (1H, d, J=5.3 Hz), 7.42-7.53 (2H, m), 7.54-7.63 (2H, m), 7.84-7.97 (2H, m), 8.08 (1H, brs), 8.17 (1H, s).
Elemental analysis (for C$_{17}$H$_{12}$F$_3$N$_5$O$_2$)
Calculated (%): C, 54.40; H, 3.22; N, 18.66.
Found (%): C, 54.27; H, 3.27; N, 18.64.

EXAMPLE 436

6-(5-methyl-1,3,4-oxadiazol-2-yl)-1-[3-(trifluoromethoxy)phenyl]-1H-benzimidazole In the same manner as in Example 239 and using 1-[3-(trifluoromethoxy)phenyl]-1H-benzimidazole-6-carbohydrazide instead of 2-[[4-(methylthio)phenyl]amino]isonicotinohydrazide, the title compound (yield 59%) was obtained as colorless crystals.

melting point 153-154° C. (recrystallized from hexane/ethyl acetate).
$^1$H NMR (CDCl$_3$) δ 2.63 (3H, s), 7.33-7.46 (2H, m), 7.49-7.56 (1H, m), 7.68 (1H, t, J=8.3 Hz), 7.93-8.07 (2H, m), 8.22 (2H, s).
Elemental analysis (for C$_{17}$H$_{11}$F$_3$N$_4$O$_2$)
Calculated (%): C, 56.67; H, 3.08; N, 15.55.
Found (%): C, 56.68; H, 3.08; N, 15.52.

EXAMPLE 437

6-[5-(methylsulfinyl)-1,3,4-oxadiazol-2-yl]-1-[4-(trifluoromethoxy)phenyl]-1H-benzimidazole In the same manner as in Example 140 and using 6-[5-(methylthio)-1,3,4-oxadiazol-2-yl]-1-[4-(trifluoromethoxy)phenyl]-1H-benzimidazole instead of 2-methyl-5-[3-[4-(methylthio)phenyl]-1-benzofuran-5-yl]-1,3,4-oxadiazole, the title compound (yield 54%) was obtained as colorless crystals.

melting point 152-153° C. (recrystallized from hexane/ethyl acetate).
$^1$H NMR (CDCl$_3$) δ 3.30 (3H, s), 7.47-7.54 (2H, d, J=8.4 Hz), 7.56-7.64 (2H, m), 8.03 (1H, d, J=8.4 Hz), 8.15 (1H, dd, J=1.7, 8.5 Hz), 8.20-8.30 (2H, m).
Elemental analysis (for C$_{17}$H$_{11}$F$_3$N$_4$O$_3$S)
Calculated (%): C, 50.00; H, 2.72; N, 13.72.
Found (%): C, 50.04; H, 2.83; N, 13.85.

EXAMPLE 438

5-[1-[3-(trifluoromethoxy)phenyl]-1H-benzimidazol-6-yl]-1,3,4-oxadiazol-2-amine

In the same manner as in Example 236 and using 1-[3-(trifluoromethoxy)phenyl]-1H-benzimidazole-6-carbohydrazide instead of 2-(2-phenylethyl)-1H-pyrrolo[2,3-b]pyridine-4-carbohydrazide, the title compound (yield 70%) was obtained as colorless crystals.

melting point 215-216° C. (recrystallized from hexane/tetrahydrofuran).
$^1$H NMR (DMSO-d$_6$) δ 7.23 (2H, s), 7.51-7.65 (1H, m), 7.72-8.00 (6H, m), 8.75 (1H, s).
Elemental analysis (for C$_{16}$H$_{10}$F$_3$N$_5$O$_2$)
Calculated (%): C, 53.19; H, 2.79; N, 19.38.
Found (%): C, 53.28; H, 2.98; N, 19.29.

EXAMPLE 439

1-[4-(difluoromethoxy)phenyl]-6-(5-methyl-1,3,4-oxadiazol-2-yl)-1H-benzimidazole In the same manner as in Example 239 and using 1-[4-(difluoromethoxy)phenyl]-1H-benzimidazole-6-carbohydrazide instead of 2-[[4-(methylthio)phenyl]amino]isonicotinohydrazide, the title compound (yield 75%) was obtained as colorless crystals.

melting point 154-155° C. (recrystallized from hexane/ethyl acetate).
$^1$H NMR (CDCl$_3$) δ 2.63 (3H, s), 6.62 (1H, t, J=72.9 Hz), 7.39 (2H, d, J=8.7 Hz), 7.56 (2H, d, J=8.7 Hz), 7.94-8.05 (2H, m), 8.19 (2H, s).
Elemental analysis (for C$_{17}$H$_{12}$F$_2$N$_4$O$_2$)
Calculated (%): C, 59.65; H, 3.53; N, 16.37.
Found (%): C, 59.76; H, 3.55; N, 16.44.

EXAMPLE 440

5-[1-[4-(difluoromethoxy)phenyl]-1H-benzimidazol-6-yl]-1,3,4-oxadiazol-2-amine

In the same manner as in Example 236 and using 1-[4-(difluoromethoxy)phenyl]-1H-benzimidazole-6-carbohydrazide instead of 2-(2-phenylethyl)-1H-pyrrolo[2,3-b]pyridine-4-carbohydrazide, the title compound (yield 72%) was obtained as colorless crystals.

melting point 242-243° C. (recrystallized from N,N-dimethylformamide/water).
$^1$H NMR (DMSO-d$_6$) δ 7.22 (2H, s), 7.38 (1H, d, J=72.0 Hz), 7.44-7.53 (2H, m), 7.76-7.87 (4H, m), 7.87-7.95 (1H, m), 8.68 (1H, s).

EXAMPLE 441

6-(5-morpholino-1,3,4-oxadiazol-2-yl)-1-[4-(trifluoromethoxy)phenyl]-1H-benzimidazole In the same manner as in Example 433 and using morpholine instead of sodium methoxide and using 1-methyl-2-pyrrolidone instead of N,N-dimethylformamide, the title compound (yield 63%) was obtained as colorless crystals.
melting point 202-203° C. (recrystallized from hexane/ethyl acetate).
$^1$H NMR (CDCl$_3$) δ 3.55-3.69 (4H, m), 3.80-3.92 (4H, m), 7.48 (2H, d, J=8.7 Hz), 7.59 (2H, d, J=8.7 Hz), 7.85-7.99 (2H, m), 8.09 (1H, s), 8.17 (1H, s).
Elemental analysis (for C$_{20}$H$_{16}$F$_3$N$_5$O$_3$)
Calculated (%): C, 55.69; H, 3.74; N, 16.24.
Found (%): C, 55.59; H, 3.90; N, 16.10.

EXAMPLE 442

1-[4-(difluoromethoxy)phenyl]-6-[5-(methylthio)-1,3,4-oxadiazol-2-yl]-1H-benzimidazole In the same manner as in Example 387 and using 1-[4-(difluoromethoxy)phenyl]-1H-benzimidazole-6-carbohydrazide instead of 3-(2-chlorophenyl)-1-benzofuran-5-carbohydrazide, the title compound (yield 90%) was obtained as colorless crystals.
melting point 202-203° C. (recrystallized from hexane/tetrahydrofuran).
$^1$H NMR (DMSO-d$_6$) δ 2.77 (3H, s), 7.39 (1H, t, J=73.5 Hz), 7.49 (2H, d, J=8.9 Hz), 7.83 (2H, d, J=8.9 Hz), 7.89-8.01 (2H, m), 8.05 (1H, s), 8.75 (1H, s).
Elemental analysis (for C$_{17}$H$_{12}$F$_2$N$_4$O$_2$S)
Calculated (%): C, 54.54; H, 3.23; N, 14.97.
Found (%): C, 54.61; H, 3.20; N, 14.94.

EXAMPLE 443

1-[4-(difluoromethoxy)phenyl]-6-[5-(methylsulfinyl)-1,3,4-oxadiazol-2-yl]-1H-benzimidazole In the same manner as in Example 140 and using 1-[4-(difluoromethoxy)phenyl]-6-[5-(methylthio)-1,3,4-oxadiazol-2-yl]-1H-benzimidazole instead of 2-methyl-5-[3-[4-(methylthio)phenyl]-1-benzofuran-5-yl]-1,3,4-oxadiazole, the title compound (yield 63%) was obtained as colorless crystals.
melting point 135-136° C. (recrystallized from hexane/ethyl acetate).
$^1$H NMR (DMSO-d$_6$) δ 3.28 (3H, s), 7.39 (1H, d, J=72.0 Hz), 7.50 (2H, d, J=8.7 Hz), 7.75-7.92 (2H, m), 7.97-8.12 (2H, m), 8.18 (1H, s), 8.80 (1H, s).

EXAMPLE 444

5-[1-[4-(difluoromethoxy)phenyl]-1H-benzimidazol-6-yl]-N-methyl-1,3,4-oxadiazol-2-amine In the same manner as in Example 433 and using 1-[4-(difluoromethoxy)phenyl]-6-[5-(methylsulfonyl)-1,3,4-oxadiazol-2-yl]-1H-benzimidazole instead of 6-[5-(methylsulfonyl)-1,3,4-oxadiazol-2-yl]-1-[4-(trifluoromethoxy)phenyl]-1H-benzimidazole, using 2M methylamine-tetrahydrofuran solution instead of sodium methoxide, and using 1-methyl-2-pyrrolidone instead of N,N-dimethylformamide, the title compound (yield 67%) was obtained as colorless crystals.
melting point 195-196° C. (recrystallized from hexane/ethyl acetate).
$^1$H NMR (DMSO-d$_6$) δ 2.86 (3H, d, J=4.9 Hz), 7.38 (1H, d, J=72.0 Hz), 7.43-7.52 (2H, m), 7.56-7.68 (1H, m), 7.76-7.85 (3H, m), 7.85-7.96 (2H, m), 8.68 (1H, s).
Elemental analysis (for C$_{17}$H$_{13}$F$_2$N$_5$O$_2$.0.1H$_2$O)
Calculated (%): C, 56.86; H, 3.70; N, 19.50.
Found (%): C, 56.83; H, 3.79; N, 19.56.

EXAMPLE 445

6-[5-(methylthio)-1,3,4-oxadiazol-2-yl]-1-[3-(trifluoromethoxy)phenyl]-1H-benzimidazole In the same manner as in Example 387 and using 1-[3-(trifluoromethoxy)phenyl]-1H-benzimidazole-6-carbohydrazide instead of 3-(2-chlorophenyl)-1-benzofuran-5-carbohydrazide, the title compound (yield 88%) was obtained as colorless crystals.
$^1$H NMR (DMSO-d$_6$) δ 2.77 (3H, s), 7.60 (1H, brs), 7.77-7.91 (3H, m), 7.91-8.04 (2H, m), 8.11 (1H, s), 8.81 (1H, s).
Elemental analysis (for C$_{17}$H$_{11}$F$_3$N$_4$O$_2$S)
Calculated (%): C, 52.04; H, 2.83; N, 14.28.
Found (%): C, 51.86; H, 2.77; N, 14.28.

EXAMPLE 446

N-methyl-5-[1-[3-(trifluoromethoxy)phenyl]-1H-benzimidazol-6-yl]-1,3,4-oxadiazol-2-amine In the same manner as in Example 433 and using 6-[5-(methylsulfonyl)-1,3,4-oxadiazol-2-yl]-1-[3-(trifluoromethoxy)phenyl]-1H-benzimidazole instead of 6-[5-(methylsulfonyl)-1,3,4-oxadiazol-2-yl]-1-[4-(trifluoromethoxy)phenyl]-1H-benzimidazole, using 2M methylamine-tetrahydrofuran solution instead of sodium methoxide, and using 1-methyl-2-pyrrolidone instead of N,N-dimethylformamide, the title compound (yield 79%) was obtained as colorless crystals.
melting point 226-227° C. (recrystallized from hexane/ethyl acetate).
$^1$H NMR (DMSO-d$_6$) δ 2.86 (3H, d, J=4.9 Hz), 7.53-7.69 (2H, m), 7.77-7.89 (4H, m), 7.90-7.97 (2H, m), 8.75 (1H, s).
Elemental analysis (for C$_{17}$H$_{12}$F$_3$N$_5$O$_2$)
Calculated (%): C, 54.40; H, 3.22; N, 18.66.
Found (%): C, 54.38; H, 3.18; N, 18.72.

EXAMPLE 447

6-(5-methyl-1,3,4-oxadiazol-2-yl)-1-[3-(trifluoromethyl)phenyl]-1H-benzimidazole In the same manner as in Example 239 and using 1-[3-(trifluoromethyl)phenyl]-1H-benzimidazole-6-carbohydrazide instead of 2-[[4-(methylthio)phenyl]amino]isonicotinohydrazide, the title compound (yield 84%) was obtained as colorless crystals.
melting point 212-213° C. (recrystallized from hexane/ethyl acetate).
$^1$H NMR (DMSO-d$_6$) δ 4.60 (2H, brs), 7.83 (2H, s), 7.91 (2H, d, J=4.9 Hz), 7.98-8.18 (3H, m), 8.78 (1H, s), 9.85 (1H, s).
Elemental analysis (for C$_{17}$H$_{11}$F$_3$N$_4$O.0.2H$_2$O)
Calculated (%): C, 58.69; H, 3.30; N, 16.10.
Found (%): C, 58.70; H, 3.11; N, 16.17.

EXAMPLE 448

5-[1-[3-(trifluoromethyl)phenyl]-1H-benzimidazol-6-yl]-1,3,4-oxadiazol-2-amine

In the same manner as in Example 236 and using 1-[3-(trifluoromethyl)phenyl]-1H-benzimidazole-6-carbohydrazide instead of 2-(2-phenylethyl)-1H-pyrrolo[2,3-b]pyridine-4-carbohydrazide, the title compound (yield 72%) was obtained as colorless crystals.
melting point 244-245° C. (recrystallized from hexane/tetrahydrofuran).
$^1$H NMR (DMSO-d$_6$) δ 7.22 (2H, s), 7.78-7.85 (1H, m), 7.88 (1H, s), 7.90-7.97 (3H, m), 8.03-8.14 (1H, m), 8.16 (1H, s), 8.78 (1H, s).

EXAMPLE 449

1-[2-chloro-5-(trifluoromethyl)phenyl]-6-(5-methyl-1,3,4-oxadiazol-2-yl)-1H-benzimidazole In the same manner as in Example 239 and using 1-[2-chloro-5-(trifluoromethyl)phenyl]-1H-benzimidazole-6-carbohydrazide instead of 2-[[4-(methylthio)phenyl]amino]isonicotinohydrazide, the title compound (yield 73%) was obtained as colorless crystals.
melting point 211-212° C. (recrystallized from hexane/ethyl acetate).
$^1$H NMR (DMSO-d$_6$) δ 2.55 (3H, s), 7.77 (1H, s), 7.90-8.03 (2H, m), 8.03-8.13 (2H, m), 8.33 (1H, d, J=1.9 Hz), 8.70 (1H, s).
Elemental analysis (for C$_{17}$H$_{10}$ClF$_3$N$_4$O.0.3H$_2$O)
Calculated (%): C, 53.15; H, 2.78; N, 14.58.
Found (%): C, 53.18; H, 2.69; N, 14.55.

EXAMPLE 450

5-[1-[2-chloro-5-(trifluoromethyl)phenyl]-1H-benzimidazol-6-yl]-1,3,4-oxadiazol-2-amine In the same manner as in Example 236 and using 1-[2-chloro-5-(trifluoromethyl)phenyl]-1H-benzimidazole-6-carbohydrazide instead of 2-(2-phenylethyl)-1H-pyrrolo[2,3-b]pyridine-4-carbohydrazide, the title compound (yield 21%) was obtained as colorless crystals.
melting point 288-289° C. (recrystallized from ethanol/diisopropylethyl ether).
$^1$H NMR (DMSO-d$_6$) δ 7.19 (2H, s), 7.52 (1H, s), 7.80 (1H, dd, J=1.5, 8.7 Hz), 7.89-7.97 (1H, m), 8.01-8.14 (2H, m), 8.32 (1H, d, J=1.9 Hz), 8.65 (1H, s).
Elemental analysis (for C$_{16}$H$_9$ClF$_3$N$_5$O)
Calculated (%): C, 50.61; H, 2.39; N, 18.44.
Found (%): C, 50.50; H, 2.41; N, 18.31.

EXAMPLE 451

1-[3-chloro-4-(trifluoromethoxy)phenyl]-6-(5-methyl-1,3,4-oxadiazol-2-yl)-1H-benzimidazole In the same manner as in Example 239 and using 1-[3-chloro-4-(trifluoromethoxy)phenyl]-1H-benzimidazole-6-carbohydrazide instead of 2-[[4-(methylthio)phenyl]amino]isonicotinohydrazide, the title compound (yield 62%) was obtained as colorless crystals.
melting point 211-212° C. (recrystallized from hexane/ethyl acetate).
$^1$H NMR (DMSO-d$_6$) δ 2.59 (3H, s), 7.89-8.01 (4H, m), 8.13 (1H, s), 8.23 (1H, dd, J=0.8, 2.1 Hz), 8.80 (1H, s).
Elemental analysis (for C$_{17}$H$_{10}$ClF$_3$N$_4$O$_2$)
Calculated (%): C, 51.73; H, 2.55; N, 14.19.
Found (%): C, 51.50; H, 2.56; N, 14.15.

EXAMPLE 452

5-[1-[3-chloro-4-(trifluoromethoxy)phenyl]-1H-benzimidazol-6-yl]-1,3,4-oxadiazol-2-amine In the same manner as in Example 236 and using 1-[3-chloro-4-(trifluoromethoxy)phenyl]-1H-benzimidazole-6-carbohydrazide instead of 2-(2-phenylethyl)-1H-pyrrolo[2,3-b]pyridine-4-carbohydrazide, the title compound (yield 54%) was obtained as colorless crystals.
melting point 238-239° C. (recrystallized from hexane/ethyl acetate).
$^1$H NMR (DMSO-d$_6$) δ 7.25 (2H, s), 7.75-7.85 (1H, m), 7.87-7.98 (4H, m), 8.23 (1H, dd, J=0.8, 2.1 Hz), 8.75 (1H, s).

EXAMPLE 453

1-methyl-1-[5-[1-[4-(trifluoromethoxy)phenyl]-1H-benzimidazol-6-yl]-1,3,4-oxadiazol-2-yl]ethyl acetate In the same manner as in Example 5 and using 1,1-dimethyl-2-oxo-2-[2-[[1-[4-(trifluoromethoxy)phenyl]-1H-benzimidazol-6-yl]carbonyl]hydrazino]ethyl acetate instead of N'-[3-[3-(trifluoromethyl)phenyl]propionyl]benzothiazole-6-carbohydrazide, the title compound (yield 50%) was obtained as colorless crystals.
melting point 150-151° C. (recrystallized from hexane/ethyl acetate).
$^1$H NMR (CDCl$_3$) δ 1.90 (6H, s), 2.09 (3H, s), 7.44-7.53 (2H, m), 7.56-7.62 (2H, m), 7.98 (2H, s), 8.20 (1H, s), 8.23 (1H, s).
Elemental analysis (for C$_{21}$H$_{17}$F$_3$N$_4$O$_4$)
Calculated (%): C, 56.50; H, 3.84; N, 12.55.
Found (%): C, 56.51; H, 3.75; N, 12.51.

EXAMPLE 454

2-[5-[1-[4-(trifluoromethoxy)phenyl]-1H-benzimidazol-6-yl]-1,3,4-oxadiazol-2-yl]propan-2-ol In the same manner as in Example 401 and using 1-methyl-1-[5-[1-[4-(trifluoromethoxy)phenyl]-1H-benzimidazol-6-yl]-1,3,4-oxadiazol-2-yl]ethyl acetate instead of [5-[3-[3-(trifluoromethoxy)phenyl]-1-benzofuran-5-yl]-1,3,4-oxadiazol-2-yl]methyl acetate, the title compound (yield 38%) was obtained as colorless crystals.
melting point 159-160° C. (recrystallized from hexane/ethyl acetate).
$^1$H NMR (CDCl$_3$) δ 1.79 (6H, s), 2.72 (1H, s), 7.43-7.53 (2H, m), 7.54-7.64 (2H, m), 7.91-8.06 (2H, m), 8.13-8.23 (2H, m).
Elemental analysis (for C$_{19}$H$_{15}$F$_3$N$_4$O$_3$)
Calculated (%): C, 56.44; H, 3.74; N, 13.86.
Found (%): C, 56.47; H, 3.69; N, 13.91.

EXAMPLE 455

5-[1-(2-chlorophenyl)-1H-benzimidazol-6-yl]-1,3,4-oxadiazol-2-amine

In the same manner as in Example 236 and using 1-(2-chlorophenyl)-1H-benzimidazole-6-carbohydrazide instead of 2-(2-phenylethyl)-1H-pyrrolo[2,3-b]pyridine-4-carbohydrazide, the title compound (yield 57%) was obtained as colorless crystals.

melting point 254-255° C. (recrystallized from hexane/ethyl acetate).

$^1$H NMR (DMSO-d$_6$) δ 7.20 (2H, s), 7.47 (1H, m) 7.60-7.74 (2H, m), 7.74-7.90 (2H, m), 7.89-7.98 (2H, m), 8.62 (1H, s).

Elemental analysis (for C$_{15}$H$_{10}$ClN$_5$O.0.2H$_2$O)
Calculated (%): C, 57.13; H, 3.32; N, 22.21.
Found (%): C, 57.15; H, 3.09; N, 22.15.

EXAMPLE 456

2-methyl-5-[3-[4-(methylthio)phenyl]-1-benzothien-5-yl]-1,3,4-oxadiazole

In the same manner as in Example 239 and using 3-[4-(methylthio)phenyl]-1-benzothiophene-5-carbohydrazide instead of 2-[[4-(methylthio)phenyl]amino]isonicotinohydrazide, the title compound (yield 93%) was obtained as colorless crystals.

melting point 198-199° C. (recrystallized from tetrahydrofuran/methanol).

$^1$H NMR (CDCl$_3$) δ 2.57 (3H, s), 2.63 (3H, s), 7.39-7.43 (2H, m), 7.47 (1H, s), 7.50-7.54 (2H, m), 8.02 (1H, dd, J=0.8, 8.5 Hz), 8.07 (1H, dd, J=1.5, 8.5 Hz), 8.49 (1H, dd, J=0.8, 1.5 Hz).

Elemental analysis (for C$_{18}$H$_{14}$N$_2$OS$_2$)
Calculated (%): C, 63.88; H, 4.17; N, 8.28.
Found (%): C, 63.75; H, 4.16; N, 8.26.

EXAMPLE 457

2-methyl-5-[3-[4-(methylsulfinyl)phenyl]-1-benzothien-5-yl]-1,3,4-oxadiazole

In the same manner as in Example 140 and using 2-methyl-5-[3-[4-(methylthio)phenyl]-1-benzothien-5-yl]-1,3,4-oxadiazole instead of 2-methyl-5-[3-[4-(methylthio)phenyl]-1-benzofuran-5-yl]-1,3,4-oxadiazole, the title compound (yield 86%) was obtained as colorless crystals.

melting point 166-167° C. (recrystallized from methanol/water).

$^1$H NMR (CDCl$_3$) δ 2.64 (3H, s), 2.84 (3H, s), 7.58 (1H, s), 7.74-7.78 (2H, m), 7.81-7.85 (2H, m), 8.05 (1H, dd, J=0.8, 8.5 Hz), 8.08 (1H, dd, J=1.5, 8.5 Hz), 8.50 (1H, dd, J=0.8, 1.5 Hz).

Elemental analysis (for C$_{18}$H$_{14}$N$_2$O$_2$S$_2$)
Calculated (%): C, 60.99; H, 3.98; N, 7.90.
Found (%): C, 60.78; H, 4.06; N, 7.83.

EXAMPLE 458

2-methyl-5-[3-[4-(methylsulfonyl)phenyl]-1-benzothien-5-yl]-1,3,4-oxadiazole

In the same manner as in Example 140 and using 2-methyl-5-[3-[4-(methylsulfinyl)phenyl]-1-benzothien-5-yl]-1,3,4-oxadiazole instead of 2-methyl-5-[3-[4-(methylthio)phenyl]-1-benzofuran-5-yl]-1,3,4-oxadiazole, the title compound (yield 85%) was obtained as colorless crystals.

melting point 231-232° C. (recrystallized from methanol/water).

$^1$H NMR (CDCl$_3$) δ 2.64 (3H, s), 3.17 (3H, s), 7.63 (1H, s), 7.78-7.82 (2H, m), 8.05-8.13 (4H, m), 8.48 (1H, dd, J=0.8, 1.3 Hz).

Elemental analysis (for C$_{18}$H$_{14}$N$_2$O$_3$S$_2$)
Calculated (%): C, 58.36; H, 3.81; N, 7.56.
Found (%): C, 58.35; H, 3.78; N, 7.56.

EXAMPLE 459

6-(5-methyl-1,3,4-oxadiazol-2-yl)-1-[4-(methylthio)phenyl]-1H-indole

A mixture of methyl 1-[4-(methylthio)phenyl]-1H-indole-6-carboxylate (2.50 g, 8.41 mmol), hydrazine monohydrate (4.08 mL, 84.1 mmol) and ethanol (40 mL) was heated under reflux overnight. After cooling, the precipitate was collected by filtration and washed with ethanol to give crude 1-[4-(methylthio)phenyl]-1H-indole-6-carbohydrazide.

A mixture of the obtained crude 1-[4-(methylthio)phenyl]-1H-indole-6-carbohydrazide and triethyl orthoacetate (20 mL) was stirred at 120° C. overnight. After cooling, the reaction mixture was purified by silica gel column chromatography (hexane/ethyl acetate=10/1-1/1) and recrystallized from hexane/ethyl acetate to give the title compound (531 mg, yield 20%) as colorless crystals.

melting point 193-194° C.

$^1$H NMR (CDCl$_3$) δ 2.57 (3H, s), 2.61 (3H, s), 6.73 (1H, d, J=4.2 Hz), 7.37-7.49 (5H, m), 7.66-7.88 (2H, m), 8.16 (1H, s).

Elemental analysis (for C$_{18}$H$_{15}$N$_3$OS)
Calculated (%): C, 67.27; H, 4.70; N, 13.07.
Found (%): C, 67.19; H, 4.78; N, 12.88.

EXAMPLE 460

6-(5-methyl-1,3,4-oxadiazol-2-yl)-1-[4-(methylsulfinyl)phenyl]-1H-indole

In the same manner as in Example 140 and using 6-(5-methyl-1,3,4-oxadiazol-2-yl)-1-[4-(methylthio)phenyl]-1H-indole instead of 2-methyl-5-[3-[4-(methylthio)phenyl]-1-benzofuran-5-yl]-1,3,4-oxadiazole, the title compound (yield 72%) was obtained as colorless crystals.

melting point 215-216° C. (recrystallized from hexane/ethyl acetate).

$^1$H NMR (DMSO-d$_6$) δ 2.57 (3H, s), 2.86 (3H, s), 6.89 (1H, d, J=3.0 Hz), 7.73-7.82 (1H, m), 7.88 (3H, d, J=8.7 Hz), 7.92-8.02 (3H, m), 8.11 (1H, s).

Elemental analysis (for C$_{18}$H$_{15}$N$_3$O$_2$S)
Calculated (%): C, 64.08; H, 4.48; N, 12.45.
Found (%): C, 64.08; H, 4.51; N, 12.30.

EXAMPLE 461

6-(5-methyl-1,3,4-oxadiazol-2-yl)-1-[4-(methylsulfonyl)phenyl]-1H-indole

In the same manner as in Example 200 and using 6-(5-methyl-1,3,4-oxadiazol-2-yl)-1-[4-(methylthio)phenyl]-1H-indole instead of 6-(5-methyl-1,3,4-oxadiazol-2-yl)-1-[4-(methylthio)phenyl]-1H-benzimidazole, the title compound (yield 57%) was obtained as colorless crystals.

melting point 228-229° C. (recrystallized from hexane/tetrahydrofuran).

$^1$H NMR (DMSO-d$_6$) δ 2.58 (3H, s), 3.34 (3H, s), 6.93 (1H, d, J=2.7 Hz), 7.73-7.83 (1H, m), 7.73-7.83 (1H, m), 7.85-7.93 (1H, m), 7.94-8.02 (2H, m), 8.13-8.22 (3H, m).

Elemental analysis (for C$_{18}$H$_{15}$N$_3$O$_3$S)
Calculated (%): C, 61.18; H, 4.28; N, 11.89.
Found (%): C, 61.09; H, 4.30; N, 11.84.

EXAMPLE 462

3-(2-chlorophenyl)-5-(5-methyl-1,3,4-oxadiazol-2-yl)furo[2,3-b]pyridine

In the same manner as in Example 239 and using 3-(2-chlorophenyl)furo[2,3-b]pyridine-5-carbohydrazide instead of 2-[[4-(methylthio)phenyl]amino]isonicotinohydrazide, the title compound (yield 22%) was obtained as colorless crystals.

melting point 141-142° C. (recrystallized from hexane/ethyl acetate).

$^1$H NMR (CDCl$_3$) δ 2.65 (3H, s), 7.35-7.46 (2H, m), 7.48-7.54 (1H, m), 7.54-7.63 (1H, m), 8.02 (1H, s), 8.60 (1H, d, J=1.9 Hz), 9.05 (1H, d, J=2.3 Hz).

EXAMPLE 463

5-(5-methyl-1,3,4-oxadiazol-2-yl)-3-[4-(methylthio)phenyl]furo[2,3-b]pyridine

In the same manner as in Example 239 and using 3-[4-(methylthio)phenyl]furo[2,3-b]pyridine-5-carbohydrazide instead of 2-[[4-(methylthio)phenyl]amino]isonicotinohydrazide, the title compound (yield 58%) was obtained as colorless crystals.

melting point 209-210° C. (recrystallized from hexane/ethyl acetate).

$^1$H NMR (DMSO-d$_6$) δ 2.55 (3H, s), 2.63 (3H, s), 7.45 (2H, d, J=8.5 Hz), 7.77 (2H, d, J=8.5 Hz), 8.71 (1H, s), 8.82 (1H, d, J=2.1 Hz), 8.98 (1H, d, J=2.1 Hz).

EXAMPLE 464

5-(5-methyl-1,3,4-oxadiazol-2-yl)-3-[4-(methylsulfonyl)phenyl]furo[2,3-b]pyridine In the same manner as in Example 241 and using 5-(5-methyl-1,3,4-oxadiazol-2-yl)-3-[4-(methylthio)phenyl]furo[2,3-b]pyridine instead of 4-(5-methyl-1,3,4-oxadiazol-2-yl)-N-[4-(methylthio)phenyl]pyridin-2-amine, the title compound (16 mg, yield 11%) was obtained as colorless crystals.

melting point 251-252° C. (recrystallized from hexane/ethyl acetate).

$^1$H NMR (DMSO-d$_6$) δ 2.84 (3H, s), 3.49 (3H, s), 8.27-8.36 (4H, m), 9.10 (1H, s), 9.12 (1H, d, J=2.1 Hz), 9.22 (1H, d, J=2.1 Hz).

EXAMPLE 465

5-(5-methyl-1,3,4-oxadiazol-2-yl)-3-[4-(methylsulfinyl)phenyl]furo[2,3-b]pyridine The eluate obtained after elution of 5-(5-methyl-1,3,4-oxadiazol-2-yl)-3-[4-(methylsulfonyl)phenyl]furo[2,3-b]pyridine by column purification (basic silica gel, hexane/ethyl acetate=4/1-1/1) in Example 464 was recrystallized from hexane/ethyl acetate to give the title compound (58 mg, yield 41%) as colorless crystals.

melting point 240-241° C.

$^1$H NMR (DMSO-d$_6$) δ 2.64 (3H, s), 2.81 (3H, s), 7.82-7.91 (2H, m), 7.98-8.08 (2H, m), 8.83 (1H, s), 8.89 (1H, d, J=2.1 Hz), 9.01 (1H, d, J=1.9 Hz).

EXAMPLE 466

5-(5-methyl-1,3,4-oxadiazol-2-yl)-3-[4-(methylthio)phenyl]furo[2,3-c]pyridine

In the same manner as in Example 132 and using 3-bromo-5-(5-methyl-1,3,4-oxadiazol-2-yl)furo[2,3-c]pyridine instead of 2-(3-bromo-1-benzofuran-5-yl)-5-methyl-1,3,4-oxadiazole and using [4-(methylthio)phenyl]boronic acid instead of (4-fluorophenyl)boronic acid, the title compound (yield 52%) was obtained as colorless crystals.

$^1$H NMR (DMSO-d$_6$) δ 2.55 (3H, s), 2.63 (3H, s), 7.46 (2H, d, J=8.3 Hz), 7.76 (2H, d, J=8.3 Hz), 8.61 (1H, s), 8.80 (1H, s), 9.21 (1H, s).

EXAMPLE 467

5-(5-methyl-1,3,4-oxadiazol-2-yl)-3-[4-(methylsulfonyl)phenyl]furo[2,3-c]pyridine In the same manner as in Example 241 and using 5-(5-methyl-1,3,4-oxadiazol-2-yl)-3-[4-(methylthio)phenyl]furo[2,3-c]pyridine instead of 4-(5-methyl-1,3,4-oxadiazol-2-yl)-N-[4-(methylthio)phenyl]pyridin-2-amine and using dichloromethane instead of N,N-dimethylacetamide, the title compound (yield 7%) was obtained as colorless crystals.

$^1$H NMR (DMSO-d$_6$) δ 2.64 (3H, s), 3.29 (3H, s), 8.11 (4H, s), 8.70 (1H, s), 9.00 (1H, s), 9.27 (1H, s).

EXAMPLE 468

5-(5-methyl-1,3,4-oxadiazol-2-yl)-3-[4-(methylsulfinyl)phenyl]furo[2,3-c]pyridine The eluate obtained after elution of 5-(5-methyl-1,3,4-oxadiazol-2-yl)-3-[4-(methylsulfonyl)phenyl]furo[2,3-c]pyridine by column purification (basic silica gel, hexane/ethyl acetate=4/1-0/1) in Example 467 was recrystallized from hexane/ethyl acetate to give the title compound (yield 67%) as colorless crystals.

melting point 247-248° C.

$^1$H NMR (DMSO-d$_6$) δ 2.64 (3H, s), 2.82 (3H, s), 7.88 (2H, d, J=8.4 Hz), 8.03 (2H, d, J=8.4 Hz), 8.66 (1H, d, J=0.9 Hz), 8.92 (1H, s), 9.24 (1H, d, J=0.9 Hz).

Elemental analysis (for C$_{17}$H$_{13}$N$_3$O$_3$S)

Calculated (%): C, 60.17; H, 3.86; N, 12.38.

Found (%): C, 59.98; H, 3.90; N, 12.22.

EXAMPLE 469

3-(2-chlorophenyl)-5-(5-methyl-1,3,4-oxadiazol-2-yl)furo[2,3-c]pyridine

In the same manner as in Example 132 and using 3-bromo-5-(5-methyl-1,3,4-oxadiazol-2-yl)furo[2,3-c]pyridine instead of 2-(3-bromo-1-benzofuran-5-yl)-5-methyl-1,3,4-oxadiazole and using (2-chlorophenyl)boronic acid instead of (4-fluorophenyl)boronic acid, the title compound (yield 21%) was obtained as colorless crystals.

melting point 162-163° C. (recrystallized from hexane/ethyl acetate).

¹NMR (CDCl₃) δ 2.67 (3H, s), 7.38-7.47 (2H, m), 7.49-7.65 (2H, m), 8.09 (1H, s), 8.53 (1H, d, J=0.9 Hz), 9.06 (1H, d, J=0.9 Hz).

EXAMPLE 470

5-(5-methyl-1,3,4-oxadiazol-2-yl)-3-[4-(trifluoromethoxy)phenyl]furo[2,3-c]pyridine In the same manner as in Example 132 and using 3-bromo-5-(5-methyl-1,3,4-oxadiazol-2-yl)furo[2,3-c]pyridine instead of 2-(3-bromo-1-benzofuran-5-yl)-5-methyl-1,3,4-oxadiazole and using [4-(trifluoromethoxy)phenyl]boronic acid instead of (4-fluorophenyl)boronic acid, the title compound (yield 25%) was obtained as colorless crystals.
¹H NMR (CDCl₃) δ 2.69 (3H, s), 7.39 (2H, d, J=7.9 Hz), 7.69 (2H, d, J=7.9 Hz), 8.04 (1H, s), 8.72 (1H, d, J=0.9 Hz), 9.06 (1H, d, J=0.9 Hz).

EXAMPLE 471

5-(5-methyl-1,3,4-oxadiazol-2-yl)-3-[4-(methylthio)phenyl]furo[3,2-b]pyridine

A solution of 3-[4-(methylthio)phenyl]furo[3,2-b]pyridine-5-carbohydrazide (0.20 g, 0.68 mmol) and triethyl orthoacetate (0.27 mL, 1.49 mmol) in n-butanol (5 mL) was heated under reflux for 1.5 hr. 1,8-Diazabicyclo[5.4.0]undec-7-ene (0.10 mL, 0.68 mmol) was added to the reaction mixture, and the mixture was further heated under reflux overnight. After cooling, the precipitate was collected by filtration and recrystallized from hexane/ethyl acetate to give the title compound (0.15 g, yield 67%) as colorless crystals.
melting point 186-187° C.
¹H NMR (CDCl₃) δ 2.55 (3H, s), 2.71 (3H, s), 7.40 (2H, d, J=8.5 Hz), 7.95 (1H, d, J=8.7 Hz), 8.06 (2H, d, J=8.5 Hz), 8.21 (1H, s), 8.28 (1H, d, J=8.7 Hz).
Elemental analysis (for $C_{17}H_{13}N_3O_2S$)
Calculated (%): C, 63.14; H, 4.05; N, 12.99.
Found (%): C, 63.14; H, 3.99; N, 13.13.

EXAMPLE 472

5-(5-methyl-1,3,4-oxadiazol-2-yl)-3-[4-(methylsulfinyl)phenyl]furo[3,2-b]pyridine In the same manner as in Example 140 and using 5-(5-methyl-1,3,4-oxadiazol-2-yl)-3-[4-(methylthio)phenyl]furo[3,2-b]pyridine instead of 2-methyl-5-[3-(4-(methylthio)phenyl)-1-benzofuran-5-yl]-1,3,4-oxadiazole, the title compound (yield 41%) was obtained as colorless crystals.
melting point 219-220° C. (recrystallized from hexane/tetrahydrofuran).
¹H NMR (CDCl₃) δ 2.71 (3H, s), 2.78 (3H, s), 7.81 (2H, d, J=8.7 Hz), 8.00 (1H, d, J=8.7 Hz), 8.27-8.35 (4H, m).
Elemental analysis (for $C_{17}H_{13}N_3O_3S$)
Calculated (%): C, 60.17; H, 3.86; N, 12.38.
Found (%): C, 60.22; H, 3.81; N, 12.47.

EXAMPLE 473

5-(5-methyl-1,3,4-oxadiazol-2-yl)-3-[4-(methylsulfonyl)phenyl]furo[3,2-b]pyridine In the same manner as in Example 200 and using 5-(5-methyl-1,3,4-oxadiazol-2-yl)-3-[4-(methylthio)phenyl]furo[3,2-b]pyridine instead of 6-(5-methyl-1,3,4-oxadiazol-2-yl)-1-[4-(methylthio)phenyl]-1H-benzimidazole, the title compound (yield 48%) was obtained as colorless crystals.
melting point 250-251° C. (recrystallized from acetone).
¹H NMR (CDCl₃) δ 2.72 (3H, s), 3.11 (3H, s), 8.02 (1H, d, J=8.7 Hz), 8.10 (2H, d, J=8.5 Hz), 8.31-8.39 (4H, m).
Elemental analysis (for $C_{17}H_{13}N_3O_4S$)
Calculated (%): C, 57.46; H, 3.69; N, 11.82.
Found (%): C, 57.27; H, 3.67; N, 11.81.

EXAMPLE 474

3-(2-chlorophenyl)-5-(5-methyl-1,3,4-oxadiazol-2-yl)furo[3,2-b]pyridine

In the same manner as in Example 132 and using 3-bromo-5-(5-methyl-1,3,4-oxadiazol-2-yl)furo[3,2-b]pyridine instead of 2-(3-bromo-1-benzofuran-5-yl)-5-methyl-1,3,4-oxadiazole, using (2-chlorophenyl)boronic acid instead of (4-fluorophenyl)boronic acid, and using [1,1'-bis(diphenylphosphino)ferrocene]palladium(II) chloride dichloromethane complex instead of tetrakis(triphenylphosphine)palladium(0), the title compound (yield 6%) was obtained as colorless crystals.
¹H NMR (CDCl₃) δ 2.67 (3H, s), 7.35 (1H, dt, J=1.7, 7.6 Hz), 7.47 (1H, dt, J=1.4, 7.6 Hz), 7.55 (1H, dd, J=1.4, 7.7 Hz), 7.99 (1H, d, J=8.7 Hz), 8.21 (1H, dd, J=1.7, 7.7 Hz), 8.30 (1H, d, J=8.7 Hz), 8.47 (1H, s).

EXAMPLE 475

3-(2,5-difluorophenyl)-5-(5-methyl-1,3,4-oxadiazol-2-yl)furo[3,2-b]pyridine

In the same manner as in Example 132 and using 3-bromo-5-(5-methyl-1,3,4-oxadiazol-2-yl)furo[3,2-b]pyridine instead of 2-(3-bromo-1-benzofuran-5-yl)-5-methyl-1,3,4-oxadiazole, using (2,5-difluorophenyl)boronic acid instead of (4-fluorophenyl)boronic acid, and using [1,1'-bis(diphenylphosphino)ferrocene]palladium(II) chloride dichloromethane complex instead of tetrakis(triphenylphosphine)palladium(0), the title compound (yield 43%) was obtained as colorless crystals.
melting point 185-186° C. (recrystallized from hexane/ethyl acetate).
¹H NMR (CDCl₃) δ 2.73 (3H, s), 6.97-7.10 (1H, m), 7.11-7.22 (1H, m), 7.99 (1H, d, J=8.7 Hz), 8.33 (1H, d, J=8.7 Hz), 8.53 (1H, d, J=3.0 Hz), 8.80 (1H, ddd, J=3.2, 6.0, 9.5 Hz).
Elemental analysis (for $C_{16}H_9F_2N_3O_2$)
Calculated (%): C, 61.35; H, 2.90; N, 13.41.
Found (%): C, 61.38; H, 2.95; N, 13.62.

EXAMPLE 476

5-(5-methyl-1,3,4-oxadiazol-2-yl)-3-[3-(trifluoromethoxy)phenyl]furo[3,2-b]pyridine In the same manner as in Example 132 and using 3-bromo-5-(5-methyl-1,3,4-oxadiazol-2-yl)furo[3,2-b]pyridine instead of 2-(3-bromo-1-benzofuran-5-yl)-5-methyl-1,3,4-oxadiazole, using [3-(trifluoromethoxy)phenyl]boronic acid instead of (4-fluorophenyl)boronic acid, and using [1,1'-bis(diphenylphosphino)ferrocene]palladium(II) chloride dichloromethane complex instead of tetrakis(triphenylphosphine)palladium(0), the title compound (yield 57%) was obtained as colorless crystals.
melting point 146-147° C. (recrystallized from hexane/ethyl acetate).

¹H NMR (CDCl₃) δ 2.70 (3H, s), 7.21-7.29 (1H, m), 7.54 (1H, t, J=8.1 Hz), 7.97 (1H, d, J=8.7 Hz), 8.01-8.06 (1H, m), 8.13 (1H, s), 8.27 (1H, s), 8.31 (1H, d, J=8.7 Hz).
Elemental analysis (for $C_{17}H_{10}F_3N_3O_3$)
Calculated (%): C, 56.52; H, 2.79; N, 11.63.
Found (%): C, 56.60; H, 2.72; N, 11.78.

EXAMPLE 477

3-[4-(ethylthio)phenyl]-5-(5-methyl-1,3,4-oxadiazol-2-yl)furo[3,2-b]pyridine

In the same manner as in Example 132 and using 3-bromo-5-(5-methyl-1,3,4-oxadiazol-2-yl)furo[3,2-b]pyridine instead of 2-(3-bromo-1-benzofuran-5-yl)-5-methyl-1,3,4-oxadiazole, using [4-(ethylthio)phenyl]boronic acid instead of (4-fluorophenyl)boronic acid, and using [1,1'-bis(diphenylphosphino)ferrocene]palladium(II) chloride dichloromethane complex instead of tetrakis(triphenylphosphine)palladium(0), the title compound (yield 12%) was obtained as colorless crystals.
melting point 174-175° C. (recrystallized from hexane/ethyl acetate).
¹H NMR (CDCl₃) δ 1.37 (3H, t, J=7.3 Hz), 2.71 (3H, s), 3.01 (2H, q, J=7.3 Hz), 7.47 (2H, d, J=8.5 Hz), 7.95 (1H, d, J=8.7 Hz), 8.06 (2H, d, J=8.5 Hz), 8.22 (1H, s), 8.28 (1H, d, J=8.7 Hz).
Elemental analysis (for $C_{18}H_{15}N_3O_2S$)
Calculated (%): C, 64.08; H, 4.48; N, 12.45.
Found (%): C, 64.24; H, 4.43; N, 12.49.

EXAMPLE 478

3-[4-(ethylsulfinyl)phenyl]-5-(5-methyl-1,3,4-oxadiazol-2-yl)furo[3,2-b]pyridine In the same manner as in Example 140 and using 3-[4-(ethylthio)phenyl]-5-(5-methyl-1,3,4-oxadiazol-2-yl)furo[3,2-b]pyridine instead of 2-methyl-5-[3-[4-(methylthio)phenyl]-1-benzofuran-5-yl]-1,3,4-oxadiazole, the title compound (yield 70%) was obtained as colorless crystals.
melting point 207-208° C. (recrystallized from hexane/ethyl acetate).
¹H NMR (CDCl₃) δ 1.26 (3H, t, J=7.3 Hz), 2.71 (3H, s), 2.75-2.89 (1H, m), 2.90-3.06 (1H, m), 7.77 (2H, d, J=8.1 Hz), 8.00 (1H, d, J=8.7 Hz), 8.25-8.37 (4H, m).
Elemental analysis (for $C_{18}H_{15}N_3O_3S$)
Calculated (%): C, 61.18; H, 4.28; N, 11.89.
Found (%): C, 61.14; H, 4.24; N, 11.89.

EXAMPLE 479

3-[4-(ethylsulfonyl)phenyl]-5-(5-methyl-1,3,4-oxadiazol-2-yl)furo[3,2-b]pyridine In the same manner as in Example 200 and using 3-[4-(ethylthio)phenyl]-5-(5-methyl-1,3,4-oxadiazol-2-yl)furo[3,2-b]pyridine instead of 6-(5-methyl-1,3,4-oxadiazol-2-yl)-1-[4-(methylthio)phenyl]-1H-benzimidazole, the title compound (yield 80%) was obtained as colorless crystals.
melting point 246-247° C. (recrystallized from hexane/ethyl acetate).
¹H NMR (CDCl₃) δ 1.33 (3H, t, J=7.5 Hz), 2.72 (3H, s), 3.17 (2H, q, J=7.5 Hz), 8.02 (1H, d, J=8.7 Hz), 8.06 (2H, d, J=8.3 Hz), 8.29-8.41 (4H, m).
Elemental analysis (for $C_{18}H_{15}N_3O_4S$)
Calculated (%): C, 58.53; H, 4.09; N, 11.38.
Found (%): C, 58.53; H, 4.08; N, 11.34.

EXAMPLE 480

3-(1-benzyl-1H-pyrazol-4-yl)-5-(5-methyl-1,3,4-oxadiazol-2-yl)furo[3,2-b]pyridine In the same manner as in Example 132 and using 3-bromo-5-(5-methyl-1,3,4-oxadiazol-2-yl)furo[3,2-b]pyridine instead of 2-(3-bromo-1-benzofuran-5-yl)-5-methyl-1,3,4-oxadiazole, using 1-benzyl-4-(4,4,5,5-tetramethyl-1,3,2-dioxaborolan-2-yl)-1H-pyrazole instead of (4-fluorophenyl)boronic acid, and using [1,1'-bis(diphenylphosphino)ferrocene]palladium(II) chloride dichloromethane complex instead of tetrakis(triphenylphosphine)palladium(0), the title compound (yield 68%) was obtained as colorless crystals.
melting point 194-195° C. (recrystallized from hexane/ethyl acetate).
¹H NMR (CDCl₃) δ 2.69 (3H, s), 5.43 (2H, s), 7.28-7.42 (5H, m), 7.91 (1H, d, J=8.7 Hz), 8.08 (1H, s), 8.10 (1H, s), 8.24 (1H, d, J=8.7 Hz), 8.30 (1H, s).
Elemental analysis (for $C_{20}H_{15}N_5O_2$)
Calculated (%): C, 67.22; H, 4.23; N, 19.60.
Found (%): C, 67.23; H, 4.20; N, 19.64.

EXAMPLE 481

2-methyl-5-[3-(1H-pyrazol-4-yl)-1-benzofuran-5-yl]-1,3,4-oxadiazole

In the same manner as in Example 132 and using tert-butyl 4-(4,4,5,5-tetramethyl-1,3,2-dioxaborolan-2-yl)-1H-pyrazole-1-carboxylate instead of (4-fluorophenyl)boronic acid, the title compound (yield 43%) was obtained as colorless crystals.
melting point 215-216° C. (recrystallized from tetrahydrofuran).
¹H NMR (DMSO-d₆) δ 2.61 (3H, s), 7.84 (1H, dd, J=0.6, 8.7 Hz), 7.97 (1H, brs), 8.00 (1H, dd, J=1.7, 8.7 Hz), 8.33 (1H, brs), 8.38-8.39 (2H, m), 13.16 (1H, s).
Elemental analysis (for $C_{14}H_{10}N_4O_2$)
Calculated (%): C, 63.15; H, 3.79; N, 21.04.
Found (%): C, 63.09; H, 3.85; N, 20.85.

EXAMPLE 482

2-methyl-5-[3-(1-methyl-1H-pyrazol-4-yl)-1-benzofuran-5-yl]-1,3,4-oxadiazole

In the same manner as in Example 132 and using 1-methyl-4-(4,4,5,5-tetramethyl-1,3,2-dioxaborolan-2-yl)-1H-pyrazole instead of (4-fluorophenyl)boronic acid, the title compound (yield 61%) was obtained as colorless crystals.
melting point 147-148° C. (recrystallized from hexane/ethyl acetate).
¹H NMR (CDCl₃) δ 2.65 (3H, s), 4.02 (3H, s), 7.62 (1H, dd, J=0.6, 8.7 Hz), 7.78 (1H, d, J=0.8 Hz), 7.80 (1H, d, J=0.8 Hz), 7.81 (1H, s), 8.02 (1H, dd, J=1.7, 8.7 Hz), 8.40 (1H, dd, J=0.6, 1.7 Hz).
Elemental analysis (for $C_{15}H_{12}N_4O_2$)
Calculated (%): C, 64.28; H, 4.32; N, 19.99.
Found (%): C, 64.35; H, 4.35; N, 19.86.

EXAMPLE 483

2-[3-(1-ethyl-1H-pyrazol-4-yl)-1-benzofuran-5-yl]-5-methyl-1,3,4-oxadiazole

In the same manner as in Example 1 and using 2-methyl-5-[3-(1H-pyrazol-4-yl)-1-benzofuran-5-yl]-1,3,4-oxadiazole instead of 5-(benzothiazol-6-yl)-1,3,4-oxadiazole-2-thiol and using iodoethane instead of 3-(trifluoromethyl)benzyl chloride, the title compound (yield 80%) was obtained as colorless crystals.

melting point 122-123° C. (crystallized from hexane/ethyl acetate).

$^1$H NMR (CDCl$_3$) δ 1.58 (3H, t, J=7.4 Hz), 2.65 (3H, s), 4.29 (2H, q, J=7.4 Hz), 7.62 (1H, dd, J=0.6, 8.7 Hz), 7.79 (1H, s), 7.81 (2H, s), 8.02 (1H, dd, J=1.7, 8.7 Hz), 8.41 (1H, dd, J=0.6, 1.7 Hz).

Elemental analysis (for C$_{16}$H$_{14}$N$_4$O$_2$)
Calculated (%): C, 65.30; H, 4.79; N, 19.04.
Found (%): C, 65.23; H, 4.72; N, 19.06.

EXAMPLE 484

2-[3-[1-(methoxymethyl)-1H-pyrazol-4-yl]-1-benzofuran-5-yl]-5-methyl-1,3,4-oxadiazole To a solution of 2-methyl-5-[3-(1H-pyrazol-4-yl)-1-benzofuran-5-yl]-1,3,4-oxadiazole (213 mg, 0.80 mmol) and (chloromethyl) methyl ether (0.091 mL, 1.2 mmol) in N,N-dimethylformamide (10 mL) was added sodium hydride (60% in oil, 60 mg, 1.2 mmol) by small portions at room temperature, and the resulting mixture was stirred for 10 min. The reaction mixture was poured into water, and the mixture was extracted with ethyl acetate. The organic layer was washed with saturated brine, dried over anhydrous magnesium sulfate and concentrated under reduced pressure. The residue was purified by basic silica gel column chromatography (hexane/ethyl acetate=1/1) and crystallized from hexane/ethyl acetate to give the title compound (128 mg, yield 52%) as colorless crystals.

melting point 128-129° C.

$^1$H NMR (CDCl$_3$) δ 2.65 (3H, s), 3.42 (3H, s), 5.50 (2H, s), 7.63 (1H, dd, J=0.6, 8.7 Hz), 7.85 (1H, s), 7.88 (1H, s), 7.98 (1H, s), 8.05 (1H, dd, J=1.7, 8.7 Hz), 8.40 (1H, dd, J=0.6, 1.7 Hz).

Elemental analysis (for C$_{16}$H$_{14}$N$_4$O$_3$)
Calculated (%): C, 61.93; H, 4.55; N, 18.06.
Found (%): C, 61.77; H, 4.53; N, 17.95.

EXAMPLE 485

2-[3-(1-benzyl-1H-pyrazol-4-yl)-1-benzofuran-5-yl]-5-methyl-1,3,4-oxadiazole

In the same manner as in Example 132 and using 1-benzyl-4-(4,4,5,5-tetramethyl-1,3,2-dioxaborolan-2-yl)-1H-pyrazole instead of (4-fluorophenyl)boronic acid, the title compound (yield 77%) was obtained as colorless crystals.

melting point 151-152° C. (recrystallized from hexane/ethyl acetate).

$^1$H NMR (CDCl$_3$) δ 2.64 (3H, s), 5.42 (2H, s), 7.29-7.42 (5H, m), 7.61 (1H, dd, J=0.6, 8.7 Hz), 7.78 (1H, s), 7.80 (1H, s), 7.87 (1H, s), 8.02 (1H, dd, J=1.7, 8.7 Hz), 8.38 (1H, dd, J=0.6, 1.7 Hz).

Elemental analysis (for C$_{21}$H$_{16}$N$_4$O$_2$)
Calculated (%): C, 70.77; H, 4.53; N, 15.72.
Found (%): C, 70.71; H, 4.48; N, 15.76.

EXAMPLE 486

2-[[4-[5-(5-methyl-1,3,4-oxadiazol-2-yl)-1-benzofuran-3-yl]-1H-pyrazol-1-yl]methyl]benzonitrile In the same manner as in Example 1 and using 2-methyl-5-[3-(1H-pyrazol-4-yl)-1-benzofuran-5-yl]-1,3,4-oxadiazole instead of 5-(benzothiazol-6-yl)-1,3,4-oxadiazole-2-thiol and using 2-(bromomethyl)benzonitrile instead of 3-(trifluoromethyl)benzyl chloride, the title compound (yield 91%) was obtained as colorless crystals.

melting point 192-193° C. (recrystallized from hexane/tetrahydrofuran).

$^1$H NMR (CDCl$_3$) δ 2.65 (3H, s), 5.63 (2H, s), 7.35 (1H, d, J=7.5 Hz), 7.45 (1H, dt, J=1.1, 7.5 Hz), 7.59-7.64 (2H, m), 7.73 (1H, dd, J=1.1, 7.5 Hz), 7.82 (1H, s), 7.89 (1H, d, J=0.6 Hz), 7.96 (1H, d, J=0.6 Hz), 8.05 (1H, dd, J=1.7, 8.7 Hz), 8.38 (1H, dd, J=0.6, 1.7 Hz).

Elemental analysis (for C$_{22}$H$_{15}$N$_5$O$_2$)
Calculated (%): C, 69.28; H, 3.96; N, 18.36.
Found (%): C, 69.06; H, 3.93; N, 18.28.

EXAMPLE 487

2-methyl-5-[3-[1-[2-(trifluoromethyl)benzyl]-1H-pyrazol-4-yl]-1-benzofuran-5-yl]-1,3,4-oxadiazole In the same manner as in Example 1 and using 2-methyl-5-[3-(1H-pyrazol-4-yl)-1-benzofuran-5-yl]-1,3,4-oxadiazole instead of 5-(benzothiazol-6-yl)-1,3,4-oxadiazole-2-thiol and using 2-(trifluoromethyl)benzyl bromide instead of 3-(trifluoromethyl)benzyl chloride, the title compound (yield 92%) was obtained as colorless crystals.

melting point 165-166° C. (recrystallized from hexane/ethyl acetate).

$^1$H NMR (CDCl$_3$) δ 2.64 (3H, s), 5.65 (2H, s), 7.09 (1H, d, J=7.6 Hz), 7.43 (1H, t, J=7.6 Hz), 7.52 (1H, t, J=7.6 Hz), 7.62 (1H, dd, J=0.6, 8.7 Hz), 7.73 (1H, d, J=7.6 Hz), 7.82 (2H, s), 7.92 (1H, s), 8.04 (1H, dd, J=1.7, 8.7 Hz), 8.38 (1H, dd, J=0.6, 1.7 Hz).

Elemental analysis (for C$_{22}$H$_{15}$F$_3$N$_4$O$_2$)
Calculated (%): C, 62.26; H, 3.56; N, 13.20.
Found (%): C, 62.20; H, 3.51; N, 13.16.

EXAMPLE 488

2-[3-[1-(2-fluorobenzyl)-1H-pyrazol-4-yl]-1-benzofuran-5-yl]-5-methyl-1,3,4-oxadiazole In the same manner as in Example 1 and using 2-methyl-5-[3-(1H-pyrazol-4-yl)-1-benzofuran-5-yl]-1,3,4-oxadiazole instead of 5-(benzothiazol-6-yl)-1,3,4-oxadiazole-2-thiol and using 2-fluorobenzyl bromide instead of 3-(trifluoromethyl)benzyl chloride, the title compound (yield 88%) was obtained as colorless crystals.

melting point 142-143° C. (recrystallized from hexane/tetrahydrofuran).

$^1$H NMR (CDCl$_3$) δ 2.64 (3H, s), 5.47 (2H, s), 7.08-7.18 (2H, m), 7.24-7.37 (2H, m), 7.61 (1H, dd, J=0.6, 8.7 Hz), 7.80 (1H, s), 7.84 (1H, d, J=0.8 Hz), 7.86 (1H, d, J=0.8 Hz), 8.03 (1H, dd, J=1.7, 8.7 Hz), 8.37 (1H, dd, J=0.6, 1.7 Hz).

Elemental analysis (for C$_{21}$H$_{15}$FN$_4$O$_2$)
Calculated (%): C, 67.37; H, 4.04; N, 14.97.
Found (%): C, 67.36; H, 4.03; N, 15.11.

EXAMPLE 489

2-[[4-[5-(5-methyl-1,3,4-oxadiazol-2-yl)-1-benzofuran-3-yl]-1H-pyrazol-1-yl]methyl]pyridine In the same manner as in Example 484 and using 2-(bromomethyl)pyridine hydrobromide instead of (chloromethyl) methyl ether, the title compound (yield 81%) was obtained as colorless crystals.

melting point 134-135° C. (crystallized from hexane/ethyl acetate).

$^1$H NMR (CDCl$_3$) δ 2.65 (3H, s), 5.55 (2H, s), 7.16 (1H, d, J=7.7 Hz), 7.25 (1H, dd, J=4.9, 7.7 Hz), 7.62 (1H, dd, J=0.6, 8.7 Hz), 7.69 (1H, dt, J=1.7, 7.7 Hz), 7.83 (1H, s), 7.89 (1H, s), 7.96 (1H, s), 8.04 (1H, dd, J=1.7, 8.7 Hz), 8.39 (1H, dd, J=0.6, 1.7 Hz), 8.62 (1H, td, J=0.8, 4.9 Hz).

Elemental analysis (for C$_{20}$H$_{15}$N$_5$O$_2$)
Calculated (%): C, 67.22; H, 4.23; N, 19.60.
Found (%): C, 67.18; H, 4.27; N, 19.62.

EXAMPLE 490

3-[[4-[5-(5-methyl-1,3,4-oxadiazol-2-yl)-1-benzofuran-3-yl]-1H-pyrazol-1-yl]methyl]pyridine In the same manner as in Example 484 and using 3-(bromomethyl)pyridine hydrobromide instead of (chloromethyl) methyl ether, the title compound (yield 47%) was obtained as colorless crystals.

melting point 137-138° C. (crystallized from hexane/ethyl acetate).

$^1$H NMR (CDCl$_3$) δ 2.64 (3H, s), 5.44 (2H, s), 7.32 (1H, dd, J=4.9, 7.7 Hz), 7.61-7.65 (2H, m), 7.81 (1H, s), 7.83 (1H, s), 7.88 (1H, s), 8.02 (1H, dd, J=1.7, 8.7 Hz), 8.38 (1H, d, J=1.7 Hz), 8.60 (1H, dd, J=1.7, 4.9 Hz), 8.62 (1H, d, J=2.3 Hz).

Elemental analysis (for C$_{20}$H$_{15}$N$_5$O$_2$)
Calculated (%): C, 67.22; H, 4.23; N, 19.60.
Found (%): C, 67.11; H, 4.05; N, 19.45.

EXAMPLE 491 optically active form of 2-[3-(3,3-dimethyl-1-oxido-2,3-dihydro-1-benzothien-5-yl)-1-benzofuran-5-yl]-5-methyl-1,3,4-oxadiazole (short retention time)

EXAMPLE 492 optically active form of 2-[3-(3,3-dimethyl-1-oxido-2,3-dihydro-1-benzothien-5-yl)-1-benzofuran-5-yl]-5-methyl-1,3,4-oxadiazole (long retention time)

2-[3-(3,3-Dimethyl-1-oxido-2,3-dihydro-1-benzothien-5-yl)-1-benzofuran-5-yl]-5-methyl-1,3,4-oxadiazole (300 mg) was optically resolved by preparative HPLC to give an optically active form (149 mg, recovery rate 99%) having a short retention time and an optically active form (150 mg, recovery rate 100%) having a long retention time.

The optical resolution by preparative HPLC was performed under the following conditions.
column: CHIRALPAK AS 50 mmID×500 mmL
mobile phase: ethanol
flow rate: 40 mL/min
temperature: 25° C.
detection: UV 220 nm
concentration: 1 mg/mL (ethanol)
injection volume: 30 mL The analysis conditions and analysis results of the separated fractions are as follows.
column: CHIRALPAK AS 4.6 mmID×250 mmL
mobile phase: ethanol
flow rate: 0.3 mL/min
temperature: 30° C.
detection: UV 220 nm
concentration: 0.25 mg/mL (ethanol)
injection volume: 10 μL retention time: 22.2 min (short retention time), 28.3 min (long retention time)
enantiomer excess: 99.8% (short retention time), 99.8% (long retention time)

Each of the obtained optically active forms was purified by basic silica gel column chromatography (tetrahydrofuran) and recrystallized from ethyl acetate to give an optically active form (131.9 mg) having a short retention time and an optically active form (136.3 mg) having a long retention time, both as colorless crystals.

melting point 237-238° C.

EXAMPLE 493

N-(3-methoxyphenyl)-4-(5-methyl-1,3,4-oxadiazol-2-yl)pyridin-2-amine

In the same manner as in Example 239 and using 2-[(3-methoxyphenyl)amino]isonicotinohydrazide instead of 2-[[4-(methylthio)phenyl]amino]isonicotinohydrazide, the title compound (yield 59%) was obtained as colorless crystals.

melting point 192-193° C. (recrystallized from hexane/ethyl acetate).

$^1$H NMR (DMSO-d$_6$) δ 2.61 (3H, s), 3.75 (3H, s), 6.45-6.59 (1H, m), 7.17-7.27 (3H, m), 7.40 (1H, s), 7.42-7.47 (1H, m), 8.36 (1H, d, J=5.5 Hz), 9.41 (1H, s).

Elemental analysis (for C$_{15}$H$_{14}$N$_4$O$_2$)
Calculated (%): C, 63.82; H, 5.00; N, 19.85.
Found (%): C, 63.87; H, 4.94; N, 19.89.

EXAMPLE 494

N-(2,5-difluorophenyl)-4-(5-methyl-1,3,4-oxadiazol-2-yl)pyridin-2-amine

In the same manner as in Example 239 and using 2-[(2,5-difluorophenyl)amino]isonicotinohydrazide instead of 2-[[4-(methylthio)phenyl]amino]isonicotinohydrazide, the title compound (yield 68%) was obtained as colorless crystals.

melting point 202-203° C. (recrystallized from hexane/ethyl acetate).

$^1$H NMR (DMSO-d$_6$) δ 2.62 (3H, s), 6.73-6.88 (1H, m), 7.16-7.41 (2H, m), 7.73 (1H, s), 8.25-8.37 (1H, m), 8.41 (1H, d, J=5.3 Hz), 9.32 (1H, s).

Elemental analysis (for C$_{14}$H$_{10}$F$_2$N$_4$O)
Calculated (%): C, 58.33; H, 3.50; N, 19.44.
Found (%): C, 58.40; H, 3.54; N, 19.50.

EXAMPLE 495

4-(5-methyl-1,3,4-oxadiazol-2-yl)-N-[3-(trifluoromethyl)phenyl]pyridin-2-amine

In the same manner as in Example 239 and using 2-[[3-(trifluoromethyl)phenyl]amino]isonicotinohydrazide instead of 2-[[4-(methylthio)phenyl]amino]isonicotinohydrazide, the title compound (yield 55%) was obtained as colorless crystals.

melting point 217-218° C. (recrystallized from hexane/ethyl acetate).

$^1$H NMR (DMSO-d$_6$) δ 2.62 (3H, s), 7.20-7.35 (2H, m), 7.44 (1H, s), 7.53 (1H, t, J=8.1 Hz), 7.90 (1H, d, J=8.3 Hz), 8.25 (1H, s), 8.42 (1H, d, J=5.3 Hz), 9.79 (1H, s).

Elemental analysis (for C$_{15}$H$_{11}$F$_3$N$_4$O)
Calculated (%): C, 56.25; H, 3.46; N, 17.49.
Found (%): C, 56.31; H, 3.37; N, 17.57.

EXAMPLE 496

4-(5-methyl-1,3,4-oxadiazol-2-yl)-N-[3-(trifluoromethyl)benzyl]pyridin-2-amine In the same manner as in Example 239 and using 2-[[3-(trifluoromethyl)benzyl]amino]isonicotinohydrazide instead of 2-[[4-(methylthio)phenyl]amino]isonicotinohydrazide, the title compound (yield 52%) was obtained as colorless crystals.

melting point 141-142° C. (recrystallized from hexane/ethyl acetate).

$^1$H NMR (DMSO-$d_6$) δ 2.58 (3H, s), 4.64 (2H, d, J=6.0 Hz), 7.00 (1H, dd, J=1.5, 5.3 Hz), 7.11 (1H, s), 7.46-7.80 (5H, m), 8.15 (1H, d, J=5.3 Hz).

Elemental analysis (for $C_{16}H_{13}F_3N_4O$)

Calculated (%): C, 57.49; H, 3.92; N, 16.76.

Found (%): C, 57.32; H, 3.86; N, 16.89.

EXAMPLE 497

4-(5-methyl-1,3,4-oxadiazol-2-yl)-N-(2-pyridylmethyl)pyridin-2-amine

In the same manner as in Example 239 and using 2-[(2-pyridylmethyl)amino]isonicotinohydrazide instead of 2-[[4-(methylthio)phenyl]amino]isonicotinohydrazide, the title compound (yield 18%) was obtained as colorless crystals.

melting point 137-138° C. (recrystallized from hexane/ethyl acetate).

$^1$H NMR (DMSO-$d_6$) δ 2.59 (3H, s), 4.63 (2H, d, J=6.0 Hz), 6.98 (1H, dd, J=1.1, 5.3 Hz), 7.15 (1H, s), 7.24 (1H, dd, J=5.3, 7.0 Hz), 7.32 (1H, d, J=7.9 Hz), 7.62 (1H, t, J=6.1 Hz), 7.73 (1H, td, J=1.7, 7.6 Hz), 8.14 (1H, d, J=5.3 Hz), 8.51 (1H, d, J=4.3 Hz).

Elemental analysis (for $C_{14}H_{13}N_5O \cdot 0.15H_2O$)

Calculated (%): C, 62.28; H, 4.97; N, 25.94.

Found (%): C, 62.55; H, 4.95; N, 25.72.

EXAMPLE 498

4-(5-methyl-1,3,4-oxadiazol-2-yl)-N-(3-pyridylmethyl)pyridin-2-amine

In the same manner as in Example 239 and using 2-[(3-pyridylmethyl)amino]isonicotinohydrazide instead of 2-[[4-(methylthio)phenyl]amino]isonicotinohydrazide, the title compound (yield 62%) was obtained as colorless crystals.

melting point 139-140° C. (recrystallized from hexane/ethyl acetate).

$^1$H NMR (DMSO-$d_6$) δ 2.62 (3H, s), 4.64 (2H, d, J=5.8 Hz), 5.11 (1H, brs), 7.04 (1H, s), 7.18 (1H, dd, J=1.3, 5.3 Hz), 7.23-7.33 (1H, m), 7.71 (1H, d, J=7.7 Hz), 8.26 (1H, d, J=5.3 Hz), 8.54 (1H, dd, J=1.4, 4.8 Hz), 8.65 (1H, d, J=1.7 Hz).

Elemental analysis (for $C_{14}H_{13}N_5O$)

Calculated (%): C, 62.91; H, 4.90; N, 26.20.

Found (%): C, 62.77; H, 4.90; N, 26.11.

EXAMPLE 499

4-[5-(methylthio)-1,3,4-oxadiazol-2-yl]-N-[3-(trifluoromethyl)phenyl]pyridin-2-amine In the same manner as in Example 387 and using 2-[[3-(trifluoromethyl)phenyl]amino]isonicotinohydrazide instead of 3-(2-chlorophenyl)-1-benzofuran-5-carbohydrazide, the title compound (yield 96%) was obtained as colorless crystals.

melting point 189-190° C. (recrystallized from hexane/ethyl acetate).

$^1$H NMR (DMSO-$d_6$) δ 2.80 (3H, s), 6.76 (1H, s), 7.28-7.40 (3H, m), 7.47 (1H, t, J=8.0 Hz), 7.65 (1H, d, J=6.2 Hz), 7.77 (1H, s), 8.39 (1H, d, J=0.8 Hz).

Elemental analysis (for $C_{15}H_{11}F_3N_4OS$)

Calculated (%): C, 51.13; H, 3.15; N, 15.90.

Found (%): C, 51.22; H, 3.12; N, 15.96.

EXAMPLE 500

4-[5-(methylsulfonyl)-1,3,4-oxadiazol-2-yl]-N-[3-(trifluoromethyl)phenyl]pyridin-2-amine To a solution of 4-[5-(methylthio)-1,3,4-oxadiazol-2-yl]-N-[3-(trifluoromethyl)phenyl]pyridin-2-amine (455 mg, 1.29 mmol) in N,N-dimethylacetamide (5 mL) was added m-chloroperbenzoic acid (70%, 619 mg, 2.58 mmol), and the resulting mixture was stirred at room temperature for 2 hr and at 50° C. overnight. A saturated aqueous sodium thiosulfate solution was added to the reaction mixture, and the mixture was stirred for 15 min and extracted with ethyl acetate. The organic layer was washed with saturated aqueous sodium hydrogen carbonate solution and saturated brine, dried over anhydrous sodium sulfate, and concentrated under reduced pressure. The residue was purified by silica gel column chromatography (hexane/ethyl acetate=9/1-0/1) and recrystallized from hexane/ethyl acetate to give the title compound (126 mg, yield 25%) as yellow crystals.

melting point 105-106° C.

$^1$H NMR (DMSO-$d_6$) δ 3.72 (3H, s), 7.28 (1H, d, J=7.5 Hz), 7.41 (1H, dd, J=1.3, 5.3 Hz), 7.47?7.63 (2H, m), 7.88 (1H, d, J=1.7 Hz), 8.27 (1H, s), 8.49 (1H, d, J=5.3 Hz), 9.90 (1H, s).

EXAMPLE 501

4-[5-(methylsulfinyl)-1,3,4-oxadiazol-2-yl]-N-[3-(trifluoromethyl)phenyl]pyridin-2-amine The eluate obtained after elution of 4-[5-(methylsulfonyl)-1,3,4-oxadiazol-2-yl]-N-[3-(trifluoromethyl)phenyl]pyridin-2-amine by column purification in Example 500 was recrystallized from hexane/ethyl acetate to give the title compound (29.8 mg, yield 6%) as yellow crystals.

melting point 198-199° C.

$^1$H NMR (DMSO-$d_6$) δ 3.28 (3H, s), 7.27 (1H, d, J=7.3 Hz), 7.40 (1H, dd, J=1.4, 5.4 Hz), 7.48-7.60 (2H, m), 7.90 (1H, d, J=8.9 Hz), 8.27 (1H, s), 8.48 (1H, d, J=5.5 Hz), 9.87 (1H, s).

The structural formulas of the compounds obtained in Examples 1-501 are shown in Tables 1-4.

TABLE 1
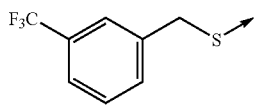
| Example | R¹ | Aa—Ba | Rb |
|---|---|---|---|
| 1 | 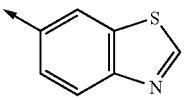 | 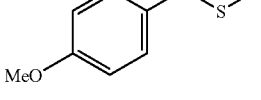 | — |
| 2 | 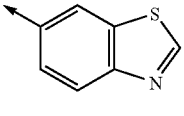 | 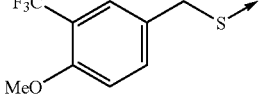 | — |
| 3 | 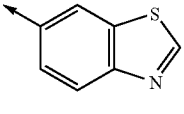 | 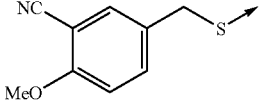 | — |
| 4 | 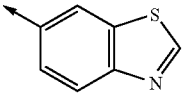 | 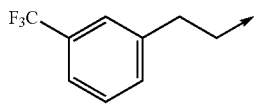 | — |
| 5 | 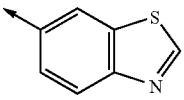 | 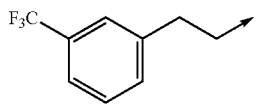 | — |
| 6 | 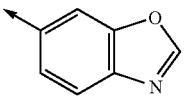 | 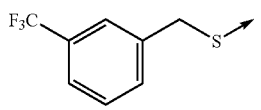 | — |
| 7 | 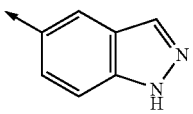 | 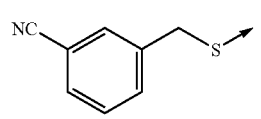 | H |
| 8 | 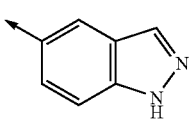 | 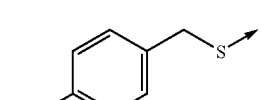 | H |
| 9 | 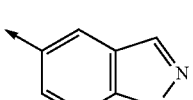 | 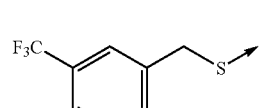 | H |
| 10 | 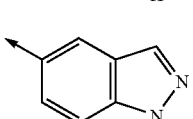 | 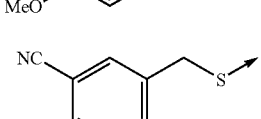 | H |
| 11 | 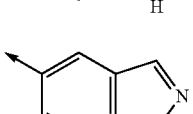 | | H |

TABLE 1-continued
| Example | R¹ | Aa—Ba | Rb |
|---|---|---|---|
| 12 | 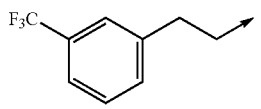 | 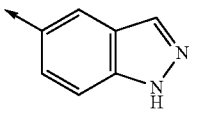 | H |
| 13 | 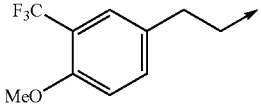 | 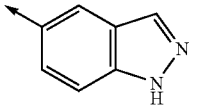 | H |
| 14 | 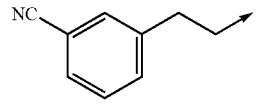 | 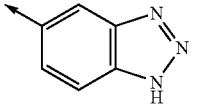 | — |
| 15 | 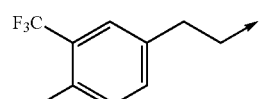 | 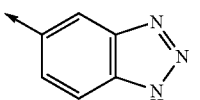 | — |
| 16 | 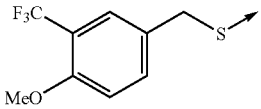 | 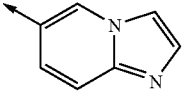 | H |
| 17 | 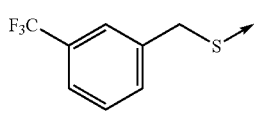 | 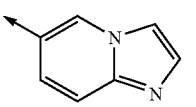 | H |
| 18 | 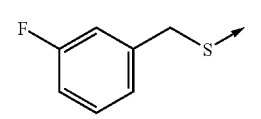 | 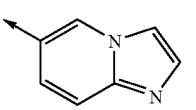 | H |
| 19 | 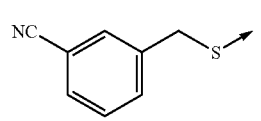 | 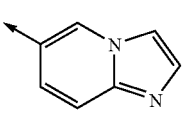 | H |
| 20 | 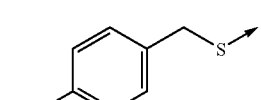 | 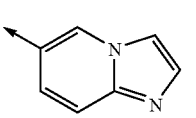 | H |
| 21 | 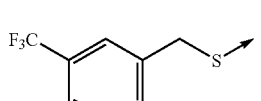 | 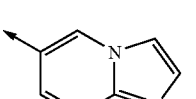 | 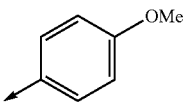 |
| 22 | 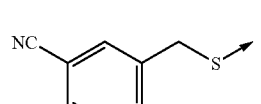 | 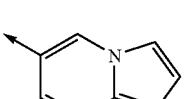 | 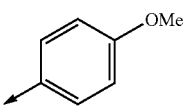 |

TABLE 1-continued

| Example | R¹ | Aa—Ba | Rb |
|---|---|---|---|
| 23 | 3-(F₃C)C₆H₄CH₂S- | imidazo[1,2-a]pyridinyl | 2-pyridyl |
| 24 | 3-(NC)C₆H₄CH₂S- | imidazo[1,2-a]pyridinyl | 2-pyridyl |
| 25 | 3-CN-4-MeO-C₆H₃CH₂S- | imidazo[1,2-a]pyridinyl | H |
| 26 | 3-(NC)C₆H₄CH₂CH₂- | imidazo[1,2-a]pyridinyl | H |
| 27 | 3-(F₃C)C₆H₄CH₂CH₂- | imidazo[1,2-a]pyridinyl | H |
| 28 | 3-F₃C-4-MeO-C₆H₃CH₂CH₂- | imidazo[1,2-a]pyridinyl | H |
| 29 | 3-(F₃C)C₆H₄CH₂S- | [1,2,4]triazolo[1,5-a]pyridinyl | — |
| 30 | 3-F₃C-4-MeO-C₆H₃CH₂S- | [1,2,4]triazolo[1,5-a]pyridinyl | — |
| 31 | 3-CN-4-MeO-C₆H₃CH₂S- | [1,2,4]triazolo[1,5-a]pyridinyl | — |
| 32 | 3-F-C₆H₄CH₂S- | [1,2,4]triazolo[1,5-a]pyridinyl | — |
| 33 | 3-(NC)C₆H₄CH₂S- | [1,2,4]triazolo[1,5-a]pyridinyl | — |
| 34 | SH | 2,3-dihydrobenzofuranyl | H |

TABLE 1-continued
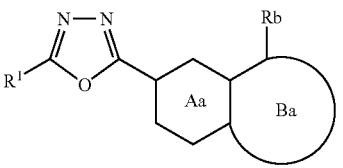
| Example | R¹ | Aa—Ba | Rb |
|---|---|---|---|
| 35 | SMe | 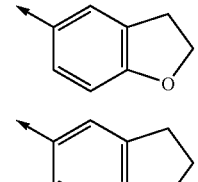 | H |
| 36 | S(O)₂Me | 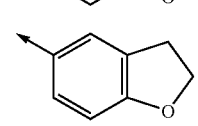 | H |
| 37 | EtO₂C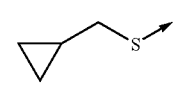 | 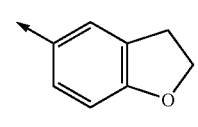 | H |
| 38 | 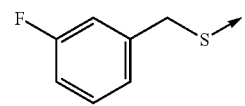 | 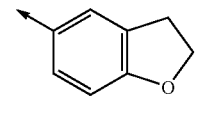 | H |
| 39 | 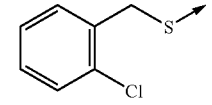 | 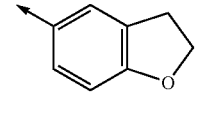 | H |
| 40 | 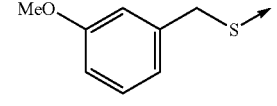 | 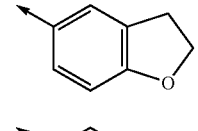 | H |
| 41 | 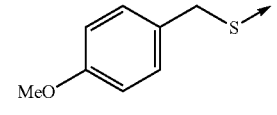 | 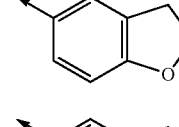 | H |
| 42 | 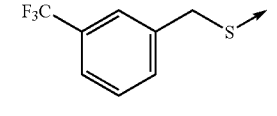 | 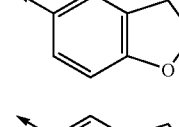 | H |
| 43 | 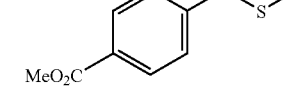 | 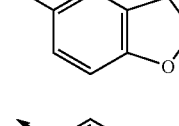 | H |
| 44 | 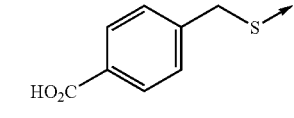 | 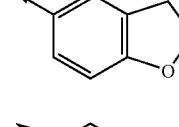 | H |
| 45 | 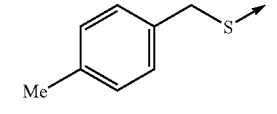 | 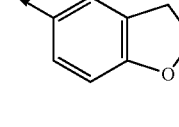 | H |
| 46 | 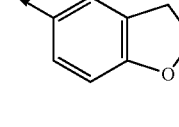 | 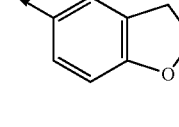 | H |

TABLE 1-continued

| Example | R¹ | Aa—Ba | Rb |
|---|---|---|---|
| 47 | 2-fluoro-4-methoxybenzyl-S- | 2,3-dihydrobenzofuran-5-yl | H |
| 48 | 3-chloro-4-methoxybenzyl-S- | 2,3-dihydrobenzofuran-5-yl | H |
| 49 | 3-cyano-4-methoxybenzyl-S- | 2,3-dihydrobenzofuran-5-yl | H |
| 50 | 3,4-difluorobenzyl-S- | 2,3-dihydrobenzofuran-5-yl | H |
| 51 | 3-trifluoromethyl-4-fluorobenzyl-S- | 2,3-dihydrobenzofuran-5-yl | H |
| 52 | 2,3-dihydrobenzofuran-5-ylmethyl-S- | 2,3-dihydrobenzofuran-5-yl | H |
| 53 | benzofuran-5-ylmethyl-S- | 2,3-dihydrobenzofuran-5-yl | H |
| 54 | pyridin-3-ylmethyl-S- | 2,3-dihydrobenzofuran-5-yl | H |
| 55 | benzyl-S- | 2,3-dihydrobenzofuran-5-yl | H |
| 56 | 3-cyanobenzyl-S- | 2,3-dihydrobenzofuran-5-yl | H |
| 57 | naphthalen-1-ylmethyl-S- | 2,3-dihydrobenzofuran-5-yl | H |

TABLE 1-continued
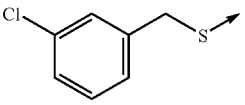
| Example | R¹ | Aa—Ba | Rb |
|---|---|---|---|
| 58 | 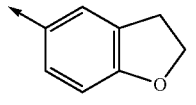 | 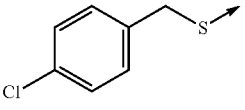 | H |
| 59 | 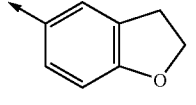 | 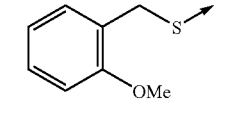 | H |
| 60 | 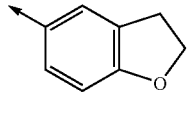 | 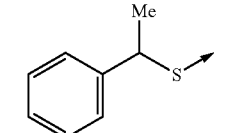 | H |
| 61 | 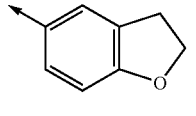 | 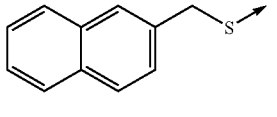 | H |
| 62 | 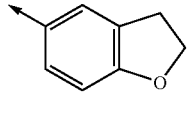 | 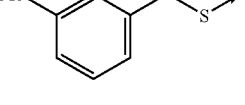 | H |
| 63 | 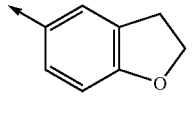 | 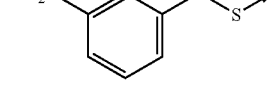 | H |
| 64 | 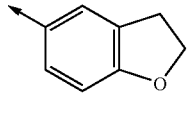 | 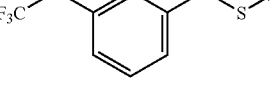 | H |
| 65 | 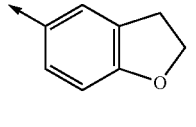 | 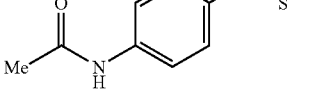 | H |
| 66 | 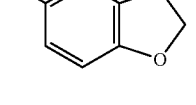 | 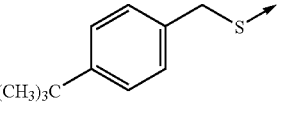 | H |
| 67 | 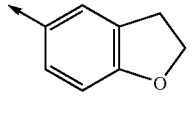 | 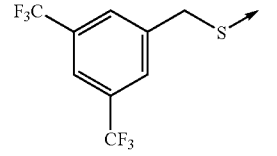 | H |
| 68 | 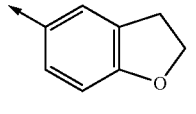 | | H |

TABLE 1-continued
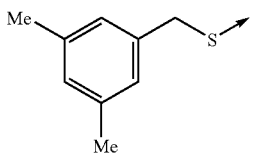
| Example | R¹ | Aa—Ba | Rb |
|---|---|---|---|
| 69 | 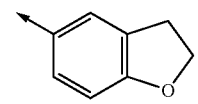 | 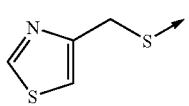 | H |
| 70 | 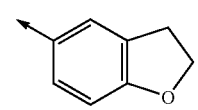 | 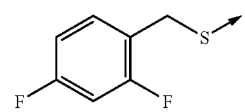 | H |
| 71 | 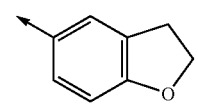 | 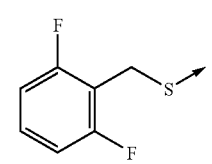 | H |
| 72 | 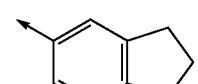 | 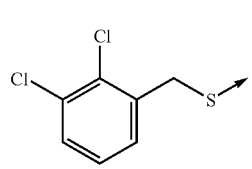 | H |
| 73 | 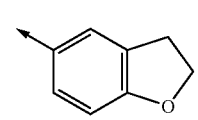 | 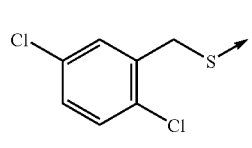 | H |
| 74 | 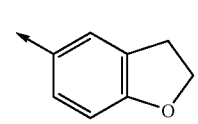 | 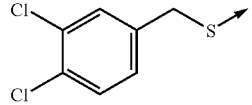 | H |
| 75 | 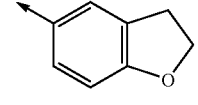 | 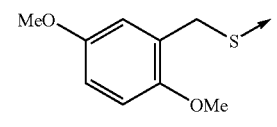 | H |
| 76 | 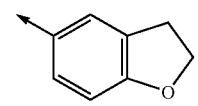 | 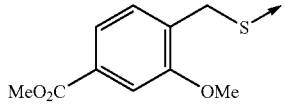 | H |
| 77 | 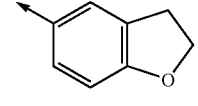 | 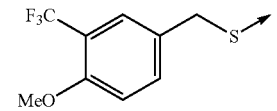 | H |
| 78 | 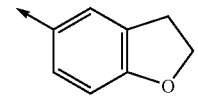 |  | H |

US 8,492,378 B2
TABLE 1-continued
| Example | R¹ | Aa—Ba | Rb |
|---|---|---|---|
| 79 | 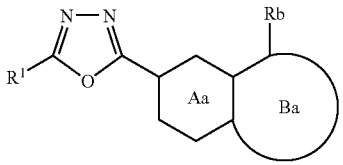 | 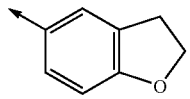 | H |
| 80 | 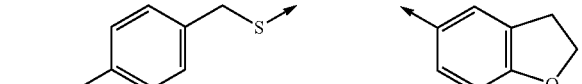 | 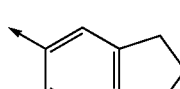 | H |
| 81 | 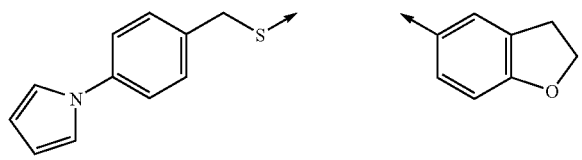 | 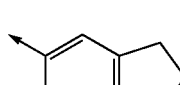 | H |
| 82 | 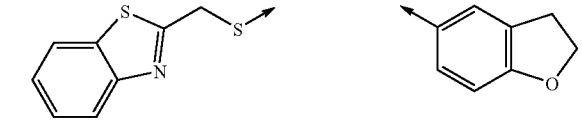 | 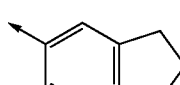 | H |
| 83 |  | 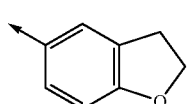 | H |
| 84 | 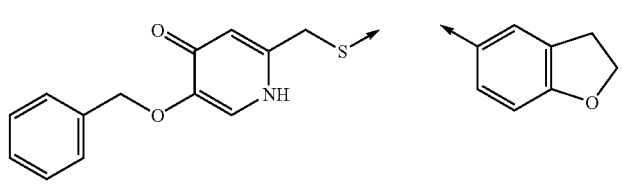 | 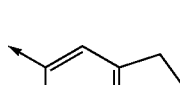 | H |
| 85 | 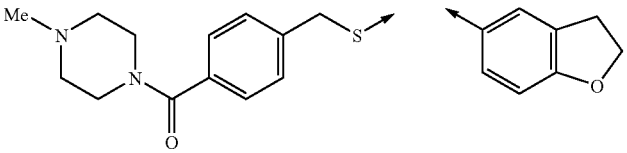 | 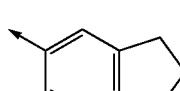 | H |
| 86 |  | 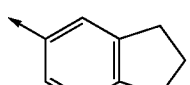 | H |
| 87 |  | 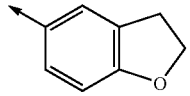 | H |

TABLE 1-continued

| Example | R¹ | Aa—Ba | Rb |
|---|---|---|---|
| 88 | thiazolo[3,2-a]pyrimidin-5(6H)-one-CH2-S- | 2,3-dihydrobenzofuran-5-yl | H |
| 89 | thieno[3,2-d]pyrimidin-4(3H)-one-CH2-S- | 2,3-dihydrobenzofuran-5-yl | H |
| 90 | 1-(prop-2-yn-1-yl)-1H-imidazol-5-yl-CH2-S- | 2,3-dihydrobenzofuran-5-yl | H |
| 91 | 1-(cyclopropylmethyl)-1H-imidazol-5-yl-CH2-S- | 2,3-dihydrobenzofuran-5-yl | H |
| 92 | 4-methyl-1-propyl-1H-imidazol-5-yl-CH2-S- | 2,3-dihydrobenzofuran-5-yl | H |
| 93 | 2-(3,4-difluorostyryl)oxazol-4-yl-CH2-S- | 2,3-dihydrobenzofuran-5-yl | H |
| 94 | 5,5-dimethyl-2,3,4,5-tetrahydro-1H-benzo[c]azepin-2-yl-C(O)-CH2-S- | 2,3-dihydrobenzofuran-5-yl | H |
| 95 | 1-methyl-3,4-dihydroisoquinolin-2(1H)-yl-C(O)-CH2-S- | 2,3-dihydrobenzofuran-5-yl | H |

TABLE 1-continued
| Example | R¹ | Aa—Ba | Rb |
|---|---|---|---|
| 96 | 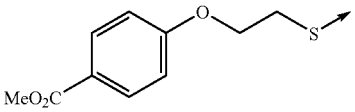 | 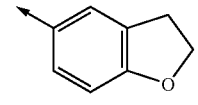 | H |
| 97 | 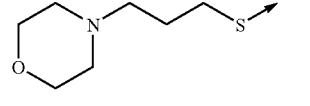 | 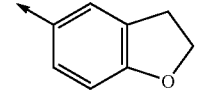 | H |
| 98 | 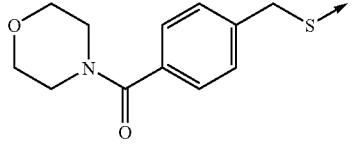 | 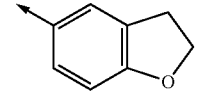 | H |
| 99 | 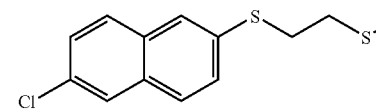 | 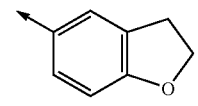 | H |
| 100 | 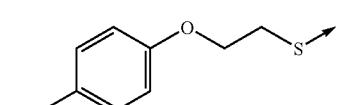 | 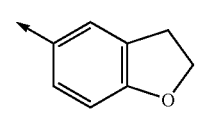 | H |
| 101 | 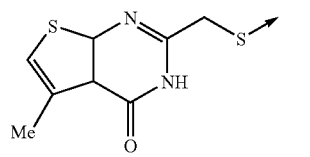 | 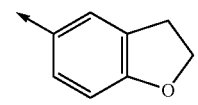 | H |
| 102 | 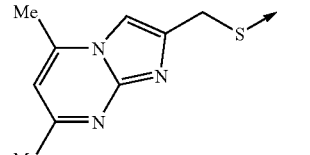 | 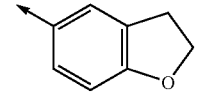 | H |
| 103 | 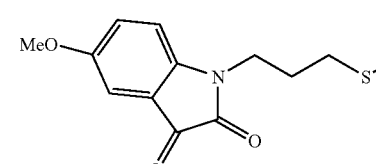 | 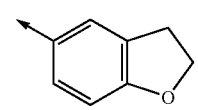 | H |
| 104 | 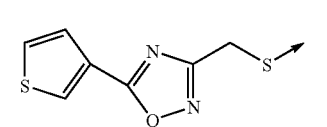 | 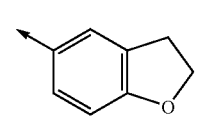 | H |

TABLE 1-continued

| Example | R¹ | Aa—Ba | Rb |
|---|---|---|---|
| 105 | 5-(2-methoxyphenyl)-1,2,4-oxadiazol-3-yl-CH₂-S- | 2,3-dihydrobenzofuran-5-yl | H |
| 106 | 3-acetyl-6-methoxyphenyl-CH₂-S- | 2,3-dihydrobenzofuran-5-yl | H |
| 107 | 3-fluorophenyl-CH₂CH₂- | 2,3-dihydrobenzofuran-5-yl | H |
| 108 | 3-fluorophenyl-S-CH₂- | 2,3-dihydrobenzofuran-5-yl | H |
| 109 | 3-fluorophenyl-CH₂-NH- | 2,3-dihydrobenzofuran-5-yl | H |
| 110 | 3-fluorophenyl-CH₂-O- | 2,3-dihydrobenzofuran-5-yl | H |
| 111 | 3-fluorophenyl-NH-CH₂- | 2,3-dihydrobenzofuran-5-yl | H |
| 112 | 3-fluorophenyl-O-CH₂- | 2,3-dihydrobenzofuran-5-yl | H |
| 113 | 3-fluorophenyl-S(O)-CH₂- | 2,3-dihydrobenzofuran-5-yl | H |
| 114 | 3-fluorophenyl-SO₂-CH₂- | 2,3-dihydrobenzofuran-5-yl | H |

TABLE 1-continued

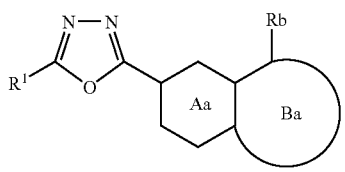

| Example | R¹ | Aa—Ba | Rb |
|---|---|---|---|
| 115 | EtO₂C-CH₂CH₂- | 2,3-dihydrobenzofuran-5-yl | H |
| 116 | HO₂C-CH₂CH₂- | 2,3-dihydrobenzofuran-5-yl | H |
| 117 | MeO(Me)N-C(O)-CH₂CH₂- | 2,3-dihydrobenzofuran-5-yl | H |
| 118 | 2-thienyl-C(O)-CH₂CH₂- | 2,3-dihydrobenzofuran-5-yl | H |
| 119 | EtO₂C-CH₂-O- | 2,3-dihydrobenzofuran-5-yl | H |
| 120 | HO₂C-CH₂-O- | 2,3-dihydrobenzofuran-5-yl | H |
| 121 | MeO(Me)N-C(O)-CH₂-O- | 2,3-dihydrobenzofuran-5-yl | H |
| 122 | 3-F-C₆H₄-CH₂-S- | benzofuran-5-yl | H |
| 123 | 3-Cl-C₆H₄-CH₂-S- | benzofuran-5-yl | H |
| 124 | 4-Cl-C₆H₄-CH₂-S- | benzofuran-5-yl | H |
| 125 | 4-MeO-C₆H₄-CH₂-S- | benzofuran-5-yl | H |

TABLE 1-continued

| Example | R¹ | Aa—Ba | Rb |
|---|---|---|---|
| 126 | 3-F-4-MeO-C₆H₃-CH₂-S- | benzofuran-5-yl | H |
| 127 | 3-CF₃-4-MeO-C₆H₃-CH₂-S- | benzofuran-5-yl | H |
| 128 | 4-MeO-C₆H₄-CH₂- | benzofuran-5-yl | H |
| 129 | 4-MeO-C₆H₄-CH₂CH₂- | benzofuran-5-yl | H |
| 130 | 4-MeO-C₆H₄-CH₂CH₂CH₂- | benzofuran-5-yl | H |
| 131 | Me | benzofuran-5-yl | 4-MeO-C₆H₄- |
| 132 | Me | benzofuran-5-yl | 4-F-C₆H₄- |
| 133 | Me | benzofuran-5-yl | 4-CO₂Me-C₆H₄- |
| 134 | Me | benzofuran-5-yl | 4-CO₂H-C₆H₄- |
| 135 | Me | benzofuran-5-yl | 4-HOCH₂-C₆H₄- |
| 136 | Me | benzofuran-5-yl | 4-MeOCH₂-C₆H₄- |
| 137 | Me | benzofuran-5-yl | 4-CONH₂-C₆H₄- |

TABLE 1-continued

| Example | R¹ | Aa—Ba | Rb |
|---|---|---|---|
| 138 | Me | benzofuran | phenyl-NMe₂ |
| 139 | Me | benzofuran | phenyl-SMe |
| 140 | Me | benzofuran | phenyl-S(O)Me |
| 141 | Me | benzofuran | phenyl-S(O)₂Me |
| 142 | Me | benzofuran | phenyl-F (meta) |
| 143 | Me | benzofuran | phenyl-OMe (meta) |
| 144 | Me | benzofuran | phenyl-CH₂OH (meta) |
| 145 | Me | benzofuran | phenyl-CH₂OMe (meta) |
| 146 | Me | benzofuran | phenyl-CF₃ (meta) |
| 147 | Me | benzofuran | phenyl-OCF₃ (meta) |
| 148 | Me | benzofuran | phenyl-Cl (meta) |
| 149 | Me | benzofuran | phenyl-CN (meta) |

TABLE 1-continued
| Example | R¹ | Aa—Ba | Rb |
|---|---|---|---|
| 150 | Me | 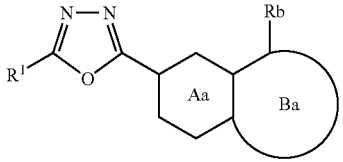 | 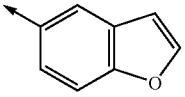 SMe |
| 151 | Me | 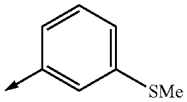 | 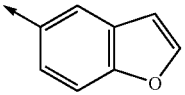 S(O)$_2$Me |
| 152 | Me | 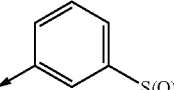 | 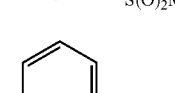 S(O)Me |
| 153 | Me | 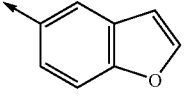 | 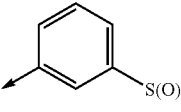 OMe, F |
| 154 | Me | 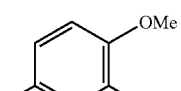 | 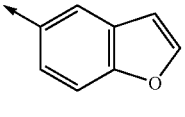 CHO, F |
| 155 | Me | 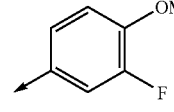 | 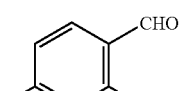 CO$_2$H, F |
| 156 | Me | 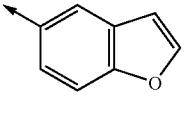 | 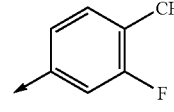 |
| 157 | Me | 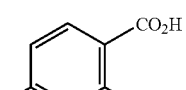 | 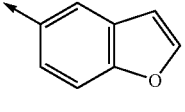 |
| 158 | Me | 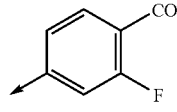 | 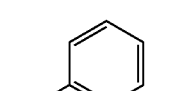 |
| 159 | Me | 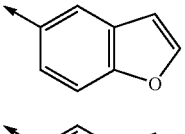 | 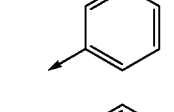 |
| 160 | Me | 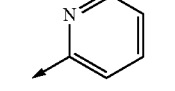 | CO$_2$Et |
| 161 | Me | 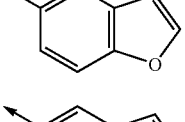 | CO$_2$H |

TABLE 1-continued

| Example | R¹ | Aa—Ba | Rb |
|---|---|---|---|
| 162 | Me | benzofuran | morpholine carbonyl |
| 163 | Me | benzofuran | -NH-CH₂CH₂-CONH₂ carbonyl ($-C(O)NHCH_2CH_2CONH_2$) |
| 164 | SH | benzofuran | 4-OMe-phenyl |
| 165 | SMe | benzofuran | 4-OMe-phenyl |
| 166 | 3-F-C₆H₄-CH₂-S- | benzofuran | 4-OMe-phenyl |
| 167 | 3-Cl-C₆H₄-CH₂-S- | benzofuran | 4-OMe-phenyl |
| 168 | 3-CF₃-C₆H₄-CH₂-S- | benzofuran | 4-OMe-phenyl |
| 169 | 3-NC-C₆H₄-CH₂-S- | benzofuran | 4-OMe-phenyl |
| 170 | 3-Me-C₆H₄-CH₂-S- | benzofuran | 4-OMe-phenyl |
| 171 | 3-MeO-C₆H₄-CH₂-S- | benzofuran | 4-OMe-phenyl |
| 172 | 4-MeO-C₆H₄-CH₂-S- | benzofuran | 4-OMe-phenyl |
| 173 | 3-F-4-MeO-C₆H₃-CH₂-S- | benzofuran | 4-OMe-phenyl |

TABLE 1-continued

| Example | R¹ | Aa—Ba | Rb |
|---|---|---|---|
| 174 | 3-CF₃-4-MeO-benzyl-S- | benzofuran-5-yl | 4-MeO-phenyl |
| 175 | SMe | benzimidazol-5-yl | 4-MeO-phenyl |
| 176 | 3-CF₃-4-MeO-benzyl-S- | benzimidazol-5-yl | 4-MeO-phenyl |
| 177 | 3-F-benzyl-S- | benzimidazol-5-yl | 4-MeO-phenyl |
| 178 | 3-CF₃-benzyl-S- | benzimidazol-5-yl | 4-MeO-phenyl |
| 179 | 3-CN-benzyl-S- | benzimidazol-5-yl | 4-MeO-phenyl |
| 180 | 3-HO₂C-benzyl-S- | benzimidazol-5-yl | 4-MeO-phenyl |
| 181 | 3-F-phenethyl- | benzimidazol-5-yl | 4-MeO-phenyl |
| 182 | 3-F-phenethyl- | benzotriazol-5-yl | 4-MeO-phenyl |
| 183 | 3-F-phenethyl- | 2-amino-benzimidazol-5-yl | 4-MeO-phenyl |
| 184 | 3-CF₃-phenethyl- | benzimidazol-5-yl | 4-MeO-phenyl |
| 185 | 3-CN-phenethyl- | benzimidazol-5-yl | 4-MeO-phenyl |

TABLE 1-continued

| Example | R¹ | Aa—Ba | Rb |
|---|---|---|---|
| 186 | 3-F-C₆H₄-CH₂-NH- | benzimidazole | 4-OMe-C₆H₄- |
| 187 | 3-F₃C-C₆H₄-CH₂-S- | benzimidazole | Me |
| 188 | 3-F-C₆H₄-CH₂CH₂- | benzimidazole | Me |
| 189 | H | benzimidazole | 4-S(O)Me-C₆H₄- |
| 190 | SH | benzimidazole | 4-S(O)Me-C₆H₄- |
| 191 | 3-F-C₆H₄-CH₂-S- | benzimidazole | 4-S(O)Me-C₆H₄- |
| 192 | 3-NC-C₆H₄-CH₂-S- | benzimidazole | 4-S(O)Me-C₆H₄- |
| 193 | 3-F₃C-C₆H₄-CH₂-S- | benzimidazole | 4-S(O)Me-C₆H₄- |
| 194 | Me | benzimidazole | 4-SMe-C₆H₄- |
| 195 | cyclopropyl | benzimidazole | 4-SMe-C₆H₄- |
| 196 | F₃C-CH₂- | benzimidazole | 4-SMe-C₆H₄- |
| 197 | Me | benzimidazole | 4-S(O)Me-C₆H₄- |

TABLE 1-continued
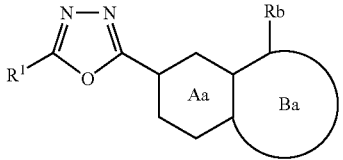
| Example | R¹ | Aa—Ba | Rb |
|---|---|---|---|
| 198 |  | 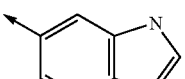 | 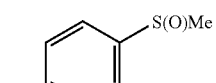 S(O)Me |
| 199 | F₃C  | 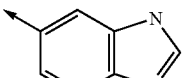 | 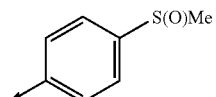 S(O)Me |
| 200 | Me | 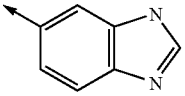 | 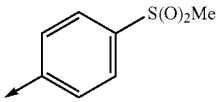 S(O)₂Me |
| 201 |  | 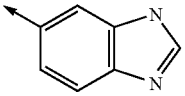 | 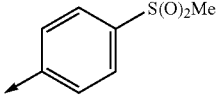 S(O)₂Me |
| 202 | F₃C  | 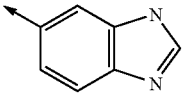 | 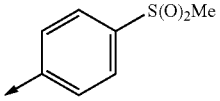 S(O)₂Me |
| 203 | 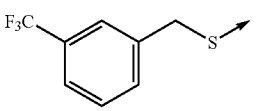 | 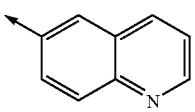 | H |
| 204 | 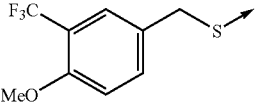 | 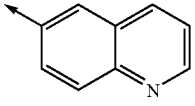 | H |
TABLE 2
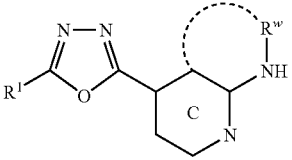
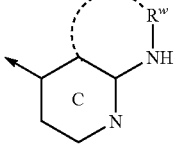
| Example | R¹ | |
|---|---|---|
| 205 | 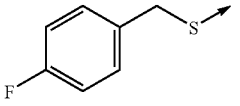 | |

TABLE 2-continued
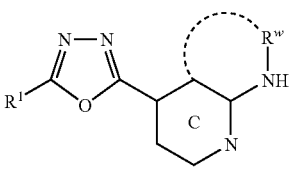
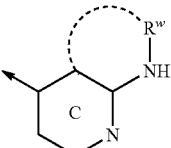
| Example | R¹ | |
|---|---|---|
| 206 | 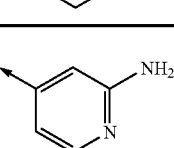 | 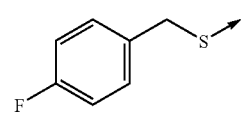 |
| 207 | 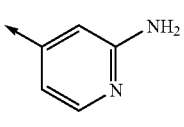 | 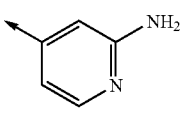 |
| 208 | 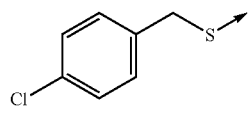 | 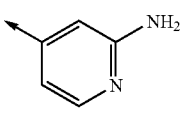 |
| 209 | 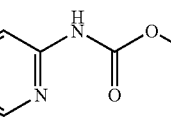 | 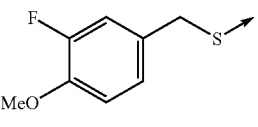 |
| 210 | 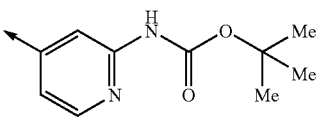 | 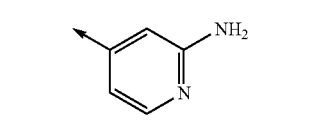 |
| 211 | 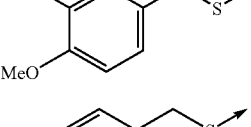 | 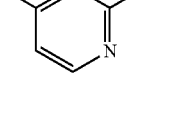 |
| 212 | 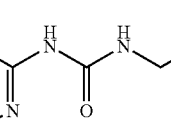 | 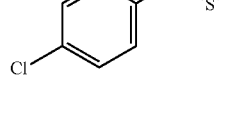 |
| 213 | 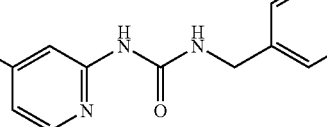 | 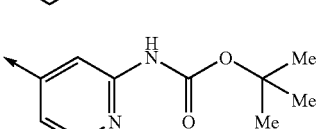 |
| 214 | 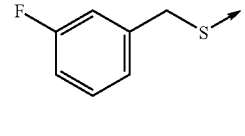 | 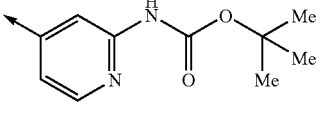 |

TABLE 2-continued
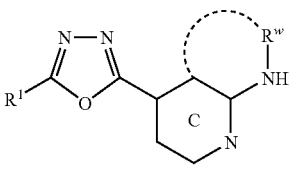
| Example | R¹ | |
|---|---|---|
| 215 | 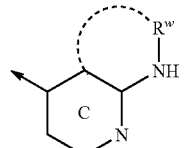 | 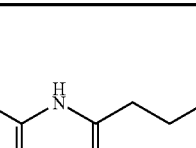 |
| 216 | 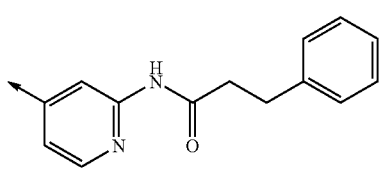 | 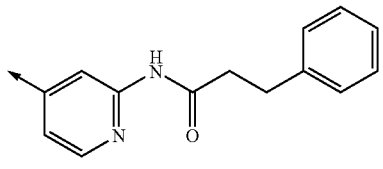 |
| 217 | 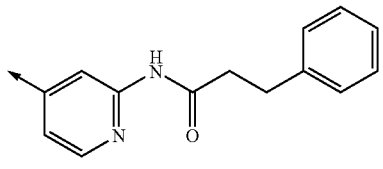 | 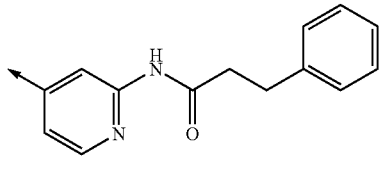 |
| 218 | 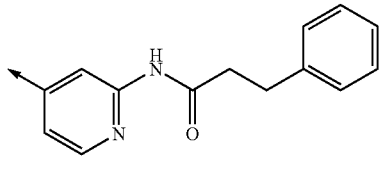 | 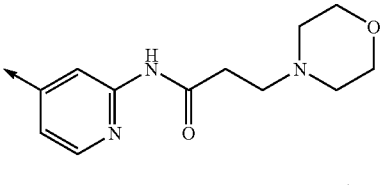 |
| 219 | 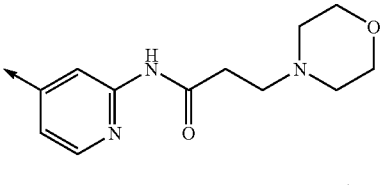 | 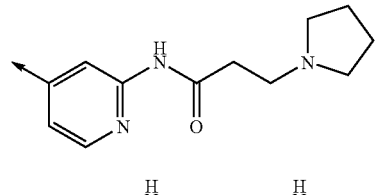 |
| 220 | 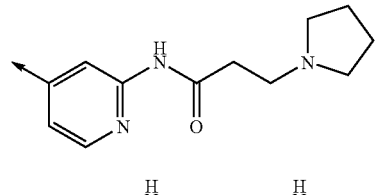 | 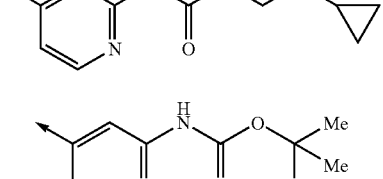 |
| 221 | 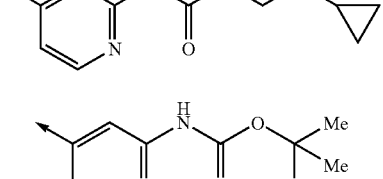 | 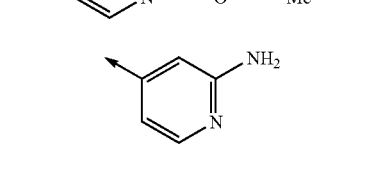 |
| 222 | 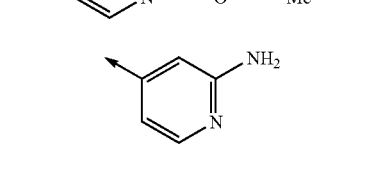 |  |

TABLE 2-continued
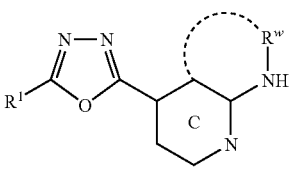
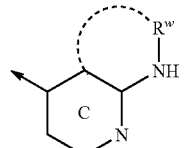
| Example | R¹ | |
|---|---|---|
| 223 | 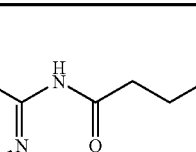 | 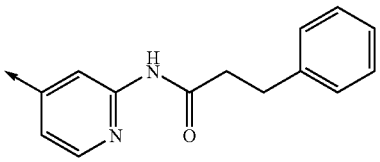 |
| 224 | 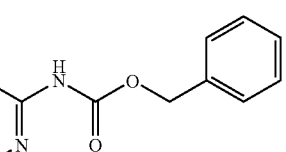 | 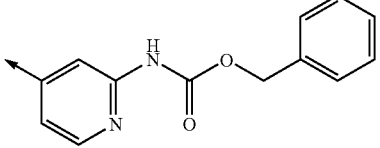 |
| 225 | 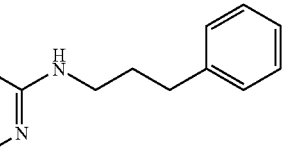 | 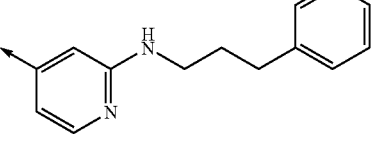 |
| 226 | 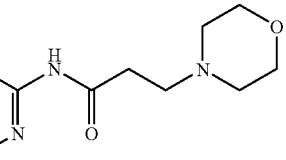 | 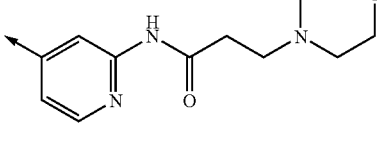 |
| 227 | 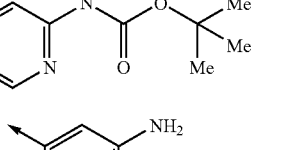 | 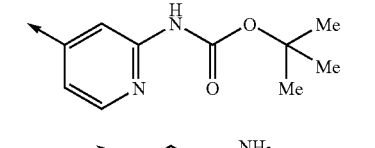 |
| 228 | 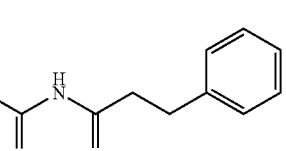 | 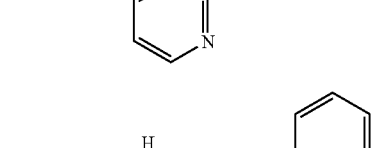 |
| 229 | 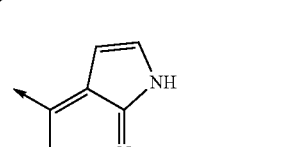 | 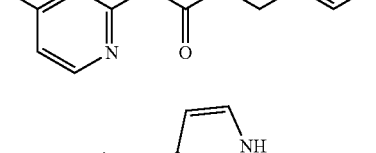 |
| 230 | 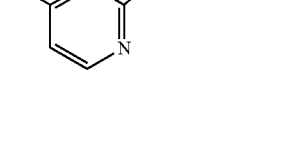 | 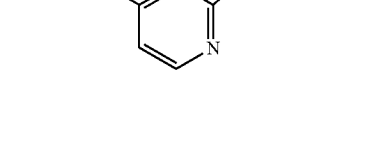 |

TABLE 2-continued
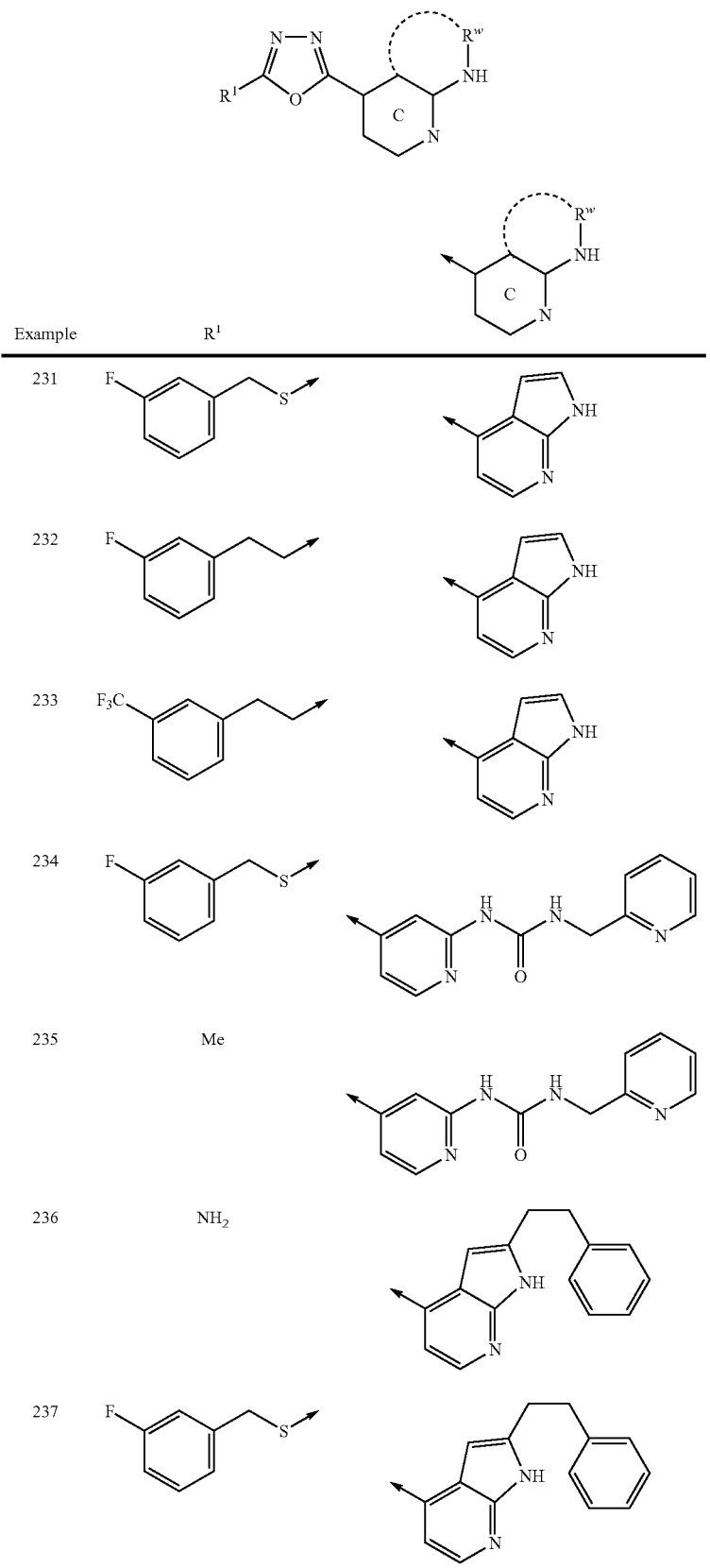

TABLE 2-continued

| Example | R¹ | |
|---|---|---|
| 238 | Me | [2-phenethyl-1H-pyrrolo[2,3-b]pyridin-4-yl] |
| 239 | Me | [2-(4-methylthiophenylamino)pyridin-4-yl] |
| 240 | Me | [2-(3-trifluoromethyl-5-methoxyphenylamino)pyridin-4-yl] |
| 241 | Me | [2-(4-methylsulfonylphenylamino)pyridin-4-yl] |
| 242 | Me | [2-(4-methylsulfinylphenylamino)pyridin-4-yl] |
| 243 | MeC(O)OC(Me)₂– | [2-(4-methylthiophenylamino)pyridin-4-yl] |
| 244 | HOC(Me)₂– | [2-(4-methylthiophenylamino)pyridin-4-yl] |
| 245 | Me | [2-(pyridin-2-ylamino)pyridin-4-yl] |

TABLE 2-continued

| Example | R¹ | | |
|---|---|---|---|
| 246 | 3-F-C₆H₄-CH₂-S- | 4-(pyridin-2-ylamino)pyridin-2-yl | | |
| 247 | 3-F-C₆H₄-CH₂-S- | 7H-pyrrolo[2,3-d]pyrimidin-4-yl | | |
| 248 | 3-F₃C-C₆H₄-CH₂-S- | 7H-pyrrolo[2,3-d]pyrimidin-4-yl | | |

TABLE 3

| Example | R¹ | Aa-Ba | Rb |
|---|---|---|---|
| 249 | 3-F₃C-4-MeS-C₆H₃-CH₂-S- | benzothiazol-6-yl | — |
| 250 | 3-F₃C-4-Me(O)S-C₆H₃-CH₂-S- | benzothiazol-6-yl | — |
| 251 | 3-F₃C-4-MeS-C₆H₃-CH₂-S- | 1H-indazol-5-yl | H |
| 252 | 3-F₃C-4-Me(O)S-C₆H₃-CH₂-S- | 1H-indazol-5-yl | H |

TABLE 3-continued
| Example | R¹ | Aa-Ba | Rb |
|---|---|---|---|
| 253 | Me | 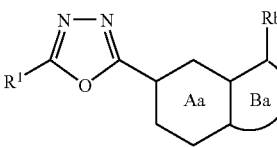 | 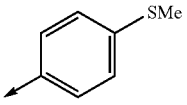 SMe |
| 254 | Me | 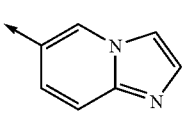 | 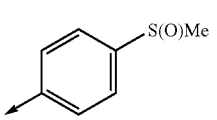 S(O)Me |
| 255 | Me | 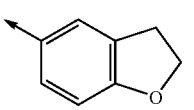 | 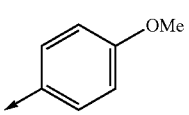 OMe |
| 256 | 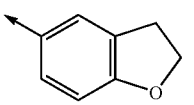 |  | H |
| 257 | 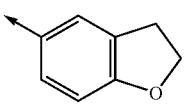 |  | H |
| 258 | SH | 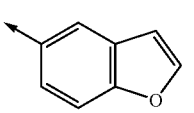 | 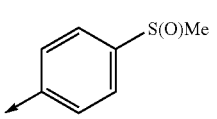 S(O)Me |
| 259 | 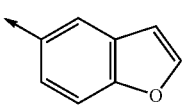 | 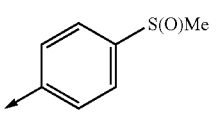 | 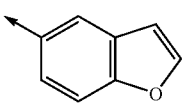 S(O)Me |
| 260 | 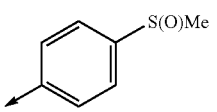 | 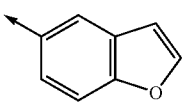 | S(O)Me |
| 261 | 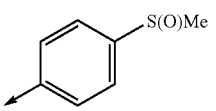 | 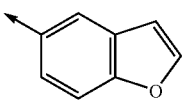 | S(O)Me |
| 262 | 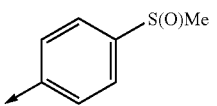 | 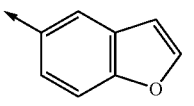 | S(O)Me |
| 263 | Me | 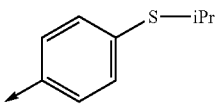 | S—iPr |
| 264 | Me | 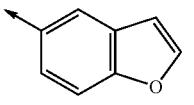 | 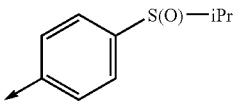 S(O)—iPr |

TABLE 3-continued
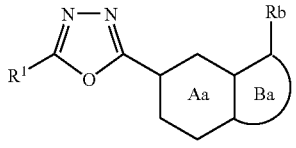
| Example | R¹ | Aa-Ba | Rb |
|---|---|---|---|
| 265 | Me | 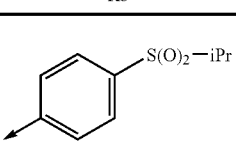 | 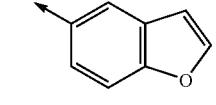 S(O)₂—iPr |
| 266 | Me | 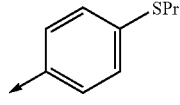 | 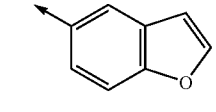 SPr |
| 267 | Me | 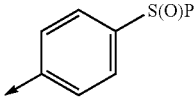 | 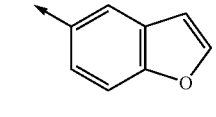 S(O)Pr |
| 268 | Me | 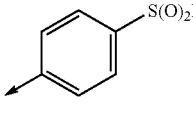 | 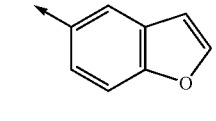 S(O)₂Pr |
| 269 | Me | 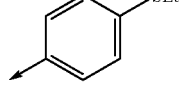 | 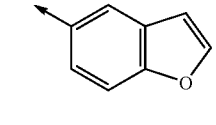 SEt |
| 270 | Me | 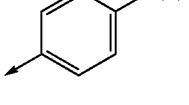 | 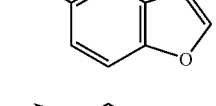 S(O)Et |
| 271 | Me | 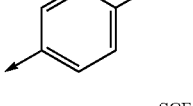 | 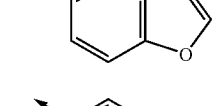 S(O)₂Et |
| 272 | Me | 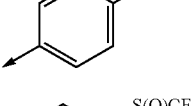 | 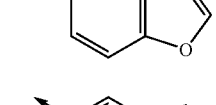 SCF₃ |
| 273 | Me | 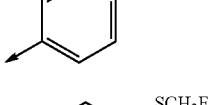 | 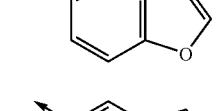 S(O)CF₃ |
| 274 | Me | 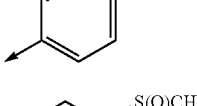 | 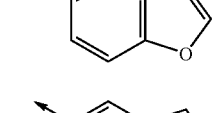 SCH₂F |
| 275 | Me | 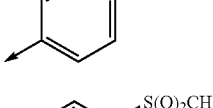 | 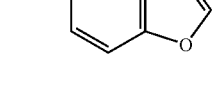 S(O)CH₂F |
| 276 | Me | 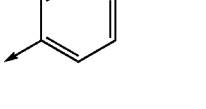 | S(O)₂CH₂F |

TABLE 3-continued

| Example | R¹ | Aa-Ba | Rb |
|---|---|---|---|
| 277 | Me | 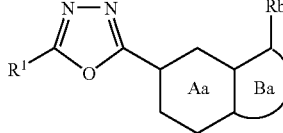 benzofuran | 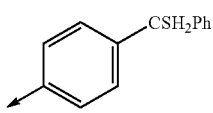 phenyl-CSH₂Ph |
| 278 | Me | 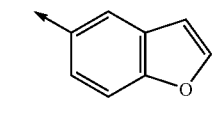 benzofuran | 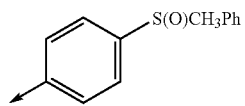 phenyl-S(O)CH₃Ph |
| 279 | Me | 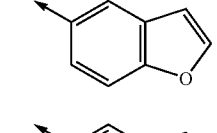 benzofuran | 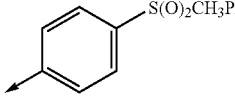 phenyl-S(O)₂CH₃Ph |
| 280 | Me | 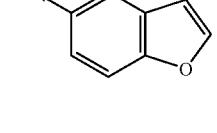 benzofuran | 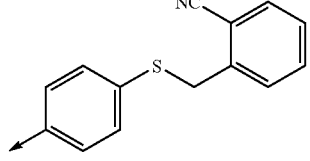 2-CN-phenyl-CH₂-S-phenyl |
| 281 | Me | 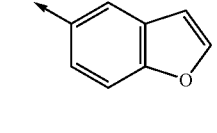 benzofuran | 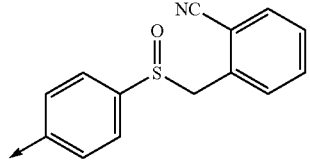 2-CN-phenyl-CH₂-S(O)-phenyl |
| 282 | Me | 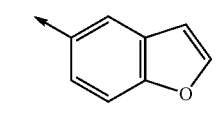 benzofuran | 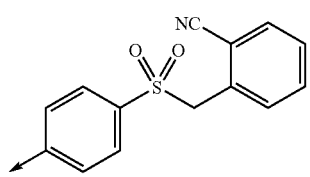 2-CN-phenyl-CH₂-S(O)₂-phenyl |
| 283 | Me | 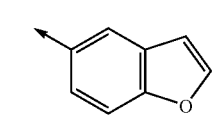 benzofuran | 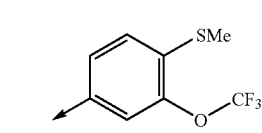 phenyl with SMe and OCF₃ |
| 284 | Me | 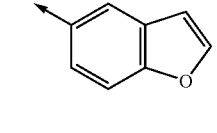 benzofuran | 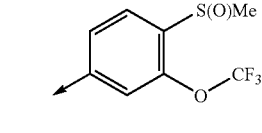 phenyl with S(O)Me and OCF₃ |
| 285 | Me | 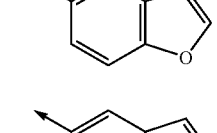 benzofuran | 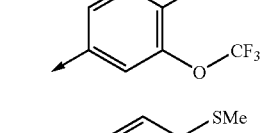 phenyl with S(O)₂Me and OCF₃ |
| 286 | Me | 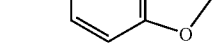 benzofuran | 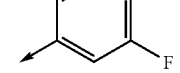 phenyl with SMe and F |

TABLE 3-continued

| Example | R¹ | Aa-Ba | Rb |
|---|---|---|---|
| 287 | Me | 5-benzofuran | 4-S(O)Me, 3-F phenyl |
| 288 | Me | 5-benzofuran | 4-S(O)₂Me, 3-F phenyl |
| 289 | Me | 5-benzofuran | 4-SEt, 3-F phenyl |
| 290 | Me | 5-benzofuran | 4-S(O)Et, 3-F phenyl |
| 291 | Me | 5-benzofuran | 4-S(O)₂Et, 3-F phenyl |
| 292 | Me | 5-benzofuran | 4-SMe, 3-Cl phenyl |
| 293 | Me | 5-benzofuran | 4-S(O)Me, 3-Cl phenyl |
| 294 | Me | 5-benzofuran | 4-S(O)₂Me, 3-Cl phenyl |
| 295 | Me | 5-benzofuran | 4-SMe, 3-Me phenyl |
| 296 | Me | 5-benzofuran | 4-S(O)Me, 3-Me phenyl |
| 297 | Me | 5-benzofuran | 4-S(O)₂Me, 3-Me phenyl |

TABLE 3-continued

| Example | R¹ | Aa-Ba | Rb | |
|---|---|---|---|---|
| 298 | Me | 5-benzofuran | 3-Cl, 4-SMe phenyl | |
| 299 | Me | 5-benzofuran | 3-Cl, 4-S(O)Me phenyl | |
| 300 | Me | 5-benzofuran | 3-Cl, 4-S(O)₂Me phenyl | |
| 301 | Me | 5-benzofuran | 3-Cl, 4-SEt phenyl | |
| 302 | Me | 5-benzofuran | 3-Cl, 4-S(O)Et phenyl | |
| 303 | Me | 5-benzofuran | 3-Cl, 4-S(O)₂Et phenyl | |
| 304 | Me | 5-benzofuran | 3,3-dimethyl-2,3-dihydrobenzothiophen-5-yl | |
| 305 | Me | 5-benzofuran | 3,3-dimethyl-2,3-dihydrobenzothiophene 1-oxide-5-yl | |
| 306 | Me | 5-benzofuran | 3,3-dimethyl-2,3-dihydrobenzothiophene 1,1-dioxide-5-yl | |
| 307 | Me | 5-benzofuran | 4-S(O)Me phenyl | (short retention time) |

TABLE 3-continued

| Example | R¹ | Aa-Ba | Rb | |
|---|---|---|---|---|
| 308 | Me | benzofuran (5-yl) | 4-S(O)Me-phenyl | (long retention time) |
| 309 | Me | benzofuran (5-yl) | 4-S(O)Et-phenyl | (short retention time) |
| 310 | Me | benzofuran (5-yl) | 4-S(O)Et-phenyl | (long retention time) |
| 311 | Me | benzofuran (5-yl) | 3-Cl-4-S(O)Me-phenyl | (short retention time) |
| 312 | Me | benzofuran (5-yl) | 3-Cl-4-S(O)Me-phenyl | (long retention time) |
| 313 | Me | benzofuran (5-yl) | 3-Cl-4-S(O)Et-phenyl | (short retention time) |
| 314 | Me | benzofuran (5-yl) | 3-Cl-4-S(O)Et-phenyl | (long retention time) |
| 315 | Me | benzofuran (5-yl) | 3-F-4-S(O)Me-phenyl | (short retention time) |
| 316 | Me | benzofuran (5-yl) | 3-F-4-S(O)Me-phenyl | (long retention time) |
| 317 | Me | benzofuran (5-yl) | 3-OCF₃-4-S(O)Me-phenyl | (short retention time) |
| 318 | Me | benzofuran (5-yl) | 3-OCF₃-4-S(O)Me-phenyl | (long retention time) |
| 319 | Me | benzofuran (5-yl) | 4-OH-phenyl | |

TABLE 3-continued
| Example | R¹ | Aa-Ba | Rb |
|---|---|---|---|
| 320 | Me | 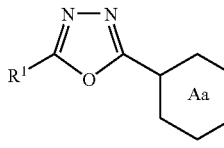 | 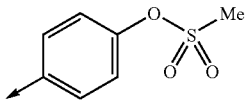 |
| 321 | Me | 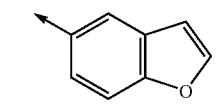 | 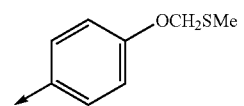 OCH₂SMe |
| 322 | Me | 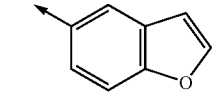 | 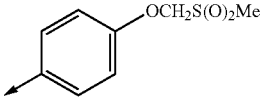 OCH₂S(O)₂Me |
| 323 | Me | 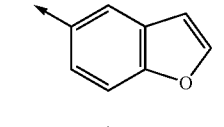 | 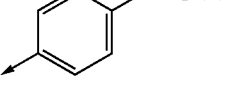 OCH₂S(O)Me |
| 324 | Me | 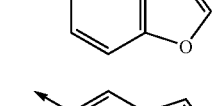 | 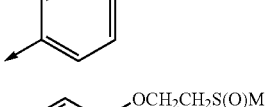 OCH₂CH₂SMe |
| 325 | Me | 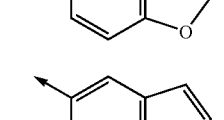 | 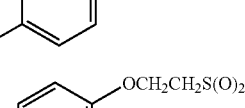 OCH₂CH₂S(O)Me |
| 326 | Me | 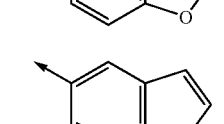 | 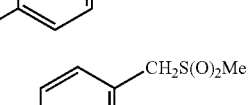 OCH₂CH₂S(O)₂Me |
| 327 | Me | 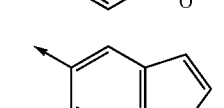 | 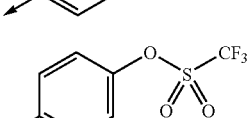 CH₂S(O)₂Me |
| 328 | Me | 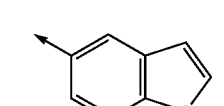 | 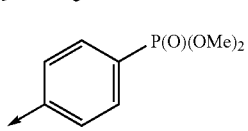 |
| 329 | Me | 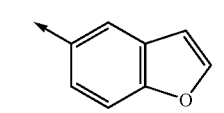 | 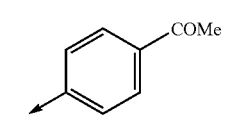 P(O)(OMe)₂ |
| 330 | Me | 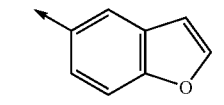 | 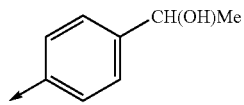 COMe |
| 331 | Me |  |  CH(OH)Me |

TABLE 3-continued
| Example | R¹ | Aa-Ba | Rb |
|---|---|---|---|
| 332 | Me | 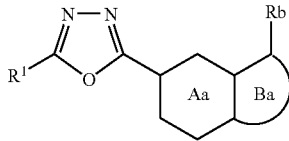 |  2-F, 4-CONHMe |
| 333 | Me |  | 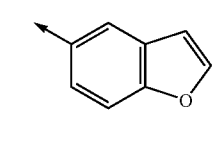 2-F, 4-CONMe₂ |
| 334 | Me | 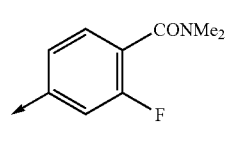 |  2-F, 4-C(O)-morpholine |
| 335 | Me | 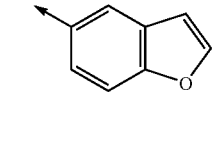 | 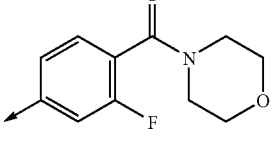 2-F, 4-NHS(O)₂Me |
| 336 | Me |  | 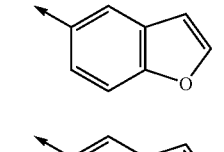 2-F, 4-C(O)-pyrrolidine |
| 337 | Me | 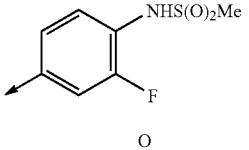 |  3-Cl, 4-CO₂Me |
| 338 | Me | 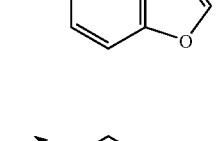 | 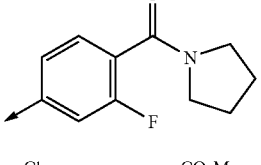 3-Cl, 4-CO₂H |
| 339 | Me |  | 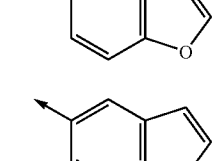 3-Cl, 4-CONHMe |
| 340 | Me | 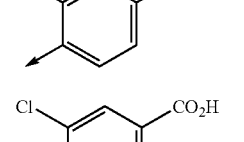 |  4-S(O)₂NHMe |
| 341 | Me | 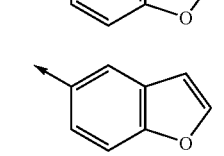 | 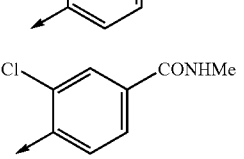 4-S(O)₂NMe₂ |
| 342 | Me |  | 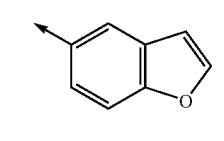 4-CN |

TABLE 3-continued
| Example | R¹ | Aa-Ba | Rb |
|---|---|---|---|
| 343 | Me | 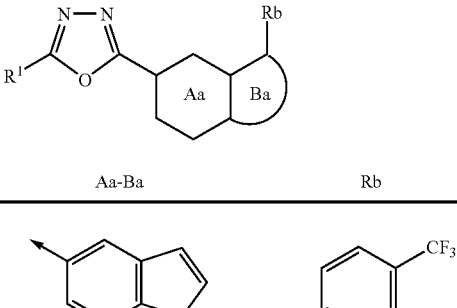 | 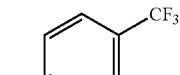 |
| 344 | Me |  | 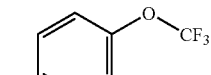 |
| 345 | Me |  | 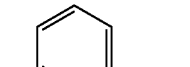 |
| 346 | Me |  | 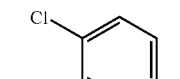 |
| 347 | Me | 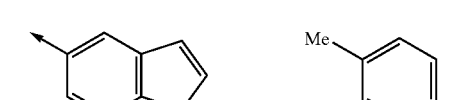 | 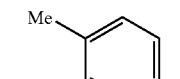 |
| 348 | Me |  | 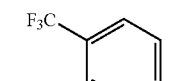 |
| 349 | Me |  | 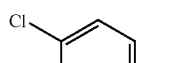 |
| 350 | Me |  | 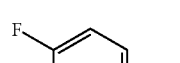 |
| 351 | Me |  | 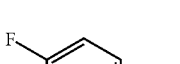 |
| 352 | Me |  |  |
| 353 | Me |  |  |

TABLE 3-continued
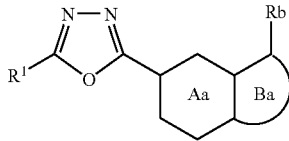
| Example | R¹ | Aa-Ba | Rb |
|---|---|---|---|
| 354 | Me | 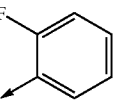 | 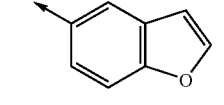 |
| 355 | Me | 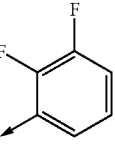 | 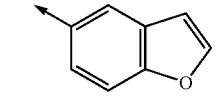 |
| 356 | Me | 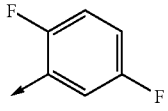 | 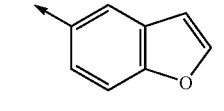 |
| 357 | Me | 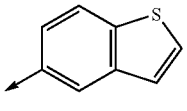 | 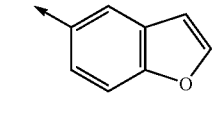 |
| 358 | Me | 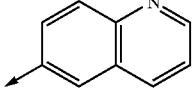 | 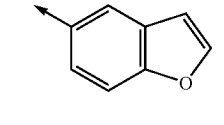 |
| 359 | Me | 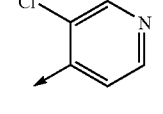 | 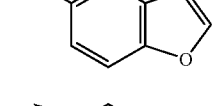 |
| 360 | Me | 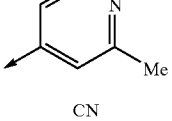 | 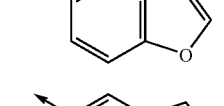 |
| 361 | Me | 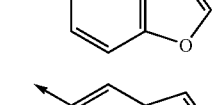 | CN |
| 362 | Me | 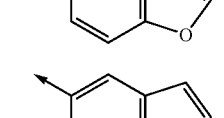 | CHO |
| 363 | Me | 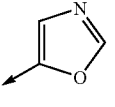 | 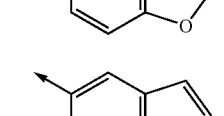 |
| 364 | Et | 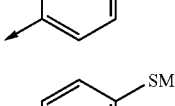 | 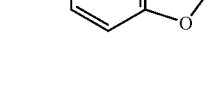 |
| 365 | NH₂ | 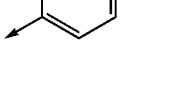 |  |

TABLE 3-continued

| Example | R¹ | Aa-Ba | Rb |
|---|---|---|---|
| 366 | NH₂ | 5-benzofuranyl | 4-(S(O)Me)phenyl |
| 367 | NH₂ | 5-benzofuranyl | 4-(S(O)₂Me)phenyl |
| 368 | NHMe | 5-benzofuranyl | 4-(SMe)phenyl |
| 369 | NHMe | 5-benzofuranyl | 4-(S(O)Me)phenyl |
| 370 | NH₂ | 5-benzofuranyl | 3-chloro-4-(SMe)phenyl |
| 371 | NH₂ | 5-benzofuranyl | 3-chloro-4-(S(O)Me)phenyl |
| 372 | NH₂ | 5-benzofuranyl | 3-chloro-4-(S(O)₂Me)phenyl |
| 373 | NH₂ | 5-benzofuranyl | 4-(OCF₃)phenyl |
| 374 | SH | 5-benzofuranyl | 4-(OCF₃)phenyl |
| 375 | SMe | 5-benzofuranyl | 4-(OCF₃)phenyl |
| 376 | S(o)Me | 5-benzofuranyl | 4-(OCF₃)phenyl |

TABLE 3-continued
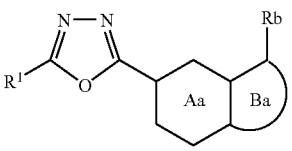
| Example | R¹ | Aa-Ba | Rb |
|---|---|---|---|
| 377 | S(O)₂Me | 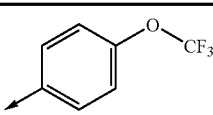 | 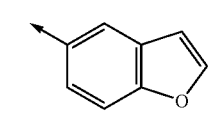 |
| 378 | NHMe | 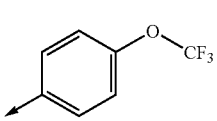 | 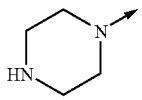 |
| 379 | 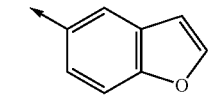 | 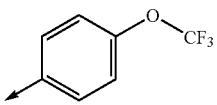 | 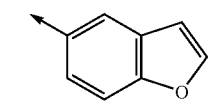 |
| 380 | NH₂ | 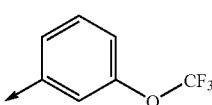 | 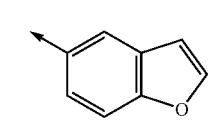 |
| 381 | SMe | 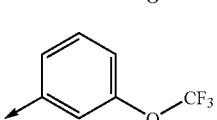 | 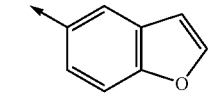 |
| 382 | S(O)Me | 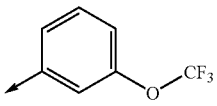 | 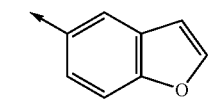 |
| 383 | NHMe | 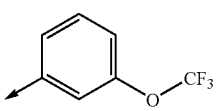 | 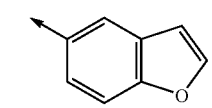 |
| 384 | NHCN | 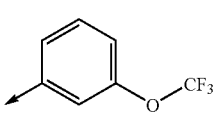 | 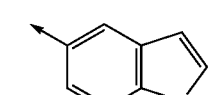 |
| 385 | NMe₂ | 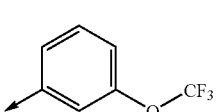 | 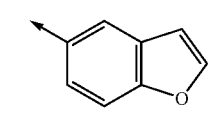 |
| 386 | NH₂ | 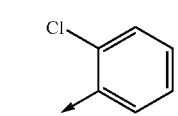 | 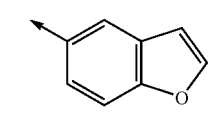 |
| 387 | SMe | 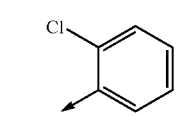 | 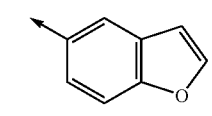 |
| 388 | NHMe | 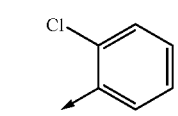 | |

TABLE 3-continued

| Example | R¹ | Aa-Ba | Rb |
|---|---|---|---|
| 389 | NH₂ | 5-benzofuran | 2,5-difluorophenyl |
| 390 | SH | 5-benzofuran | 2,5-difluorophenyl |
| 391 | SMe | 5-benzofuran | 2,5-difluorophenyl |
| 392 | S(O)Me | 5-benzofuran | 2,5-difluorophenyl |
| 393 | CH₂SMe | 5-benzofuran | 3-(OCF₃)phenyl |
| 394 | CH₂S(O)Me | 5-benzofuran | 3-(OCF₃)phenyl |
| 395 | CH₂S(O)₂Me | 5-benzofuran | 3-(OCF₃)phenyl |
| 396 | OH | 5-benzofuran | 4-(SMe)phenyl |
| 397 | OH | 5-benzofuran | 4-(S(O)Me)phenyl |
| 398 | OH | 5-benzofuran | 4-(S(O)₂Me)phenyl |
| 399 | OMe | 5-benzofuran | 4-(OCF₃)phenyl |
| 400 | MeC(O)OCH₂ | 5-benzofuran | 3-(OCF₃)phenyl |

TABLE 3-continued
| Example | R¹ | Aa-Ba | Rb |
|---|---|---|---|
| 401 |  | 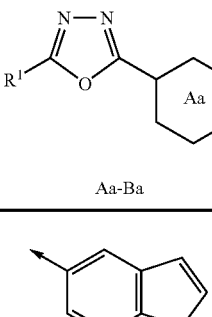 | 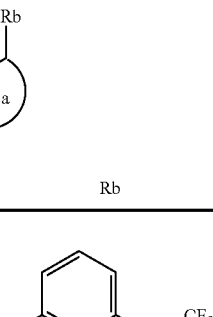 |
| 402 |  |  | 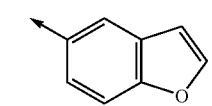 |
| 403 | 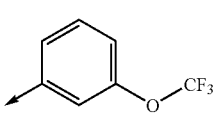 |  |  |
| 404 | 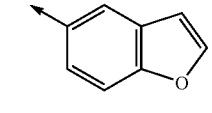 | 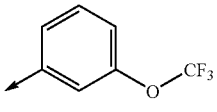 |  |
| 405 | 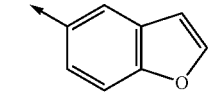 | 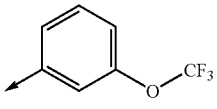 |  |
| 406 | 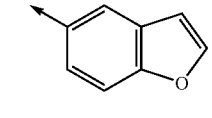 | 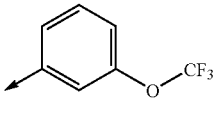 |  |
| 407 | 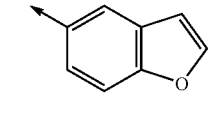 | 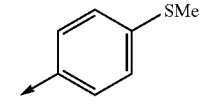 |  |
| 408 | 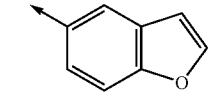 | 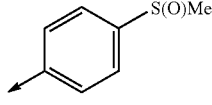 |  |
| 409 | 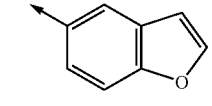 | 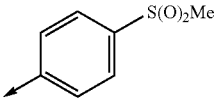 |  |
| 410 | 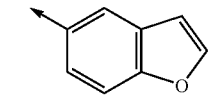 | 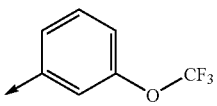 |  |
| 411 | 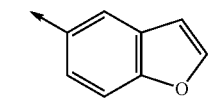 | 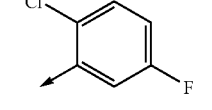 |  |

TABLE 3-continued

| Example | R¹ | Aa-Ba | Rb |
|---|---|---|---|
| 412 | HOC(Me)₂– | benzofuran-5-yl | 2,5-difluorophenyl |
| 413 | CH₂OMe | benzofuran-5-yl | 3-(trifluoromethoxy)phenyl |
| 414 | CH₂NHMe | benzofuran-5-yl | 3-(trifluoromethoxy)phenyl |
| 415 | Me | benzimidazol-5-yl | 1-benzylpiperidin-4-yl |
| 416 | 3-cyanophenethyl | benzimidazol-5-yl | 4-(SMe)phenyl |
| 417 | 3-cyanophenethyl | benzimidazol-5-yl | 4-S(O)Me-phenyl |
| 418 | 3-cyanophenethyl | benzimidazol-5-yl | 4-S(O)₂Me-phenyl |
| 419 | 3-(trifluoromethyl)phenethyl | benzimidazol-5-yl | 4-(SMe)phenyl |
| 420 | 3-(trifluoromethyl)phenethyl | benzimidazol-5-yl | 4-S(O)Me-phenyl |
| 421 | 3-(trifluoromethyl)phenethyl | benzimidazol-5-yl | 4-S(O)₂Me-phenyl |
| 422 | NH₂ | benzimidazol-5-yl | 4-(SMe)phenyl |
| 423 | NH₂ | benzimidazol-5-yl | 4-S(O)Me-phenyl |

TABLE 3-continued

| Example | R¹ | Aa-Ba | Rb |
|---|---|---|---|
| 424 | Me | benzimidazole | piperidine-N-S(O)₂Me |
| 425 | Me | benzimidazole | piperidine-N-COPh |
| 426 | Me | benzimidazole | piperidine-N-COMe |
| 427 | Me | benzimidazole | piperidine-N-CO₂Et |
| 428 | Me | benzimidazole | phenyl-OCF₃ |
| 429 | NHMe | benzimidazole | phenyl-SMe |
| 430 | NHEt | benzimidazole | phenyl-SMe |
| 431 | NH₂ | benzimidazole | phenyl-OCF₃ |
| 432 | SMe | benzimidazole | phenyl-OCF₃ |
| 433 | OMe | benzimidazole | phenyl-OCF₃ |
| 434 | NMe₂ | benzimidazole | phenyl-OCF₃ |
| 435 | NHMe | benzimidazole | phenyl-OCF₃ |

TABLE 3-continued

| Example | R¹ | Aa-Ba | Rb |
|---|---|---|---|
| 436 | Me | benzimidazole | phenyl-OCF₃ (meta) |
| 437 | S(O)Me | benzimidazole | phenyl-OCF₃ (para) |
| 438 | NH₂ | benzimidazole | phenyl-OCF₃ (meta) |
| 439 | Me | benzimidazole | phenyl-OCHF₂ (para) |
| 440 | NH₂ | benzimidazole | phenyl-OCHF₂ (para) |
| 441 | morpholinyl | benzimidazole | phenyl-OCF₃ (para) |
| 442 | SMe | benzimidazole | phenyl-OCHF₂ (para) |
| 443 | S(O)ME | benzimidazole | phenyl-OCHF₂ (para) |
| 444 | NHMe | benzimidazole | phenyl-OCHF₂ (para) |
| 445 | SMe | benzimidazole | phenyl-OCF₃ (meta) |
| 446 | NHMe | benzimidazole | phenyl-OCF₃ (meta) |
| 447 | Me | benzimidazole | phenyl-CF₃ (meta) |

TABLE 3-continued

| Example | R[1] | Aa-Ba | Rb |
|---|---|---|---|
| 448 | NH$_2$ | benzimidazole | 3-CF$_3$-phenyl |
| 449 | Me | benzimidazole | 2-Cl-5-CF$_3$-phenyl |
| 450 | NH$_2$ | benzimidazole | 2-Cl-5-CF$_3$-phenyl |
| 451 | Me | benzimidazole | 4-OCF$_3$-3-Cl-phenyl |
| 452 | NH$_2$ | benzimidazole | 4-OCF$_3$-3-Cl-phenyl |
| 453 | MeC(O)O-C(Me)$_2$- | benzimidazole | 4-OCF$_3$-phenyl |
| 454 | HO-C(Me)$_2$- | benzimidazole | 4-OCF$_3$-phenyl |
| 455 | NH$_2$ | benzimidazole | 2-Cl-phenyl |
| 456 | Me | benzothiophene | 4-SMe-phenyl |
| 457 | Me | benzothiophene | 4-S(O)Me-phenyl |
| 458 | Me | benzothiophene | 4-S(O)$_2$Me-phenyl |

TABLE 3-continued
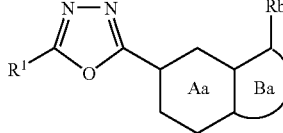
| Example | R¹ | Aa-Ba | Rb |
|---|---|---|---|
| 459 | Me | 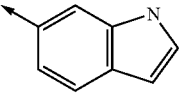 | 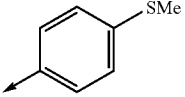 |
| 460 | Me | 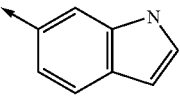 | 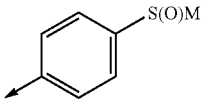 |
| 461 | Me | 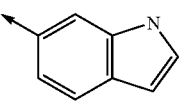 | 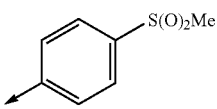 |
| 462 | Me | 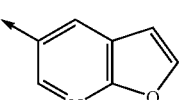 | 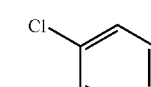 |
| 463 | Me | 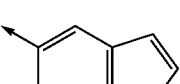 | 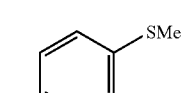 |
| 464 | Me | 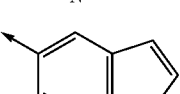 | 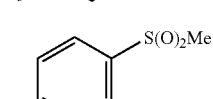 |
| 465 | Me | 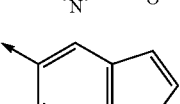 | 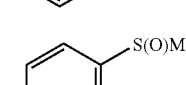 |
| 466 | Me | 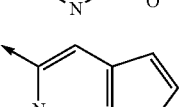 | 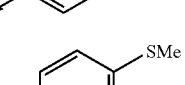 |
| 467 | Me | 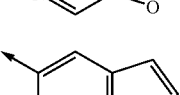 | 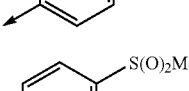 |
| 468 | Me | 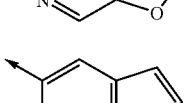 | 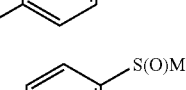 |
| 469 | Me | 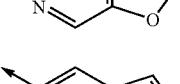 | 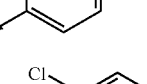 |
| 470 | Me | 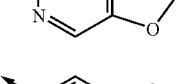 | 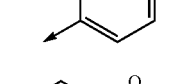 |

TABLE 3-continued
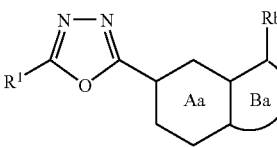
| Example | R¹ | Aa-Ba | Rb |
|---|---|---|---|
| 471 | Me | 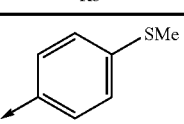 | 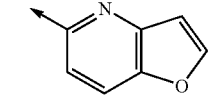 SMe |
| 472 | Me | 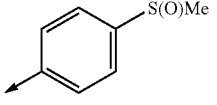 | 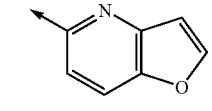 S(O)Me |
| 473 | Me | 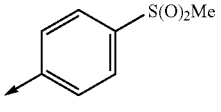 | 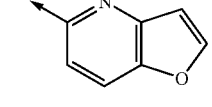 S(O)₂Me |
| 474 | Me | 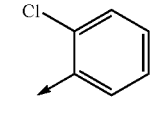 | 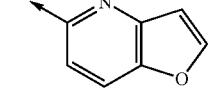 Cl |
| 475 | Me | 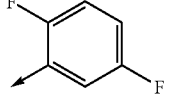 | 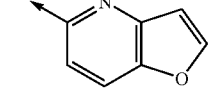 F, F |
| 476 | Me | 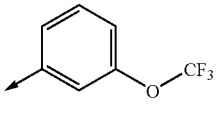 | 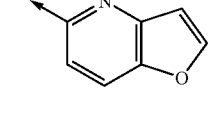 OCF₃ |
| 477 | Me | 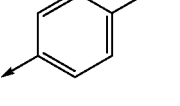 | 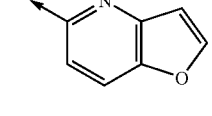 SEt |
| 478 | Me | 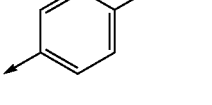 | 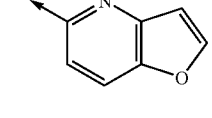 S(O)Et |
| 479 | Me | 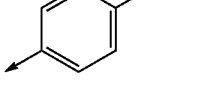 | 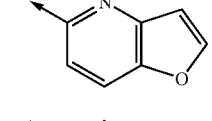 S(O)₂Et |
| 480 | Me | 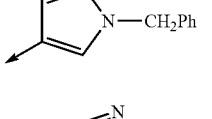 | 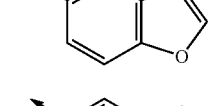 N—CH₂Ph |
| 481 | Me | 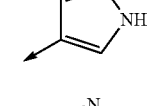 | 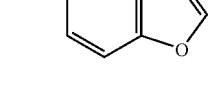 NH |
| 482 | Me | 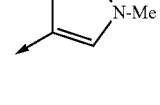 | N-Me |

TABLE 3-continued

| Example | R¹ | Aa-Ba | Rb | |
|---|---|---|---|---|
| 483 | Me | 5-benzofuran | 1-ethyl-pyrazol-4-yl | |
| 484 | Me | 5-benzofuran | 1-(CH₂OMe)-pyrazol-4-yl | |
| 485 | Me | 5-benzofuran | 1-(CH₂Ph)-pyrazol-4-yl | |
| 486 | Me | 5-benzofuran | 1-(2-cyanobenzyl)-pyrazol-4-yl | |
| 487 | Me | 5-benzofuran | 1-(2-CF₃-benzyl)-pyrazol-4-yl | |
| 488 | Me | 5-benzofuran | 1-(2-fluorobenzyl)-pyrazol-4-yl | |
| 489 | Me | 5-benzofuran | 1-(pyridin-2-ylmethyl)-pyrazol-4-yl | |
| 490 | Me | 5-benzofuran | 1-(pyridin-3-ylmethyl)-pyrazol-4-yl | |
| 491 | Me | 5-benzofuran | 3,3-dimethyl-1-oxo-2,3-dihydrobenzothiophen-5-yl | (short retention time) |

TABLE 3-continued

| Example | R¹ | Aa-Ba | Rb | |
|---|---|---|---|---|
| 492 | Me | 5-benzofuranyl | 3,3-dimethyl-2,3-dihydrobenzo[b]thiophene 1-oxide | (long retention time) |

TABLE 4

| Example | R¹ | |
|---|---|---|
| 493 | Me | 4-pyridyl-NH-(3-methoxyphenyl) |
| 494 | Me | 4-pyridyl-NH-(2,5-difluorophenyl) |
| 495 | Me | 4-pyridyl-NH-(3-trifluoromethylphenyl) |
| 496 | Me | 4-pyridyl-NH-CH₂-(3-trifluoromethylphenyl) |
| 497 | Me | 4-pyridyl-NH-CH₂-(2-pyridyl) |
| 498 | Me | 4-pyridyl-NH-CH₂-(3-pyridyl) |
| 499 | SMe | 4-pyridyl-NH-(3-trifluoromethylphenyl) |
| 500 | S(O)₂Me | 4-pyridyl-NH-(3-trifluoromethylphenyl) |
| 501 | S(O)Me | 4-pyridyl-NH-(3-trifluoromethylphenyl) |

FORMULATION EXAMPLE 1

| | |
|---|---|
| (1) compound of Example 17 | 50.0 mg |
| (2) lactose | 34.0 mg |

-continued

| | |
|---|---|
| (3) cornstarch | 10.6 mg |
| (4) cornstarch (paste) | 5.0 mg |
| (5) magnesium stearate | 0.4 mg |
| (6) calcium carboxymethylcellulose | 20.0 mg |
| total | 120.0 mg |

According to a conventional method, the above-mentioned (1)-(6) are mixed and tableted by a tableting machine to give a tablet.

FORMULATION EXAMPLE 2

| | |
|---|---|
| (1) compound of Example 17 | 10.0 mg |
| (2) lactose | 60.0 mg |
| (3) cornstarch | 35.0 mg |
| (4) gelatin | 3.0 mg |
| (5) magnesium stearate | 2.0 mg |

A mixture of the compound (10.0 mg) of Example 17, lactose (60.0 mg) and cornstarch (35.0 mg) is granulated using 10% aqueous gelatin solution (0.03 mL, 3.0 mg as gelatin) and by passing through a 1 mm mesh sieve, dried at 40° C. and passed through a sieve again. The thus-obtained granules are mixed with magnesium stearate (2.0 mg), and the mixture is compressed. The obtained core tablet is coated with a sugar coating of a suspension of saccharose, titanium dioxide, talc and gum arabic in water. The coated tablet is polished with beeswax to give a coated tablet.

FORMULATION EXAMPLE 3

| | |
|---|---|
| (1) compound of Example 17 | 10.0 mg |
| (2) lactose | 70.0 mg |
| (3) cornstarch | 50.0 mg |
| (4) soluble starch | 7.0 mg |
| (5) magnesium stearate | 3.0 mg |

The compound of Example 17 (10.0 mg) and magnesium stearate (3.0 mg) are granulated with an aqueous soluble starch solution (0.07 mL, 7.0 mg as soluble starch), dried, and mixed with lactose (70.0 mg) and cornstarch (50.0 mg). The mixture is compressed to give a tablet.

FORMULATION EXAMPLE 4

| | |
|---|---|
| (1) compound of Example 215 | 50.0 mg |
| (2) lactose | 34.0 mg |
| (3) cornstarch | 10.6 mg |
| (4) cornstarch (paste) | 5.0 mg |
| (5) magnesium stearate | 0.4 mg |
| (6) calcium carboxymethylcellulose | 20.0 mg |
| total | 120.0 mg |

According to a conventional method, the above-mentioned (1)-(6) are mixed and tableted by a tableting machine to give a tablet.

FORMULATION EXAMPLE 5

| | |
|---|---|
| (1) compound of Example 215 | 10.0 mg |
| (2) lactose | 60.0 mg |
| (3) cornstarch | 35.0 mg |
| (4) gelatin | 3.0 mg |
| (5) magnesium stearate | 2.0 mg |

A mixture of the compound (10.0 mg) of Example 215, lactose (60.0 mg) and cornstarch (35.0 mg) is granulated using 10% aqueous gelatin solution (0.03 mL, 3.0 mg as gelatin) and by passing through a 1 mm mesh sieve, dried at 40° C. and passed through a sieve again. The thus-obtained granules are mixed with magnesium stearate (2.0 mg), and the mixture is compressed. The obtained core tablet is coated with a sugar coating of a suspension of saccharose, titanium dioxide, talc and gum arabic in water. The coated tablet is polished with beeswax to give a coated tablet.

FORMULATION EXAMPLE 6

| | |
|---|---|
| (1) compound of Example 215 | 10.0 mg |
| (2) lactose | 70.0 mg |
| (3) cornstarch | 50.0 mg |
| (4) soluble starch | 7.0 mg |
| (5) magnesium stearate | 3.0 mg |

The compound of Example 215 (10.0 mg) and magnesium stearate (3.0 mg) are granulated with an aqueous soluble starch solution (0.07 mL, 7.0 mg as soluble starch), dried, and mixed with lactose (70.0 mg) and cornstarch (50.0 mg). The mixture is compressed to give a tablet.

FORMULATION EXAMPLE 7

| | |
|---|---|
| (1) compound of Example 140 | 50.0 mg |
| (2) lactose | 34.0 mg |
| (3) cornstarch | 10.6 mg |
| (4) cornstarch (paste) | 5.0 mg |
| (5) magnesium stearate | 0.4 mg |
| (6) calcium carboxymethylcellulose | 20.0 mg |
| total | 120.0 mg |

According to a conventional method, the above-mentioned (1)-(6) are mixed and tableted by a tableting machine to give a tablet.

FORMULATION EXAMPLE 8

| | |
|---|---|
| (1) compound of Example 140 | 10.0 mg |
| (2) lactose | 60.0 mg |
| (3) cornstarch | 35.0 mg |
| (4) gelatin | 3.0 mg |
| (5) magnesium stearate | 2.0 mg |

A mixture of the compound (10.0 mg) of Example 140, lactose (60.0 mg) and cornstarch (35.0 mg) is granulated using 10% aqueous gelatin solution (0.03 mL, 3.0 mg as gelatin) and by passing through a 1 mm mesh sieve, dried at 40° C. and passed through a sieve again. The thus-obtained granules are mixed with magnesium stearate (2.0 mg), and the mixture is compressed. The obtained core tablet is coated with a sugar coating of a suspension of saccharose, titanium dioxide, talc and gum arabic in water. The coated tablet is polished with beeswax to give a coated tablet.

FORMULATION EXAMPLE 9

| (1) compound of Example 140 | 10.0 mg |
|---|---|
| (2) lactose | 70.0 mg |
| (3) cornstarch | 50.0 mg |
| (4) soluble starch | 7.0 mg |
| (5) magnesium stearate | 3.0 mg |

The compound of Example 140 (10.0 mg) and magnesium stearate (3.0 mg) are granulated with an aqueous soluble starch solution (0.07 mL, 7.0 mg as soluble starch), dried, and mixed with lactose (70.0 mg) and cornstarch (50.0 mg). The mixture is compressed to give a tablet.

FORMULATION EXAMPLE 10

| (1) compound of Example 3 | 50.0 mg |
|---|---|
| (2) lactose | 34.0 mg |
| (3) cornstarch | 10.6 mg |
| (4) cornstarch (paste) | 5.0 mg |
| (5) magnesium stearate | 0.4 mg |
| (6) calcium carboxymethylcellulose | 20.0 mg |
| total | 120.0 mg |

According to a conventional method, the above-mentioned (1)-(6) are mixed and tableted by a tableting machine to give a tablet.

FORMULATION EXAMPLE 11

| (1) compound of Example 3 | 10.0 mg |
|---|---|
| (2) lactose | 60.0 mg |
| (3) cornstarch | 35.0 mg |
| (4) gelatin | 3.0 mg |
| (5) magnesium stearate | 2.0 mg |

A mixture of the compound (10.0 mg) of Example 3, lactose (60.0 mg) and cornstarch (35.0 mg) is granulated using 10% aqueous gelatin solution (0.03 mL, 3.0 mg as gelatin) and by passing through a 1 mm mesh sieve, dried at 40° C. and passed through a sieve again. The thus-obtained granules are mixed with magnesium stearate (2.0 mg), and the mixture is compressed. The obtained core tablet is coated with a sugar coating of a suspension of saccharose, titanium dioxide, talc and gum arabic in water. The coated tablet is polished with beeswax to give a coated tablet.

FORMULATION EXAMPLE 12

| (1) compound of Example 3 | 10.0 mg |
|---|---|
| (2) lactose | 70.0 mg |
| (3) cornstarch | 50.0 mg |
| (4) soluble starch | 7.0 mg |
| (5) magnesium stearate | 3.0 mg |

The compound of Example 3 (10.0 mg) and magnesium stearate (3.0 mg) are granulated with an aqueous soluble starch solution (0.07 mL, 7.0 mg as soluble starch), dried, and mixed with lactose (70.0 mg) and cornstarch (50.0 mg). The mixture is compressed to give a tablet.

FORMULATION EXAMPLE 13

| (1) compound of Example 270 | 50.0 mg |
|---|---|
| (2) lactose | 34.0 mg |
| (3) cornstarch | 10.6 mg |
| (4) cornstarch (paste) | 5.0 mg |
| (5) magnesium stearate | 0.4 mg |
| (6) calcium carboxymethylcellulose | 20.0 mg |
| total | 120.0 mg |

According to a conventional method, the above-mentioned (1)-(6) are mixed and tableted by a tableting machine to give a tablet.

FORMULATION EXAMPLE 14

| (1) compound of Example 270 | 10.0 mg |
|---|---|
| (2) lactose | 60.0 mg |
| (3) cornstarch | 35.0 mg |
| (4) gelatin | 3.0 mg |
| (5) magnesium stearate | 2.0 mg |

A mixture of the compound (10.0 mg) of Example 270, lactose (60.0 mg) and cornstarch (35.0 mg) is granulated using 10% aqueous gelatin solution (0.03 mL, 3.0 mg as gelatin) and by passing through a 1 mm mesh sieve, dried at 40° C. and passed through a sieve again. The thus-obtained granules are mixed with magnesium stearate (2.0 mg), and the mixture is compressed. The obtained core tablet is coated with a sugar coating of a suspension of saccharose, titanium dioxide, talc and gum arabic in water. The coated tablet is polished with beeswax to give a coated tablet.

FORMULATION EXAMPLE 15

| (1) compound of Example 270 | 10.0 mg |
|---|---|
| (2) lactose | 70.0 mg |
| (3) cornstarch | 50.0 mg |
| (4) soluble starch | 7.0 mg |
| (5) magnesium stearate | 3.0 mg |

The compound of Example 270 (10.0 mg) and magnesium stearate (3.0 mg) are granulated with an aqueous soluble starch solution (0.07 mL, 7.0 mg as soluble starch), dried, and mixed with lactose (70.0 mg) and cornstarch (50.0 mg). The mixture is compressed to give a tablet.

EXPERIMENTAL EXAMPLE 1

GSK-3β Inhibitory Activity Evaluation (1) Cloning of Human GSK-3β Gene and Preparation of Recombinant Baculovirus Human GSK-3β gene was cloned by PCR using human brain cDNA (Clontech; trade name: QUICK-Clone cDNA) as a template and a primer set (GSK3β-U: 5'-AAAGAAT-TCACCATGGACTACAAGGACGACGATGA-CAAGTCAGGGCGGCCCAGAACCACCTCCTT-3' (SEQ ID NO: 1) and GSK3β-L: 5'-AAAAGTCGACTCAGGTG-GAGTTGGAAGCTGATGCAGAAG-3' (SEQ ID NO: 2)) prepared by reference to the base sequence of GSK-3β gene registered under an accession No. NM_002093 in the GenBank.

PCR was performed according to the protocol attached to KOD plus DNA polymerase (TOYOBO CO., LTD.). The obtained PCR product was subjected to agarose gel (1%) electrophoresis, and DNA fragment (1.2 kb) containing GSK-3β gene was recovered from the gel, and digested with restriction enzymes EcoR I and Sal I. DNA after treatment with restriction enzymes was subjected to agarose gel (1%) electrophoresis, and the obtained DNA fragment was recovered, and ligated to plasmid pFASTBAC1 (Invitrogen) digested with restriction enzymes EcoR I and Sal I to give expression plasmid pFB-GSK3β. The base sequence of the inserted fragment was confirmed to match the object sequence. Using BAC-TO-BAC Baculovirus Expression System (Invitrogen), virus stock BAC-GSK3β of recombinant Baculovirus was prepared.

(2) Preparation of Recombinant GSK-3β Enzyme

Sf-21 cells (Invitrogen) were inoculated to 150 ml Sf-900 II SFM medium (Invitrogen) containing 10% fetal bovine serum to $1\times10^6$ cells/ml and cultured at 27° C. for 24 hr. To the obtained culture medium was added the virus stock BAC-GSK3β of recombinant Baculovirus obtained above by 150 μl each, and the cells were further cultured for 60 hr. The culture medium was centrifuged (3000 rpm, 10 min) to separate the cells, and the cells were washed once with PBS. The cells were suspended in 10 ml of cell lysis buffer (25 mM HEPES (pH 7.5), 1% Triton X, 130 mM sodium chloride, 1 mM EDTA, 1 mM Dithiothreitol, 25 mM β-glycerophosphate, Protease inhibitor Complete (Boehringer), 1 mM sodium orthovanadate), treated 4 times in a homogenizer (POLY-TRON) at 20000 rpm, 30 sec to disrupt the cells. The cell disrupt solution was centrifuged (40000 rpm, 45 min), and GSK-3β was purified from the obtained supernatant using Anti-FLAG M2 Affinity Gel (Sigma Ltd.).

(3) Experiment Method

To 37.5 μl of a reaction solution (25 mM HEPES (pH 7.5), 10 mM magnesium acetate, 1 mM DTT, 0.01% bovine serum albumin (Wako Pure Chemical Industries, Ltd.)) containing recombinant GSK-3β enzyme (100 ng) obtained above and substrate peptide (YR-RAAVPPSPSLSRHSSPHQpSEDEEE, pS is phosphorylated serine) (100 ng) derived from glycogen synthase was added a test compound (2.5 μl) dissolved in DMSO, and the mixture was incubated at room temperature for 5 min. To the obtained mixture was added ATP solution (2.5 μM ATP, 10 μl), and the mixture was reacted at room temperature for 30 min. After the reaction, the reaction was quenched by adding 50 μL of Kinase Glo Reagent (Promega) to the reaction solution. After reaction at room temperature for 10 min, the luminescence amount was measured using an ARVO multilabel counter (PerkinElmer Life Sciences). The concentration of the test compound necessary for inhibiting the luminescence amount by 50% ($IC_{50}$ value) was calculated by PRISM 3.0 (Graphpad software).

As a result, the compounds obtained in Reference Examples 71, 72, Examples 1-13, 16-18, 20, 22, 24, 27-30, 39, 43, 47-51, 56-58, 78, 79, 83, 122, 123, 127, 131, 132, 134, 135, 137-143, 145-149, 153-156, 159, 166-174, 176-182, 184-188, 190-193, 204, 210-220, 223, 229-231, 233, 234, 237, 246, 249-252, 256-262, 264, 265, 267-271, 273-276, 278, 279, 281-294, 296-303, 305, 306, 308, 310-314, 316-318, 320, 322, 330, 333-336, 338-343, 346, 347, 349, 350, 352, 354-356, 358, 359, 365-373, 376-378, 380, 382, 383, 385, 386, 388-392, 398, 401, 403, 405, 409, 410, 416-423, 429-431, 435-438, 440, 443-446, 448, 451, 452, 455, 476, 485, 486, 488, 490-492 and 499-501 showed an $IC_{50}$ value of not more than 100 nM.

EXPERIMENTAL EXAMPLE 2

Measurement of Serine Threonine Kinase Inhibitory Activity

Inhibitory action on various purified proteins of serine, threonine kinases (p38α, JNK1, IKKβ, ASK1, TAK1, MEKK1, PKCθ, GSK-3β, PLK1, TTK, Aurora A, MEK1, MEK5, B-RAF, ERK1) was examined. As a reaction mixture, 37.5 μL of 25 mM HEPES (pH 7.5), 10 mM magnesium acetate, 1 mM DTT, each concentration of purified protein and a synthesis substrate were used. The mixture was reacted in the presence or absence of a test compound (2.5 μL/the reaction mixture) dissolved in DMSO at each concentration at room temperature for 5 min. Further, 10 μL of a mixture of 2.5 μM ATP and 10 μCi/ml [γ-$^{33}$P]ATP (DAIICHI PURE CHEMICALS) was added and the mixture was reacted at room temperature for 30 min. After quenching the reaction, the amount of phosphorylated peptide was measured by Top-Count (Packard). The concentration of the test compound necessary for 50% inhibition ($IC_{50}$ value) was calculated by PRISM 3.0 (GraphPad Software).

As a result, the compounds obtained in Reference Example 71, Example 165 and Example 209 showed $IC_{50}$ values of 0.065 μM, 0.19 μM and 0.14 μM, respectively, against GSK-3β, but did not show 50% inhibitory activity against other kinases even at a concentration of 10 μM. Therefrom it was found that the GSK-3β inhibitor of the present invention has superior kinase selectivity.

EXPERIMENTAL EXAMPLE 3

Evaluation of Intracellular GSK-3β Inhibitory Activity with Tau Phosphorylation as Index Cerebral cortex-derived neuronal cell was prepared from SD rat fetus (TP-17), suspended in a neuronal cell culture medium (SUMITOMO BALELITE) to 100,000 cells/mL, and plated on a poly-D-Lysin/Laminin-coated 96 well plate at 100 μL/well. After culture at 37° C., 5% $CO_2$ for 4 days, the test compound was diluted with a neuronal cell culture medium (SUMITOMO BAKELITE), added to the neuronal cell at 100 μL/well, and allowed to react at 37° C., 5% $CO_2$ for 2 hr (final 0, 0.1, 0.5, 1, 2, 5, 10, 20 μM, each n=3 wells). After 2 hr, the medium was removed, and the cells were washed with cooled 1×PBS (−) and fixed with 4% para-formaldehyde for 30 min. After washing with 1× PBS (−), 2% BSA, 0.1% Triton X-100-containing PBS (blocking solution) was added by 200 μL/well and blocking was performed at room temperature for 1 hr. Calf intestine alkaline phosphatase was added at 10 U/well to a 100% inhibition control group. The blocking solution was removed, MAb anti-PHF Tau AT-8 (phosphorylated Tau) (Innogenetics, mouse monoclonal antibody), which was 200-fold diluted with a blocking solution, and Tau Ab-3 (total Tau) (NeoMarker, rabbit polyclonal antibody), which was 500-fold diluted therewith, were added at 50 μL/well. After reaction at room temperature for 2 hr, the cells were washed 4 times with 0.1% Tween 20-containing PBS (PBST). Then, Alexa Fluoro 680 goat anti-mouse IgG (Invitrogen), which was 200-fold diluted with a blocking solution and IR Dye 800CW anti-rabbit IgG (Rockland, 1 mg/mL), which was 800-fold diluted therewith, were added at 50 μL/well, and the mixture was reacted at room temperature for 1 hr. The cells were washed 4 times with PBST, and the fluorescence at 700 nm (phosphorylated Tau: AT-8) and 800 nm (total Tau) was measured using a near-infrared imaging system Odyssey (LI-COR). The amount of phosphorylated Tau (AT-8) was amended with total Tau, and the ratio (%) of Tau phosphorylation was calculated with the amount of phosphorylation at 0 μM as 100% and the amount of phosphorylation of the alkaline phosphatase treatment group as 0%, based on which the $IC_{50}$ value was calculated using preclinical package.

As a result, the compounds obtained in Examples 3, 16, 24, 176-179, 181, 184-187, 191-193, 213-215, 218-220, 234, 259-262, 310, 367, 376, 380, 386, 389, 416-421, 423, 437, 438, 440, 443, 446, 448 and 455 showed $IC_{50}$ values of not more than 10 μM.

EXPERIMENTAL EXAMPLE 4

In Vivo Evaluation of GSK-3β Inhibitor in Cold Water Stress (CWS) Model

A test compound suspended in 0.5% methylcellulose was orally administered to C57BL/6N mice (7- to 10-week-old, male). After 30 min, the mice were placed in cold water at 1-2° C. and made to swim for 4 min. At 30 min after the cold swimming, the hippocampus was removed from the mice, homogenized with 300 μL of RIPA buffer, and centrifuged at 4° C., 15000 rpm×10 min. The protein concentration of the supernatant was measured using a BCA protein Assay Reagent (PIERCE), adjusted to protein 1 mg/mL, and preserved at −80° C. until measurement. SDS-PAGE sample buffer was added to and blended with the cryopreserved sample, treated at 42° C. for 30 min, and centrifuged at 15000 rpm×10 min, and the supernatant was applied to 10% polyacrylamide gel (4% stacking gel) to a protein amount of 10 μg/lane and electrophoresed (at 45 mA for 90 min per one sheet of gel). Using Trans Blot SD-cell (BIO RAD), the protein on the gel after electrophoresis was transferred onto a PVDF membrane (Immobilon-P, Millipore) at 120 mA for 45 min. A membrane after completion of transfer was soaked in TBS with 0.05% Tween-20 (TBS-T), and shaken gently at room temperature for 15 min. The membrane was soaked in Block Ace (Yukijirushi), blocked at room temperature for 45 min, soaked in a primary antibody (anti-phosphorylated Tau pT205 antibody (Biosource), which was 1000-fold diluted with 3% BSA-containing TBS), and shaken gently at room temperature for 1 hr or overnight at 4° C. After washing with TBS-T (3 min×3), the membrane was soaked in a secondary antibody (HRP-labeled anti-rabbit antibody (Amersham), which was 20000-fold diluted with TBS-T) and shaken gently at room temperature for 1 hr. After washing with TBS-T (3 min×3), the membrane was soaked in ImmunoStar reagent (Wako Pure Chemical Industries, Ltd.) and agitated for 3 min. The luminescence signal was detected with LAS1000 (Fujifilm), and the band was quantified with the application attached to LAS1000 (ImageGauge). Then the membrane was soaked in Reblotting buffer, shaken for 10 min, and washed with TBS-T (3 min×3), and the above-mentioned procedure was repeated using anti-total Tau antibody Ab-3 (NeoMarkers) 5000-fold diluted with 3% BSA-containing TBS as the primary antibody. As for the quantified image data, the phosphorylated Tau (pT205) data was amended with total Tau (Ab-3) data, and the ratio (%) of Tau phosphorylation was calculated with the amount of CWS treatment vehicle group as 100% and the normal group as 0%, and a significant difference was detected using preclinical package, where $p \leq 0.05$ meant a significant difference.

INDUSTRIAL APPLICABILITY

The GSK-3β inhibitor of the present invention is useful as an agent for the prophylaxis or treatment of GSK-3β-related pathology or diseases.

This application is based on a patent application No. 2006-212642 filed in Japan, the contents of which are incorporated in full herein by this reference. In addition, the patent documents and non-patent documents cited in the present specification are hereby incorporated in their entireties by reference, to the extent that they have been disclosed in the present specification.

The invention claimed is:

1. A GSK-3β inhibitor comprising a compound represented by the formula (I):

wherein
R$^1$ is a group represented by the formula: R$^{1a}$—Y—
   wherein
   Y is a bond, a sulfur atom, or —NR$^y$— (R$^y$ is a hydrogen atom, or a lower alkyl group), and
   R$^{1a}$ is (1) a hydrogen atom, or (2) a C$_{1-2}$ alkyl group optionally substituted by one or more substituents selected from the group consisting of a halogen atom, an optionally substituted carbamoyl group, an optionally substituted C$_{6-10}$ aryl group and an optionally substituted 5- to 10-membered aromatic heterocyclic group, and
W is a group represented by the formula:

wherein
ring A is a 6-membered aromatic ring,
X is an oxygen atom, and
ring B is a 5-membered heterocycle represented by wherein
Rb is an optionally substituted phenyl group, or an optionally substituted 5- or 6-membered heterocyclic group, and Rb$^1$ is a hydrogen atom, an amino group, or a monosubstituted amino group, or a salt thereof.

2. A method of inhibiting GSK-3β, comprising administering a compound represented by the formula (I):

wherein
R$^1$ is a group represented by the formula: R$^{1a}$—Y—
   wherein
   Y is a bond, a sulfur atom, or —NR$^y$— (R$^y$ is a hydrogen atom, or a lower alkyl group), and
   R$^{1a}$ is (1) a hydrogen atom, or (2) a C$_{1-2}$ alkyl group optionally substituted by one or more substituents selected from the group consisting of a halogen atom, an optionally substituted carbamoyl group, an optionally substituted C$_{6-10}$ aryl group and an optionally substituted 5- to 10-membered aromatic heterocyclic group, and
W is a group represented by the formula:

wherein
ring A is a 6-membered aromatic ring,
X is an oxygen atom, and
ring B is a 5-membered heterocycle represented by wherein
Rb is an optionally substituted phenyl group, or an optionally substituted 5- or 6-membered heterocyclic group, and Rb' is a hydrogen atom, an amino group, or a monosubstituted amino group, or a salt thereof to a subject.

3. The method of claim 2, wherein the subject suffers from a neurodegenerative disease.

4. The method of claim 2, wherein the subject suffers from Alzheimer's disease.

5. A pharmaceutical composition comprising the GSK-3β inhibitor of claim 1, and a pharmacologically acceptable carrier.

* * * * *

UNITED STATES PATENT AND TRADEMARK OFFICE
CERTIFICATE OF CORRECTION

PATENT NO.        : 8,492,378 B2
APPLICATION NO.   : 12/309906
DATED             : July 23, 2013
INVENTOR(S)       : Fumio Itoh Page 1 of 2

It is certified that error appears in the above-identified patent and that said Letters Patent is hereby corrected as shown below:

In the Claims

In claim 1, col. 409, the two formulas in lines 48-53, of "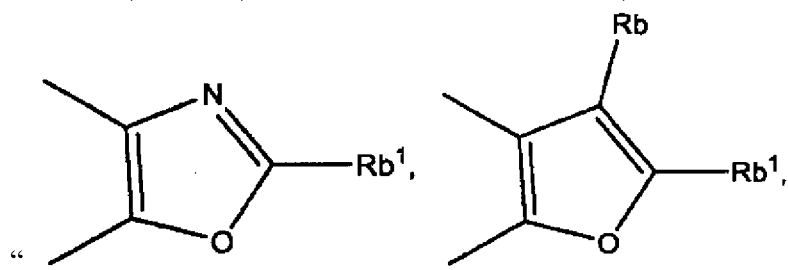", should be deleted and the following two formulas should be added:

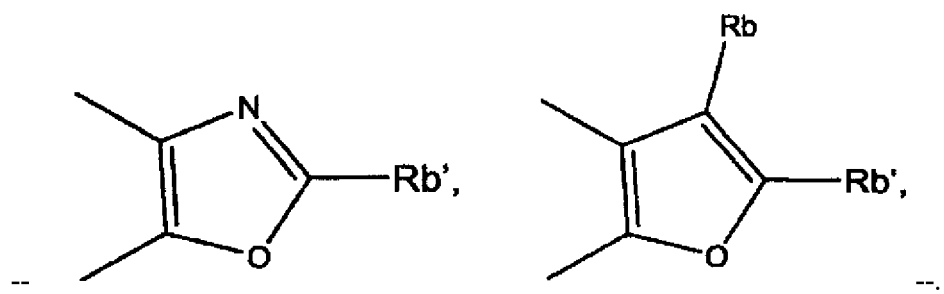

--.

In claim 1, in col. 410, line 14,
"Rb' is a hydrogen atom" should be deleted, and
--Rb' is a hydrogen atom-- should be added.

Signed and Sealed this
First Day of July, 2014

Michelle K. Lee
*Deputy Director of the United States Patent and Trademark Office*

In claim 2, col. 410, the two formulas in lines 53-58, of
" 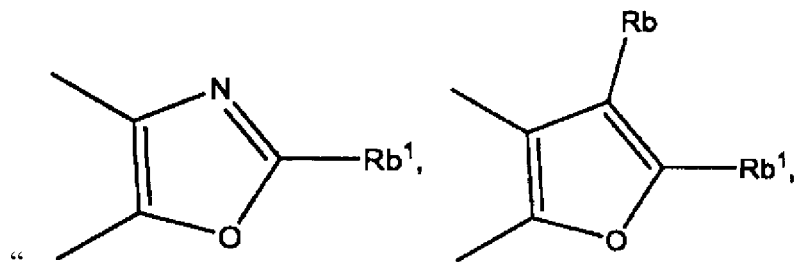 ", should be deleted and the following two formulas should be added:
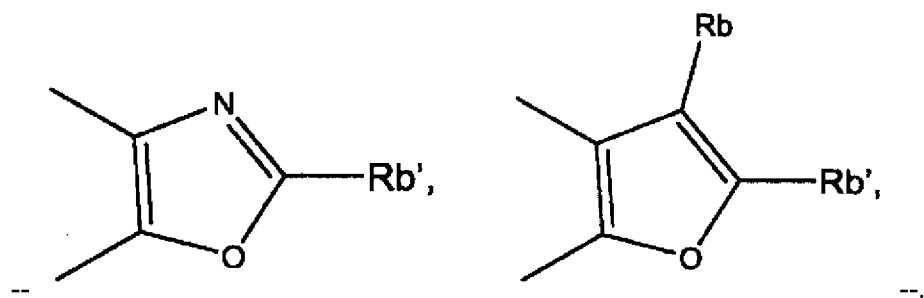
--     --.
In claim 2, in col. 411, line 5,
"Rb' is a hydrogen atom" should be deleted, and
--Rb' is a hydrogen atom-- should be added.

UNITED STATES PATENT AND TRADEMARK OFFICE
CERTIFICATE OF CORRECTION

PATENT NO.        : 8,492,378 B2
APPLICATION NO.   : 12/309906
DATED             : July 23, 2013
INVENTOR(S)       : Fumio Itoh Page 1 of 1

It is certified that error appears in the above-identified patent and that said Letters Patent is hereby corrected as shown below:

In the Claims

In claim 2, col. 410, lines 40-45, the formula

"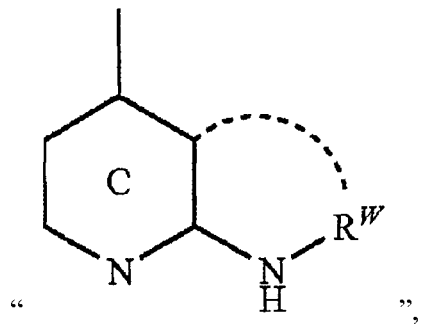", should be deleted and the following formula should be added:

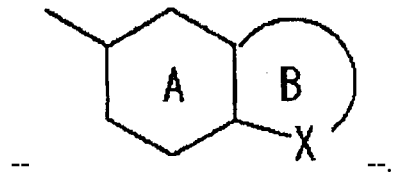.

Signed and Sealed this
Eighteenth Day of November, 2014

Michelle K. Lee
*Deputy Director of the United States Patent and Trademark Office*